(12) United States Patent
Rodgers et al.

(10) Patent No.: US 10,640,506 B2
(45) Date of Patent: *May 5, 2020

(54) CYCLOBUTYL SUBSTITUTED PYRROLOPYRIDINE AND PYRROLOPYRIMIDINES DERIVATIVES AS JAK INHIBITORS

(71) Applicants: Incyte Corporation, Wilmington, DE (US); Incyte Holdings Corporation, Wilmington, DE (US)

(72) Inventors: James D. Rodgers, Jupiter, FL (US); Stacey Shepard, Wilmington, DE (US); Lixin Shao, Wilmington, DE (US); Joseph Glenn, Mount Royal, NJ (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/047,544

(22) Filed: Jul. 27, 2018

(65) Prior Publication Data

US 2019/0135813 A1    May 9, 2019

Related U.S. Application Data

(60) Continuation of application No. 14/556,775, filed on Dec. 1, 2014, now abandoned, which is a division of application No. 13/300,094, filed on Nov. 18, 2011, now Pat. No. 8,933,085.

(60) Provisional application No. 61/415,705, filed on Nov. 19, 2010.

(51) Int. Cl.
| | |
|---|---|
| *C07D 487/04* | (2006.01) |
| *A61K 31/519* | (2006.01) |
| *A01N 43/90* | (2006.01) |
| *C07D 491/107* | (2006.01) |
| *A61P 19/02* | (2006.01) |
| *A61P 29/00* | (2006.01) |
| *A61P 35/04* | (2006.01) |
| *A61P 27/04* | (2006.01) |
| *C07D 471/04* | (2006.01) |

(52) U.S. Cl.
CPC ........... *C07D 487/04* (2013.01); *A01N 43/90* (2013.01); *A61K 31/519* (2013.01); *A61P 19/02* (2018.01); *A61P 27/04* (2018.01); *A61P 29/00* (2018.01); *A61P 35/04* (2018.01); *C07D 471/04* (2013.01); *C07D 491/107* (2013.01)

(58) Field of Classification Search
CPC ........................... C07D 487/04; A61K 31/519
USPC ...................................... 544/280; 514/265.1
See application file for complete search history.

(56) References Cited

U.S. PATENT DOCUMENTS

| | | | |
|---|---|---|---|
| 2,985,589 | A | 5/1961 | Broughton et al. |
| 3,832,460 | A | 8/1974 | Kosti |
| 4,140,755 | A | 2/1979 | Sheth |
| 4,402,832 | A | 9/1983 | Gerhold |
| 4,498,991 | A | 2/1985 | Oroskar |
| 4,512,984 | A | 4/1985 | Seufert et al. |
| 4,548,990 | A | 10/1985 | Mueller et al. |
| 4,814,477 | A | 3/1989 | Wijnberg et al. |
| 5,378,700 | A | 1/1995 | Sakuma et al. |
| 5,472,949 | A | 12/1995 | Arasaki |

(Continued)

FOREIGN PATENT DOCUMENTS

| | | |
|---|---|---|
| CN | 102026999 | 4/2011 |
| CN | 102458581 | 5/2012 |

(Continued)

OTHER PUBLICATIONS

"FDA prescribing information for Jakafi (Ruxolitinib dosage form)", (Nov. 1, 2011) Retrieved from the Internet: URL: http://www.accessdata.fda.gov/drugsatfda_docs/labels/2011/2021921b1.pdf [retrieved on Sep. 25, 2013] 22 pages.

(Continued)

*Primary Examiner* — Susanna Moore
(74) *Attorney, Agent, or Firm* — Fish & Richardson P.C.

(57) ABSTRACT

The present invention provides cyclobutyl substituted pyrrolopyrimidines and pyrrolopyridines of Formula I:

wherein X, Y, Z, L, A, $R^5$, n and m are defined above, as well as their compositions and methods of use, that modulate the activity of Janus kinases (JAKs) and are useful in the treatment of diseases related to the activity of JAKs includ- (Continued)

ing, for example, inflammatory disorders, autoimmune disorders, cancer, and other diseases.

20 Claims, No Drawings

(56) References Cited

U.S. PATENT DOCUMENTS

| | | |
|---|---|---|
| 5,510,101 A | 4/1996 | Stroppolo |
| 5,521,184 A | 5/1996 | Zimmermann |
| 5,630,943 A | 5/1997 | Grill |
| 5,795,909 A | 8/1998 | Shashoua et al. |
| 5,856,326 A | 1/1999 | Anthony |
| 5,919,779 A | 7/1999 | Proudfoot et al. |
| 6,025,366 A | 2/2000 | Walsh et al. |
| 6,060,038 A | 5/2000 | Burns |
| 6,075,056 A | 6/2000 | Quigley, Jr. et al. |
| 6,136,198 A | 10/2000 | Adam et al. |
| 6,217,895 B1 | 4/2001 | Guo et al. |
| 6,335,342 B1 | 1/2002 | Longo et al. |
| 6,375,839 B1 | 4/2002 | Adam et al. |
| 6,413,419 B1 | 7/2002 | Adam et al. |
| 6,486,322 B1 | 11/2002 | Longo et al. |
| 6,518,265 B1 | 2/2003 | Kato et al. |
| 6,548,078 B2 | 4/2003 | Guo |
| 6,569,443 B1 | 5/2003 | Dawson |
| 6,579,882 B2 | 6/2003 | Stewart et al. |
| 6,624,138 B1 | 9/2003 | Sung et al. |
| 6,635,762 B1 | 10/2003 | Blumenkopf et al. |
| 6,712,973 B2 | 3/2004 | Adam et al. |
| 6,713,089 B1 | 3/2004 | Bertelsen et al. |
| 6,852,727 B2 | 2/2005 | Goulet et al. |
| 6,953,776 B2 | 10/2005 | Di Napoli |
| 7,005,436 B2 | 2/2006 | Lloyd et al. |
| 7,167,750 B2 | 1/2007 | Knudson et al. |
| 7,265,108 B2 | 9/2007 | Ozaki |
| 7,335,667 B2 | 2/2008 | Rodgers et al. |
| 7,358,255 B2 | 4/2008 | Nakamura |
| 7,517,870 B2 | 4/2009 | Auricchio |
| 7,598,257 B2 | 10/2009 | Rodgers et al. |
| 7,683,171 B2 | 3/2010 | Pitts et al. |
| 7,745,437 B2 | 6/2010 | Ren et al. |
| 7,750,007 B2 | 7/2010 | Bearss et al. |
| 7,834,022 B2 | 11/2010 | Rodgers et al. |
| 8,053,433 B2 | 11/2011 | Rodgers et al. |
| 8,158,616 B2 | 4/2012 | Rodgers et al. |
| 8,309,718 B2 | 11/2012 | Li et al. |
| 8,410,265 B2 | 4/2013 | Zhou et al. |
| 8,415,362 B2 | 4/2013 | Rodgers et al. |
| 8,420,629 B2 | 4/2013 | Rodgers et al. |
| 8,440,679 B2 | 5/2013 | McAllister |
| 8,445,488 B2 | 5/2013 | Rodger et al. |
| 8,486,902 B2 | 7/2013 | Rodgers et al. |
| 8,513,270 B2 | 8/2013 | Arvanitis et al. |
| 8,530,485 B2 | 9/2013 | Rodgers et al. |
| 8,541,425 B2 | 9/2013 | Rodgers et al. |
| 8,563,541 B2 | 10/2013 | Arvanitis et al. |
| 8,604,043 B2 | 12/2013 | Li et al. |
| 8,637,529 B2 | 1/2014 | Woller |
| 8,691,807 B2 | 4/2014 | Yao et al. |
| 8,716,303 B2 | 5/2014 | Rodgers et al. |
| 8,722,693 B2 | 5/2014 | Rodgers et al. |
| 8,741,895 B2 | 6/2014 | Rodgers et al. |
| 8,748,401 B2 | 6/2014 | Rodgers et al. |
| 8,765,734 B2 | 7/2014 | Huang et al. |
| 8,822,481 B1 | 9/2014 | Rodgers et al. |
| 8,829,013 B1 | 9/2014 | Rodgers et al. |
| 8,835,423 B2 | 9/2014 | Arvanitis et al. |
| 8,841,318 B2 | 9/2014 | Arvanitis et al. |
| 8,883,806 B2 | 11/2014 | Zhou et al. |
| 8,889,697 B2 | 11/2014 | Rodgers et al. |
| 8,933,085 B2 | 1/2015 | Rodgers et al. |
| 8,933,086 B2 | 1/2015 | Rodgers et al. |
| 8,946,245 B2 | 2/2015 | Rodgers et al. |
| 8,987,442 B2 | 3/2015 | Tung et al. |
| 8,987,443 B2 | 3/2015 | Liu |
| 8,993,582 B2 | 3/2015 | Zhou et al. |
| 9,000,161 B2 | 4/2015 | Zhou et al. |
| 9,023,840 B2 | 5/2015 | Yao et al. |
| 9,034,884 B2 | 5/2015 | Rodgers et al. |
| 9,079,912 B2 | 7/2015 | Rodgers et al. |
| 9,090,611 B2 | 7/2015 | Rodgers et al. |
| 9,181,271 B2 | 11/2015 | Li et al. |
| 9,206,187 B2 | 12/2015 | Rodgers et al. |
| 9,216,984 B2 | 12/2015 | Li |
| 9,221,845 B2 | 12/2015 | Cao |
| 9,290,506 B2 | 3/2016 | Zhou et al. |
| 9,334,274 B2 | 5/2016 | Rodgers |
| 9,359,358 B2 | 6/2016 | Rodgers |
| 9,376,439 B2 | 6/2016 | Rodgers |
| 9,464,088 B2 | 10/2016 | Huang |
| 9,487,521 B2 | 11/2016 | Zhou et al. |
| 9,498,467 B2 | 11/2016 | Leopold et al. |
| 9,611,269 B2 | 4/2017 | Yao et al. |
| 9,623,029 B2 | 4/2017 | Li et al. |
| 9,655,854 B2 | 5/2017 | Yeleswaram |
| 9,974,790 B2 | 5/2018 | Rodgers et al. |
| 9,999,619 B2 | 6/2018 | Huang et al. |
| 10,398,699 B2 | 9/2019 | Rodgers et al. |
| 2002/0111353 A1 | 8/2002 | Ledeboer et al. |
| 2003/0064969 A1 | 4/2003 | Bhagwat et al. |
| 2003/0100756 A1 | 5/2003 | Adams et al. |
| 2003/0144309 A1 | 7/2003 | Choon-Moon |
| 2003/0165576 A1 | 9/2003 | Fujii et al. |
| 2004/0009222 A1 | 1/2004 | Chou et al. |
| 2004/0009983 A1 | 1/2004 | Cox et al. |
| 2004/0029857 A1 | 2/2004 | Hale et al. |
| 2004/0077654 A1 | 4/2004 | Bouillot |
| 2004/0099204 A1 | 5/2004 | Nestor |
| 2004/0198737 A1 | 10/2004 | Cox et al. |
| 2004/0204404 A1 | 10/2004 | Zelle |
| 2004/0214928 A1 | 10/2004 | Aronov |
| 2004/0235862 A1 | 11/2004 | Burns |
| 2005/0014966 A1 | 1/2005 | Tabe |
| 2005/0054568 A1 | 3/2005 | Ling |
| 2005/0153989 A1 | 7/2005 | Grotzfeld et al. |
| 2006/0004010 A1 | 1/2006 | Habashita et al. |
| 2006/0020011 A1 | 1/2006 | Wu et al. |
| 2006/0079511 A1 | 4/2006 | Liu et al. |
| 2006/0106020 A1 | 5/2006 | Rodgers et al. |
| 2006/0106027 A1 | 5/2006 | Furet et al. |
| 2006/0128803 A1 | 6/2006 | Klimko |
| 2006/0135537 A1 | 6/2006 | Knegtel et al. |
| 2006/0178393 A1 | 8/2006 | Pitts |
| 2006/0183761 A1 | 8/2006 | Ledeboer et al. |
| 2006/0183906 A1 | 8/2006 | Rodgers et al. |
| 2006/0223864 A1 | 10/2006 | Biju |
| 2006/0293311 A1 | 12/2006 | Li et al. |
| 2007/0135461 A1 | 6/2007 | Rodgers et al. |
| 2007/0135466 A1 | 6/2007 | Ledeboer et al. |
| 2007/0149506 A1 | 6/2007 | Arvanitis et al. |
| 2007/0149561 A1 | 6/2007 | Dhanak et al. |
| 2007/0191364 A1 | 8/2007 | Braun et al. |
| 2007/0191405 A1 | 8/2007 | Noronha |
| 2007/0208053 A1 | 9/2007 | Wang et al. |
| 2007/0225286 A1 | 9/2007 | Ren et al. |
| 2007/0259904 A1 | 11/2007 | Noronha |
| 2008/0021026 A1 | 1/2008 | Borchardt et al. |
| 2008/0085898 A1 | 4/2008 | Lu |
| 2008/0096852 A1 | 4/2008 | Yanni |
| 2008/0119496 A1 | 5/2008 | Ohlmeyer |
| 2008/0161346 A1 | 7/2008 | Cheng |
| 2008/0188500 A1 | 8/2008 | Arvanitis et al. |
| 2008/0194468 A1 | 8/2008 | Bodor |
| 2008/0207570 A1 | 8/2008 | Segura-Orsoni |
| 2008/0207584 A1 | 8/2008 | Habashita et al. |
| 2008/0280876 A1 | 11/2008 | Hobson et al. |
| 2008/0312258 A1 | 12/2008 | Rodgers et al. |
| 2008/0312259 A1 | 12/2008 | Rodgers et al. |
| 2009/0018156 A1 | 1/2009 | Tang et al. |
| 2009/0076070 A1 | 3/2009 | Harada et al. |
| 2009/0088410 A1 | 4/2009 | Zeldis |
| 2009/0088445 A1 | 4/2009 | Ledeboer et al. |
| 2009/0131403 A1 | 5/2009 | Kusuda |

(56) References Cited

U.S. PATENT DOCUMENTS

| | | |
|---|---|---|
| 2009/0181959 A1 | 7/2009 | Rodgers et al. |
| 2009/0197869 A1 | 8/2009 | Arvanitis et al. |
| 2009/0203637 A1 | 8/2009 | Hocek et al. |
| 2009/0215766 A1 | 8/2009 | Rodgers et al. |
| 2009/0221608 A1 | 9/2009 | Cui et al. |
| 2009/0233903 A1 | 9/2009 | Rodgers et al. |
| 2009/0318405 A1 | 12/2009 | Li et al. |
| 2010/0022522 A1 | 1/2010 | Rodgers et al. |
| 2010/0069381 A1 | 3/2010 | Itoh et al. |
| 2010/0113416 A1 | 5/2010 | Friedman et al. |
| 2010/0190981 A1 | 7/2010 | Zhou et al. |
| 2010/0210627 A1 | 8/2010 | Mao et al. |
| 2010/0298334 A1 | 11/2010 | Rodgers et al. |
| 2010/0298355 A1 | 11/2010 | Li et al. |
| 2011/0059951 A1 | 3/2011 | Rodgers et al. |
| 2011/0082159 A1 | 4/2011 | Rodgers et al. |
| 2011/0086810 A1 | 4/2011 | Rodgers et al. |
| 2011/0086835 A1 | 4/2011 | Rodgers et al. |
| 2011/0201593 A1 | 8/2011 | Babu et al. |
| 2011/0207754 A1 | 8/2011 | Li et al. |
| 2011/0223210 A1 | 9/2011 | Rodgers et al. |
| 2011/0224157 A1 | 9/2011 | Rodgers et al. |
| 2011/0224190 A1 | 9/2011 | Huang et al. |
| 2011/0288107 A1 | 11/2011 | Parikh et al. |
| 2012/0014989 A1 | 1/2012 | Rodgers |
| 2012/0077798 A1 | 3/2012 | Rodgers et al. |
| 2012/0149681 A1 | 6/2012 | Rodgers |
| 2012/0149682 A1 | 6/2012 | Rodgers et al. |
| 2012/0149825 A1 | 6/2012 | Bandyopadhyay |
| 2012/0214825 A1 | 8/2012 | Vannucchi et al. |
| 2012/0225057 A1 | 9/2012 | Flynn |
| 2012/0252779 A1 | 10/2012 | Ramsden |
| 2012/0301464 A1 | 11/2012 | Friedman et al. |
| 2012/0329782 A1 | 12/2012 | Arvanitis et al. |
| 2013/0018034 A1 | 1/2013 | Yao et al. |
| 2013/0040973 A1 | 2/2013 | Vannucchi et al. |
| 2013/0045963 A1 | 2/2013 | Rodgers et al. |
| 2013/0060026 A1 | 3/2013 | Zhou et al. |
| 2013/0137681 A1 | 5/2013 | Rodgers et al. |
| 2013/0225556 A1 | 8/2013 | Rodgers et al. |
| 2013/0253190 A1 | 9/2013 | Zhou et al. |
| 2013/0253191 A1 | 9/2013 | Zhou et al. |
| 2013/0253193 A1 | 9/2013 | Zhou et al. |
| 2013/0274257 A1 | 10/2013 | Arvanitis et al. |
| 2013/0296299 A1 | 11/2013 | Rodgers et al. |
| 2014/0004516 A1 | 1/2014 | Sattler et al. |
| 2014/0005166 A1 | 1/2014 | Rodgers et al. |
| 2014/0005210 A1 | 1/2014 | Rodgers et al. |
| 2014/0018374 A1 | 1/2014 | Rodgers et al. |
| 2014/0031344 A1 | 1/2014 | Arvanitis et al. |
| 2014/0073657 A1 | 3/2014 | Li et al. |
| 2014/0094477 A1 | 4/2014 | Rodgers et al. |
| 2014/0121198 A1 | 5/2014 | Li et al. |
| 2014/0135350 A1 | 5/2014 | Ni et al. |
| 2014/0171409 A1 | 6/2014 | Yao et al. |
| 2014/0221379 A1 | 8/2014 | Rodgers et al. |
| 2014/0228346 A1 | 8/2014 | Rodgers et al. |
| 2014/0243360 A1 | 8/2014 | Rodgers et al. |
| 2014/0256941 A1 | 9/2014 | Liu et al. |
| 2014/0275031 A1 | 9/2014 | Huang et al. |
| 2014/0303196 A1 | 10/2014 | Rodgers et al. |
| 2014/0343030 A1 | 11/2014 | Li et al. |
| 2014/0378400 A1 | 12/2014 | Rodgers et al. |
| 2015/0065447 A1 | 3/2015 | Sandor |
| 2015/0065484 A1 | 3/2015 | Yeleswaram et al. |
| 2015/0087632 A1 | 3/2015 | Rodgers et al. |
| 2015/0087662 A1 | 3/2015 | Li et al. |
| 2015/0152117 A1 | 6/2015 | Gibbons |
| 2015/0164900 A1 | 6/2015 | Rodgers et al. |
| 2015/0183805 A1 | 7/2015 | Liu et al. |
| 2015/0225411 A1 | 8/2015 | Yao et al. |
| 2015/0225412 A1 | 8/2015 | Brameld |
| 2015/0238492 A1 | 8/2015 | Rodgers et al. |
| 2015/0246046 A1 | 9/2015 | Vaddi |
| 2015/0250790 A1 | 9/2015 | Parikh et al. |
| 2015/0315185 A1 | 11/2015 | Rodgers et al. |
| 2015/0342952 A1 | 12/2015 | Leopold |
| 2015/0344497 A1 | 12/2015 | Zhou et al. |
| 2016/0000795 A1 | 1/2016 | Scherle |
| 2016/0015695 A1 | 1/2016 | Li et al. |
| 2016/0024109 A1 | 1/2016 | Li |
| 2016/0067253 A1 | 3/2016 | Li et al. |
| 2016/0272648 A1 | 9/2016 | Rodgers et al. |
| 2016/0346286 A1 | 12/2016 | Rodgers et al. |
| 2016/0347734 A1 | 12/2016 | Liu et al. |
| 2017/0015674 A1 | 1/2017 | Zhou et al. |
| 2017/0071947 A1 | 3/2017 | Rodgers et al. |
| 2017/0087158 A1 | 3/2017 | Friedman et al. |
| 2017/0246157 A1 | 8/2017 | Huang et al. |
| 2017/0253598 A1 | 9/2017 | Yao et al. |
| 2017/0319487 A1 | 11/2017 | Yeleswaram et al. |
| 2018/0338978 A1 | 11/2018 | Rodgers et al. |
| 2018/0353499 A1 | 12/2018 | Huang et al. |
| 2019/0111058 A1 | 4/2019 | Vaddi |
| 2019/0125750 A1 | 5/2019 | Rodgers et al. |

FOREIGN PATENT DOCUMENTS

| | | |
|---|---|---|
| CN | 102985417 | 3/2013 |
| DE | 30 36 390 | 5/1982 |
| EA | 201590272 | 5/2015 |
| EP | 0223420 | 5/1987 |
| EP | 0587473 | 3/1994 |
| EP | 0727217 | 8/1996 |
| EP | 0795556 | 9/1997 |
| EP | 1104764 | 6/2001 |
| JP | 07-010876 | 1/1995 |
| JP | 2003-155285 | 5/2003 |
| JP | 2004-531513 | 10/2004 |
| JP | 2006-502183 | 1/2006 |
| JP | 2006-518341 | 8/2006 |
| JP | 2008-508241 | 3/2008 |
| JP | 2008-545660 | 12/2008 |
| JP | 2009-504619 | 2/2009 |
| JP | 2010-529209 | 8/2010 |
| JP | 2011-503194 | 1/2011 |
| JP | 2011-514909 | 5/2011 |
| JP | 2013-522214 | 6/2013 |
| JP | 2013-543007 | 11/2013 |
| MX | 2015005428 | 7/2015 |
| MX | 2015015738 | 3/2016 |
| WO | WO 96/030343 | 10/1996 |
| WO | WO 97/002262 | 1/1997 |
| WO | WO 97/036587 | 10/1997 |
| WO | WO 97/038664 | 10/1997 |
| WO | WO 97/045412 | 12/1997 |
| WO | WO 98/044797 | 10/1998 |
| WO | WO 98/051391 | 11/1998 |
| WO | WO 99/000654 | 1/1999 |
| WO | WO 99/062908 | 12/1999 |
| WO | WO 99/065909 | 12/1999 |
| WO | WO 00/009495 | 2/2000 |
| WO | WO 00/051614 | 9/2000 |
| WO | WO 00/053595 | 9/2000 |
| WO | WO 00/063168 | 10/2000 |
| WO | WO 01/014402 | 3/2001 |
| WO | WO 01/027104 | 4/2001 |
| WO | WO 01/042246 | 6/2001 |
| WO | WO 01/064655 | 9/2001 |
| WO | WO 01/081345 | 11/2001 |
| WO | WO 2001/081346 | 11/2001 |
| WO | WO 01/098344 | 12/2001 |
| WO | WO 02/000196 | 1/2002 |
| WO | WO 02/000661 | 1/2002 |
| WO | WO 02/016370 | 2/2002 |
| WO | WO 02/046184 | 6/2002 |
| WO | WO 02/055084 | 7/2002 |
| WO | WO 02/055496 | 7/2002 |
| WO | WO 02/060492 | 8/2002 |
| WO | WO 02/080926 | 10/2002 |
| WO | WO 02/092573 | 11/2002 |
| WO | WO 02/096909 | 12/2002 |
| WO | WO 03/000695 | 1/2003 |
| WO | WO 2003/000688 | 1/2003 |

(56) References Cited

FOREIGN PATENT DOCUMENTS

| | | |
|---|---|---|
| WO | WO 03/011285 | 2/2003 |
| WO | WO 03/024967 | 3/2003 |
| WO | WO 03/037347 | 5/2003 |
| WO | WO 03/048162 | 6/2003 |
| WO | WO 03/092595 | 11/2003 |
| WO | WO 03/099771 | 12/2003 |
| WO | WO 03/099796 | 12/2003 |
| WO | WO 04/003026 | 1/2004 |
| WO | WO 04/005281 | 1/2004 |
| WO | WO 04/005282 | 1/2004 |
| WO | WO 04/026406 | 4/2004 |
| WO | WO 04/041814 | 5/2004 |
| WO | WO 04/046120 | 6/2004 |
| WO | WO 04/047843 | 6/2004 |
| WO | WO 04/056786 | 7/2004 |
| WO | WO 04/072063 | 8/2004 |
| WO | WO 04/080980 | 9/2004 |
| WO | WO 04/092154 | 10/2004 |
| WO | WO 04/099204 | 11/2004 |
| WO | WO 04/099205 | 11/2004 |
| WO | WO 05/005988 | 1/2005 |
| WO | WO 05/013986 | 2/2005 |
| WO | WO 05/020921 | 3/2005 |
| WO | WO 05/026129 | 3/2005 |
| WO | WO 05/028444 | 3/2005 |
| WO | WO 05/049033 | 6/2005 |
| WO | WO 05/051393 | 6/2005 |
| WO | WO 05/060972 | 7/2005 |
| WO | WO 05/061463 | 7/2005 |
| WO | WO 05/062795 | 7/2005 |
| WO | WO 05/089502 | 9/2005 |
| WO | WO 05/095400 | 10/2005 |
| WO | WO 05/105146 | 11/2005 |
| WO | WO 05/105814 | 11/2005 |
| WO | WO 05/105988 | 11/2005 |
| WO | WO 05/110410 | 11/2005 |
| WO | WO 05/117909 | 12/2005 |
| WO | WO 05/121130 | 12/2005 |
| WO | WO 05/123719 | 12/2005 |
| WO | WO 06/004984 | 1/2006 |
| WO | WO 06/013114 | 2/2006 |
| WO | WO 06/022459 | 3/2006 |
| WO | WO 06/039718 | 4/2006 |
| WO | WO 06/046023 | 5/2006 |
| WO | WO 06/046024 | 5/2006 |
| WO | WO 06/052913 | 5/2006 |
| WO | WO 06/056399 | 6/2006 |
| WO | WO 06/067445 | 6/2006 |
| WO | WO 06/069080 | 6/2006 |
| WO | WO 06/077499 | 7/2006 |
| WO | WO 06/096270 | 9/2006 |
| WO | WO 06/101783 | 9/2006 |
| WO | WO 06/108103 | 10/2006 |
| WO | WO 06/122806 | 11/2006 |
| WO | WO 06/127587 | 11/2006 |
| WO | WO 06/129199 | 12/2006 |
| WO | WO 06/136823 | 12/2006 |
| WO | WO 07/002433 | 1/2007 |
| WO | WO 07/025090 | 3/2007 |
| WO | WO 07/041130 | 4/2007 |
| WO | WO 07/043677 | 4/2007 |
| WO | WO 07/044894 | 4/2007 |
| WO | WO 2007/044050 | 4/2007 |
| WO | WO 07/049041 | 5/2007 |
| WO | WO 07/062459 | 6/2007 |
| WO | WO 07/070514 | 6/2007 |
| WO | WO 07/076423 | 7/2007 |
| WO | WO 07/077949 | 7/2007 |
| WO | WO 07/080766 | 7/2007 |
| WO | WO 07/084557 | 7/2007 |
| WO | WO 07/090141 | 8/2007 |
| WO | WO 07/090748 | 8/2007 |
| WO | WO 07/116313 | 10/2007 |
| WO | WO 07/117494 | 10/2007 |
| WO | WO 07/129195 | 11/2007 |
| WO | WO 07/135461 | 11/2007 |
| WO | WO 07/140222 | 12/2007 |
| WO | WO 08/013925 | 1/2008 |
| WO | WO 08/028937 | 3/2008 |
| WO | WO 08/035376 | 3/2008 |
| WO | WO 08/043031 | 4/2008 |
| WO | WO 08/058126 | 5/2008 |
| WO | WO 08/064157 | 5/2008 |
| WO | WO 08/067119 | 6/2008 |
| WO | WO 08/077712 | 7/2008 |
| WO | WO 08/079291 | 7/2008 |
| WO | WO 08/079292 | 7/2008 |
| WO | WO 08/082198 | 7/2008 |
| WO | WO 08/082839 | 7/2008 |
| WO | WO 08/082840 | 7/2008 |
| WO | WO 08/106692 | 9/2008 |
| WO | WO 08/124323 | 10/2008 |
| WO | WO 08/139161 | 11/2008 |
| WO | WO 08/145681 | 12/2008 |
| WO | WO 08/145688 | 12/2008 |
| WO | WO 08/157207 | 12/2008 |
| WO | WO 08/157208 | 12/2008 |
| WO | WO 09/007839 | 1/2009 |
| WO | WO 09/016460 | 2/2009 |
| WO | WO 09/049028 | 4/2009 |
| WO | WO 09/064486 | 5/2009 |
| WO | WO 09/064835 | 5/2009 |
| WO | WO 09/071577 | 6/2009 |
| WO | WO 09/100130 | 8/2009 |
| WO | WO 09/109576 | 9/2009 |
| WO | WO 09/114512 | 9/2009 |
| WO | WO 09/115572 | 9/2009 |
| WO | WO 09/155156 | 12/2009 |
| WO | WO 09/158687 | 12/2009 |
| WO | WO 10/000978 | 1/2010 |
| WO | WO 10/001169 | 1/2010 |
| WO | WO 10/020905 | 2/2010 |
| WO | WO 10/022076 | 2/2010 |
| WO | WO 10/022081 | 2/2010 |
| WO | WO 10/026121 | 3/2010 |
| WO | WO 10/026122 | 3/2010 |
| WO | WO 10/026124 | 3/2010 |
| WO | WO 10/039939 | 4/2010 |
| WO | WO 2010/043052 | 4/2010 |
| WO | WO 10/081692 | 7/2010 |
| WO | WO 10/083283 | 7/2010 |
| WO | WO 10/135621 | 11/2010 |
| WO | WO 10/135650 | 11/2010 |
| WO | WO 11/003418 | 1/2011 |
| WO | WO 11/025685 | 3/2011 |
| WO | WO 11/028685 | 3/2011 |
| WO | WO 11/029802 | 3/2011 |
| WO | WO 11/031554 | 3/2011 |
| WO | WO 11/035900 | 3/2011 |
| WO | WO 11/044481 | 4/2011 |
| WO | WO 11/057784 | 5/2011 |
| WO | WO 11/069141 | 6/2011 |
| WO | WO 2011/066369 | 6/2011 |
| WO | WO 11/112662 | 9/2011 |
| WO | WO 11/130146 | 10/2011 |
| WO | WO 11/144338 | 11/2011 |
| WO | WO 11/146808 | 11/2011 |
| WO | WO 12/003457 | 1/2012 |
| WO | WO 2012/045010 | 4/2012 |
| WO | WO 12/068440 | 5/2012 |
| WO | WO 2012/071612 | 6/2012 |
| WO | WO 12/177606 | 12/2012 |
| WO | WO 13/007765 | 1/2013 |
| WO | WO 13/007768 | 1/2013 |
| WO | WO 13/023119 | 2/2013 |
| WO | WO 13/026025 | 2/2013 |
| WO | WO 13/036611 | 3/2013 |
| WO | WO 13/173720 | 11/2013 |
| WO | WO 2014/016396 | 1/2014 |
| WO | WO 14/071031 | 5/2014 |
| WO | WO 14/138168 | 9/2014 |
| WO | WO 2014/186706 | 11/2014 |
| WO | WO 2015/184305 | 12/2015 |
| WO | WO 2015/184087 | 4/2018 |

(56) References Cited

FOREIGN PATENT DOCUMENTS

OTHER PUBLICATIONS

26th Annual JPMorgan Healthcare Conference presentation dated Jan. 8, 2008, 28 pages.
Abe et al., "Effective Methods for Introducing Some Aryl and Heteroaryl Substituent onto 1-Azaazulene Nuclei", Heterocycles, 2005, 66: 229-240.
Abelson et al., "Alternate reference values for tear film break-up time in normal and dry eye populations, Lacrimal Gland, Tear Film, and Dry Eye Syndromes 3 Part B", Adv Exp Med Biol, 2002, 506: 1121-1125.
Abelson et al., "Dry eye syndrome: diagnosis, clinical trials, and pharmaceutical treatment—'improving clinical trials'. Lacrimal Gland, Tear Film, and Dry Eye Syndromes 3 Part B", Adv Exp Med Biol, 2002, 506: 1079-86.
Abstract of Chilean patent application No. 3496-06 published in Official Gazette of the Republic of Chile (Jun. 1, 2007) and publication (2 pages).
Ahmed et al., "Treatment of Pemphigus Vulgaris with Rituximab and Intravenous Immune Globulin," The New England Journal of Medicine, 2006, 1772-1779.
Aho et al., Expression of human pim family genes is selectively up-regulated by cytokines promoting T helper type 1, but not T helper type 2, cell differentiation, Immunology, 2005, 116: 82-88.
Albach et al., "Diagnosis of keratoconjunctivitis sicca in rheumatoid arthritis. The value of various tests", Ophthalmologe, Apr. 1994; 91(2):229-34—in German (with English abstract/summary contained therein).
Anonymous, "Ruxolitinib for Patients with Low or Intermediate-1 Risk Myelodysplastic Syndrome (MDS)," ClinicalTrials.gov archive, Aug. 2013, XP002739581, Retrieved from the Internet: URL: clinicaltrials.gov/archive/NCT01895842/2013_08_19 [retrieved on Apr. 30, 2015], 5 pages.
Arber et al., "The 2016 revision to the World Health Organization classification of myeloid neoplasms and acute leukemia," Blood, May 2016, 2391-2405.
Australian Office Action in Australian Application No. 2013344780, dated May 5, 2017, 5 pages.
Australian Office Action in Australian Application No. 2016204689, dated Mar. 22, 2017, 4 pages.
Bachmann et al., "The serine/threonine kinase Pim-1," The International Journal of Biochemistry and Cell Biology, 2005, 37: 726-730.
Bain et al., "Chronic neutrophilic leukaemia," in: Swerdlow, et al., eds. WHO Classification of Tumors of Haematopoietic and Lymphoid Tissues (ed 4th). Lyon: IARC Press, 2008: 38-39.
Banker et al., "Modern Pharmaceuticals" Third Edition, 1996, 596.
Barabino et al., "Tear film and ocular surface tests in animal models of dry eye; uses and limitations," Experimental Eye Research, 2004, 79: 613-621.
Barr et al., "Corneal scarring in the Collaborative Longitudinal Evaluation of Keratoconus (CLEK) Study: baseline prevalence and repeatability of detection", Cornea, 1999, 18(1):34-46.
Baudouin et al., "Flow cytometry in impression cytology specimens. A new method for evaluation of conjunctival Inflammation," Invest Ophthalmol Vis Sci, 1997, 38: 1458-1464.
Baxter et al., "Acquired mutation of the tyrosine kinase JAK2 in human myeloproliferative disorders," Lancet., 2005, 365:1054-1061.
Baxter et al., "Reductive Aminations of Carbonyl Compounds with Borohydride and Borane Reducing Agents," Organic Reactions, 2002, 1-57.
Baytel et al., "The human Pim-2 proto-oncogene and its testicular expression," Biochimica et Biophysica Acta, 1998, 1442: 274-285.
Beck et al., "Brief Report: Alleviation of Systemic Manifestations of Castleman's Disease by Monoclonal Anti-Interleukin-6 Antibody," N. Engl. J. Med., 1994, 330(9):602-605.

Begley et al., "Use of the dry eye questionnaire to measure symptoms of ocular irritation in patients with aqueous tear deficient dry eye", Cornea, 2002, 21: 664-70.
Bell and Zalay, "Synthesis of Substituted 3-Amino[6, 5-b] triazinoindoles." Journal of Heterocyclic Chemistry, Oct. 1975, 12(5):1001-1004.
Bennett et al., "Proposals for the classification of the myelodysplastic syndromes," British Journal of Haematology, 1982, 51: 189-199.
Berge et al., "Pharmaceutical salts", J. Pharma. Science, 1977, 66(1): 1-19.
Beyer, "Uber die Synthese von 2-Methylmercapto-1,3,4-thiodiazinen und deren Umlagerung in Pyrazolderivate (The synthesis of 2-methylthio-1,3,4-thiadiazines and their rearrangement to pyrazole derivatives)", Chem. Berichte Jahrg., 92:2593-2599 (1959) (abstract provided).
Bhattacharya et al., "Polymorphism in Pharmaceutical Solids," Second Edition, 2009, 192:327-345.
Bhovi et al., "1,3-Dipolar Cycloaddition Reaction: Synthesis and Antimicrobial, Activity of Some New 3-Ethoxycarbonyl-s-Methoxy-6-Bromo-2-Triazolylmethylindoles", Indian Journal of Heterocyclic Chemistry, Jul.-Sep. 2004, 14: 15-18.
Edward B. Roche, "Bioreversible Carriers in Drug Design," American Pharmaceutical Association and Pergamon Press, 1987, Front Matter, 4 pages.
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blom, "Two-Pump at-Column-Dilution Configuration for Preparative Liquid Chromatography—Mass Spectrometry," J. Comb. Chem., 2002, 4: 295-301.
Blume-Jensen et al, "Oncogenic kinase signaling", Nature, 2001, 411(6835):355-365.
Bock et al. "Managing drug resistance in cancer: lessons from HIV therapy." Nature, Jul. 2012, 12: 494-501.
Bolen, "Nonreceptor tyrosine protein kinases", Oncogene, 1993, 8(8):2025-31.
Bollrath et al., "gp130-Mediated Stat3 Activation in Enterocytes Regulates Cell Survival and Cell-Cycle Progression during Colitis-Associated Tumorigenesis," Cancer Cell, 2009, 15:91-102.
Bondoux et al., "Palladium-catalyzed C-C coupling: efficient preparation of new 5-thio-B-D-xylopyranosides as oral venous antithrombotic drugs," Tetrahedron Letters, 2009, 50(27): 3872-3876.
Borie et al., "Combined Use of the Jak3 Inhibitor CP-690, 550 with Mycophenolate Mofetil to Prevent Kidney Allograft Rejection in Nonhuman Primates", Transplantation, Dec. 2005, 80(12):1756-64.
Bosworth, "JAK1/JAK2 Inhibitor Ruxolitinib Is a Rising Start," Clinical Oncology, Apr. 2011, 06:04, 3 pages.
Boudny et al., "JAK/STAT signaling pathways and cancer," Neoplasm, 2002, 49:349-355.
Bourcier et al., "Expression of CD40 and CD40 ligand in the human conjunctival epithelium", Invest Ophthalmol Vis Sci, 2000, 41:120-126.
Bowman et al. "STATs in oncogenesis", Oncogene, 2000, 19:2474-2488.
Brett et al., "Structural chemistry of polycyclic heteroaromatic compound. Part 4. Electronic structures of angular dithienopyridines," J Chem Soc, Perkin Trans 2, Jan. 1, 1994, 9:2045.
Brignole et al., "Expression of Fas-Fas Ligand Antigens and Apoptotic Marker APO2-7 by the Human Conjunctival Epithelium. Positive correlation with class II HLA DR expression in inflammatory Ocular Surface Disorders", Exp Eye Res, 1998, 67:687-697.
Brignole et al., "Flow cytometric analysis of inflammatory markers in conjunctival epithelial cells of patients with dry eyes," Invest Ophthalmol Vis Sci, 2000, 41:1356-1363.
Brignole et al., "Flow cytometric analysis of inflammatory markers in KCS: 6-month treatment with topical cyclosporin A," Invest Ophthalmol Vis Sci, 2001, 42:90-95.
Brignole et al., "Flow cytometry in conjunctival impression cytology: a new tool for exploring ocular surface pathologies," Exp Eye Res, 2004, 78:473-481.

(56) References Cited

OTHER PUBLICATIONS

Bromberg et al., "Inflammation and Cancer: IL-6 and STAT3 Complete the Link," Cancer Cell, 2009, 15:79-80.

Bron et al., "Grading of corneal and conjunctival staining in the context of other dry eye tests", Cornea, 2003, 22(7):640-50.

Bron et al., "Methodologies to Diagnose and Monitor Dry Eye Disease: Report of the Diagnostic Methodology Subcommittee of the International Dry Eye Workshop (2007)", The Ocular Surface, Apr. 2007, 5(2): 108-152.

Brunning et al., "Myelodysplastic syndromes/neoplasms, overview," WHO Classification of Tumours of Haematopoietic and Lymphoid Tissues, 4th edition, 2008, 88-103.

Brunton et al., "Chemotherapy of Neoplastic Diseases," Goodman & Gillman's. The Pharmacological Basis of Therapeutics, 11th edition, 2008, 853-908.

Burger et al., "Gp130 and ras mediated signaling in human plasma cell line IN/a-6: a cytokine-regulated tumor model for plasmacytoma", Hematol J., 2001, 2:42-53.

Burger et al., "Janus kinase inhibitor INCB20 has antiproliferative and apoptotic effects on human myeloma cells in vitro and in vivo", Mol. Cancer Ther., Jan. 2009, 8(1): 26-35.

Campas-Moya, "Ruxolitinib. Tyrosine-protein kinase JAK1/2 inhibitor, treatment of myelofibrosis, treatment of myeloproliferative neoplasms, treatment of psoriasis", Drugs of the Future, Jun. 2010, 35(6):457-465.

Canadian Office Action in Canadian Application No. 2,738,520, dated Jul. 16, 2018, 7 pages.

Cancer.org "Breast Cancer," American Cancer Society, [retrieved on Dec. 1, 2014] retrieved from URL <http://www.cancer.org.cancer/breastcancer/detailedguide/breast-cancer-prevention>, 4 pages.

Candotti et al., "Molecular aspects of primary immuno-deficiencies: lessons from cytokine and other signaling pathways.", J Clin Invest, May 2002, 109(10): 1261-9.

Candotti et al., "Structural and functional basis for JAK3-deficient severe combined immunodeficiency.", Blood, 1997, 90(10): 3996-4003.

Carey and Sundberg, Advanced Organic Chemistry, Part B: Reactions and Synthesis, 4th ed., Kluwer Academic/Plenum Publishers:New York, 2001, 111-119.

Carey and Sundberg, Advanced Organic Chemistry, Part B: Reactions and Synthesis, Oxidations, 4th ed., Kluwer Academic/Plenum Publishers:New York, 2001, 747-757.

Cazzola et al., American Society of Hematology (ASH Education Book), 2011(1), 2011, 264-272.

Cermak et al, "Is complete androgen insensitivity syndrome associated with alterations in the meibomian gland and ocular surface," Cornea, 2003, 22:516-521.

Cervantes et al., "Three-year efficacy, safety, and survival findings from COMFORT-II, a phase 3 study comparing ruxolitinib with best available therapy for mylefibrosis," Blood, Dec. 12, 2013, 122(25):4047-4053.

Cetkovic-Cvrlje et al., "Targeting JAK3 with JANEX-1 for prevention of autoimmune type 1 diabetes in NOD mice.", Clin Immunol, 2003, 106(3): 213-25.

Chalandon, "Targeting mutated protein tyrosine kinases and their signaling pathways in hematologic malignancies," Haematologica, 2005, 90(7):949-68.

Chan, "Skin inflammatory disorders," in In Vivo Models of Inflammation, 2006, 85-120.

Changelian et al., "Prevention of Organ Allograft Rejection by a Specific Janus Kinase 3 Inhibitor", Science, 2003, 302: 875-878.

Chari et al., "Complete Remission Achieved with Single Agent CNTO 328, an Anti-IL-6 Monoclonal Antibody, in Relapsed and Refractory Myeloma," *Clinical Lymphoma, Myeloma & Leukemia,* 2013, 13(3):333-337.

Chauhan et al, "Autoimmunity in Dry Eye due to resistance of Th17 to Treg Suppression", J. Immunology, 2009, 182(3):1247-52.

Chauhan et al., "A concise review on sustained drug delivery system and its opportunities," International Journal on Pharmtech Research, Mar. 2012, 2: 227-238.

Chemical encyclopedia publication "Soviet Encyclopedia," Moscow, 1988, 1:242-243.

Chen et al., "Blockade of interleukin-6 signaling augments regulatory T-cell reconstitution and attenuates the severity of graft-versus-host disease," Blood, Jul. 2009, 114(4): 891-900.

Chen et al., "Stat3 Activation in Human Endometrial and Cervical Cancer", British Journal of Cancer, 2007, 96: 591-599.

Chen et al., "Induction of myelodysplasia by myeloid-derived suppressor cells," J Clin Invest, Nov. 2013, 123(11): 4595-611.

Cheson et al., "Report of an international working group to standardize response criteria for myelodysplastic syndromes," Blood, Dec. 2000, 96(12): 3671-4.

Chew et al., "An instrument for quantifying meibomian lipid on the lid margin: the Meibometer", Curr Eye Res, 1993, 12:247-254.

Chew et al., "The casual level of meibomian lipids in humans", Current Eye Research, 1993, 12:255-259.

Chinese Notice of Reexamination in Chinese Application No. 201080033675.6, dated May 10, 2016, 18 pages (English Translation).

Chinese Office Action in Chinese Application No. 201380070296.8, dated Feb. 16, 2017, 19 pages.

Chinese Office Action in Chinese Application No. 201480024761.9, dated Oct. 8, 2016, 21 pages (English Translation).

Chinese Office Action in Chinese Application No. 201480052299.3, dated Jan. 25, 2018, 13 pages.

Chinese Office Action in Chinese Application No. 201610989522.8, dated Jun. 4, 2018, 19 pages.

Chinese Office Action in Chinese Application No. 201580017178, dated Nov. 8, 2018, 10 pages.

Cho et al, "Review of the tear break-up time and a closer look at the tear break-up time of Hong Kong Chinese", Optom Vis Sci, 1993, 70(1):30-8.

Choi Ha-Soon et al., "Design and synthesis of 7H-pyrrolo[2,3-d]pyrimidines as focal adhesion kinase inhibitors. Part 1", Bioorg. & Med. Chem. Lett., 2006, 16(8):2173-2176.

Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.

Chu-Moyer et al., "Preparation of the Four Regioisomeric 2-(Methylthio)oxazolopyridines: Useful Synthons for Elaboration to 2-(Amino substituted)oxazolopyridines", J. Org. Chem., 1995, 60(17): 5721-5725.

Cilloni et al., "Emerging drugs for chronic myeloid leukemia", Expert Opinion on Emerging Drugs, Jun. 2010, 15(2): 175-184.

Claessens et al., "In vitro proliferation and differentitation of erythyroid progenitors from patients with myelodysplastic syndromes: evidence for Fas-dependent apoptosis," Blood, Mar. 2002, 1594-1601.

Claridge et al., "Discovery of a novel and potent series of thieno[3,2-b]pyridine-based inhibitors of c-Met and VEGFR2 tyrosine kinases," Bioorganic & Medicinal Chemistry Letters, 2008, 2793-2798.

Clark et al., "Discovery and Development of Janus Kinase (JAK) inhibitors for Inflammatory Diseases," J Med Chem., 2014, A-P.

Clevelandclinic.org, "Lupus," Feb. 2001, [retrieved on Dec. 15, 2018] retrieved from URL <https://my.clevelandclinic.org/health/diseases/4875-lupus>, 7 pages.

Clinical Trial NCT01787487 ('487 Trial), dated Feb. 7, 2013, 6 pages.

ClinicalTrials.gov, <http:clinicaltrials.gov/ct2/show/NCT00227591>, downloaded Dec. 6, 2016.

ClinicalTrials.gov, "Topical Ruxolitinib for the Treatment of Vitiligo," Retrieved on Dec. 19, 2018, retrieved from URL <clinicaltrials.gov/ct2/show/NCT02809976>, 6 pages.

ClinicalTrials.gov, "A Study to Evaluate the Safety and Efficacy of INCB018424 Phosphate Cream Applied Topically to Adults With Atopic Dermatitis," Retrieved on Dec. 19, 2018, retrieved from URL <https://clinicaltrials.gov/ct2/show/NCT03011892>, 7 pages.

Winyard, P.G. and Willoughby, D.A., "Inflammation Protocols," Humana Press, Methods in Molecular Biology:, 2003, vol. 225, 359 pages.

Columbian Office Action in Columbian Application No. 12-213.010, dated Jun. 17, 2014, 20 pages.

(56) References Cited

OTHER PUBLICATIONS

Columbian Office Action in Columbian Application No. 15-114.028, dated Apr. 18, 2017, 7 pages.
Columbian Office Action in Columbian Application No. 15-114.028, dated Sep. 20, 2017, 8 pages.
Communication dated Jan. 22, 2009 for European Appln. No. 06839328.9 (5 pgs.).
Conklyn et al., "The JAK3 inhibitor CP-0690550 selectively reduces NK and CD8+ cell numbers in cynomolgus monkey blood following chronic oral dosing," Journal of Leukocyte Biology, Dec. 2004, 76: 1248-1255.
Costa Rican Office Action in Costa Rican Application No. 10065, dated Jul. 16, 2013, 8 pages.
Cottet and Schlosser, "Three Chloro(trifluoromethyl)pyridines as Model Substrates for Regioexhaustive Functionalization," Eur J Org Chem, 2004, 18:3793-3798.
Craig et al. "Tear lipid layer structure and stability following expression of the meibomian glands ", Ophthalmic Physiol Opt, 1995, 15(6):569-74.
Coligan, "Current Protocols in Immunology," Wiley Press, 1988, vol. 3, Chapter abstracts only, 21 pages.
Daniels et al., "Imatinib mesylate inhibits the profibrogenic activity of TGF-? and prevents bleomycinmediated lung fibrosis," J. Clin. Invest., Nov. 2004, 114(9):1308-1316.
Danjo et al., "Observation of precorneal tear film in patients with Sjogren's syndrome", Acta Ophthalmol Scand, 1995, 73:501-505.
De Paiva et al, "IL-17 disrupts corneal barrier following desiccating stress," Mucosal Immunol., 2009, 2(3):243-53.
De Vos et al., "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 2000, 109(4): 823-8.
Deisseroth et al., "U.S. Food and Drug Administration Approval: Ruxolitinib for the Treatment of Patients with Intermediate and High-Risk Myelofibrosis," Clin. Cancer Res., Jun. 2012, 18(12):3212-3217.
Deng Jun et al, "Rh-catalyzed asymmetric hydrogenation of gamma-phthalimido-substituted esters: an efficient enantioselective synthesis of beta-aryl-gamma-amino acids", Org. Lett., 2007, 9(23):4825-4827.
Deuse et al., "Novel Immunosuppression: R348, a JAK3- and Syk-Inhibitor Attenuates Acute Cardiac Allograft Rejection," Transplantation, 2008, 85(6): 885-892.
Divkovic et al., "Hapten-protein binding: from theory to practical application in the in vitro prediction of skin sensitization," Contact Dermatitis, 2005, 189-200.
Doane, "An instrument for in vivo tear film interferometry", Optom Vis Sci, 1989, 66: 383-8.
Doleschall et al., "Thermal and Acid Catalysed Degradations of 3-alkylthio-6,7-dihydro[1.2.4]triazino[1,6-c]quinazolin-5-ium-1-olates," Tetrahedron, 1974, 30:3997-4012.
Dorwald, "Side Reactions in Organic Synthesis: A Guide to Successful Synthesis Design," Wiley-VCH, 2005, Chapter 1, 32 pages.
Dudley et al. "A VEGF/JAK2/STAT5 axis may partially mediate endothelial cell tolerance to hypoxia", Biochem. J., 2005, 390(Pt 2):427-36.
Ecuador Examination Report in Ecuador Application No. SP-08-8540, dated Jun. 13, 2017, 30 pages.
Eghtedar et al., "Phase 2 study of the JAK kinase inhibitor ruxolitinib in patients with refractory leukemias, including postmyeloproliferative neoplasm acute myeloid leukemia," Blood, May 2012, 119(20): 4614-4618.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Einmahl et al., "Therapeutic applications of viscous and injectable poly(ortho esters)," Adv. Drug. Deliv. Rev., 2001, 53:45-73.
Eliason et al., "Staining of the conjunctiva and conjunctival tear film," Br J Ophthalmol, 1990, 74:519-22.
Elliott et al., "WHO-defined chronic neutrophilic leukemia: a long-term analysis of 12 cases and a critical review of the literature," Leukemia, 2005, 19:313-317.
Eurasian Office Action in Eurasian Application No. 201291310, dated Mar. 9, 2017, 4 pages (English Translation).
Eurasian Office Action in Eurasian Application No. 201590930, dated Apr. 5, 2016, 6 pages (English Translation).
Eurasian Search Report in Eurasian Application No. 201200132, dated Sep. 1, 2016, 6 pages (English Translation).
Eurasian Office Action in Eurasian Application No. 201691745, dated Mar. 20, 2019, 4 pages.
European Communication in European Application No. 06839328.5, dated Jan. 22, 2009, 5 pages.
European Communication in European Application No. 13798840.8, dated May 11, 2018, 5 pages.
European Communication pursuant to Article 94(3) EPC in European Application No. 14753182.6, dated Nov. 6, 2017, 10 pages.
European Communication pursuant to Article 94(3) EPC in European Application No. 14753182.6, dated Sep. 10, 2018, 7 pages.
European Office Action in European Application No. 15195698.4, dated Mar. 15, 2017, 4 pages.
European Search Report in European Application No. 16197502.4, dated Mar. 20, 2017, 15 pages.
European Extended Search Report in European Application No. 18191992.9, dated Jan. 18, 2019, 10 pages.
Expert Scientific Group on Phase One Clinical Trials Final Report, Nov. 30, 2006, pp. C1, C35-C38.
Farrell et al., "A classification for dry eyes following comparison of tear thinning time with Schirmer tear test," Acta Ophthalmol (Copenh), 1992, 70(3):357-60.
Farrell et al., "A clinical procedure to predict the value of temporary occlusion therapy in keratoconjunctivitis sicca," Ophthal Physiol Opt, 2003, 23:1-8.
Farris, "Tear osmolarity—a new gold standard?" Adv Exp Med Biol, 1994, 350:495-503.
Fayad et al., "Interleukin-6 and interleukin-10 levels in chronic lymphocytic leukemia: correlation with phenotypic characteristics and outcome," Blood, Jan. 2001, 97(1): 256-263.
Fenaux et al., "A randomized phase 3 study of lenalidomide versus placebo in RBC transfusion-dependent patients with Low-/Intermediate-1-risk myelodysplastic syndromes with del5q," Blood, Oct. 2011, 118(14): 3765-76.
Fenaux et al., "Efficacy of azacitidine compared with that of conventional care regimens in the treatment of higher-risk myelodysplastic syndromes: a randomised, open-label, phase III study," Lancet Oncol, Mar. 2009, 10: 223-32.
Fiskus et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov. 1, 2010 p. 349, XP002667216, ISSN: 0002-7863 (1 page).
Fleischman et al., "The CSF3R T618I mutation causes a lethal neutrophilic neoplasia in mice that is responsive to therapeutic JAK inhibition," Blood, Nov. 2013, 122: 3628-3632.
Flex et al., "Somatically acquired JAK1 mutations in adult acute lymphoblastic leukemia", J. Exp Med., 2008, 205:751-8.
Fonseca et al., "Interleukin-6 as a key player in systemic inflammation and joint destruction", Autoimmunity Reviews, 2009, 8:538-42.
Forbes et al., "Synthesis and evaluation of a series of aryl [e] fused pyrazolo [4,3-c]pyridines with potential anxiolytic activity," J Medicinal Chem., Jan. 1, 1990, 33(9):2640-2645.
Foucar, "Myelodysplastic/Myeloproliferative Neoplasms," Am J Olin Pathol, 2009, 132:281-289.
Fridman et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).

(56) References Cited

OTHER PUBLICATIONS

Fridman et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman et al., "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman et al., "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009 (1 page).
Fridman et al., "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).
Fridman et al., "Preclinical evaluation of local JAK1 and JAK2 inhibition in cutaneous inflammation", Journal of Investigative Dermatology, Sep. 2011, 131(9): 1838-1844.
Froberg et al., "Demonstration of clonality in neutrophils using FISH in a case of chronic neutrophilic leukemia," Leukemia, 1998, 12:623-626.
Fujihara et al., "Evaluation of human conjunctival epithelium by a combination of brush cytology and flow cytometry: an approach to the quantitative technique", Diagn Cytopathol, 1997, 17:456-60.
Fujii et al., "Aberrant expression of serine/threonine kinase Pim-3 in hepatocellular carcinoma development and its role in the proliferation of human hepatoma cell lines" International Journal of Cancer, 2005, 114: 209-218.
Fukagawa et al., "Histological evaluation of brush cytology of rabbit conjunctiva", Nippon Ganka Gakkai Zasshi, 1993, 97:1173-8 (contains English abstract within the article).
Furqan et al., "Dysregulation of JAK-STAT pathway in hematological malignancies and JAK inhibitors for clinical application," Biomarker Research 2013, 1(1):1-10.
Gadamasetti et al., "Process Chemistry in the Pharmaceutical Industry," Challenges in an Ever Changing Climate, 2008, vol. 2, pp. 49-63.
Gaertner, "Cyclization of 1-Alkylamino-3-halo-2-alkanols to 1-Alkyl-3-azetidinols," J. Org. Chem., 1967, 32: 2972-76.
Gaestel et al., "Targeting innate immunity protein kinase signalling in inflammation," Nat Rev Drug Discov., Jun. 2009, 8(6):480-99.
Ghelardi et al., "A Mucoadhesive Polymer Extracted from Tamarind Seed Improves the Intraocular Penetration and Efficacy of Rufloxacin in Topical Treatment of Experimental Bacterial Keratitis", Antimicrob. Agents Chemother., 2004, 48:3396-3401.
Gilchrist et al., "5H-2-Pyrindines from 2-Bromocyclopentene-1-carboxaldehyde," Tetrahedron, Jan. 1, 1995, 9119-9126.
Glasson et al., "Differences in clinical parameters and tear film of tolerant and intolerant contact lens wearers," Invest Ophthalmol Vis Sci, 2003, 44:5116-5124.
Glattfeld, "Improvements in the Preparation of DL-Threonic and DL-Erythronic Acids", J. Am. Chem. Soc., 1940, 62:974-977.
Gobbels et al., "Tear secretion in dry eyes as assessed by objective fluorophotometry.," Ger J Ophthalmol, 1992, 1:350-353.
Golding et al., "X-ray and scanning electron microscopic analysis of the structural composition of tear ferns", Cornea, Jan. 1994, 13(1):58-66.
Gomtsyan et al, "Design, synthesis, and structure-activity relationship of 6-alkynylpyrimidines as potent adenosine kinase inhibitors," J. Med. Chem., 2002, 45(17):3639-3648.
Goodman et al., "IL-6 Signaling in Psoriasis Prevents Immune Suppression by Regulatory T Cells," J. Immunol., Sep. 2009, 183: 3170-3176.
Gooseman et al., "The intramolecular b-fluorine . . . ammonium interaction in 4- and 8-membered rings", Chem. Commun, 2006, 30:3190-3192.
Gorre et al., "Clinical Resistance to STI-571 Cancer Therapy Caused by BCR-ABL Gene Mutation or Amplification." Science, 2001, 293:876-880.
Gotlieb, Alice, Presentation at the 2008 American Academy of Dermatology, 66th Annual Meeting, San Antonio, TX. Feb. 1, 2008, symposium-303 (12 pp.).
Goto et al., "Color mapping of tear lipid layer thickness distribution from the image analysis in DR-1 tear lipid layer interference images," ARVO abstract, 2004, 2 pages.
Goto et al., "Computer-synthesis of an interference color chart of human tear lipid layer by a colorimetric approach," Invest Ophthalmol Vis Sci, 2003, 44:4693-7.
Goto et al., "Differentiation of lipid tear deficiency dry eye by kinetic analysis of tear interference images,",Arch Ophthalmol, 2003, 121:173-80.
Goto et al., "Evaluation of the tear film stability after laser in situ keratomileusis using the tear film stability analysis system," Am J Ophthalmol, Jan. 2004, 137(1):116-20.
Goto et al., "Kinetic analysis of tear interference images in aqueous tear deficiency dry eye before and after punctal occlusion," Invest Ophthalmol Vis Sci, 2003, 44:1897-905.
Goto et al., "Tear Film Stability Analysis System: Introducing a new application for videokeratography", Cornea, Nov. 2004, 23(8):S65-S70.
Gottlieb, "Psoriasis: Emerging Therapeutic Strategies," Nat Rev Drug Disc., Jan. 2005, 4:19-34.
Grabbe et al., "Immunoregulatory mechanisms involved in elicitation of allergic-contact hypersensitivity," Immunol Today, Jan. 1998, 19(1):37-44 (only 1 page provide and marked "best available copy").
Greenberg, "The Role of Hemopoietic Growth Factors in the Treatment of Myelodysplastic Syndromes," International Journal of Pediatric Hematology/Oncology, 1997, 4(3): 231-238.
Greenberg, "The myelodysplastic syndromes" in Hoffman, et al, eds. Hematology: Basic Principles and Practice (3rd ed.), Churchill Livingston; 2000:1106-1129.
Greene et al., Greene's Protective Groups in Organic Synthesis, 2007, 4th Edition, 54-55.
Gregory et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, 2003, 58, 1101-1113.
Grossman et al., "Interleukin 6 is expressed in high levels in psoriatic skin and stimulates proliferation of cultured human keratinocytes," Proc. Natl. Acad., Sci. USA, Aug. 1989, 86: 6367-6371.
Guillon, "Tear film photography and contact lens wear", J Br Contact Lens Assoc, 1982;5:84-7.
Gura, "Systems for Identifying New Drugs Are Often Faulty," Science, Nov. 1997, 278(5340): 1041-1042.
Gurram et al., "C-C Cross-Coupling Reactions of )6-Alkyl-2-Haloinosine Derivatives and a One-Pot Cross-Coupling/)6-Deprotection Procedure," Chem Asian J., Aug. 2012, 7(8): 1853-1861.
Guschin et al, "A major role for the protein tyrosine kinase JAK1 in the JAK/STAT signal transduction pathway in response to interleukin-6", Embo J 14:1421-1429 (1995).
Hamze' et al., "Synthesis of Various 3-Substituted 1,2,4-Oxadiazole-Containing Chiral β3- and r-Amino Acids from Fmoc-Protected Aspartic Acid," J. Org. Chem., 2003, 68(19), pp. 7316-7321.
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Harper Collins Publishers, Collins English Dictionary, "in vitro" and "in vivo", p. 852, 2007.

(56) References Cited

OTHER PUBLICATIONS

Harris et al., "Alkyl 4-Chlorobenzoyloxycalbamates as Highly Effective Nitrogen Source Reagents for the Base-Free, Intermolecular Aminohydroxylation Reaction," J. Org. Chem., 2011, 76:358-372.

Harris et al., "World Health Organization classification of neoplastic diseases of the hematopoietic and lymphoid tissues: report of the Clinical Advisory Committee meeting—Airlie House, Virginia, Nov. 1997," J Clin Oncol, 1999, 17:3835-3849.

Harrison et al., "JAK Inhibition with Ruxolitinib versus Best Available Therapy for Myelofibrosis," The New England Journal of Medicine, Mar. 2012, 366(9): 787-798.

Heine et al., "The JAK-inhibitor ruxolitinib impairs dendritic cell function in vitro and in vivo," Blood, 2013, 122(7): 1192-1202.

Helal et al., "Stereoselective Synthesis of cis-1,3-Disubstituted Cyclobutyl Kinase Inhibitors," Organic Letters, (2004), 6(11), pp. 1853-1856.

Hengge et al., "Adverse Effects of Topical Glucocorticosteroids," J Am Acad Dermatol., Jan. 2006, 54(1):1-15.

Hernandez et al., "Clinical, hematological and cytogenetic characteristics of atypical chronic myeloid leukemia," Ann. Oncol., Apr. 2000, 11(4): 441-444.

Hickenbottom "Reactions of organic compounds," State Scientific-Technical Publishing Association, Chemical Literature Section, Moscow, 1939, pp. 360-362.

Holly et al., "Lacrimation kinetics in Humans as determined by a novel technique", in Holly FJ (ed). The preocular tear film. Lubbock TX, Lubbock Dry Eye Institute, 1986, pp. 76-88).

Hong et al., "Total Synthesis of Onnamide A", J. Am. Chem. Soc., 113:9693-94 (1991).

Huang, "Inhibition of STAT3 activity with AG490 decreases the invasion of human pancreatic cancer cells in vitro", Cancer Sci. 97(12):1417-23 (2006).

Huttel, et al., "Lithium pyrazole compounds", Liebigs Ann. Chem. Bd., 625:55-65 (1959) (abstract provided).

Hyung-Bae et al., "CP-690550, a Janus Kinase Inhibitor, Suppresses CD4+ T-Cell-Mediated Acute Graft-Versus-Host Disease by Inhibiting the Interferon-Y Pathway," Transplantation, 2010, 90(8):825-835.

Indian Office Action in Indian Application No. 2177/DELNP/2014, dated May 8, 2018, 4 pages.

International Preliminary Report on Patentability (with Written Opinion) dated Nov. 22, 2011 for International Appln. No. PCT/US2010/035728, 8 pages.

International Preliminary Report on Patentability (with Written Opinion) dated Nov. 22, 2011 for International Appln. No. PCT/US2010/035783, 5 pages.

International Preliminary Report on Patentability (with Written Opinion) in International Application No. PCT/US2006/047369, dated Jun. 18, 2008, 10 pages.

International Preliminary Report on Patentability (with Written Opinion) in International Application No. PCT/US2010/047252, dated Mar. 6, 2012, 7 pages.

International Preliminary Report on Patentability for International Appln. No. PCT/US2008/066662 dated Dec. 17, 2009, 7 pages.

International Preliminary Report on Patentability for PCT/US2008/66658 dated Dec. 17, 2009, 7 pages.

International Preliminary Report on Patentability for PCT/US2009/036635 dated Sep. 14, 2010, 6 pages.

International Preliminary Report on Patentability for PCT/US2009/059203 dated Apr. 5, 2011, 6 pages.

International Preliminary Report on Patentability for PCT/US2010/021003 dated Jul. 19, 2011, 11 pages.

International Preliminary Report on Patentability for PCT/US2010/052011 dated Apr. 11, 2012, 4 pages.

International Preliminary Report on Patentability for PCT/US2011/025433 dated Aug. 21, 2012, 7 pages.

International Preliminary Report on Patentability for PCT/US2011/027665 dated Sep. 11, 2012, 7 pages.

International Preliminary Report on Patentability for PCT/US2011/037291 dated Nov. 27, 2012, 7 pages.

International Preliminary Report on Patentability for PCT/US2011/061351 dated May 30, 2013, 7 pages.

International Preliminary Report on Patentability for PCT/US2011/061374 dated May 30, 2013, 5 pages.

International Preliminary Report on Patentability for PCT/US2012/043099 dated Dec. 23, 2013, 6 pages.

International Preliminary Report on Patentability for PCT/US2012/050210 dated Feb. 11, 2014, 8 pages.

International Preliminary Report on Patentability for PCT/US2012/051439 dated Feb. 27, 2014, 7 pages.

International Preliminary Report on Patentability for PCT/US2012/053921 dated Mar. 20, 2014, 8 pages.

International Preliminary Report on Patentability for PCT/US2013/041601, dated Nov. 18, 2014, 7 pages.

International Preliminary Report on Patentability for PCT/US2013/070012, dated May 19, 2015, 8 pages.

International Preliminary Report on Patentability in International Application No. PCT/US2014/049940, dated Feb. 9, 2016, 9 pages.

International Preliminary Report on Patentability in International Application No. PCT/US2014/051678, dated Mar. 3, 2016, 15 pages.

International Preliminary Report on Patentability in International Application No. PCT/US2015/028224, dated Nov. 10, 2016, 7 pages.

International Search Report and the Written Opinion, PCT/US2012/051439, dated Nov. 30, 2012, 15 pages.

International Search Report and the Written Opinion, PCT/US2012/053921, dated Nov. 7, 2012, 19 pages.

International Search Report and Written Opinion dated Feb. 9, 2010 for International Appln. No. PCT/US2009/059203, 10 pages.

International Search Report and Written Opinion for International Appln. No. PCT/US2005/046207 dated May 15, 2007, 6 pages.

International Search Report and Written Opinion for International Appln. No. PCT/US2008/066662 dated Dec. 23, 2008, 11 pages.

International Search Report and Written Opinion for International Appln. No. PCT/US2009/036635 dated Jun. 3, 2009, 14 pages.

International Search Report and Written Opinion for PCT/US2006/047369, 16 pages (dated Apr. 24, 2007).

International Search Report and Written Opinion for PCT/US2008/083319, 29 pages dated Mar. 13, 2009.

International Search Report and Written Opinion for PCT/US2011/025433, 12 pages (dated Jul. 20, 2011).

International Search Report and Written Opinion for PCT/US2011/027665 dated Jun. 27, 2011, 14 pages.

International Search Report and Written Opinion for PCT/US2011/037291, 11 pages (dated Apr. 19, 2012).

International Search Report and Written Opinion for PCT/US2011/061351 dated Feb. 17, 2012, 12 pages.

International Search Report and Written Opinion for PCT/US2011/061374 dated Mar. 27, 2012, 12 pages.

International Search Report and Written Opinion for PCT/US2012/025581, 16 pages (dated Apr. 26, 2012).

International Search Report and Written Opinion for PCT/US2012/043099, 11 pages (dated Sep. 13, 2012).

International Search Report and Written Opinion for PCT/US2012/050252 dated Jan. 2, 2013, 17 pages.

International Search Report and Written Opinion in International Application No. PCT/US2013/067794, dated Dec. 17, 2013, 14 pages.

International Search Report and Written Opinion in International Application No. PCT/US2013/070012, dated Jan. 23, 2014, 10 pages.

International Search Report and Written Opinion in International Application No. PCT/US2014/020554, dated Jul. 16, 2014, 17 pages.

International Search Report and Written Opinion in International Application No. PCT/US2014/049940, dated Nov. 4, 2014, 13 pages.

International Search Report and Written Opinion in International Application No. PCT/US2014/051678, dated Feb. 11, 2015, 22 pages.

(56) References Cited

OTHER PUBLICATIONS

International Search Report and Written Opinion in International Application No. PCT/US2015/017963, dated Jun. 5, 2015, 13 pages.
International Search Report and Written Opinion in International Application No. PCT/US2015/028224, dated Jul. 21, 2015, 9 pages.
International Search Report and Written Opinion in International Application No. PCT/US2015/033254, dated Oct. 7, 2015, 12 pages.
International Search Report for PCT/US2008/66658 dated Dec. 23, 2008, 4 pages.
International Search Report for PCT/US2010/021003 dated Aug. 16, 2010, 8 pages.
International Search Report for PCT/US2010/035728 dated Jul. 8, 2010, 3 pages.
International Search Report for PCT/US2010/035783 dated Aug. 23, 2010, 4 pages.
International Search Report for PCT/US2010/047252 dated Nov. 17, 2010, 4 pages.
International Search Report for PCT/US2010/052011 dated Nov. 30, 2010, 3 pages.
International Search Report in International Application No. PCT/US2013/041601, dated Sep. 3, 2013, 3 pages.
Iranpoor, "A Rapid and Facile Conversion of Primary Amides and Aldoximes to Nitriles and Ketoximes to Amides with Triphenylphosphine and N-Chlorosuccinimide," G Syn., 2002, Commun 32:2535-41.
Ishizaki et al., "Pharmacological Properties of Y-27632, a Specific Inhibitor of Rho-Associated Kinases", Molecular Pharmacology, 2000, 57, 976-983.
Itagaki et al, "Expedient Synthesis of Potent Cannabinoid Receptor Agonist (-)-CP55,940", Organic Letters, 2005, 7(19): 4181-4183
Jädersten et al., "Long-term outcome of treatment of anemia in MDS with erythropoietin and G-CSF," Blood, Aug. 2005, 106(3): 803-11.
Jakavi, Highlights of Prescribing Information, Incyte Corporation, 2011, revised Mar. 2016, 11 pages.
No Author, Jakavi, Novatis, 2015, 19 pages.
James et al., "A unique clonal JAK2 mutation leading to constitutive signalling causes polycythaemia vera", Nature, 434 (7037):1144-8 (2005).
Janes et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Japanese Office Action in Japanese Application No. 2013-540049, dated Aug. 11, 2015, 3 pages (English Translation).
Japanese Office Action in Japanese Application No. 2015-042933, dated Feb. 2, 2016, 6 pages (English Translation).
Japanese Office Action in Japanese Application No. 2015-219637, dated Oct. 4, 2016, 6 pages.
Japanese Office Action in Japanese Application No. 2015-241393, dated Sep. 27, 2016, 5 pages (English Translation).
Japanese Office Action in Japanese Application No. 2015-542764, dated Jul. 25, 2017, 5 Pages.
Japanese Office Action in Japanese Application No. 2015-561582, dated Feb. 13, 2018, 9 pages (English Translation).
Japanese Office Action in Japanese Application No. 2016-143513, dated May 23, 2017, 3 pages (English Summary).
Japanese Office Action in Japanese Application No. 2017-000685, dated Jan. 31, 2017, 7 pages (with English translation).
Japanese Office Action in Japanese Application No. 2017-246-134, dated Oct. 16, 2018, 12 pages.
Japanese Office Action in Japanese Application No. 2016-554471, dated Nov. 27, 2018, 8 pages.
Jee et al., "Overview: animal models of osteopenia and osteoporosis", J Musculoskel. Neuron, Interact., 2001, 1(3):193-207.
Jester et al., "In vivo biomicroscopy and photography of meibomian glands in a rabbit model of meibomian gland dysfunction", Invest Ophthalmol Vis Sci, 1982, 22:660-7.
Johnson et al., "The effect of instilled fluorescein solution volume on the values and repeatability of TBUT measurements", Cornea, 2005, 24:811-7.
Kaddis et al., "Second-Line Treatment for Pancreatic Cancer," Journal of the Pancreas, Jul. 2014, XP055147286, Retrieved from the Internet: URL: http://www.serena.unina.it/index.php/jop/article/viewFile/2691/2737 [retrieved on Oct. 17, 2014].
Kaercher, "Ocular symptoms and signs in patients with ectodermal dysplasia syddromes", Graefe's Arch Clin Exp Ophthalmol, 2004, 495-500.
Kamb, "What's wrong with our cancer models?," Nature Reviews, Feb. 2005, 161-165.
Kantarjian et al., "Ruxolitinib for Myelofibrosis—An Update of Its Clinical Effects," Clinical Lymphoma, Myeloma & Leukemia, Dec. 2013, 638-645.
Kantarjian et al., "Decitabine improves patient outcomes in myelodysplastic syndromes: results of phase III randomized study," Cancer, Apr. 2006, 106(8): 1794-803.
Kaushansky, "Lineage-Specific Hematopoietic Growth Factors," NEJM, 2006, 354:2034-45.
Kawamura et al., "Molecular cloning of L-JAK, a Janus family protein-tyrosine kinase expressed in natural killer cells and activated leukocytes," Proc Natl Acad Sci USA, 1994, 91(14): 6374-8.
Kharas et al., "ABL Oncogenes and Phosphoinositide 3-Kinase: Mechanism of Activation and Downstream Effectors," Cancer Res., Mar. 2005, 65(6):2047-2053.
Killedar et al., "Early pathogenic events associated with Sjogren's syndrome (SjS)-like disease of the NOD mouse using microarray analysis," Lab Invest, Dec. 2006, 86(12): 1243-1260.
Kim et al., Abstract #1956, "A Phase 2, Randomized, Dose-Ranging, Vehicle-and Active-Controlled Study to Evaluate the Safety and Efficacy of Ruxolitinib Cream in Adult Patients with Atopic Dermatitis," Presentation, Presented at the 27th European Academy of Dermatology and Venereology Congress, Sep. 12-16, 2018, Paris, France, 11 pages.
Kim et al., "Clinical significances of preoperative serum interleukin-6 and C-reactive protein level in operable gastric cancer," BMC Cancer, May 20, 2009, 9(155):1-9.
Kim et al., "Zinc-Modified Cyanoborohydride as a Selective Reducing Agent," J. Org. Chem., 1985, 50: 1927-1932.
King-Smith et al., "Three interferometric methods for measuring the thickness of layers of the tear film," Optom Vis Sci, 1999, 76:19-32.
Kiss, "Recent developments on JAK2 inhibitors: A patent review", Expert Opinion on Therapeutic Patents, Apr. 2010, 20(4):471-495.
Kojima et al., "A new noninvasive tear stability analysis system for the assessment of dry eyes", Invest Ophthalmol Vis Sci, 2004, 45(5):1369-74.
Kola, "Can the pharmaceutical industry reduce attrition rates?" Nature Reviews Drug Discovery, 2004, 3:711-715.
Komuro et al., "Assessment of meibomian gland function by a newly developed laser meibometer", Adv Exp Med Biol, 2002, 506:517-520.
Kontzias et al., "Jakinibs: a new class of kinase inhibitors in cancer and autoimmune disease," Curr. Opin. Pharm., 2012, 12: 464-470.
Korb et al., "Increase in tear film lipid layer thickness following treatment of meibomian gland dysfunction", Adv Exp Med Biol, 1994, 350:293-8.
Korb et al., "The effect of two novel lubricant eye drops on tear film lipid layer thickness in subjects with dry eye symptoms", Optom Vis Sci, 2005, 82: 594-601.
Korean Office Action in Korean Application No. 10-2012-7033308, dated Mar. 21, 2017, 6 pages (English Translation Only).
Korolev et al., "Pd-EDTA as an efficient catalyst for Suzuki-Miyaura reactions in water", Tet. Lett., 2005, 46: 5751-5754.
Kortylewski et al., "Regulation of the IL-23 and IL-12 balance by Stat3 signaling in the tumor microenvironment", Cancer Cell, 2009, 15:114-123.
Kruh et al., "The complete coding sequence of arg defines the Abelson subfamily of cytoplasmic tyrosine kinases.", Proc. Natl. Acad. Sci., Aug. 1990, 87:5802-5806.
Kubinyi, "QSAR: Hansch Analysis and Related Approaches," Methods and Principles in Medicinal Chemistry, Manhold, R. ed. Weinheim, NY, 1993, 42 pages.

(56) References Cited

OTHER PUBLICATIONS

Kudelacz et al. "The JAK-3 inhibitor CP-690550 is a potent anti-inflammatory agent in a murine model of pulmonary eosinophilia", European Journal of Pharmacology, 2008, 582: 154-161.
Kumar, "Kinase drug discovery approaches in chronic myeloproliferative disorders", Oncogene, Jun. 2009, 28(24): 2305-23.
Kuo et al., "Pd-EDTA as an efficient catalyst for Suzuki-Miyaura reactions in water", Chem Commun, 2007, 301-3.
Kuppens et al., "Basal tear turnover and topical timolol in glaucoma patients and healthy controls by Fluorophotometry", Invest Ophthalmol Vis Sci, 1992, 33:3442-3448.
Kurzrock et al., "Serum Interleukin 6 Levels Are Elevated in Lymphoma Patients and Correlate with Survival in Advanced Hodgkin's Disease and with B Symptoms," Cancer Res., May 1993, 52: 2118-2122.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Kuster, "Kinase Inhibitors," Methods and Protocols, 2012, 46 pages.
Lai et al., "Mechanistic Study on the Inactivation of General Acyl-CoA Dehydrogenase by a Metabolite of Hypoglycin A," J. Am. Chem. Soc., 1991, 113: 7388-7397.
Lam et al, "Tear Cytokine Profiles in Dysfunctional Tear Syndrome", Am J Ophthalmol., 2009, 147(2):198-205.
Larock, "Comprehensive Organic Transformations", Wiley-VCH, 2nd Ed. (1999) pp. 1949-1950, 1958-1959, 1976, and 1983-1985.
Larson, "Myelodysplasia: when to treat and how," Best Pract Res Clin Haematol, 2006, 19(2): 293-300.
Lasho et al., "Chronic neutrophilic leukemia with concurrent CSF3R and SETBP1 mutations: single colony clonality studies, in vitro sensitivity to JAK inhibitors and lack of treatment response to ruxolitinib," Leukemia, 2014, 3 pages.
Leaf, "Why are we losing the war on cancer (and how to win it)," Clifton, Health Administrator vol. XVII, 2005, 1:172-183.
Lemp "Report of National Eye Institute/Industry Workshop on clinical trials in dry eyes," CLAO J, 1995, 21:221-232.
Lemp et al., "Corneal desiccation despite normal tear volume", Ann Ophthalmol, 1970 (2) pp. 258-261 & 284.
Lemp et al., "The Definition and Classification of Dry Eye Disease: Report of the Definition and Classification Subcommittee of the International Dry Eye WorkShop", The Ocular Surface, 5(2), 75-92 Apr. 2007.
Letter translation of Office Action, Chilean Application No. 3496-2006 as received from the foreign associate (dated Jul. 5, 2010) (4 pages).
Levine et al., "Activating mutation in the tyrosine kinase JAK2 in polycythemia vera, essential thrombocythemia, and myeloid metaplasia with myelofibrosis", Cancer Cell, 2005, 7:387-397.
Levitzki, "Tyrosine kinases as targets for cancer therapy", Eur. J. Cancer, 2002, 38(suppl. 5):S11-S18.
Levy et al. "INCB018424 A Selective Janus Kinase 1/2 Inhibitor" Presentation at the 50th American Society of Hematology Annual Meeting (ASH), Dec. 8, 2008, 27 pages.
Levy, et al., INCB18424 Discussion presentation at the American Society of Hematology, 49th Annual Meeting and Exposition, Atlanta, GA. Abstract #558, Dec. 10, 2007 (25 pages).
Li et al., "Pim-3, a proto-oncogene with serine/threonine kinase activity, is aberrantly expressed in human pancreatic cancer and phosphorylates Bad-mediated apoptosis in human pancreatic cell lines," Cancer Research, 2006, 66(13): 6741-7.
Li et al., "The synthesis and the antitumor activity of 5,7-disubstituted pyrazolo [1,5-a] pyrimidines," Chinese J Med Chem., Feb. 28, 2007, 17(1):18-22.
Liesveld and Lichtman, Chapter 88. "Myelodysplastic Syndromes (Clonal Cytopenias and Oligoblastic Myelogenous Leukemia)", in Prchal et al, eds. Williams Hematology. 8th ed., New York: McGraw-Hill; 2010.
Lima and Barreiro, "Bioisosterism: a useful strategy for molecular modification and drug design," Curr Med Chem., 2005, 12(1):23-49.
Lin et al., "Enantioselective synthesis of Janus kinase inhibitor INCB018424 via an organocatalytic aza-Michael reaction," Organic Letters, 2009, 11(9): 1999-2002.
Lin, "Constitutive Activation of JAK3/STAT3 in Colon Carcinoma Tumors and Cell Lines," Am J Pathol., 2005, 167(4):969-80.
Ling et al., "Knockdown of STAT3 Expression by RNA Interference Inhibits the Induction of Breast Tumors in Immunocompetent Mice," Cancer Res, Apr. 2005 65:2532.
List et al., "Efficacy of lenalidomide in myelodysplastic syndromes," N Engl J Med, Feb. 2005, 352(6): 549-57.
Liu et al., "Combined Inhibition of Janus Kinase 1/2 for the Treatment of JAK2V617F-Driven Neoplasms: Selective Effects on Mutant Cells and Improvements in Measures of Disease Severity," Clin Cancer Res, 2009, 15(22):6891-6900.
Lübbert et al., "Cytogenic responses in high-risk myelodysplastic syndrome following low-dose treatment with the DNA methylation inhibitor 5-aza-2'-deoxycytidine," Br J Haematol, Aug. 2001, 114(2): 349-57.
Lübbert et al., "Low-dose decitabine versus best supportive care in elderly patients with intermediate- or high-risk myelodysplastic syndrome (MDS) ineligible for intensive chemotherapy: final results of the randomized phase III study of the European Organisation for Research and Treatment of Cancer Leukemia Group and the German MDS Study Group," J Clin Oncol, May 2011, 29(15): 1987-96.
Lucet et al., "The structural basis of Janus kinas 2 inhibition by a potent and specific pan-Janus kinase inhibitor," Blood, 2006, 107(1):176-183.
Macchi et al., "Mutations of Jak-3 gene in patients with autosomal severe combined immune deficiency (SCID)", Nature, 1995, 377:65-8.
Madden et al., "Comparative study of two non-invasive tear film stability techniques," Curr Eye Res, 1994, 13(4):263-9.
Madhusudan et al., "Tyrosine kinase inhibitors in cancer therapy," Clin Biochem., 2004, 37(7):618-35.
Maffioli et al., "Mild and Reversible Dehydration of Primary Amides with PdCl2 in Aqueous Acetonitrile", Organic Letters, 2005, 7(23): 5237-39.
Main et al, "High throughput synthesis of diverse 2,5-disubstituted indoles using titanium carbenoids bearing boronate functionality", Tetrahedron, 2007, 64(5):901-914.
Mainstone et al., "Tear meniscus measurement in the diagnosis of dry eye", Curr Eye Res, 1996, 15:653-661.
Malaysian Examination Report in Malaysian Application No. PI2013002970, dated May 31, 2016, 4 pages.
Malhotra, "Janus Activated Kinase Inhibition in Myelofibrosis," Indian Journal of Cancer, Sep. 2012, 49(3):260-265.
Mancini et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Mandal, "Cancer Classification," 2014. Available from: <http://www.news-medical.net/health/Cancer-Classification.aspx, 6 pages.
Manjula et al., "Rapid Method of Converting Primary Amides to Nitriles and Nitriles to Primary Amides by ZnCl2 using Microwaves under Different Reaction Conditions", Syn. Commun, 2007, 37:1545-50.
Manning et al., "The Protein Kinase Complement of the Human Genome," Science, 2002, 298(5600):1912-16 and 1933-34.
Mao et al., "Advances in research of tyrosine kinases inhibitor of vascular endothelial growth factor receptor," Chinese J New Drugs, Dec. 31, 2008, 17(7):544-550.
March, Jerry, Advanced Organic Chemistry: Reactions, Mechanisms, and Structure, 3rd ed., John Wiley & Sons:New York, pp. 845-855 (1985).
Marelli et al., "Tumor targeting via integrin ligands," Frontiers in Oncology, 2013, 1-12.
Marquardt et al., "Modification of tear film break-up time test for increased reliability" in Holly ed. The Preocular Tear Film in Health, Disease and Contact Lens Wear. Lubbock, Texas: Dry Eye Institute, 1986:57-63.

(56) References Cited

OTHER PUBLICATIONS

Maruyama et al., "Effect of environmental conditions on tear dynamics in soft contact lens wearers," Invest Ophthalmol Vis Sci, 2004, 45(8):2563-8.
Mascarenhas et al., "Ruxolitinib: The First FDA Approved Therapy for the Treatment of Myelofibrosis," Clinical Cancer Research, Jun. 2012, 18(11): 3008-3014.
Matano et al., "Deletion of the long arm of chormosome 20 in a patient with chronic neutrophilic leukemia: cytogenetic findings in chronic neutrophilic leukemia," Am. J. Hematol., Jan. 1997, 54(1): 72-5.
Mathers et al., "Assessment of the tear film with tandem scanning confocal microscopy", Cornea, 1997;16:162-8.
Mathers et al., "Tear film changes associated with normal aging", Cornea, 1996; 15:229-334.
Mathers et al., "Tear flow and evaporation in patients with and without dry eye", Ophthalmology, 1996, 103:664-669.
Mathers et al., "Video imaging of the meibomian gland", Arch Ophthalmol, 1994, 112:448-9.
Mathers, "Evaporation from the ocular surface", Exp Eye Res, 2004, 78:389-394.
Maxson et al., "Oncogenic CSF3R Mutations in Chronic Neutrophilic Leukemia and Atypical CML," *N. Engl. J. Med.,* 2013, 368(19):1781-1790.
MayoClinic.org, "Heart Transplant," 2018, [retrieved Dec. 8, 2018] retrieved from URL <https://www.mayoclinic.org/tests-procedures/heart-transplant/about/pac-20384750>, 18 pages.
Mayo Clinic. Available at: < http://www.mayoclinic.com/health/pancreatic-cancer/DS00357 >. 2 pages, retrieved from the Internet Apr. 3, 2013.
Mayo Clinic. Available at: < http://www.mayoclinic.com/health/prostate-cancer-prevention/MC00027 >. 3 pages, retrieved from the Internet Apr. 3, 2013.
Mayo Clinic. Available at: <http://www.mayoclinic.com/health/crohns-disease/DS00104/DSECTION=treatments-and-drugs> 6 pages, retrieved from the Internet May 27, 2013.
Mayo Clinic. Available at: <http://www.mayoclinic.com/health/multiple-sclerosis/DS00188/DSECTION=treatments-and-drugs>. 3 pages, retrieved from the Internet May 27, 2013.
Mayo Clinic. Available at: <http://www.mayoclinic.com/health/myasthenia-gravis/DS00375> 2 pages, retrieved from the Internet May 27, 2013.
Mayo Clinic. Available at: <http://www.mayoclinic.com/health/rheumatoid-arthritis/DS00020/DSECTION=treatments-and-drugs> 3 pages, retrieved from the Internet Jun. 26, 2013.
Mayo Clinic. Available at: <http://www.mayoclinic.org/diseases-conditions/type-1-diabetes/basics/prevention> 2014, 19 pages.
McMillan, "The systemic inflammation-based Glasgow Prognostic Score: a decade of experience in patients with cancer," Cancer Treat Rev, Aug. 2013, 39(5): 534-40.
McNamara et al., "Fluorometry in contact lens research: The next step," Optom Vis Sci, 1998, 75:316-322.
MD Anderson Cancer Center. "Leukemia Prevention and Screening," 2014, 2 pages.
MD Anderson Cancer Center. "Myeloproliferative Disease Prevention and Screening," 2014, 2 pages.
Mengher et al., "Non-invasive tear film break-up time: sensitivity and specificity", Acta Ophthalmol (Copenh), 1986, 64(4):441-4.
Mesa et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa et al., "Emerging drugs for the therapy of primary and post essential thrombocythemia, post polycythemia vera myelofibrosis", Expert Opinion on Emerging Drugs England, 2009, 14(3): 471-479.
Mesa et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, Nov. 2011, 117(21): 4869-4877.
Meydan et al., "Inhibition of acute lymphoblastic leukaemia by a Jak-2 inhibitor", Nature, Feb. 1996, 379(6566):645-8.
Meyer et al., "Anti-inflammatory activity and neutrophil reductions mediated by the JAK1/JAK3 inhibitor, CP-690,550, in rat adjuvant-induced arthritis," Journal of Inflammation, 2010, 1-12.
Miethchen, "Micelle-activated reactions. I. Micelle-activated iodination and partial dehalogenation of pyrazoles and 1,2,4-triazoles", Journal F. prakt. Chemie, Band 331, Heft 5, S. 799-805 (1989) (1 page abstract also provided).
Milici et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi et al., "Human Tyrosine Kinase 2 Deficiency Reveals Its Requisite Roles in Multiple Cytokine Signals Involved in Innate and Acquired Immunity", Immunity, 2006, 25:745-55.
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol., Sep. 2010, 85(3):192-9 Epub Jun. 2, 2010.
Mishima et al., "Determination of tear volume and tear flow", Invest Ophthalmol, 1966, 5:264-276.
Mishima, "Some physiological aspects of the precorneal tear film", Arch Ophthalmol, 1965, 73:233-241.
Mitsunobu, "The Use of Diethyl Azodicarboxylate and Triphenylphosphine in Synthesis and Transformation of Natural Products." Synthesis, 1981, (1): 1-28.
Miyata et al., "Stereospecific nucleophilic addition reactions to olefins.", J. Org. Chem., 1991, 56:6556-6564.
Miyaura et al., "Palladium-Catalyzed Cross-Coupling Reactions of Organoboron Compounds," Chem. Rev., 1995, 95: 2457-2483.
Miyoshi et al., "Interleukin-8 concentrations in conjunctival epithelium brush cytology samples correlate with neutrophil, eosinophil infiltration, and corneal damage", Cornea, 2001, 20:743-7.
Molldrem et al., "Antithymocyte globulin for patients with myelodysplastic syndrome," Br J Haematol, Dec. 1997, 99(3): 699-705.
Moreland et al. "A Randomized Placebo-Controlled Study of INCB018424, a Selective Janus Kinase 1&2 (JAK 1&2) Inhibitor in Rheumatoid Arthritis (RA)" Presentation at the American College of Rheumatology meeting, Oct. 26, 2008. (20 pages).
Moriarty et al., "The synthesis and SAR of 2-amino-pyrrolo[2,3-d]pyrimidines: A new class of Aurora-A kinase inhibitors", Bioorganic and Medicinal Chemistry Letters, 2006, 16(22), 5778-5783.
Mosby's Dictionary of Medicine, Nursing, & Health Professions, sicca complex, 2009, Elsevier, printed from http://www.credoreference.com/entry/ehsmosbymed/sicca_complex, 2 pages.
Mullighan et al, "JAK mutations in high-risk childhood acute lymphoblastic leukemia", Proc Natl Acad Sci USA, 2009, 106:9414-8.
Mundle et al., "Evidence for Involvement of Tumor Necrosis Factor-α in Apoptotic Death of Bone Marrow Cells in Myelodysplastic Syndromes," Am J Hematol, 1999, 60:36-47.
Naka, "The paradigm of IL-6: from basic science to medicine", Arthritis Res., 2002, 4 Suppl 3:S233-42.
Nakagawara, "Trk receptor tyrosine kinases: A bridge between cancer and neural development." Cancer Letters, 2001, 169:107-114.
Nally et al., "Ocular discomfort and tear film break-up time in dry eye patients: A correlation," Invest Ophthalmol Vis Sci, 2000, 41:4:1436 (Poster Presentation).
Namour et al., "Once-daily High Dose Regimens of GLPG0634 in Healthy Volunteers are Safe and Provide Continuous Inhibition of JAK1 but not JAK2," ACR/ARHP Annual Meeting 12, Nov. 9-14, 2012, Abstract No. 1331.
Naqvi et al., "A potential role of ruxolitinib in leukemia", Expert Opinion on Investigational Drugs, Aug. 2011, 20(8): 1159-1166.
National Cancer Institute, "Cancer Types by Site," Mar. 14, 2011, [retrieved from Dec. 15, 2018] retrieved from URL <https://web.

(56) References Cited

OTHER PUBLICATIONS archive.org/web/20110314030905/https://training.seer.cancer.gov/disease/categories/site.html>, 3 pages.
National Cancer Institute, "FDA Approval for Ruxolitinib Phosphate", http://www.cancer.gov/cancertopics/druginfo/fda-ruxolitinibphosphate posted Nov. 18, 2011 (3 pages).
National Institutes of Health, "Study of Ruxolitinib Sustained release formulations in Myelofibrosis Patients," Sep. 25, 2013, Retrieved from the Internet: URL:http://clinicaltrials.gov/ct2/show/results/NCT01340651 [retrieved on Jan. 2, 2014], 4 pages.
Naus et al., "6-(Het)aryl-7-Deazapurine Ribonucleosides as Novel Potent Cytostatic Agents", J. Med. Chem., 2010, 53(1):460-470.
NavigatingCancer.com "List of Cancer Chemotherapy Drugs," Navigating Care, [retrieved on Nov. 26, 2013] retrieved from URL <https://www.navigatingcancer.com/library/all/chemotherapy_drugs>, 6 pages.
Neidle Cancer Drug Design and Discovery, (Elsevier/Academic Press, 2008) 427-431.
Nelson et al., "Tear film osmolality determination: an evaluation of potential errors in measurement," Curr Eye Res, 1986, 5(9):677-81.
Neubauer et al., "Jak2 Deficiency Defines an Essential Developmental Checkpoint in Definitive Hematopoiesis", Cell, 1998, 93(3): 397-409.
Neuner et al., "Increased IL-6 Production by Monocytes and Keratinocytes in Patients with Psoriasis," J. Invest. Dermatol., 1991, 97: 27-33.
Nicholoff et al., "Recent Insights into the immunopathogenesis of psoriasis provide new therapeutic opportunities", J. Clin. Invest., 2004, 113: 1664-1675.
Nichols et al., "The lack of association between signs and symptoms in patients with dry eye disease", Cornea, 2004, 23(8):762-770.
Nichols et al., "The repeatability of clinical measurements of dry eye", Cornea, 2004, 23(3):272-85.
Nishimoto et. al., "Improvement in Castleman's disease by humanized anti-interleukin-6 receptor antibody theraphy," *Blood,* 2000, 95(1):56-61.
Nishio et al., "Tyrosine kinase-dependent modulation by interferon-α of the ATP-sensitive K+ current in rabbit ventricular myocytes", FEBS Letters, 1999, 445: 87-91.
Nitta et al., "Peptide-Titanium Complex as Catalyst for Asymmetric Addition of Hydrogen Cyanide to Aldehyde", J. Am. Chem. Soc., 1992, 114: 7969-75.
Nokhodchi et al., "The role of oral controlled release matrix tablets in drug delivery systems," BioImpacts, 2012, 2(4): 175-187.
Norman, "Selective JAK1 inhibitor and selective Tyk2 inhibitor patents," *Expert Opinion,* Informa Healthcare. 2012, available at: <http://informahealthcare.com/dol/pdfplus/10.1517/13543776.2012.723693>.
Norn, "Quantitative tear ferning. Clinical investigations", Acta Ophthalmol (Copenh), 1994, 72(3):369-72.
Notice of Allowance and Fee(s) Due dated Sep. 21, 2007 in connection with U.S. Appl. No. 11/313,394, 6 pages.
Notice of Hearing and Preliminary Report for EP Patent 1966202, dated Mar. 18, 2013 (7 pages).
Office Action (Non-final) dated Aug. 22, 2007 in connection with U.S. Appl. No. 11/115,702, 9 pages.
Office Action (Non-final) dated Dec. 3, 2007 in connection with U.S. Appl. No. 11/524,641, 13 pages.
Office Action (Non-final) dated Feb. 25, 2009 for U.S. Appl. No. 12/137,892, 13 pages.
Office Action (Final) dated Feb. 7, 2008 for U.S. Appl. No. 11/115,702, 5 pages.
Office Action (Final) dated Jan. 29, 2014 in U.S. Appl. No. 13/043,986, 10 pages.
Office Action (Final) dated Nov. 30, 2009 for U.S. Appl. No. 12/137,892 (9 pgs.).
Office Action (Non-final) dated Apr. 20, 2007 in connection with U.S. Appl. No. 11/313,394, 16 pages.
Office Action in U.S. Appl. No. 14/186,338, dated May 5, 2014, 18 pages.
Office Action received for European Application No. 06 839 328.9 (dated Jan. 22, 2009), 5 pages.
Office Action received for Japanese Application No. 2008-545733 dated Oct. 11, 2011 (5 pages).
Office Action received for New Zealand Application No. 569015 dated Feb. 24, 2010, 2 pages.
Office Action Received for New Zealand Application No. 748000, dated Dec. 24, 2018, 2 pages.
Office Action received for Singapore Application No. 2008-04386-1 (dated Aug. 24, 2010).
Office Action received for Vietnamese Patent Application No. 1-2011-03188 dated Mar. 8, 2012 as translated by foreign associate (10 pages).
Office Action, Canadian Patent Office, Application No. 2,632,466, dated May 8, 2012, 3 pages.
Office Action, China, Patent Application No. 201080033308.6 dated Aug. 2, 2013, 10 pages.
Office Action, Eurasian Patent Office Application No. 200870048, dated Feb. 5, 2010.
Office Action, European Patent Office, Application No. 06 839 328.9 dated Oct. 21, 2010.
Office Action, European Patent Office, dated Nov. 6, 2009 (Application 06839328.9).
Office Action, Intellectual Property Office of Singapore, Application No. 2012043428, dated Sep. 26, 2014 (25 pages).
Office Action, Mexico, Patent Appl. No. MX/a/2008/007635 as received from foreign associate dated Jun. 15, 2010, 1 page.
Office Action, Mexico, Patent Appl. No. MX/a/2008/007635 as received from foreign associate dated Nov. 13, 2009, 4 pages.
Office Action/Examination Report received for Pakistan Application No. 211/2009 dated Jan. 18, 2010, 1 page.
Oguz et al., "The height and radius of the tear meniscus and methods for examining these parameters", Cornea, 2000, 19:497-500.
Opposition (Actavis), European Patent Office, EP Patent No. EP2173752, mailed Jan. 20, 2015, 20 pages.
Opposition (Generics), European Patent Office, EP2173752, mailed Jan. 20, 2015, 18 pages.
Opposition for EP Patent 1966202, filed on Jun. 21, 2012, 30 pages.
Opposition for India Patent Application No. 2365/KOLNP/2008 dated Nov. 12, 2012 (received by Applicants from Indian associate on Apr. 17, 2013) 37 pages.
Opposition, Costa Rica, translation from Foreign Associate Dated Jun. 13, 2012, 6 pages.
Opposition, Costa Rica, translation from Foreign Associate Dated Nov. 20, 2013, 9 pages.
Opposition, Ecuador Patent Office, mailed Nov. 18, 2008, 6 pages (English Translation).
Ortmann et al., "Janus kinases and signal transducers and activators of transcription: their roles in cytokine signaling, development and immunoregulation," Arthritis Res, 2000, 2(1): 16-32.
O'shea et al., "Janus Kinase Inhibitors in Autoimmune Diseases," Ann Theum Dis., Apr. 2013, 72(Suppl 2):ii111-ii115.
Osteoporosis.aaos.org[online], "Osteoporosis," Feb. 2001, [retrieved on Dec. 15, 2018] retrieved from URL <https://orthoinfo.aaos.org/en/diseases--conditions/osteoporosis/>, 7 pages.
Ostojic et al., "Ruxolitinib: a new JAK1/2 inhibitor that offers promising options for treatment of myelofibrosis," Future Oncology, 2011, 7(9): 1035-1043.
Ostojic et al., "Ruxolitinib for the treatment of myelofibrosis," Drugs of Today, Nov. 2011, 47(11): 817-827.
Ousler et al., "Factors that influence the inter-blink interval (IBI) as measured by the ocular protection index (OPI)", Invest Ophthalmol Vis Sci 2001; 43: E-abstract 56 (Poster presentation) ARVO (2002) 2 pages, downloaded from http://abstracts.iov.s.org/cgi/content/abstract/43/12/56?maxtoshow on Aug. 14, 2009.
Palmer et al., "Multiple roles of ephrins in morphogenesis, neuronal networking, and brain function," Genes & Dev., 2003, 17:1429-1450.
Panteli et al., "Serum interleukin (IL)-1, IL-2, sIL-2Ra, IL-6 and thrombopoietin levels in patients with chronic myeloproliferative diseases," British Journal of Haematology, 2005, 130: 709-715.

(56) References Cited

OTHER PUBLICATIONS

Pardanani et al., "CSF3R T618I is a highly prevalent and specific mutation in chronic neutrophilic leukemia," Leukemia, 2013, 27: 1870-1873.
Pardanani, "JAK2 inhibitor therapy in myeloproliferative disorders: rationale, preclinical studies and ongoing clinical trials JAK2 inhibitor therapy in MPD," Leukemia, Jan. 2008, 22: 23-30.
Parganas et al., "Jak2 is Essential for Signaling through a Variety of Cytokine Receptors," Cell, 1998, 93(3): 385-95.
Park et al., "Homogeneous Proximity Tyrosine Kinase Assays: Scintillation Proximity Assay versus Homogeneous Time-Resolved Fluorescence", Analytical Biochemistry, 1999, 269: 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Patani et al., "Bioisosterism: A Rational Approach in Drug Design", Chem. Rev., 1996, 96: 3147-3176.
Patel et al., "Formulation and Evaluation of Controlled Release Matrix Tablet of a Model Antibiotic Drug," Am. J. PharmTech. Res., 2012 2(2).
Patrick, "An Introduction to medicinal chemistry" *Oxford University Press Inc.*, New York, 1995 (31 pages) (cited in Opposition from India dated Nov. 12, 2012.
Pearce et al., "An improved fluorophotometric method for tear turnover assessment", Optom Vis Sci, 2001, 78(1):30-36.
Pearce et al., "Spatial location studies on the chemical composition of human tear ferns", Ophthalmic Physiol Opt, 2000, 20(4):306-13.
Pedranzini et al., "Pyridone 6, A Pan-Janus-Activated Kinase Inhibitor, Induces Growth Inhibition of Multiple Myeloma Cells," Cancer Res., 2006, 66(19):9714-9721.
Pensyl et al., "The repeatability of tear mucus ferning grading", Optom Vis Sci, 1998, 75(8):600-4.
Pernis et al., "JAK-STAT signaling in asthma" J Clin Invest, 2002, 109(10): 1279-83.
Peters et al., "Functional Significance of Tie2 Signaling in the Adult Vasculature", 2004, © The Endocrine Society (21 pages).
Pflugfelder et al., "Evaluation of subjective assessments and objective diagnostic tests for diagnosing tear-film disorders known to cause ocular irritation," Cornea, 1998, 17(1):38-56.
Philippines Examination Report in Philippines Application No. 1-2013-501001, dated Mar. 23, 2017, 3 pages.
Pillonel "Evaluation of phenylaminopyrimidines as antifungal protein kinase inhibitors," Pest Management Science, Wiley & Sons, Jun. 2005, 61: 1069-1076.
Pirard et al., "Classification of Kinase Inhibitors Using BCUT Descriptors", J. Chem. Inf. Comput. Sci., 2000, 40: 1431-1440.
Pisella et al., "Conjunctival proinflammatory and proapoptotic effects of latanoprost, preserved timolol and unpreserved timolol: an ex vivo and in vitro study." Invest Ophthalmol Vis Sci, 2004, 45:1360-1368.
Pisella et al., "Flow cytometric analysis of conjunctival epithelium in ocular rosacea and keratoconjunctivitis sicca," Ophthalmology, 2000, 107:1841-1849.
Portnaya et. al., "Azomethine dyes. IV. Indoaniline dyes derived from heterocyclic N-substituted 1-hydroxy-2-naphthamide," Ts Vses Nauchn Issled Kinofotoinst, 1960, Issue 40, 106-8 (with English abstract 20 pages total).
Press Release dated Sep. 18, 2008: "Incyte's Topical JAK Inhibitor Demonstrates Positive Proof-of-Concept Results in Patients with Mild to Moderate Psoriasis" (4 pages).
Press Release dated Sep. 13, 2018: "Incyte Announces Positive Data from Phase 2b Trial of Ruxolitinib Cream in Patients with Atopic Dermatitis" (2 pages).
Prezent et al., "Boron chelates as intermediates in the synthesis of new functionalized pyridines and pyrimidines from a, a-dioxoketene aminals", Proceedings of the International Conference on the Chemistry of Boron, vol. 11 (2003) (abstract only—1 page).

Product Monograph, "Jakavi," Prepared Jun. 15, 2012, Last revised, Sep. 28, 2018, 51 pages.
PubChem CID: 222786, "Cortisone," retrieved on Mar. 6, 2019, retrieved from URL<https://pubchem.ncbi.nih.gov/compound/cortisone#section=Chemical-and-Physical-Properties>, 39 pages.
PubChem CID: 5865, "Prednisone," retrieved on Mar. 6, 2019, retrieved from URL<https://pubchem.ncbi.nlm.nih.gov/compound/prednisone#section=Top>, 90 pages.
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Punwani, Naresh, et al. "Efficacy and safety of topical INCB018424, a selective Janus kinase 1 & 2 (JAK1&2) inhibitor in psoriasis." Journal of the American Academy of Dermatology. vol. 60. No. 3. 360 Park Avenue South, New York, NY 10010-1710 USA: Mosby-Elsevier, 2009.
Quesada et al, "One-pot conversion of activated alcohols into 1,1-dibromoalkenes and terminal alkynes using tandem oxidation processes with manganese dioxide", Tetrahedron, 2006, 62: 6673-6680.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Ravin, "Preformulation", Remington's Pharmaceutical Sciences, 17th ed., Mack Publishing Company, Easton, Pa., 1985, Chapter 76, 1409-1423.
Raza et al., "Novel insights into the biology of myelodyplastic syndromes: excessive apoptosis and the role of cytokines," Int J Hematol, 1996, 63:265-278.
Raza et al., "The Myelodysplastic Syndromes in 1996: Complex Stem Cell Disorders Confounded by Dual Actions of Cytokines," Leuk Res, 1996, 20:881-890.
Raza et al., "Apoptosis in bone marrow biopsy samples involving stromal and hematopoietic cells in 50 patients with myelodysplastic syndromes," Blood, Jul. 1995, 86(1): 268-76.
Raza et al., "Phase 2 Study of lenalidomide in transfusion-dependent, low-risk, and intermediate-1 risk myelodysplastic syndromes with karyotypes other than deletion 5q," Blood, Jan. 2008, 111(1): 86-93.
Ren et al., "Compounds and Compositions as Protein Kinase Inhibitors," U.S. Appl. No. 60/578,491, filed Jun. 10, 2004 (56 pages).
Research Gate, "What is the difference between Ex vivo and In vitro?", Dec. 18, 2014, available at http://www.researchgate.net/post/What_is_the_difference_between_Ex_vivo_and_in_vitro, 6 pages.
Response and Amendment dated Aug. 25, 2009 to non-final Office Action for U.S. Appl. No. 12/137,892, 34 pages.
Response and Amendment in Reply to Action of Apr. 20, 2007 filed Jul. 17, 2007 for U.S. Appl. No. 11/313,394, 39 pages.
Response to Action of Aug. 22, 2007 dated Nov. 19, 2007, U.S. Appl. No. 11/115,702, 7 pages.
Response to Restriction Requirement dated May 29, 2007, U.S. Appl. No. 11/115,702, 8 pages.
Restriction Requirement dated Mar. 6, 2007 in connection with U.S. Appl. No. 11/115,702, 8 pages.
Reuters, "Jakafi (ruxolitinib) improved advanced pancreas cancer outcomes in mid-stage trial," Internet Citation, Aug. 21, 2013, pp. 1-2, XP002717211, Retrieved from Internet: URL: http://www.curetoday.com/index.cfm/fuseaction/news.showNewsArticle/id/13/news_id/3785 [retrieved on Nov. 29, 2013].
Riese et al., "Inhibition of JAK kinases in patients with rheumatoid arthritis: scientific rationale and clinical outcomes," Best Practice & Research Clinical Rheumatology, 2010, 513-526.
Roberts et al., "Trends in the Risks and Benefits to Patients With Cancer Participating in Phase 1 Clinical Trials," JAMA, 2004, 292(17):2130-2140.

(56) References Cited

OTHER PUBLICATIONS

Robin et al., "In vivo transillumination biomicroscopy and photography of meibomian gland dysfunction," Ophthalmology, 1985, 92:1423-6.
Rodig et al., "Disruption of the Jak1 gene demonstrates obligatory and nonredundant roles of the Jaks in cytokine-induced biologic responses." Cell, 1998, 93(3): 373-83.
Rolando et al., "Tear mucus crystallization in children with cystic fibrosis", Ophthalmologica, 1988, 197(4):202-6.
Rolando et al., "Tear mucus ferning test in keratoconjunctivitis sicca", Holly FJ, Lamberts DW, MacKeen DL (eds.): The preocular tear film in health, disease, and contact lens wear,. 1st Intern Tear Film Symposium. Lubbock (Texas, USA), Dry Eye Institute, 1986, 203-210.
Rolando et al., "The effect of hyperosmolarity on tear mucus ferning", Fortschr Ophthalmol, 1986, 83:644-646.
Rolando et al., "The Ocular Surface and Tear Film and Their Dysfunction in Dry Eye Disease," Survey of Ophthalmology, Mar. 2001, 45(Supplement 2): S203-S210.
Rolando, "Tear mucus ferning test in normal and keratoconjunctivitis sicca eyes," Chibret Int J Ophthalmol, 1984, 2(4):32-41.
Rollison et al., "Epidemiology of myelodysplastic syndromes and chronic myeloproliferative disorders in the United States, 2001-2004, using data from the NAACCR and SEER programs," Blood, Jul. 2008, 112(1): 45-52.
Roudebush et al., "Pharmacologic manipulation of a four day marine delayed type hyper sensitivity model", Agents Actions, 1993, 38(1-2):116-21.
Rousvoal et al. "Janus kinase 3 inhibition with CP-690,550 prevents allograft vasculopathy", Transpl Int., 2006, 19(12):1014-21.
Rowe et al., "Handbook of Pharmaceutical Excipients," Pharmaceutical Excipients, 2009, 6:697-699.
Roy et al., "Formulation and design of sustained release matrix tablets of metformin hydrochloride: Influence of hypromellose and polyacrylate polymers," Int J Appl Basic Med Res., Jan. 2013, 3(1):55-63.
Saemann et al., "Suppression of early T-cell-receptor-triggered cellular activation by the Janus kinase 3 inhibitor MHI-P-154," Transplantation, 2003, 75(11): 1864-1872.
Saemann et al., "Prevention of CD40-triggered dendritic cell maturation and induction of T-cell hyporeactivity by targeting of Janus kinase 3," Am J Transplant, 2003, 3(11): 1341-9.
Saettone and Salminen, "Ocular inserts for topical delivery", Advanced Drug Delivery Reviews, 1995, 16:95-106.
Saettone et al., "Ocular inserts for topical delivery," Advanced Drug Delivery Reviews, 1995, 16: 95-106.
Samanta et al., "Janus kinase 2: a critical target in chronic myelogenous leukemia," Cancer Res., Jul. 2006, 66(13):6468-72.
Santini et al., "Hepcidin Levels and Their Determinants in Different Types of Myelodysplastic Syndromes," PLoS One, 2011, 6(8): e23109, pp. 1-8.
Sawada et al, "Increased Lipophilicity and Subsequent Cell Partitioning Decrease Passive Transcellular Diffusion of Novel, Highly Lipophilic Antioxidants", The Journal of Pharmacology and Experimental Therapeutics, 1999, 288(3):1317-1326, p. 1321, compound 26.
Schiffer, "Clinical issues in the management of patients with myelodysplasia," Hematology Am Soc Hematol Educ Program, 2006, 205-10.
Schiffer, "Myelodysplasia: the good, the fair and the ugly," Best Pract Res Clin Haematol, Mar. 2007, 20(1): 49-55.
Schindler et al., "Hormones and Signaling: Cytokines and STAT Signaling," Adv Pharmacol., 2000, 47:113-74.
Schmidt et al., "Rituximab in autoimmune bullous diseases: mixed responses and adverse effects," British Journal of Dermatology, 2007, 352-356.
Schrader et al., "Animal Models of Dry Eye," Developmental Ophthalmology, 2008, 41: 298-312.
Scott et al., "Jaks, STATs, Cytokines, and Sepsis." Clin Diagn Lab Immunol, 2002, 9(6): 1153-9.
Scott et al., "Prolonged responses in patients with MDS and CMML treated with azacitidine and etanercept," (British Journal of Haematology), Mar. 2010, 148(6): 944-947.
Search Report in TW Application No. 100117866, dated Dec. 2014, 1 page.
Seefeld et al, "Discovery of 5-pyrrolopyridinyl-2-thiophenecarboxamides as potent AKT kinase," Bioorganic & Medicinal Chemistry Letters, 2009, 19(8):2244-2248.
Seela et al., "Synthesis of Pyrrolo[2,3-d]pyrimidine 2', 3'-Dideoxyribenucleosides Related to 2',3'-Dideoxyadenosine and 2',3'-Dideoxgtuanosine and Inhibitory Activity of 5'-Triphosphates on HIV-1 Reverse Transcriptase", Helvetica Chimica Acta, 1991, 74(3), 554-64.
Seki, "STAT3 and MAPK in human lung cancer tissues and suppression of oncogenic growth by JAB and dominant negative STAT3", Int J Oncol., 2004, 24(4):931-4.
Seto et al., "Enhanced Th2 cell-mediated allergic inflammation in Tyk2-deficient mice." J Immunol, 2003, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia," Cancer Cell, Aug. 2002, 2:117-125.
Shi et al., "The effect of CYP3A4 inhibition or induction on the pharmacokinetics and pharmacodynamics of orally administered ruxolitinib (INCB018424 Phosphate) in Healthy Volunteers,"J. Clin. Pharmacol. Jun. 2012;52(6):809-818.
Shi et al., "The pharmacokinetics, pharmacodynamics, and safety of orally dosed INCB018424 phosphate in healthy volunteers", Journal of Clinical Pharmacology, Dec. 2011, 51(12): 1644-1654.
Shimazaki et al., "Meibomian gland dysfunction in patients with Sjogren syndrome", Ophthalmology, 1998, 105(8):1485-8.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Sloand et al., "Factors affecting response and survival in patients with myelodysplasia treated with immunosuppressive therapy," J Clin Oncol, May 2008, 26(15): 2505-11.
Smith et al, "Basic pathogenic mechanisms operating in experimental model acute anterior uveitis," Immunology and Cell Biology, 1998, 76: 497-512.
Smolen et al, "Effect of interleukin-6 receptor inhibition with tocilizumab in patients with rheumatoid arthritis (OPTION study): a double-blind, placebo-controlled, randomized trial", Lancet, 2008, 371:987.
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., "Activity of therapeutic JAK 1/2 blockade in graft-versus-host disease," *Blood,* 2014, 123(24): 3832-3842.
Srdan et al., "Safety and Efficacy of INCB018424, a JAK1 and JAK2 Inhibitor, in Myelfibrosis," The New England Journal of Medicine, Sep. 16, 2010, 363:1117-1127.
Sriram et al., "Induction of gp130-related Cytokines and Activation of JAK2/STAT3 Pathway in Astrocytes Precedes Up-regulation of Glial Fibrillary, Acidic Protein in the 1-Methyl-4-phenyl-1,2,3,6-tetrahydropyridine Model of Neurodegeneration", J. Biol. Chem., 2004, 279(19):19936-47.
Staerk et. al., "JAK1 and Tyk2 activation by the homologous polycythemia vera JAK2 V617F mutation: cross-talk with IGF1 receptor", J Biol Chem, 2005, 280:41893-41899.
State Intellectual Property Office, PR China, Office Action, dated Sep. 3, 2010 Pat. Appl. No. 200680052750.7 (8 +A601+A597.

(56) References Cited

OTHER PUBLICATIONS

Steensma et al., "The JAK2 V617F activating tyrosine kinase mutation is an infrequent event in both "atypical" myeloproliferative disorders and mylodysplastic syndromes," Blood, Aug. 2005, 106(4): 1207-9.
Stirewalt et al., "Predictors of relapse and overall survival in Philadelphia chromosome-positive acute lymphoblastic leukemia after transplantation", Biol Blood Marrow Transplant., Mar. 2003, 9(3):206-12.
STN Search conducted Aug. 30, 2010 (17 pages).
STN Search conducted Jun. 24, 2011 (24 pages).
STN Search conducted Nov. 5, 2010 (5 pages).
STN Search conducted Nov. 9, 2010 (43 pages).
STN Search, Nov. 12, 2009 (180 pages).
STN Search, Oct. 20, 2009 (601 pages).
STN Search, Sep. 20, 2009 (864 pages).
Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Submission in Opposition Proceedings in European Application No. 08770794.9, Actavis Group PTC ehf, dated Mar. 19, 2014, 7 pages.
Submission in Opposition Proceedings in European Application No. 08770794.9, Incyte Corporation, dated Jun. 5, 2015, 14 pages.
Sullivan et al., "4th International Conference on the Lacrimal Gland, Tear Film & Ocular Surface and Dry Eye Syndromes, Nov. 20, 2004" (2 pages).
Summons to Attend Oral Proceedings in European Application No. 08770794.9, dated Jan. 29, 2016, 18 pages.
Summons to Attend Oral Proceedings in European Application No. 08770794.9, dated Nov. 30, 2015, 18 pages.
Swerdlow, et al., WHO Classification of Tumours of Haematopoietic and Lymphoid Tissues. 4th Edition. Lyon France: IARC Press; 2008:88-103.
Symington et al., "The relationship of serum IL-6 levels to acute graft-versus-host disease and hepatorenal disease after human bone marrow transplantation," Transplantation, 1992, 54(3): 457-462 (Abstract only).
Taiwan Search Report in Taiwanese Application No. 102141524, dated Apr. 27, 2017, 12 pages.
Taiwanese Office Action in Taiwanese Application No. 103126987, dated Dec. 28, 2017, 9 pages (English Translation).
Taiwanese Office Action in Taiwanese Application No. 103126987, dated Oct. 22, 2018, 5 pages (English Translation).
Takahashi et al., "Solvent-Free Reaction Using Phosphonium Salts: Chlorination of Hydroxyheteroaromatics and dehydration of Primary Amides", Heterocycles, 2006, 68: 1973-1979.
Takano et al., "Inflammatory cells in brush cytology samples correlate with the severity of corneal lesions in atopic keratoconjunctivitis", Br J Ophthalmol, 2004, 88:1504-5.
Takemoto et al., "Proliferation of adult T cell leukemia/lymphoma cells is associated with the constitutive activation of JAK/STAT proteins." Proc Natl Acad Sci USA, 1997, 94(25): 13897-902.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Tan et al, "Racemization processes at a quaternary carbon center in the context of the asymmetric Michael reaction", Tetrahedron Lett., 2001, 42(30):5021-5023.
Tang et al., "Knowledge-based design of 7-azaindoles as selective B-Raf inhibitors", Bioorganic & Medicinal Chemistry Letters, 2008, 18(16):4610-4614.
Tasian et al., "Understanding the biology of CRLF2-overexpressing acute lymphoblastic leukemia", Critical Reviews in Oncogenesis, 2011, 16(1): 13-24.
Tefferi et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi et al., "Serious adverse events during ruxolitinib treatment discontinuation in patients with myelofibrosis", Mayo Clinic Proceedings, Dec. 2011, 86(12): 1188-1191.
Tefferi, "Primary myelofibrosis: 2012 update on diagnosis, risk stratification, and management," American Journal of Hematology, Dec. 2011, 86(12): 1017-1026.
Textbook of Clinical Trials 264 (D. Machin et al., eds., 2nd ed., 2006).
Thailand Office Action in Thailand Application No. 1501002638, dated Jul. 17, 2017 2 pages (English Translation).
Thompson et al., "Photochemical Preparation of a Pyridone Containing Tetracycle: A Jak Protein Kinase Inhibitor", Bioorganic & Medicinal Chemistry Letters, 2002, 12: 1219-1223.
Tiffany et al., Meniscectomy using the Tearscope-plus (ARVO abstract). Invest Ophthalmol Vis Sci, 2001,42: s37 (1 page).
Tiffany, "Refractive index of meibomian and other lipids", Curr Eye Res, 1986, 5:887-9.
Ting et al., "The Synthesis of substituted bipiperidine amide compounds as CCR3 antagonists", Bioorg. Med. Chem. Lett., 2005, 15(5): 1375-1378.
Toyonaga, "Blockade of constitutively activated Janus kinase/signal transducer and activator of transcription-3 pathway inhibits growth of human pancreatic cancer", Cancer Lett., 2003, 201(1):107-16.
Trikha et al., "Targeted anti-interleukin-6 monoclonal antibody therapy for cancer: a review of the rationale and clinical evidence," Clinical Cancer Research, 2003, 9: 4653-4665.
Tsubota et al., "Brush cytology for the evaluation of dry-eye", Nippon Ganka Gakkai Zasshi, 1990, 94:224-30 (English Abstract).
Tsubota et al., "Conjunctival brush cytology", Acta Cytol, 1990, 34(2):233-5.
Tsubota et al., "Detection by brush cytology of mast cells and eosinophils in allergic and vernal conjunctivitis," Cornea, 1991, 10(6):525-31.
UCSFHealth.org, "Liver Cancer," UCSF Medical Center, [retreived on Nov. 9, 2018], retreived from URL <https://www.ucsfhealth.org/conditions/liver_cancer/<, 3 pages.
U.S. Natinoal Institute of Health, "Single-Agent Glasdegib in Patients With Myelofibrosis Previously Treated With Ruxolitinib," dated Aug. 25, 2014, available at www.clinicaltrials.gov, 4 pages.
U.S. National Insitute of Health, "Phase I/II Study of Nilotinib/Ruxolitinb Therapy for TKI Resistant Ph-Leukemia," dated Jul. 28, 2013, available at www.clinicaltrials.gov, 5 pages.
U.S. National Insitute of Health, "Phase III Study Investigating the Efficacy and Safety of Ruxolitnib in Early Myelofibrosis Patients With High Molecular Risk Mutations," dated Oct. 27, 2015, available at www.clinicaltrials.gov, 4 pages.
U.S. National Insitute of Health, "Ruxolitinib and Pomalidomide Combination Therapy in Patients With Primary and Secondary MF (POMINC)," dated Jul. 16, 2012, available at www.clinicaltrials.gov, 4 pages.
U.S. National Institute of Health, "A Clinical Study of Ruxolitinib in Patients With Primary Myelofibrosis (PM), Post-polycythemia Vera (PV) Myelofibrosis, or Post-essential Thrombocythemia (ET) Myelofibrosis," dated Mar. 12, 2014, available at www.clinicaltrials.gov, 4 pages.
U.S. National Institute of Health, "A Dose Ranging Study of the Effect of INCB018424 Phosphate Cream When Applied to Patients With Plaque Psoriasis," dated Oct. 21, 2008, available at www.clinicaltrials.gov, 3 pages.
U.S. National Institute of Health, "A Phase Ib/II Dose-finding Study to Assess the Safety and Efficacy of LDE225 + INC424 in Patients With MF," dated Feb. 6, 2013, available at www.clinicaltrials.gov, 5 pages.
U.S. National Institute of Health, "A Phase II Study of Oral JAK1/JAK2 Inhibitor INC424 in Adult Patients With Relapsed/Refractory Classical Hodgkin's Lymphoma (HIJAK)," dated Jun. 11, 2013, available at www.clinicaltrials.gov, 4 pages.
U.S. National Institute of Health, "A Phase II Study of Re-treatment of Myelofibrosis Patients With Ruxolitinib/Jakavi After Treatment Interruption Due to Loss of Response and/or Adverse Event (Re Treatment Trial)," dated Mar. 6, 2014, available at www.clinicaltrials.gov, 3 pages.

(56) References Cited

OTHER PUBLICATIONS

U.S. National Institute of Health, "A Pilot Study of Ruxolitinib in Secondary Hemophagocytic Syndrome," dated Jan. 22, 2015, available at www.clinicaltrials.gov, 3 pages.
U.S. National Institute of Health, "A Sequential Two-Stage Dose Escalation Study to Evaluate the Safety and Efficacy of Ruxolitinib," dated Jan. 24, 2013, available at www.clinicaltrials.gov, 5 pages.
U.S. National Institute of Health, "A Study Exploring the Safety, Tolerability and Efficacy of a 4 Week Course of INCB018424 in Subjects With Active Rheumatoid Arthritis," dated Oct. 24, 2007, available at www.clinicaltrials.gov, 4 pages.
U.S. National Institute of Health, "A Study of INCB018424 Phosphate Cream When Applied to Patients With Plaque Psoriasis," dated Jan. 8, 2009, available at www.clinicaltrials.gov, 3 pages.
U.S. National Institute of Health, "A Study of LY2784544 in Participants With Myeloproliferative Neoplasms," dated May 1, 2012, available at www.clinicaltrials.gov, 3 pages.
U.S. National Institute of Health, "A Study of Ruxolitinib in Pancreatic Cancer Patients," dated Apr. 17, 2014, available at www.clinicaltrials.gov, 3 pages.
U.S. National Institute of Health, "A Study of Ruxolitnib in Combination With Capecitabine in Subjects With Advanced or Metastatic HER2-negative Breast Cancer," dated Apr. 18, 2014, available at www.clinicaltrials.gov, 3 pages.
U.S. National Institute of Health, "A Study to Determine the Effect and Safety of an Oral Janus Kinase 2 (JAK2)-Inhibitor (Ruxolitinib; INBC018424) in Patients With Multiple Myeloma," dated Mar. 12, 2008, available at www.clinicaltrials.gov, 3 pages.
U.S. National Institute of Health, "A Study to Evaluate Efficacy and Safety of Vismodegib (Erivedge) in Combination With Ruxolitinib for the Treatment of Intermediate- or High-Risk Myelofibrosis (MF)," dated Oct. 29, 2015, available at www.clinicaltrials.gov, 3 pages.
U.S. National Institute of Health, "A Study With INCB018424 Phosphate Cream Applied Topically to Subjects With Alopecia Areata (AA)," dated Sep. 16, 2015, available at www.clinicaltrials.gov, 3 pages.
U.S. National Institute of Health, "Adding Ruxolitinib to a Combination of Dasatinib Plus Dexamethasone in Remission Induction Therapy in Newly Diagnosed Philadelphia Chromosome-Positive Acute Lymphoblastic Leukemia Patients Aged 40 Years or Older," dated Jul. 8, 2015, available at www.clinicaltrials.gov, 4 pages.
U.S. National Institute of Health, "Administration of Jakafi (Ruxolitnib) for Symptom Control of Patients With Chronic Lymphocytic Leukemia (CLL): Phase II," dated May 2, 2014, available at www.clinicaltrials.gov, 4 pages.
U.S. National Institute of Health, "Alternative Dosing Strategy of Ruxolitinib in Patients With Myelofibrosis," dated Sep. 23, 2011, available at www.clinicaltrials.gov, 6 pages.
U.S. National Institute of Health, "An Open-Label Study of Ruxolitinib Given With Chemotherapy in Patients With Advanced Solid Tumors," dated Mar. 28, 2013, available at www.clinicaltrials.gov, 3 pages.
U.S. National Institute of Health, "Asian Phase II Study of INC424 in Patients With Primary Myelofibrosis (MF), Post-PV MF or Post-ET MF," dated Jul. 11, 2011, available at www.clinicaltrials.gov, 4 pages.
U.S. National Institute of Health, "CINC424A2X01B Rollover Protocol," dated Mar. 6, 2015, available at www.clinicaltrials.gov, 4 pages.
U.S. National Institute of Health, "Controlled MyeloFibrosis Study with Oral JAK Inhibitor Treatment: The COMFORT-I Trial," dated Aug. 4, 2009, available at www.clinicaltrials.gov, 5 pages.
U.S. National Institute of Health, "Controlled Myelofibrosis Study With Oral Janus-associated Kinase (JAK) Inhibitor Treatment-II: The COMFORT-II Trial," dated Jul. 6, 2009, available at www.clinicaltrials.gov, 4 pages.
U.S. National Institute of Health, "Dose Escalation Study to Determine the Maxiumum Tolerated Dose of the Combination of Ruxolitinib and Bortezomib in Patients with Relapsed or Refractory Lymphoma," dated Nov. 20, 2015, available at www.clinicaltrials.gov, 4 pages.
U.S. National Institute of Health, "Efficacy and Safety of Simtuzumab in Adults With Primary, Post Polycythemia Vera or Post Essential Thrombocythemia Myelofibrosis," dated Jun. 6, 2011, available at www.clinicaltrials.gov, 4 pages.
U.S. National Institute of Health, "Efficacy of Momelotinib Versus Best Available Therapy in Anemic or Thrombocytopenic Subjects With Primary Myelofibrosis (MF), Post-polycythemia Vera MF, or Post-essential Thrombocythemia MF (Simplify 2)," dated Mar. 28, 2014, available at www.clinicaltrials.gov, 4 pages.
U.S. National Institute of Health, "Evaluating the Safety and Tolerability of Ruxolitinib in Antiretroviral-Treated HIV-Infected Adults," dated Jun. 16, 2015, availabe at www.clinicaltrials.gov, 6 pages.
U.S. National Institute of Health, "Evaluation of RUX and AZA Combination as a Therapy for Patients With Myelofibrosis and Myelodysplastic Syndrome/ Myeloproliferative Neoplasm," dated Feb. 6, 2013, available at www.clinicaltrials.gov, 5 pages.
U.S. National Institute of Health, "Expanded Treatment Protocol (ETP) of Ruxolitinib in Patients With Polycythemia Vera Who Are Hydroxyurea Resistant or Intolerant and for Whom no Treatment Alternatives Are Available," dated Nov. 5, 2014, availabe at www.clinicaltrials.gov, 3 pages.
U.S. National Institute of Health, "Exploratory Phase II Study of INC424 Patients With Primary Myelofibrosis (PMF) or Post Polycythaemia Myelofibrosis (PPV MF) or Post Essential Thrombocythaemia Myelofibrosis (PET-MF) (MACS2030)," dated Mar. 16, 2012, available at www.clinicaltrials.gov, 4 pages.
U.S. National Institute of Health, "Genomics-Based Target Therapy for Children With Relapsed or Refractory Malignancy," dated Nov. 29, 2015, available at www.clinicaltrials.gov, 3 pages.
U.S. National Institute of Health, "High Throughput Drug Sensitivity Assay and Genomics-Guided Treatment of Patients With Relapsed or Refractory Acute Leukemia," dated Aug. 25, 2015, available at www.clinicaltrials.gov, 4 pages.
U.S. National Institute of Health, "INC424 for Patients With Myelofibrosis, Post Polycythemia Myelofibrosis or Post-essential Thrombocythemia Myelofibrosis (JUMP)," dated Dec. 13, 2011, available at www.clinicaltrials.gov, 3 pages.
U.S. National Institute of Health, "INCB018424 in Patients With Advanced Hematologic Malignancies," dated May 5, 2008, available at www.clinicaltrials.org, 4 pages.
U.S. National Institute of Health, "INCB18424 in Treating Young Patients With Relapsed or Refractory Solid Tumor, Leukemia, or Myeloproliferative Disease," dated Jul. 15, 2010, available at www.clinicaltrials.gov, 5 pages.
U.S. National Institute of Health, "JAK2 Inhibitors Ruxolitinib in Patients With Myelofibrosis," dated Dec. 21, 2012, available at www.clinicaltrials.gov, 4 pages.
U.S. National Institute of Health, "JAK-inhibition in Recurrent Classical Hodgkin Lymphoma (JeRiCHO)," dated Jun. 12, 2014, available at www.clinicaltrials.gov, 3 pages.
U.S. National Institute of Health, "Momelotinib Versus Ruxolitinib in Subjects With Myelofibrosis (Simplify 1)," dated Oct. 22, 2013, available at www.clinicaltrials.gov, 4 pages.
U.S. National Institute of Health, "N-of-1 Trial: Actionable Target Identification in Metastatic Cancer for Palliative Systemic Therapy (MetAction)," dated Apr. 13, 2014, available at www.clinicaltrials.gov, 4 pages.
U.S. National Institute of Health, "Open Label Ruxolitinib (INCB018424) in Patients With Myelofibrosis and Post Polycythemia Vera/Essential Thombrocythemia Myelofibrosis," dated Jul. 30, 2007, available at www.clinicaltrials.gov, 4 pages.
U.S. National Institute of Health, "Open Label, Safety and Efficacy Study of Topical Investigational Drug to Treat Patients With Psoriasis," dated Jan. 21, 2008, available at www.clinicaltrials.gov, 3 pages.
U.S. National Institute of Health, "Oral Pacritinib Versus Best Available Therapy to Treat Myelofibrosis With Thrombocytopenia (PAC326)," dated Feb. 3, 2014, available at www.clinicaltrials.gov, 3 pages.

(56) References Cited

OTHER PUBLICATIONS

U.S. National Institute of Health, "Panobinostat and Ruxolitinib in MyElofibrosis (PRIME Trial) (PRIME)," dated Sep. 14, 2012, available at www.clinicaltrials.gov, 4 pages.

U.S. National Institute of Health, "Panobinostat and Ruxolitinib in Primary Myelofibrosis, Post-polycythemia Vera-myelofibrosis or Post-essential Thrombocythemia-myelofibrosis," dated Jun. 27, 2011, available at www.clinicaltrials.gov, 4 pages.

U.S. National Institute of Health, "Pharmacodynamic Effects and Predictive Biomarkers With Ruxolitinib in Operable Head and Neck Cancer," dated Oct. 14, 2015, available at www.clinicaltrials.gov, 4 pages.

U.S. National Institute of Health, "Phase I Study of the Combination of Afatinib and Ruxolitinib in Patients With Treatment-refractory Non-Small Cell Lung Cancer (NSCLC)," dated Apr. 23, 2014, available at www.clinicaltrials.gov, 3 pages.

U.S. National Institute of Health, "Phase I/II Study of Ruxolitinib for Acute Leukemia," dated Nov. 30, 2010, available at www.clinicaltrials.gov, 3 pages.

U.S. National Institute of Health, "Phase II, Open Label, Single Arm Study of SAR302503 in Myelofibrosis Patients Previously Treated With Ruxolitinib (JAKARTA2)," dated Jan. 27, 2012, available at www.clinicaltrials.gov, 4 pages.

U.S. National Institute of Health, "Pilot Study of Ruxolitinib in Relapsed or Refractory Hodgkin Lymphoma and Primary Mediastinal Large B-cell Lymphoma (JAK2)," dated Oct. 9, 2013, available at www.clinicaltrials.gov, 4 pages.

U.S. National Institute of Health, "Pilot Study to Evaluate of Ruxolitinib in Alopecia Areata," dated Sep. 23, 2013, available at www.clinicaltrials.gov, 4 pages.

U.S. National Institute of Health, "Randomized Switch Study From Hydroxyurea to Ruxolitinib for RELIEF of Polycythemia Vera Symptoms: The Relief Study," dated Jun. 29, 2012, available at www.clinicaltrials.gov, 3 pages.

U.S. National Institute of Health, "Ruxolitinib (INCB018424) in Subjects With Primary Myelofibrosis, Post Essential Thrombocythemia-myelofibrosis and Post Polycythemia Vera-myelofibrosis," dated May 4, 2011, available at www.clinicaltrials.gov, 3 pages.

U.S. National Institute of Health, "Ruxolitinib and Lenalidomide for Patients With Myelofibrosis," dated Jun. 14, 2011, available at www.clinicaltrials.gov, 4 pages.

U.S. National Institute of Health, "Ruxolitinib Efficacy and Safety in Patients With HU Resistant or Intolerant Polycythemia Vera vs Best Available Therapy. (RESPONSE 2)," dated Jan. 14, 2014, available at www.clinicaltrials.gov, 4 pages.

U.S. National Institute of Health, "Ruxolitinib for Adult T-Cell Leukemia," dated Oct. 20, 2012, available at www.clinicaltrials.gov, 4 pages.

U.S. National Institute of Health, "Ruxolitinib for Chronic Myeloid Leukemia (CML) With Minimal Residual Disease (MRD)," Dec. 14, 2012, available at www.clinicaltrials.gov, 4 pages.

U.S. National Institute of Health, "Ruxolitinib for Chuvash Polycythemia," dated Nov. 7, 2012, available at www.clinicaltrials.gov, 2 pages.

U.S. National Institute of Health, "Ruxolitinib for Patients With Low or Intermediate-1 Risk Myelodysplastic Syndrome (MDS)," dated Jul. 5, 2013, available at www.clinicaltrials.gov, 3 pages.

U.S. National Institute of Health, "Ruxolitinib for Pracinostat Combination Therapy for Patients With Myelofibrosis (MF)," dated Oct. 14, 2014, available at www.clinicaltrials.gov, 4 pages.

U.S. National Institute of Health, "Ruxolitinib in Combination With Autotransplant," dated May 28, 2015, available at www.clinicaltrials.gov, 4 pages.

U.S. National Institute of Health, "Ruxolitinib in Combination With Nilotinib in Chronic Myeloid Leukemia (CML) Patients," dated Oct. 3, 2012, available at www.clinicaltrials.gov, 4 pages.

U.S. National Institute of Health, "Ruxolitinib in Combination With Pemetrexed/Cisplatin in Non Small Cell Lung Cancer," dated Apr. 17, 2014, available at www.clinicaltrials.gov, 4 pages.

U.S. National Institute of Health, "Ruxolitinib in Combination With Trastuzumab in Metastatic HER2 Positive Breast Cancer," dated Feb. 18, 2014, available at www.clinicaltrials.gov, 5 pages.

U.S. National Institute of Health, "Ruxolitinib in Estrogen Receptor Positive Breast Cancer," dated May 7, 2012, available at www.clinicaltrials.gov, 3 pages.

U.S. National Institute of Health, "Ruxolitinib in GvHD (RIG)," dated Mar. 10, 2015, available at www.clinicaltrials.gov, 4 pages.

U.S. National Institute of Health, "Ruxolitinib in Patients With Breast Cancer," dated Mar. 20, 2012, available at www.clinicaltrials.gov, 3 pages.

U.S. National Institute of Health, "Ruxolitinib in the Treatment of Chronic Lymphocytic Leukemia," dated Dec. 3, 2013, available at www.clinicaltrials.gov, 4 pages.

U.S. National Institute of Health, "Ruxolitinib or Dasatinib With Chemotherapy in Patients With Philadelphia Chromosome (Ph)-Like Acute Lymphoblastic Leukemia (ALL)," dated Apr. 15, 2015, available at www.clinicaltrials.gov, 8 pages.

U.S. National Institute of Health, "Ruxolitinib Phosphate (Oral JAK Inhibitor INCB18424) in Treating Patients With Relapsed or Refractory Diffuse Large B-Cell or Peripheral T-Cell Non-Hodgkin Lymphoma," dated Sep. 5, 2011, available at www.clinicaltrials.gov, 4 pages.

U.S. National Institute of Health, "Ruxolitinib Phosphate and Danazol in Treating Anemia in Patients With Myelofibrosis," dated Nov. 19, 2012, available at www.clinicaltrials.gov, 5 pages.

U.S. National Institute of Health, "Ruxolitinib Phosphate in Treating Patients With Chronic Neutrophilic Leukemia or Atypical Chronic Myeloid Leukemia," dated Mar. 18, 2014, available at www.clinicaltrials.gov, 5 pages.

U.S. National Institute of Health, "Ruxolitinib Phosphate, Tacrolimus and Sirolimus in Preventing Acute Graft-versus-Host Disease During Reduced Intensity Donor Hematopoietic Cell Transplant in Patients With Myelofibrosis," dated Aug. 18, 2015, available at www.clinicaltrials.gov, 6 pages.

U.S. National Institute of Health, "Ruxolitinib Prior to Transplant in Patients With Myelofibrosis," dated Feb. 8, 2013, available at www.clinicaltrials.gov, 6 pages.

U.S. National Institute of Health, "Ruxolitinib W/ Preop Chemo for Triple Negative Inflammatory Brca," dated Jan. 11, 2014, available at www.clinicaltrials.gov, 4 pages.

U.S. National Institute of Health, "Safety and Tolerability of Combined Treatment With Nilotinib and Ruxolitinib in CML and Ph+ ALL Patients (CoRNea)," dated Sep. 17, 2014, available at www.clinicaltrials.gov, 4 pages.

U.S. National Institute of Health, "Safety, Tolerability, and Pharmacokinetics of Idelalisib in Adults Receiving Ruxolitinib as Therapy for Primary, Post-Polycythemia Vera, or Post-Essential Thrombocythemia Myelofibrosis With Progressive or Relapsed Disease," dated May 1, 2015, available at www.clinicaltrials.gov, 4 pages.

U.S. National Institute of Health, "Study of Combination Ruxolitinib and Decitabine Treatment for Accelerated Phase MPN or Post-MPN AML," dated Feb. 27, 2014, available at www.clinicaltrials.gov, 4 pages.

U.S. National Institute of Health, "Study of Efficacy and Safety of INC424 in Regularly Transfused Patients With Thalassemia," dated Jan. 28, 2014, available at www.clinicaltrials.gov, 3 pages.

U.S. National Institute of Health, "Study of Ruxolitinib (INCB018424) Administered Orally to Patients With Androgen Independent Metastatic Prostate Cancer," dated Mar. 12, 2008, available at www.clinicaltrials.gov, 4 pages.

U.S. National Institute of Health, "Study of Ruxolitinib (INCB018424) Sustained Release Formulation in Myelofibrosis Patients," dated Apr. 21, 2011, available at www.clinicaltrials.gov, 4 pages.

U.S. National Institute of Health, "Study of Ruxolitinib in Colorectal Cancer Patients," dated Apr. 17, 2014, available at www.clinicaltrials.gov, 4 pages.

U.S. National Institute of Health, "Study of Ruxolitinib in Pancreatic Cancer Patients (Janus 1)," dated Apr. 16, 2014, available at www.clinicaltrials.gov, 3 pages.

(56) References Cited

OTHER PUBLICATIONS

U.S. National Institute of Health, "Study of Ruxolitinib in Pancreatic Cancer Patients (RECAP)," dated Aug. 22, 2011, available at www.clinicaltrials.gov, 3 pages.
U.S. National Institute of Health, "Study of Ruxolitinib in the Treatment of Cachexia in Patients With Tumor-Associated Chronic Wasting Diseases," dated Feb. 21, 2014, available at www.clinicaltrials.gov, 4 pages.
U.S. National Institute of Health, "Study of Ruxolitinib Plus Decitabine in Patients With Acute Myeloid Leukemia (AML)," dated Sep. 26, 2014, available at www.clinicaltrials.gov, 4 pages.
U.S. National Institute of Health, "Study of the JAK Inhibitor Ruxolitinib Administered Orally to Patients With Primary Myelofibrosis (PMF), Post-Polycythemia Vera-Myelofibrosis (PPV-MF) or Post-Essential Thrombocythemia-Myelofibrosis (PET-MF)," dated Mar. 14, 2011, available at www.clinicaltrials.gov, 4 pages.
U.S. National Institute of Health, "Study of the Safety of PIM447 in Combination With Ruxolitinib (INC424) and LEE011 in Patients With Myelofibrosis," dated Feb. 6, 2015, available at www.clinicaltrials.gov, 5 pages.
U.S. National Institute of Health, "Study to Determine the Safety and Efficacy of Ruxolitinib (INCB018424) in Patients With Polycythemia Vera or Essential Thrombocythemia," dated Jul. 29, 2008, available at www.clinicaltrials.gov, 5 pages.
U.S. National Institute of Health, "TGR-1202 + Ruxolitinib PMF PPV-MF PET-MF MDS/MPN Polycythemia Vera Resistant to Hydroxyurea," dated Jul. 1, 2015, availabe at www.clinicaltrials.gov, 4 pages.
U.S. National Institute of Health, "The Role of JAK2 in Alveolar Macrophages (AM's) in Chronic Beryllium Disease (CBD)," dated Oct. 29, 2015, available at www.clinicaltrials.gov, 4 pages.
U.S. National Institute of Health, "The Ruxo-BEAT Trial in Patients With High-risk Polycythemia Vera or High-risk Essential Thrombocythemia (Ruxo-BEAT)," dated Oct. 1, 2015, available at www.clinicaltrials.gov, 5 pages.
U.S. National Institute of Health, "Trial of Ruxolitinib and Erlotinib in Patients With EGFR-mutant Lung Adenocarcinoma With Acquired Resistance to Erlotinib," dated Jun. 2, 2014, available at www.clinicaltrials.gov, 4 pages.
U.S. National Institute of Health, "Open Label Ruxolitinib (INCB018424) in Patients with Myelofibrosis and Post Polycythemia Vera/Essential Thrombocythemia Myelofibrosis," Dec. 19, 2014, available at www.clinicaltrials.gov, 4 pages.
U.S. National Institute of Health, "Study of Ruxolitinib," Dec. 3, 2008, available at www.clinicaltrials.gov, 11 pages.
U.S. National Institute of Helath, "Study of Efficacy and Safety in Polycythemia Vera Subjects Who Are Resistant to or Intolerant of Hydroxyurea: JAK Inhibitor INC424 (INCB018424) Tablets Versus Best Available Care: (The RESPONSE Trial)," dated Nov. 17, 2010, available at www.clinicaltrials.gov, 4 pages.
Ueda et al., "1,2-Benzisoxazol-3-yl Diphenyl Phosphate: A New, Reactive Activating Agent for the Synthesis of Amides, Esters, and Peptides via Condensation", J. Org. Chem., 1985, 50:760-763.
Ukraine Office Action in Ukraine Application No. a 2015 05798, dated Nov. 20, 2017, 9 pages (English Translation).
Vaillant et al., "Turbidity of pulpy fruit juice: A key factor for predicting cross-flow microfiltration performance," J Membrane Sci., 2008, 325:404-412.
van Best et al., "Measurement of basal tear turnover using a standardized protocol", Graefe's Arch Clin Exp Ophthalmol, 1995, 233:1-7.
van Bijsterveld, "Diagnostic tests in the sicca syndrome", Arch Ophthalmol, 1969, 82:10-14.
van Rhee et al., "Anti-Interleukin-6 Monoclonal man's Disease," J. Clin. Oncol., 2010, 28(23):3701-3708.
Vanhoutte, "Selective JAK1 Inhibition in the Treatment of Rheumatoid Arthritis: Proof of Concept with GLPG0634," Arthritis Rheum, 2012, 64.10: S1051-1.
Vannucchi et al., "Inhibitors of PI3K/Akt and/or mTOR Inhibit the Growth of Cells of Myeloproliferative Neoplasms and Synergize with JAK2 Inhibitor and Interferon", Blood, 2011, 118(21): 1638-1639, XP008150742ASH Annual Meeting Abstract 3835 American Society of Hematology.
Vannucchi et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, 2009, 114(22), 2 pages.
Vannucchi et al., "The mTOR Inhibitor, RAD001, Inhibits the Growth of Cells From Patients with Myeloproliferative Neoplasms", Blood: ASH Annual Meeting Abstracts, $51^{st}$ Annual Meeting of the American Society of Hematology, 2009, 114(22), 2 pages.
Vardiman et al., "Atypical chronic myeloid leukaemia, BCR-ABL1 negative," in: Swerdlow, et al., WHO Classification of Tumors of Haematopoietic and Lymphoid Tissues (ed 4th). Lyon: IARC Press; 2008:80-81.
Vardiman et al., "The 2008 revision of the World Health Organization (WHO) Classification of myeloid neoplasms and acute leukemia: rationale and important changes," Blood, 2009, 114:937-951.
Vardiman et al., "The World Health Organization (WHO) classification of the myeloid neoplasms," Blood, 2002, 100:2292-2302.
Vasilevsky et al., "Ethyl Vinyl Ether—an Agent for Protection of the Pyrazole NH-Fragment. A Convenient Method for the Preparation of N-Unsubstituted 6Alkynylpyrazoles", Heterocycles, 2003, 60(4):879-886.
Venugopal et al., "Special clinical concerns/problems in the management of MDS and secondary acute myeloid leukemias," Cancer Treat Res, 2001, 108: 257-65.
Verma et al., "Jak family of kinases in cancer", Cancer and Metastasis Reviews, 2003, 22(4): 423-434, DOI: 10.1023/A:1023805715476.
Verstovsek, "Therapeutic Potential of JAK2 Inhibitors", Hematology Am Soc Hematol Educ Program, 2009:636-42.
Verstovsek, et al., Blood (ASH Annual Meeting Abstracts) 2007 110: Abstract 558.
Verstovsek, et al., Blood (ASH Annual Meeting Abstracts) 2009 114: Abstract 311.
Verstovsek, et al., Blood (ASH Annual Meeting Abstracts) 2010 116: Abstract 313.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, Srdan et al., "Characterization of JAKS V617F Allele Burden in Advanced Myelofibrosis (MT) Patients: No Change in V617F:WT JAK2 Ratio in Patients with High Allele Burdens despite Profound Clinical Improvement Following Treatment with the JAKL Inhibitor, INCB018424, "50th ASH Annual Meeting and Exposition, Abstract No. 2802 (2008).
Verstovsek et al., "Efficacy, safety and survival with ruxolitinib in patients with mylefibrosis:resuts of a median 2-year follow-up of COMFORT-I," Haematologica, 2013, 98(12):1865-1871.
Vietnamese Office Action in Vietnamese Application No. 1-2013-01872, dated Sep. 25, 2018.
Vitali et al. "The European Community Study Group on diagnostic criteria for Sjogren's syndrome. Sensitivity and specificity of tests

(56) References Cited

OTHER PUBLICATIONS for ocular and oral involvement in Sjogren's syndrome," Ann Rheum Dis, 1994, 53(10): 637-47.
Wagh et al., "Polymers used in ocular dosage form and drug delivery systems", Asian J. Pharm., Jan. 2008, 12-17.
Wang and Deisboeck, "Mathematical modeling in cancer drug discovery," Drug Discovery Today, 2014, 145-150.
WebMD. "Diabetes Health Center." Available at: < http://diabetes.webmd.com/guide/diabetestreatment_care >. 3 pages, retrieved from the Internet May 28, 2013.
Webster's New World Medical Dictionary, Sjogren's syndrome, 2003, Wiley Publishing, printed fro http://www.credoreference.com/entry/webstermed/sjogren_s_syndrome, 2 pages.
Weiss et al., "Evaluation of a Series of Naphthamides as Potent, Orally Active Vascular Endothelial Growth Factor Receptor-2 Tyrosine Kinase Inhibitors", J. Med Chem., 2008, 51:1668-1680.
Welch et al., "An approach to a more standardized method of evaluating tear film break-up time", Invest Ophthalmol Vis Sci, 2003, 2485/B324 (abstract only—2 pages).
White et al., "Human basic tear fluid osmolality. I. Importance of sample collection strategy", Acta Ophthalmol (Copenh), Aug. 1993, 71(4):524-9.
Wilks, "The JAK kinases. Not just another kinase drug discovery target," Seminars in Cell & Developmental Biology, 2008, 319-328.
Williams and Ibrahim, "Carbodiimide Chemistry: Recent Advances", Chem. Rev., 1981, 81:589-636.
Williams et al., "Dissecting Specificity in the Janus Kinases: The Structures of JAK-Specific Inhibitors Complexed to the JAK1 and JAK2 Protein Tyrosine Kinase Domains," Journal of Molecular Biology, 2009, 219-232.
Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Winfield, Pharmaceutical Practice, Ophthalmic Products-pH adjustment, Churchill Livingstone, 2004, 264-271.
Wolff et al., "Burger's Medicinal Chemistry and Drug Discovery", 5th Ed. Part I, 1995, 975-977.
Wu et al., One-Pot Two-Step Microwave-Assisted Reaction in Construction 4,5-Disubstituted Pyrazolopyrimidines Organic Letters, 2003, 5(20): 3587-3590.
Xiaoyang et al., "Knockdown of STAT3 Expression by RNA Interference Inhibits the Induction of Breast Tumors in Immunocompetent Mice", Cancer Res Apr. 1, 2005 65; 2532.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Yamamura et al., "Circulating interleukin-6 levels are elevated in adult T-cell leukaemia/lymphoma patients and correlate with adverse clinical features and survival," Br. J. Haematol., 1998, 100: 129-134.
Yamaoka et al., "Janus kinase (JAK) inhibitors in rheumatoid arthritis", Current Rheumatology Reviews, Nov. 2011, 7(4): 306-312.
Yang et al., "Constitutive NF-KB activation confers interleukin 6 (IL6) independence and resistance to dexamethasone and Janus kinase inhibitor INCB018424 in murine plasmacytoma cells", Journal of Biological Chemistry, Aug. 2011, 286(32):27988-27997.
Yao et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 2008, 58(11):3485-3497.
Yao, et al., "Glucocorticoid Excess in Mice Results in Early Activation of Osteoclastogenesis and Adipogenesis and Prolonged Suppression of Osteogenesis", Arthritis and Rheumatism, 2008, 58(6), 1674-1686.
Ye et al., "The synthesis and the antitumor activity of 5,7-disubstituted pyrazolo [1,5-a] pyrimidines," Chinese J Med Chem., Feb. 28, 2007, 17(1):18-22.

Yokoi et al., "A newly developed video-meibography system featuring a newly designed probe", Jpn J Ophthalmol, 2007, 51: 53-6.
Yokoi et al., "Assessment of meibomian gland function in dry eye using meibometry", Arch Ophthalmol, 1999, 117:723-9.
Yokoi et al., "Correlation of tear lipid layer interference patterns with the diagnosis and severity of dry eye", Am J Ophthalmol, 1996, 122:818-24.
Yokoi et al., "Non-invasive methods of assessing the tear film", Exp Eye Res, 2004, 78:399-407.
Yongjun et al., "Advances in research of tyrosine kinases inhibitor of vascular endothelial growth factor receptor," Chinese J New Drugs, Dec. 31, 2008, 17(7):544-550.
Younes et al., "Phase I Study of a Novel Oral Janus Kinase 2 Inhibitor, SB1518, in Patients With Relapsed Lymphoma: Evidence of Clinical and Biologic Activity in Multiple Lymphoma Subtypes," J. Clin. Oncol., 2012, 30(33):4161-4167.
Yu et al., "Role of Janus Kinase/Signal Transducers and Activators of Transcription in the Pathogenesis of Pancreatitis and Pancreatic Cancer," Gut and Liver, Oct. 2012, 6(4): 417-422.
Yu et al., "Constitutive activation of the Janus kinase-STAT pathway in T lymphoma overexpressing the Lck protein tyrosine kinase," J Immunol., 1997, 159(11):5206-10.
Zaidi et al., "Dermatology in Clinical Practice," Springer, 2010, 157 pages.
Zheng et al., "Discovery of INCB108201PF-4178903, a potent, selective, and orally bioavailable dual CCR2 and CCR5 antagonist", Bioorganic & Medicinal Chemistry Letters, 2011, 21: 1442-45.
Zoppellaro et al., "A Multifunctional High-Spin Biradical Pyrazolylbipyridine-bisnitronylnitroxide", Org. Lett., 2004, 6(26):4929-4932.
Zou et al., "Signaling Pathways Activated by Oncogenic Forms of Abl Tyrosine Kinase " Journal of Biological Chemistry, 1999, 274(26):18141-18144.
Argentina Office Action in Argentina Application No. P110100737, dated Mar. 21, 2019, 10 pages.
Argentina Office Action in Argentina Application No. P110101747, dated Jun. 10, 2019, 5 pages.
Argentina Office Action in Argentina Application No. 20120102175, dated Jul. 22, 2019, 10 pages.
Australian Office Action in Australian Application No. 2015222913, dated Jun. 17, 2019, 5 pages.
Brazil Office Action in Brazil Application No. BR11201303270-0, dated Jul. 30, 2019, 5 pages.
Chilean Office Action in Chilean Application No. 292-02016, dated Jul. 18, 2019, 5 pages.
Chinese Office Action in Chinese Application No. 2015/0017178.X, dated Jul. 24, 2019, 24 pages.
Ecuador Examination Report in Ecuador Application No. SP-12-12546, dated Mar. 29, 2019, 12 pages.
European Opposition in European Application No. 16197502.4, dated Jul. 18, 2019, 22 pages.
Higuchi et al., "Pro-drugs as Novel Delivery Systems," vol. 14 of the A.C.S. Symposium Series (1975), Front Matter Only, 6 pages.
Indonesian Office Action in Indonesian Application No. P00201605769, dated May 13, 2019, 6 pages.
Indonesian Office Action in Indonesian Application No. P00201506279, dated Jul. 11, 2019, 5 pages.
Japanese Office Action in Japanese Application No. 2018-070780, dated Jul. 2, 2019, 5 pages.
Korean Office Action in Korean Application No. 10-2018-7030015, dated May 17, 2019, 7 pages.
Mexican Office Action in Mexican Application No. MX/a/2016/011103, dated Jul. 18, 2019, 3 pages.
Mexican Office Action in Mexican Application No. MX/a/2016/001639, dated Jun. 7, 2019, 2 pages.
Office Action received for New Zealand Application No. 749437, dated Jul. 8, 2019, 2 pages.
Peruvian Office Action in Peruvian Application No. 1872.15, dated Aug. 19, 2019, 27 pages.
Philippines Notice of Allowance in Philippines Application No. 1/2015502575, dated Jun. 27, 2019, 3 pages.
Philippines Office Action in Philippines Application No. 1/2016/500243, dated Jun. 25, 2019, 4 pages.

(56) References Cited

OTHER PUBLICATIONS

Philippines Office Action in Philippine Application No. 1/2015/502575, dated Aug. 9, 2019, 3 pages.
Raoof et al., "12-Week Efficacy and Safety Data of Ruxolitinib Cream in Adult Patients with Atopic Dermatitits: Results from a Phase 2 Study," Presented at the 24th World Congress of Dermatology, Milan, Italy, Jun. 10-15, 2019, 15 pages.
Sri Lanka Office Action in Sri Lanka Application No. 18621, dated May 16, 2019, 1 pages.
Stahl et al., "Topical Administration," Handbook of Pharmaceutical Salts, 22(43):110, (2008).
Vietnamese Office Action in Vietnamese Application No. 1-2011-02964, dated Jun. 26, 2019, 2 pages.
Vietnamese Office Action in Vietnamese Application No. 1-2019-03042, dated Jun. 21, 2019, 2 pages.
Vietnamese Office Action in Vietnamese Application No. 1-2015-03693, dated Jun. 4, 2019, 2 pages.
Vietnamese Office Action in Vietnamese Application No. 1-2014-00977, dated Jul. 22, 2019, 2 pages.
Wuts and Greene, Protective Groups in Organic Synthesis, 4th ed., John Wiley & Sons: New Jersey, (2007), Front Matter Only, 27 pages.

CYCLOBUTYL SUBSTITUTED PYRROLOPYRIDINE AND PYRROLOPYRIMIDINES DERIVATIVES AS JAK INHIBITORS

This application is a continuation of Ser. No. 14/556,775, filed Dec. 1, 2014, which is a continuation of Ser. No. 13/300,094, filed Nov. 18, 2011, which claims the benefit of priority of U.S. Provisional Application No. 61/415,705, filed Nov. 19, 2010, each of which is incorporated herein by reference in its entirety.

TECHNICAL FIELD

The present invention provides cyclobutyl substituted pyrrolopyrimidines and pyrrolopyridines, as well as their compositions and methods of use, that modulate the activity of Janus kinases (JAKs) and are useful in the treatment of diseases related to the activity of JAKs including, for example, inflammatory disorders, autoimmune disorders, cancer, and other diseases.

BACKGROUND OF THE INVENTION

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, Jak1−/− mice are runted at birth, fail to nurse, and die perinatally (Rodig, S. J., M. A. Meraz, et al. (1998) *Cell* 93(3): 373-83). Jak2−/− mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell*, vol. 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacol.* 2000; 47:113-74).

Accordingly, inhibitors of Janus kinases or related kinases are widely sought. For example, certain JAK inhibitors, including pyrrolopyridine and pyrrolopyrimidines, are reported in U.S. Ser. No. 11/637,545, filed Dec. 12, 2006.

Thus, new or improved agents which inhibit kinases such as JAKs are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases, diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. The compounds of the invention, as well as its compositions and methods described herein are directed toward these needs and other ends.

SUMMARY OF THE INVENTION

The present invention provides, inter alia, compounds of Formula I:

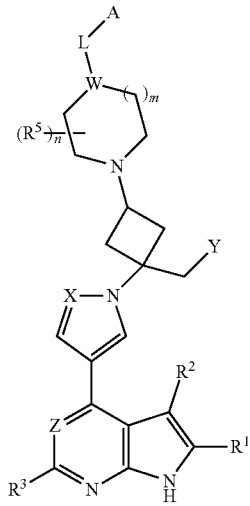

and pharmaceutically acceptable salts thereof; wherein A, L, W, X, Y, Z, $R^2$, $R^3$, $R^5$, n and m are defined herein.

The present invention further provides pharmaceutical compositions comprising a compound of Formula I as described herein, or a pharmaceutically acceptable salt thereof, and at least one pharmaceutically acceptable carrier.

The present invention further provides methods of modulating an activity of JAK1 comprising contacting JAK1 with a compound of Formula I as described herein, or a pharmaceutically acceptable salt thereof.

The present invention further provides methods of treating a disease or a disorder associated with abnormal kinase expression or activity in a patient by administering to a patient a therapeutically effective amount of a compound of Formula I as described herein, or a pharmaceutically acceptable salt thereof.

The present invention further provides methods of treating an autoimmune disease, a cancer, a myeloproliferative disorder, an inflammatory disease, a bone resorption disease, or organ transplant rejection in a patient in need thereof, comprising administering to said patient a therapeutically effective amount of a compound of Formula I as described herein, or a pharmaceutically acceptable salt thereof.

The present invention also provides compounds of Formula I as described herein, or pharmaceutically acceptable salts thereof, as described herein for use in methods of treating autoimmune diseases, cancer, myeloproliferative disorders, inflammatory diseases, a bone resorption disease, or organ transplant rejection.

The present invention further provides compounds of Formula I as described herein, or pharmaceutically acceptable salts thereof, for use in methods of modulating a JAK1.

The present invention also provides uses of compounds of Formula I as described herein, or pharmaceutically acceptable salts thereof, for the preparation of medicaments for use in treating autoimmune diseases, cancer, myeloproliferative disorders, inflammatory diseases, a bone resorption disease, or organ transplant rejection.

The present invention further provides uses of compounds of Formula I as described herein, or pharmaceutically acceptable salts thereof, for the preparation of medicaments for use in methods of modulating a JAK1.

DETAILED DESCRIPTION

The present invention provides, inter alia, a compound of Formula I:

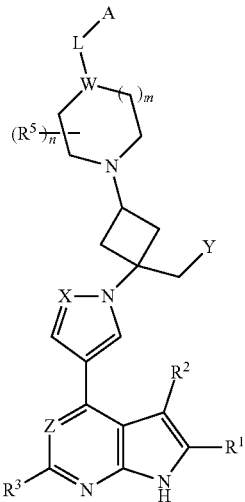

I or a pharmaceutically acceptable salt thereof; wherein:
X is CH or N;
Y is H, cyano, halo, $C_{1-3}$ alkyl, or $C_{1-3}$ haloalkyl;
Z is $CR^4$ or N;
W is CH or N;
when W is CH, then L is O, S, $C(R^6)_2$, C(=O), C(=O)N($R^7$), C(=O)O, C(=O)C($R^6)_2$, S(=O), S(=O)$_2$, S(=O)N($R^7$), S(=O)$_2$N($R^7$), or C(=$NR^{7a}$)N($R^7$); or
when W is N, then L is $C(R^6)_2$, C(=O), C(=O)O, C(=O)N($R^7$), C(=O)C($R^6)_2$, S(=O), S(=O)$_2$, S(=O)N($R^7$), S(=O)$_2$N($R^7$), or C(=$NR^{7a}$)N($R^7$);

$R^1$, $R^2$, $R^3$, and $R^4$ are each independently H, hydroxy, halo, $C_{1-3}$ alkyl, or $C_{1-3}$ haloalkyl;

each $R^5$ is independently hydroxy, $C_{1-4}$ alkoxy, fluorine, $C_{1-4}$ alkyl, hydroxy-$C_{1-4}$-alkyl, $C_{1-4}$ alkoxy-$C_{1-4}$-alkyl, or $C_{1-4}$ fluoroalkyl;

each $R^6$ is, independently, H or $C_{1-4}$ alkyl; or two $R^6$ groups, together with the carbon atom to which they are attached, form a 3-, 4-, 5-, or 6-membered cycloalkyl ring;

$R^7$ is H or $C_{1-4}$ alkyl;

$R^{7a}$ is H, OH, CN, $C_{1-4}$ alkoxy, or $C_{1-4}$ alkyl;

or $R^7$ and $R^{7a}$, taken together with the C(=N)N moiety to which they are attached, form a 4-, 5-, 6-, or 7-membered heterocycloalkyl ring or a 5- or 6-membered heteroaryl ring;

A is H, $C_{1-6}$ alkyl, $C_{3-10}$ cycloalkyl, $C_{2-10}$ heterocycloalkyl, $C_{6-10}$ aryl, or $C_{1-10}$ heteroaryl; wherein said $C_{1-6}$ alkyl, $C_{3-10}$ cycloalkyl, $C_{2-10}$ heterocycloalkyl, $C_{6-10}$ aryl, and $C_{1-10}$ heteroaryl are each optionally substituted with p independently selected $R^8$ substituents; wherein p is 1, 2, 3, 4, or 5; provided when L is O, S, C(=O), C(=O)O, S(=O), or S(=O)$_2$, then A is not H;

each $R^8$ is independently selected from halo, cyano, nitro, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, $C_{1-10}$ heteroaryl-$C_{1-4}$-alkyl, $-OR^a$, $-SR^a$, $-S(=O)R^b$, $-S(=O)_2R^b$, $-S(=O)_2NR^eR^f$, $-C(=O)R^b$, $-C(=O)OR^a$, $-C(=O)NR^eR^f$, $-OC(=O)R^b$, $-OC(=O)NR^eR^f$, $-NR^eR^f$, $-NR^cC(=O)R^d$, $-NR^cC(=O)OR^d$, $-NR^cC(=O)NR^d$, $-NR^cS(=O)_2R^d$, and $-NR^cS(=O)_2NR^eR^f$; wherein said $C_{1-6}$ alkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by 1, 2, 3, or 4 independently selected $R^g$ groups;

each $R^a$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl; wherein said $C_{1-6}$ alkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by 1, 2, 3, or 4 independently selected $R^g$ groups;

each $R^b$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl; wherein said $C_{1-6}$ alkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by 1, 2, 3, or 4 independently selected $R^g$ groups;

each $R^g$ is independently selected from halo, cyano, nitro, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, $C_{1-7}$ heteroaryl-$C_{1-3}$-alkyl, —$OR^{a1}$, —$SR^{a1}$, —$S(=O)R^{b1}$, —$S(=O)_2R^{b1}$, —$S(=O)_2NR^{e1}R^{f1}$, —$C(=O)R^{b1}$, —$C(=O)OR^{a1}$, —$C(=O)NR^{e1}R^{f1}$, —$OC(=O)R^{b1}$, —$OC(=O)NR^{e1}R^{f1}$, —$NR^{e1}R^{f1}$, —$NR^{c1}C(=O)R^{d1}$, —$NR^{c1}C(=O)OR^{d1}$, —$NR^{c1}C(=O)NR^{d1}$, —$NR^{c1}S(=O)_2R^{d1}$, and —$NR^{c1}S(=O)_2NR^{e1}R^{f1}$; wherein said $C_{1-6}$ alkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl are each optionally substituted with 1, 2, 3, or 4 independently selected $R^h$ groups;

each $R^{a1}$, $R^{c1}$, $R^{d1}$, $R^{e1}$, and $R^{f1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl; wherein said $C_{1-6}$ alkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl are each optionally substituted by 1, 2, 3, or 4 independently selected $R^h$ groups;

each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl; wherein said $C_{1-6}$ alkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl are each optionally substituted by 1, 2, 3, or 4 independently selected $R^h$ groups;

each $R^h$ is independently selected from cyano, halo, hydroxy, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$-alkylamino, hydroxy-$C_{1-4}$ alkyl, $C_{1-4}$ alkoxy-$C_{1-4}$ alkyl, cyano-$C_{1-4}$ alkyl, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

m is 0, 1, or 2; and n is 0, 1, 2, 3, or 4.

In some embodiments:

X is CH or N;

Y is H, cyano, halo, $C_{1-3}$ alkyl, or $C_{1-3}$ haloalkyl;

Z is $CR^4$ or N;

W is CH or N;

when W is CH, then L is O, S, $C(R^6)_2$, $C(=O)$, $C(=O)N(R^7)$, $C(=O)O$, $C(=O)C(R^6)_2$, $S(=O)$, $S(=O)_2$, $S(=O)N(R^7)$, or $S(=O)_2N(R^7)$; or when W is N, then L is $C(R^6)_2$, $C(=O)$, $C(=O)O$, $C(=O)N(R^7)$, $C(=O)C(R^6)_2$, $S(=O)$, $S(=O)_2$, $S(=O)N(R^7)$, or $S(=O)_2N(R^7)$;

$R^1$, $R^2$, $R^3$, and $R^4$ are each independently H, hydroxy, halo, $C_{1-3}$ alkyl, or $C_{1-3}$ haloalkyl;

each $R^5$ is independently hydroxy, $C_{1-4}$ alkoxy, fluorine, $C_{1-4}$ alkyl, hydroxy-$C_{1-4}$-alkyl, $C_{1-4}$ alkoxy-$C_{1-4}$-alkyl, or $C_{1-4}$ fluoroalkyl;

each $R^6$ is, independently, H or $C_{1-4}$ alkyl; or two $R^6$ groups, together with the carbon atom to which they are attached, form a 3-, 4-, 5-, or 6-membered cycloalkyl ring;

$R^7$ is H or $C_{1-4}$ alkyl;

A is $C_{1-6}$ alkyl, $C_{3-10}$ cycloalkyl, $C_{2-10}$ heterocycloalkyl, $C_{6-10}$ aryl, or $C_{1-10}$ heteroaryl; wherein said $C_{1-6}$ alkyl, $C_{3-10}$ cycloalkyl, $C_{2-10}$ heterocycloalkyl, $C_{6-10}$ aryl, and $C_{1-10}$ heteroaryl are each optionally substituted with p independently selected $R^8$ substituents; wherein p is 1, 2, 3, 4, or 5;

each $R^8$ is independently selected from halo, cyano, nitro, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, $C_{1-10}$ heteroaryl-$C_{1-4}$-alkyl, —$OR^a$, —$SR^a$, —$S(=O)R^b$, —$S(=O)_2R^b$, —$S(=O)_2NR^eR^f$, —$C(=O)R^b$, —$C(=O)OR^a$, —$C(=O)NR^eR^f$, —$OC(=O)R^b$, —$OC(=O)NR^eR^f$, —$NR^eR^f$, —$NR^cC(=O)R^d$, —$NR^cC(=O)OR^d$, —$NR^cC(=O)NR^d$, —$NR^cS(=O)_2R^d$, and —$NR^cS(=O)_2NR^eR^f$; wherein said $C_{1-6}$ alkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by 1, 2, 3, or 4 independently selected $R^g$ groups;

each $R^a$, $R^c$, $R^d$, $R^e$, and $R^f$ is independently selected from H, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl; wherein said $C_{1-6}$ alkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by 1, 2, 3, or 4 independently selected $R^g$ groups;

each $R^b$ is independently selected from $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl; wherein said $C_{1-6}$ alkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by 1, 2, 3, or 4 independently selected $R^g$ groups;

each $R^g$ is independently selected from halo, cyano, nitro, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, $C_{1-7}$ heteroaryl-$C_{1-3}$-alkyl, —$OR^{a1}$, —$SR^{a1}$, —$S(=O)R^{b1}$, —$S(=O)_2R^{b1}$, —$S(=O)_2NR^{e1}R^{f1}$, —$C(=O)R^{b1}$, —$C(=O)OR^{a1}$, —$C(=O)NR^{e1}R^{f1}$, —$OC(=O)R^{b1}$, —$OC(=O)NR^{e1}R^{f1}$, —$NR^{e1}R^{f1}$, —$NR^{c1}C(=O)R^{d1}$, —$NR^{c1}C(=O)OR^{d1}$, —$NR^{c1}C(=O)NR^{d1}$, —$NR^{c1}S(=O)_2R^{d1}$, and —$NR^{c1}S(=O)_2NR^{e1}R^{f1}$; wherein said $C_{1-6}$ alkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl are each optionally substituted with 1, 2, 3, or 4 independently selected $R^h$ groups;

each $R^{a1}$, $R^{c1}$, $R^{d1}$, $R^{e1}$, and $R^{f1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl; wherein said $C_{1-6}$ alkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl are each optionally substituted by 1, 2, 3, or 4 independently selected $R^h$ groups;

each $R^{b1}$ is independently selected from $C_{1-6}$ alkyl, $C_{1-6}$ haloalkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl; wherein said $C_{1-6}$ alkyl, $C_{2-6}$ alkenyl, $C_{2-6}$ alkynyl, $C_{3-7}$ cycloalkyl, $C_{3-7}$ cycloalkyl-$C_{1-3}$-alkyl, $C_{2-7}$ heterocycloalkyl, $C_{2-7}$ heterocycloalkyl-$C_{1-3}$-alkyl, phenyl, phenyl-$C_{1-3}$-alkyl, $C_{1-7}$ heteroaryl, and $C_{1-7}$ heteroaryl-$C_{1-3}$-alkyl are each optionally substituted by 1, 2, 3, or 4 independently selected $R^h$ groups;

each $R^h$ is independently selected from cyano, halo, hydroxy, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$-alkylamino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino;

m is 0, 1, or 2; and n is 0, 1, 2, 3, or 4.

In some embodiments, when W is CH, then L is O or S; and when W is N, then L is $C(R^6)_2$, $C(=O)$, $C(=O)N(R^7)$, $C(=O)C(R^6)_2$, $S(=O)$, $S(=O)_2$, $S(=O)N(R^7)$, or $S(=O)_2N(R^7)$.

In some embodiments, X is N.

In some embodiments, Z is N.

In some embodiments, Z is CH.

In some embodiments, W is N.

In some embodiments, L is $C(R^6)_2$, $C(=O)$, $C(=O)N(R^7)$, $S(=O)_2$, or $S(=O)_2N(R^7)$.

In some embodiments, L is $C(R^6)_2$.

In some embodiments, L is $C(=O)N(R^7)$.

In some embodiments, L is $S(=O)_2N(R^7)$.

In some embodiments, L is $C(R^6)_2$, $C(=O)$, $C(=O)O$, $C(=O)N(R^7)$, $S(=O)_2$, $S(=O)_2N(R^7)$ or $C(=NR^{7a})N(R^7)$.

In some embodiments, L is $C(=O)O$.

In some embodiments, L is $C(=NR^{7a})N(R^7)$.

In some embodiments, $R^6$ is H.

In some embodiments, $R^7$ is H or methyl.

In some embodiments, $R^{7a}$ is CN.

In some embodiments, $R^6$ is H, $R^7$ is H or methyl, and $R^{7a}$ is CN.

In some embodiments, L is $S(=O)_2$.

In some embodiments, L is $C(=O)$.

In some embodiments, W is CH.

In some embodiments, L is O.

In some embodiments, Y is cyano.

In some embodiments, $R^1$, $R^2$, $R^3$, and $R^4$ are each H.

In some embodiments, n is 0, 1, or 2.

In some embodiments, n is 0.

In some embodiments, m is 1.

In some embodiments, A is $C_{1-6}$ alkyl, optionally substituted with p independently selected $R^8$ substituents.

In some embodiments, A is $C_{3-10}$ cycloalkyl, optionally substituted with p independently selected $R^8$ substituents.

In some embodiments, A is $C_{6-10}$ aryl, optionally substituted with p independently selected $R^8$ substituents.

In some embodiments, A is $C_{2-10}$ heterocycloalkyl, optionally substituted with p independently selected $R^8$ substituents.

In some embodiments, A is $C_{1-10}$ heteroaryl, optionally substituted with p independently selected $R^8$ substituents.

In some embodiments, A is methyl, ethyl, cyclopropyl, phenyl, a pyrrolidine ring, a piperidine ring, a pyridine ring, a pyrimidine ring, a thiazole ring, or a pyrazine ring; each of which is optionally substituted with p independently selected $R^8$ substituents.

In some embodiments, A is H, methyl, ethyl, propyl, isopropyl, isobutyl, sec-butyl, 1,2-dimethylpropyl, 1-(tert-butyl)methyl, cyclopropyl, cyclobutyl, cyclopentyl, cyclohexyl, phenyl, a tetrahydropyran ring, a pyrrolidine ring, a piperidine ring, a pyridine ring, a pyrimidine ring, a thiazole ring, or a pyrazine ring; each of which is optionally substituted with p independently selected $R^8$ substituents; provided when L is O, S, $C(=O)$, $C(=O)O$, $S(=O)$, or $S(=O)_2$, then A is not H.

In some embodiments, each $R^8$ is independently selected from halo, cyano, nitro, $C_{1-6}$ alkyl, $C_{1-6}$ haloalkyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, $C_{1-10}$ heteroaryl-$C_{1-4}$-alkyl, —$OR^a$, —$SR^a$, —$S(=O)R^b$, —$S(=O)_2R^b$, —$S(=O)_2NR^eR^f$, —$C(=O)R^b$, —$C(=O)OR^a$, —$C(=O)NR^eR^f$, —$OC(=O)R^b$, —$OC(=O)NR^eR^f$, —$NR^eR^f$, —$NR^cC(=O)R^d$, —$NR^cC(=O)OR^d$, —$NR^cC(=O)NR^d$, —$NR^cS(=O)_2R^d$, and —$NR^cS(=O)_2NR^eR^f$; wherein said $C_{1-6}$ alkyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, and $C_{1-10}$ heteroaryl-$C_{1-4}$-alkyl are each optionally substituted by 1, 2, 3, or 4 independently selected $R^g$ groups.

In some embodiments, each $R^8$ is independently selected from halo, cyano, nitro, $C_{1-6}$ alkyl, $C_{1-6}$ haloalkyl, —$OR^a$, —$SR^a$, —$S(=O)R^b$, —$S(=O)_2R^b$, —$S(=O)_2NR^eR^f$, —$C(=O)R^b$, —$C(=O)OR^a$, —$C(=O)NR^eR^f$, —$OC(=O)R^b$, —$OC(=O)NR^eR^f$, —$NR^eR^f$, —$NR^cC(=O)R^d$, —$NR^cC(=O)OR^d$, —$NR^cC(=O)NR^d$, —$NR^cS(=O)_2R^d$, and —$NR^cS(=O)_2NR^eR^f$; wherein said $C_{1-6}$ alkyl is optionally substituted by 1, 2, 3, or 4 independently selected $R^g$ groups.

In some embodiments, each $R^8$ is independently selected from halo, cyano, $C_{1-6}$ alkyl, $C_{1-6}$ haloalkyl, —$OR^a$, or —$NR^eR^f$; wherein said $C_{1-6}$ alkyl is optionally substituted by 1, 2, 3, or 4 independently selected $R^g$ groups.

In some embodiments, each $R^8$ is independently selected from halo, cyano, $C_{1-6}$ alkyl, $C_{1-6}$ haloalkyl, $C_{3-7}$ cycloalkyl, $C_{2-7}$ heterocycloalkyl, —$OR^a$, —$C(=O)OR^a$, or —$NR^eR^f$; wherein said $C_{1-6}$ alkyl is optionally substituted by 1, 2, 3, or 4 independently selected $R^g$ groups.

In some embodiments, each $R^8$ is independently selected from halo, cyano, $C_{1-6}$ alkyl, $C_{1-6}$ haloalkyl, $C_{3-7}$ cycloalkyl, $C_{2-7}$ heterocycloalkyl, —$OR^a$, —$C(=O)OR^a$, or —$NR^eR^f$; wherein said $C_{1-6}$ alkyl is optionally substituted by 1, 2, 3, or 4 independently selected $R^g$ groups; and wherein each $R^a$, $R^c$, and $R^f$ is independently selected from H, $C_{1-6}$ alkyl, and $C_{1-6}$ haloalkyl.

In some embodiments, each $R^g$ is independently selected from halo, cyano, $C_{1-6}$ alkyl, $C_{1-6}$ haloalkyl, $C_{3-7}$ cycloalkyl, $C_{2-7}$ heterocycloalkyl, $-OR^{a1}$, $-S(=O)_2R^{b1}$, $-S(=O)_2NR^{e1}R^{f1}$, $-C(=O)R^{b1}$, $-C(=O)OR^{a1}$, $-C(=O)NR^{e1}R^{f1}$, $-OC(=O)R^{b1}$, $-OC(=O)NR^{e1}R^{f1}$, $-NR^{e1}R^{f1}$, $-NR^{c1}C(=O)R^{d1}$, $-NR^{c1}C(=O)OR^{d1}$, $-NR^{c1}C(=O)NR^{d1}$, $-NR^{c1}S(=O)_2R^{d1}$, and $-NR^{c1}S(=O)_2NR^{e1}R^{f1}$; wherein said $C_{1-6}$ alkyl and $C_{2-7}$ heterocycloalkyl is optionally substituted with 1, 2, 3, or 4 independently selected $R^h$ groups.

In some embodiments, each $R^g$ is independently selected from halo, cyano, $C_{1-6}$ alkyl, $C_{1-6}$ haloalkyl, $C_{3-7}$ cycloalkyl, $C_{2-7}$ heterocycloalkyl, $-OR^{a1}$, $-S(=O)_2R^{b1}$, $-S(=O)_2NR^{e1}R^{f1}$, $-C(=O)R^{b1}$, $-C(=O)OR^{a1}$, and $-NR^{e1}R^{f1}$; wherein said $C_{1-6}$ alkyl, $C_{3-7}$ cycloalkyl, $C_{2-7}$ heterocycloalkyl and are each optionally substituted by 1, 2, 3, or 4 independently selected $R^h$ groups.

In some embodiments, each $R^g$ is independently selected from $C_{2-7}$ heterocycloalkyl and $-NR^{e1}R^{f1}$; wherein said $C_{2-7}$ heterocycloalkyl is optionally substituted by 1, 2, 3, or 4 independently selected $R^h$ groups.

In some embodiments, each $R^g$ is independently selected from $C_{2-7}$ heterocycloalkyl, $-NR^{e1}R^{f1}$; wherein said $C_{2-7}$ heterocycloalkyl is optionally substituted by 1 or 2 $R^h$ groups independently selected from fluoro, OH, $C_{1-3}$ alkyl, $C_{1-3}$ alkoxy, and hydroxy-$C_{1-4}$ alkyl; and wherein each $R^{a1}$, $R^{e1}$ and $R^{f1}$ are independently selected from H, $C_{3-7}$ cycloalkyl, and $C_{1-6}$ alkyl.

In some embodiments, each $R^h$ is independently $C_{1-4}$ alkyl.

In some embodiments, each $R^h$ is independently selected from fluoro, OH, $C_{1-3}$ alkyl, $C_{1-3}$ alkoxy, and hydroxy-$C_{1-4}$ alkyl.

In some embodiments:
each $R^a$, $R^c$, $R^d$, $R^e$, and $R^f$ is independently selected from H, $C_{1-6}$ alkyl, and $C_{1-6}$ haloalkyl;
each $R^b$ is independently selected from $C_{1-6}$ alkyl and $C_{1-6}$ haloalkyl;
each $R^{a1}$, $R^{c1}$, $R^{d1}$, $R^{e1}$, and $R^{f1}$ is independently selected from H, $C_{1-6}$ alkyl, and $C_{1-6}$ haloalkyl;
each $R^{b1}$ is independently selected from $C_{1-6}$ alkyl and $C_{1-6}$ haloalkyl.

In some embodiments, p is 1, 2, or 3.
In some embodiments:
X is N;
Z is N;
$R^1$, $R^2$, and $R^3$ are each H;
Y is cyano;
W is N and L is $C(R^6)_2$, $C(=O)$, $C(=O)N(R^7)$, $S(=O)_2$, or $S(=O)_2N(R^7)$; or
W is CH and L is O;
A is $C_{1-6}$ alkyl, $C_{3-10}$ cycloalkyl, $C_{2-10}$ heterocycloalkyl, $C_{6-10}$ aryl, or $C_{1-10}$ heteroaryl; wherein said $C_{1-6}$ alkyl, $C_{3-10}$ cycloalkyl, $C_{2-10}$ heterocycloalkyl, $C_{6-10}$ aryl, and $C_{1-10}$ heteroaryl are each optionally substituted with p independently selected $R^8$ substituents; wherein p is 1, 2, 3, 4, or 5;
each $R^8$ is independently selected from halo, cyano, nitro, $C_{1-6}$ alkyl, $C_{1-6}$ haloalkyl, $-OR^a$, $-SR^a$, $-S(=O)R^b$, $-S(=O)_2R^b$, $-S(=O)_2NR^eR^f$, $-C(=O)R^b$, $-C(=O)OR^a$, $-C(=O)NR^eR^f$, $-OC(=O)R^b$, $-OC(=O)NR^eR^f$, $-NR^eR^f$, $-NR^cC(=O)R^d$, $-NR^cC(=O)OR^d$, $-NR^cC(=O)NR^d$, $-NR^cS(=O)_2R^d$, and $-NR^cS(=O)_2NR^eR^f$; wherein said $C_{1-6}$ alkyl is optionally substituted by 1, 2, 3, or 4 independently selected $R^g$ groups;
each $R^g$ is independently selected from halo, cyano, $C_{1-6}$ alkyl, $C_{1-6}$ haloalkyl, $C_{3-7}$ cycloalkyl, $C_{2-7}$ heterocycloalkyl, $-OR^{a1}$, $-S(=O)_2R^{b1}$, $-S(=O)_2NR^{e1}R^{f1}$, $-C(=O)R^{b1}$, $-C(=O)OR^{a1}$, $-C(=O)NR^{e1}R^{f1}$, $-OC(=O)R^{b1}$, $-OC(=O)NR^{e1}R^{f1}$, $-NR^{e1}R^{f1}$, $-NR^{c1}C(=O)R^{d1}$, $-NR^{c1}C(=O)OR^{d1}$, $-NR^{c1}C(=O)NR^{d1}$, $-NR^{c1}S(=O)_2R^{d1}$, and $-NR^{c1}S(=O)_2NR^{e1}R^{f1}$; wherein said $C_{1-6}$ alkyl and $C_{2-7}$ heterocycloalkyl is optionally substituted with 1, 2, 3, or 4 independently selected $R^h$ groups;
each $R^a$, $R^c$, $R^d$, $R^e$, and $R^f$ is independently selected from H, $C_{1-6}$ alkyl, and $C_{1-6}$ haloalkyl;
each $R^b$ is independently selected from $C_{1-6}$ alkyl and $C_{1-6}$ haloalkyl;
each $R^{a1}$, $R^{c1}$, $R^{d1}$, $R^{e1}$, and $R^{f1}$ is independently selected from H, $C_{1-6}$ alkyl, and $C_{1-6}$ haloalkyl;
n is 0; and
m is 1.

In some embodiments:
X is N;
Z is N;
$R^1$, $R^2$, and $R^3$ are each H;
Y is cyano;
W is N and L is $C(R^6)_2$, $C(=O)$, $C(=O)N(R^7)$, $S(=O)_2$, or $S(=O)_2N(R^7)$; or
W is CH and L is O;
A is $C_{1-6}$ alkyl, $C_{3-10}$ cycloalkyl, $C_{2-10}$ heterocycloalkyl, $C_{6-10}$ aryl, or $C_{1-10}$ heteroaryl; wherein said $C_{1-6}$ alkyl, $C_{3-10}$ cycloalkyl, $C_{2-10}$ heterocycloalkyl, $C_{6-10}$ aryl, and $C_{1-10}$ heteroaryl are each optionally substituted with p independently selected $R^8$ substituents; wherein p is 1, 2, 3, 4, or 5;
each $R^8$ is independently selected from halo, cyano, $C_{1-6}$ alkyl, $C_{1-6}$ haloalkyl, $-OR^a$, or $-NR^eR^f$; wherein said $C_{1-6}$ alkyl is optionally substituted by 1, 2, 3, or 4 independently selected $R^g$ groups;
each $R^g$ is independently selected from halo, cyano, $C_{1-6}$ alkyl, $C_{1-6}$ haloalkyl, $C_{3-7}$ cycloalkyl, $C_{2-7}$ heterocycloalkyl, $-OR^{a1}$, $-S(=O)_2R^{b1}$, $-S(=O)_2NR^{e1}R^{f1}$, $-C(=O)R^{b1}$, $-C(=O)OR^{a1}$, and $-NR^{e1}R^{f1}$; wherein said $C_{1-6}$ alkyl, $C_{3-7}$ cycloalkyl, $C_{2-7}$ heterocycloalkyl and are each optionally substituted by 1, 2, 3, or 4 independently selected $R^h$ groups;
each $R^a$, $R^c$, $R^d$, $R^e$, and $R^f$ is independently selected from H, $C_{1-6}$ alkyl, and $C_{1-6}$ haloalkyl;
each $R^b$ is independently selected from $C_{1-6}$ alkyl and $C_{1-6}$ haloalkyl; each $R^{a1}$, $R^{c1}$, $R^{d1}$, $R^{e1}$, and $R^{f1}$ is independently selected from H, $C_{1-6}$ alkyl, and $C_{1-6}$ haloalkyl;
each $R^{b1}$ is independently selected from $C_{1-6}$ alkyl and $C_{1-6}$ haloalkyl;
n is 0; and
m is 1.

In some embodiments:
X is N;
Z is N;
$R^1$, $R^2$, and $R^3$ are each H;
Y is cyano;
W is N and L is $C(R^6)_2$, $C(=O)$, $C(=O)N(R^7)$, $S(=O)_2$, or $S(=O)_2N(R^7)$; or
W is CH and L is O;
A is $C_{1-6}$ alkyl, $C_{3-10}$ cycloalkyl, $C_{2-10}$ heterocycloalkyl, $C_{6-10}$ aryl, or $C_{1-10}$ heteroaryl; wherein said $C_{1-6}$ alkyl, $C_{3-10}$ cycloalkyl, $C_{2-10}$ heterocycloalkyl, $C_{6-10}$ aryl, and $C_{1-10}$ heteroaryl are each optionally substituted with p independently selected $R^8$ substituents; wherein p is 1, 2, 3, 4, or 5;
each $R^8$ is independently selected from halo, cyano, $C_{1-6}$ alkyl, $C_{1-6}$ haloalkyl, $-OR^a$, or $-NR^eR^f$; wherein said $C_{1-6}$ alkyl is optionally substituted by 1, 2, 3, or 4 independently selected $R^g$ groups;

each $R^g$ is independently selected from $C_{2-7}$ heterocycloalkyl and —$NR^{e1}R^{f1}$; wherein said $C_{2-7}$ heterocycloalkyl is optionally substituted by 1, 2, 3, or 4 independently selected $R^h$ groups;

each $R^h$ is independently selected from $C_{1-4}$ alkyl;

each $R^a$, $R^e$, and $R^f$ is independently selected from H, $C_{1-6}$ alkyl, and $C_{1-6}$ haloalkyl;

each $R^{a1}$, $R^{e1}$, and $R^{f1}$ is independently selected from H, $C_{1-6}$ alkyl, and $C_{1-6}$ haloalkyl;

n is 0; and m is 1.

In some embodiments:

X is N;

Z is N;

$R^1$, $R^2$, and $R^3$ are each H;

Y is cyano;

W is N and L is $C(R^6)_2$, $C(=O)$, $C(=O)N(R^7)$, $S(=O)_2$, or $S(=O)_2N(R^7)$;

$R^6$ is H;

$R^7$ is H or methyl;

A is methyl, ethyl, cyclopropyl, phenyl, a pyrrolidine ring, a piperidine ring, a pyridine ring, a pyrimidine ring, a thiazole ring, or a pyrazine ring; each of which is optionally substituted with p independently selected $R^8$ substituents; wherein p is 1, 2, or 3;

each $R^8$ is independently selected from halo, cyano, $C_{1-6}$ alkyl, $C_{1-6}$ haloalkyl, —$OR^a$, or —$NR^eR^f$; wherein said $C_{1-6}$ alkyl is optionally substituted by 1, 2, 3, or 4 independently selected $R^g$ groups;

each $R^g$ is independently selected from $C_{2-7}$ heterocycloalkyl and —$NR^{e1}R^{f1}$; wherein said $C_{2-7}$ heterocycloalkyl is optionally substituted by 1, 2, 3, or 4 independently selected $R^h$ groups;

each $R^h$ is independently $C_{1-4}$ alkyl;

each $R^a$, $R^e$, and $R^f$ is independently selected from H, $C_{1-6}$ alkyl, and $C_{1-6}$ haloalkyl;

each $R^{a1}$, $R^{e1}$ and $R^{f1}$ is independently selected from H, $C_{1-6}$ alkyl, and $C_{1-6}$ haloalkyl;

n is 0; and m is 1.

In some embodiments:

X is N;

Z is N;

$R^1$, $R^2$, and $R^3$ are each H;

Y is cyano;

W is CH and L is O;

$R^6$ is H;

$R^7$ is H or methyl;

A is phenyl, which is optionally substituted with p independently selected $R^8$ substituents; wherein p is 1, 2, or 3;

each $R^8$ is independently selected from halo, cyano, $C_{1-6}$ alkyl, $C_{1-6}$ haloalkyl, —$OR^a$, or —$NR^eR^f$; wherein said $C_{1-6}$ alkyl is optionally substituted by p independently selected $R^g$ groups;

each $R^g$ is independently selected from $C_{2-7}$ heterocycloalkyl and —$NR^{e1}R^{f1}$; wherein said $C_{2-7}$ heterocycloalkyl is optionally substituted by 1, 2, 3, or 4 independently selected $R^h$ groups;

each $R^h$ is independently $C_{1-4}$ alkyl;

each $R^a$, $R^e$, and $R^f$ is independently selected from H, $C_{1-6}$ alkyl, and $C_{1-6}$ haloalkyl;

each $R^{a1}$, $R^{e1}$ and $R^{f1}$ is independently selected from H, $C_{1-6}$ alkyl, and $C_{1-6}$ haloalkyl;

n is 0; and m is 1.

In some embodiments:

X is N;

Z is N;

$R^1$, $R^2$, and $R^3$ are each H;

Y is cyano;

W is N and L is $C(R^6)_2$, $C(=O)$, $C(=O)O$, $C(=O)N(R^7)$, $S(=O)_2$, $S(=O)_2N(R^7)$ or $C(=NR^{7a})N(R^7)$; or W is CH and L is O;

$R^6$ is H;

$R^7$ is H or methyl;

$R^{7a}$ is CN;

A is H, methyl, ethyl, propyl, isopropyl, isobutyl, sec-butyl, 1,2-dimethylpropyl, 1-(tert-butyl)methyl, cyclopropyl, cyclobutyl, cyclopentyl, cyclohexyl, phenyl, a tetrahydropyran ring, a pyrrolidine ring, a piperidine ring, a pyridine ring, a pyrimidine ring, a thiazole ring, or a pyrazine ring; wherein said methyl, ethyl, propyl, isopropyl, isobutyl, sec-butyl, 1,2-dimethylpropyl, 1-(tert-butyl)methyl, cyclopropyl, cyclobutyl, cyclopentyl, cyclohexyl, phenyl, a tetrahydropyran ring, pyrrolidine ring, piperidine ring, pyridine ring, pyrimidine ring, thiazole ring, and pyrazine ring are each optionally substituted with p independently selected $R^8$ substituents; provided when L is O, S, $C(=O)$, $C(=O)O$, $S(=O)$, or $S(=O)_2$, then A is not H;

each $R^8$ is independently selected from halo, cyano, $C_{1-6}$ alkyl, $C_{1-6}$ haloalkyl, $C_{3-7}$ cycloalkyl, $C_{2-7}$ heterocycloalkyl, —$OR^a$, —$C(=O)OR^a$, or —$NR^eR^f$; wherein said $C_{1-6}$ alkyl is optionally substituted by 1, 2, 3, or 4 independently selected $R^g$ groups; and wherein each $R^a$, $R^e$, and $R^f$ is independently selected from H, $C_{1-6}$ alkyl, and $C_{1-6}$ haloalkyl;

each $R^g$ is independently selected from $C_{2-7}$ heterocycloalkyl, —$OR^{a1}$, —$NR^{e1}R^{f1}$; wherein said $C_{2-7}$ heterocycloalkyl is optionally substituted by 1 or 2 $R^h$ groups independently selected from fluoro, OH, $C_{1-3}$ alkyl, $C_{1-3}$ alkoxy, and hydroxy-$C_{1-4}$ alkyl; and wherein each $R^{a1}$, $R^{e1}$ and $R^{f1}$ are independently selected from H, $C_{3-7}$ cycloalkyl, and $C_{1-6}$ alkyl;

p is 1, 2, or 3;

m is 1; and n is 0.

In some embodiments:

X is N;

Z is N;

$R^1$, $R^2$, and $R^3$ are each H;

Y is cyano;

W is N and L is $C(R^6)_2$, $C(=O)$, $C(=O)O$, $C(=O)N(R^7)$, $S(=O)_2$, or $S(=O)_2N(R^7)$; or W is CH and L is O;

$R^6$ is H;

$R^7$ is H or methyl;

A is methyl, ethyl, propyl, isopropyl, isobutyl, sec-butyl, 1,2-dimethylpropyl, 1-(tert-butyl)methyl, cyclopropyl, cyclobutyl, cyclopentyl, cyclohexyl, phenyl, a tetrahydropyran ring, a pyrrolidine ring, a piperidine ring, a pyridine ring, a pyrimidine ring, a thiazole ring, or a pyrazine ring; each of which is optionally substituted with p independently selected $R^8$ substituents;

each $R^8$ is independently selected from halo, cyano, $C_{1-6}$ alkyl, $C_{1-6}$ haloalkyl, $C_{3-7}$ cycloalkyl, $C_{2-7}$ heterocycloalkyl, —$OR^a$, —$C(=O)OR^a$, or —$NR^eR^f$; wherein said $C_{1-6}$ alkyl is optionally substituted by 1, 2, 3, or 4 independently selected $R^g$ groups; and wherein each $R^a$, $R^e$, and $R^f$ is independently selected from H, $C_{1-6}$ alkyl, and $C_{1-6}$ haloalkyl;

each $R^g$ is independently selected from $C_{2-7}$ heterocycloalkyl, —$OR^{a1}$, —$NR^{e1}R^{f1}$; wherein said $C_{2-7}$ heterocycloalkyl is optionally substituted by 1 or 2 $R^h$ groups independently selected from fluoro, OH, $C_{1-3}$ alkyl, $C_{1-3}$ alkoxy, and hydroxy-$C_{1-4}$ alkyl; and wherein each $R^{a1}$, $R^{e1}$ and $R^{f1}$ are independently selected from H, $C_{3-7}$ cycloalkyl, and $C_{1-6}$ alkyl;

p is 1, 2, or 3;
m is 1; and
n is 0.

In some embodiments, the compound is a compound of Formula II:

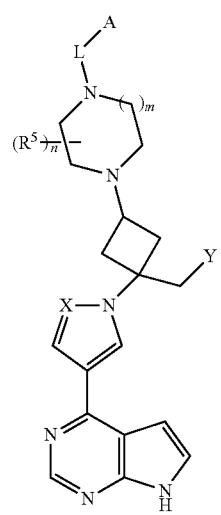

II or a pharmaceutically acceptable salt thereof.

In some embodiments, the compound is a compound of Formula III:

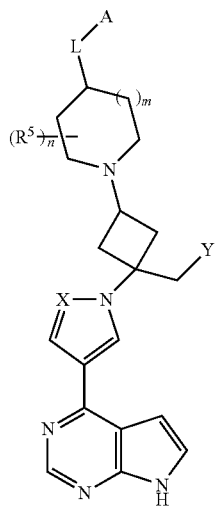

III or a pharmaceutically acceptable salt thereof.

In some embodiments, the compound is a compound of Formula IV:

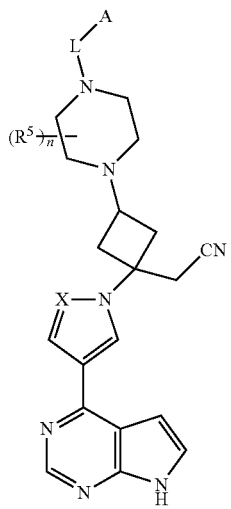

IV or a pharmaceutically acceptable salt thereof.

In some embodiments, the compound is a compound of V:

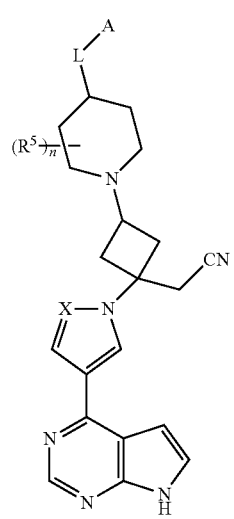

V or a pharmaceutically acceptable salt thereof.

In some embodiments, the compound is a compound selected from:

3-[(4-{3-(cyanomethyl)-3-[4-(7H-pyrrolo[2,3-d]pyrimidin-4-yl)-1H-pyrazol-1-yl]cyclobutyl}piperazin-1-yl) methyl]-5-fluorobenzonitrile;

3-[(4-{3-(cyanomethyl)-3-[4-(7H-pyrrolo[2,3-d]pyrimidin-4-yl)-1H-pyrazol-1-yl]cyclobutyl}piperazin-1-yl) methyl]-6-(dimethylamino)-2-fluorobenzonitrile;

4-{3-(cyanomethyl)-3-[4-(7H-pyrrolo[2,3-d]pyrimidin-4-yl)-1H-pyrazol-1-yl]cyclobutyl}-N-[4-fluoro-2-(trifluoromethyl)phenyl]piperazine-1-carboxamide;

{3-(4-{[(2S)-2-methylpyrrolidin-1-yl]carbonyl}piperazin-1-yl)-1-[4-(7H-pyrrolo[2,3-d]pyrimidin-4-yl)-1H-pyrazol-1-yl]cyclobutyl}acetonitrile;

{3-(4-{[(2S)-2-ethylpyrrolidin-1-yl]carbonyl}piperazin-1-yl)-1-[4-(7H-pyrrolo[2,3-d]pyrimidin-4-yl)-1H-pyrazol-1-yl]cyclobutyl}acetonitrile;

{3-{4-[3-fluoro-2-(trifluoromethyl)isonicotinoyl]piperazin-1-yl}-1-[4-(7H-pyrrolo[2,3-d]pyrimidin-4-yl)-1H-pyrazol-1-yl]cyclobutyl}acetonitrile;

[1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile;

{3-[4-(3,5-difluorobenzoyl)piperazin-1-yl]-1-[4-(7H-pyrrolo[2,3-d]pyrimidin-4-yl)-1H-pyrazol-1-yl]cyclobutyl}acetonitrile;

{3-{4-[(2-chloro-5-fluoropyridin-3-yl)carbonyl]piperazin-1-yl}-1-[4-(7H-pyrrolo[2,3-d]pyrimidin-4-yl)-1H-pyrazol-1-yl]cyclobutyl}acetonitrile;

{3-{4-[(5-fluoropyridin-3-yl)carbonyl]piperazin-1-yl}-1-[4-(7H-pyrrolo[2,3-d]pyrimidin-4-yl)-1H-pyrazol-1-yl]cyclobutyl}acetonitrile;

{3-{4-[2-(difluoromethyl)-3-fluoroisonicotinoyl]piperazin-1-yl}-1-[4-(7H-pyrrolo[2,3-d]pyrimidin-4-yl)-1H-pyrazol-1-yl]cyclobutyl}acetonitrile;

3-[(4-{3-(cyanomethyl)-3-[4-(7H-pyrrolo[2,3-d]pyrimidin-4-yl)-1H-pyrazol-1-yl]cyclobutyl}piperazin-1-yl)carbonyl]-5-fluorobenzonitrile;

[1-[4-(7H-pyrrolo[2,3-d]pyrimidin-4-yl)-1H-pyrazol-1-yl]-3-(4-{[4-(trifluoromethyl)-1,3-thiazol-2-yl]carbonyl}piperazin-1-yl)cyclobutyl]acetonitrile;

[1-[4-(7H-pyrrolo[2,3-d]pyrimidin-4-yl)-1H-pyrazol-1-yl]-3-(4-{[6-(trifluoromethyl)pyrazin-2-yl]carbonyl}piperazin-1-yl)cyclobutyl]acetonitrile;

{3-[4-(3,4-difluorobenzoyl)piperazin-1-yl]-1-[4-(7H-pyrrolo[2,3-d]pyrimidin-4-yl)-1H-pyrazol-1-yl]cyclobutyl}acetonitrile;

{3-[4-(2-chloro-3,6-difluorobenzyl)piperazin-1-yl]-1-[4-(7H-pyrrolo[2,3-d]pyrimidin-4-yl)-1H-pyrazol-1-yl]cyclobutyl}acetonitrile;

{3-{4-[3-fluoro-5-(trifluoromethyl)benzoyl]piperazin-1-yl}-1-[4-(7H-pyrrolo[2,3-d]pyrimidin-4-yl)-1H-pyrazol-1-yl]cyclobutyl}acetonitrile;

{3-{4-[2-fluoro-4-(trifluoromethyl)benzoyl]piperazin-1-yl}-1-[4-(7H-pyrrolo[2,3-d]pyrimidin-4-yl)-1H-pyrazol-1-yl]cyclobutyl}acetonitrile;

{3-[4-(pyrrolidin-1-ylcarbonyl)piperazin-1-yl]-1-[4-(7H-pyrrolo[2,3-d]pyrimidin-4-yl)-1H-pyrazol-1-yl]cyclobutyl}acetonitrile;

{1-[4-(7H-pyrrolo[2,3-d]pyrimidin-4-yl)-1H-pyrazol-1-yl]-3-(4-{[6-(trifluoromethyl)pyridin-2-yl]carbonyl}piperazin-1-yl)cyclobutyl}acetonitrile;

{3-(4-{[6-(difluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile;

{3-{4-[2-fluoro-3-(trifluoromethyl)benzoyl]piperazin-1-yl}-1-[4-(7H-pyrrolo[2,3-d]pyrimidin-4-yl)-1H-pyrazol-1-yl]cyclobutyl}acetonitrile;

{3-{4-[(5-fluoropyridin-3-yl)methyl]piperazin-1-yl}-1-[4-(7H-pyrrolo[2,3-d]pyrimidin-4-yl)-1H-pyrazol-1-yl]cyclobutyl}acetonitrile;

{3-{4-[(2-isopropylpyrimidin-4-yl)carbonyl]piperazin-1-yl}-1-[4-(7H-pyrrolo[2,3-d]pyrimidin-4-yl)-1H-pyrazol-1-yl]cyclobutyl}acetonitrile;

{3-[4-(piperidin-1-ylcarbonyl)piperazin-1-yl]-1-[4-(7H-pyrrolo[2,3-d]pyrimidin-4-yl)-1H-pyrazol-1-yl]cyclobutyl}acetonitrile;

{3-{4-[4-fluoro-3-(trifluoromethoxy)benzoyl]piperazin-1-yl}-1-[4-(7H-pyrrolo[2,3-d]pyrimidin-4-yl)-1H-pyrazol-1-yl]cyclobutyl}acetonitrile;

{3-(4-{[3-fluoro-5-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile;

{3-{4-[4-chlorobenzoyl]piperazin-1-yl}-1-[4-(7H-pyrrolo[2,3-d]pyrimidin-4-yl)-1H-pyrazol-1-yl]cyclobutyl}acetonitrile;

{3-{4-[2-fluoro-4-(trifluoromethyl)benzoyl]piperazin-1-yl}-1-[4-(7H-pyrrolo[2,3-d]pyrimidin-4-yl)-1H-pyrazol-1-yl]cyclobutyl}acetonitrile;

4-{3-(cyanomethyl)-3-[4-(7H-pyrrolo[2,3-d]pyrimidin-4-yl)-1H-pyrazol-1-yl]cyclobutyl}-N,N-dimethylpiperazine-1-carboxamide;

{3-(4-{3-[(dimethylamino)methyl]-5-fluorobenzoyl}piperazin-1-yl)-1-[4-(7H-pyrrolo[2,3-d]pyrimidin-4-yl)-1H-pyrazol-1-yl]cyclobutyl}acetonitrile;

{3-(4-{3-[(dimethylamino)methyl]-5-fluorobenzyl}piperazin-1-yl)-1-[4-(7H-pyrrolo[2,3-d]pyrimidin-4-yl)-1H-pyrazol-1-yl]cyclobutyl}acetonitrile;

{3-[4-(ethylsulfonyl)piperazin-1-yl]-1-[4-(7H-pyrrolo[2,3-d]pyrimidin-4-yl)-1H-pyrazol-1-yl]cyclobutyl}acetonitrile;

{3-[4-(cyclopropylsulfonyl)piperazin-1-yl]-1-[4-(7H-pyrrolo[2,3-d]pyrimidin-4-yl)-1H-pyrazol-1-yl]cyclobutyl}acetonitrile;

4-{3-(cyanomethyl)-3-[4-(7H-pyrrolo[2,3-d]pyrimidin-4-yl)-1H-pyrazol-1-yl]cyclobutyl}-N,N-dimethylpiperazine-1-sulfonamide;

4-{3-(cyanomethyl)-3-[4-(7H-pyrrolo[2,3-d]pyrimidin-4-yl)-1H-pyrazol-1-yl]cyclobutyl}-N-ethyl-N-methylpiperazine-1-carboxamide;

{3-{4-[3-[(dimethylamino)methyl]-5-(trifluoromethyl)benzoyl]piperazin-1-yl}-1-[4-(7H-pyrrolo[2,3-d]pyrimidin-4-yl)-1H-pyrazol-1-yl]cyclobutyl}acetonitrile;

{3-[4-(3-fluoro-5-{[(2S)-2-methylpyrrolidin-1-yl]methyl}phenoxy)piperidin-1-yl]-1-[4-(7H-pyrrolo[2,3-d]pyrimidin-4-yl)-1H-pyrazol-1-yl]cyclobutyl}acetonitrile;

{3-(4-{3-[(dimethylamino)methyl]-5-fluorophenoxy}piperidin-1-yl)-1-[4-(7H-pyrrolo[2,3-d]pyrimidin-4-yl)-1H-pyrazol-1-yl]cyclobutyl}acetonitrile;

[cis-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile-d1; and

[trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile-d1;

or a pharmaceutically acceptable salt of any of the aforementioned.

In some embodiments, the cyclobutyl ring in Formula I is the cis form.

In some embodiments, the cyclobutyl ring in Formula I is the trans form.

In some embodiments, if $R^5$ is hydroxy or $C_{1-4}$ alkoxy and n is not 0, then $R^5$ is not attached to a carbon adjacent to a nitrogen ring member.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

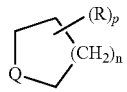

then it is to be understood that substituent R can occur p number of times on the ring, and R can be a different moiety at each occurrence. It is to be understood that each R group may replace any hydrogen atom attached to a ring atom, including one or both of the $(CH_2)_n$ hydrogen atoms. Further, in the above example, should the variable Q be defined to include hydrogens, such as when Q is the to be $CH_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. As used herein, the term "substituted" means that a hydrogen atom is removed and replaced by a substituent. It is to be understood that substitution at a given atom is limited by valency. Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like.

As used herein, the term "alkylene", employed alone or in combination with other terms, refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, "$C_{n-m}$ alkenyl" refers to an alkyl group having one or more double carbon-carbon bonds and having n to m carbons. In some embodiments, the alkenyl moiety contains 2 to 6 or to 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6 or 1 to 4 carbon atoms.

As used herein, the term "di-$C_{n-m}$-alkylamino" refers to a group of formula —N(alkyl)$_2$, wherein the two alkyl groups each has, independently, n to m carbon atoms. In some embodiments, each alkyl group independently has 1 to 6 or 1 to 4 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6 or 1 to 4 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6 or 1 to 4 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6 or 1 to 4 carbon atoms.

As used herein, the term "aminosulfonyl", employed alone or in combination with other terms, refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6 or 1 to 4 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6 or 1 to 4 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6 or 1 to 4 carbon atoms.

As used herein, the term "aminocarbonylamino" refers to a group of formula —NHC(O)NH$_2$.

As used herein, the term "$C_{n-m}$ alkylaminocarbonylamino" refers to a group of formula —NHC(O)NH (alkyl), wherein the alkyl group has n to m carbon atoms. In some embodiments, the alkyl group has 1 to 6 or 1 to 4 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6 or 1 to 4 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6 or 1 to 4 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6 or 1 to 4 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6 or 1 to 4 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6 or 1 to 4 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6 or 1 to 4 carbon atoms.

As used herein, the term "amino" refers to a group of formula —NH$_2$.

As used herein, the term "hydroxy-$C_{n-m}$-alkyl" refers to a group of formula -alkylene-OH, wherein said alkylene group has n to m carbon atoms. In some embodiments, the alkylene group has 1 to 4 carbon atoms.

As used herein, the term "$C_{o-p}$ alkoxy-$C_{n-m}$-alkyl" refers to a group of formula -alkylene-O-alkyl, wherein said alkylene group has n to m carbon atoms and said alkyl group has o to p carbon atoms. In some embodiments, the alkyl and alkylene groups each independently have 1 to 4 carbon atoms.

As used herein, the term "cyano-$C_{n-m}$-alkyl" refers to a group of formula -alkylene-CN, wherein said alkylene group has n to m carbon atoms. In some embodiments, the alkylene group has 1 to 4 carbon atoms.

As used herein, the term "aryl", employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "arylalkyl" refers to a group of formula -alkylene-aryl. In some embodiments, arylalkyl is $C_{6-10}$ aryl-$C_{1-3}$ alkyl. In some embodiments, arylalkyl is benzyl.

As used herein, the term "carbamyl" refers to a group of formula —C(O)NH$_2$.

As used herein, the term "carbonyl", employed alone or in combination with other terms, refers to a —C(O)— group.

As used herein, the term "carboxy" refers to a group of formula —C(O)OH.

As used herein, the term "cycloalkyl", employed alone or in combination with other terms, refers to a non-aromatic cyclic hydrocarbon moiety, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-12}$ cycloalkyl, which is monocyclic or bicyclic. Examplary cycloalkyl groups include 1,2,3,4-tetrahydro-naphthalene, cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is cyclopropyl, cyclobutyl, cyclopentyl, or cyclohexyl.

As used herein, the term "cycloalkylalkyl" refers to a group of formula -alkylene-cycloalkyl. In some embodiments, cycloalkylalkyl is $C_{3-12}$ cycloalkyl-$C_{1-3}$ alkyl, wherein the cycloalkyl portion is monocyclic or bicyclic.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6 or 1 to 4 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6 or 1 to 4 carbon atoms.

As used herein, the term "$C_{n-m}$ fluoroalkyl" refers to a $C_{n-m}$ haloalkyl wherein the halogen atoms are selected from fluorine. In some embodiments, fluorinated $C_{n-m}$ haloalkyl is fluoromethyl, difluoromethyl, or trifluoromethyl. In some embodiments, the alkyl group has 1 to 6 or 1 to 4 carbon atoms.

As used herein, the term "heteroaryl", employed alone or in combination with other terms, refers to a monocyclic or polycyclic (e.g., having 2, 3 or 4 fused rings) aromatic hydrocarbon moiety, having one or more heteroatom ring members selected from nitrogen, sulfur and oxygen. In some embodiments, heteroaryl is 5- to 10-membered $C_{1-9}$ heteroaryl, which is monocyclic or bicyclic and which has 1, 2, 3, or 4 heteroatom ring members independently selected from nitrogen, sulfur and oxygen. When the heteroaryl group contains more than one heteroatom ring member, the heteroatoms may be the same or different. Example heteroaryl groups include, but are not limited to, pyridine, pyrimidine, pyrazine, pyridazine, pyrrole, pyrazole, azolyl, oxazole, thiazole, imidazole, furan, thiophene, quinoline, isoquinoline, indole, benzothiophene, benzofuran, benzisoxazole, imidazo[1,2-b]thiazole, purine, or the like.

A five-membered ring heteroaryl is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered ring heteroaryl is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, the term "heteroarylalkyl" refers to a group of formula alkylene-heteroaryl. In some embodiments, heteroarylalkyl is $C_{1-9}$ heteroaryl-$C_{1-3}$ alkyl, wherein the heteroaryl portion is monocyclic or bicyclic and has 1, 2, 3, or 4 heteroatom ring members independently selected from nitrogen, sulfur and oxygen.

As used herein, the term "heterocycloalkyl", employed alone or in combination with other terms, refers to non-aromatic ring system, which may optionally contain one or more alkenylene or alkynylene groups as part of the ring structure, and which has at least one heteroatom ring member independently selected from nitrogen, sulfur and oxygen. When the heterocycloalkyl groups contains more than one heteroatom, the heteroatoms may be the same or different. Heterocycloalkyl groups can include mono- or poly-cyclic (e.g., having 2, 3 or 4 fused rings) ring systems. Also included in the definition of heterocycloalkyl are moieties that have one or more aromatic rings fused (i.e., having a bond in common with) to the non-aromatic ring, for example, 1,2,3,4-tetrahydro-quinoline and the like. The carbon atoms or heteroatoms in the ring(s) of the heterocycloalkyl group can be oxidized to form a carbonyl, or sulfonyl group (or other oxidized linkage) or a nitrogen atom can be quaternized. In some embodiments, heterocycloalkyl is 5- to 10-membered $C_{2-9}$ heterocycloalkyl, which is mono-cyclic or bicyclic and which has 1, 2, 3, or 4 heteroatom ring members independently selected from nitrogen, sulfur and oxygen. Examples of heterocycloalkyl groups include 1,2,3,4-tetrahydro-quinoline, azetidine, azepane, pyrrolidine, piperidine, piperazine, morpholine, thiomorpholine, pyran, and a 2-oxo-1,3-oxazolidine ring.

As used herein, the term "heterocycloalkylalkyl" refers to a group of formula -alkylene-heterocycloalkyl. In some embodiments, heterocycloalkylalkyl is $C_{2-9}$ heterocycloalkyl-$C_{1-3}$ alkyl, wherein the heterocycloalkyl portion is monocyclic or bicyclic and has 1, 2, 3, or 4 heteroatom ring members independently selected from nitrogen, sulfur and oxygen.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone enol pairs, amide-imidic acid pairs, lactam lactim pairs, amide-imidic acid pairs, enamine imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. In some embodiments, 1, 2, or 3 $CH_2$ or CH groups in the cyclobutyl ring of Formula I are replaced by a CHD or $CD_2$ group. In some embodiments, 1, 2, or 3 $CH_2$ or CH groups in the moiety

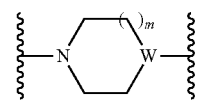

of Formula I are replaced by a CHD, $CD_2$ or CD group, respectively.

For example, some embodiments of the compounds of Formula I may have a deuterium atom attached to one atom of the cyclobutyl ring:

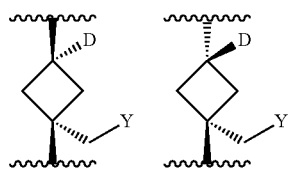

The term, "compound," as used herein is meant to include all stereoisomers, geometric iosomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

Compounds of the invention, including salts and N-oxides thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2007), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC) or thin layer chromatography (TLC).

Useful intermediates 3-4 can be made according to the methods outlined in Scheme 1. The heterocycloalkyl ring compound 3-1 (such as tert-butyl 4-hydroxypiperidine-1-carboxylate) can be reacted with phenol 7-2 under Mitsunobu coupling reaction condition to afford ether 3-3. [See, Mitsunobu, O. (1981). "The Use of Diethyl Azodicarboxylate and Triphenylphosphine in Synthesis and Transformation of Natural Products". *Synthesis* 1982 (1): 1-28.] The amino protecting group $Pg^1$ can be removed to afford intermediate 3-4.

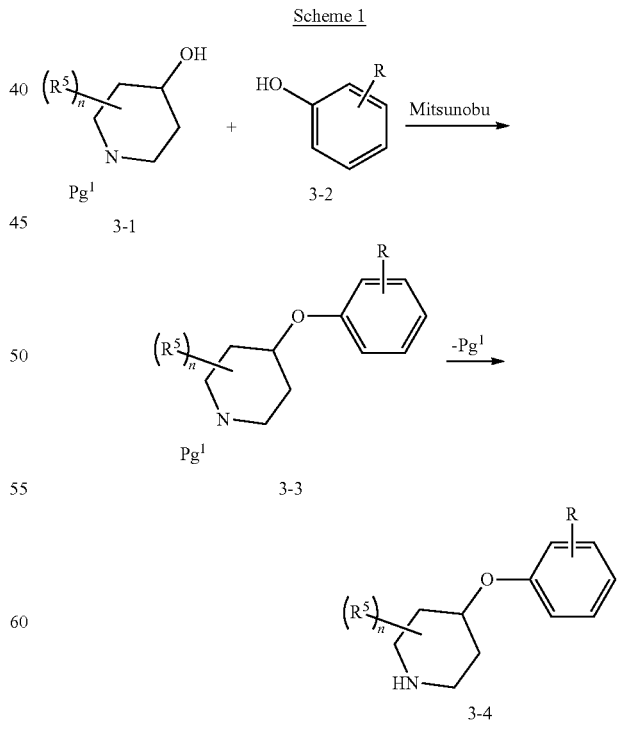

$Pg^1$ is an amine protecting group such as Boc

Compounds of Formula I, wherein W is CH, can also be made by the methods shown in Scheme 2. Accordingly, compound 4-2 can be formed by reaction of the cyclobutanone 4-1 with a Horner-Wadsworth-Emmons reagent. A protected pyrazol-4-yl-pyrrolo[2,3-d]pyrimidineor pyrrol-3-yl-pyrrolo[2,3-d]pyrimidine of formula 4-3 is reacted with a protected alkene 4-2 in a Michael addition in the presence of a coupling agent to give compound 4-4. The ether protecting group can be removed from compound 4-4 to give an alcohol derivative 4-5, which can be oxidized to give the compound 4-6. Compound 4-6 can be converted to compound of formula 4-7 and 4-8 via reductive amination, which can be deprotected to remove P₁ to give the compound of Formula I.

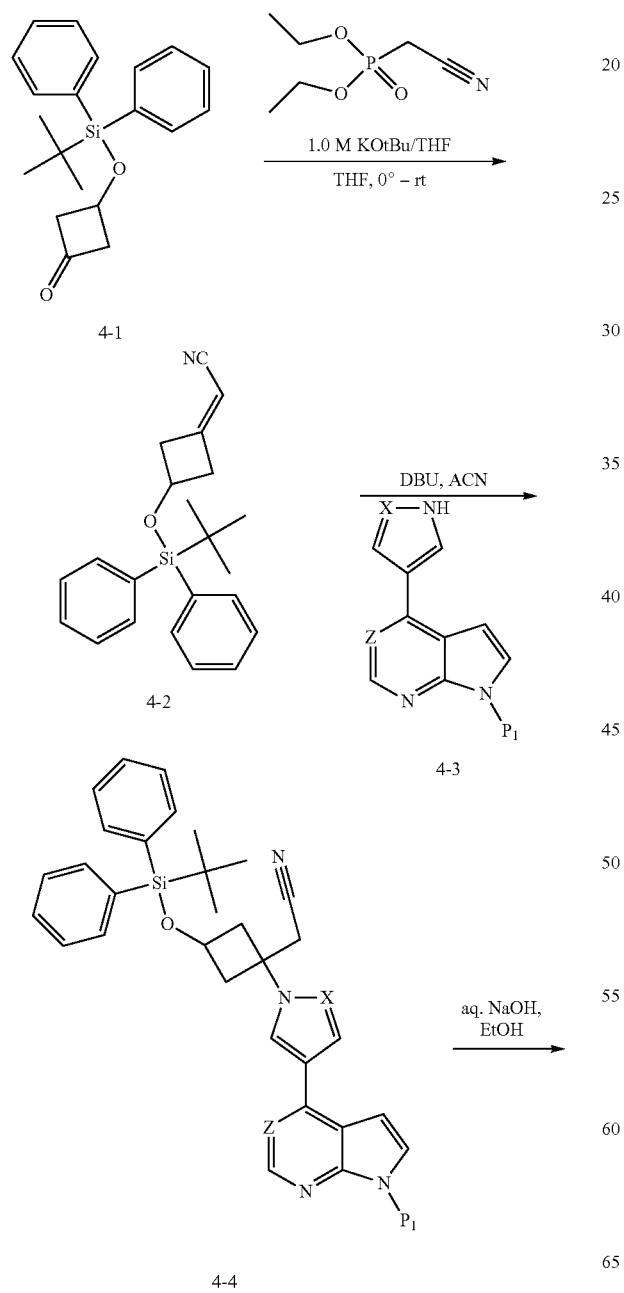

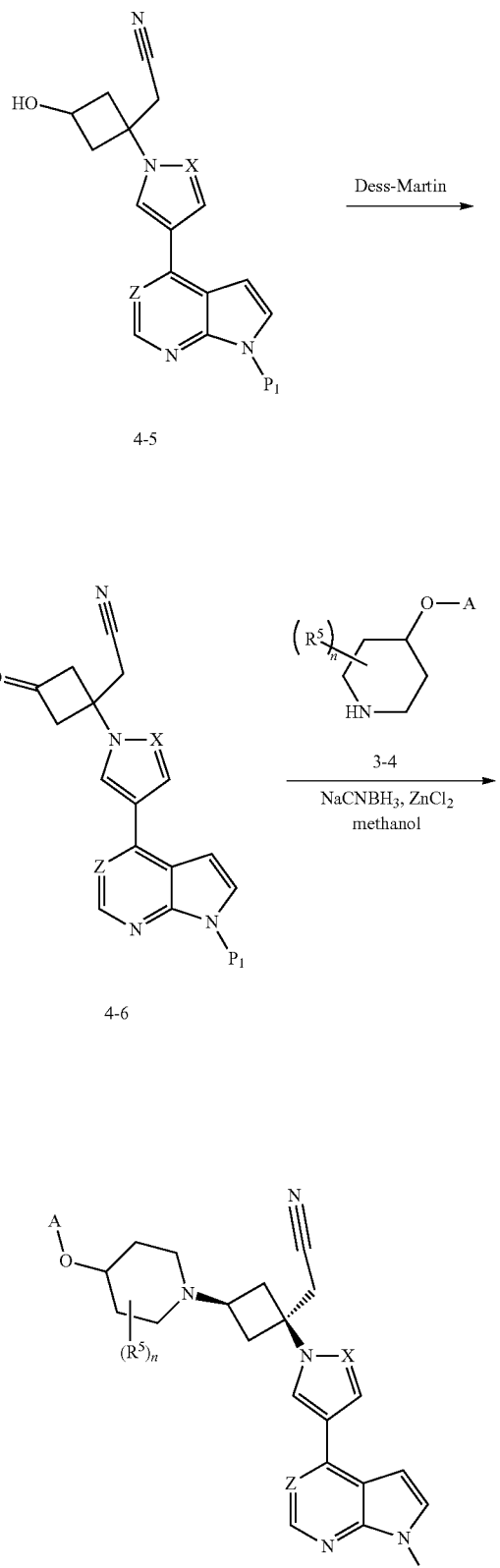

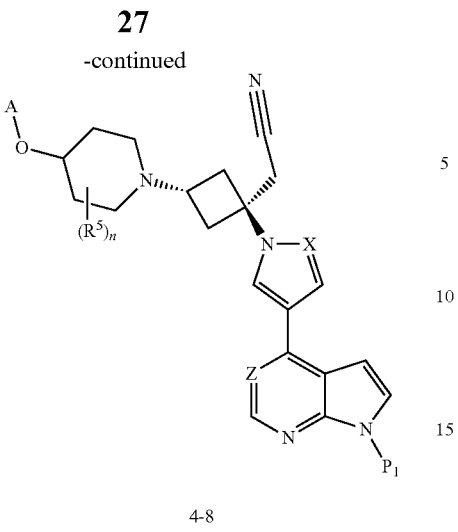

4-8

Further compounds of Formula I, wherein W is N, can be prepared as shown in Scheme 3. 1,3-dibromopropan-2-ol can be protected as its tert-butyldiphenylsilyl ether by reaction with tert-butylchlorodiphenylsilane, 1H-imidazole and 4-dimethylaminopyridine in DCM at 0° C. to afford [2-bromo-1-(bromomethyl)ethoxy](tert-butyl)diphenylsilane a. By reaction with 2 equivalents of the anion derived from reaction of (methylsulfinyl)(methylthio)methane with n-butyllithium, tert-butyl{[3-(methylsulfinyl)-3-(methylthio)cyclobutyl]oxy}diphenylsilane b may be formed. Hydrolysis of this intermediate using perchloric acid in water may afford 3-{[tert-butyl(diphenyl)silyl]oxy}cyclobutanone c. Horner-Wadsworth-Emmons reaction employing the appropriate phosphonate gives the conjugate acceptor d. Conjugate addition of 4-(1H-pyrazol-4-yl)-7-{[2-(trimethylsilyl)ethoxy]methyl}-7H-pyrrolo[2,3-d]pyrimidine to this acceptor, mediated by DBU in acetonitrile can provide the TBDPS-protected alcohol e. The silyl protecting group could be removed by action of aqueous NaOH, followed by oxidation of the resulting alcohol to the corresponding ketone f by the action of Dess-Martin periodinane. Reductive alkylation of a Boc-protected compound g with this ketone, employing a zinc-modified reducing reagent produced by the combination of zinc (II) chloride and sodium cyanoborohydride (J. Org. Chem. 1985, 50, pp. 1927-1932) can provide the cis- and trans-isomers h and i in roughly equal proportions. These may be separated by chiral HPLC into the individual isomers, and the stereochemistry can be determined by nOe. Removal of the Boc protecting group can be effected by stirring with aqueous HCl in THF to afford the base, which can then be functionalized according to the following methods, then deprotected by the use of TFA in DCM followed by ethylenediamine in methanol to afford compounds described herein.

The NH-heterocycle could be reacted with acid chlorides in the presence of base (such as TEA or Hunig's base) to afford amides. Alternatively, amides can be formed by reaction with carboxylic acids using BOP or HATU as coupling agents, in the presence of either of the aforementioned bases. Ureas are formed from the cis- or trans-cyclobutylpiperazine starting materials either by reaction (in the presence of base) with an isocyanate, or with an intermediate formed by the combination of phosgene with an amine, or with a carbamoyl chloride. Sulfonamides are formed by reaction of the piperazine with sulfonyl chlorides or sulfamoyl chlorides in the presence of base. Alkylated piperazines (L=CH$_2$) were prepared by the combination of an aldehyde, the piperazine, and sodium triacetoxyborohydride in DCM. Where the desired reactants were not commercially available, the preparation used is described in the Examples.

Scheme 3

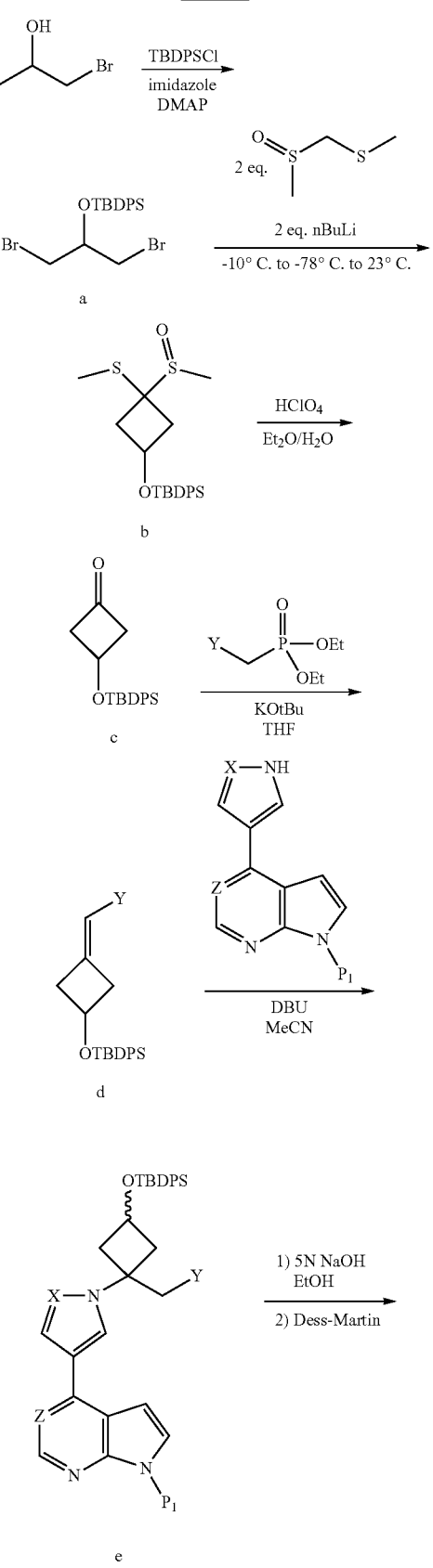

29
-continued

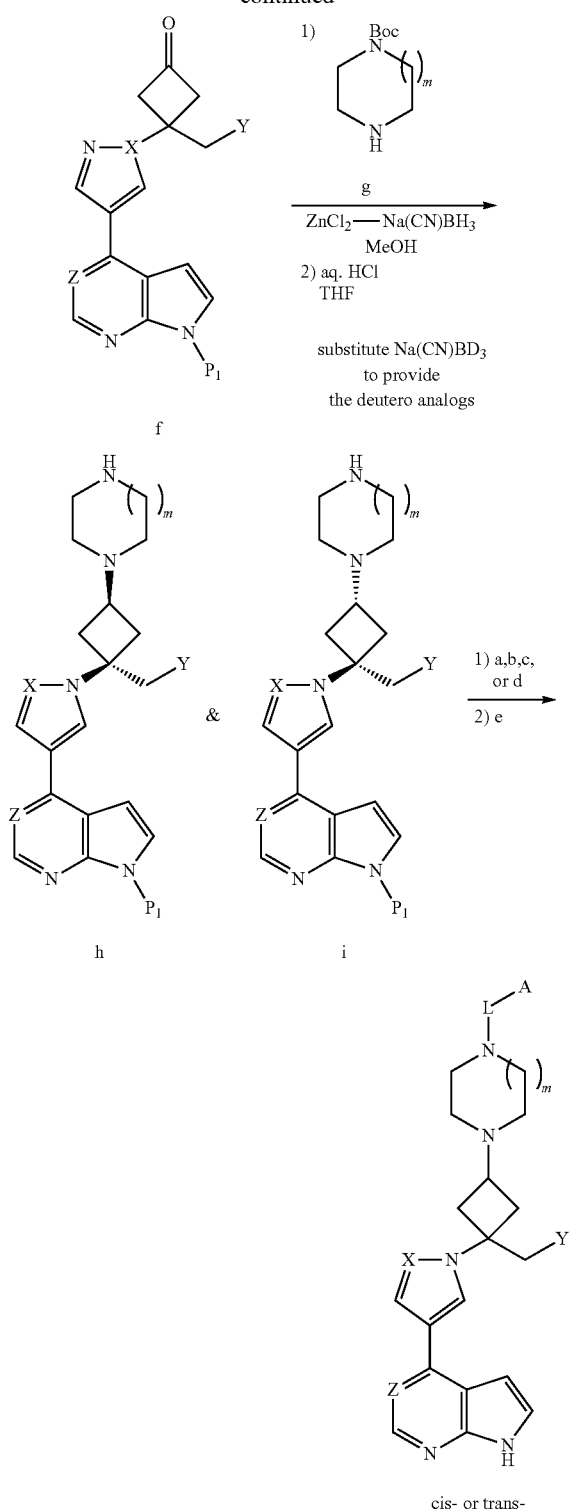

a) L = CO for amides: ACO$_2$H, BOP or HATU, TEA or DIPEA; or ACOCl, base
b) L = CO for ureas: ANCO, base; or A-H, COCl$_2$, base; or ACOCl, base (e.g. carbamoyl chloride)
c) L = SO$_2$ for sulfonamides: ASO$_2$Cl, base (also sulfamoyl chloride)
d) L = CH$_2$: ACHO, NA(OAc)BH$_3$
e) 1) TFA, DCM 2) ethylenediamine, MeOH

30

Compound of Formula I can also be made by the methods shown in Scheme IV. Accordingly formula 4-2 can be formed by reaction of the cyclobutanone of formula 4-1 with a Horner-Wadsworth-Emmons reagent. A protected pyrazol-4-yl-pyrrolo[2,3-d]pyrimidine or pyrrol-3-yl-pyrrolo[2,3-d]pyrimidine of formula 4-3 is reacted with a protected alkene of formula 4-2 in a Michael addition in the presence of a coupling agent to give the compound of formula 4-4. Removal of ether protecting group of formula 4-4 gives an alcohol derivative of formula 4-5, which can be oxidized to give the compound of formula 4-6. The compound of formula 4-6 can be converted to compound of formula 4-7 and 4-8 via reductive amination, which can be deprotected to remove P$_1$ to give the compound of Formula I.

Scheme 4

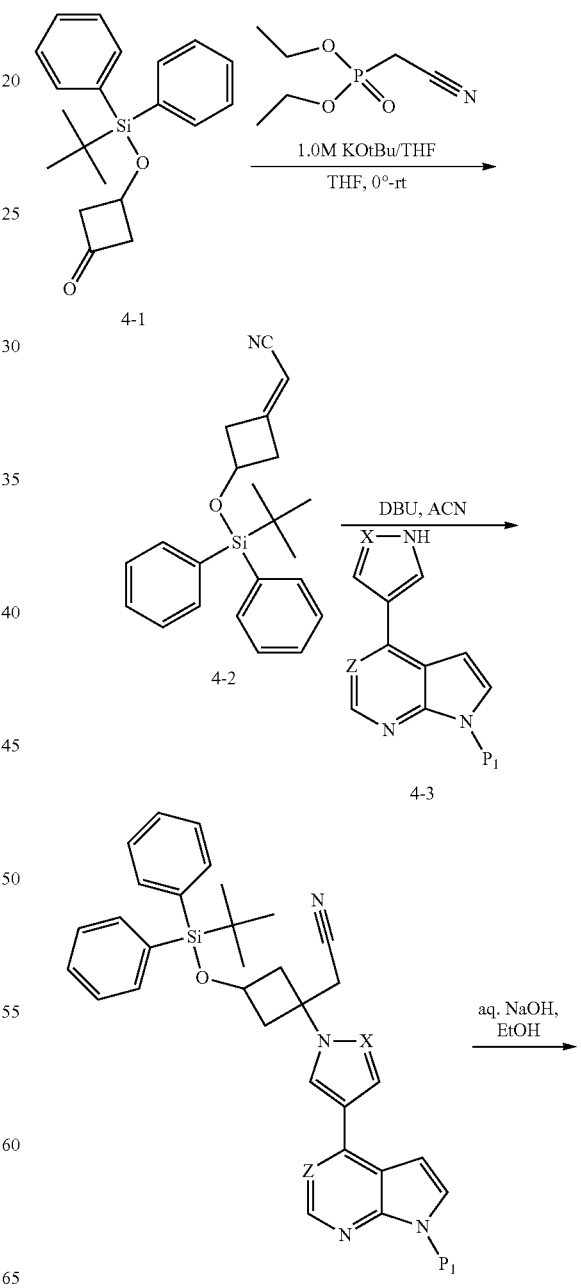

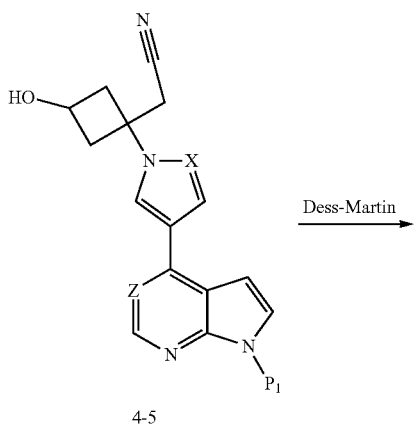

4-5

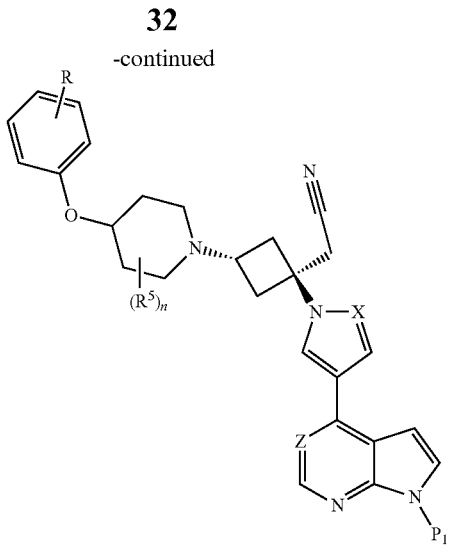

4-8

Methods

Compounds of the invention are JAK inhibitors, and the majority of the compounds of the invention are JAK1 selective inhibitors. A JAK1 selective inhibitor is a compound that inhibits JAK1 activity preferentially over other Janus kinases. For example, the compounds of the invention preferentially inhibit JAK1 over one or more of JAK2, JAK3, and TYK2. In some embodiments, the compounds inhibit JAK1 preferentially over JAK2 (e.g., have a JAK1/JAK2 $IC_{50}$ ratio>1).

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci USA. 106: 9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present invention pertains to methods of treating a JAK-associated disease or disorder in an individual (e.g., patient) by administering to the individual in need of such treatment a therapeutically effective amount or dose of a compound of the present invention or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity. In some embodiments, the JAK-associated disease is a JAK1-associated disease.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, atopic dermatitis and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chondrolysis, chrondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the invention together with the agent causing unwanted sensitization can be helpful in treating such unwanted sensitization or dermatitis. In some embodiments, the skin disorder is treated by topical administration of at least one JAK inhibitor of the invention.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, melanoma etc.), hematological cancers (e.g., lymphoma, leukemia such as acute lymphoblastic leukemia, acute myelogenous leukemia (AML) or multiple myeloma), and skin cancer such as cutaneous T-cell lymphoma (CTCL) and cutaneous B-cell lymphoma. Example CTCLs include Sezary syndrome and mycosis fungoides.

In some embodiments, the JAK inhibitors described herein, or in combination with other JAK inhibitors, such as those reported in U.S. Ser. No. 11/637,545, which is incorporated herein by reference in its entirety, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of: JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/ET MF)).

The present invention further provides methods of treating psoriasis or other skin disorders by administration of a topical formulation containing a compound of the invention.

In some embodiments, JAK inhibitors described herein can be used to treat pulmonary arterial hypertension.

The present invention further provides a method of treating dermatological side effects of other pharmaceuticals by administration of the compound of the invention. For example, numerous pharmaceutical agents result in unwanted allergic reactions which can manifest as acneiform rash or related dermatitis. Example pharmaceutical agents that have such undesirable side effects include anti-cancer drugs such as gefitinib, cetuximab, erlotinib, and the like. The compounds of the invention can be administered systemically or topically (e.g., localized to the vicinity of the dermatitis) in combination with (e.g., simultaneously or sequentially) the pharmaceutical agent having the undesirable dermatological side effect. In some embodiments, the compound of the invention can be administered topically together with one or more other pharmaceuticals, where the other pharmaceuticals when topically applied in the absence of a compound of the invention cause contact dermatitis, allergic contact sensitization, or similar skin disorder. Accordingly, compositions of the invention include topical formulations containing the compound of the invention and a further pharmaceutical agent which can cause dermatitis, skin disorders, or related side effects.

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases.

The JAK inhibitors described herein can further be used to treat ischemia reperfusion injuries or a disease or condition related to an inflammatory ischemic event such as stroke or cardiac arrest. The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J.* 2005, 390 (Pt 2):427-36 and Sriram, K. et al. *J. Biol. Chem.* 2004, 279(19):19936-47. Epub 2004 Mar. 2, both of which are incorporated herein by reference in their entirety. The JAK inhibitors described herein can be used to treat Alzheimer's disease.

The JAK inhibitors described herein can further be used to treat other inflammatory diseases such as systemic inflammatory response syndrome (SIRS) and septic shock.

The JAK inhibitors described herein can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the JAK inhibitors can be about 10%, about 20%, about 30%, about 40%, about 50%, about 60%, about 70%, about 80%, or about 90%.

In some embodiments, JAK inhibitors described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface*, 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present invention provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted sub-epithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound of the invention, or a pharmaceutically acceptable salt thereof.

Additionally, the compounds of the invention, or in combination with other JAK inhibitors, such as those reported in U.S. Ser. No. 11/637,545, which is incorporated herein by reference in its entirety, can be used to treat respiratory dysfunction or failure associated with viral infection, such as influenza and SARS.

In some embodiments, the present invention provides a compound of Formula I, pharmaceutically acceptable salt thereof, as described in any of the embodiments herein, for use in a method of treating any of the diseases or disorders described herein. In some embodiments, the present invention provides the use of a compound of Formula I as described in any of the embodiments herein, for the preparation of a medicament for use in a method of treating any of the diseases or disorders described herein.

In some embodiments, the present invention provides a compound of Formula I as described herein, or a pharmaceutically acceptable salt thereof, for use in a method of modulating a JAK1. In some embodiments, the present invention also provides use of a compound of Formula I as described herein, or a pharmaceutically acceptable salt thereof, for the preparation of a medicament for use in a method of modulating a JAK1.

As used herein, the term "contacting" refers to the bringing together of indicated moieties in an in vitro system or an in vivo system. For example, "contacting" a JAK with a compound of the invention includes the administration of a compound of the present invention to an individual or patient, such as a human, having a JAK, as well as, for example, introducing a compound of the invention into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, RAF and FAK kinase inhibitors such as, for example, those described in WO 2006/056399, which is incorporated herein by reference in its entirety, or other agents can be used in combination with the compounds described herein for treatment of JAK-associated diseases, disorders or conditions. The one or more additional pharmaceutical agents can be administered to a patient simultaneously or sequentially.

Example chemotherapeutic include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, one or more of the compounds of the invention can be used in combination with one or more other kinase inhibitors including imatinib, particularly for treating patients resistant to imatinib or other kinase inhibitors.

In some embodiments, one or more JAK inhibitors of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present invention with an additional agent. Furthermore, resistance of multiple myeloma cells to agents such as dexamethasone may be reversible upon treatment with a JAK inhibitor of the present invention. The agents can be combined with the present compounds in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of one or more JAK inhibitors of the invention with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxycline).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; cortico steroids; diclofenac; flurbiprofen; ketorolac; suprofen; cromolyn; lodoxamide; levocabastin; naphazoline; antazoline; pheniramine; or azalide antibiotic.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions of the invention contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions of the invention contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tert, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

In some embodiments, the compound, or pharmaceutically acceptable salt thereof, is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is an topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the invention can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydropropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases.

In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly(dimethyl siloxane), polyethylene oxide, poly(lactide-co-glycolide), poly(2-hydroxyethylmethacrylate), poly(vinyl alcohol), or poly(propylene fumarate). In some embodiments, the insert comprises Gelfoam® R. In some embodiments, the insert is a polyacrylic acid of 450 kDa-cysteine conjugate.

In some embodiments, the ophthalmic composition is a ophthalmic film. Polymers suitable for such films include, but are not limited to, those described in Wagh, et al. (ibid). In some embodiments, the film is a soft-contact lens, such as ones made from copolymers of N,N-diethylacrylamide and methacrylic acid crosslinked with ethyleneglycol dimethacrylate.

In some embodiments, the ophthalmic compositon comprises microspheres or nanoparticles. In some embodiment, the microspheres comprise gelatin. In some embodiments, the microspheres are injected to the posterior segment of the eye, in the chroroidal space, in the sclera, intravitreally or sub-retinally. In some embodiments, the microspheres or nanoparticles comprises a polymer including, but not limited to, those described in Wagh, et al. (ibid), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al. (ibid), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating JAK in tissue samples, including human, and for identifying JAK ligands by inhibition binding of a labeled compound. Accordingly, the present invention includes JAK assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro JAK labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is to be understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a JAK by monitoring its concentration variation when contacting with the JAK, through tracking of the labeling. For example, a test compound (labeled) can be evaluated for its ability to reduce binding of another compound which is known to bind to a JAK (i.e., standard compound). Accordingly, the ability of a test compound to compete with the standard compound for binding to the JAK directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of JAK-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to be JAK inhibitors according to at least one assay described herein. At points throughout the Examples, the stereochemistry of the cyclobutyl ring has been indicated, as currently under-

Example 1a

3-[(4-{cis-3-(cyanomethyl)-3-[4-(7H-pyrrolo[2,3-d]pyrimidin-4-yl)-1H-pyrazol-1-yl]cyclobutyl}piperazin-1-yl)methyl]-5-fluorobenzonitrile stood after nOe experiments Boc-protected piperazine intermediates (e.g., products of Example 1a, Step 8).

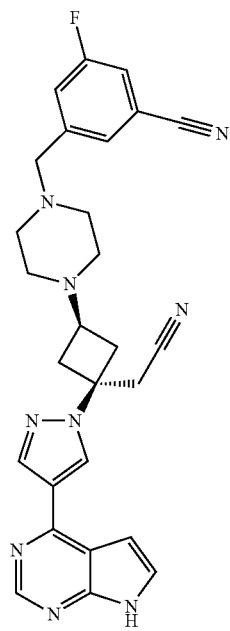

Step 1. [2-bromo-1-(bromomethyl)ethoxy](tert-butyl)diphenylsilane

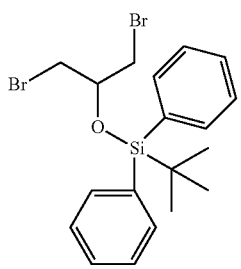 [SMILES: CC(C)(C)[Si](OC(CBr)CBr)(c1ccccc1)c1ccccc1]

To a solution of 1,3-dibromo-2-propanol (20.00 g, 91.79 mmol) in methylene chloride (DCM) (100 mL) cooled to 0° C. was added 1H-imidazole (6.56 g, 96.4 mmol) followed by tert-butylchlorodiphenylsilane (25.1 mL, 96.4 mmol) and 4-dimethylaminopyridine (1.12 g, 9.18 mmol). The reaction was stirred with warming to room temperature overnight. The reaction mixture was diluted with diethyl ether, washed with water, and the aqueous layer was again extracted once with ether. The combined organic extracts were washed with water, followed by brine, dried over sodium sulfate, decanted and concentrated. Flash chromatography (eluting with a gradient from 0-15% ethyl acetate/hexanes) afforded desired product (42 g, 100%). $^1$H NMR (300 MHz, CDCl$_3$): δ 7.72-7.66 (m, 4H), 7.51-7.37 (m, 6H), 4.00-3.91 (m, 1H), 3.49-3.45 (m, 4H), 1.09 (s, 9H).

Step 2. tert-butyl{[3-(methylsulfinyl)-3-(methylthio)cyclobutyl]oxy}diphenylsilane

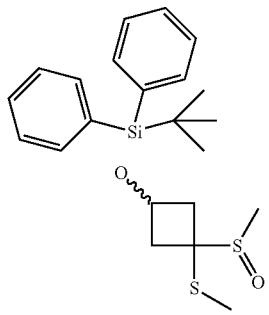

To a solution of (methylsulfinyl)(methylthio)methane (27.70 g, 223.0 mmol) in tetrahydrofuran (90 mL) at −10° C. was added dropwise, a solution of 2.5 M n-butyllithium in hexane (89.2 mL, 223 mmol). The mixture was stirred at −10° C. for 2 hours. It was then cooled to −78° C. and transferred by cannula in a slow manner to a solution of [2-bromo-1-(bromomethyl)ethoxy](tert-butyl)diphenylsilane (42 g, 93 mmol, from Step 1) in tetrahydrofuran (70 mL, 900 mmol) held at −78° C. The mixture was stirred with warming to room temperature over 2 nights. Water was added, and then the product was extracted with three portions of DCM. The combined extracts were dried over sodium sulfate, filtered and concentrated. Flash chromatography (eluting with a gradient from 0-100% ethyl acetate/hexanes) afforded desired product as a mixture of diastereomers (34.1 g, 88%). $^1$H NMR (300 MHz, CDCl$_3$), diastereomers: δ 7.74-7.58 (m, 8H), 7.48-7.31 (m, 10H), 4.52 (tt, 1H), 4.42 (tt, 1H), 3.05-1.99 (m, 8H), 2.47 (s, 3H), 2.42 (s, 3H), 2.13 (s, 3H), 2.00 (s, 3H), 1.05 (s, 9H), 1.02 (s, 9H).

Step 3. 3-{[tert-butyl(diphenyl)silyl]oxy}cyclobutanone

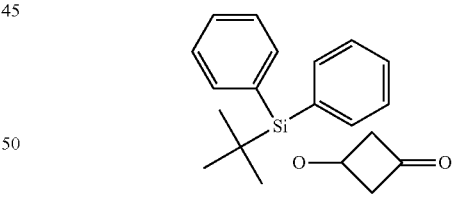

A solution of tert-butyl{[3-(methylsulfinyl)-3-(methylthio)cyclobutyl]oxy}diphenylsilane (17.05 g, 40.7 mmol, from Step 2) in ether (350 mL) cooled to 0° C. was treated with a solution of 6 M perchloric acid in water (10 mL) that was pre-diluted with water (7 mL). The bath was removed and stirred overnight. The mixture was poured into pH 7 buffer, and the product was extracted with diethyl ether. The combined extracts were dried over sodium sulfate, decanted and concentrated. The reaction was performed again on the same scale and the two batches were combined for purification. Flash chromatography, eluting with a gradient from 0-5% ethyl acetate/hexanes afforded desired product (15.7 g, 59%). $^1$H NMR (300 MHz, CDCl$_3$): δ 7.75-7.62 (m, 4H), 7.49-7.33 (m, 6H), 4.59 (tt, 1H), 3.22-3.03 (m, 4H), 1.07 (s, 9H).

Step 4. (3-{[tert-butyl(diphenyl)silyl]oxy}cyclobutylidene)acetonitrile

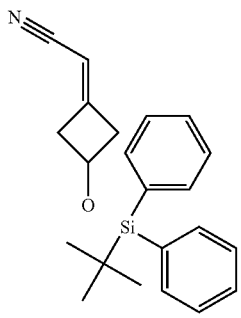

To a solution of 1.0 M potassium tert-butoxide in tetrahydrofuran (46.0 mL, 46.0 mmol) at 0° C. was added diethyl cyanomethylphosphonate (7.8 mL, 48 mmol). The bath was removed and the reaction mixture was allowed to warm to room temperature over 1 hour. The reaction was re-cooled to 0° C., and a solution of 3-{[tert-butyl(diphenyl)silyl]oxy}cyclobutanone (15.7 g, 48.4 mmol, from Step 3) in tetrahydrofuran (80 mL) was added. During the course of the addition, additional tetrahydrofuran (50 mL) was added into the receiving flask to facilitate stirring. Upon complete addition of the ketone, the bath was removed and the reaction allowed to reach room temperature and stirred overnight. The reaction mixture was partitioned between water and ethyl acetate and the aqueous was extracted with ethyl acetate a total of three times. The combined extracts were washed with brine, dried over sodium sulfate, decanted and concentrated. Flash chromatography, eluting with a gradient of 0-10% ethyl acetate in hexanes afforded product (16.1 g, 96%). $^1$H NMR (300 MHz, CDCl$_3$): δ 7.74-7.58 (m, 4H), 7.49-7.34 (m, 6H), 5.13 (dddd, 1H), 4.34 (tt, 1H), 3.16-2.90 (m, 4H), 1.05 (s, 9H).

Step 5. cis and trans {3-{[tert-butyl(diphenyl)silyl]oxy}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile

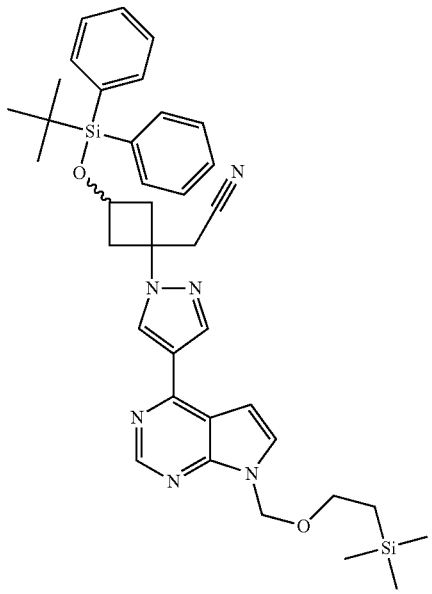 [SMILES: CC(C)(C)[Si](OC1CC(CC#N)(n2cc(-c3ncnc4c3ccn4COCC[Si](C)(C)C)cn2)C1)(c1ccccc1)c1ccccc1]

To a solution of (3-{[tert-butyl(diphenyl)silyl]oxy}cyclobutylidene)acetonitrile (16.1 g, 35.2 mmol, from Step 4) and 4-(1H-pyrazol-4-yl)-7-{[2-(trimethylsilyl)ethoxy]methyl}-7H-pyrrolo[2,3-d]pyrimidine (11.1 g, 35.2 mmol) (prepared as in WO2007/070514 Example 65, Step 2) in acetonitrile (100 mL) was added 1,8-diazabicyclo[5.4.0]undec-7-ene (5.3 mL, 35 mmol). The reaction was stirred over three nights. The acetonitrile was removed in vacuo. Flash chromatography, eluting with 25% ethyl acetate in hexanes until product began to elute, then 40 to 66% ethyl acetate in hexanes was used to elute desired product as a mixture of diastereomers (17.4 g, 75%). $^1$H NMR (300 MHz, CDCl$_3$), diastereomers (M=major, min=minor): δ 8.86 (s, 1H M), 8.81 (s, 1H min), 8.37 (s 1H, M), 8.30 (s, 1H M), 8.26 (s, 1H min), 8.25 (s, 1H min), 7.67-7.35 (m, 11H M & 11H min), 6.81 (d, 1H M), 6.73 (d, 1H min), 5.68 (s, 2H M), 5.66 (s, 2H min), 4.45 (tt, 1H min), 4.33 (tt, 1H M), 3.59-3.50 (m, 2H M & 2H min), 3.23 (s, 2H min), 3.11-3.00 (m, 2H min), 2.90 (s, 2H M), 2.88-2.80 (m, 4H M), 2.64-2.54 (m, 2H min), 1.08 (s, 9H min), 1.03 (s, 9H M), 0.97-0.88 (m, 2H M & 2H min), −0.06 (s, 9H M), −0.07 (s, 9H min); LCMS (M+H)$^+$: 663.3.

Step 6. cis and trans {3-hydroxy-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile

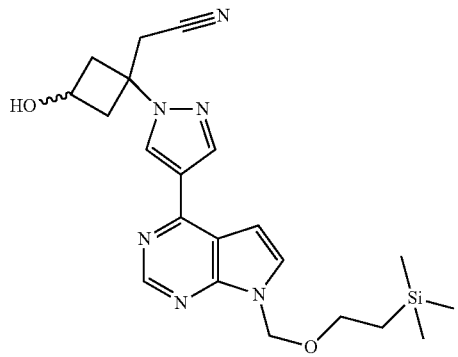 [SMILES: C[Si](C)(C)CCOCn1ccc2c(-c3cnn(C4(CC#N)CC(O)C4)c3)ncnc21]

To {3-{[tert-butyl(diphenyl)silyl]oxy}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (8.7 g, 13.1 mmol, as a mixture of diastereomers from Step 5) in ethanol (355 mL) was added 5.0 M sodium hydroxide in water (90 mL, 450 mmol). The reaction was stirred for 5 hours. Additional water was added and then the ethanol was removed using rotary evaporation. The mixture was then partitioned between ethyl acetate and water. The aqueous portion was extracted with ethyl acetate a total of three times. The combined organic extracts were washed with water, then brine, dried over sodium sulfate, decanted and concentrated. The residue was azeotroped with benzene. This reaction was performed again on the same scale and the crude product of both runs was combined for purification. Flash chromatography, eluting with a gradient from 0-10% MeOH in DCM afforded product as an off-white foam (9.3 g, 83%). $^1$H NMR (300 MHz, CDCl$_3$), diastereomers (M=major, min=minor): δ 8.84 (s, 1H M & 1H min), 8.41 (s, 1H min), 8.39 (s, 1H M), 8.31 (s, 1H min), 8.30 (s, 1H M), 7.40 (d, 1H M & 1H min), 6.80 (d, 1H M & 1H min), 5.67 (s, 2H M & 2H min), 4.60-4.44 (m, 1H M & 1H min), 3.59-3.46 (m, 2H M & 2H min), 3.25 (s, 2H min), 3.25-3.16

(m, 2H min), 3.08 (s, 2H M), 3.10-3.00 (m, 2H M), 2.84-2.73 (m, 2H M), 2.64-2.51 (m, 2H min), 0.97-0.87 (m, 2H M & 2H min), −0.06 (s, 9H M & 9H min); LCMS (M+H)+: 425.0.

Step 7. {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile

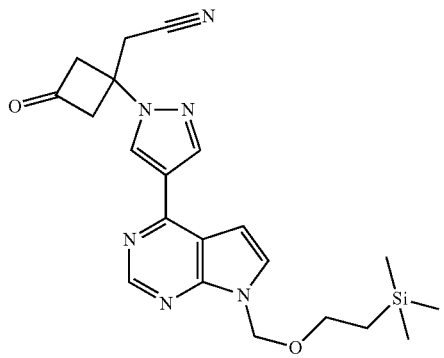 [SMILES: C[Si](C)(C)CCOCn1ccc2c(-c3cnn(C4(CC#N)CC(=O)C4)c3)ncnc21]

To a solution of {3-hydroxy-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (9.3 g, 22 mmol, as a mixture of diastereomers from Step 6) in methylene chloride (300 mL) at 0° C. was added Dess-Martin periodinane (10.0 g, 24 mmol). After a reaction time of 2 hours, the mixture was poured into 1N NaOH and extracted with three portions of DCM. The combined extracts were washed with further 1N NaOH, dried over sodium sulfate, decanted and the solvent removed in vacuo. Flash chromatography, eluting with a gradient from 0-10% MeOH in DCM afforded product as a yellow foam. Theoretical yield assumed for use in Step 8. $^1$H NMR (300 MHz, CDCl$_3$): δ 8.85 (s, 1H), 8.50 (s, 1H), 8.35 (s, 1H), 7.42 (d, 1H), 6.80 (d, 1H), 5.68 (s, 2H), 4.11-4.00 (m, 2H), 3.74-3.61 (m, 2H), 3.59-3.50 (m, 2H), 3.31 (s, 2H), 0.96-0.88 (m, 2H), −0.06 (s, 9H); LCMS (M+H)+: 423.0.

Step 8. tert-butyl 4-{cis-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperazine-1-carboxylate; and tert-butyl 4-{trans-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperazine-1-carboxylate

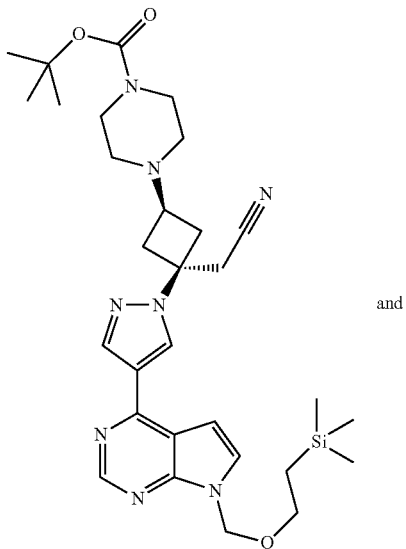

and

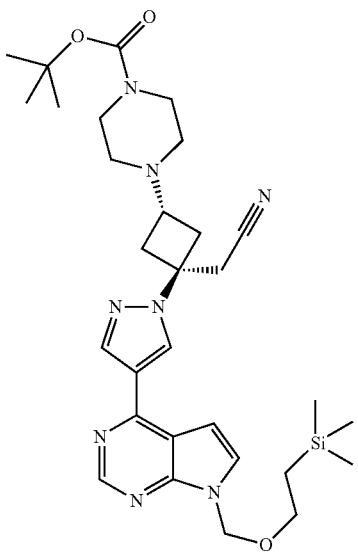

Sodium cyanoborohydride (0.693 g, 11.0 mmol) and zinc dichloride (0.752 g, 5.51 mmol) were precombined in methanol and stirred for 2 hours as described in *J. Org. Chem.* 1985, 50, pp. 1927-1932. {3-Oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (4.66 g, 11.0 mmol, from Step 7) and tert-butyl piperazine-1-carboxylate (4.11 g, 22.0 mmol) were dissolved in methanol (200 mL), then the pre-mixed solution of sodium cyanoborohydride and zinc dichloride was added. The reaction was left to stir over 4 nights. The methanol was removed in vacuo. The residue was partitioned between ethyl acetate and saturated sodium bicarbonate solution. The aqueous layer was extracted with two further portions of ethyl acetate. The combined organic extracts were dried over sodium sulfate, filtered and concentrated. Flash chromatograpy, eluting with a gradient from 0-10% MeOH in DCM afforded the product as a mixture of diastereomers. Chiral HPLC (Chiralcel OJ-H, 20×250 mm, 5 u packing, 30% EtOH/70% Hexanes at a flow rate of 12 mL/min, with a loading of about 31 mg/injection) was used to separate the cis and trans diastereomers. Peak 1, cis: (retention time 9.80 min): 1.48 g, 23%; and Peak 2, trans: (retention time 13.54 min): 1.58 g, 24%.

$^1$H NMR peak 1 (300 MHz, CD$_3$OD): δ 8.70 (s, 1H), 8.63 (s, 1H), 8.35 (s, 1h), 7.58 (d, 1H), 7.01 (d, 1H), 5.65 (s, 2H), 3.60-3.52 (m, 2H), 3.46-3.38 (m, 4H), 2.92 (tt, 1H), 2.83-2.72) m, 2H), 2.72-2.60 (m, 2H), 2.40-2.29 (m, 4H), 1.44 (s, 9H), 0.90-0.82 (m, 2H), −0.10 (s, 9H); LCMS (M+H)+: 593.4.

$^1$H NMR peak 2 (400 MHz, d$_6$-dmso): δ 8.72 (s, 1H), 8.71 (s, 1H), 8.39 (s, 1H), 7.61 (d, 1H), 7.04 (d, 1H), 5.67 (s, 2H), 3.62-3.53 (m, 2H), 3.50-3.40 (m, 4H), 3.32 (dd, 2H), 3.11-3.01 (m, 2H), 2.89 (tt, 1H), 2.53-2.42 (m, 2H), 2.40-2.31 (m, 4H), 1.44 (s, 9H), 0.92-0.82 (m, 2H), −0.09 (s, 9H); LCMS (M+H)+: 593.4.

Step 9. {cis-3-piperazin-1-yl-1-[4-(7-{[2-(trimethyl-silyl)ethoxy]methyl}-7H-pyrrolo[2,3-d]pyrimidin-4-yl)-1H-pyrazol-1-yl]cyclobutyl}acetonitrile

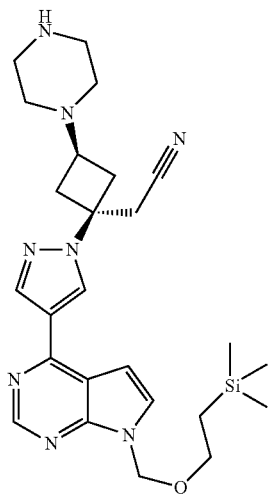 [SMILES: C[Si](C)(C)CCOCn1ccc2c(-c3cnn([C@]4(CC#N)C[C@H](N5CCNCC5)C4)c3)ncnc21]

To a solution of tert-butyl 4-{cis-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperazine-1-carboxylate (1.48 g, 2.50 mmol, Peak 1 from Step 8) in 1,4-dioxane (90 mL) was added 4.0 M HCl in water (20 mL, 60 mmol) and was stirred over two nights. The reaction mixture was poured into saturated sodium bicarbonate, sufficient quantity to become basic. Dioxane was removed in vacuo. The product was extracted with three portions of ethyl acetate. The combined organic extracts were washed with brine, dried over sodium sulfate, decanted and concentrated. The product was used without further purification (1.18 g, 96%). LCMS (M+H)+: 493.1.

Step 10. 3-[(4-{cis-3-(cyanomethyl)-3-[4-(7H-pyrrolo[2,3-d]pyrimidin-4-yl)-1H-pyrazol-1-yl]cyclobutyl}piperazin-1-yl)methyl]-5-fluorobenzonitrile

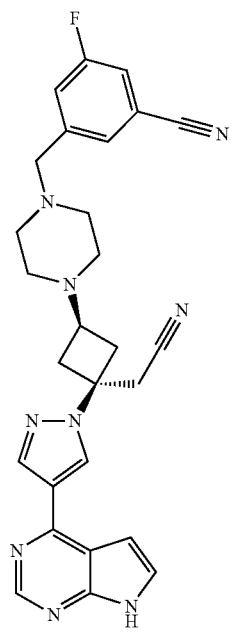 [SMILES: N#CC[C@]1(n2cc(-c3ncnc4[nH]ccc34)cn2)C[C@@H](N2CCN(Cc3cc(F)cc(C#N)c3)CC2)C1]

{cis-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.080 g, 0.16 mmol, from Step 9) and 3-bromo-5-fluorobenzaldehyde (0.046 g, 0.23 mmol, Matrix Scientific) were combined in methylene chloride (3 mL) and after 10 minutes, sodium triacetoxyborohydride (0.138 g, 0.649 mmol) was added. The reaction was continued overnight. 1N NaOH was added into the mixture, and then the product was extracted with three portions of ethyl acetate. The combined extracts were dried over sodium sulfate, decanted and concentrated. The crude product was then dissolved in N,N-dimethylformamide (2 mL), and zinc cyanide (0.114 g, 0.974 mmol) was added. The mixture was degassed by bubbling a stream of nitrogen through the mixture for 10 minutes. Tetrakis(triphenylphosphine)palladium(0) (0.04 g, 0.03 mmol) was added, the reaction vessel was sealed and heated in the microwave to 120° C. for 30 minutes. The mixture was partitioned between water and ethyl acetate. The aqueous was extracted with ethyl acetate a total of three times. The combined extracts were washed with water, then brine, dried over sodium sulfate, decanted and concentrated. The crude product was stirred in a 1:1 mix of TFA:DCM (4 mL) for 2 hours. The solvents were evaporated, and the residue was stirred with 0.3 mL ethylenediamine in methanol (4 mL) overnight. The mixture was filtered and purified by preparative HPLC-MS (C18 eluting with a gradient of $H_2O$/MeCN containing 0.15% $NH_4OH$). The eluent containing the desired mass was frozen and lyophilized to afford desired product as the free base (0.01 g, 10%). $^1$H NMR (300 MHz, $CD_3OD$): δ 8.66 (s, 1H), 8.65 (s, 1H), 8.37 (s, 1H), 7.57 (dd, 1H), 7.51 (d, 1H), 7.50-7.43 (m, 2H), 6.98 (d, 1H), 3.62 (s, 2H), 3.35 (s, 2H), 3.13-2.99 (m, 1H), 2.88-2.77 (m, 2H), 2.77-2.66 (m, 2H), 2.65-2.40 (br, 8H); $^{19}$F NMR (376 MHz, $d_6$-dmso): δ −111.45 (dd, 1F); LCMS (M+H)+: 496.3.

Example 1b

3-[(4-{trans-3-(cyanomethyl)-3-[4-(7H-pyrrolo[2,3-d]pyrimidin-4-yl)-1H-pyrazol-1-yl]cyclobutyl}piperazin-1-yl)methyl]-5-fluorobenzonitrile

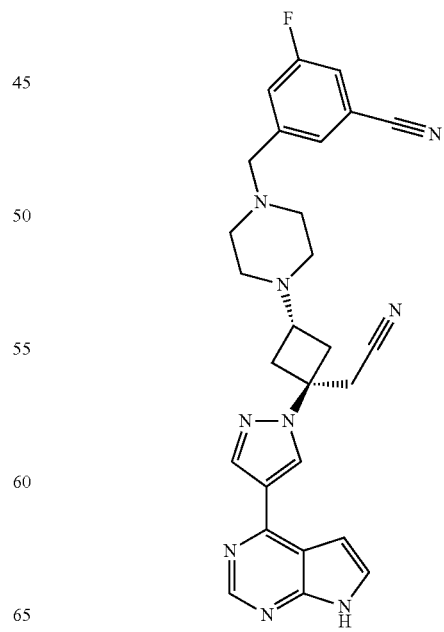

Step 1. {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile

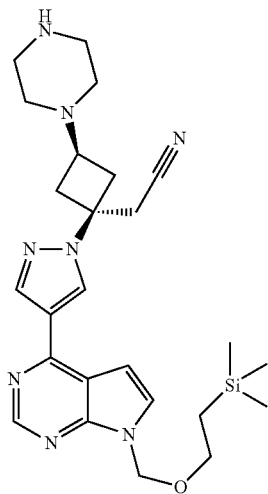 [SMILES: C[Si](C)(C)CCOCn1ccc2c(-c3cnn([C@]4(CC#N)C[C@H](N5CCNCC5)C4)c3)ncnc21]

To a solution of tert-butyl 4-{trans-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperazine-1-carboxylate (1.58 g, 2.66 mmol, Peak 2 from Example 1a, Step 8) in 1,4-dioxane (100 mL) was added 4.0 M hydrogen chloride in water (20 mL) and stirred overnight for two nights. The reaction mixture was poured into saturated sodium bicarbonate in sufficient quantity to neutralize and become basic. Dioxane was then removed from the mixture in vacuo. The product was extracted with three portions of ethyl acetate. The combined extracts were washed with brine, dried over sodium sulfate, decanted and concentrated. The product was used without further purification (1.3 g, 100%). LCMS (M+H)$^+$: 493.1.

Step 2. 3-[(4-{trans-3-(cyanomethyl)-3-[4-(7H-pyrrolo[2,3-d]pyrimidin-4-yl)-1H-pyrazol-1-yl]cyclobutyl}piperazin-1-yl)methyl]-5-fluorobenzonitrile

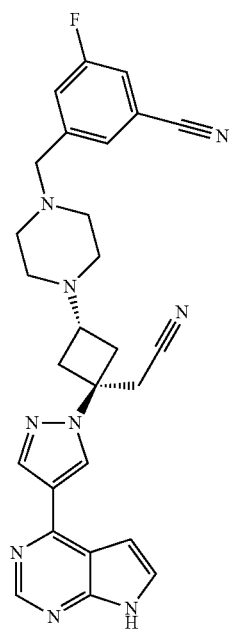 [SMILES: N#CC[C@]1(n2cc(-c3ncnc4[nH]ccc34)cn2)C[C@H](N2CCN(Cc3cc(F)cc(C#N)c3)CC2)C1]

{trans-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.047 g, 0.095 mmol, from Step 1) and 3-bromo-5-fluorobenzaldehyde (0.027 g, 0.13 mmol, Matrix Scientific) were stirred in methylene chloride (1 mL) for 10 minutes, then sodium triacetoxyborohydride (0.0809 g, 0.382 mmol) was added. The reaction was continued overnight. 1N NaOH was added, and then the product was extracted with three portions of ethyl acetate. The combined extracts were dried over sodium sulfate, decanted and concentrated. The crude product was dissolved in N,N-dimethylformamide (2 mL), zinc cyanide (0.12 g, 1.0 mmol) was added, then the mixture was degassed by passing a stream of nitrogen through for 10 minutes. Tetrakis(triphenylphosphine)palladium(0) (0.040 g, 0.035 mmol) was added. The reaction vessel was sealed and heated in the microwave for 30 minutes at 120° C. The reaction mixture was partitioned between water and ethyl acetate. The product was extracted with a total of three portions of ethyl acetate. The combined extracts were washed with water, then brine, dried over sodium sulfate, decanted and concentrated. The residue was stirred in a 1:1 mix of trifluoroacetic (TFA):DCM (4 mL) for 2 hours, and the solvents were removed in vacuo. The residue was then stirred with 0.3 mL ethylenediamine in 4 mL methanol overnight. The reaction mixture was filtered and purified by preparative HPLC-MS (C18, eluting with a gradient of H$_2$O/MeCN containing 0.15% NH$_4$OH). The eluent containing desired mass was frozen and lyophilized to afford product as the free base (0.01 g, 10%). $^1$H NMR (300 MHz, CD$_3$OD): δ 8.72 (s, 1H), 8.67 (s, 1H), 8.40 (s, 1H), 7.57 (dd, 1H), 7.51 (d, 1H), 7.50-7.42 (m, 2H), 6.98 (d, 1H), 3.61 (s, 2H), 3.32 (s, 2H), 3.11-3.01 (m, 2H), 2.94 (tt, 1H), 2.63-2.36 (m, 10H); $^{19}$F NMR (376 MHz, d$_6$-dmso): δ −111.43 (dd, 1F); LCMS (M+H)$^+$: 496.3.

Example 2a

3-[(4-{cis-3-(cyanomethyl)-3-[4-(7H-pyrrolo[2,3-d]pyrimidin-4-yl)-1H-pyrazol-1-yl]cyclobutyl}piperazin-1-yl)methyl]-6-(dimethylamino)-2-fluorobenzonitrile

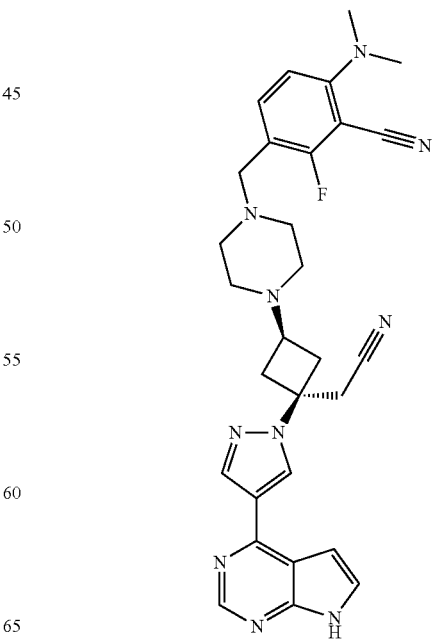

To a solution of {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Example 1a, Step 9) and 6-(dimethylamino)-2-fluoro-3-formylbenzonitrile (0.018 g, 0.091 mmol) in methylene chloride (1 mL) was added sodium triacetoxyborohydride (0.052 g, 0.24 mmol) and the reaction was stirred overnight. The reaction mixture was partitioned between 1N NaOH, brine and DCM. The layers were separated, and the aqueous layer was extracted with a further two portions of DCM. The combined organic extracts were dried over sodium sulfate, decanted and concentrated. The product was deprotected by stirring with 1:1 TFA:DCM for 2 hours. The solvent was then removed in vacuo, and the residue was stirred in a solution of methanol (1.5 mL) containing 0.3 mL ethylenediamine. The product was purified via preparative HPLC-MS (C18, eluting with a gradient of $H_2O$/MeCN containing 0.15% $NH_4OH$). The eluent containing the desired mass was frozen and lyophilized to afford product as the free base (0.015 g, 40%). $^1$H NMR (400 MHz, $CDCl_3$): δ 9.50 (s, 1H), 8.81 (s, 1H), 8.34 (s, 1H), 8.28 (s, 1H), 7.36 (dd, 1H), 7.32 (t, 1H), 6.77 (dd, 1H), 6.57 (d, 1H), 3.50 (s, 2H), 3.12 (s, 2H). 3.08 (s, 6H), 2.87 (tt, 1H), 2.82-2.74 (m, 2H), 2.72-2.64 (m, 2H), 2.60-2.20 (br m, 8H); $^{19}$F NMR (376 MHz, $d_6$-dmso): δ −112.00 (d, 1F); LCMS (M+H)$^+$: 539.3.

Example 2b

3-[(4-{trans-3-(cyanomethyl)-3-[4-(7H-pyrrolo[2,3-d]pyrimidin-4-yl)-1H-pyrazol-1-yl]cyclobutyl}piperazin-1-yl)methyl]-6-(dimethylamino)-2-fluorobenzonitrile

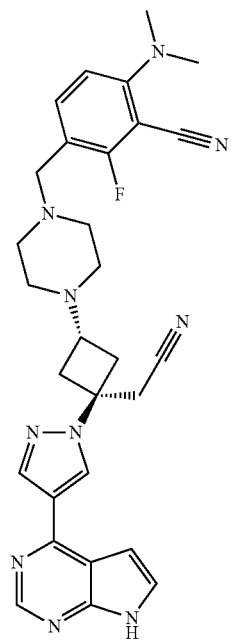

The procedure as for Example 2a was followed, using {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Example 1b, Step 1) as starting material to afford product as the free base, in the same yield (0.015 g, 46%). $^1$H NMR (400 MHz, $CDCl_3$): δ 10.22 (s, 1H), 8.83 (s, 1H), 8.46 (s, 1H), 8.33 (s, 1H), 7.39 (dd, 1H), 7.35 (t, 1H), 6.79 (dd, 1H), 6.58 (d, 1H), 3.54 (s, 2H), 3.21 (s, 2H), 3.10 (s, 6H), 3.04-2.96 (m, 2H), 2.95-2.86 (m, 1H), 2.80-1.60 (br m, 10H); $^{19}$F NMR (376 MHz, $d_6$-dmso): −112.08 (d, 1F); δ LCMS (M+H)$^+$: 539.0.

Example 3a

4-{cis-3-(cyanomethyl)-3-[4-(7H-pyrrolo[2,3-d]pyrimidin-4-yl)-1H-pyrazol-1-yl]cyclobutyl}-N-[4-fluoro-2-(trifluoromethyl)phenyl]piperazine-1-carboxamide 2.4×(trifluoroacetate) Salt

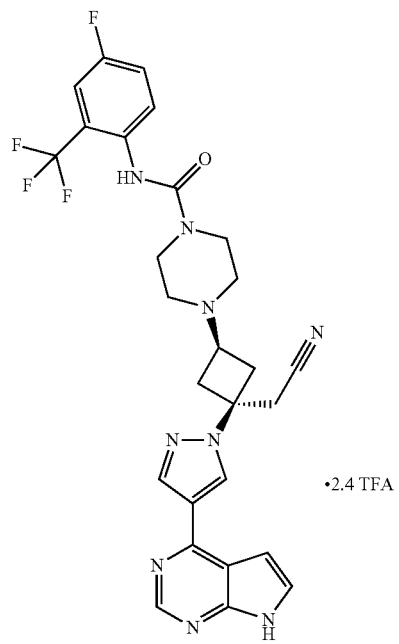 [SMILES: N#CC[C@]1(n2cc(-c3ncnc4[nH]ccc34)cn2)C[C@@H](N2CCN(C(=O)Nc3ccc(F)cc3C(F)(F)F)CC2)C1]

•2.4 TFA

{cis-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.027 g, 0.055 mmol, prepared as in Example 1a, Step 9) was dissolved in tetrahydrofuran (2 mL) and triethylamine (23 μL, 0.16 mmol) followed by 4-fluoro-1-isocyanato-2-(trifluoromethyl)benzene (10 mg, 0.06 mmol, Aldrich) were added. The reaction was stirred for 1 hour. Solvent was removed in vacuo. The residue was stirred with TFA/DCM 1:1 for 1 hour, followed by evaporation and stirring with excess ethylenediamine in MeOH until the deprotection was complete. HPLC-MS (C18, eluting with a gradient of $H_2O$/MeCN containing 0.1% TFA) was used to purify the product. The eluent containing the desired mass was frozen and lyophilized to afford product as the 2.4×TFA salt (10 mg, 22%). $^1$H NMR (300 MHz, $d_6$-dmso): δ 12.33 (br s, 1H), 8.86 (s, 1H), 8.76 (s, 1H), 8.62 (s, 1H), 8.49 (s, 1H), 7.69 (dd, 1H), 7.63 (dd, 1H), 7.55 (dd, 1H), 7.47 (dd, 1H), 7.11 (dd, 1H), 5.24-2.78 (m, 15H); $^{19}$F NMR (282 MHz, $d_6$-dmso): δ −59.88 (s, 3F), −74.61 (s, 7.2F), −114.58 (dd, 1F); LCMS (M+H)$^+$: 568.3.

Example 3b

4-{3-(cyanomethyl)-3-[4-(7H-pyrrolo[2,3-d]pyrimidin-4-yl)-1H-pyrazol-1-yl]cyclobutyl}-N-[4-fluoro-2-(trifluoromethyl)phenyl]piperazine-1-carboxamide 2.3×(trifluoroacetate) Salt

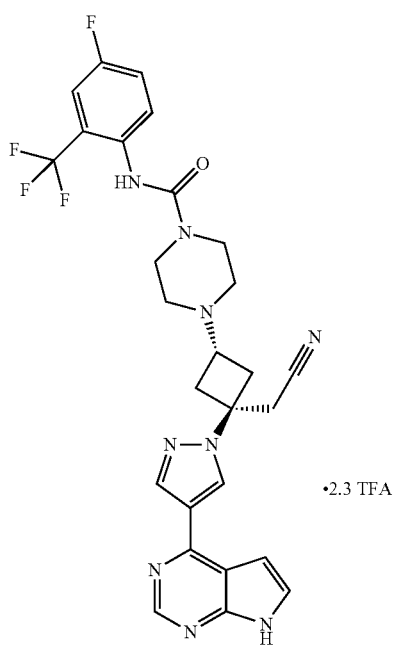 [SMILES: N#CC[C@]1(n2cc(-c3ncnc4[nH]ccc34)cn2)C[C@H](N2CCN(C(=O)Nc3ccc(F)cc3C(F)(F)F)CC2)C1]

·2.3 TFA

{trans-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.015 g, 0.030 mmol, prepared as in Example 1b, Step 1) was dissolved in tetrahydrofuran (1 mL) and triethylamine (13 μL, 0.091 mmol) followed by 4-fluoro-1-isocyanato-2-(trifluoromethyl)benzene (7 mg, 0.03 mmol, Aldrich) were added. The reaction was stirred for 1 hour. Solvent was removed in vacuo. The residue was stirred with 1:1 DCM; TFA for 1 hour, then with excess ethylenediamine in methanol HPLC-MS (C18, eluting with a gradient of H₂O/MeCN containing 0.1% TFA) was used to purify the product. The eluent containing the desired mass was frozen and lyophilized to afford product as the 2.3×trifluoroacetate salt (7 mg, 28%). ¹H NMR (300 MHz, d₆-dmso): δ 12.31 (br s, 1H), 8.97 (s, 1H), 8.75 (s, 1H), 8.60 (s, 1H), 8.51 (s, 1H), 7.68 (dd, 1H), 7.62 (dd, 1H), 7.58-7.50 (m, 1H), 7.45 (dd, 1H), 7.14 (dd, 1H), 5.57-2.73 (m, 15H); ¹⁹F NMR (282 MHz, d₆-dmso): δ -59.91 (s, 3F), -74.58 (s, 6.9F), -114.62 (dd, 1F); LCMS (M+H)⁺: 568.2.

Example 4a

{cis-3-(4-{[(2S)-2-methylpyrrolidin-1-yl]carbonyl}piperazin-1-yl)-1-[4-(7H-pyrrolo[2,3-d]pyrimidin-4-yl)-1H-pyrazol-1-yl]cyclobutyl}acetonitrile

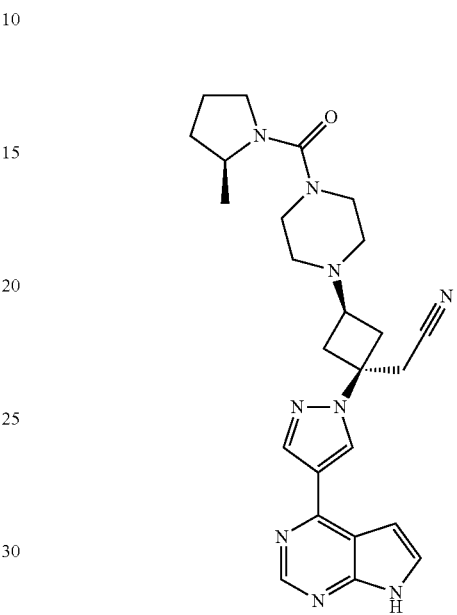

To a mixture of (2S)-2-methylpyrrolidine (0.0142 mL, 0.142 mmol) in methylene chloride (0.13 mL) and tetrahydrofuran (0.38 mL) was added triethylamine (0.099 mL, 0.710 mmol) followed by 1.89 M phosgene in toluene (0.113 mL, 0.213 mmol). The reaction mixture was stirred for 1 hour, followed by evaporation and hyvac to remove excess reagents. Triethylamine (0.040 mL, 0.28 mmol) was again added followed by acetonitrile (0.4 mL) and tetrahydrofuran (0.38 mL). To this solution was added {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.035 g, 0.071 mmol, from Example 1a, Step 9) and the reaction was stirred overnight. The solvent was then removed in vacuo. The residue was stirred with 1:1 TFA:DCM for 2 hours, then evaporated and stirred with 0.2 nth ethylenediamine in methanol (1.5 mL) until the deprotection complete. The product was purified via preparative HPLC-MS (C18, eluting with a gradient of H₂O/MeCN containing 0.15% NH₄OH). The eluent containing the desired mass was frozen and lyophilized to afford product as the free base (0.007 g, 20%). ¹H NMR (300 MHz, d₆-dmso): δ 12.12 (br s, 1H), 8.70 (s, 1H), 8.68 (s, 1H), 8.39 (s, 1H), 7.60 (d, 1H), 7.06 (d, 1H), 3.89-3.78 (m, 1H), 3.47 (s, 2H), 3.36-2.99 (m, 6H), 2.92 (tt, 1H), 2.71-2.53 (m, 4H), 2.42-2.19 (m, 4H), 2.06-1.95 (m, 1H), 1.86-1.71 (m, 1H), 1.69-1.48 (m, 1H), 1.43-1.26 (m, 1H), 1.06 (d, 3H); LCMS (M+H)⁺: 474.0.

Example 4b

{trans-3-(4-{[(2S)-2-methylpyrrolidin-1-yl]carbonyl}piperazin-1-yl)-1-[4-(7H-pyrrolo[2,3-d]pyrimidin-4-yl)-1H-pyrazol-1-yl]cyclobutyl}acetonitrile

Example 5

{trans-3-(4-{[(2S)-2-ethylpyrrolidin-1-yl]carbonyl}piperazin-1-yl)-1-[4-(7H-pyrrolo[2,3-d]pyrimidin-4-yl)-1H-pyrazol-1-yl]cyclobutyl}acetonitrile

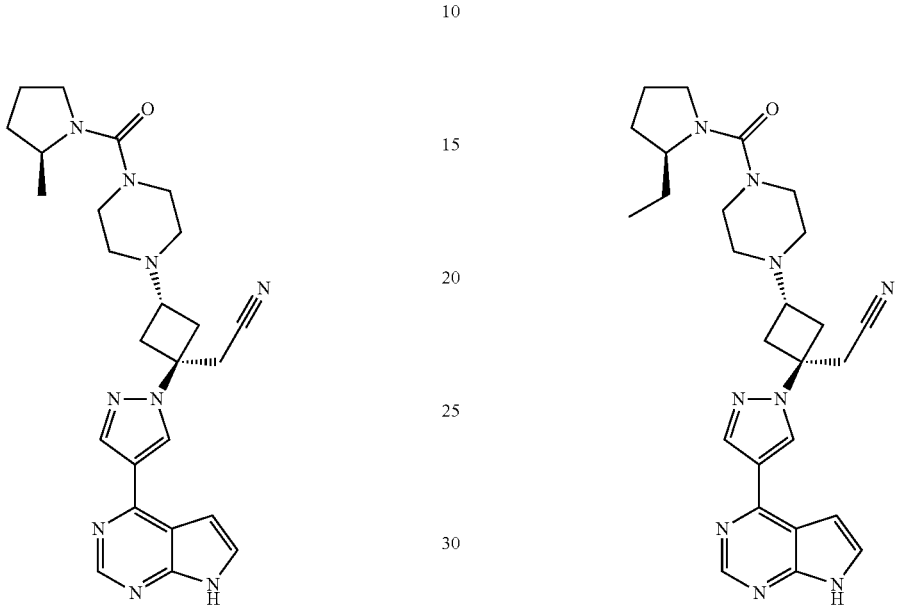

To a mixture of (2S)-2-methylpyrrolidine (0.0122 mL, 0.122 mmol) in methylene chloride (0.11 mL) and tetrahydrofuran (0.32 mL) was added triethylamine (0.0849 mL, 0.609 mmol) followed by 1.89 M phosgene in toluene (0.0966 mL, 0.183 mmol). The reaction mixture was stirred for 1 hour, followed by evaporation and hyvac to remove excess reagents. Triethylamine (0.0339 mL, 0.244 mmol) was again added followed by acetonitrile (0.3 mL) and tetrahydrofuran (0.32 mL). To this solution was added {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Example 1b, Step 1) and the reaction was stirred overnight. The solvent was then removed in vacuo. The residue was stirred with 1:1 TFA:DCM for 2 hours, then evaporated and stirred with 0.2 mL ethylenediamine in methanol (1.5 mL) until the deprotection complete. The product was purified via preparative HPLC-MS (C18, eluting with a gradient of $H_2O$/MeCN containing 0.15% $NH_4OH$). The eluent containing the desired mass was frozen and lyophilized to afford product as the free base (0.007 g, 20%). $^1$H NMR (300 MHz, $d_6$-dmso): δ 12.12 (br s, 1H), 8.82 (s, 1H), 8.69 (s, 1H), 8.42 (s, 1H), 7.60 (d, 1H), 7.07 (d, 1H), 3.91-3.76 (m, 1H), 3.42 (s, 2H), 3.30-3.18 (m, 4H), 3.15-3.05 (m, 2H), 3.04-2.94 (m, 2H), 2.78 (tt, 1H), 2.41-2.18 (m, 6H), 2.06-1.94 (m, 1H), 1.83-1.70 (m, 1H), 1.67-1.49 (m, 1H), 1.42-1.26 (m, 1H), 1.06 (d, 3H); LCMS (M+H)$^+$: 474.2.

1.89 M Phosgene in toluene (0.0966 mL, 0.183 mmol) was added to a solution of triethylamine (0.0849 mL, 0.609 mmol) in methylene chloride (0.11 mL) and tetrahydrofuran (0.32 mL). A solution of (2S)-2-ethylpyrrolidine hydrochloride (0.0165 g, 0.122 mmol, prepared as described in Chemistry—A European Journal, 12(28), 7398-7410; 2006 and WO2005/103020) in methylene chloride (0.7 mL) was added and the reaction mixture was stirred for 1 hour. {trans-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, prepared as in Example 1b, Step 1) was added in a solution of acetonitrile (0.5 mL). The reaction was stirred overnight. Solvent was removed in vacuo. The residue was stirred with 1:1 TFA:DCM for 2 hours, then evaporated and stirred with 0.2 mL ethylenediamine in methanol (1.5 mL) until deprotection was complete. The product was purified via preparative HPLC-MS (C18, eluting with a gradient of $H_2O$/MeCN containing 0.15% $NH_4OH$). The eluent containing the desired mass was frozen and lyophilized to afford product as the free base (0.01 g, 30%).

$^1$H NMR (300 MHz, $d_6$-dmso): δ 12.12 (br s, 1H), 8.82 (s, 1H), 8.69 (s, 1H), 8.41 (s, 1H), 7.60 (d, 1H), 7.07 (d, 1H), 3.86-3.75 (m, 1H), 3.42 (s, 2H), 3.32-3.18 (m, 4H), 3.15-2.94 (m, 4H), 2.78 (tt, 1H), 2.41-2.18 (m, 6H), 2.03-1.90 (m, 1H), 1.83-1.72 (m, 1H), 1.67-1.49 (m, 2H), 1.46-1.31 (m, 1H), 1.30-1.15 (m, 1H), 0.77 (t, 3H); LCMS (M+H)$^+$: 488.3.

Example 6a

{cis-3-{4-[3-fluoro-2-(trifluoromethyl)isonicotinoyl]piperazin-1-yl}-1-[4-(7H-pyrrolo[2,3-d]pyrimidin-4-yl)-1H-pyrazol-1-yl]cyclobutyl}acetonitrile

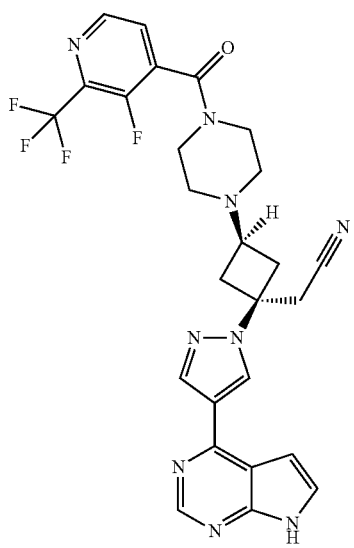 [SMILES: N#CC[C@]1(n2cc(-c3ncnc4[nH]ccc34)cn2)C[C@@H](N2CCN(C(=O)c3ccnc(C(F)(F)F)c3F)CC2)C1]

To a mixture of 3-fluoro-2-(trifluoromethyl)isonicotinic acid (0.270 g, 1.29 mmol, Oakwood) and benzotriazol-1-yloxytris(dimethylamino)phosphonium hexafluorophosphate (0.636 g, 1.44 mmol, Advanced ChemTech) in N,N-dimethylformamide (5 mL) was added Triethylamine (0.417 mL, 2.99 mmol) and this was stirred for 10 minutes, followed by the addition of {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.590 g, 1.20 mmol, from Example 1a, Step 9) in a solution of N,N-dimethylformamide. The reaction was stirred overnight. Additional triethylamine (1.2 mL, 8 mmol), 3-fluoro-2-(trifluoromethyl)isonicotinic acid (0.270 g, 1.29 mmol), and benzotriazol-1-yloxytris(dimethylamino)phosphonium hexafluorophosphate (0.636 g, 1.44 mmol) were combined in N,N-dimethylformamide (5 mL, 60 mmol) on the side and the incomplete reaction mixture was added to it. After stirring for a few hours, the now complete reaction mixture was partitioned between ethyl acetate and saturated sodium bicarbonate solution. The layers were separated, and the aqueous portion was extracted with ethyl acetate a total of three times. The combined organic extracts were dried over sodium sulfate, decanted and concentrated. The crude product was deprotected by stirring with 1:1 TFA in DCM (40 mL) for 3 hours, then solvents were removed in vacuo. The deprotection was completed by stirring with excess ethylenediamine (2.4 mL total added in portions) in methanol (20 mL). The reaction mixture was partitioned between water and ethyl acetate. The aqueous portion was extracted three times. The combined extracts were washed with brine, dried over sodium sulfate, decanted and concentrated. Flash chromatography, eluting with a gradient from 0-10% MeOH in DCM was used to purify product. The product, as a glass, was reconstituted in MeCN/H$_2$O, frozen and lyophilized (260 mg, 39%). $^1$H NMR (400 MHz, d$_6$-dmso): δ 12.13 (br s, 1H), 8.70 (s, 1H), 8.69-8.67 (m, 2H), 8.39 (s, 1H), 7.91 (t, 1H), 7.60 (dd, 1H), 7.06 (dd, 1H), 3.76-3.58 (m, 2H), 3.47 (s, 2H), 3.31-3.23 (m, 2H), 2.97 (tt, 1H), 2.70-2.55 (m, 4H), 2.47-2.20 (m, 4H); $^{19}$F NMR (376 MHz, d$_6$-dmso): δ −64.52 (d, 3F), −129.01 (qd, 1F); LCMS (M+H)$^+$: 554.3.

Example 6b

{trans-3-{4-[3-fluoro-2-(trifluoromethyl)isonicotinoyl]piperazin-1-yl}-1-[4-(7H-pyrrolo[2,3-d]pyrimidin-4-yl)-1H-pyrazol-1-yl]cyclobutyl}acetonitrile

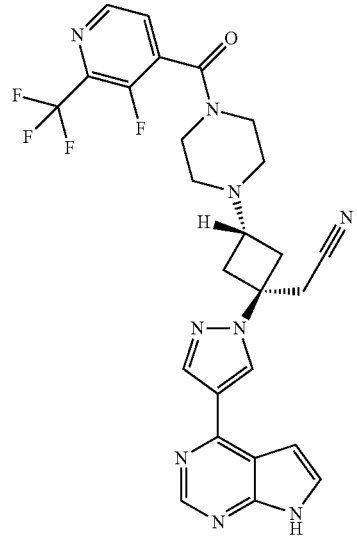 [SMILES: N#CC[C@]1(n2cc(-c3ncnc4[nH]ccc34)cn2)C[C@H](N2CCN(C(=O)c3ccnc(C(F)(F)F)c3F)CC2)C1]

A mixture of 3-fluoro-2-(trifluoromethyl)isonicotinic acid (0.331 g, 1.58 mmol, Oakwood), benzotriazol-1-yloxytris(dimethylamino)phosphonium hexafluorophosphate (0.700 g, 1.58 mmol, Advanced ChemTech), and triethylamine (0.68 mL, 4.9 mmol) in N,N-dimethylformamide (6 mL) was prestirred for 10 minutes, followed by the addition of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.600 g, 1.22 mmol, from Example 1b, Step 1) in N,N-dimethylformamide (6 mL). The reaction was stirred overnight. The reaction mixture was partitioned between saturated sodium bicarbonate and ethyl acetate. The layers were separated and the aqueous portion was extracted with a further two portions of ethyl acetate. The combined organic extracts were dried over sodium sulfate, decanted and concentrated. Flash chromatography, eluting with a gradient from 0-10% MeOH in DCM afforded SEM-protected intermediate. The product was deprotected by first stirring with trifluoroacetic Acid (5 mL) in methylene chloride (5 mL) for 4 hours, then evaporation, followed by stirring with ethylenediamine (1.63 mL, 24.4 mmol) in methanol (10 mL) until deprotection was complete. The reaction mixture was partitioned between water and ethyl acetate, and the aqueous portion extracted a total of three times with ethyl acetate. The combined organic extracts were dried over sodium sulfate, decanted and concentrated. Flash chromatography, eluting with a gradient from 0-10% MeOH/DCM was used to purify product. The product so obtained was re-purified by preparative HPLC-MS (C18, eluting with a gradient of H$_2$O/MeCN containing 0.15% NH$_4$OH). The eluent containing the desired mass was frozen and lyophilized to afford product as the free base (0.2 g, 30%). $^1$H NMR (300 MHz, CD$_3$OD): δ 8.70 (s, 1H), 8.66 (s, 1H), 8.61 (d, 1H), 8.39 (s, 1H), 7.75 (t, 1H), 7.51 (d, 1H), 6.98 (d, 1H), 3.90-3.81 (m, 2H), 3.43-3.37 (m, 2H), 3.34 (s, 2H), 3.13-3.02 (m, 2H), 2.96 (tt, 1H), 2.58-2.46 (m, 4H), 2.46-2.38 (m, 2H); $^{19}$F NMR (282 MHz, CD$_3$OD): δ −67.40 (d, 3F), −129.37 (qd, 1F); LCMS (M+H)$^+$: 553.8.

Example 7a

[cis-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile

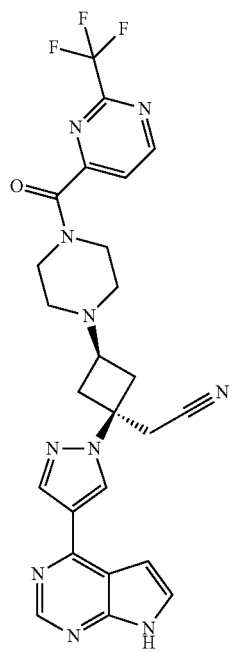 [SMILES: N#CC[C@]1(n2cc(-c3ncnc4[nH]ccc34)cn2)C[C@@H](N2CCN(C(=O)c3ccnc(C(F)(F)F)n3)CC2)C1]

A solution of 2-(trifluoromethyl)pyrimidine-4-carboxylic acid (0.015 g, 0.076 mmol, prepared by hydrolysis of the methyl ester obtained from Apollo as described in WO2006/067445), N,N,N',N'-tetramethyl-O-(7-azabenzotriazol-1-yl) uronium hexafluorophosphate (0.023 g, 0.061 mmol, Aldrich) and triethylamine (0.021 mL, 0.15 mmol) in tetrahydrofuran (0.5 mL) was prestirred, then to this was added {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.025 g, 0.051 mmol, from Example 1a, Step 9) in a solution of Tetrahydrofuran (1 mL). The reaction was stirred overnight, then was diluted with ethyl acetate, and saturated sodium bicarbonate and brine were added. The layers separated and the organic layer was washed with dilute HCl, dried over sodium sulfate, decanted and concentrated. The crude product was deprotected by stirring with 1:1 TFA:DCM for 2 hours, then solvents were evaporated and the deprotection was completed by stirring with excess ethylenediamine in methanol. The product was purified by preparative HPLC-MS (C18, eluting with a gradient of H$_2$O/MeCN containing 0.15% NH$_4$OH). The eluent containing the desired mass was frozen and lyophilized to afford product as the free base (0.007 g, 20%). $^1$H NMR (300 MHz, d$_6$-dmso): δ 12.12 (br s, 1H), 9.22 (d, 1H), 8.70 (s, 1H), 8.68 (s, 1H), 8.39 (s, 1H), 8.00 (d, 1H), 7.60 (d, 1H), 7.06 (d, 1H), 3.72-3.63 (m, 2H), 3.47 (s, 2H), 3.39-3.32 (m, 2H), 2.97 (tt, 1H), 2.74-2.56 (m, 4H), 2.47- 2.39 (m, 2H), 2.36-2.27 (m, 2H); $^{19}$F NMR (282 MHz, d$_6$-dmso): δ −69.57 (s, 3F); LCMS (M+H)$^+$: 537.2.

Example 7b

[trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile

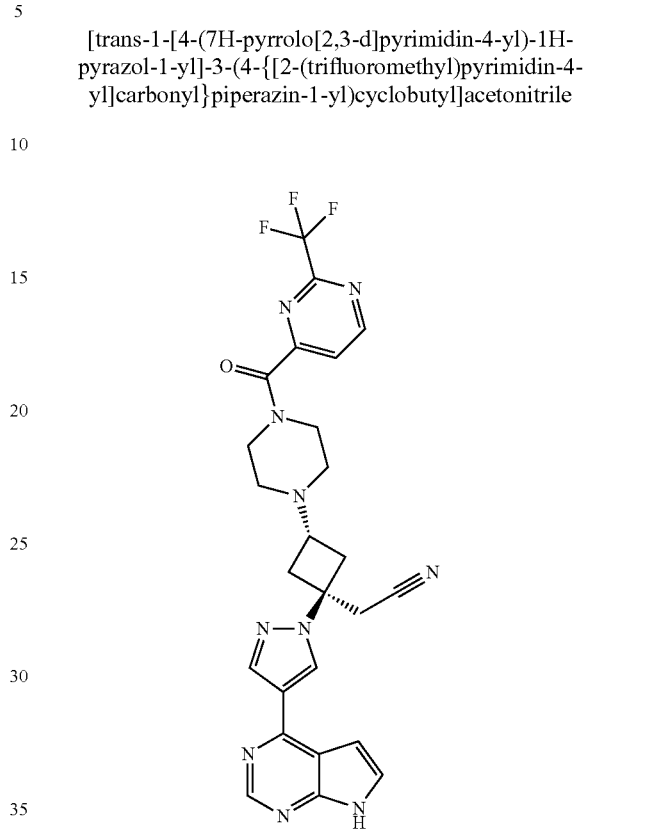

A mixture of 2-(trifluoromethyl)pyrimidine-4-carboxylic acid (0.225 g, 1.17 mmol, prepared by hydrolysis of the methyl ester obtained from Apollo as described in WO2006/067445), N,N,N',N'-tetramethyl-O-(7-azabenzotriazol-1-yl) uronium hexafluorophosphate (0.29 g, 0.76 mmol, Aldrich), and triethylamine (0.26 mL, 1.9 mmol) in tetrahydrofuran (6 mL) was prestirred for 15 minutes, followed by the addition of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.188 g, 0.380 mmol, prepared as in Example 1b, Step 1) in tetrahydrofuran (10 mL). The reaction was stirred overnight. THF was removed in vacuo. The residue was partitioned between saturated sodium bicarbonate and ethyl acetate. The aqueous portion was extracted a total of three times. The combined organic extracts were dried over sodium sulfate, decanted and concentrated. Flash chromatography, eluting with a gradient from 0-10% MeOH in DCM was used to purify the SEM-protected intermediate. Deprotection was effected by first stirring with trifluoroacetic acid (10 mL) in methylene chloride (10 mL) for 2 hours, followed by evaporation of solvent in vacuo, then stirring with methanol (6 mL, 200 mmol) containing ethylenediamine (0.5 mL, 7 mmol) overnight. The reaction mixture was partitioned between water and ethyl acetate, and the aqueous portion was extracted a further two times with ethyl acetate. The combined extracts were dried over sodium sulfate, filtered and concentrated. Flash chromatography was used to purify product, eluting with a gradient from 0-10% MeOH in DCM. The product was repurified preparative HPLC-MS (C18, eluting with a gradient of H₂O/MeCN containing 0.1% TFA). Acetonitrile was removed from the eluent containing the desired mass via rotary evaporation, then the remaining aqueous solution was neutralized by the addition of sodium bicarbonate and extracted with ethyl acetate several times. The combined organic extracts were dried over sodium sulfate, filtered and concentrated. The product was re-purified by preparative HPLC-MS (C18, eluting with a gradient of H₂O/MeCN containing 0.15% NH₄OH). The eluent containing the desired mass was frozen and lyophilized to afford product as the free base (99 mg, 48%). $^1$H NMR (300 MHz, CD₃OD): δ 9.13 (d, 1H), 8.71 (s, 1H), 8.66 (s, 1H), 8.39 (s, 1H), 7.88 (d, 1H), 7.50 (d, 1H), 6.98 (d, 1H), 3.89-3.81 (m, 2H), 3.59-3.52 (m, 2H), 3.34 (s, 2H), 3.13-3.03 (m, 2H), 2.97 (tt, 1H), 2.59-2.42 (m, 6H); $^{19}$F NMR (282 MHz, CD₃OD): δ −72.43 (s, 3F); LCMS (M+H)⁺: 537.0.

Example 8a

{cis-3-[4-(3,5-difluorobenzoyl)piperazin-1-yl]-1-[4-(7H-pyrrolo[2,3-d]pyrimidin-4-yl)-1H-pyrazol-1-yl]cyclobutyl}acetonitrile

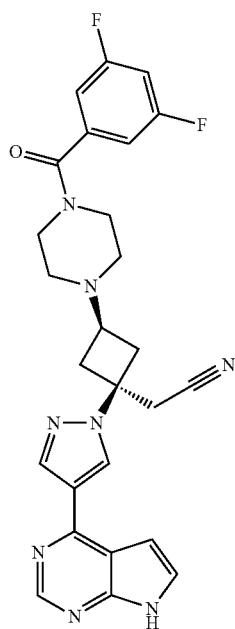 [SMILES: N#CC[C@]1(n2cc(-c3ncnc4[nH]ccc34)cn2)C[C@@H](N2CCN(C(=O)c3cc(F)cc(F)c3)CC2)C1]

To a solution of 3,5-difluorobenzoyl chloride (54 mg, 0.30 mmol, Aldrich) and {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.100 g, 0.203 mmol, from Example 1a, Step 9) in tetrahydrofuran (4 mL) was added triethylamine (0.085 mL, 0.61 mmol). The reaction was stirred overnight and solvent removed in vacuo. The product was then deprotected by stirring with 1:1 TFA:DCM for 2 hours, then evaporated and stirred with excess ethylenediamine in methanol until hydroxymethyl removal complete. The compound was then purified via preparative HPLC-MS (C18, eluting with a gradient of H₂O/MeCN containing 0.15% NH₄OH). The eluent containing the desired mass was frozen and lyophilized to afford product as the free base (16 mg, 16%). $^1$H NMR (400 MHz, d₆-dmso): δ 8.70 (s, 1H), 8.68 (s, 1H), 8.39 (s, 1H), 7.60 (d, 1H), 7.36 (tt, 1H), 7.20-7.13 (m, 2H), 7.06 (d, 1H), 3.67-3.56 (br m, 2H), 3.47 (s, 2H), 3.32-3.23 (m, 2H), 2.95 (tt, 1H), 2.70-2.55 (m, 4H), 2.43-2.24 (m, 4H); $^{19}$F NMR (376 MHz, d₆-dmso): δ −109.01 (dd, 2F); LCMS (M+H)⁺: 503.2.

Example 8b

{trans-3-[4-(3,5-difluorobenzoyl)piperazin-1-yl]-1-[4-(7H-pyrrolo[2,3-d]pyrimidin-4-yl)-1H-pyrazol-1-yl]cyclobutyl}acetonitrile

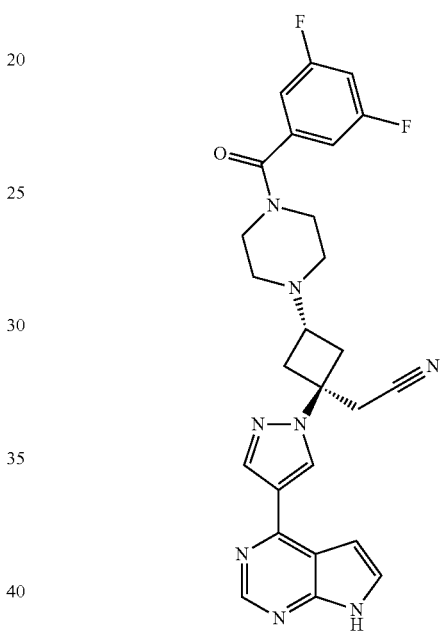

To a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Example 1b, Step 1) in tetrahydrofuran (1 mL) was added triethylamine (0.025 mL, 0.18 mmol) followed by 3,5-difluorobenzoyl chloride (0.012 mL, 0.091 mmol, Aldrich). The reaction was stirred for a few hours, then concentrated via rotary evaporation. The product was then deprotected by first stirring with 1:1 TFA:DCM for 1 hour, followed by evaporation and stirring with excess ethylenediamine in methanol until deprotection of SEM was complete. The compound was purified via preparative HPLC-MS (C18, eluting with a gradient of H₂O/MeCN containing 0.15% NH₄OH). The eluent containing the desired mass was frozen and lyophilized to afford product as the free base (20 mg, 60%). $^1$H NMR (300 MHz, d₆-dmso): δ 12.12 (br s, 1H), 8.83 (s, 1H), 8.69 (s, 1H), 8.42 (s, 1H), 7.60 (dd, 1H), 7.36 (tt, 1H), 7.21-7.12 (m, 2H), 7.07 (dd, 1H), 3.72-3.56 (m, 2H), 3.43 (s, 2H), 3.37-3.25 (m, 2H), 3.08-2.94 (m, 2H), 2.83 (tt, 1H), 2.46-2.24 (m, 6H); $^{19}$F NMR (282 MHz, d₆-dmso): δ −109.00 (dd, 2F); LCMS (M+H)⁺: 503.2.

Example 9b

{trans-3-{4-[(2-chloro-5-fluoropyridin-3-yl)carbonyl]piperazin-1-yl}-1-[4-(7H-pyrrolo[2,3-d]pyrimidin-4-yl)-1H-pyrazol-1-yl]cyclobutyl}acetonitrile

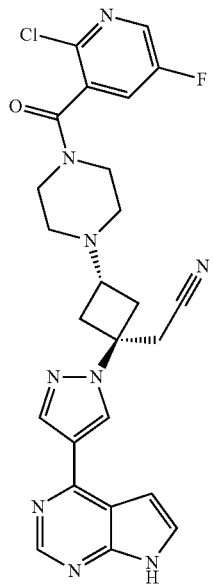 [SMILES: N#CC[C@]1(n2cc(-c3ncnc4[nH]ccc34)cn2)C[C@H](N2CCN(C(=O)c3cc(F)cnc3Cl)CC2)C1]

A mixture of 2-chloro-5-fluoronicotinic acid (0.027 g, 0.15 mmol, Matrix), triethylamine (0.041 g, 0.40 mmol) and N,N,N',N'-tetramethyl-O-(7-azabenzotriazol-1-yl)uronium hexafluorophosphate (0.046 g, 0.12 mmol, Aldrich) in tetrahydrofuran (0.6 mL) was stirred for 10 minutes, followed by the addition of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.050 g, 0.10 mmol, from Example 1b, Step 1) in tetrahydrofuran (0.6 mL). The reaction was stirred for 3 hours, the solvent was evaporated, and the mixture was stirred with 1:1 TFA:DCM for 1 hour, followed by evaporation and stirring with 0.2 mL ethylenediamine in methanol until deprotection complete. The product was purified via preparative HPLC-MS (C18, eluting with a gradient of $H_2O$/MeCN containing 0.15% $NH_4OH$). The eluent containing the desired mass was frozen and lyophilized to afford product as the free base (23 mg, 43%). $^1$H NMR (300 MHz, $d_6$-dmso): δ 12.12 (br s, 1H), 8.82 (s, 1H), 8.69 (s, 1H), 8.55 (d, 1H), 8.41 (s, 1H), 8.04 (dd, 1H), 7.60 (d, 1H), 7.07 (d, 1H), 3.77-3.57 (m, 2H), 3.42 (s, 2H), 3.27-3.16 (m, 2H), 3.08-2.94 (m, 2H), 2.84 (tt, 1H), 2.45-2.23 (m, 6H); $^{19}$F NMR (282 MHz, $d_6$-dmso): δ −128.62 (d, 1F); LCMS (M+H)$^+$: 520.1/522.1.

Example 10a

{cis-3-{4-[(5-fluoropyridin-3-yl)carbonyl]piperazin-1-yl}-1-[4-(7H-pyrrolo[2,3-d]pyrimidin-4-yl)-1H-pyrazol-1-yl]cyclobutyl}acetonitrile

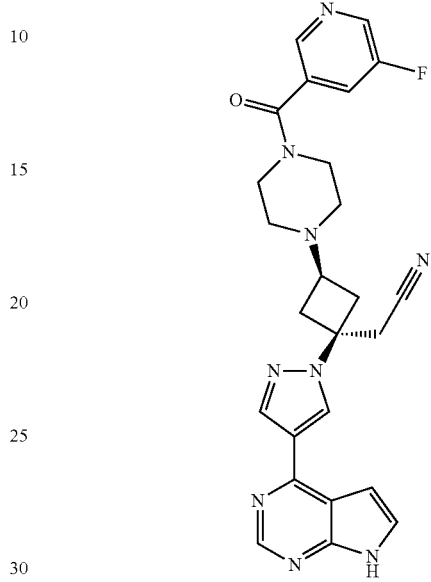

A mixture of 2-chloro-5-fluoronicotinic acid (0.027 g, 0.15 mmol, Matrix), triethylamine (0.041 g, 0.40 mmol) and N,N,N',N'-tetramethyl-O-(7-azabenzotriazol-1-yl)uronium hexafluorophosphate (0.046 g, 0.12 mmol, Aldrich) in tetrahydrofuran (0.6 mL) was stirred for 10 minutes, followed by the addition of {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.050 g, 0.10 mmol, Example 1a, Step 9) in tetrahydrofuran (0.6 mL). The reaction was stirred for 3 hours, and was purified via preparative HPLC-MS (C18, eluting with a gradient of $H_2O$/MeCN containing 0.15% $NH_4OH$). The eluent containing the desired mass was evaporated to afford the clean SEM-protected intermediate. This was hydrogenated under 55 psi of hydrogen overnight in a degassed mixture of ethanol (5 mL) containing palladium on carbon (0.011 g, 0.010 mmol, 10%, wet Degussa type) and sodium bicarbonate (0.0259 g, 0.304 mmol). The reaction mixture was filtered, rinsed well with ethanol and the solvent was removed in vacuo. The residue was then azeotroped once with toluene. The deprotection was effected by stirring with 1:1 TFA:DCM for 1 hour, evaporation, then stirring with 0.4 mL ethylenediamine in methanol until the deprotection was complete. The product was purified via preparative HPLC-MS (C18, eluting with a gradient of $H_2O$/MeCN containing 0.15% $NH_4OH$). The eluent containing the desired mass was frozen and lyophilized to afford product as the free base (0.01 g, 20%) $^1$H NMR (400 MHz, $d_6$-dmso): δ 12.12 (br s, 1H), 8.70 (s, 1H), 8.68 (s, 1H), 8.67 (d, 1H), 8.49 (t, 1H), 8.39 (s, 1H), 7.85 (ddd, 1H), 7.60 (d, 1H), 7.06 (d, 1H), 3.64 (br, 2H), 3.47 (s, 2H), 3.37-3.28 (br, 2H), 2.96 (tt, 1H), 2.69-2.56 (m, 4H), 2.41 (br, 2H), 2.32 (br, 2H); $^{19}$F NMR (376 MHz, $d_6$-dmso): δ −126.62 (dd, 1F); LCMS (M+H)$^+$: 486.4.

Example 10b

{trans-3-{4-[(5-fluoropyridin-3-yl)carbonyl]piperazin-1-yl}-1-[4-(7H-pyrrolo[2,3-d]pyrimidin-4-yl)-1H-pyrazol-1-yl]cyclobutyl}acetonitrile tris(trifluoroacetate) Salt

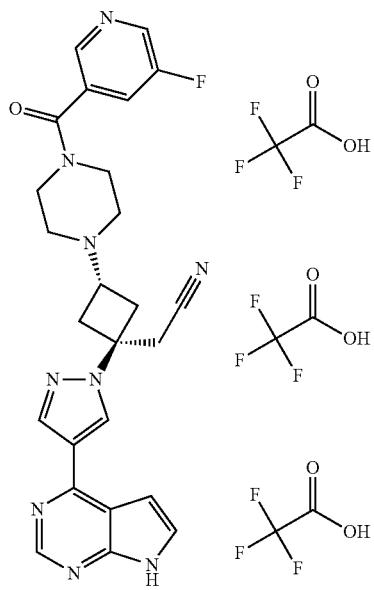 [SMILES: N#CC[C@]1(n2cc(-c3ncnc4[nH]ccc34)cn2)C[C@H](N2CCN(C(=O)c3cncc(F)c3)CC2)C1 ; O=C(O)C(F)(F)F ; O=C(O)C(F)(F)F ; O=C(O)C(F)(F)F]

To a solution of {trans-3-{4-[(2-chloro-5-fluoropyridin-3-yl)carbonyl]piperazin-1-yl}-1-[4-(7H-pyrrolo[2,3-d]pyrimidin-4-yl)-1H-pyrazol-1-yl]cyclobutyl}acetonitrile (18 mg, 0.035 mmol, from Example 9b) in ethanol (5 mL) was added sodium bicarbonate (0.0259 g, 0.304 mmol), and the mixture was degassed. Palladium on carbon (0.011 g, 0.010 mmol, 10% on carbon, wet, Degussa type) was added and the mixture stirred and shaken under 55 psi of hydrogen overnight. The reaction mixture was filtered, rinsed with methanol and evaporated, then purified via preparative HPLC-MS (C18, eluting with a gradient of H$_2$O/MeCN containing 0.1% TFA). The eluent containing the desired mass was frozen and lyophilized to afford product as the 3×TFA salt (5 mg, 10%). $^1$H NMR (400 MHz, CDCl$_3$): δ 10.02 (s, 1H), 8.85 (s, 1H), 8.48 (s, 1H), 8.37 (d, 1H), 8.36 (dd, 1H), 8.34 (s, 1H), 7.44 (ddd, 1H), 7.40 (d, 1H), 6.81 (dd, 1H), 3.56 (s, 2H), 3.22 (s, 2H), 3.05-2.96 (m, 2H), 2.92 (tt, 1H), 2.66-2.25 (m, 10H); $^{19}$F NMR (282 MHz, d$_6$-dmso): δ −74.75 (s, 9F), −126.45 (d, 1F); LCMS (M+H)$^+$: 486.2.

Example 11a

{cis-3-{4-[2-(difluoromethyl)-3-fluoroisonicotinoyl]piperazin-1-yl}-1-[4-(7H-pyrrolo[2,3-d]pyrimidin-4-yl)-1H-pyrazol-1-yl]cyclobutyl}acetonitrile

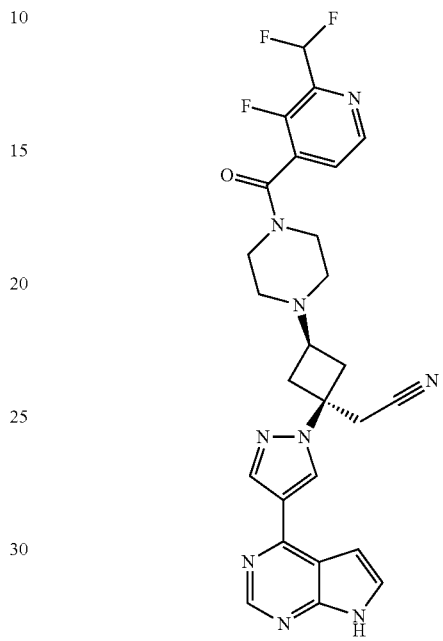

Step 1. 3-fluoro-2-vinylisonicotinic acid

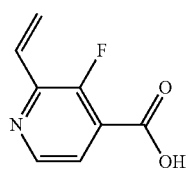

A solution of 2-chloro-3-fluoroisonicotinic acid (1.50 g, 8.55 mmol, Matrix), dibutyl vinylboronate (2.82 mL, 12.8 mmol, Aldrich), and potassium carbonate (1.42 g, 10.25 mmol) in N,N-dimethylacetamide (9 mL) and water (3 mL) was degassed by bubbling a stream of nitrogen through the solution for 20 minutes. Tetrakis(triphenylphosphine)palladium(0) (0.59 g, 0.51 mmol) was added and the mixture was similarly degassed for a further 10 minutes. The reaction vessel was sealed and heated in the microwave for 25 minutes at 135° C. The reaction mixture was filtered and purified using preparative HPLC (UV-detection) eluting with a gradient of H$_2$O/MeCN containing 0.1% TFA. This reaction was run again on the same scale and the product of both runs were pooled. Solvent was removed from the eluent containing desired product in vacuo (1.3 g, 46%). $^1$H NMR (300 MHz, CD$_3$OD): δ 8.45 (d, 1H), 7.69 (dd, 1H), 7.07 (ddd, 1H), 6.44 (dd, 1H), 5.65 (dd, 1H); $^{19}$F NMR (282 MHz, CD$_3$OD): δ −129.64 (d, 1F); LCMS (M+H)$^+$: 167.9.

Step 2. methyl 3-fluoro-2-vinylisonicotinate

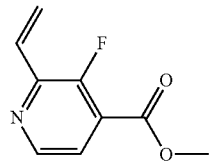

To a solution of 3-fluoro-2-vinylisonicotinic acid (1.3 g, 7.8 mmol, from Step 1) in methanol (20 mL) cooled to 0° C., was added dropwise 2.0 M trimethylsilyldiazomethane in ether (21.6 mL, 44 mmol). When the reaction was complete, acetic acid was added dropwise to quench excess reagent and the volume of solvent was reduced in vacuo. The mixture was partitioned between saturated sodium bicarbonate solution and DCM. The aqueous portion was extracted with a total of three portions of DCM. The combined extracts were dried over sodium sulfate, decanted and concentrated and The product was used without further purification (1.4 g, 100%). $^1$H NMR (300 MHz, CDCl$_3$): δ 8.47 (d, 1H), 7.62 (dd, 1H), 7.08 (ddd, 1H), 6.48 (dd, 1H), 5.65 (dd, 1H), 3.97 (s, 3H); LCMS (M+H)$^+$: 182.0.

Step 3. methyl 3-fluoro-2-formylisonicotinate

Ozone was bubbled through a solution of methyl 3-fluoro-2-vinylisonicotinate (1.4 g, 7.73 mmol, from Step 2) in methylene chloride (100 mL) at −78° C. until the blue color of excess ozone persisted. Nitrogen was bubbled through the solution for 1 minute to purge excess ozone and then triphenylphosphine (3.9 g, 15 mmol) was added and the solution was warmed to room temperature and stirred overnight. The compound was dry loaded onto silica gel. Flash chromatography eluting with 40% ethyl acetate in hexanes afforded product (0.8 g, 57%) as an off-white crystalline solid. $^1$H NMR (300 MHz, CDCl$_3$): δ 10.27 (s, 1H), 8.73 (d, 1H), 8.01 (dd, 1H), 4.01 (s, 3H).

Step 4. methyl 2-(difluoromethyl)-3-fluoroisonicotinate

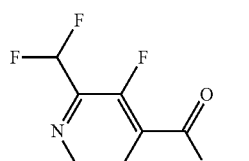

To a solution of methyl 3-fluoro-2-formylisonicotinate (0.80 g, 4.4 mmol, from Step 3) in methylene chloride (30 mL) and ethanol (0.06 mL) at 0° C. was added Deoxo-Fluor® (Aldrich (3 mL, 20 mmol). The reaction was continued at this temperature for 2 hours. Water was added into the cold reaction mixture. The product was extracted with three portions of DCM. The extracts were washed with water, dried over sodium sulfate, decanted and concentrated. The crude product was used without further purification (0.44 g, 49%). $^1$H NMR (300 MHz, CDCl$_3$): δ 8.59 (d, 1H), 7.92 (dd, 1H), 6.85 (t, 1H), 4.00 (s, 3H); $^{19}$F NMR (282 MHz, CDCl$_3$): δ −117.85 (dd, 2F), −125.97 (td, 1F).

Step 5. 2-(difluoromethyl)-3-fluoroisonicotinic acid

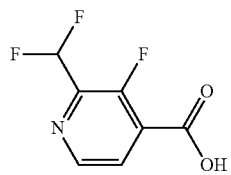 [SMILES: O=C(O)c1ccnc(C(F)F)c1F]

To a solution of methyl 2-(difluoromethyl)-3-fluoroisonicotinate (0.44 g, 2.1 mmol, from Step 4) in tetrahydrofuran (10 mL) was added a solution of lithium hydroxide monohydrate (0.45 g, 11 mmol) in water (10 mL). The reaction was stirred for 2 hours. The reaction mixture was acidified by the addition of a solution of citric acid.

The product was extracted with three portions of DCM. The combined extracts were dried over sodium sulfate, decanted and concentrated to afford product, which was used without further purification in Step 6. $^1$H NMR (300 MHz, CD$_3$OD): δ 8.57 (d, 1H), 7.99 (dd, 1H), 6.96 (t, 1H).

Step 6. {cis-3-{4-[2-(difluoromethyl)-3-fluoroisonicotinoyl]piperazin-1-yl}-1-[4-(7H-pyrrolo[2,3-d]pyrimidin-4-yl)-1H-pyrazol-1-yl]cyclobutyl}acetonitrile

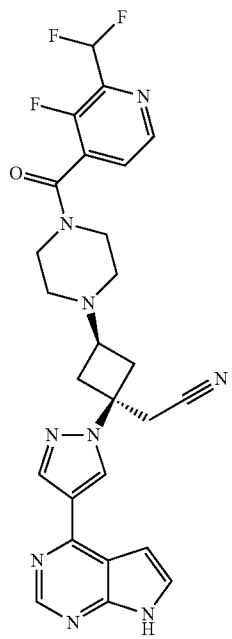 [SMILES: N#CC[C@]1(n2cc(-c3ncnc4[nH]ccc34)cn2)C[C@@H](N2CCN(C(=O)c3ccnc(C(F)F)c3F)CC2)C1]

To a prestirred combination of 2-(difluoromethyl)-3-fluoroisonicotinic acid (0.014 g, 0.076 mmol, from Step 5), N,N,N',N'-tetramethyl-O-(7-azabenzotriazol-1-yl)uronium hexafluorophosphate (0.023 g, 0.061 mmol, Aldrich) and triethylamine (0.027 mL, 0.19 mmol) in tetrahydrofuran (1.5 mL) was added {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.025 g, 0.051 mmol, Example 1a, Step 9) as a solid. The reaction was stirred overnight. The mixture was diluted with ethyl acetate, and was washed with saturated sodium bicarbonate and brine, followed by dilute HCl. The organic portion was dried over sodium sulfate, decanted and concentrated. The crude product was deprotected by stirring with 1:1 TFA:DCM for 2 hours, then solvent was removed in vacuo, and the residue was stirred with excess ethylenediamine in methanol until the deprotection was complete. The product was purified via preparative HPLC-MS (C18, eluting with a gradient of $H_2O$/MeCN containing 0.15% $NH_4OH$). The eluent containing the desired mass was frozen and lyophilized to afford product as the free base (0.007 g, 20%). $^1$H NMR (300 MHz, $d_6$-dmso): δ 12.08 (br s, 1H), 8.70 (s, 1H), 8.68 (s, 1H), 8.61 (d, 1H), 8.39 (s, 1H), 7.74 (dd, 1H), 7.60 (d, 1H), 7.19 (t, 1H), 7.05 (d, 1H), 3.67 (br, 2H), 3.47 (s, 2H), 3.28-3.20 (m, 2H), 2.97 (tt, 1H), 2.70-2.54 (m, 4H), 2.41 (br, 2H), 2.30 (br, 2H); $^{19}$F NMR (282 MHz, $d_6$-dmso): δ −117.95 (dd, 2F), −131.83−−131.97 (m, 1F); LCMS $(M+H)^+$: 536.3.

Example 11b

{trans-3-{4-[2-(difluoromethyl)-3-fluoroisonicotinoyl]piperazin-1-yl}-1-[4-(7H-pyrrolo[2,3-d]pyrimidin-4-yl)-1H-pyrazol-1-yl]cyclobutyl}acetonitrile

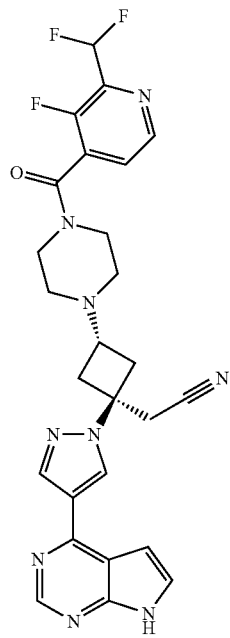 [SMILES: N#CC[C@]1(n2cc(-c3ncnc4[nH]ccc34)cn2)C[C@H](N2CCN(C(=O)c3ccnc(C(F)F)c3F)CC2)C1]

A mixture of 2-(difluoromethyl)-3-fluoroisonicotinic acid (0.34 g, 1.8 mmol, from Example 11a, Step 5), N,N,N',N'-tetramethyl-O-(7-azabenzotriazol-1-yl)uronium hexafluorophosphate (0.72 g, 1.9 mmol, Aldrich) and triethylamine (0.81 mL, 5.8 mmol) in tetrahydrofuran (20 mL) was prestirred for 15 min, then to this was added {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.581 g, 1.18 mmol, prepared as in Example 1b, Step 1) in a solution of tetrahydrofuran (30 mL). The reaction was stirred overnight, and then THF was removed in vacuo. The residue was partitioned between ethyl acetate and saturated sodium bicarbonate solution. The layers were separated and the aqueous was extracted with two further portions of ethyl acetate. The combined organic extracts were washed with brine, then dried over sodium sulfate, decanted and concentrated. Flash chromatography, eluting with a gradient from 0-10% MeOH in DCM afforded the SEM-protected intermediate. Deprotection was effected by stirring with 1:1 TFA:DCM for 2 hours, then removal of solvent in vacuo followed by stirring with excess ethylenediamine in methanol until deprotection complete. The product was purified via preparative HPLC-MS (C18, eluting with a gradient of $H_2O$/MeCN containing 0.15% $NH_4OH$). The eluent containing the desired mass was frozen and lyophilized to afford product as the free base (0.137 g, 22%). $^1$H NMR (400 MHz, $CD_3OD$): δ 8.70 (s, 1H), 8.66 (s, 1H), 8.56 (d, 1H), 8.39 (d, 1H), 7.63 (dd, 1H), 7.50 (d, 1H), 6.97 (d, 1H), 6.94 (t, 1H), 3.85 (dd, 2H), 3.38 (dd, 2H), 3.34 (s, 2H), 3.10-3.02 (m, 2H), 2.95 (tt, 1H), 2.55-2.46 (m, 4H), 2.41 (dd, 2H); $^{19}$F NMR (376 MHz, $CD_3OD$): δ −119.68 (ddd, 2F), −132.42 (td, 1F); LCMS $(M+H)^+$: 536.0.

Example 12a

3-[(4-{cis-3-(cyanomethyl)-3-[4-(7H-pyrrolo[2,3-d]pyrimidin-4-yl)-1H-pyrazol-1-yl]cyclobutyl}piperazin-1-yl)carbonyl]-5-fluorobenzonitrile

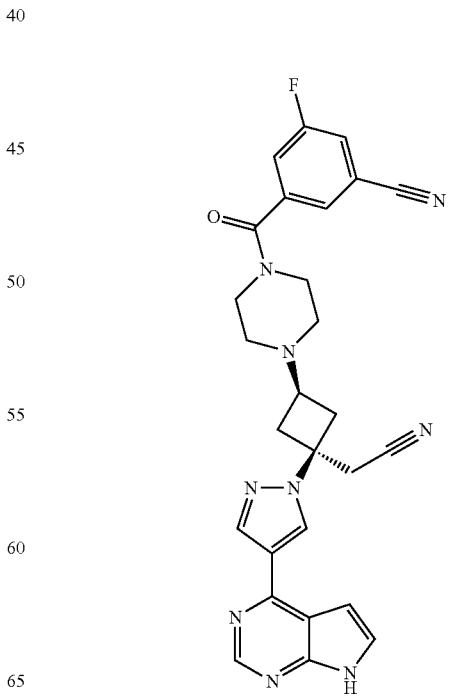

3-Cyano-5-fluorobenzoic acid (12 mg, 0.076 mmol, Oakwood) was coupled with {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.025 g, 0.051 mmol, prepared as in Example 1a, Step 9) by the procedure outlined in Step 6 of Example 11a, to afford 3-[(4-{cis-3-(cyanomethyl)-3-[4-(7H-pyrrolo[2,3-d]pyrimidin-4-yl)-1H-pyrazol-1-yl]cyclobutyl}piperazin-1-yl)carbonyl]-5-fluorobenzonitrile as the free base (11 mg, 41%). $^1$H NMR (400 MHz, d$_6$-dmso): δ 12.08 (br s, 1H), 8.70 (s, 1H), 8.68 (s, 1H), 8.40 (s, 1H), 7.97 (ddd, 1H), 7.78 (t, 1H), 7.69 (ddd, 1H), 7.60 (d, 1H), 7.06 (d, 1H), 3.69-3.56 (m, 2H), 3.50-3.22 (br m, 4H), 2.96 (tt, 1H), 2.69-2.56 (m, 4H), 2.44-2.24 (br m, 4H); $^{19}$F NMR (376 MHz, d$_6$-dmso): δ −109.87 (t, 1F); LCMS (M+H)$^+$: 509.9.

Example 12b

3-[(4-{trans-3-(cyanomethyl)-3-[4-(7H-pyrrolo[2,3-d]pyrimidin-4-yl)-1H-pyrazol-1-yl]cyclobutyl}piperazin-1-yl)carbonyl]-5-fluorobenzonitrile

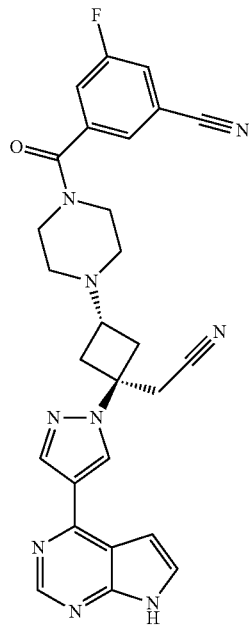 [SMILES: N#CC[C@]1(n2cc(-c3ncnc4[nH]ccc34)cn2)C[C@H](N2CCN(C(=O)c3cc(F)cc(C#N)c3)CC2)C1]

The procedure of Example 11a, Step 6 was followed, using {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, prepared as in Example 1b, Step 1) and 3-cyano-5-fluorobenzoic acid (0.015 g, 0.091 mmol, Oakwood) to afford product (0.01 g, 30%). $^1$H NMR (300 MHz, d$_6$-dmso): δ 12.12 (br s, 1H), 8.83 (s, 1H), 8.69 (s, 1H), 8.42 (s, 1H), 7.97 (ddd, 1H), 7.78 (s, 1H), 7.69 (ddd, 1H), 7.60 (d, 1H), 7.07 (d, 1H), 3.71-3.57 (m, 2H), 3.42 (s, 2H), 3.35-3.25 (m, 2H), 3.07-2.94 (m, 2H), 2.84 (tt, 1H), 2.46-2.24 (m, 6H); $^{19}$F NMR (282 MHz, d$_6$-dmso): δ −109.86 (t, 1F); LCMS (M+H)$^+$: 510.2.

Example 13a

[cis-1-[4-(7H-pyrrolo[2,3-d]pyrimidin-4-yl)-1H-pyrazol-1-yl]-3-(4-{[4-(trifluoromethyl)-1,3-thiazol-2-yl]carbonyl}piperazin-1-yl)cyclobutyl]acetonitrile

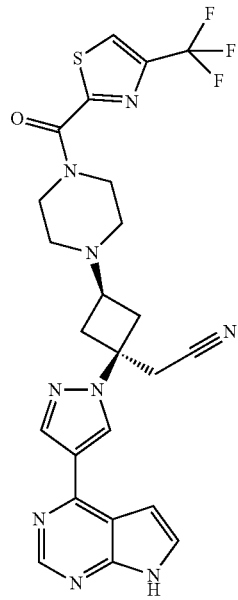 [SMILES: N#CC[C@]1(n2cc(-c3ncnc4[nH]ccc34)cn2)C[C@@H](N2CCN(C(=O)c3nc(C(F)(F)F)cs3)CC2)C1]

Using 4-(trifluoromethyl)-1,3-thiazole-2-carboxylic acid (15 mg, 0.076 mmol, SynQuest), and {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.025 g, 0.051 mmol, prepared as in Example 1a, Step 9) by the procedure analogous to Example 11a, Step 6, afforded [cis-1-[4-(7H-pyrrolo[2,3-d]pyrimidin-4-yl)-1H-pyrazol-1-yl]-3-(4-{[4-(trifluoromethyl)-1,3-thiazol-2-yl]carbonyl}piperazin-1-yl)cyclobutyl]acetonitrile (10 mg, 38%). $^1$H NMR (400 MHz, d$_6$-dmso): δ 12.11 (br s, 1H), 8.79 (d, 1H), 8.71 (s, 1H), 8.69 (s, 1H), 8.40 (s, 1H), 7.60 (d, 1H), 7.06 (d, 1H), 4.24-4.13 (m, 2H), 3.72-3.63 (m, 2H), 3.48 (s, 2H), 2.96 (tt, 1H), 2.71-2.56 (m, 4H), 2.48-2.39 (m, 4H); $^{19}$F NMR (376 MHz, d$_6$-dmso): δ −62.71 (s, 3F); LCMS (M+H)$^+$: 541.8.

Example 13b

[trans-1-[4-(7H-pyrrolo[2,3-d]pyrimidin-4-yl)-1H-pyrazol-1-yl]-3-(4-{[4-(trifluoromethyl)-1,3-thiazol-2-yl]carbonyl}piperazin-1-yl)cyclobutyl]acetonitrile

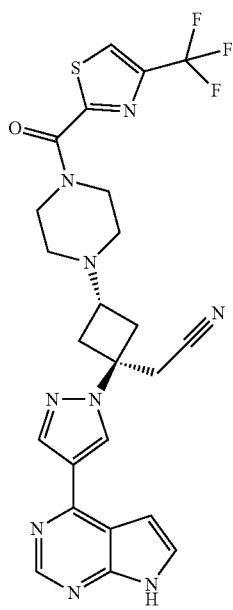 [SMILES: N#CC[C@]1(n2cc(-c3ncnc4[nH]ccc34)cn2)C[C@H](N2CCN(C(=O)c3nc(C(F)(F)F)cs3)CC2)C1]

To a solution of 4-(trifluoromethyl)-1,3-thiazole-2-carboxylic acid (0.021 g, 0.11 mmol, SynQuest), Triethylamine (0.038 mL, 0.27 mmol) and N,N,N',N'-tetramethyl-O-(7-azabenzotriazol-1-yl)uronium hexafluorophosphate (0.032 g, 0.085 mmol) in tetrahydrofuran (0.5 mL) was added {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.035 g, 0.071 mmol, prepared as in Example 1b, Step 1) as a solution in an aliquot of tetrahydrofuran (0.5 mL). The reaction was worked up by a partition between 1N NaOH and ethyl acetate. The aqueous portion was extracted with ethyl acetate three times. The combined organic extracts were dried over sodium sulfate, decanted and concentrated. The product was deprotected by stirring with 1:1 TFA:DCM for 2 hours, followed by removal of solvent in vacuo, then stirred with ethylenediamine 0.2 mL in methanol until deprotection was complete. The product was purified via preparative HPLC-MS (C18, eluting with a gradient of H$_2$O/MeCN containing 0.15% NH$_4$OH). The eluent containing the desired mass was frozen and lyophilized to afford product as the free base (0.007 g, 20%). $^1$H NMR (300 MHz, d6-dmso): δ 8.82 (s, 1H), 8.77 (d, 1H), 8.68 (s, 1H), 8.42 (s, 1H), 7.59 (d, 1H), 7.07 (d, 1H), 4.27-4.16 (m, 2H), 3.75-3.66 (m, 2H), 3.43 (s, 2H), 3.07-2.97 (m, 2H), 2.85 (tt, 1H), 2.48-2.34 (m, 6H); $^{19}$F NMR (282 MHz, d$_6$-dmso): δ −62.73 (s, 3F); LCMS (M+H)$^+$: 542.2.

Example 14a

[cis-1-[4-(7H-pyrrolo[2,3-d]pyrimidin-4-yl)-1H-pyrazol-1-yl]-3-(4-{[6-(trifluoromethyl)pyrazin-2-yl]carbonyl}piperazin-1-yl)cyclobutyl]acetonitrile

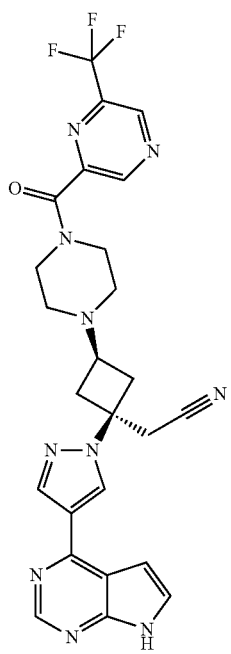 [SMILES: N#CC[C@]1(n2cc(-c3ncnc4[nH]ccc34)cn2)C[C@@H](N2CCN(C(=O)c3cncc(C(F)(F)F)n3)CC2)C1]

A solution of 6-(trifluoromethyl)pyrazine-2-carboxylic acid (15 mg, 0.076 mmol, Anichem), and {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.025 g, 0.051 mmol, prepared as in Example 1a, Step 9) were coupled and purified according to the procedure described for Example 11a, Step 6, to afford the product as the free base (7 mg, 20%). $^1$H NMR (300 MHz, d$_6$-dmso): δ 12.12 (br s, 1H), 9.30 (s, 1H), 9.20 (s, 1H), 8.70 (s, 1H), 8.68 (s, 1H), 8.40 (s, 1H), 7.60 (d, 1H), 7.06 (d, 1H), 3.75-3.65 (m, 2H), 3.48 (s, 2H), 3.46-3.40 (m, 2H), 2.97 (tt, 1H), 2.72-2.55 (m, 4H), 2.48-2.39 (m, 2H), 2.37-2.29 (m, 2H); $^{19}$F NMR (282 MHz, d$_6$-dmso): δ −66.71 (s, 3F); LCMS (M+H)$^+$: 537.2.

Example 14b

[trans-1-[4-(7H-pyrrolo[2,3-d]pyrimidin-4-yl)-1H-pyrazol-1-yl]-3-(4-{[6-(trifluoromethyl)pyrazin-2-yl]carbonyl}piperazin-1-yl)cyclobutyl]acetonitrile

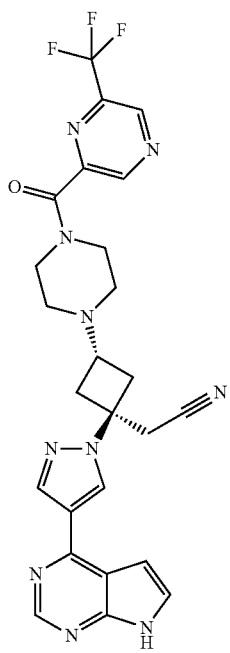 [SMILES: N#CC[C@]1(n2cc(-c3ncnc4[nH]ccc34)cn2)C[C@H](N2CCN(C(=O)c3cncc(C(F)(F)F)n3)CC2)C1]

A solution of 6-(trifluoromethyl)pyrazine-2-carboxylic acid (12 mg, 0.061 mmol, Anichem), and {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.025 g, 0.051 mmol, prepared as in Example 1b, Step 1) were coupled and purified according to the procedure described for Example 11a, Step 6, to afford the product as the free base (6 mg, 30%). $^1$H NMR (300 MHz, $d_6$-dmso): δ 12.12 (br s, 1H), 9.30 (s, 1H), 9.20 (s, 1H), 8.83 (s, 1H), 8.69 (s, 1H), 8.42 (s, 1H), 7.60 (d, 1H), 7.07 (d, 1H), 3.77-3.68 (m, 2H), 3.50-3.44 (m, 2H), 3.43 (s, 2H), 3.08-2.95 (m, 2H), 2.85 (tt, 1H), 2.48-2.29 (m, 6H); $^{19}$F NMR (282 MHz, $d_6$-dmso): δ −66.71 (s, 3F); LCMS (M+H)$^+$: 536.8.

Example 15a

{cis-3-[4-(3,4-difluorobenzoyl)piperazin-1-yl]-1-[4-(7H-pyrrolo[2,3-d]pyrimidin-4-yl)-1H-pyrazol-1-yl]cyclobutyl}acetonitrile

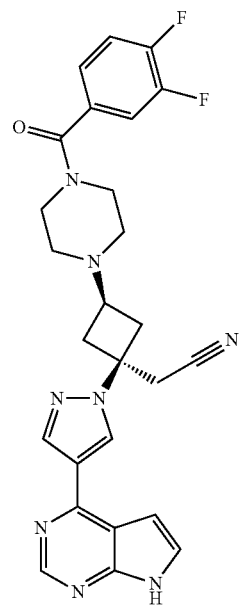 [SMILES: N#CC[C@]1(n2cc(-c3ncnc4[nH]ccc34)cn2)C[C@@H](N2CCN(C(=O)c3ccc(F)c(F)c3)CC2)C1]

To a solution of {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, prepared as in Example 1a, Step 9) in tetrahydrofuran (1 mL) was added triethylamine (0.025 mL, 0.18 mmol) followed by 3,4-difluorobenzoyl chloride (0.011 mL, 0.091 mmol, Aldrich). The reaction was stirred overnight, and then solvent was removed in vacuo. The crude product was deprotected by stirring with 1:1 TFA:DCM for 2 hours, then removal of solvent in vacuo, followed by stirring with excess ethylenediamine (0.2 mL) in methanol for 2 hours. The product was purified via preparative HPLC-MS (C18, eluting with a gradient of $H_2O$/MeCN containing 0.15% $NH_4OH$). The eluent containing the desired mass was frozen and lyophilized to afford product as the free base (0.01 g, 30%). $^1$H NMR (400 MHz, $d_6$-dmso): δ 12.11 (br s, 1H), 8.70 (s, 1H), 8.68 (s, 1H), 8.39 (s, 1H), 7.60 (d, 1H), 7.56-7.47 (m, 2H), 7.29-7.24 (m, 1H), 7.06 (d, 1H), 3.61 (br, 2H), 3.47 (s, 2H), 3.40-3.26 (br, 2H), 2.95 (tt, 1H), 2.69-2.55

(m, 4H), 2.44-2.21 (br m, 4H); ¹⁹F NMR (376 MHz, d₆-dmso): δ −137.34 (dddd, 1F), −138.23 (ddd, 1F); LCMS (M+H)⁺: 503.1.

Example 15b

{trans-3-[4-(3,4-difluorobenzoyl)piperazin-1-yl]-1-[4-(7H-pyrrolo[2,3-d]pyrimidin-4-yl)-1H-pyrazol-1-yl]cyclobutyl}acetonitrile The procedure of Example 15a was followed, on the same scale, using {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (prepared as in Example 1b, Step 1) to afford product as the free base (0.01 g, 30%). ¹H NMR (400 MHz, d₆-dmso): δ 8.83 (s, 1H), 8.69 (s, 1H), 8.42 (s, 1H), 7.60 (d, 1H), 7.56-7.46 (m, 2H), 7.29-7.24 (m, 1H), 7.07 (d, 1H), 3.63 (br, 2H), 3.42 (s, 2H), 3.40-3.27 (br, 2H), 3.05-2.97 (m, 2H), 2.83 (tt, 1H), 2.43-2.22 (m, 6H); ¹⁹F NMR (376 MHz, d₆-dmso): δ −137.32 (dddd, 1F), −138.22 (ddd, 1F); LCMS (M+H)⁺: 503.1.

Example 16a

{cis-3-[4-(2-chloro-3,6-difluorobenzyl)piperazin-1-yl]-1-[4-(7H-pyrrolo[2,3-d]pyrimidin-4-yl)-1H-pyrazol-1-yl]cyclobutyl}acetonitrile

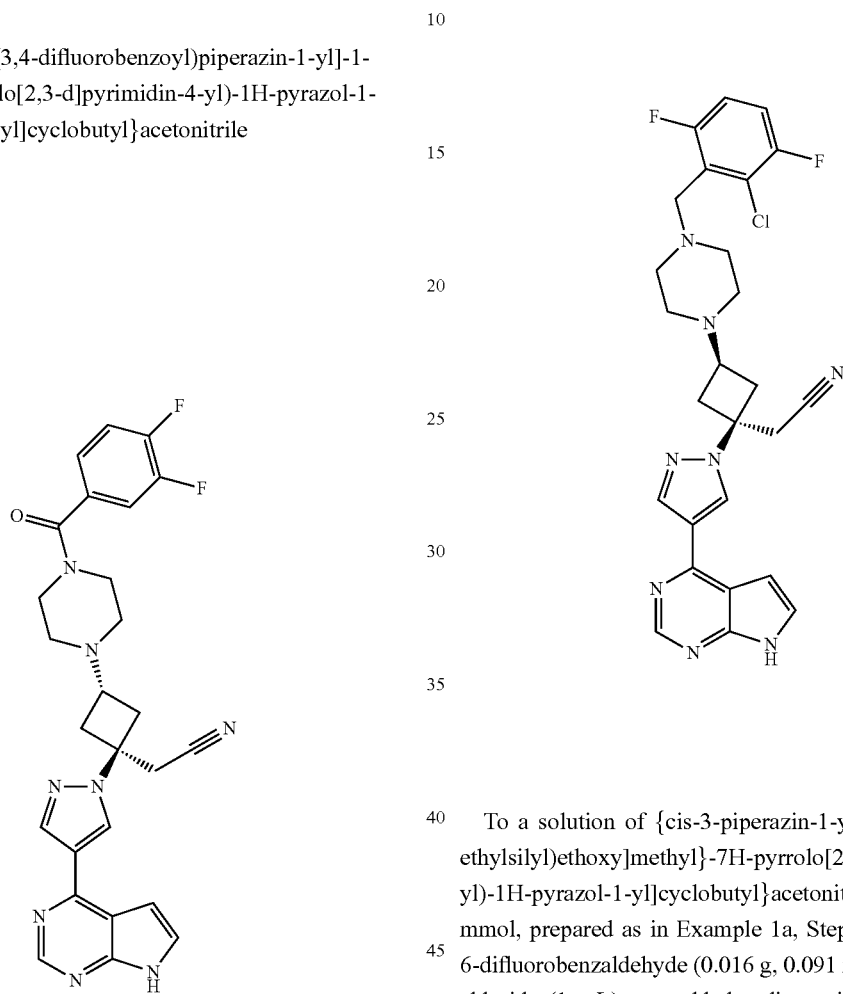

To a solution of {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, prepared as in Example 1a, Step 9) and 2-chloro-3,6-difluorobenzaldehyde (0.016 g, 0.091 mmol) in methylene chloride (1 mL) was added sodium triacetoxyborohydride (0.052 g, 0.24 mmol) and the reaction was stirred overnight. The reaction mixture was partitioned between 1N NaOH, brine and DCM. The aqueous portion was extracted with three portions of DCM. The combined extracts were dried over sodium sulfate, decanted and concentrated. The crude product was deprotected by stirring with 1:1 TFA:DCM for 2 hours. Solvent was then removed in vacuo, and the residue was stirred with 0.3 mL ethylenediamine in methanol until the deprotection was complete. The product was purified via preparative HPLC-MS (C18, eluting with a gradient of H₂O/MeCN containing 0.15% NH₄OH). The eluent containing the desired mass was frozen and lyophilized to afford product as the free base (0.015 g, 47%). ¹H NMR (400 MHz, d₆-dmso): δ 12.11 (br s, 1H), 8.68 (s, 2H), 8.38 (s, 1H), 7.60 (d, 1H), 7.44 (ddd, 1H), 7.30 (ddd, 1H), 7.05 (d, 1H), 3.61

(s, 2H), 3.45 (s, 2H), 2.87 (tt, 1H), 2.61-2.13 (m, 12H); $^{19}$F NMR (376 MHz, d$_6$-dmso): δ −117.52−−117.64 (m, 1F), −118.99 (ddd, 1F); LCMS (M+H)$^+$: 523.2/525.2.

Example 16b

{trans-3-[4-(2-chloro-3,6-difluorobenzyl)piperazin-1-yl]-1-[4-(7H-pyrrolo[2,3-d]pyrimidin-4-yl)-1H-pyrazol-1-yl]cyclobutyl}acetonitrile

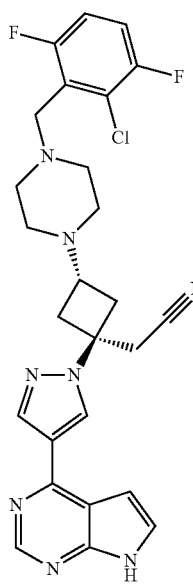

The procedure of Example 16a was followed, on the same scale, using {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, prepared as in Example 1b, Step 1) to afford product as the free base (0.015 g, 47%). $^1$H NMR (400 MHz, d$_6$-dmso): δ 12.11 (br s, 1H), 8.80 (s, 1H), 8.68 (s, 1H), 8.40 (s, 1H), 7.59 (d, 1H), 7.45 (td, 1H), 7.30 (td, 1H), 7.06 (d, 1H), 3.62 (s, 2H), 3.40 (s, 2H), 3.50-2.92 (m, 2H), 2.74 (tt, 1H), 2.58-2.18 (m, 10H); $^{19}$F NMR (376 MHz, d$_6$-dmso): δ −117.46−−117.65 (m, 1F), −118.89−−119.07 (m, 1F); LCMS (M+H)$^+$: 522.9.

Example 17

{cis-3-{4-[3-fluoro-5-(trifluoromethyl)benzoyl]piperazin-1-yl}-1-[4-(7H-pyrrolo[2,3-d]pyrimidin-4-yl)-1H-pyrazol-1-yl]cyclobutyl}acetonitrile

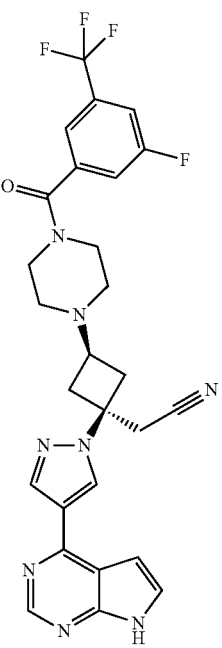 [SMILES: N#CC[C@]1(n2cc(-c3ncnc4[nH]ccc34)cn2)C[C@@H](N2CCN(C(=O)c3cc(F)cc(C(F)(F)F)c3)CC2)C1]

The procedure of Example 15a was followed, using 3-fluoro-5-(trifluoromethyl)benzoyl chloride (17 mg, 0.076 mmol, Aldrich) and {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.025 g, 0.051 mmol, prepared as in Example 1a, Step 9) to afford product as the free base (11 mg, 40%). $^1$H NMR (400 MHz, d$_6$-dmso): δ 12.12 (br s, 1H), 8.70 (s, 1H), 8.68 (s, 1H), 8.39 (s, 1H), 7.83-7.79 (m, 1H), 7.68-7.64 (m, 1H), 7.63 (br s, 1H), 7.60 (d, 1H), 7.06 (d, 1H), 3.64 (br, 2H), 3.47 (s, 2H), 3.29 (br, 2H), 2.96 (tt, 1H), 2.68-2.56 (m, 4H), 2.41 (br, 2H), 2.30 (br, 2H); $^{19}$F NMR (376 MHz, d$_6$-dmso): δ −61.61 (s, 3F), −109.91 (dd, 1F); LCMS (M+H)$^+$: 553.0.

Example 18

{trans-3-{4-[2-fluoro-4-(trifluoromethyl)benzoyl]
piperazin-1-yl}-1-[4-(7H-pyrrolo[2,3-d]pyrimidin-4-
yl)-1H-pyrazol-1-yl]cyclobutyl}acetonitrile 2.3×
(trifluoroacetate) Salt

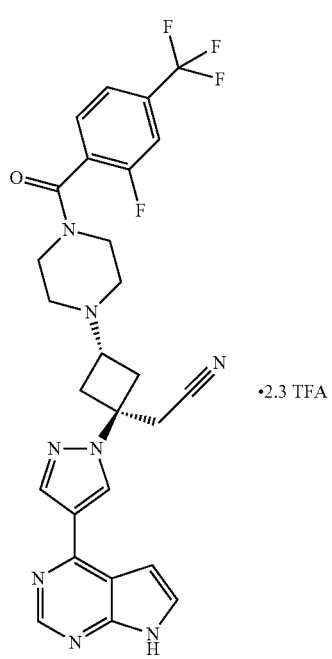 [SMILES: N#CC[C@]1(n2cc(-c3ncnc4[nH]ccc34)cn2)C[C@H](N2CCN(C(=O)c3ccc(C(F)(F)F)cc3F)CC2)C1]

·2.3 TFA

To a solution of {trans-3-piperazin-1-yl-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.033 g, 0.067 mmol, prepared as in Example 1b, Step 1) and triethylamine (0.0373 mL, 0.268 mmol) in acetonitrile (0.5 mL) was added 2-fluoro-4-(trifluoromethyl)benzoyl chloride (0.018 g, 0.080 mmol, Aldrich). The reaction was stirred for 2 hours, then was worked up by partition between 1 N NaOH and ethyl acetate. The organic layer was dried over sodium sulfate, decanted and concentrated. The crude product was deprotected by stirring with 1:1 DCM:TFA for 1 hour, followed by removal of solvents in vacuo, and stirring with excess ethylenediamine in methanol. The product was purified via preparative HPLC-MS (C18, eluting with a gradient of $H_2O$/MeCN containing 0.1% TFA). The eluent containing the desired mass was frozen and lyophilized to afford product as the 2.3×TFA salt (0.01 g, 20%). $^1$H NMR (400 MHz, $d_6$-dmso): δ 12.41 (s, 1H), 8.98 (s, 1H), 8.77 (s, 1H), 8.51 (s, 1H), 7.87 (d, 1H), 7.74-7.72 (m, 2H), 7.71 (dd, 1H), 7.16 (dd, 1H), 3.96-2.73 (m, 15H); $^{19}$F NMR (376 MHz, $d_6$-dmso): δ −61.78 (s, 3F), −74.59 (s, 6.9 F), −113.97 (br s, 1F); LCMS (M+H)$^+$: 553.3.

Example 19

{trans-3-[4-(pyrrolidin-1-ylcarbonyl)piperazin-1-yl]-
1-[4-(7H-pyrrolo[2,3-d]pyrimidin-4-yl)-1H-pyrazol-
1-yl]cyclobutyl}acetonitrile

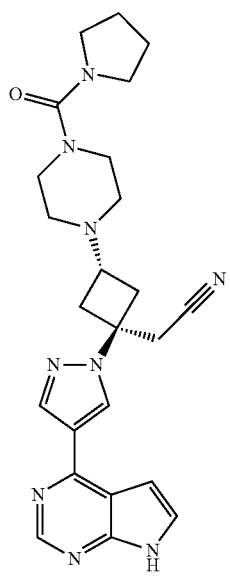 [SMILES: N#CC[C@]1(n2cc(-c3ncnc4[nH]ccc34)cn2)C[C@H](N2CCN(C(=O)N3CCCC3)CC2)C1]

To a solution of {trans-3-piperazin-1-yl-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.035 g, 0.071 mmol, prepared as in Example 1b, Step 1) and Triethylamine (0.030 mL, 0.21 mmol) in Methylene chloride (1 mL) was added 1-pyrrolidinecarbonyl chloride (0.010 mL, 0.092 mmol, Aldrich). After stirring overnight, solvent was removed in vacuo. The residue was stirred with 1:1 TFA:DCM for 2 hours, then solvents were again evaporated and the residue stirred with 0.2 mL ethylenediamine in methanol until the deprotection was complete. The product was purified via preparative HPLC-MS (C18, eluting with a gradient of $H_2O$/MeCN containing 0.15% $NH_4OH$). The eluent containing the desired mass was frozen and lyophilized to afford product as the free base (0.007 g, 20%). $^1$H NMR (300 MHz, $d_6$-dmso): δ 12.11 (br s, 1H), 8.82 (s, 1H), 8.69 (s, 1H), 8.41 (s, 1H), 7.60 (d, 1H), 7.07 (d, 1H), 3.42 (s, 2H), 3.38-3.10 (m, 8H), 3.06-2.93 (m, 2H), 2.78 (tt, 1H), 2.44-2.23 (m, 6H), 1.79-1.67 (m, 4H); LCMS (M+H)$^+$: 460.0.

Example 20a

{cis-1-[4-(7H-pyrrolo[2,3-d]pyrimidin-4-yl)-1H-pyrazol-1-yl]-3-(4-{[6-(trifluoromethyl)pyridin-2-yl]carbonyl}piperazin-1-yl)cyclobutyl}acetonitrile

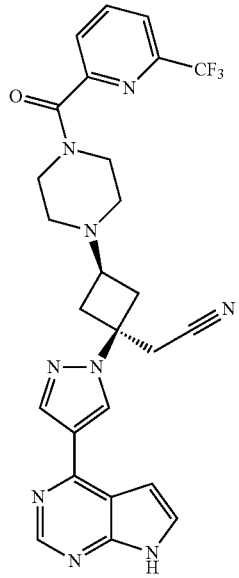 [SMILES: N#CC[C@]1(n2cc(-c3ncnc4[nH]ccc34)cn2)C[C@@H](N2CCN(C(=O)c3cccc(C(F)(F)F)n3)CC2)C1]

The method of Example 11a, Step 6 was followed, using 6-(trifluoromethyl)pyridine-2-carboxylic acid (0.014 g, 0.076 mmol, Matrix) and {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.025 g, 0.051 mmol, prepared as in Example 1a, Step 9) to afford product as the free base (0.007 g, 20%). $^1$H NMR (300 MHz, $d_6$-dmso): δ 12.11 (br s, 1H), 8.70 (s, 1H), 8.68 (s, 1H), 8.39 (s, 1H), 8.24 (t, 1H), 8.01 (dd, 1H), 7.90 (d, 1H), 7.60 (d, 1H), 7.06 (d, 1H), 3.72-3.62 (m, 2H), 3.48 (s, 2H), 3.40-3.28 (m, 2H), 2.96 (tt, 1H), 2.70-2.55 (m, 4H), 2.47-2.39 (m, 2H), 2.36-2.25 (m, 2H); $^{19}$F NMR (282 MHz, $d_6$-dmso): δ −66.96 (s, 3F); LCMS (M+H)$^+$: 536.2.

Example 20b

{trans-1-[4-(7H-pyrrolo[2,3-d]pyrimidin-4-yl)-1H-pyrazol-1-yl]-3-(4-{[6-(trifluoromethyl)pyridin-2-yl]carbonyl}piperazin-1-yl)cyclobutyl}acetonitrile

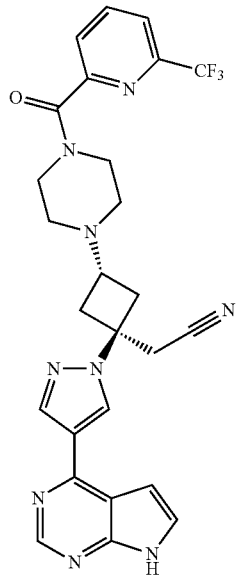 [SMILES: N#CC[C@]1(n2cc(-c3ncnc4[nH]ccc34)cn2)C[C@H](N2CCN(C(=O)c3cccc(C(F)(F)F)n3)CC2)C1]

The method of Example 11a was followed, using 6-(trifluoromethyl)pyridine-2-carboxylic acid (0.012 g, 0.061 mmol, Matrix) and {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.020 g, 0.040 mmol, prepared as in Example 1b, Step 1) to afford product as the free base (0.006 g, 30%). $^1$H NMR (300 MHz, $d_6$-dmso): δ 12.13 (br s, 1H), 8.82 (s, 1H), 8.69 (s, 1H), 8.42 (s, 1H), 8.24 (t, 1H), 8.01 (d, 1H), 7.90 (d, 1H), 7.60 (d, 1H), 7.07 (d, 1H), 3.76-3.65 (m, 2H), 3.43 (s, 2H), 3.42-3.36 (m, 2H), 3.07-2.94 (m, 2H), 2.84 (tt, 1H), 2.47-2.24 (m, 6H); $^{19}$F NMR (282 MHz, $d_6$-dmso): δ −66.95 (s, 3F); LCMS (M+H)$^+$: 535.9.

Example 21a

{cis-3-(4-{[6-(difluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

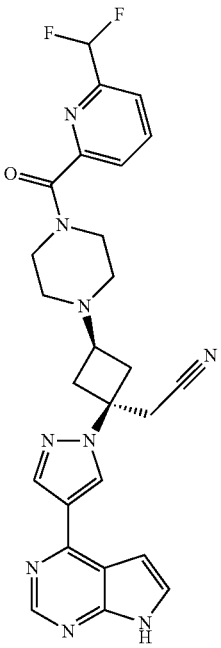 [SMILES: N#CC[C@]1(n2cc(-c3ncnc4[nH]ccc34)cn2)C[C@@H](N2CCN(C(=O)c3cccc(C(F)F)n3)CC2)C1]

Step 1. methyl 6-(difluoromethyl)pyridine-2-carboxylate

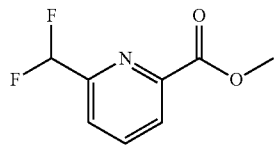

To a solution of methyl 6-formylpyridine-2-carboxylate (1.00 g, 6.06 mmol) (ChemBridge Building Blocks) in methylene chloride (35 mL) containing a small amount of ethanol (0.1 mL) at 0° C. was added Deoxo-Fluor® (4.46 mL, 24.2 mmol, Aldrich). After 3 hours, the reaction was cooled in an ice bath and quenched by the addition of water.

The product was extracted with three portions of DCM. The combined extracts were washed with water, dried over sodium sulfate, decanted and concentrated, to afford product which was used without further purification (1.1 g, 100%). $^1$H NMR (300 MHz, CDCl$_3$): δ 8.27-8.22 (m, 1H), 8.02 (t, 1H), 7.85 (dd, 1H), 6.75 (t, 1H), 4.03 (s, 3H); LCMS (M+H)$^+$: 187.9.

Step 2. 6-(difluoromethyl)pyridine-2-carboxylic acid

To a solution of methyl 6-(difluoromethyl)pyridine-2-carboxylate (0.58 g, 3.1 mmol, from Step 1) in Water (22 mL) and Tetrahydrofuran (20 mL, 250 mmol) was added Lithium hydroxide, monohydrate (0.65 g, 15 mmol). The reaction was stirred for 2 hours. The basic mixture was extracted with ether, which was discarded. The mixture was then acidified by the addition of 1 N HCl and the volume of solvent reduced in vacuo. The product was purified via preparative HPLC-MS (C18, eluting with a gradient of H$_2$O/MeCN containing 0.1% TFA). The eluent containing the desired mass was evaporated by rotary evaporation to afford a solid product (0.35 g, 65%). $^1$H NMR (400 MHz, CD$_3$OD): δ 8.27 (ddd, 1H), 8.17 (dd, 1H), 7.92 (dd, 1H), 6.78 (t, 1H); $^1$H NMR (400 MHz, CD$_3$OD): δ −117.52 (d, 2F); LCMS (M+H)$^+$: 173.9.

Step 3. {cis-3-(4-{[6-(difluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

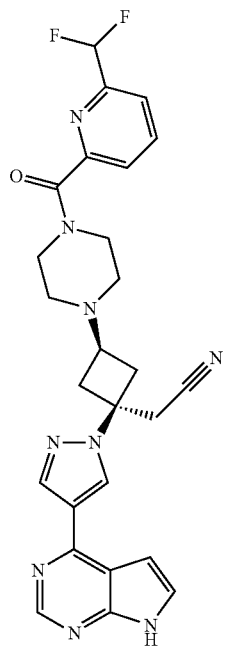 [SMILES: N#CC[C@]1(n2cc(-c3ncnc4[nH]ccc34)cn2)C[C@@H](N2CCN(C(=O)c3cccc(C(F)F)n3)CC2)C1]

The procedure of Example 11a (Step 6) was followed, using 6-(difluoromethyl)pyridine-2-carboxylic acid (0.016 g, 0.091 mmol, from Step 2) and {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, prepared as in Example 1a, Step 9), except that in the work up after coupling, dilute HCl wash was omitted. The purification afforded product as the free base (0.01 g, 30%). $^1$H NMR (300 MHz, CD$_3$OD): δ 8.66 (s, 1H), 8.64 (s, 1H), 8.37 (s, 1H), 8.11 (dd, 1H), 7.76 (dd, 1H), 7.51 (d, 1H), 6.98 (d, 1H), 6.73 (t, 1H), 3.86-3.77 (m, 2H), 3.60-3.49 (m, 2H), 3.34 (s, 2H), 3.01 (tt, 1H), 2.89-2.76 (m, 2H), 2.76-2.65 (m, 2H), 2.61-2.52 (m, 2H), 2.51-2.42 (m, 2H); $^{19}$F NMR (282 MHz, CD$_3$OD): δ −118.19 (d, 2F); LCMS (M+H)$^+$: 517.9.

Example 21b

{trans-3-(4-{[6-(difluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

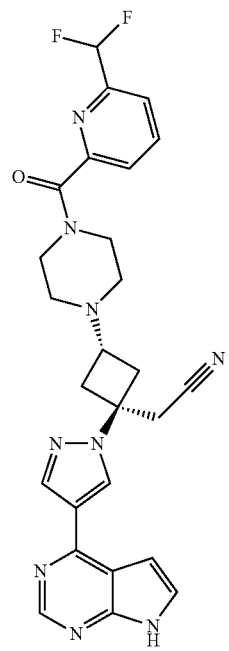 [SMILES: N#CC[C@]1(n2cc(-c3ncnc4[nH]ccc34)cn2)C[C@H](N2CCN(C(=O)c3cccc(C(F)F)n3)CC2)C1]

The procedure of Example 11a (Step 6) was followed, using 6-(difluoromethyl)pyridine-2-carboxylic acid (0.016 g, 0.091 mmol, Example 21a, Step 2) and {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, prepared as in Example 1b, Step 1) except that in the workup after coupling, the dilute HCl wash was omitted. The purification afforded product as the free base (0.01 g, 30%). $^1$H NMR (400 MHz, d$_6$-dmso): δ 12.11 (br s, 1H), 8.83 (s, 1H), 8.69 (s, 1H), 8.42 (s, 1H), 8.13 (dd, 1H), 7.79 (d, 1H), 7.75 (d, 1H), 7.60 (d, 1H), 7.07 (d, 1H), 6.98 (t, 1H), 3.73-3.66 (m, 2H), 3.43 (s, 2H), 3.41-3.37 (m, 2H), 3.05-2.96 (m, 2H), 2.84 (tt, 1H), 2.46-2.27 (m, 6H); $^{19}$F NMR (376 MHz, d$_6$-dmso): δ −116.20 (d, 2F); LCMS (M+H)$^+$: 517.8.

Example 22

{cis-3-{4-[2-fluoro-3-(trifluoromethyl)benzoyl]piperazin-1-yl}-1-[4-(7H-pyrrolo[2,3-d]pyrimidin-4-yl)-1H-pyrazol-1-yl]cyclobutyl}acetonitrile

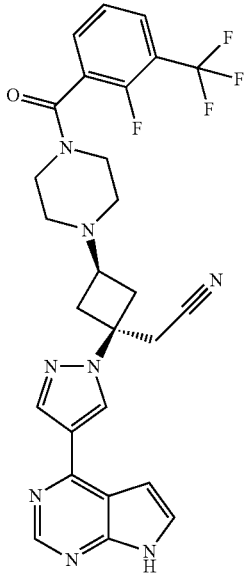 [SMILES: N#CC[C@]1(n2cc(-c3ncnc4[nH]ccc34)cn2)C[C@@H](N2CCN(C(=O)c3cccc(C(F)(F)F)c3F)CC2)C1]

The procedure of Example 8b was followed, using {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (25 mg, 0.051 mmol, from Example 1a, Step 9) and 2-fluoro-3-(trifluoromethyl)benzoyl chloride (23 mg, 0.101 mmol). Purification afforded product as the free base (15 mg, 54%). $^1$H NMR (300 MHz, d$_6$-dmso): δ 12.10 (br s, 1H), 8.70 (s, 1H), 8.68 (s, 1H), 8.39 (s, 1H), 7.88 (ddd, 1H), 7.77 (ddd, 1H), 7.60 (d, 1H), 7.50 (dd, 1H), 7.06 (d, 1H), 3.67 (br, 2H), 3.47 (s, 2H), 3.26-3.19 (m, 2H), 2.96 (tt, 1H), 2.69-2.54 (m, 4H), 2.40 (br s, 2H), 2.29 (br s, 2H); LCMS (M+H)$^+$: 553.3.

Example 23a

{cis-3-{4-[(5-fluoropyridin-3-yl)methyl]piperazin-1-yl}-1-[4-(7H-pyrrolo[2,3-d]pyrimidin-4-yl)-1H-pyrazol-1-yl]cyclobutyl}acetonitrile

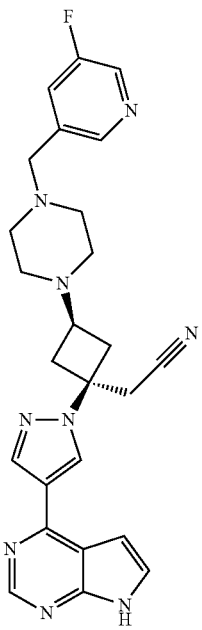 [SMILES: N#CC[C@]1(n2cc(-c3ncnc4[nH]ccc34)cn2)C[C@@H](N2CCN(Cc3cncc(F)c3)CC2)C1]

{cis-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, prepared as in Example 1a, Step 9) and 5-fluoronicotinaldehyde (0.011 g, 0.085 mmol) were combined in methylene chloride (1 mL) and after 10 minutes, sodium triacetoxyborohydride (0.0516 g, 0.244 mmol) was added. The reaction was continued overnight. The reaction mixture was partitioned between water and ethyl acetate. The aqueous portion was extracted a further two times with ethyl acetate. The combined extracts were washed with water, then brine, dried over sodium sulfate, decanted and concentrated. The crude product was deprotected by first stirring the residue in a 1:1 mix of TFA:DCM (4 mL) for 2 hours, followed by removal of the solvents in vacuo and then stirring with 0.2 mL ethylenediamine in 2 mL methanol overnight. The solution was filtered and the product was purified via preparative HPLC-MS (C18, eluting with a gradient of H$_2$O/MeCN containing 0.15% NH$_4$OH). The eluent containing the desired mass was frozen and lyophilized to afford product as the free base (0.01 g, 30%). $^1$H NMR (400 MHz, CDCl$_3$): δ 10.13 (br s, 1H), 8.82 (s, 1H), 8.37 (d, 1H), 8.35 (dd, 1H), 8.33 (s, 1H), 8.27 (s, 1H), 7.43 (ddd, 1H), 7.37 (dd, 1H), 6.76 (dd, 1H), 3.54 (s, 2H), 3.13 (s, 2H), 2.89 (tt, 1H), 2.84-2.76 (m, 2H), 2.75-2.67 (m, 2H), 2.64-2.27 (br, 8H); $^{19}$F NMR (376 MHz, d$_6$-dmso): δ −128.43 (dd, 1F); LCMS (M+H)$^+$: 472.5.

Example 23b

{trans-3-{4-[(5-fluoropyridin-3-yl)methyl]piperazin-1-yl}-1-[4-(7H-pyrrolo[2,3-d]pyrimidin-4-yl)-1H-pyrazol-1-yl]cyclobutyl}acetonitrile

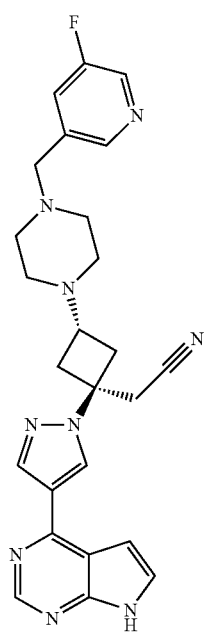 [SMILES: N#CC[C@]1(n2cc(-c3ncnc4[nH]ccc34)cn2)C[C@H](N2CCN(Cc3cncc(F)c3)CC2)C1]

The procedure of Example 23a was followed, using {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, prepared as in Example 1b, Step 1) and 5-fluoronicotinaldehyde (0.011 g, 0.085 mmol). Purification by the same method afforded product as the free base (0.01 g, 30%). $^1$H NMR (400 MHz, CDCl$_3$): δ 10.02 (br s, 1H), 8.85 (s, 1H), 8.48 (s, 1H), 8.37 (d, 1H), 8.36 (dd, 1H), 8.34 (s, 1H), 7.44 (ddd, 1H), 7.40 (dd, 1H), 6.81 (dd, 1H), 3.56 (s, 2H), 3.22 (s, 2H), 3.05-2.96 (m, 2H), 2.92 (tt, 1H), 2.68-2.22 (m, 10H); $^{19}$F NMR (376 MHz, d$_6$-dmso): δ −128.41 (dd, 1F); LCMS (M+H)$^+$: 472.5.

Example 24a

{cis-3-{4-[(2-isopropylpyrimidin-4-yl)carbonyl]piperazin-1-yl}-1-[4-(7H-pyrrolo[2,3-d]pyrimidin-4-yl)-1H-pyrazol-1-yl]cyclobutyl}acetonitrile

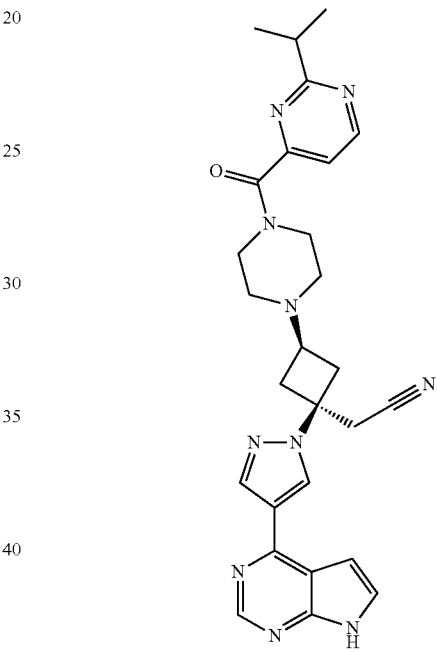

Step 3 of Example 21a was followed, using 2-isopropylpyrimidine-4-carboxylic acid (0.013 g, 0.076 mmol, ChemBridge), and {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.025 g, 0.051 mmol, prepared according to the procedure in Example 1a) to afford the product as the free base (0.010 g, 38%). $^1$H NMR (300 MHz, d$_6$-dmso): δ 12.13 (br s, 1H), 8.88 (d, 1H), 8.70 (s, 1H), 8.68 (s, 1H), 8.40 (s, 1H), 7.60 (d, 1H), 7.45 (d, 1H), 7.06 (d, 1H), 3.69-3.60 (m, 2H), 3.47 (s, 2H), 3.38-3.32 (m, 2H), 3.15 (sept, 1H), 2.96 (tt, 1H), 2.69-2.54 (m, 4H), 2.45-2.38 (m, 2H), 2.37-2.29 (m, 2H), 1.27 (d, 6H); LCMS (M+H)$^+$: 511.4.

Example 25

{trans-3-[4-(piperidin-1-ylcarbonyl)piperazin-1-yl]-1-[4-(7H-pyrrolo[2,3-d]pyrimidin-4-yl)-1H-pyrazol-1-yl]cyclobutyl}acetonitrile

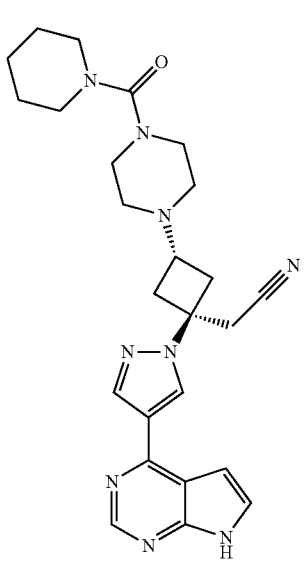 [SMILES: N#CC[C@]1(n2cc(-c3ncnc4[nH]ccc34)cn2)C[C@H](N2CCN(C(=O)N3CCCCC3)CC2)C1]

Piperidine (0.020 mL, 0.203 mmol, Aldrich) was dissolved in methylene chloride (0.18 mL) and acetonitrile (0.5 mL), and 1.89 M phosgene in toluene (0.161 mL, 0.304 mmol) was introduced, followed by diisopropylethylamine (0.177 mL, 1.01 mmol). The reaction mixture was stirred for 1 hour, and the solvent and excess phosgene was removed in vacuo. N,N-Diisopropylethylamine (0.100 mL, 0.574 mmol) was again added, followed by acetonitrile (0.5 mL). To this solution was added {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.050 g, 0.10 mmol, prepared as in Example 1b, Step 1) in acetonitrile (1 mL). The reaction was stirred overnight and then solvent and excess reagents were removed by evaporation. The crude product was deprotected by stirring with 1:1 TFA:DCM for 2 hours, then evaporation, followed by stirring with excess ethylenediamine in methanol until deprotection was complete. The product was purified via preparative HPLC-MS (C18, eluting with a gradient of H$_2$O/MeCN containing 0.15% NH$_4$OH). The eluent containing the desired mass was frozen and lyophilized to afford product as the free base (0.02 g, 40%). $^1$H NMR (300 MHz, d$_6$-dmso): δ 12.12 (br s, 1H), 8.82 (s, 1H), 8.69 (s, 1H), 8.42 (s, 1H), 7.60 (d, 1H), 7.07 (d, 1H), 3.42 (s, 2H), 3.17-3.05 (m, 8H), 3.04-2.94 (m, 2H), 2.79 (tt, 1H), 2.41-2.24 (m, 6H), 1.57-1.39 (m, 6H); LCMS (M+H)$^+$: 474.1.

Example 26

{cis-3-{4-[4-fluoro-3-(trifluoromethoxy)benzoyl]piperazin-1-yl}-1-[4-(7H-pyrrolo[2,3-d]pyrimidin-4-yl)-1H-pyrazol-1-yl]cyclobutyl}acetonitrile To a mixture of 4-fluoro-3-(trifluoromethoxy)benzoic acid (17.0 mg, 0.0761 mmol, JRD Fluorochem), N,N,N',N'-tetramethyl-O-(7-azabenzotriazol-1-yl)uronium hexafluorophosphate (23.2 mg, 0.0609 mmol) and triethylamine (42.4 μL, 0.304 mmol) in tetrahydrofuran (0.50 mL) that was pre-stirred at room temperature for 15 minutes, was added {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (25 mg, 0.051 mmol, prepared as in Example 1a). The mixture was stirred for one hour and was diluted with ethyl acetate and water. The mixture was shaken and the layers separated. The organic layer was washed with water, 0.1N NaOH and sat. NaCl solution, dried over sodium sulfate, decanted and concentrated. The residue was dissolved in a 1:1 mixture of DCM:TFA, and stirred for 1 hour. The solvents were removed in vacuo and the residue was dissolved in 1 mL methanol and 0.2 ml ethylenediamine. This solution was stirred for one hour. The product was purified via preparative HPLC-MS (C18, eluting with a gradient of H$_2$O/MeCN containing 0.15% NH$_4$OH). The eluent containing the desired mass was frozen and lyophilized to afford product as the free base (0.012 g, 42%). $^1$H NMR (300 MHz, d$_6$-dmso): δ 8.70 (s, 1H), 8.68 (s, 1H), 8.39 (s, 1H), 7.64 (ddd, 1H), 7.60 (d, 1H), 7.59 (dd, 1H), 7.51 (ddd, 1H), 7.05 (d, 1H), 3.61 (br, 2H), 3.47 (s, 2H), 2.95 (tt, 1H), 2.70-2.54 (m, 4H), 2.42-2.22 (m, 4H); LCMS (M+H)$^+$: 569.3.

Example 27

{cis-3-(4-{[3-fluoro-5-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

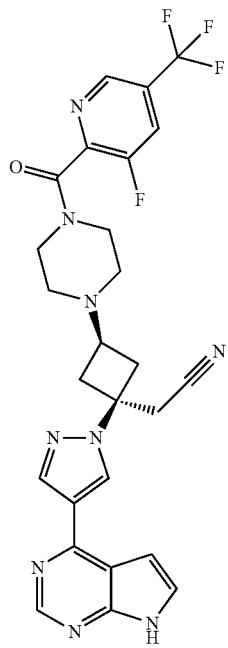 [SMILES: N#CC[C@]1(n2cc(-c3ncnc4[nH]ccc34)cn2)C[C@@H](N2CCN(C(=O)c3ncc(C(F)(F)F)cc3F)CC2)C1]

Step 1.
2-bromo-3-fluoro-5-(trifluoromethyl)pyridine

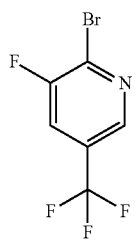

A mixture of 3-fluoro-5-(trifluoromethyl)pyridin-2-ol (1.0 g, 5.5 mmol, Matrix) and phosphoric tribromide (1.6 g, 5.5 mmol) in N,N-dimethylformamide (2.9 mL, 38 mmol) was heated to 130° C. for 70 minutes. After cooling to room temperature, the mixture was poured onto a mixture of ice and sodium bicarbonate solution (final pH=8). The product was extracted with diethyl ether. The extract was washed with water (twice), followed by brine, dried and solvent removed in vacuo. Flash chromatography, eluting with a gradient from 0-10% ethyl acetate in hexanes afforded product as a colorless oil (0.59 g, 44%). $^1$H NMR (400 MHz, CDCl$_3$): δ 8.53-8.50 (m, 1H), 7.66 (dd, 1H).

Step 2.
3-fluoro-5-(trifluoromethyl)pyridine-2-carboxylic acid

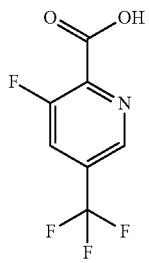

2.5 M n-Butyllithium in hexane (1.1 mL, 2.7 mmol) was added to toluene (3.0 mL, 29 mmol) at −75° C. A solution of 2-bromo-3-fluoro-5-(trifluoromethyl)pyridine (0.59 g, 2.4 mmol, from Step 1) in toluene (0.50 mL) was added. After one hour at −75° C., CO$_2$ gas (generated by the evaporation of dry ice in a flask on the side and directed into the reaction flask, sub-surface, via cannula) was bubbled through the solution at −75° C. for 15 minutes, and continued as the reaction warmed to ambient temperature. Solvent was evaporated. The residue was mixed with 4 mL of water, and this aqueous mixture was washed with ether (2×2 ml), and these extracts discarded. The aqueous was then acidifed by the addition of concentrated HCl to pH 1. The resulting light yellow precipitate was collected by filtration (0.30 g, 59%). $^1$H NMR (300 MHz, CDCl$_3$): δ 8.78 (s, 1H), 7.93 (d, 1H); LCMS (M+H)$^+$: 210.1.

Step 3. {cis-3-(4-{[3-fluoro-5-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

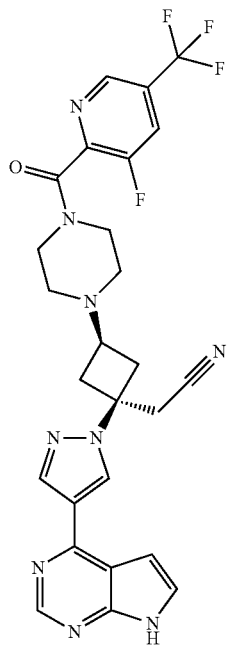 [SMILES: N#CC[C@]1(n2cc(-c3ncnc4[nH]ccc34)cn2)C[C@@H](N2CCN(C(=O)c3ncc(C(F)(F)F)cc3F)CC2)C1]

3-Fluoro-5-(trifluoromethyl)pyridine-2-carboxylic acid (16 mg, 0.076 mmol), and {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (25 mg, 0.051 mmol, prepared as described in Example 1a) were coupled, deprotected and purified according to the procedure of Example 26 to afford product as the free base (13 mg, 46%). $^1$H NMR (400 MHz, d$_6$-dmso): δ 12.06 (br s, 1H), 8.91 (s, 1H), 8.70 (s, 1H), 8.68 (s, 1H), 8.51 (dd, 1H), 8.39 (s, 1h), 7.60 (d, 1H), 7.06 (d, 1H), 3.74-3.63 (m, 2H), 3.47 (s, 2H), 3.28-3.19 (m, 2H), 2.97 (tt, 1H), 2.70-2.54 (m, 4H), 2.46-2.35 (m, 2H), 2.33-2.21 (m, 2H); LCMS (M+H)$^+$: 554.2.

Example 24b

{trans-3-{4-[(2-isopropylpyrimidin-4-yl)carbonyl]piperazin-1-yl}-1-[4-(7H-pyrrolo[2,3-d]pyrimidin-4-yl)-1H-pyrazol-1-yl]cyclobutyl}acetonitrile

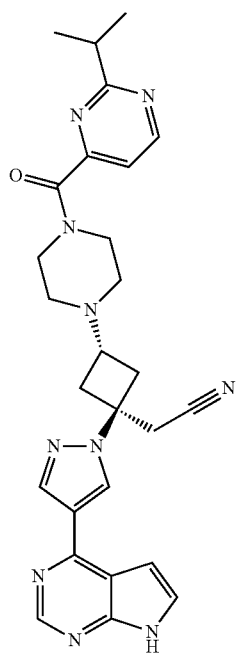 [SMILES: CC(C)c1nccc(C(=O)N2CCN([C@H]3C[C@](CC#N)(n4cc(-c5ncnc6[nH]ccc56)cn4)C3)CC2)n1]

Step 3 of Example 21a was followed, using 2-isopropylpyrimidine-4-carboxylic acid (0.010 g, 0.061 mmol, ChemBridge), and {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.020 g, 0.040 mmol, prepared according to the procedure in Example 1b, Step 1) to afford the product as the free base (0.008 g, 40%). $^1$H NMR (300 MHz, d$_6$-dmso): δ 12.13 (br s, 1H), 8.88 (d, 1H), 8.83 (s, 1H), 8.69 (s, 1H), 8.42 (s, 1H), 7.60 (d, 1H), 7.45 (d, 1H), 7.07 (d, 1H), 3.72-3.64 (m, 2H), 3.43 (s, 2H), 3.41-3.35 (m, 2H), 3.15 (sept, 1H), 3.07-2.96 (m, 2H), 2.84 (tt, 1H), 2.46-2.29 (m, 6H); LCMS (M+H)$^+$: 511.4.

Example 9a

{cis-3-{4-[(2-chloro-5-fluoropyridin-3-yl)carbonyl]piperazin-1-yl}-1-[4-(7H-pyrrolo[2,3-d]pyrimidin-4-yl)-1H-pyrazol-1-yl]cyclobutyl}acetonitrile

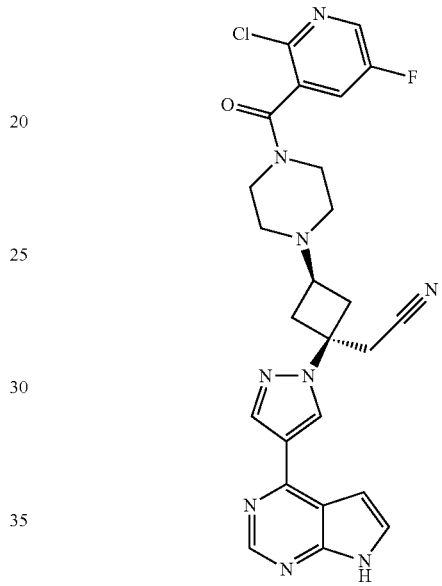

A mixture of 2-chloro-5-fluoronicotinic acid (0.027 g, 0.15 mmol, Matrix), triethylamine (0.041 g, 0.40 mmol) and N,N,N',N'-tetramethyl-O-(7-azabenzotriazol-1-yl)uronium Hexafluorophosphate (0.046 g, 0.12 mmol, Aldrich) in tetrahydrofuran (0.6 mL) was stirred for 10 minutes, followed by the addition of {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.050 g, 0.10 mmol, prepared as in Example 1a) in tetrahydrofuran (0.6 mL). Solvent was removed in vacuo, the residue was stirred in a solution of 1:1 TFA:DCM for 1 hour, evaporated, and then stirred with 0.2 mL ethylenediamine in methanol until deprotection complete. The product was purified via preparative HPLC-MS (C18, eluting with a gradient of H$_2$O/MeCN containing 0.15% NH$_4$OH). The eluent containing the desired mass was frozen and lyophilized to afford product as the free base (22 mg, 42%). $^1$H NMR (300 MHz, d$_6$-dmso): δ 12.12 (br s, 1H), 8.70 (s, 1H), 8.68 (s, 1h), 8.55 (d, 1H), 8.39 (s, 1H), 8.04 (dd, 1H), 7.60 (d, 1H), 7.06 (d, 1H), 3.77-3.52 (m, 2H), 3.47 (s, 2H), 3.25-3.15 (m, 2H), 2.96 (tt, 1H), 2.75-2.56 (m, 4H), 2.48-2.21 (m, 4H); $^{19}$F NMR (282 MHz, d$_6$-dmso): δ −128.61 (d, 1H); LCMS (M+H)$^+$: 520.1/522.1.

Example 28

{cis-3-{4-[4-chlorobenzoyl]piperazin-1-yl}-1-[4-(7H-pyrrolo[2,3-d]pyrimidin-4-yl)-1H-pyrazol-1-yl]cyclobutyl}acetonitrile

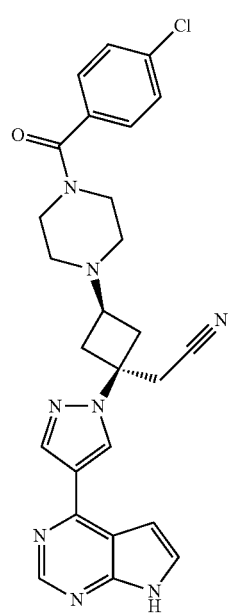 [SMILES: N#CC[C@]1(n2cc(-c3ncnc4[nH]ccc34)cn2)C[C@@H](N2CCN(C(=O)c3ccc(Cl)cc3)CC2)C1]

The procedure of Example 8b was followed, using {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (25 mg, 0.051 mmol, from Example 1a, Step 9) and 4-Chlorobenzoic acid chloride (17.8 mg, 0.101 mmol), to afford product as the free base (15 mg, 59%). $^1$H NMR (300 MHz, d$_6$-dmso): δ 12.13 (br s, 1H), 8.70 (s, 1H), 8.68 (s, 1H), 8.39 (s, 1H), 7.60 (s, 1H), 7.53-7.47 (m, 2H), 7.45-7.39 (m, 2H), 7.06 (d, 1H), 3.61 (br, 2H), 3.47 (s, 2H), 3.36-3.23 (br, 2H), 2.95 (tt, 1H), 2.70-2.53 (m, 4H), 2.45-2.20 (m, 4H); LCMS (M+H)$^+$: 501.2/503.2.

Example 29

{cis-3-{4-[2-fluoro-4-(trifluoromethyl)benzoyl]piperazin-1-yl}-1-[4-(7H-pyrrolo[2,3-d]pyrimidin-4-yl)-1H-pyrazol-1-yl]cyclobutyl}acetonitrile 2.3×(trifluoroacetate) Salt

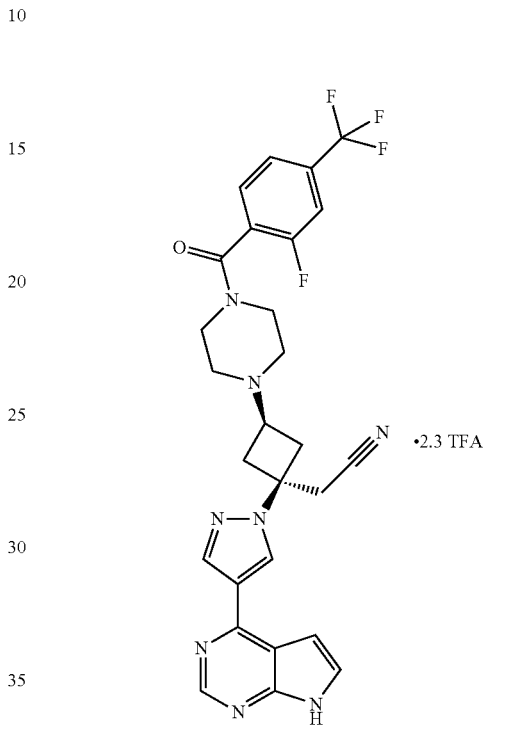

To a solution of {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.033 g, 0.067 mmol, prepared as in Example 1a) and triethylamine (0.0373 mL, 0.268 mmol) in acetonitrile (0.5 mL) was added 2-fluoro-4-(trifluoromethyl)benzoyl chloride (0.018 g, 0.080 mmol). The reaction was stirred for 2 hours. The reaction mixture was partitioned between 1 N NaOH and ethyl acetate. The organic layer was dried over sodium sulfate, decanted and concentrated. The crude product was deprotected by stirring in a solution of 1:1 DCM:TFA for 1 hour, then evaporation, and stirring with excess ethylenediamine in methanol until deprotection was complete. The product was purified via preparative HPLC-MS (C18, eluting with a gradient of H$_2$O/MeCN containing 0.1% TFA). The eluent containing the desired mass was frozen and lyophilized to afford product as the 2.3×TFA salt. $^1$H NMR (400 MHz, d$_6$-dmso): δ 12.35 (s, 1H), 8.80 (s, 1H), 8.70 (s, 1H), 8.42 (s, 1H), 7.81 (d, 1H), 7.72-7.65 (m, 2H), 7.64 (dd, 1H), 7.07 (dd, 1H), 3.91-2.73 (br m, 15H); $^{19}$F NMR (376 MHz, d$_6$-dmso): δ −61.77 (s, 3F), −74.60 (s, 6.9 F), −113.98 (br s, 1F); LCMS (M+H)$^+$: 553.2.

Example 30

[cis-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile-d1

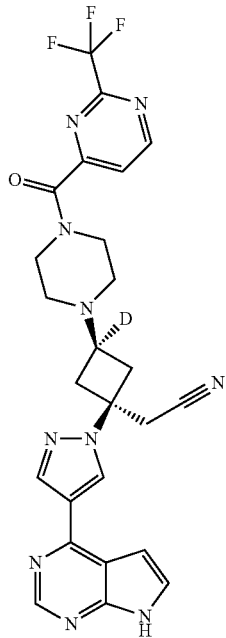 [SMILES: [2H][C@]1(N2CCN(C(=O)c3ccnc(C(F)(F)F)n3)CC2)C[C@@](CC#N)(n2cc(-c3ncnc4[nH]ccc34)cn2)C1]

Step 1. tert-butyl 4-{cis-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperazine-1-carboxylate-d1 and tert-butyl 4-{trans-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperazine-1-carboxylate-d1

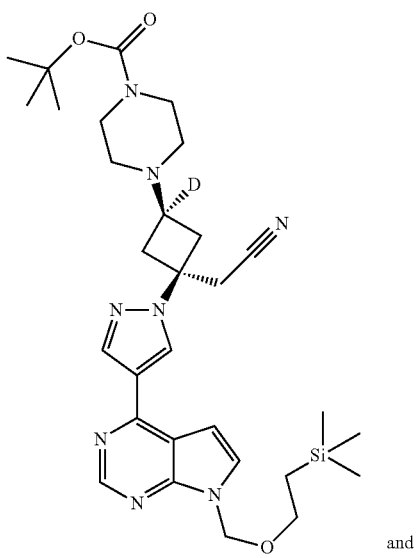

and

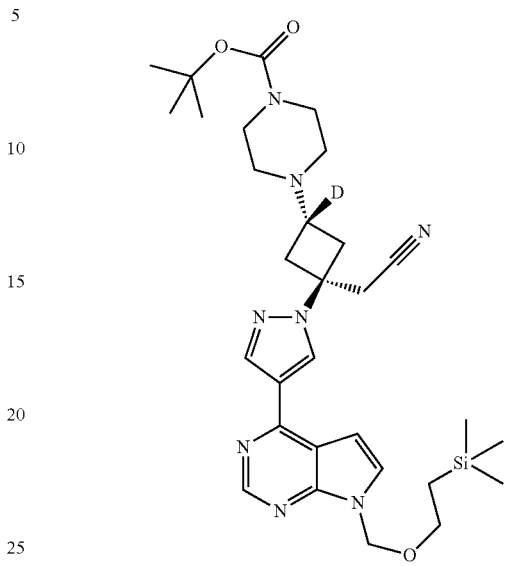

Sodium cyano(trihydrido)borate(1-)-d3 (0.02 g, 0.2 mmol, Aldrich) and zinc dichloride (0.02 g, 0.1 mmol) were precombined in a small quantity of methanol and were stirred for 2 hours. {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.100 g, 0.237 mmol, Example 1a, Step 7) and tert-butyl piperazine-1-carboxylate (0.0882 g, 0.473 mmol) were combined in methanol (4 mL, 100 mmol) and stirred for 15 minutes to dissolve. The mixture of sodium cyano(trihydrido)borate(1-)-d3 and zinc dichloride was then added. The reaction was continued for 4 hours. Methanol was removed in vacuo. The residue was reconstituted in ethyl acetate, and this solution was washed with saturated sodium bicarbonate solution. The aqueous basic solution was extracted with five further portions of ethyl acetate, which were combined with the original organic layer. The combined extracts were dried over sodium sulfate, filtered and concentrated. The cis and trans isomers were separated by chiral HPLC (Chiralcel OJ-H, 20×250 mm, 5 u packing, 30% EtOH/70% Hexanes at a flow rate of 12 mL/min). Peak 1, cis-: retention time 10.58 minutes, 55 mg (39%). Peak 2, trans-: retention time 14.95 minutes, 51 mg (36%).

$^1$H NMR peak 1, cis, (300 MHz, CDCl$_3$): δ 8.83 (s, 1H), 8.37 (s, 1H), 8.28 (s, 1H), 7.39 (d, 1H), 6.79 (d, 1H), 5.66 (s, 2H), 3.53 (dd, 2H), 3.45-3.38 (m, 4H), 3.12 (s, 2H), 2.78 (d, 2H), 2.67 (d, 2H), 2.35-2.26 (m, 4H), 1.45 (s, 9H), 0.91 (dd, 2H), −0.07 (s, 9H); LCMS (M+H)$^+$: 594.1.

1H NMR peak 2, trans, (300 MHz, CDCl₃): δ 8.84 (s, 1H), 8.46 (s, 1H), 8.32 (s, 1H), 7.40 (d, 1H), 6.81 (d, 1H), 5.67 (s, 2H), 3.54 (dd, 2H), 3.50-3.43 (m, 4H), 3.21 (s, 2H), 3.02 (d, 2H), 2.51 (d, 2H), 2.40-2.31 (m, 4H), 1.45 (s, 9H), 0.91 (dd, 2H), −0.07 (s, 9H); LCMS (M+H)⁺: 594.0.

Step 2. {cis-3-piperazin-1-yl-1-[4-(7-{[2-(trimethyl-silyl)ethoxy]methyl}-7H-pyrrolo[2,3-d]pyrimidin-4-yl)-1H-pyrazol-1-yl]cyclobutyl}acetonitrile-d1

To a solution of tert-butyl 4-{cis-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperazine-1-carboxylate-d1 (0.083 g, 0.14 mmol, Peak 1, prepared according to the method of Step 1) in 1,4-dioxane (5 mL) was added 4.0 M hydrogen chloride in water (0.7 mL, 3 mmol), and the deprotection reaction was stirred over two nights. The reaction mixture was then poured into sufficient saturated sodium bicarbonate solution to make the mixture basic, and this was extracted with ethyl acetate three times. The combined extracts were washed with brine, dried over sodium sulfate, filtered and concentrated, to afford product, which was used without further purification (0.07 g, 100%). LCMS (M+H)⁺: 494.0.

Step 3 of Example 30. [cis-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile-d1

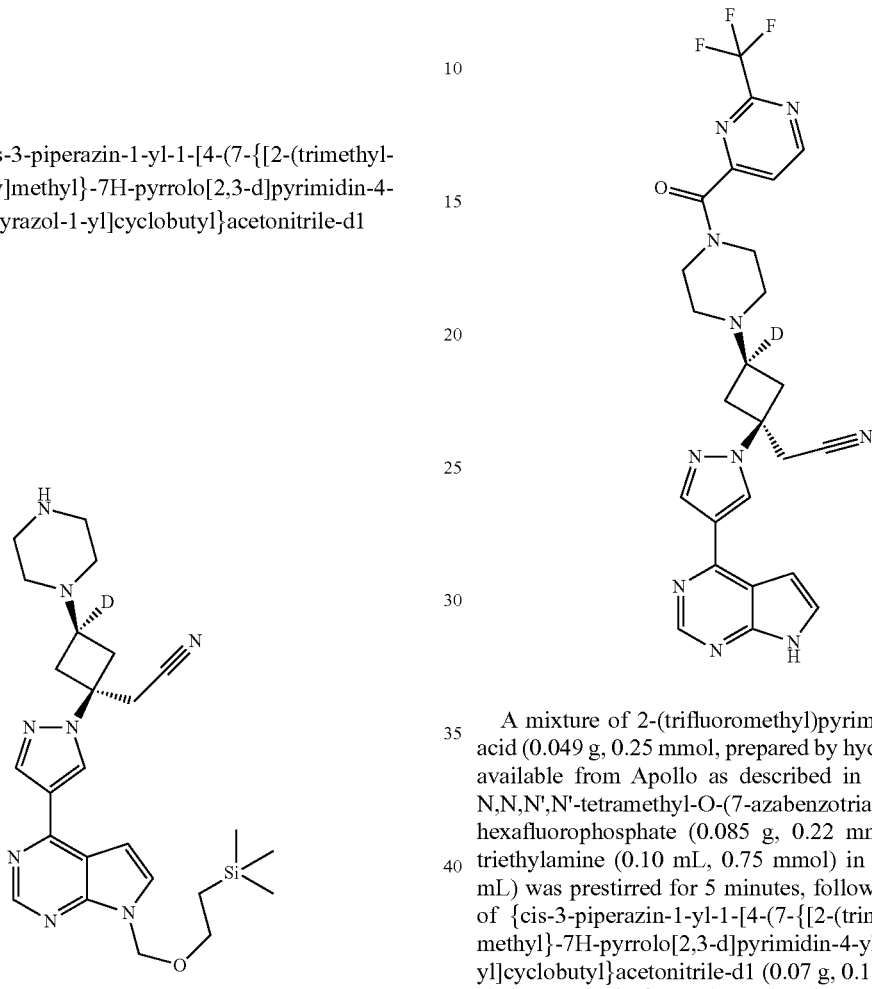

A mixture of 2-(trifluoromethyl)pyrimidine-4-carboxylic acid (0.049 g, 0.25 mmol, prepared by hydrolysis of the ester available from Apollo as described in WO2006/067445), N,N,N',N'-tetramethyl-O-(7-azabenzotriazol-1-yl)uronium hexafluorophosphate (0.085 g, 0.22 mmol, Aldrich), and triethylamine (0.10 mL, 0.75 mmol) in tetrahydrofuran (1 mL) was prestirred for 5 minutes, followed by the addition of {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile-d1 (0.07 g, 0.15 mmol, from Step 2) in tetrahydrofuran (4 mL). The reaction was stirred overnight. The THF was removed in vacuo, and the residue was partitioned between saturated sodium bicarbonate solution and ethyl acetate. The layers were separated and the aqueous was extracted with two further portions of ethyl acetate. The combined extracts were dried over sodium sulfate, decanted and concentrated. Flash chromatography, eluting with a gradient from 0-10% MeOH in DCM was used to purify the SEM-protected intermediate. This product was stirred with trifluoroacetic acid (2 mL) in methylene chloride (2 mL) for 2 hours. The solvents were removed in vacuo. The residue was reconstituted in methanol (4 mL) and ethylenediamine (0.2 mL, 3 mmol) was added. The second step of the deprotection was continued overnight. The reaction was worked up by partition between water and ethyl acetate, and the aqueous portion was extracted with ethyl acetate a total of three times. The combined extracts were dried over sodium sulfate, filtered and concentrated. The product was purified via preparative HPLC-MS (C18, eluting with a gradient of H₂O/MeCN containing 0.15% NH₄OH). The eluent containing the desired mass was frozen and lyophilized to afford product as the free base (0.010 g, 12%). ¹H NMR (300 MHz, CD₃OD): δ 9.13 (d, 1H), 8.66 (s, 1H), 8.63 (s, 1H), 8.37 (s, 1H), 7.88 (d, 1H), 7.51 (d, 1H), 6.98 (d, 1H), 3.82 (dd, 2H), 3.53 (dd, 2H), 3.34 (s, 2H), 2.81 (dd, 2H), 2.69 (dd, 2H), 2.57 (dd, 2H), 2.49 (dd, 2H); $^{19}$F NMR (282 MHz, CD$_3$OD): δ −72.46 (s, 3F); LCMS (M+H)$^+$: 537.8.

Example 31

[trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile-d1

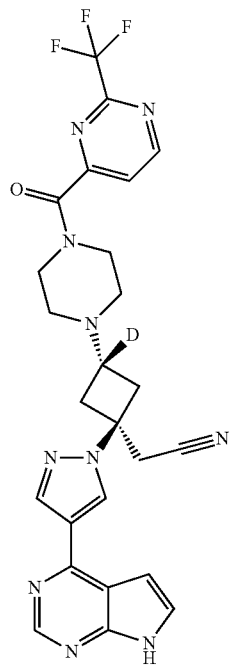 [SMILES: [2H][C@]1(N2CCN(C(=O)c3ccnc(C(F)(F)F)n3)CC2)C[C@](CC#N)(n2cc(-c3ncnc4[nH]ccc34)cn2)C1]

Step 1. {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile-d1

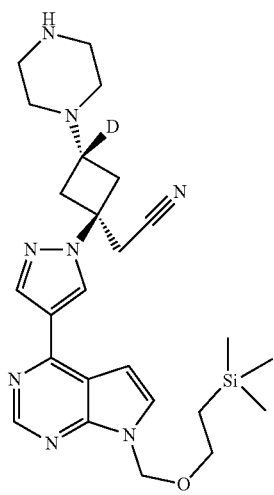 [SMILES: [2H][C@]1(N2CCNCC2)C[C@](CC#N)(n2cc(-c3ncnc4c3ccn4COCC[Si](C)(C)C)cn2)C1]

The procedure of Example 30, Step 2 was followed, using Peak 2 produced in Example 30, Step 1: tert-butyl 4-{trans-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperazine-1-carboxylate-d1 (0.076 g, 0.13 mmol) to afford the trans-product, which was used without further purification (47 mg, 74%). LCMS (M+H)$^+$: 494.0.

Step 2. [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile-d1

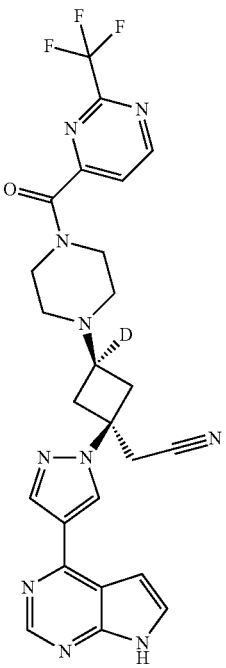 [SMILES: [2H][C@]1(N2CCN(C(=O)c3ccnc(C(F)(F)F)n3)CC2)C[C@@](CC#N)(n2cc(-c3ncnc4[nH]ccc34)cn2)C1]

The product of Step 1, {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile-d1 (0.047 g, 0.095 mmol), was coupled with 2-(trifluoromethyl)pyrimidine-4-carboxylic acid (0.046 g, 0.24 mmol, prepared by hydrolysis of the ester available from Apollo as described in WO2006/067445) according to the procedure of Example 30, Step 3 (10 mg, 20%). $^1$H NMR (300 MHz, CD$_3$OD): δ 9.13 (d, 1H), 8.71 (s, 1H), 8.66 (s, 1H), 8.40 (s, 1H), 7.88 (d, 1H), 7.51 (d, 1H), 6.98 (d, 1H), 3.94-3.79 (m, 2H), 3.64-3.50 (m, 2H), 3.34 (s, 2H), 3.07 (d, 2H), 2.64-2.43 (m, 6H); $^{19}$F NMR (282 MHz, CD$_3$OD): δ −72.45 (s, 3F); LCMS (M+H)$^+$: 537.8.

Example 32

4-{trans-3-(cyanomethyl)-3-[4-(7H-pyrrolo[2,3-d]pyrimidin-4-yl)-1H-pyrazol-1-yl]cyclobutyl}-N,N-dimethylpiperazine-1-carboxamide

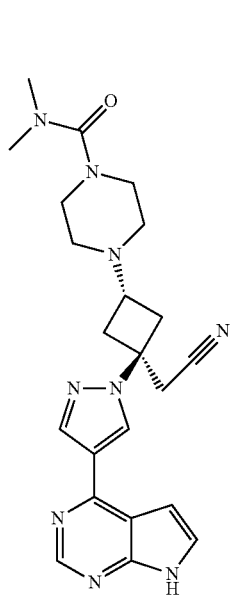 [SMILES: CN(C)C(=O)N1CCN([C@H]2C[C@](CC#N)(n3cc(-c4ncnc5[nH]ccc45)cn3)C2)CC1]

{trans-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Example 1b, Step 1) was dissolved in acetonitrile (1 mL) and Methylene chloride (0.5 mL). N,N-Diisopropylethylamine (0.10 mL, 0.57 mmol) followed by N,N-Dimethylcarbamoyl chloride (25 μL, 0.27 mmol, Aldrich) were added. After a reaction time of 1.5 hours, solvent was removed in vacuo. The crude product was stirred with 1:1 TFA:DCM for 2 hours, then evaporated and stirred with excess ethylenediamine (0.2 mL) in methanol until deprotection was complete. The product was purified via preparative HPLC-MS (C18, eluting with a gradient of H$_2$O/MeCN containing 0.15% NH$_4$OH). The eluent containing the desired mass was frozen and lyophilized to afford product as the free base (0.012 g, 45%). $^1$H NMR (300 MHz, d$_6$-dmso): δ 12.10 (s, 1H), 8.82 (s, 1H), 8.69 (s, 1H), 8.41 (s, 1H), 7.60 (d, 1H), 7.07 (d, 1H), 3.42 (s, 2H), 3.16-3.07 (m, 4H), 3.05-2.94 (m, 2H), 2.78 (tt, 1H), 2.71 (s, 6H), 2.40-2.24 (m, 6H); LCMS (M+H)$^+$: 434.2.

Example 33

{trans-3-(4-{3-[(dimethylamino)methyl]-5-fluorobenzoyl}piperazin-1-yl)-1-[4-(7H-pyrrolo[2,3-d]pyrimidin-4-yl)-1H-pyrazol-1-yl]cyclobutyl}acetonitrile

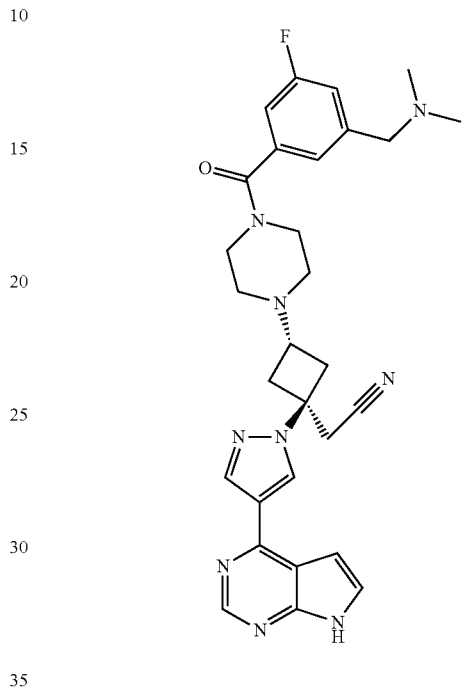

Step 1. methyl 3-fluoro-5-methylbenzoate

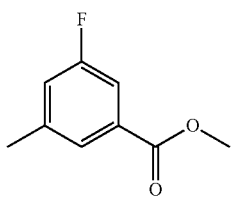

To a solution of 3-fluoro-5-methylbenzoic acid (1.50 g, 9.73 mmol, Oakwood) in Acetone (40 mL) was added Potassium carbonate (1.34 g, 9.73 mmol) followed by Methyl iodide (0.73 mL, 12 mmol). The reaction mixture was heated to 65° C. for 1 hour, heating discontinued and stirred overnight, then heating resumed at that temperature for a further 2 hours. Additional Methyl iodide (0.5 mL, 8 mmol) was added and heating was continued for 6 hours. Solids were removed by filtration and acetone was removed in vacuo. The residue was partitioned between 1N NaOH and ethyl acetate. The aqueous portion was extracted with a further two portions of ethyl acetate. The combined extracts were washed with brine, then dried over sodium sulfate, decanted and concentrated. The product so obtained was used without further purification (1.64 g, 100%). $^1$H NMR (300 MHz, CDCl$_3$): δ 7.66-7.63 (m, 1H), 7.51 (d, 1H), 7.10-7.04 (m, 1H), 3.91 (s, 3H), 2.40 (s, 3H).

Step 2. methyl 3-(bromomethyl)-5-fluorobenzoate

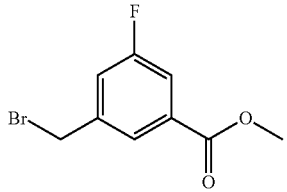

To a solution of methyl 3-fluoro-5-methylbenzoate (1.64 g, 9.75 mmol, from Step 1) and N-bromosuccinimide (2.05 g, 11.5 mmol) in carbon tetrachloride (20 mL) was added benzoyl peroxide (0.1 g, 0.6 mmol) and the mixture was heated to reflux for four hours. The reaction was then cooled to room temperature, filtered, and diluted with DCM. The solution was washed successively with sodium thiosulfate, 1N NaOH, water, and brine, dried over sodium sulfate, decanted and concentrated. Flash chromatography, eluting with a gradient from 0-20% ethyl acetate in hexanes, afforded a partially purified product. The cleanest fractions were used in the displacement with amine in Step 3. $^1$H NMR (300 MHz, CDCl$_3$): δ 7.87-7.85 (m, 1H), 7.68-7.62 (m, 1H), 7.31 (ddd, 1H), 4.47 (s, 2H), 3.93 (s, 3H).

Step 3. methyl 3-[(dimethylamino)methyl]-5-fluorobenzoate

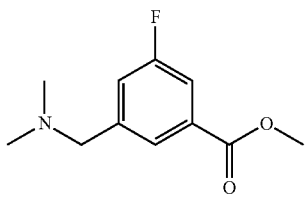

To a solution of 2.0 M dimethylamine in THF (3.24 mL, 6.48 mmol) was added methylene chloride (2 mL) and methyl 3-(bromomethyl)-5-fluorobenzoate (0.200 g, 0.810 mmol from Step 2). The reaction was heated in a sealed reaction vessel in an oil bath held at 60° C. for 2 hours. Solvent and excess reagent were removed in vacuo and the residue was subjected to flash chromatography, eluting with a gradient from 0-20% MeOH in DCM containing some NH$_4$OH (50 mg, 29%). $^1$H NMR (300 MHz, CDCl$_3$): δ 7.80-7.77 (m, 1H), 7.62 (ddd, 1H), 7.29 (ddd, 1H), 3.90 (s, 3H), 3.53 (s, 2H), 2.29 (s, 6H); $^{19}$F NMR (282 MHz, CDCl$_3$): δ −113.10 (t, 1F); LCMS (M+H)$^+$: 212.1.

Step 4. 3-[(dimethylamino)methyl]-5-fluorobenzoic acid

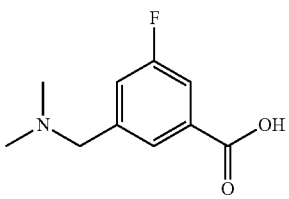

Methyl 3-[(dimethylamino)methyl]-5-fluorobenzoate (0.040 g, 0.19 mmol from Step 3) was dissolved in tetrahydrofuran (3 mL) and lithium hydroxide monohydrate (0.0954 g, 2.27 mmol) dissolved in water (1 mL) was added. The reaction was stirred for 3 hours. The crude reaction mixture was purified by preparative HPLC-MS (C18, eluting with a gradient of H$_2$O/MeCN containing 0.15% NH$_4$OH). The eluent containing the desired mass was evaporated using rotary evaporation to afford product (22 mg, 59%), which was used directly in Step 5. LCMS (M+H)$^+$: 198.1.

Step 5. {trans-3-(4-{3-[(dimethylamino)methyl]-5-fluorobenzoyl}piperazin-1-yl)-1-[4-(7H-pyrrolo[2,3-d]pyrimidin-4-yl)-1H-pyrazol-1-yl]cyclobutyl}acetonitrile

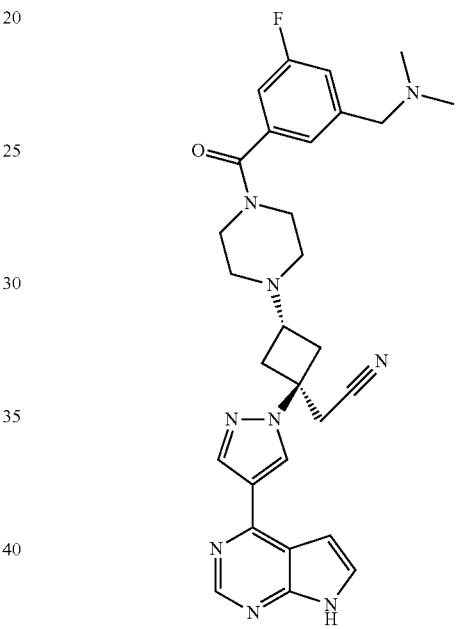

To a mixture of 3-[(dimethylamino)methyl]-5-fluorobenzoic acid (0.018 g, 0.091 mmol, from Step 4) in N,N-dimethylformamide (1.5 mL, 19 mmol) and triethylamine (0.06 mL, 0.4 mmol) was added N,N,N',N'-tetramethyl-O-(7-azabenzotriazol-1-yl)uronium hexafluorophosphate (0.028 g, 0.073 mmol). After stirring for 5 minutes, {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Example 1b, Step 1) in tetrahydrofuran (1.5 mL, 18 mmol) was added, and the reaction was stirred for 3 hours. Saturated sodium bicarbonate solution was added, and the product was extracted with three portions of ethyl acetate. The combined extracts were dried over sodium sulfate, decanted and concentrated. The residue was stirred with 1:1 TFA:DCM for 1 hour, evaporated, and then stirred with 0.2 mL ethylenediamine in methanol until deprotection was complete. The product was purified by preparative HPLC-MS (C18, eluting with a gradient of H$_2$O/MeCN containing 0.15% NH$_4$OH). The eluent containing the desired mass was frozen and lyophilized to afford the product as the free base (15 mg, 45%). $^1$H NMR (500 MHz, CD$_3$OD): δ 8.69 (s, 1H), 8.66 (s, 1H), 8.38 (s, 1H), 7.49 (d, 1H), 7.22-7.19 (m, 1H), 7.18 (s, 1H), 7.09 (ddd, 1H), 6.96 (d, 1H), 3.87-3.72 (br s, 2H), 3.51 (s, 2H), 3.52-3.43 (br s, 2H), 3.33 (s, 2H), 3.10-3.03 (m, 2H) 2.95 (tt, 1H), 2.55-2.34 (m, 6H), 2.24 (s, 6H); $^{19}$F NMR (282 MHz, d$_6$-dmso): δ −113.45 (dd, 1F); LCMS (M+H)$^+$: 542.3.

Example 34

{trans-3-(4-{3-[(dimethylamino)methyl]-5-fluorobenzyl}piperazin-1-yl)-1-[4-(7H-pyrrolo[2,3-d]pyrimidin-4-yl)-1H-pyrazol-1-yl]cyclobutyl}acetonitrile

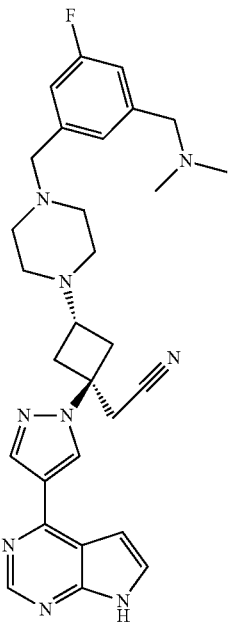

Step 1. {3-[(dimethylamino)methyl]-5-fluorophenyl}methanol

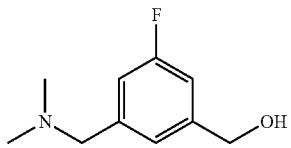

To a solution of methyl 3-[(dimethylamino)methyl]-5-fluorobenzoate (0.14 g, 0.66 mmol, Example 33, Step 3) in Ether (4 mL) at 0° C. in an ice bath was added dropwise 1.0 M lithium tetrahydroaluminate in THF (1.32 mL, 1.32 mmol). The reaction was allowed to warm to room temperature and stirred for 1.5 hours. The reaction mixture was re-cooled in an ice bath and methanol, followed by 1 N NaOH, were added to quench the reaction. The product was extracted from the reaction mixture with three portions of ethyl acetate. The combined extracts were dried over sodium sulfate, decanted and concentrated, to afford product which was used without further purification (0.100 g, 82%). $^1$H NMR (300 MHz, CD$_3$OD): δ 7.13-6.94 (m, 3H), 4.59 (s, 2H), 3.47 (s, 2H), 2.24 (s, 6H); $^{19}$F NMR (282 MHz, CD$_3$OD): δ −116.41 (t, 1F); LCMS (M+H)$^+$: 184.0.

Step 2. 3-[(dimethylamino)methyl]-5-fluorobenzaldehyde

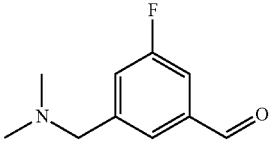

To a solution of {3-[(dimethylamino)methyl]-5-fluorophenyl}methanol (0.100 g, 0.546 mmol, from Step 1) in Chloroform (3 mL) was added manganese(IV) oxide (0.145 g, 1.42 mmol) and the mixture was heated in an oil bath held at 80° C. for 7 hours. The reaction mixture was filtered, rinsing with copious CHCl$_3$ and the solvent was removed from the filtrate in vacuo. The product of the reaction, containing approximately 50% aldehyde and 50% unreacted alcohol was used without further purification in Step 3. $^1$H NMR (300 MHz, CDCl$_3$): δ 9.99 (d, 1H), 7.78 (dd, 1H), 7.67 (ddd, 1H), 7.52 (ddd, 1H), 4.28 (s, 2H), 2.84 (s, 6H); LCMS (M+H)$^+$: 182.0.

Step 3. {trans-3-(4-{3-[(dimethylamino)methyl]-5-fluorobenzyl}piperazin-1-yl)-1-[4-(7H-pyrrolo[2,3-c]pyrimidin-4-yl)-1H-pyrazol-1-yl]cyclobutyl}acetonitrile

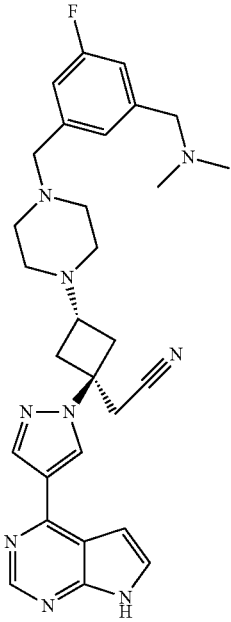 [SMILES: CN(C)Cc1cc(F)cc(CN2CCN([C@H]3C[C@](CC#N)(n4cc(-c5ncnc6[nH]ccc56)cn4)C3)CC2)c1]

A solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, Example 1b, Step 1) and 3-[(dimethylamino)methyl]-5-fluorobenzaldehyde (0.022 g, 0.12 mmol, from Step 2) in methylene chloride (1 mL, 20 mmol) was treated with sodium triacetoxyborohydride (0.0645 g, 0.304 mmol) and Example 35

{trans-3-[4-(ethylsulfonyl)piperazin-1-yl]-1-[4-(7H-pyrrolo[2,3-d]pyrimidin-4-yl)-1H-pyrazol-1-yl]cyclobutyl}acetonitrile

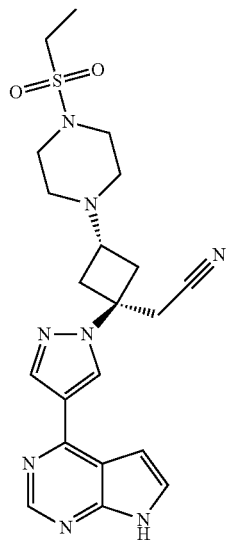 [SMILES: CCS(=O)(=O)N1CCN([C@H]2C[C@](CC#N)(n3cc(-c4ncnc5[nH]ccc45)cn3)C2)CC1]

{trans-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (30.0 mg, 0.061 mmol, prepared as in Example 1b, Step 1) was dissolved in methylene chloride (0.50 mL), then triethylamine (17 µL, 0.12 mmol) and ethanesulfonyl chloride (7.5 µL, 0.079 mmol) were added. The reaction was stirred for 1 hour, and the mixture was concentrated. The residue was stirred in 1:1 TFA/DCM for 1 hour, then was concentrated, dissolved in 1 mL methanol, and 0.2 mL ethylenediamine was added. Purification via preparative HPLC-MS (C18 eluting with a gradient of MeCN/H₂O containing 0.15% NH₄OH) followed by lyophilization afforded the product as the free base (15 mg, 54%). ¹H NMR (400 MHz, d₆-dmso): δ 12.10 (br s, 1H), 8.83 (s, 1H), 8.69 (s, 1H), 8.42 (s, 1H), 7.60 (d, 1H), 7.07 (d, 1H), 3.42 (s, 2H), 3.23-3.16 (m, 4H), 3.06 (q, 2H), 3.06-2.96 (m, 2H), 2.84 (tt, 1H), 2.43-2.29 (m, 6H), 1.21 (t, 3H); LCMS (M+H)⁺: 455.3.

stirred overnight. Solvent was removed in vacuo. The SEM-protected intermediate was reconstituted in methanol and purified by preparative HPLC-MS (C18, eluting with a gradient of H₂O/MeCN containing 0.15% NH₄OH). The eluent containing the desired mass subjected to rotary evaporation to remove solvent. To deprotect, the product was stirred with 1:1 TFA:DCM for 1 hour, evaporated, and then stirred with 0.2 mL ethylenediamine in methanol for 30 minutes. The deprotected product was purified by preparative HPLC-MS (C18, eluting with a gradient of H₂O/MeCN containing 0.15% NH₄OH). The eluent containing the desired mass was frozen and lyophilized to afford the product as the free base (8 mg, 20%). ¹H NMR (500 MHz, CD₃OD): δ 8.69 (s, 1H), 8.66 (s, 1H), 8.38 (s, 1H), 7.49 (d, 1H), 7.10 (s, 1H), 7.02 (ddd, 1H), 6.98 (ddd, 1H), 6.96 (d, 1H), 3.55 (s, 2H), 3.46 (s, 2H), 3.31 (s, 2H), 3.08-3.01 (m, 2H), 2.93 (tt, 1H), 2.61-2.40 (m, 10H), 2.23 (s, 6H); ¹⁹F NMR (282 MHz, d₆-dmso): δ -115.07 (t, 1F); LCMS (M+H)⁺: 528.3.

Example 36

{trans-3-[4-(cyclopropylsulfonyl)piperazin-1-yl]-1-[4-(7H-pyrrolo[2,3-d]pyrimidin-4-yl)-1H-pyrazol-1-yl]cyclobutyl}acetonitrile

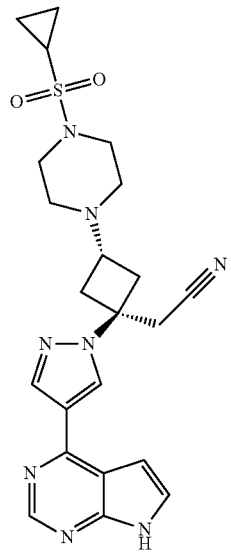 [SMILES: N#CC[C@]1(n2cc(-c3ncnc4[nH]ccc34)cn2)C[C@H](N2CCN(S(=O)(=O)C3CC3)CC2)C1]

The compound was prepared as in Example 35, using cyclopropanesulfonyl chloride (8.1 µL, 0.079 mmol). (10.2 mg, 36%). ¹H NMR (400 MHz, d₆-dmso): δ 12.12 (br s, 1H), 8.83 (s, 1H), 8.69 (s, 1H), 8.42 (s, 1H), 7.60 (d, 1H), 7.07 (d, 1H), 3.42 (s, 2H), 3.26-3.16 (m, 4H), 3.06-2.97 (m, 2H), 2.84 (tt, 1H), 2.61 (tt, 1H), 2.44-2.30 (m, 6H), 1.03-0.88 (m, 4H); LCMS (M+H)⁺: 467.1.

Example 37

4-{trans-3-(cyanomethyl)-3-[4-(7H-pyrrolo[2,3-d]pyrimidin-4-yl)-1H-pyrazol-1-yl]cyclobutyl}-N,N-dimethylpiperazine-1-sulfonamide

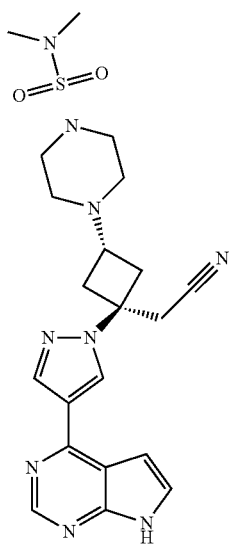

The compound was prepared as in Example 35, using dimethylsulfamoyl chloride (8.5 μL, 0.079 mmol). (13 mg, 45%). $^1$H NMR (400 MHz, $d_6$-dmso): δ 12.12 (br s, 1H), 8.83 (s, 1H), 8.69 (s, 1H), 8.42 (s, 1H), 7.60 (d, 1H), 7.07 (d, 1H), 3.42 (s, 2H), 3.21-3.15 (m, 4H), 3.05-2.96 (m, 2H), 2.83 (tt, 1H), 2.76 (s, 6H), 2.40-2.29 (m, 6H); LCMS (M+H)$^+$: 470.0.

Example 38

4-{trans-3-(cyanomethyl)-3-[4-(7H-pyrrolo[2,3-d]pyrimidin-4-yl)-1H-pyrazol-1-yl]cyclobutyl}-N-ethyl-N-methylpiperazine-1-carboxamide

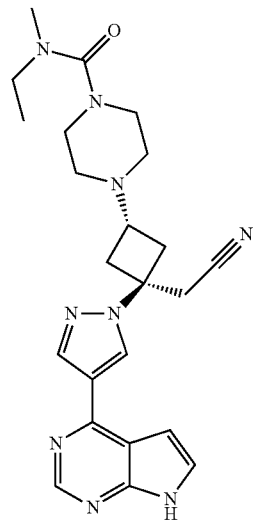 [SMILES: CCN(C)C(=O)N1CCN([C@H]2C[C@](CC#N)(n3cc(-c4ncnc5[nH]ccc45)cn3)C2)CC1]

{trans-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, prepared as in Example 1b, Step 1) was dissolved in methylene chloride (0.50 mL), and Triethylamine (0.0339 mL, 0.244 mmol) and ethyl(methyl)carbamic chloride (14.8 mg, 0.122 mmol, Toronto Research Chemicals) were added. The reaction mixture was stirred for 2 hours, and solvent was removed in vacuo. The residue was stirred with 1:1 TFA:DCM for 1 hour, then evaporated and stirred with 0.2 mL ethylenediamine in methanol until the deprotection was complete. Purification via preparative HPLC-MS (C18 eluting with a gradient of MeCN/H$_2$O containing 0.15% NH$_4$OH) followed by lyophilization afforded the product as the free base (15.4 mg, 56%). $^1$H NMR (400 MHz, $d_6$-dmso): δ 12.08 (br s, 1H), 8.82 (s, 1H), 8.69 (s, 1H), 8.42 (s, 1H), 7.60 (d, 1H), 7.07 (d, 1H), 3.42 (s, 2H), 3.14-3.05 (m, 6H), 3.04-2.95 (m, 2H), 2.78 (tt, 1H), 2.70 (s, 3H), 2.40-2.25 (m, 6H), 1.03 (t, 3H); LCMS (M+H)$^+$: 448.2.

Example 39

{trans-3-{4-[3-[(dimethylamino)methyl]-5-(trifluoromethyl)benzoyl]piperazin-1-yl}-1-[4-(7H-pyrrolo[2,3-d]pyrimidin-4-yl)-1H-pyrazol-1-yl]cyclobutyl}acetonitrile

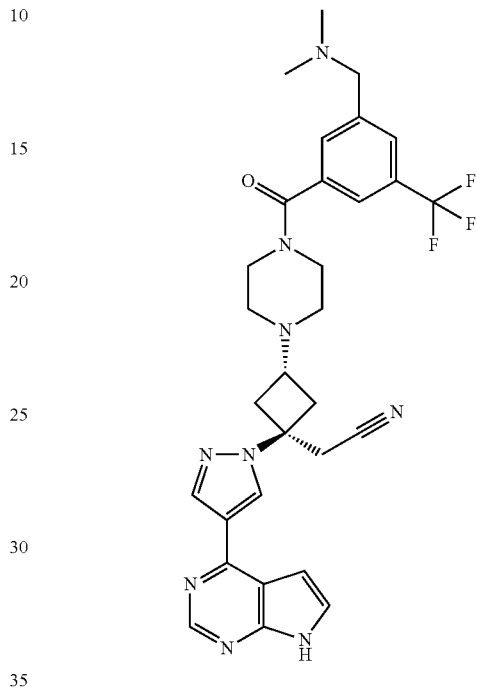

Lithium 3-[(dimethylamino)methyl]-5-(trifluoromethyl)benzoate (23.1 mg, 0.0913 mmol, US 2010/197924) was dissolved in tetrahydrofuran (0.67 mL), triethylamine (33.9 μL, 0.244 mmol) and N,N,N',N'-tetramethyl-O-(7-azabenzotriazol-1-yl)uronium hexafluorophosphate (32.4 mg, 0.0852 mmol) were added, and after stirring for 15 minutes, {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (30.0 mg, 0.0609 mmol, prepared as in Example 1b, Step 1) was added. The reaction was continued for 2 hours. The reaction mixture was diluted with ethyl acetate and water, shaken, and the layers separated. The organic layer was washed with water, 0.1N NaOH and saturated NaCl solution, dried over sodium sulfate and concentrated. The residue was dissolved in a 1:1 mixture of DCM:TFA, stirred for 1 hour, and solvents were removed in vacuo. The residue was dissolved in 1 mL methanol, and 0.2 mL of ethylenediamine was added. The reaction was stirred until deprotection was complete. Purification via preparative HPLC-MS (C18 eluting with a gradient of MeCN/H$_2$O containing 0.15% NH$_4$OH) followed by lyophilization afforded the product as the free base (20 mg, 56%). $^1$H NMR (400 MHz, $d_6$-dmso): δ 12.08 (br s, 1H), 8.83 (s, 1H), 8.69 (s, 1H), 8.42 (s, 1H), 7.71 (s, 1H), 7.62 (s, 1H), 7.60 (d, 1H), 7.59 (s, 1H), 7.07 (d, 1H), 3.67 (br s, 2H), 3.51 (s, 2H), 3.43 (s, 2H), 3.40-3.27 (m, 4H), 3.05-2.96 (m, 2H), 2.84 (tt, 1H), 2.46-2.23 (m, 6H), 2.15 (s, 6H); $^{19}$F NMR (376 MHz, $d_6$-dmso): δ −61.48 (s, 3F); LCMS (M+H)$^+$: 592.3.

Example 40

{cis-3-(4-{3-[(dimethylamino)methyl]-5-fluorophenoxy}piperidin-1-yl)-1-[4-(7H-pyrrolo[2,3-d]pyrimidin-4-yl)-1H-pyrazol-1-yl]cyclobutyl}acetonitrile; and {trans-3-(4-{3-[(dimethylamino)methyl]-5-fluorophenoxy}piperidin-1-yl)-1-[4-(7H-pyrrolo[2,3-d]pyrimidin-4-yl)-1H-pyrazol-1-yl]cyclobutyl}acetonitrile

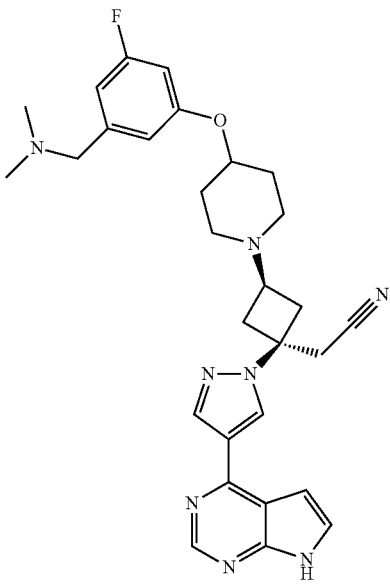

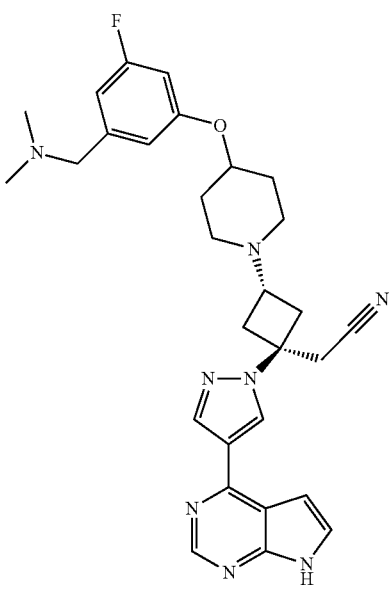

Step 1. (3-{[tert-butyl(diphenyl)silyl]oxy}cyclobutylidene)acetonitrile

To a solution of 1.0 M potassium tert-butoxide in tetrahydrofuran (5.95 mL, 5.95 mmol) at 0° C. was added diethyl cyanomethylphosphonate (1.05 g, 5.95 mmol). The bath was removed and reaction allowed to warm to room temperature for 1 hour. The reaction was cooled to 0° C. and a solution of 3-{[tert-butyl(diphenyl)silyl]oxy}cyclobutanone (1.95 g, 6.01 mmol) in THF (10 mL) was added. Upon complete addition, the bath was removed and the reaction was allowed to warm to room temperature and stir overnight. The reaction solution was diluted with water and ethyl acetate. The aqueous layer was extracted with ethyl acetate three times. The combined extracts were washed with brine, dried over sodium sulfate, decanted and concentrated. The crude was purified silica gel column to give the desired product (2.07 g, 90%) as an oil. LCMS (M+H)$^+$: 348.2.

Step 2. {3-{[tert-butyl(diphenyl)silyl]oxy}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile To a solution of (3-{[tert-butyl(diphenyl)silyl]oxy}cyclobutylidene)acetonitrile (1.859 g, 4.065 mmol) and 4-(1H-pyrazol-4-yl)-7-{[2-(trimethylsilyl)ethoxy]methyl}-7H-pyrrolo[2,3-d]pyrimidine (1.28 g, 4.06 mmol) in acetonitrile (10 mL) was added 1,8-diazabicyclo[5.4.0]undec-7-ene (0.61 mL, 4.1 mmol). The reaction was stirred overnight. The solvent was remove in vacuo. The crude was purified with silica gel column to give of the product (2.7 g, 79%) as an oil. LCMS (M+H)$^+$: 663.3.

Step 3. {3-hydroxy-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile To {3-{[tert-butyl(diphenyl)silyl]oxy}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (2.85 g, 4.30 mmol) in ethanol (120 mL) was added 5.0 M sodium hydroxide in water (29 mL, 150 mmol). The reaction was stirred for 3 hours and diluted with water. The ethanol was removed under reduced pressure. The aqueous layer was extracted with ethyl acetate three times. The combine organic solutions were washed with brine, dried over Na$_2$SO$_4$, filtered and concentrated. The crude was purified with silica gel column eluting with a gradient from 0-10% MeOH/DCM.to give of the product (1.62 g, 88%) as .off-white foam. LCMS (M+H)$^+$: 425.2.

Step 4. {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile To a solution of {3-hydroxy-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (1.62 g, 3.82 mmol) in DCM (50 mL) at 0° C. was added Dess-Martin periodinane (2.1 g, 5.0 mmol). After stirring for 2 hours, the reaction solution was diluted with ether and saturated NaHCO$_3$ solution. The aqueous layer was extracted with ethyl acetate three times. The combined extracts were washed with brine, dried over sodium sulfate, decanted and evaporated. The crude was used in the next step without purification. LCMS (M+H)$^+$: 423.2.

Step 5. tert-butyl 4-(3-bromo-5-fluorophenoxy)piperidine-1-carboxylate

To a mixture of triphenylphosphine (1.75 g, 6.66 mmol) and 3-bromo-5-fluorophenol (795 mg, 4.16 mmol) and tert-butyl 4-hydroxypiperidine-1-carboxylate (922 mg, 4.58 mmol) in THF (20. mL) was added di-tert-butyl azodicarboxylate (1.53 g, 6.66 mmol) (DBAD) at 0° C. The reaction was stirred overnight at room temperature. The solvent was removed and the residue was dissolved in methanol and purified by preparative-LCMS (C18 column eluting with a gradient of ACN/H$_2$O containing 0.15% NH$_4$OH) to give the desired product (1.09 g, 70%). LCMS (M+Na)$^+$: 396.0, 398.0.

Step 6. tert-butyl 4-{3-[(dimethylamino)methyl]-5-fluorophenoxy}piperidine-1-carboxylate To a microwave vial was added tert-butyl 4-(3-bromo-5-fluorophenoxy)piperidine-1-carboxylate (215 mg, 0.574 mmol), cesium carbonate (562 mg, 1.72 mmol), dicyclohexyl(2',4',6'-triisopropylbiphenyl-2-yl)phosphine (130 mg, 0.27 mmol), potassium [(dimethylamino)methyl](trifluoro)borate(1-) (114 mg, 0.689 mmol), palladium acetate (30.7 mg, 0.137 mmol) and 5.05 M water in THF (3.5 mL). The tube was sealed and evacuated and refilled with N$_2$ (3×). The sealed tube was then heated at 80° C. for 20 hours. The reaction was diluted with water and ethyl acetate. The aqueous layer was extracted with ethyl acetate once. The combined organic solutions were washed with brine, dried over Na$_2$SO$_4$, filtered and concentrated. The crude was purified with preparative LCMS (C18 column eluting with a gradient of ACN/H$_2$O containing 0.1% TFA) to afford the desired product (180 mg, 89%). LCMS (M+H)$^+$: 353.2.

Step 7. 1-[3-fluoro-5-(piperidin-4-yloxy)phenyl]-N,N-dimethylmethanamine dihydrochloride To a solution of tert-butyl 4-{3-[(dimethylamino)methyl]-5-fluorophenoxy}piperidine-1-carboxylate (180 mg, 0.51 mmol) in DCM (2.4 mL) was added 4.0 M hydrogen chloride in dioxane (1.0 mL, 4.1 mmol). The reaction solution was stirred at room temperature for 6 hours. The solvent was removed to give the desired product as white solid (145 mg, 87%). LCMS (M+H)$^+$: 253.1.

Step 8. {cis-3-(4-{3-[(dimethylamino)methyl]-5-fluorophenoxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile; and {trans-3-(4-{3-[(dimethylamino)methyl]-5-fluorophenoxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile To a solution of zinc dichloride (14.8 mg, 0.109 mmol) in methanol (2 mL) was added sodium cyanoborohydride (13.7 mg, 0.218 mmol). After stirring for 2 hours, a solution of {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (91.9 mg, 0.217 mmol) and 1-[3-fluoro-5-(piperidin-4-yloxy)phenyl]-N,N-dimethylmethanamine (78 mg, 0.31 mmol) in methanol (0.50 mL) was added to reaction vial. The resulting mixture was stirred overnight at room temperature. The mixture was diluted with methanol and purified with prep-LCMS (C18 column eluting with a gradient of ACN/H$_2$O containing 0.15% NH$_4$OH) to give two isomers.

Isomer 1 (first to elute): LCMS (M+H)$^+$: 659.4.

Isomer 2 (second to elute): LCMS (M+H)$^+$: 659.4.

Step 9. {cis-3-(4-{3-[(dimethylamino)methyl]-5-fluorophenoxy}piperidin-1-yl)-1-[4-(7H-pyrrolo[2,3-d]pyrimidin-4-yl)-1H-pyrazol-1-yl]cyclobutyl}acetonitrile; and {trans-3-(4-{3-[(dimethylamino)methyl]-5-fluorophenoxy}piperidin-1-yl)-1-[4-(7H-pyrrolo[2,3-d]pyrimidin-4-yl)-1H-pyrazol-1-yl]cyclobutyl}acetonitrile To a solution of {cis-3-(4-{3-[(dimethylamino)methyl]-5-fluorophenoxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (isomer 1 from last step) (23.1 mg, 0.0350 mmol) in DCM (0.5 mL) was added trifluoroacetic acid (0.5 mL). The reaction solution was stirred for 1 h. The solvent was then removed and residue was dissolved in methanol (1.0 mL) and ethylenediamine (100. μL, 1.50 mmol) was added. The reaction solution was stirred for 2 h and diluted with methanol and purified with prep-LCMS (C18 column eluting with a gradient of ACN/H$_2$O containing 0.15% NH$_4$OH) to give the desired product as white solid.

Isomer 1 (first to elute): $^1$H NMR (400 MHz, CD$_3$OD): δ 8.67 (d, 1H), 8.66 (s, 1H), 8.37 (s, 1H), 7.51 (d, 1H), 7.00 (d, 1H), 6.74 (s, 1H), 6.63 (m, 2H), 4.46 (m, 1H), 3.42 (s, 2H), 3.35 (s, 2H), 3.00 (m, 1H), 2.85-2.66 (m, 6H), 2.36 (m, 2H), 2.23 (s, 6H), 2.04 (m, 2H), 1.81 (m, 2H); LCMS (M+H)$^+$: 529.3.

Trans isomer was prepared in same manner, using {trans-3-(4-{3-[(dimethylamino)methyl]-5-fluorophenoxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (isomer 2 from last step) as starting material.

Isomer 2 (second to elute): $^1$H NMR (400 MHz, CD$_3$OD): δ 8.74 (s, 1H), 8.67 (s, 1H), 8.41 (s, 1H), 7.51 (d, 1H), 6.99 (d, 1H), 6.73 (s, 1H), 6.63 (m, 2H), 4.44 (m, 1H), 3.41 (s, 2H), 3.31 (s, 2H), 3.10 (m, 2H), 2.95 (m, 1H), 2.71 (m, 2H), 2.47 (m, 2H), 2.31 (m, 2H), 2.23 (s, 6H), 2.04 (m, 2H), 1.80 (m, 2H); LCMS (M+H)$^+$: 529.3.

Example 41

{cis-3-[4-(3-fluoro-5-{[(2S)-2-methylpyrrolidin-1-yl]methyl}phenoxy)piperidin-1-yl]-1-[4-(7H-pyrrolo[2,3-d]pyrimidin-4-yl)-1H-pyrazol-1-yl]cyclobutyl}acetonitrile; and {trans-3-[4-(3-fluoro-5-{[(2S)-2-methylpyrrolidin-1-yl]methyl}phenoxy)piperidin-1-yl]-1-[4-(7H-pyrrolo[2,3-d]pyrimidin-4-yl)-1H-pyrazol-1-yl]cyclobutyl}acetonitrile

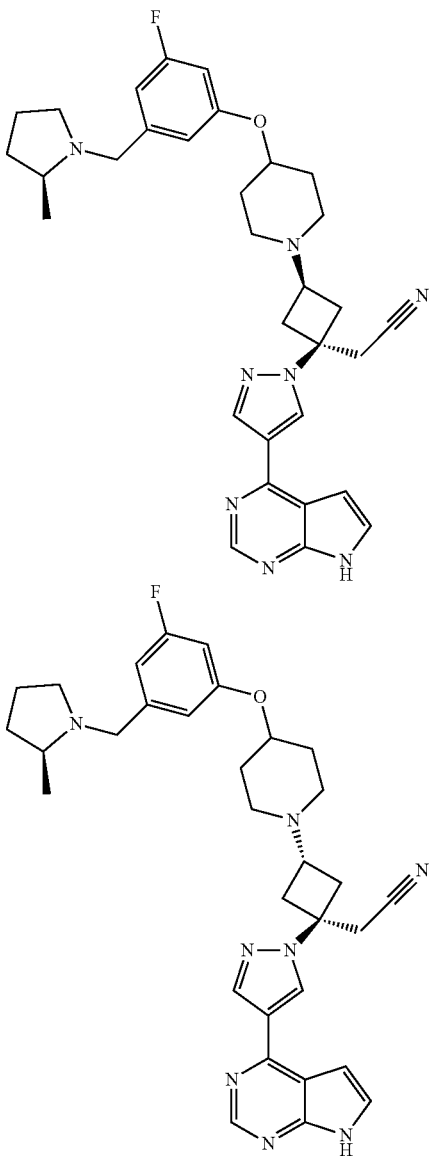

Step 1. tert-butyl 4-(3-fluoro-5-formylphenoxy)piperidine-1-carboxylate

To a solution of tert-butyl 4-(3-bromo-5-fluorophenoxy)piperidine-1-carboxylate (0.666 g, 1.78 mmol) in THF (9.0 mL) at −78° C. was added 2.5 M n-butyllithium in hexane (0.78 mL, 2.0 mmol). The solution was stirred at same temperature for 30 minutes, then N,N-dimethylformamide (1.4 mL, 18 mmol) was added to reaction flask. The reaction solution was allowed to warm to room temperature and stirred overnight. The reaction was quenched with water, and aqueous layer was extracted with ethyl acetate twice. The combined organic solutions were washed with brine, dried over $Na_2SO_4$, filtered and concentrated. The residue was diluted with methanol and purified with prep-LCMS (C18 column eluting with a gradient of $ACN/H_2O$ containing 0.15% $NH_4OH$) to give the desired product as an oil (75 mg, 13%). LCMS (M+H-100)$^+$: 224.1.

Step 2. tert-butyl 4-(3-fluoro-5-{[(2S)-2-methylpyrrolidin-1-yl]methyl}phenoxy)piperidine-1-carboxylate trifluoroacetate To a mixture of (2S)-2-methylpyrrolidine (30. μL, 0.30 mmol) and tert-butyl 4-(3-fluoro-5-formylphenoxy)piperidine-1-carboxylate (90.0 mg, 0.278 mmol) in DCM (1.3 mL) was added resin of sodium triacetoxyborohydride (13 mg, 0.032 mmol). The resulting mixture was stirred overnight. The reaction mixture was filtered, washing with additional DCM, and concentrated. The residue was purified by preparative-LCMS (C18 column eluting with a gradient of acetonitrile (ACN)/$H_2O$ containing 0.1% trifluoroacetic acid (TFA)) to give the desired product (98 mg, 70%). LCMS (M+H)$^+$: 393.2.

Step 3. (3-fluoro-5-{[(2S)-2-methylpyrrolidin-1-yl]methyl}phenoxy)piperidine This compound was prepared according to the method of Example 40, Step 7 using tert-butyl 4-(3-fluoro-5-{[(2S)-2-methylpyrrolidin-1-yl]methyl}phenoxy)piperidine-1-carboxylate trifluoroacetate as starting material. LCMS (M+H)$^+$: 293.1.

Step 4. {cis-3-[4-(3-fluoro-5-{[(2S)-2-methylpyrrolidin-1-yl]methyl}phenoxy)piperidin-1-yl]-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile; and {trans-3-[4-(3-fluoro-5-{[(2S)-2-methylpyrrolidin-1-yl]methyl}phenoxy)piperidin-1-yl]-[4-(7-{[2-(trimethylsilyl)ethoxy]methyl}-7H-pyrrolo[2,3-d]pyrimidin-4-yl)-1H-pyrazol-1-yl]cyclobutyl}acetonitrile These compounds were prepared according to the method of Example 40, Step 8 using (3-fluoro-5-{[(2S)-2-methylpyrrolidin-1-yl]methyl}phenoxy)piperidine as starting material. LCMS (M+H)$^+$: 699.5.

Step 5. {cis-3-[4-(3-fluoro-5-{[(2S)-2-methylpyrrolidin-1-yl]methyl}phenoxy)piperidin-1-yl]-1-[4-(7H-pyrrolo[2,3-d]pyrimidin-4-yl)-1H-pyrazol-1-yl]cyclobutyl}acetonitrile; and {trans-3-[4-(3-fluoro-5-{[(2S)-2-methylpyrrolidin-1-yl]methyl}phenoxy)piperidin-1-yl]-1-[4-(7H-pyrrolo[2,3-d]pyrimidin-4-yl)-1H-pyrazol-1-yl]cyclobutyl}acetonitrile These compounds were prepared according to the method of Example 40, Step 9 using {cis-3-[4-(3-fluoro-5-{[(2S)-2-methylpyrrolidin-1-yl]methyl}phenoxy)piperidin-1-yl]-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile and {trans-3-[4-(3-fluoro-5-{[(2S)-2-methylpyrrolidin-1-yl]methyl}phenoxy)piperidin-1-yl]-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile as starting materials.

Isomer 1 (first to elute): $^1$H NMR (500 MHz, CD$_3$CN): δ 10.41 (bs, 1H), 8.68 (s, 1H), 8.34 (s, 1H), 8.27 (s, 1H), 7.43 (d, 1H), 6.82 (d, 1H), 6.70 (s, 1H), 6.65 (m, 1H), 6.54 (m, 1H), 4.35 (m, 1H), 3.92 (d, 1H), 3.20 (s, 2H), 3.09 (d, 1H), 2.90-2.82 (m, 2H), 2.74-2.62 (m, 5H), 2.40 (m, 1H), 2.21 (m, 3H), 2.07 (m, 1H), 1.92 (m, 3H), 1.66 (m, 4H), 1.38 (m, 1H), 1.09 (d, 3H); LCMS (M+H)$^+$: 569.3.

Isomer 2 (second to elute): $^1$H NMR (500 MHz, CD$_3$CN): δ 10.18 (bs, 1H), 8.74 (s, 1H), 8.56 (s, 1H), 8.37 (s, 1H), 7.43 (d, 1H), 6.90 (d, 1H), 6.73 (s, 1H), 6.64 (m, 1H), 6.56 (m, 1H), 4.36 (m, 1H), 3.94 (d, 1H), 3.22 (s, 2H), 3.08 (d, 1H), 2.96 (m, 2H), 2.82 (m, 2H), 2.64 (m, 2H), 2.40 (m, 3H), 2.35-2.08 (m, 4H), 2.04 (m, 1H), 1.91 (m, 1H), 1.64 (m, 4H), 1.38 (m, 1H), 1.07 (d, 3H); LCMS (M+H)$^+$: 569.3.

Example 42

3-[(4-{cis-3-(cyanomethyl)-3-[4-(7H-pyrrolo[2,3-d]pyrimidin-4-yl)-1H-pyrazol-1-yl]cyclobutyl}piperazin-1-yl)carbonyl]-5-[(dimethylamino)methyl]benzonitrile

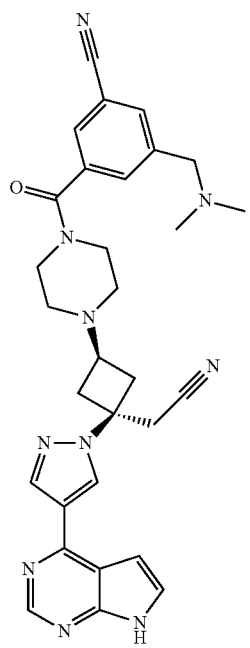 [SMILES: CN(C)Cc1cc(C#N)cc(C(=O)N2CCN([C@H]3C[C@@](CC#N)(n4cc(-c5ncnc6[nH]ccc56)cn4)C3)CC2)c1]

The title compound was prepared according to the method of Example 136, using {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (40.0 mg, 0.0812 mmol, from Step 9 of Example 1a) to afford product as the free base (12.3 mg, 28%). $^1$H NMR (400 MHz, dmso) δ 12.12 (br s, 1H), 8.70 (s, 1H), 8.68 (s, 1H), 8.39 (s, 1H), 7.80 (dd, 1H), 7.77 (dd, 1H), 7.62 (dd, 1H), 7.60 (d, J=3.6 Hz, 1H), 7.06 (d, J=3.6 Hz, 1H), 3.63 (br m, 2H), 3.47 (s, 4H), 3.29 (br m, 2H), 2.96 (tt, J=7.5, 7.6 Hz, 1H), 2.68-2.52 (m, 4H), 2.40 (br m, 2H), 2.30 (br m, J=5.6 Hz, 2H), 2.15 (s, 6H); LCMS (M+H)$^+$: 549.2.

Example 43

3-[(4-{trans-3-(cyanomethyl)-3-[4-(7H-pyrrolo[2,3-d]pyrimidin-4-yl)-1H-pyrazol-1-yl]cyclobutyl}piperazin-1-yl)methyl]-5-[(dimethylamino)methyl]benzonitrile

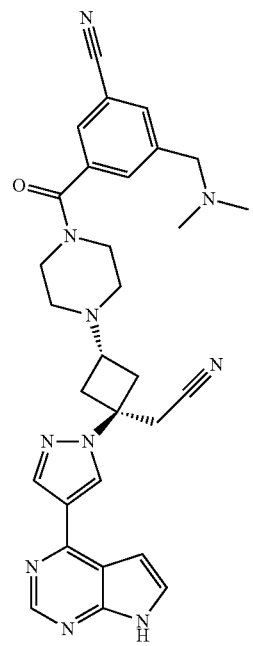 [SMILES: CN(C)Cc1cc(C#N)cc(C(=O)N2CCN([C@H]3C[C@](CC#N)(n4cc(-c5ncnc6[nH]ccc56)cn4)C3)CC2)c1]

Step A. Methyl 3-bromo-5-[(dimethylamino)methyl]benzoate

To a solution of methyl 3-bromo-5-formylbenzoate (1.8 g, 7.4 mmol, prepared as described in WO2003/048111 starting from dimethyl 5-bromoisophthalate (Alfa Aesar) in methylene chloride (20 mL) was added a solution of 2.0 M dimethylamine in tetrahydrofuran (7.4 mL, 15 mmol) and the reaction was stirred for 15 min. Sodium triacetoxyborohydride (4.7 g, 22 mmol) was then added and the resulting mixture was stirred overnight. Saturated sodium bicarbonate solution was added and the resulting mixture was extracted with ethyl acetate. The organic extract was washed twice with water, once with brine, dried over sodium sulfate, filtered and concentrated to afford product as a light yellow oil (1.87 g, 93%). $^1$H NMR (400 MHz, CDCl$_3$) δ 8.08-8.03 (m, 1H), 7.90-7.87 (m, 1H), 7.70-7.67 (m, 1H), 3.91 (s, 3H), 3.42 (s, 2H), 2.24 (s, 6H); LCMS (M+H)$^+$: 272.0, 274.0.

Step B. {3-Bromo-5-[(dimethylamino)methyl]phenyl}methanol 1.0 M Diisobutylaluminum hydride in hexanes (6.2 mL, 6.2 mmol) was added dropwise to a solution of methyl 3-bromo-5-[(dimethylamino)methyl]benzoate (0.50 g, 1.8 mmol, from Step A) in tetrahydrofuran (10 mL) at −78° C. After stirring for 2 hours, the mixture was quenched with saturated potassium sodium tartrate solution and was allowed to warm to room temperature. Ethyl acetate was added and the mixture was then stirred until a biphasic solution formed. The ethyl acetate layer was washed with water (3×), followed by brine, was dried over sodium sulfate and concentrated to give a light yellow oil (0.41 g, 93%). $^1$H NMR (300 MHz, CDCl$_3$) δ 7.41 (dd, J=1.7 Hz, 1H), 7.37 (dd, J=1.8 Hz, 1H), 7.24 (dd, J=1.4, 0.7 Hz, 1H), 4.65 (s, 2H), 3.37 (s, 2H), 2.22 (s, 6H). LCMS (M+H)$^+$: 244.0, 246.0.

Step C. 3-Bromo-5-[(dimethylamino)methyl]benzaldehyde

Manganese(IV) oxide (0.71 g, 8.2 mmol) was added to a solution of {3-bromo-5-[(dimethylamino)methyl]phenyl}methanol (0.40 g, 1.6 mmol, from Step B) in toluene (10 mL). The mixture was heated to 105° C. for 2 hours, then was cooled to room temperature and was filtered and concentrated to afford a light yellow oil (0.31 g, 80%). $^1$H NMR (400 MHz, CDCl$_3$) δ 9.95 (s, 1H), 7.90 (dd, J=1.7 Hz, 1H), 7.82-7.69 (m, 2H), 3.46 (s, 2H), 2.25 (s, 6H).

LCMS (M+H)$^+$: 241.9, 243.9.

Step D. 3-[(4-{trans-3-(Cyanomethyl)-3-[4-(7H-pyrrolo[2,3-d]pyrimidin-4-yl)-1H-pyrazol-1-yl]cyclobutyl}piperazin-1-yl)methyl]-5-[(dimethylamino)methyl]benzonitrile A solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (40. mg, 0.081 mmol, from Step 1 of Example 1b) and 3-bromo-5-[(dimethylamino)methyl]benzaldehyde (39.3 mg, 0.162 mmol, from Step C) in methylene chloride (1 mL) was treated with sodium triacetoxyborohydride (86.0 mg, 0.406 mmol) and was stirred for two hours. The reaction mixture was partitioned between ethyl acetate and water. The organic layer was washed with water, 0.1 N NaOH and sat. NaCl, dried over sodium sulfate and concentrated. The residue was dissolved in N,N-dimethylformamide (1.0 mL) and zinc cyanide (57 mg, 0.48 mmol) was added. The reaction mixture was degassed by bubbling a stream of nitrogen through the mixture for 10 minutes. Tetrakis(triphenylphosphine)palladium(0) (19 mg, 0.016 mmol) was added. The reaction was heated in the microwave to 120° C. for 30 minutes. The reaction was worked up by partition between water and ethyl acetate. The ethyl acetate layer was washed twice with water, once with brine, dried over sodium sulfate and concentrated. The residue was then stirred with 1:1 TFA:DCM for 1 hour, evaporated and stirred with 0.2 nth ethylenediamine in methanol for 30 minutes. Purification via preparative HPLC-MS (C18 eluting with a gradient of MeCN/H$_2$O containing 0.15% NH$_4$OH) followed by lyophilization afforded product as the free base (12 mg, 28%). $^1$H NMR (400 MHz, dmso) δ 12.11 (br s, 1H), 8.81 (s, 1H), 8.69 (s, 1H), 8.41 (s, 1H), 7.63-7.58 (m, 3H), 7.57 (s, 1H), 7.07 (d, J=3.6 Hz, 1H), 3.52 (s, 2H), 3.42 (s, 2H), 3.41 (s, 2H), 3.04-2.95 (m, 2H), 2.77 (tt, J=7.1, 7.2 Hz, 1H), 2.47-2.17 (m, 10H), 2.13 (s, 6H); LCMS (M+H)$^+$: 535.3.

Example 44

3-[(4-{cis-3-(cyanomethyl)-3-[4-(7H-pyrrolo[2,3-d]pyrimidin-4-yl)-1H-pyrazol-1-yl]cyclobutyl}piperazin-1-yl)methyl]-5-[(dimethylamino)methyl]benzonitrile

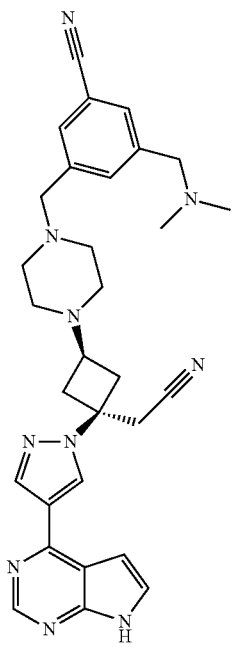 [SMILES: CN(C)Cc1cc(C#N)cc(CN2CCN([C@H]3C[C@@](CC#N)(n4cc(-c5ncnc6[nH]ccc56)cn4)C3)CC2)c1]

The title compound was prepared by the procedure of Example 43, Step D, using {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (40. mg, 0.081 mmol, from Step 9 of Example 1a) and 3-bromo-5-[(dimethylamino)methyl]benzaldehyde (39.3 mg, 0.162 mmol, Example 43, Step C) to afford product as the free base (14.5 mg, 33%). $^1$H NMR (400 MHz, dmso) δ 12.11 (br s, 1H), 8.68 (s, 2H), 8.38 (s, 1H), 7.62-7.58 (m, 3H), 7.56 (s, 1H), 7.06 (d, J=3.6 Hz, 1H), 3.50 (s, 2H), 3.46 (s, 3H), 3.42 (s, 2H), 2.90 (tt, J=7.5, 7.6 Hz, 1H), 2.67-2.53 (m, 4H), 2.47-2.16 (m, 8H), 2.13 (s, 6H); LCMS (M+H)$^+$: 535.2.

Example 45

{trans-3-{4-[3-[(dimethylamino)methyl]-5-(trifluoromethyl)benzyl]piperazin-1-yl}-1-[4-(7H-pyrrolo[2,3-d]pyrimidin-4-yl)-1H-pyrazol-1-yl]cyclobutyl}acetonitrile

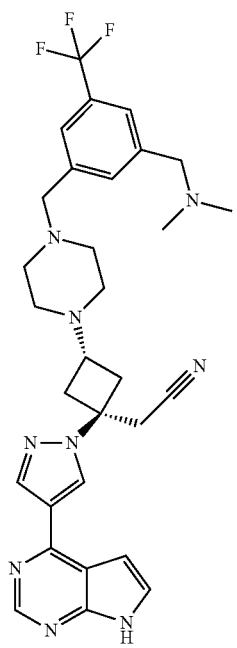 [SMILES: CN(C)Cc1cc(CN2CCN([C@H]3C[C@](CC#N)(n4cc(-c5ncnc6[nH]ccc56)cn4)C3)CC2)cc(C(F)(F)F)c1]

Step A. 1-[3-Bromo-5-(trifluoromethyl)phenyl]-N,N-dimethylmethanamine

To a solution of 3-bromo-5-(trifluoromethyl)benzaldehyde (2.0 g, 7.9 mmol, Combi-blocks) in methylene chloride (10 mL) was added a solution of 2.0 M dimethylamine in tetrahydrofuran (7.9 mL, 16 mmol) and the reaction was stirred for 15 minutes at room temperature. The reaction was then cooled to 0° C. and sodium triacetoxyborohydride (2.5 g, 12 mmol) was added. The resulting mixture was warmed to room temperature and was stirred for 24 hours. The solvents were removed in vacuo. Saturated sodium bicarbonate solution was added and the resulting mixture was extracted three times with ethyl acetate. The combined organic extracts were washed with brine, dried over sodium sulfate, filtered and concentrated. Purification by silica gel column chromatography, eluting with a gradient from 10-40% ethyl acetate in hexanes afforded product as a colorless oil (1.58 g, 71%). $^1$H NMR (300 MHz, CDCl$_3$) δ 7.68 (s, 1H), 7.65 (s, 1H), 7.57-7.46 (m, 1H), 3.45 (s, 2H), 2.25 (s, 6H); $^{19}$F NMR (282 MHz, CDCl$_3$) δ −63.10 (s); LCMS (M+H)$^+$: 282.0, 284.0.

Step B. 3-[(Dimethylamino)methyl]-5-(trifluoromethyl)benzaldehyde 2.5 M n-Butyllithium in hexanes (0.47 mL, 1.2 mmol) was added dropwise to a solution of 1-[3-bromo-5-(trifluoromethyl)phenyl]-N,N-dimethylmethanamine (0.30 g, 1.1 mmol, from Step A) in THF (6.0 mL) at −78° C. After stirring at this temperature for 20 minutes, N,N-dimethylformamide (160 μL, 2.1 mmol) was added dropwise. After a total reaction time of 50 minutes at −78° C., the reaction was quenched with 1.0 M Hydrogen chloride in water (2.1 mL, 2.1 mmol). After warming to room temperature, the mixture was diluted with more water, treated with saturated sodium bicarbonate to achieve pH 7, then extracted with ethyl acetate (EtOAc). The combined extracts were washed with water (3×), brine, dried over sodium sulfate and concentrated to give a light yellow oil, a 4:1 mixture of the desired together with de-bromination byproduct, which was used without further purification (0.2 g, 60%).

$^1$H NMR (300 MHz, CDCl$_3$) δ 10.06 (d, J=0.9 Hz, 1H), 8.03 (s, 2H), 7.87 (s, 1H), 3.55 (s, 2H), 2.27 (s, 6H); $^{19}$F NMR (282 MHz, CDCl$_3$) δ −63.15 (s); LCMS (M+H)$^+$: 232.1.

Step C. {trans-3-{4-[3-[(Dimethylamino)methyl]-5-(trifluoromethyl)benzyl]piperazin-1-yl}-1-[4-(7H-pyrrolo[2,3-d]pyrimidin-4-yl)-1H-pyrazol-1-yl]cyclobutyl}acetonitrile A solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Step 1 of Example 1b) and 3-[(dimethylamino)methyl]-5-(trifluoromethyl)benzaldehyde (0.0352 g, 0.122 mmol, from Step B) in methylene chloride (DCM) (1 mL) was treated with sodium triacetoxyborohydride (0.0645 g, 0.304 mmol) and stirred overnight. The mixture was quenched with 0.1 N NaOH and extracted with DCM. The combined organic extracts were washed with three portions of water, followed by brine, dried over sodium sulfate and concentrated. The residue was stirred with 1:1 TFA:DCM for 1 hour, evaporated and then stirred with 0.2 mL ethylenediamine in methanol for 30 minutes. Purification via preparative HPLC-MS (C18 eluting with a gradient of MeCN/H$_2$O containing 0.15% NH$_4$OH), followed by lyophilization afforded product as the free base (21.4 mg, 61%).

$^1$H NMR (400 MHz, dmso) δ 12.13 (br s, 1H), 8.82 (s, 1H), 8.69 (s, 1H), 8.41 (s, 1H), 7.60 (d, J=3.6 Hz, 1H), 7.55-7.47 (m, 3H), 7.08 (d, J=3.6 Hz, 1H), 3.56 (s, 2H), 3.46 (s, 2H), 3.41 (s, 2H), 3.04-2.93 (m, 2H), 2.77 (tt, J=7.2, 7.2 Hz, 1H), 2.48-2.18 (m, 10H), 2.14 (s, 6H); $^{19}$F NMR (376 MHz, dmso) δ −61.25 (s); LCMS (M+H)$^+$: 578.3.

Example 46

{cis-3-{4-[3-[(dimethylamino)methyl]-5-(trifluoromethyl)benzyl]piperazin-1-yl}-1-[4-(7H-pyrrolo[2,3-d]pyrimidin-4-yl)-1H-pyrazol-1-yl]cyclobutyl}acetonitrile

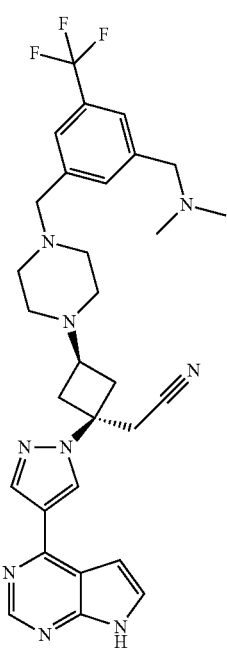 [SMILES: CN(C)Cc1cc(CN2CCN([C@H]3C[C@@](CC#N)(n4cc(-c5ncnc6[nH]ccc56)cn4)C3)CC2)cc(C(F)(F)F)c1]

The title compound was prepared by the method of Example 45, using {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Step 9 of Example 1a) and 3-[(dimethylamino)methyl]-5-(trifluoromethyl)benzaldehyde (0.0352 g, 0.122 mmol, from Example 45, Step B) to afford product as the free base (29.4 mg, 84%). $^1$H NMR (400 MHz, dmso) δ 12.14 (br s, 1H), 8.69 (s, 1H), 8.68 (s, 1H), 8.39 (s, 1H), 7.60 (d, J=3.5 Hz, 1H), 7.54-7.46 (m, 3H), 7.06 (d, J=3.6 Hz, 1H), 3.54 (s, 2H), 3.46 (s, 4H), 2.89 (tt, J=7.8, 8.0 Hz, 1H), 2.64-2.16 (m, 12H), 2.13 (s, 6H). $^{19}$F NMR (376 MHz, dmso) δ −61.25 (s); LCMS (M+H)$^+$: 578.2.

Example 47

{trans-3-(4-{[6-[(ethylamino)methyl]-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

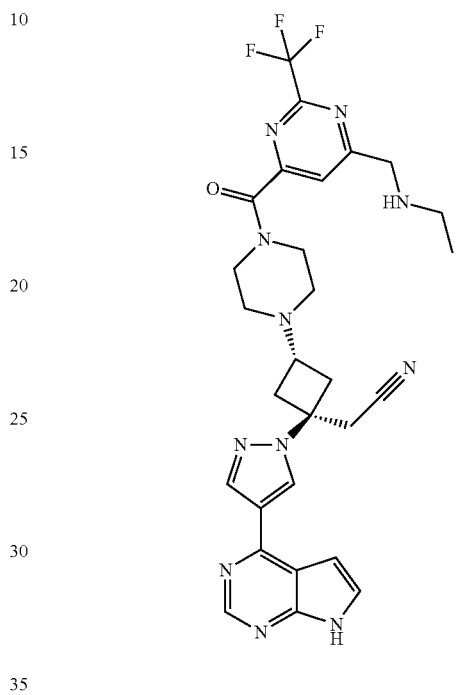

Step A. Ethyl 6-(bromomethyl)-2-(trifluoromethyl)pyrimidine-4-carboxylate

A solution of ethyl 6-methyl-2-(trifluoromethyl)pyrimidine-4-carboxylate (2.00 g, 8.54 mmol, prepared as described in WO2007/090748) in acetic acid (12 mL) was treated with bromine (1.36 g, 8.54 mmol) and the reaction was heated to 80° C. in a sealed vial for 30 minutes, at which time, the color of bromine was dissipated. The acetic acid was removed in vacuo and was followed by dissolving of the residue in toluene and removal of solvent in vacuo. The percent by weight of desired component in the mixture (containing unreacted starting material and overbrominated product) was determined by NMR and the mixture used without further purification (1.62 g, 61%). $^1$H NMR (300 MHz, CDCl$_3$): δ 8.32 (s, 1H), 4.60 (s, 2H), 4.54 (q, 2H), 1.46 (t, 3H); LCMS (M+H)$^+$: 313.0, 315.0

Step B. Ethyl 6-[(acetyloxy)methyl]-2-(trifluoromethyl)pyrimidine-4-carboxylate

Ethyl 6-(bromomethyl)-2-(trifluoromethyl)pyrimidine-4-carboxylate (1.62 g, 5.17 mmol, from Step A) was dissolved in acetonitrile (15 mL) and sodium acetate (2.8 g, 34 mmol) was added. The mixture was heated to 80° C. for 4 hours, then allowed to stand at room temperature overnight. Acetonitrile was removed in vacuo. The residue was partitioned between water and ethyl acetate and the aqueous layer was extracted with two further portions of ethyl acetate. The combined extracts were washed with water, then brine, dried over sodium sulfate, filtered and concentrated. Flash chromatography, eluting with a gradient from 0-60% EtOAc/hexanes afforded purified product (0.95 g, 63%). $^1$H NMR (300 MHz, CDCl$_3$): δ 8.15 (s, 1H), 5.36 (s, 2H), 4.53 (q, 2H), 2.25 (s, 3H), 1.46 (t, 3H); LCMS (M+H)$^+$: 293.0.

Step C. 6-[(Acetyloxy)methyl]-2-(trifluoromethyl)pyrimidine-4-carboxylic acid A solution of ethyl 6-[(acetyloxy)methyl]-2-(trifluoromethyl)pyrimidine-4-carboxylate (0.95 g, 3.2 mmol, from Step B) in tetrahydrofuran (8.7 mL) at 0° C. was treated with lithium hydroxide, monohydrate (140 mg, 3.2 mmol) in water (1.3 mL). The reaction was stirred for 15 minutes, then was treated with 1N HCl to pH~4 while still in the ice bath. THF was removed from the mixture in vacuo. The product was extracted first with ethyl acetate, then with several portions of 10% iPrOH in CHCl$_3$, including periodic adjustment of pH as necessary. The extracts were combined and dried over sodium sulfate, filtered and concentrated to afford a yellow oil, which was used without further purification (0.86 g, 100%). $^1$H NMR (300 MHz, CDCl$_3$): δ 8.25 (s, 1H), 5.35 (s, 2H), 2.23 (s, 3H); LCMS (M+H)$^+$: 265.0.

Step D. {trans-3-(4-{[6-(Hydroxymethyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile Triethylamine (3.5 mL, 25 mmol) and benzotriazol-1-yloxytris(dimethylamino)phosphonium hexafluorophosphate (3.11 g, 7.02 mmol) were added to a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (3.01 g, 6.11 mmol, from Step 1 of Example 1b) and 6-[(acetyloxy)methyl]-2-(trifluoromethyl)pyrimidine-4-carboxylic acid (1.91 g, 7.23 mmol, from Step C) in N,N-Dimethylformamide (50. mL). After stirring for 1 hour, the reaction mixture was partitioned between ethyl acetate and water. The aqueous portion was extracted with two further portions of ethyl acetate. The combined organic extracts were washed with water, brine, dried over sodium sulfate, filtered and concentrated. The product was purified by flash chromatography, eluting with a gradient from 0-5% MeOH/ethyl acetate to give 4.5 g brown oil. The oil was dissolved in tetrahydrofuran (50.0 mL), and a solution of lithium hydroxide, monohydrate (0.31 g, 7.3 mmol) in water (12 mL, 670 mmol) was added. After stirring for 30 minutes, 1 N HCl was used to adjust the pH to 7. The mixture was diluted with water, and extracted with EtOAc. The combined organic extracts were washed twice with water, once with brine, dried over sodium sulfate and concentrated to afford the product as a light yellow solid (3.24 g, 76%).
$^1$H NMR (300 MHz, CDCl$_3$) δ0 8.84 (s, 1H), 8.46 (s, 1H), 8.32 (s, 1H), 7.97 (s, 1H), 7.41 (d, J=3.7 Hz, 1H), 6.81 (d, J=3.7 Hz, 1H), 5.67 (s, 2H), 4.91 (s, 2H), 3.92-3.78 (m, 2H), 3.71-3.57 (m, 2H), 3.59-3.43 (m, 2H), 3.34 (br s, 1H), 3.20 (s, 2H), 3.12-2.83 (m, 3H), 2.55-2.36 (m, 6H), 0.99-0.84 (m, 2H), −0.06 (s, 9H). $^{19}$F NMR (282 MHz, CDCl$_3$) δ −70.74 (s); LCMS (M+H)$^+$: 697.3.

Step E. {trans-3-(4-{[6-[(Ethylamino)methyl]-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile A solution of methanesulfonyl chloride (22 μL, 0.28 mmol) in methylene chloride (1.5 mL) was added to a mixture of {trans-3-(4-{[6-(hydroxymethyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.15 g, 0.22 mmol, from Step D) and triethylamine (0.060 mL, 0.43 mmol) in methylene chloride (7.1 mL). After stirring for 15 minutes, ethylamine (0.5 mL, 9 mmol) was added. After 1 hour, solvents were removed in vacuo and the residue was dissolved in a 1:1 mixture of TFA/DCM, stirred for one hour, then concentrated again. The residue was redissolved in 10 ml MeOH, and 0.5 ml ethylenediamine was added. After deprotection was complete, the product was purified via preparative HPLC-MS (C18 eluting with a gradient of MeCN/H$_2$O containing 0.15% NH$_4$OH) and lyophilized to afford product as the free base (37 mg, 28%).
$^1$H NMR (400 MHz, dmso) δ 12.13 (s, 1H), 8.83 (s, 1H), 8.69 (s, 1H), 8.42 (s, 1H), 7.96 (s, 1H), 7.60 (dd, J=3.6, 2.3 Hz, 1H), 7.07 (dd, J=3.6, 1.7 Hz, 1H), 3.95 (s, 2H), 3.77-3.63 (m, 2H), 3.43 (s, 2H), 3.41-3.35 (m, 2H), 3.06-2.95 (m, 2H), 2.85 (tt, J=7.3, 7.3 Hz, 1H), 2.58 (q, J=7.1 Hz, 2H), 2.47-2.40 (m, 2H), 2.40-2.33 (m, 2H), 2.33-2.25 (m, 2H), 1.04 (t, J=7.1 Hz, 3H); $^{19}$F NMR (376 MHz, dmso) δ −69.43 (s); LCMS (M+H)$^+$: 594.3

Example 48

6-[(4-{trans-3-(cyanomethyl)-3-[4-(7H-pyrrolo[2,3-d]pyrimidin-4-yl)-1H-pyrazol-1-yl]cyclobutyl}piperazin-1-yl)carbonyl]-2-(trifluoromethyl)pyrimidine-4-carboxylic acid

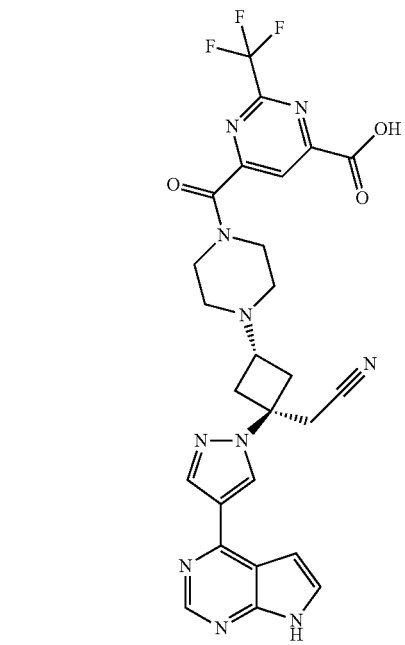 [SMILES: N#CC[C@]1(n2cc(-c3ncnc4[nH]ccc34)cn2)C[C@H](N2CCN(C(=O)c3cc(C(=O)O)nc(C(F)(F)F)n3)CC2)C1]

6-[(4-{trans-3-(Cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperazin-1-yl)carbonyl]-2-(trifluoromethyl)pyrimidine-4-carboxylic acid was produced as a byproduct of the hydrolysis reaction described in Example 47, Step D. This product could be purified from that reaction mixture via preparative HPLC-MS (C18 eluting with a gradient of MeCN/H$_2$O containing 0.15% NH$_4$OH). The product was deprotected by stirring with 1:1TFA:DCM for 1 hour, followed by evaporation and stirring with excess ethylenediamine in methanol. After deprotection was complete, the product was again purified via preparative HPLC-MS (C18 eluting with a gradient of MeCN/H$_2$O containing 0.15% NH$_4$OH) and lyophilized to afford product. $^1$H NMR (400 MHz, CD$_3$OD) δ 8.71 (s, 1H), 8.66 (s, 1H), 8.39 (s, 1H), 8.21 (s, 1H), 7.50 (d, J=3.6 Hz, 1H), 6.98 (d, J=3.7 Hz, 1H), 3.91-3.77 (m, 2H), 3.61-3.46 (m, 2H), 3.35 (s, 2H), 3.14-3.02 (m, 2H), 3.03-2.88 (m, 1H), 2.63-2.36 (m, 6H); LCMS (M+H)$^+$: 581.2

Example 49

{trans-3-(4-{[6-(azetidin-1-ylmethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

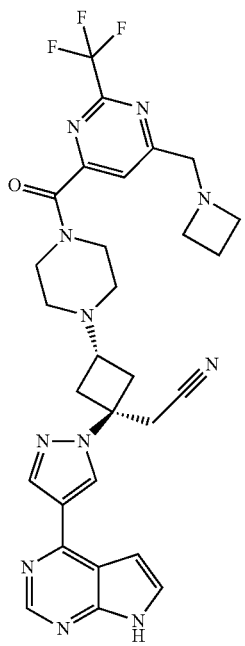 [SMILES: N#CC[C@]1(n2cc(-c3ncnc4[nH]ccc34)cn2)C[C@H](N2CCN(C(=O)c3cc(CN4CCC4)nc(C(F)(F)F)n3)CC2)C1]

Step A. Ethyl 6-(azetidin-1-ylmethyl)-2-(trifluoromethyl)pyrimidine-4-carboxylate Azetidine (0.62 mL, 9.2 mmol, Aldrich) was added to a solution of ethyl 6-(bromomethyl)-2-(trifluoromethyl)pyrimidine-4-carboxylate (1.76 g, 4.16 mmol, prepared in the manner outlined in Example 47, Step A) in methylene chloride (39 mL). and the reaction was stirred for 20 minutes. Solvent was removed in vacuo and the residue was purified by flash chromatography on silica gel, eluting with a gradient from 0-5% MeOH in DCM to afford product (0.74 g, 61%); LCMS (M+H)$^+$: 290.0.

Step B. 6-(Azetidin-1-ylmethyl)-2-(trifluoromethyl)pyrimidine-4-carboxylic acid dihydrochloride Lithium hydroxide, monohydrate (108 mg, 2.57 mmol) was added to a mixture of ethyl 6-(azetidin-1-ylmethyl)-2-(trifluoromethyl)pyrimidine-4-carboxylate (0.34 g, 1.2 mmol, from Step A) in tetrahydrofuran (6.0 mL) and water (1.5 mL). After 15 minutes, the THF was removed in vacuo and the mixture was treated with 1.0 M hydrogen chloride in water (5.3 mL, 5.3 mmol), and acetonitrile (7.0 mL). The mixture was then filtered and concentrated to afford the product as a yellow solid. LCMS (M+H)$^+$: 262.1.

Step C. {trans-3-(4-{[6-(Azetidin-1-ylmethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile {trans-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (20.0 mg, 0.0406 mmol, from Step 1 of Example 1b) was added to a mixture of 6-(azetidin-1-ylmethyl)-2-(trifluoromethyl)pyrimidine-4-carboxylic acid dihydrochloride (27 mg, 0.061 mmol, from Step B), triethylamine (33.9 μL, 0.244 mmol) and N,N,N',N'-tetramethyl-O-(7-azabenzotriazol-1-yl)uronium Hexafluorophosphate (21.6 mg, 0.0568 mmol) in DCM (0.4 mL) and THF (0.45 mL) that was pre-stirred for 15 minutes. After stirring overnight, the mixture was diluted with EtOAc, washed successively with water, 0.1 N NaOH, and brine, dried over sodium sulfate, decanted and concentrated. The crude product was deprotected by stirring with 1:1 DCM/TFA for one hour, removal of solvents in vacuo, and stirring with ethylenediamine (0.1 mL) in MeOH (1 mL). Purification via preparative HPLC-MS (C18 eluting with a gradient of MeCN/H$_2$O containing 0.15% NH$_4$OH) followed by lyophilization afforded the product as the free base (6.2 mg, 25%). $^1$H NMR (400 MHz, dmso) δ 12.13 (s, 1H), 8.83 (s, 1H), 8.69 (s, 1H), 8.42 (s, 1H), 7.82 (s, 1H), 7.60 (d, J=3.6 Hz, 1H), 7.07 (d, J=3.6 Hz, 1H), 3.82 (s, 2H), 3.75-3.64 (m, 2H), 3.43 (s, 2H), 3.39-3.35 (m, 2H), 3.28 (t, J=7.0 Hz, 4H), 3.06-2.96 (m, 2H), 2.85 (tt, J=7.0, 7.4 Hz, 1H), 2.47-2.40 (m, 2H), 2.40-2.33 (m, 2H), 2.33-2.26 (m, 2H), 2.04 (p, J=7.1 Hz, 2H); $^{19}$F NMR (376 MHz, dmso) δ −69.49 (s); LCMS (M+H)$^+$: 606.2.

Example 50

{trans-3-(4-{[6-[(methylamino)methyl]-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

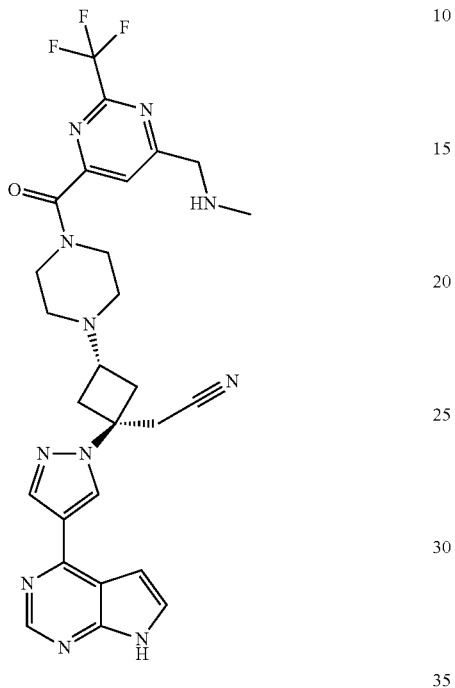

Methanesulfonyl chloride (0.006 mL, 0.08 mmol) was added to a solution of {trans-3-(4-{[6-(hydroxymethyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.043 mmol, from Example 47, Step D) and N,N-diisopropylethylamine (0.025 g, 0.19 mmol) in methylene chloride (1 mL). When mesylate formation was complete as determined by LCMS, 10.6 M methylamine in ethanol (0.20 mL, 2.2 mmol) was added (33 wt % in ethanol, Aldrich). After stirring for a total of 2 hours, solvent and excess reagents were removed in vacuo. To deprotect, trifluoroacetic Acid (1 mL) was added. After stirring for 2 hours, the solvents were evaporated and the residue was dissolved in methanol (1 mL) and ethylenediamine (0.2 mL, 3 mmol) was added. After 30 minutes, the deprotection was complete and the product was purified via preparative HPLC-MS (C18 eluting with a gradient of MeCN/H$_2$O containing 0.15% NH$_4$OH) and lyophilized to afford the product as the free base (5 mg, 20%). $^1$H NMR (400 MHz, CD$_3$OD) δ 8.71 (s, 1H), 8.66 (s, 1H), 8.40 (s, 1H), 7.88 (s, 1H), 7.51 (d, J=3.6 Hz, 1H), 6.98 (d, J=3.6 Hz, 1H), 4.00 (s, 2H), 3.89-3.79 (m, 2H), 3.58-3.50 (m, 2H), 3.34 (s, 2H), 3.13-3.02 (m, 2H), 2.97 (tt, J=7.0, 7.1 Hz, 1H), 2.58-2.43 (m, 6H); $^{19}$F NMR (376 MHz, CD$_3$OD) δ −72.35 (s); LCMS (M+H)$^+$: 580.2.

Example 51

{trans-3-(4-{[6-(hydroxymethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

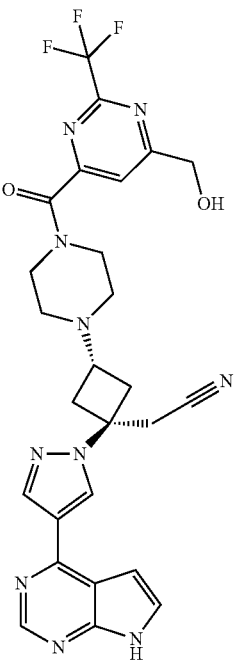

{trans-3-(4-{[6-(Hydroxymethyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (prepared as in Example 47, Step D) was stirred with 1:1 TFA/DCM for 1 hour. Solvents were removed in vacuo and the residue was then stirred with excess ethylenediamine in methanol overnight. Purification via preparative HPLC-MS (C18 eluting with a gradient of MeCN/H$_2$O containing 0.15% NH$_4$OH) followed by lyophilization afforded the product as the free base. $^1$H NMR (500 MHz, CDCl$_3$) δ 9.08 (s, 1H), 8.84 (s, 1H), 8.50 (s, 1H), 8.33 (s, 1H), 7.96 (s, 1H), 7.38 (dd, J=3.7, 2.1 Hz, 1H), 6.82 (dd, J=3.7, 1.8 Hz, 1H), 4.93 (d, J=4.6 Hz, 2H), 3.87 (br m, 2H), 3.68 (br m, 2H), 3.22 (s, 2H), 3.14-2.88 (m, 3H), 2.80 (t, J=5.6 Hz, 1H), 2.66-2.27 (m, 6H); $^{19}$F NMR (376 MHz, CDCl$_3$) δ −70.77 (s); LCMS (M+H)$^+$: 551.2

Example 52

{trans-3-(4-{[6-[(dimethylamino)methyl]-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

Example 53

{trans-3-(4-{[6-(pyrrolidin-1-ylmethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

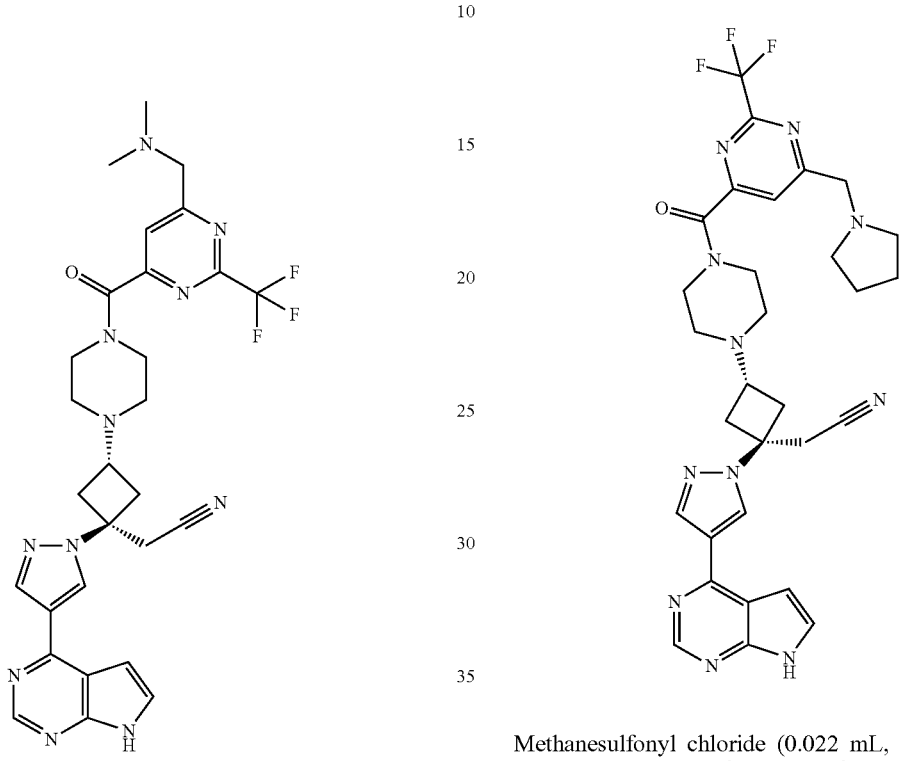

Triethylamine (0.16 mL, 1.1 mmol) and methanesulfonyl chloride (58 µL, 0.75 mmol) were added sequentially to a solution of {trans-3-(4-{[6-(hydroxymethyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.4 g, 0.6 mmol, prepared as in Example 47, Step D) in methylene chloride (19 mL, 3.0E2 mmol). After 15 minutes, 2.0 M dimethylamine in THF (2.87 mL, 5.74 mmol, Aldrich) was added. After 2 hours, the mixture was concentrated, the residue was dissolved in a 1:1 mixture of TFA/DCM, stirred for one hour, then concentrated again. The residue was redissolved in 10 mL MeOH, and 1.0 mL of ethylenediamine was added. After complete deprotection, the product was purified via preparative HPLC-MS (C18 eluting with a gradient from 20-38% MeCN/H$_2$O containing 0.15% NH$_4$OH and lyophilized to afford product as the free base (134 mg, 38%). $^1$H NMR (400 MHz, CD$_3$OD) δ 8.71 (s, 1H), 8.66 (s, 1H), 8.40 (s, 1H), 7.94 (s, 1H), 7.51 (d, J=3.6 Hz, 1H), 6.98 (d, J=3.7 Hz, 1H), 3.92-3.77 (m, 4H), 3.64-3.45 (m, 2H), 3.35 (s, 2H), 3.16-3.02 (m, 2H), 2.97 (tt, J=7.1, 7.3 Hz, 1H), 2.62-2.41 (m, 6H), 2.40 (s, 6H); $^{19}$F NMR (376 MHz, CD$_3$OD) δ −72.31 (s); LCMS (M+H)$^+$: 594.2

Methanesulfonyl chloride (0.022 mL, 0.29 mmol) was added to a solution of {trans-3-(4-{[6-(hydroxymethyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.100 g, 0.144 mmol, prepared as in Example 47, Step D) and N,N-diisopropylethylamine (0.083 g, 0.64 mmol) in DCM (3 mL). When mesylate formation was complete as determined by LCMS, pyrrolidine (0.120 mL, 1.44 mmol, Aldrich) was added. The reaction was stirred for 40 hours. The reaction was partitioned between water and ethyl acetate and the aqueous portion was extracted a further two times with ethyl acetate. The combined extracts were dried over sodium sulfate, decanted and concentrated. The crude product was stirred with 1:1 TFA:DCM for 2 hours. The solvents were evaporated and replaced with methanol (3 mL) and ethylenediamine (0.7 mL, 10 mmol) and the deprotection stirred for 30 minutes. Purification via preparative HPLC-MS (C18 eluting with a gradient of MeCN/H$_2$O containing 0.15% NH$_4$OH). followed by purification via preparative HPLC-MS (C18 eluting with a gradient of MeCN/H$_2$O containing 0.1% TFA). followed by purification again via preparative HPLC-MS (C18 eluting with a gradient of MeCN/H$_2$O containing 0.15% NH$_4$OH) afforded product, after lyophilization, as the free base. $^1$H NMR (400 MHz, CD$_3$OD) δ 8.71 (s, 1H), 8.66 (s, 1H), 8.40 (s, 1H), 7.93 (s, 1H), 7.51 (d, J=3.6 Hz, 1H), 6.98 (d, J=3.6 Hz, 1H), 3.94 (s, 2H), 3.89-3.77 (m, 2H), 3.59-3.46 (m, 2H), 3.34 (s, 2H), 3.13-3.03 (m, 2H), 2.97 (tt, J=7.0, 7.2 Hz, 1H), 2.72-2.61 (m, 4H), 2.62-2.40 (m, 6H), 1.91-1.71 (m, 4H); $^{19}$F NMR (376 MHz, CD$_3$OD) δ −72.31 (s); LCMS (M+H)$^+$: 620.3

Example 54

{trans-3-(4-{[6-(aminomethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

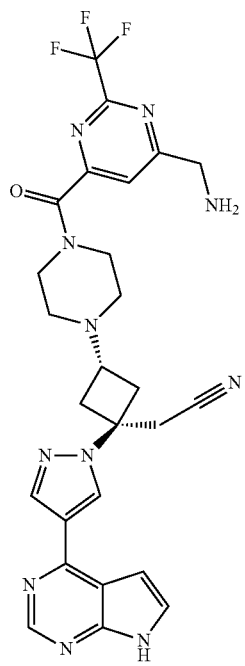 [SMILES: N#CC[C@]1(n2cc(-c3ncnc4[nH]ccc34)cn2)C[C@H](N2CCN(C(=O)c3cc(CN)nc(C(F)(F)F)n3)CC2)C1]

Triethylamine (0.012 mL, 0.089 mmol) and methanesulfonyl chloride (4.5 μL, 0.058 mmol) were added to a solution of {trans-3-(4-{[6-(hydroxymethyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (31 mg, 0.044 mmol, prepared as in Example 47, Step D) in methylene chloride (1.5 mL). After 15 minutes, the mixture was concentrated in vacuo and 7.0 M ammonia in methanol (0.6 mL, 4 mmol) was added. After 2 hours, solvents and excess reagents were removed in vacuo and the residue was dissolved in a 1:1 mixture of TFA/DCM and stirred for one hour, then concentrated again. Deprotection was completed by stirring the resulting residue in 1 mL MeOH containing 0.2 mL of ethylenediamine. Purification via preparative HPLC-MS (C18 eluting with a gradient of MeCN/H$_2$O containing 0.15% NH$_4$OH) followed by lyophilization afforded product as the free base (2.6 mg, 10%).

$^1$H NMR (400 MHz, dmso) δ 12.13 (br s, 1H), 8.83 (s, 1H), 8.69 (s, 1H), 8.42 (s, 1H), 8.03 (s, 1H), 7.60 (d, J=3.6 Hz, 1H), 7.07 (d, J=3.6 Hz, 1H), 3.94 (s, 2H), 3.79-3.65 (m, 2H), 3.43 (s, 2H), 3.40-3.36 (m, 2H), 3.09-2.96 (m, 2H), 2.84 (tt, J=7.3, 7.4 Hz, 1H), 2.47-2.24 (m, 6H); $^{19}$F NMR (376 MHz, dmso) δ −69.42 (s); LCMS (M+H)$^+$: 566.3.

Example 55

{trans-3-(4-{[6-[(isopropylamino)methyl]-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

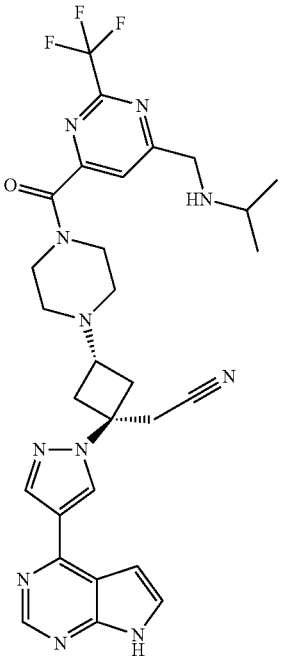 [SMILES: CC(C)NCc1cc(C(=O)N2CCN([C@H]3C[C@](CC#N)(n4cc(-c5ncnc6[nH]ccc56)cn4)C3)CC2)nc(C(F)(F)F)n1]

Triethylamine (0.012 mL, 0.089 mmol) and methanesulfonyl chloride (4.5 μL, 0.058 mmol) were added to a solution of {trans-3-(4-{[6-(hydroxymethyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (31 mg, 0.044 mmol, prepared as in Example 47, Step D) in methylene chloride (1.5 mL). After 15 minutes, 2-propanamine (37.9 μL, 0.445 mmol, Aldrich) was added. After stirring overnight, solvent and excess reagents were removed in vacuo. The residue was dissolved in a 1:1 mixture of TFA/DCM, stirred for one hour, then concentrated again. The residue was redissolved in 1 mL MeOH and 0.2 mL of ethylenediamine was added. Purification via preparative HPLC-MS (C18 eluting with a gradient of MeCN/H$_2$O containing 0.15% NH$_4$OH) followed by lyophilization afforded product as the free base (4.3 mg, 16%). $^1$H NMR (400 MHz, dmso) δ 12.14 (s, 1H), 8.83 (s, 1H), 8.69 (s, 1H), 8.42 (s, 1H), 7.99 (s, 1H), 7.61 (d, J=3.6 Hz, 1H), 7.08 (d, J=3.6 Hz, 1H), 3.94 (s, 2H), 3.78-3.63 (m, 2H), 3.43 (s, 2H), 3.41-3.37 (m, 2H), 3.07-2.96 (m, 2H), 2.84 (tt, J=7.2, 7.2 Hz, 1H), 2.74 (hept, J=6.7, 6.3 Hz, 1H), 2.48-2.40 (m, 2H), 2.40-2.32 (m, 2H), 2.32-2.21 (m, 2H), 1.00 (d, J=6.2 Hz, 6H); LCMS (M+H)$^+$: 608.3.

145

Example 56

{trans-3-(4-{[6-[(cyclobutylamino)methyl]-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

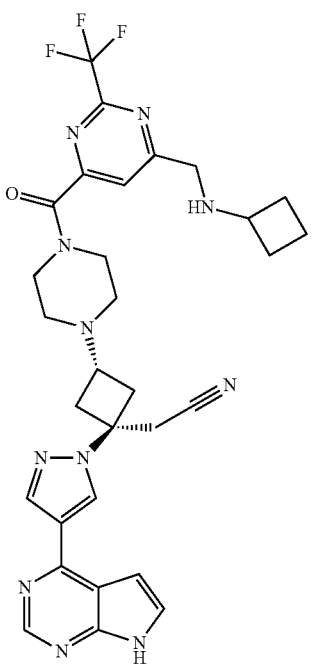 [SMILES: N#CC[C@]1(n2cc(-c3ncnc4[nH]ccc34)cn2)C[C@H](N2CCN(C(=O)c3cc(CNC4CCC4)nc(C(F)(F)F)n3)CC2)C1]

The title compound was prepared by a modification of Example 55, starting from {trans-3-(4-{[6-(hydroxymethyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (31 mg, 0.044 mmol, prepared as in Example 47, Step D) and using cyclobutanamine (40 µL, 0.4 mmol, Aldrich), but with stirring at 40° C. overnight after addition of the amine, to afford product as the free base (9.0 mg, 33%). $^1$H NMR (300 MHz, dmso) δ 12.12 (br s, 1H), 8.83 (s, 1H), 8.69 (s, 1H), 8.42 (s, 1H), 7.95 (s, 1H), 7.60 (d, J=3.6 Hz, 1H), 7.07 (d, J=3.6 Hz, 1H), 3.86 (s, 2H), 3.76-3.60 (m, 2H), 3.26-3.10 (m, 1H), 3.43 (s, 2H), 3.40-3.35 (m, 2H), 3.10-2.93 (m, 2H), 2.84 (tt, J=6.7, 6.5 Hz, 1H), 2.75 (br s, 1H), 2.46-2.20 (m, 6H), 2.14-1.94 (m, 2H), 1.80-1.38 (m, 4H); $^{19}$F NMR (282 MHz, dmso) δ −69.43 (s); LCMS (M+H)$^+$: 620.2.

146

Example 57

{trans-3-(4-{[6-[(tert-butylamino)methyl]-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

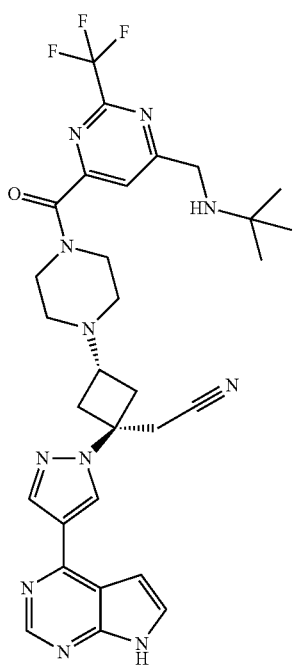 [SMILES: CC(C)(C)NCc1cc(C(=O)N2CCN([C@H]3C[C@](CC#N)(n4cc(-c5ncnc6[nH]ccc56)cn4)C3)CC2)nc(C(F)(F)F)n1]

The title compound was prepared as in Example 56, starting with {trans-3-(4-{[6-(hydroxymethyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (81 mg, 0.12 mmol, prepared as in Example 47, Step D) and using tert-Butylamine (100 µL, 1 mmol, Aldrich) to afford product as the free base (19.5 mg, 26%). $^1$H NMR (400 MHz, dmso) δ 12.13 (br s, 1H), 8.83 (s, 1H), 8.69 (s, 1H), 8.42 (s, 1H), 8.02 (s, 1H), 7.60 (d, J=3.6 Hz, 1H), 7.07 (d, J=3.6 Hz, 1H), 3.92 (s, 2H), 3.73-3.60 (m, 2H), 3.43 (s, 2H), 3.40-3.35 (m, 2H), 3.07-2.94 (m, 2H), 2.84 (tt, J=7.1, 7.2 Hz, 1H), 2.46-2.40 (m, 2H), 2.40-2.33 (m, 3H), 2.33-2.25 (m, 2H), 1.07 (s, 9H); $^{19}$F NMR (376 MHz, dmso) δ −69.41 (s); LCMS (M+H)$^+$: 622.2.

Example 58

{trans-3-(4-{[6-(1-hydroxy-1-methylethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

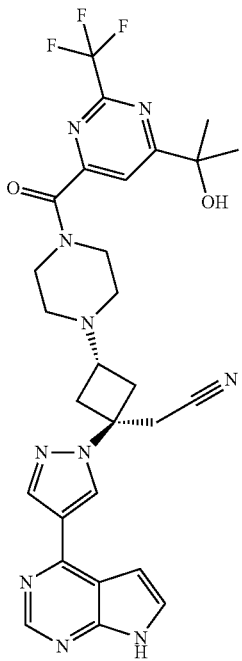 [SMILES: CC(C)(O)c1cc(C(=O)N2CCN([C@H]3C[C@](CC#N)(n4cc(-c5ncnc6[nH]ccc56)cn4)C3)CC2)nc(C(F)(F)F)n1]

Step A. Ethyl 6-isopropyl-2-(trifluoromethyl)pyrimidine-4-carboxylate

To a solution of 2,2,2-trifluoroethanimidamide (7.08 g, 53.7 mmol, Matrix) in ethanol (85 mL, 1400 mmol) was added ethyl (3Z)-4-hydroxy-5-methyl-2-oxohex-3-enoate (10.00 g, 53.70 mmol, Alfa Aesar). The mixture was then cooled in an ice bath, and a solution of hydrogen chloride in ethanol (84 mL, prepared by bubbling HCl gas through the ethanol for 10 minutes) was added. The reaction was allowed to warm to room temperature and stir overnight. The mixture was added dropwise to a saturated solution of sodium bicarbonate. After complete neutralization was achieved, ethanol was removed in vacuo. The product was extracted with three portions of DCM. The combined extracts were dried over sodium sulfate, filtered and evaporated. The crude product was purified by flash chromatography on silica gel, eluting with a gradient from 0-25% EtOAc/Hexanes (9.14 g, 65%). $^1$H NMR (300 MHz, CDCl$_3$) δ 8.02 (s, 1H), 4.52 (q, J=7.1 Hz, 2H), 3.22 (hept, J=6.9 Hz, 1H), 1.45 (t, J=7.1 Hz, 3H), 1.38 (d, J=6.9 Hz, 6H); LCMS (M+H)$^+$: 263.1

Step B. 6-(1-Hydroxy-1-methylethyl)-2-(trifluoromethyl)pyrimidine-4-carboxylic acid A solution of ethyl 6-isopropyl-2-(trifluoromethyl)pyrimidine-4-carboxylate (2.00 g, 7.63 mmol, from Step A) in tetrahydrofuran (40 mL) was added to 1.0 M potassium tert-butoxide in THF (22.9 mL, 22.9 mmol) held at −40° C. After stirring for 45 minutes at this temperature, oxygen was introduced below the surface of the reaction solution via a syringe attached to a balloon containing oxygen. The oxygen was bubbled subsurface periodically (by addition and removal of an outlet) for 20 minutes, while maintaining the reaction temperature between −40 to −30° C. The reaction was then allowed to slowly reach room temperature with periodic bubbling of oxygen through the solution. Near a temperature of −30 deg C., the reaction turned from purple to orange in color. The reaction was kept under atmosphere of oxygen overnight, at which time the reaction was quenched with water and sodium sulfite (2 g, 20 mmol) was added. Lithium hydroxide, monohydrate (0.928 g, 22.1 mmol) was also added and the reaction was stirred overnight. Concentrated HCl was added dropwise into the reaction to achieve pH between 3 and 4. The layers were separated and the THF layer was reserved for addition to the subsequent two ethyl acetate extractions. The combined extracts were washed with brine, dried over sodium sulfate, filtered and concentrated, then azeotroped twice with MeOH to afford a yellow syrup which was used without further purification (1.7 g, 62%). $^1$H NMR (400 MHz, CD$_3$OD) δ 8.51 (s, 1H), 1.57 (s, 6H); LCMS (M+H)$^+$: 251.0

Step C. {trans-3-(4-{[6-(1-Hydroxy-1-methylethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile {trans-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (1.145 g, 2.324 mmol, from Step 1 of Example 1b), benzotriazol-1-yloxytris(dimethylamino)phosphonium hexafluorophosphate (1214 mg, 2.746 mmol) and triethylamine (1.6 mL, 11 mmol) were added to a solution of 6-(1-hydroxy-1-methylethyl)-2-(trifluoromethyl)pyrimidine-4-carboxylic acid (0.572 g, 2.29 mmol, from Step B) in N,N-dimethylformamide (60 mL, 700 mmol). After stirring overnight, the reaction mixture was partitioned between ethyl acetate and brine, and the aqueous was extracted three times with ethyl acetate. The combined organic extracts were dried over sodium sulfate, filtered and concentrated. The SEM-protected product was purified by flash chromatography on silica gel, eluting with a gradient from 0-10% MeOH in DCM. The product was stirred with TFA:DCM (1:1) for 1 hour, and solvents were removed in vacuo. The resulting residue was stirred with excess ethylenediamine in methanol until the deprotection was complete. The solution was filtered and purified via successive preparative HPLC-MS runs at pH10 (C18 eluting with a gradient of MeCN/H$_2$O containing 0.15% NH$_4$OH), then pH2 (C18 eluting with a gradient of MeCN/H$_2$O containing 0.1% TFA). After lyophilization, the product was free based by dissolution in ethyl acetate and washing with saturated sodium bicarbonate, then extraction of the basic aqueous layer with two further portions of ethyl acetate. The combined extracts were washed with water, then brine, dried over sodium sulfate, filtered and concentrated. To afford an easily handled solid, the sample was re-dissolved in MeCN and H$_2$O, frozen and lyophilized to afford desired compound as the free base (0.18 g, 13%). $^1$H NMR (400 MHz, CDCl$_3$) δ 9.77 (s, 1H), 8.85 (s, 1H), 8.48 (s, 1H), 8.34 (s, 1H), 8.05 (s, 1H), 7.40 (dd, J=3.8, 1.6 Hz, 1H), 6.81 (d, J=3.4 Hz, 1H), 3.91-3.76 (m, 2H), 3.72-3.57 (m, 2H), 3.21 (s, 2H), 3.11-

3.01 (m, 2H), 2.97 (tt, J=6.4, 7.2 Hz, 1H), 2.60-2.37 (m, 6H), 1.62 (s, 6H); $^{19}$F NMR (376 MHz, CDCl$_3$) δ −70.70 (s); LCMS (M+H)$^+$: 595.1

Example 59

{cis-3-(4-{[6-(1-hydroxy-1-methylethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

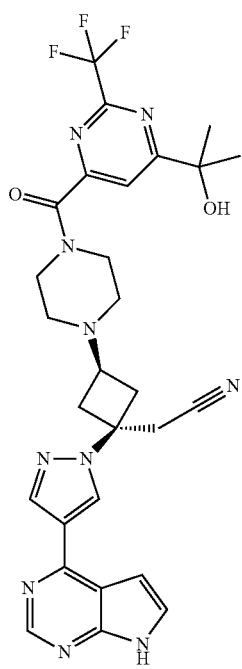 [SMILES: CC(C)(O)c1cc(C(=O)N2CCN([C@H]3C[C@@](CC#N)(n4cc(-c5ncnc6[nH]ccc56)cn4)C3)CC2)nc(C(F)(F)F)n1]

6-(1-Hydroxy-1-methylethyl)-2-(trifluoromethyl)pyrimidine-4-carboxylic acid (0.010 g, 0.040 mmol, Example 58, Step B) was dissolved in N,N-dimethylformamide (1 mL, 10 mmol) and to this was added {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.020 g, 0.040 mmol, from Step 9 of Example 1a), followed by benzotriazol-1-yloxytris(dimethylamino)phosphonium hexafluorophosphate (21.2 mg, 0.0480 mmol) and triethylamine (0.028 mL, 0.20 mmol). After stirring overnight, the reaction mixture was partitioned between ethyl acetate and water, and the aqueous portion was extracted a further two times. The combined extracts were dried over sodium sulfate, filtered and concentrated. The product was deprotected by stirring with TFA:DCM (1:1) for 1 hour, followed by evaporation and stirring with excess ethylenediamine in methanol until the deprotection was complete. The product was purified via preparative HPLC-MS (C18 eluting with a gradient of MeCN/H$_2$O containing 0.15% NH$_4$OH) to afford product as the free base (0.01 g, 40%). $^1$H NMR (400 MHz, dmso) δ 12.13 (s, 1H), 8.70 (s, 1H), 8.68 (s, 1H), 8.40 (s, 1H), 8.06 (s, 1H), 7.60 (dd, J=3.6, 2.3 Hz, 1H), 7.06 (dd, J=3.6, 1.8 Hz, 1H), 5.78 (s, 1H), 3.76-3.62 (m, 2H), 3.47 (s, 2H), 3.41-3.24 (m, 2H), 2.97 (br m, 1H), 2.62 (br m, 4H), 2.44 (br m, 2H), 2.32 (br m, 2H), 1.47 (s, 6H); $^{19}$F NMR (376 MHz, dmso) δ −69.40 (s); LCMS (M+H)$^+$: 595.2

Example 60

{trans-3-(4-{[6-(methoxymethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

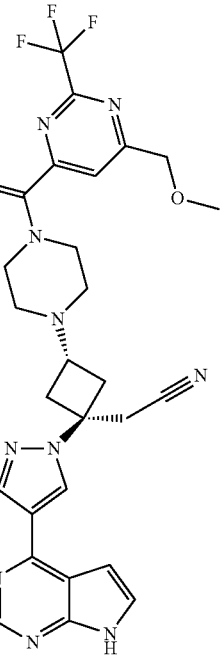

Step A. 6-(Methoxymethyl)-2-(trifluoromethyl)pyrimidine-4-carboxylic acid

Potassium carbonate (1.2 g, 8.7 mmol) was added to a solution of ethyl 6-(bromomethyl)-2-(trifluoromethyl)pyrimidine-4-carboxylate (0.65 g, 1.2 mmol, prepared in the manner outlined in Example 47, Step A) in methanol (10 mL). After stirring for 2 hours, the reaction was then treated with 1N HCl to achieve pH 4, was diluted with water and extracted with six portions of 10% isopropanol in chloroform. The combined extracts were dried over sodium sulfate and concentrated to afford product as an oil which was used without further purification (0.25 g, 88%). $^1$H NMR (300 MHz, CDCl$_3$) δ 8.48 (s, 1H), 4.74 (s, 2H), 3.58 (s, 3H); LCMS (M+H)$^+$: 237.1.

Step B. {trans-3-(4-{[6-(Methoxymethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile Triethylamine (36 µL, 0.26 mmol) and benzotriazol-1-yloxytris(dimethylamino)phosphonium hexafluorophosphate (34.5 mg, 0.0779 mmol) were added to a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (32 mg, 0.065 mmol, from Step 1 of Example 1b) and 6-(methoxymethyl)-2-(trifluoromethyl)pyrimidine-4-carboxylic acid (18 mg, 0.078 mmol, from Step A) in N,N-dimethylformamide (0.64 mL, 8.3 mmol). After stirring for 1 hour, the mixture was diluted with EtOAc, washed with water (3×), then brine, then dried over sodium sulfate, filtered and concentrated. The crude mixture was stirred in a 1:1 mixture of TFA:DCM for one hour, then was concentrated. The residue was dissolved in 1.0 mL MeOH, and 200 μl ethylenediamine was added. When deprotection was complete, the product was purified via preparative HPLC-MS (C18 eluting with a gradient of MeCN/H$_2$O containing 0.15% NH$_4$OH) to afford product as the free base (5.0 mg, 13%). $^1$H NMR (300 MHz, dmso) δ 12.12 (br s, 1H), 8.82 (s, 1H), 8.69 (s, 1H), 8.42 (s, 1H), 7.87 (s, 1H), 7.60 (d, J=3.5 Hz, 1H), 7.07 (d, J=3.6 Hz, 1H), 4.68 (s, 2H), 3.77-3.58 (m, 2H), 3.46-3.36 (m, 7H), 3.11-2.94 (m, 2H), 2.85 (tt, J=7.1, 7.2 Hz, 1H), 2.46-2.24 (m, 6H); $^{19}$F NMR (282 MHz, dmso) δ −69.49 (s); LCMS (M+H)$^+$: 581.3

Example 61

{trans-3-(4-{[6-(1-aminocyclobutyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

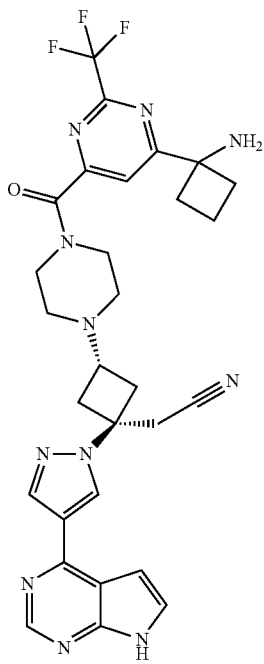 [SMILES: N#CC[C@]1(n2cc(-c3ncnc4[nH]ccc34)cn2)C[C@H](N2CCN(C(=O)c3cc(C4(N)CCC4)nc(C(F)(F)F)n3)CC2)C1]

Step A.
Ethyl-4-cyclobutyl-4-hydroxy-2-oxobut-3-enoate

Ethanol (4.39 mL, 75.2 mmol) was added dropwise to a suspension of sodium hydride (0.607 g, 15.2 mmol, 60% in mineral oil) in a flask that was held in an ice bath. Ten minutes after complete addition, a mixture of 1-cyclobutylethanone (1.5 mL, 14 mmol, Aldrich) and diethyl oxalate (2.01 g, 13.8 mmol, Aldrich) was added dropwise. After stirring overnight, 4.0 M sulfuric acid in water (0.00759 L, 30.4 mmol) was added. The product was extracted into diethyl ether. The combined organic extracts were washed with water and brine, dried over sodium sulfate, filtered and concentrated. The material was used without further purification in Step B.

Step B. Ethyl 6-cyclobutyl-2-(trifluoromethyl)pyrimidine-4-carboxylate

To a solution of 2,2,2-trifluoroethanimidamide (1.80 g, 13.6 mmol, Matrix) in ethanol (22 mL, 370 mmol) was added a solution of ethyl (3Z)-4-cyclobutyl-4-hydroxy-2-oxobut-3-enoate (2.7 g, 14 mmol, from Step A) in a small volume of ethanol. The solution was cooled in an ice bath and a solution of hydrogen chloride in ethanol (21 mL, 360 mmol, prepared by bubbling HCl gas through the ethanol for 10 minutes) was added. The reaction was allowed to warm to room temperature and stirred overnight. The mixture was added slowly to a saturated solution of sodium bicarbonate. Additional solid potassium carbonate was added. After neutralization was complete, ethanol was removed in vacuo. The product was extracted with three portions of DCM. The combined extracts were dried over sodium sulfate, filtered and evaporated. The product was purified by flash chromatography on silica gel, eluting with a gradient from 0-25% EtOAc/hexanes to afford a yellow oil (1.8 g, 48%). $^1$H NMR (400 MHz, CDCl$_3$) δ 7.98 (s, 1H), 4.51 (q, J=7.1 Hz, 2H), 3.81 (p, J=8.6 Hz, 1H), 2.48-2.33 (m, 4H), 2.21-2.08 (m, 1H), 2.03-1.93 (m, 1H), 1.45 (t, J=7.1 Hz, 3H); LCMS (M+H)$^+$: 275.1

Step C. 6-(1-Bromocyclobutyl)-2-(trifluoromethyl)pyrimidine-4-carboxylic acid

Bromine (0.13 mL, 2.6 mmol) was added to a solution of ethyl 6-cyclobutyl-2-(trifluoromethyl)pyrimidine-4-carboxylate (0.65 g, 2.4 mmol, from Step B) in acetic acid (2.0 mL) and the reaction was heated to 80° C. for one hour. The mixture was concentrated and the resulting oil was dissolved in THF (8.0 mL) and cooled to 0° C. A solution of lithium hydroxide, monohydrate (0.20 g, 4.7 mmol) in water (2.0 mL) was added. After stirring for 20 minutes, 1N HCl was added to achieve pH 4. Additional water was introduced and the product was extracted with six portions of 10% isopropanol in chloroform. The combined extracts were dried over sodium sulfate, filtered and concentrated to afford product which was used without further purification (0.64 g, 80%). $^1$H NMR (400 MHz, dmso) δ 8.27 (s, 1H), 3.17-2.97 (m, 2H), 2.92-2.71 (m, 2H), 2.34 (dtt, J=10.9, 9.1, 6.9 Hz, 1H), 1.84 (dtt, J=11.0, 8.6, 5.6 Hz, 1H); LCMS (M+H)$^+$: 324.9, 326.7.

Step D. {trans-3-(4-{[6-(1-Bromocyclobutyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile Triethylamine (0.14 mL, 0.97 mmol) and benzotriazol-1-yloxytris(dimethylamino)phosphonium hexafluorophosphate (0.129 g, 0.292 mmol) were added to a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.12 g, 0.24 mmol, from Step 1 of Example 1b) and 6-(1-bromocyclobutyl)-2-(trifluoromethyl)pyrimidine-4-carboxylic acid (0.095 g, 0.29 mmol, from Step C) in N,N-dimethylformamide (2.4 mL). After a reaction time of 1 hour, the mixture was diluted with EtOAc and washed with water (3×), followed by brine, dried over sodium sulfate, filtered and concentrated. Flash chromatography on silica gel, eluting with a gradient from 0-5% MeOH in EtOAc afforded product as an oil (0.068 g, 35%). $^1$H NMR (300 MHz, CDCl$_3$) δ 8.85 (s, 1H), 8.47 (s, 1H), 8.33 (s, 1H), 8.04 (s, 1H), 7.41 (d, J=3.7 Hz, 1H), 6.81 (d, J=3.7 Hz, 1H), 5.68 (s, 2H), 3.91-3.80 (m, 2H), 3.75-3.63 (m, 2H), 3.59-3.48 (m, 2H), 3.21 (s, 2H), 3.20-1.85 (m, 15H), 1.05-0.74 (m, 2H), −0.06 (s, 9H); LCMS (M+H)$^+$: 799.3, 801.2.

Step E. {trans-3-(4-{[6-(1-Aminocyclobutyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile Sodium azide (16 mg, 0.24 mmol) was added to a solution of {trans-3-(4-{[6-(1-bromocyclobutyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.065 g, 0.081 mmol, from Step D) in dimethyl sulfoxide (0.42 mL). After stirring for 4 hours, the reaction was worked up by partitioning between ethyl acetate and brine. The EtOAc layer was washed with additional brine, dried over sodium sulfate, filtered and concentrated. The resulting product was dissolved in THF (1.8 mL) and water (0.4 mL) and 1.0 M trimethylphosphine in THF (0.098 mL, 0.098 mmol) was added dropwise. After 20 minutes, the solvent was removed in vacuo, and the residue was purified by flash chromatography on silica gel, eluting with a gradient from 0-5% MeOH in DCM to afford product as an oil (14 mg, 24%). $^1$H NMR (300 MHz, CDCl$_3$) δ 8.85 (s, 1H), 8.46 (s, 1H), 8.33 (s, 1H), 8.03 (s, 1H), 7.41 (d, J=3.7 Hz, 1H), 6.81 (d, J=3.7 Hz, 1H), 5.68 (s, 2H), 3.93-3.79 (m, 2H), 3.72-3.57 (m, 2H), 3.21 (s, 2H), 3.12-2.79 (m, 3H), 2.75-2.57 (m, 2H), 2.56-2.37 (m, 6H), 2.30-2.10 (m, 3H), 2.05-1.90 (m, 1H), 1.01-0.77 (m, 2H), −0.06 (s, 9H); LCMS (M+H)$^+$: 736.3.

Step F. {trans-3-(4-{[6-(1-Aminocyclobutyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile {trans-3-(4-{[6-(1-Aminocyclobutyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (14 mg, 0.019 mmol, from Step E) was stirred with 1:1 mixture of TFA:DCM for one hour and then solvents were removed in vacuo. The residue was dissolved in 0.5 mL MeOH, and 0.1 mL of ethylenediamine was added. Purification via preparative HPLC-MS (C18 eluting with a gradient of MeCN/H$_2$O containing 0.15% NH$_4$OH) afforded product as the free base (3.5 mg, 30%). $^1$H NMR (400 MHz, dmso) δ 12.13 (br s, 1H), 8.83 (s, 1H), 8.69 (s, 1H), 8.42 (s, 1H), 8.06 (s, 1H), 7.60 (d, J=3.6 Hz, 1H), 7.07 (d, J=3.6 Hz, 1H), 3.78-3.63 (m, 2H), 3.43 (s, 2H), 3.41-3.31 (m, 2H), 3.08-2.94 (m, 2H), 2.84 (tt, J=7.2, 7.2 Hz, 1H), 2.59-2.51 (m, 2H), 2.46-2.24 (m, 6H), 2.14-1.97 (m, 3H), 1.92-1.77 (m, 1H). $^{19}$F NMR (376 MHz, dmso) δ −69.41 (s); LCMS (M+H)$^+$: 606.2.

Example 62

{cis-3-(4-{[6-(1-aminocyclobutyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

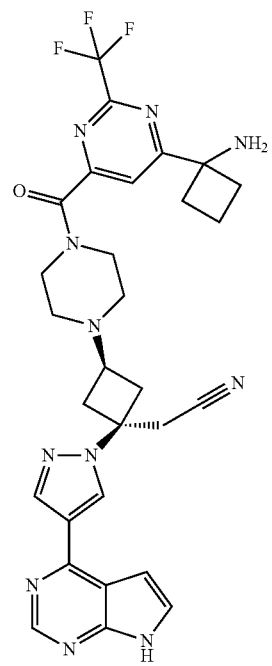 [SMILES: N#CC[C@]1(n2cc(-c3ncnc4[nH]ccc34)cn2)C[C@@H](N2CCN(C(=O)c3cc(C4(N)CCC4)nc(C(F)(F)F)n3)CC2)C1]

The title compound was prepared by the method of Example 61, using {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (from Step 9 of Example 1a). $^1$H NMR (400 MHz, dmso) δ 12.12 (br s, 1H), 8.68 (s, 1H), 8.66 (s, 1H), 8.38 (s, 1H), 8.05 (s, OH), 7.94 (s, OH), 7.58 (d, J=3.5 Hz, 1H), 7.04 (d, J=3.6 Hz, 1H), 3.76-3.57 (m, 2H), 3.45 (s, 2H), 3.40-3.19 (m, 2H), 2.95 (tt, J=7.6, 7.9 Hz, 1H), 2.72-2.45 (m, 7H), 2.44-2.34 (m, 2H), 2.34-2.24 (m, 2H), 2.13-1.91 (m, 1H), 1.95-1.68 (m, 1H), 1.32-1.18 (m, 1H), 1.18-1.05 (m, 1H); LCMS (M+H)⁺: 606.2.

Example 63

{trans-3-(4-{[6-[1-(dimethylamino)cyclobutyl]-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

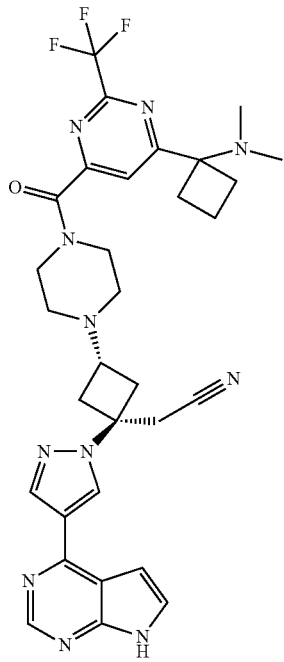 [SMILES: CN(C)C1(c2cc(C(=O)N3CCN([C@H]4C[C@](CC#N)(n5cc(-c6ncnc7[nH]ccc67)cn5)C4)CC3)nc(C(F)(F)F)n2)CCC1]

{trans-3-(4-{[6-(1-Aminocyclobutyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (15 mg, 0.020 mmol, Example 61, Step E) was dissolved in methanol (0.86 mL, 21 mmol), and acetic acid (0.013 mL, 0.22 mmol), sodium cyanoborohydride (7.7 mg, 0.12 mmol) and 37 wt % formaldehyde in water (5.4 mg, 0.066 mmol, Sigma-Aldrich) were added. After 20 minutes, the mixture was concentrated. The residue was stirred in a solution of TFA:DCM (1:1) for one hour and concentrated again. The residue was dissolved in 0.5 mL MeOH to which 100 μL ethylenediamine was added, and stirred until deprotection was complete. Purification via preparative HPLC-MS (C18 eluting with a gradient of MeCN/H₂O containing 0.15% NH₄OH) afforded product as the free base (5.3 mg, 40%). ¹H NMR (400 MHz, dmso) δ 12.12 (br s, 1H), 8.83 (s, 1H), 8.69 (s, 1H), 8.42 (s, 1H), 7.89 (s, 1H), 7.60 (d, J=3.6 Hz, 1H), 7.07 (d, J=3.6 Hz, 1H), 3.84-3.61 (m, 2H), 3.43 (s, 2H), 3.41-3.36 (m, 2H), 3.07-2.97 (m, 2H), 2.85 (tt, J=7.2, 7.2 Hz, 1H), 2.48-2.19 (m, 10H), 1.96 (s, 6H), 1.88-1.73 (m, 1H), 1.65-1.49 (m, 1H); ¹⁹F NMR (376 MHz, dmso) δ −69.52 (s); LCMS (M+H)⁺: 634.2.

Example 64

{cis-3-(4-{[6-[1-(dimethylamino)cyclobutyl]-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

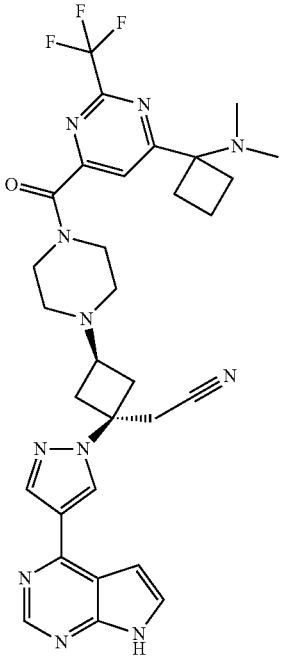 [SMILES: CN(C)C1(c2cc(C(=O)N3CCN([C@H]4C[C@@](CC#N)(n5cc(-c6ncnc7[nH]ccc67)cn5)C4)CC3)nc(C(F)(F)F)n2)CCC1]

The title compound was prepared in the manner of Example 63 starting with the product of Example 62 (22 mg, 0.030 mmol) to afford purified product (7.4 mg, 33%). ¹H NMR (400 MHz, dmso) δ 12.17 (br s, 1H), 8.68 (s, 1H), 8.66 (s, 1H), 8.38 (s, 1H), 7.88 (s, 1H), 7.58 (d, J=3.6 Hz, 1H), 7.04 (d, J=3.6 Hz, 1H), 3.72-3.60 (m, 2H), 3.45 (s, 2H), 3.41-3.00 (m, 2H), 2.95 (tt, J=7.4, 7.6 Hz, 1H), 2.76-2.16 (m, 12H), 1.94 (s, 6H), 1.86-1.68 (m, 1H), 1.64-1.46 (m, 1H); ¹⁹F NMR (376 MHz, dmso) δ −69.53 (s), −73.86 (s); LCMS (M+H)⁺: 597.0

Example 65

{trans-3-(4-{[4-[(dimethylamino)methyl]-6-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

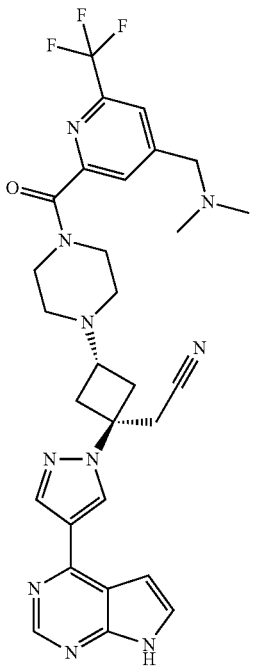 [SMILES: CN(C)Cc1cc(C(=O)N2CCN([C@H]3C[C@](CC#N)(n4cc(-c5ncnc6[nH]ccc56)cn4)C3)CC2)nc(C(F)(F)F)c1]

Step A.
6-(Trifluoromethyl)-4-vinylpyridine-2-carboxylic acid

A mixture of 4-bromo-6-(trifluoromethyl)pyridine-2-carboxylic acid (0.50 g, 1.8 mmol, Anichem), (2-Ethenyl)tri-n-butyltin (919 µL, 3.14 mmol, Aldrich) and tetrakis(triphenylphosphine)palladium(0) (428 mg, 0.370 mmol, Strem) in toluene (4.2 mL) was degassed by a stream of nitrogen through the solution for 15 minutes. Triethylamine (774 µL, 5.56 mmol) was added and the mixture was heated to 80° C. for 2 hours. After cooling to ambient temperature, water and 1N NaOH were added and the product was extracted with four portions of ethyl acetate. The aqueous layer was then treated with 1N HCl to achieve a pH between 4 and 5, and was extracted with six portions of 10% isopropanol in chloroform. The combined organic extracts were dried over sodium sulfate, filtered and concentrated to afford crude product, which was used without further purification in Step B. $^1$H NMR (300 MHz, CDCl$_3$) δ 8.40 (d, J=1.3 Hz, 1H), 7.88 (d, J=1.5 Hz, 1H), 6.82 (dd, J=17.6, 10.9 Hz, 1H), 6.23 (d, J=17.4 Hz, 1H), 5.78 (d, J=10.9 Hz, 1H); LCMS (M+H)$^+$: 218.1.

Step B.
4-formyl-6-(trifluoromethyl)pyridine-2-carboxylic acid 6-(Trifluoromethyl)-4-vinylpyridine-2-carboxylic acid (0.30 g, 0.69 mmol, the crude product from Step A) was dissolved in 1,4-dioxane (20. mL) and water (5.0 mL), then sodium periodate (0.44 g, 2.1 mmol, Aldrich) was added, followed by 4 wt % osmium tetraoxide in water (0.152 mL, 0.0240 mmol, Aldrich). The reaction was stirred overnight. Sodium thiosulfate solution was added and the mixture was stirred for 30 minutes. 1N HCl was added to adjust the pH to between 4 and 5, and the product was extracted with ten portions of 10% isopropanol in CHCl$_3$. The combined extracts were dried over sodium sulfate, filtered and concentrated. Flash chromatography on silica gel, eluting with a gradient from 0-10% MeOH in DCM afforded a partially purified product (94 mg, 20% yield over Steps A & B). $^1$H NMR (300 MHz, CDCl$_3$) δ 10.25 (s, 1H), 8.83 (d, J=0.8 Hz, 1H), 8.38 (d, J=1.3 Hz, 1H).

Step C. {trans-3-(4-{[4-Formyl-6-(trifluoromethyl)pyridin-2-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile Triethylamine (0.095 mL, 0.68 mmol) and benzotriazol-1-yloxytris(dimethylamino)phosphonium hexafluorophosphate (0.14 g, 0.31 mmol) were added to a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.15 g, 0.31 mmol, from Step 1 of Example 1b) and 4-formyl-6-(trifluoromethyl)pyridine-2-carboxylic acid (90 mg, 0.2 mmol, from Step B) in N,N-dimethylformamide (1.7 mL). After stirring for 30 minutes, the mixture was diluted with EtOAc and was washed with water (3×), followed by brine, then dried over sodium sulfate, filtered and concentrated. Flash chromatography on silica gel, eluting with a gradient from 0-10% MeOH in DCM afforded product as a light yellow solid (52 mg, 24%). $^1$H NMR (400 MHz, CDCl$_3$) δ 10.17 (s, 1H), 8.85 (s, 1H), 8.47 (s, 1H), 8.38 (s, 1H), 8.33 (s, 1H), 8.15 (d, J=1.3 Hz, 1H), 7.41 (d, J=3.7 Hz, 1H), 6.81 (d, J=3.7 Hz, 1H), 5.68 (s, 2H), 3.96-3.81 (m, 2H), 3.79-3.59 (m, 2H), 3.59-3.49 (m, 2H), 3.21 (s, 2H), 3.09-3.01 (m, 2H), 2.97 (tt, J=6.3, 6.7 Hz, 1H), 2.57-2.38 (m, 6H), 0.95-0.86 (m, 2H), −0.06 (s, 9H); LCMS (M+H)$^+$: 694.2.

Step D. {trans-3-(4-{[4-[(Dimethylamino)methyl]-6-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile 2.0 M Dimethylamine in THF (130 µL, 0.26 mmol, Aldrich) and sodium triacetoxyborohydride (27 mg, 0.129 mmol) were added to a solution of {trans-3-(4-{[4-formyl-6-(trifluoromethyl)pyridin-2-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (15 mg, 0.022 mmol, from Step C) in methylene chloride (1.0 mL) and the reaction was stirred overnight. The mixture was concentrated, then the solvent was replaced with isopropyl alcohol (0.50 mL). This was followed by the addition of 2.0 M dimethylamine in THF (22 µL, 0.043 mmol) and excess sodium triacetoxyborohydride. After stirring for 24 hours, 0.1 N NaOH was added and the product was extracted with EtOAc. The combined extracts were washed twice with water, once with brine, dried over sodium sulfate, filtered and concentrated. The residue was stirred in a 1:1 mixture of DCM:TFA for one hour, was concentrated, then was redissolved in 1 mL methanol to which 0.15 mL ethylenediamine was subsequently added. Purification via preparative HPLC-MS (C18 eluting with a gradient of MeCN/H$_2$O containing 0.15% NH$_4$OH) afforded product as the free base (2.0 mg, 16%). $^1$H NMR (400 MHz, CD$_3$OD) δ 8.71 (s, 1H), 8.66 (s, 1H), 8.40 (s, 1H), 7.89 (d, J=1.3 Hz, 1H), 7.82 (s, 1H), 7.51 (d, J=3.6 Hz, 1H), 6.99 (d, J=3.6 Hz, 1H), 3.91-3.81 (m, 2H), 3.64 (s, 2H), 3.60-3.55 (m, 2H), 3.35 (s, 2H), 3.11-3.04 (m, 2H), 2.97 (tt, J=6.9, 7.1 Hz, 1H), 2.62-2.38 (m, 6H), 2.28 (s, 6H); $^{19}$F NMR (376 MHz, CD$_3$OD) δ −71.39 (s); LCMS (M+H)$^+$: 593.2

Example 66

{trans-3-(4-{[4-(hydroxymethyl)-6-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

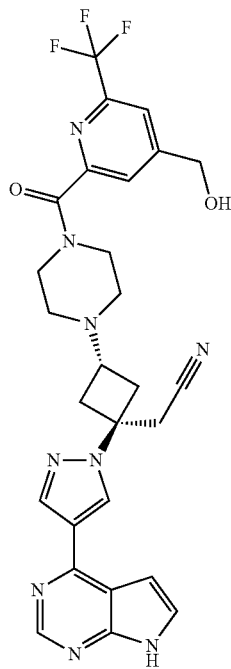 [SMILES: N#CC[C@]1(n2cc(-c3ncnc4[nH]ccc34)cn2)C[C@H](N2CCN(C(=O)c3cc(CO)cc(C(F)(F)F)n3)CC2)C1]

Example 66 was obtained as a byproduct in the reaction of Example 65, Step D and was isolated during the HPLC purification as described above in that Example (2.5 mg, 20%). $^1$H NMR (400 MHz, CD$_3$OD) δ 8.72 (s, 1H), 8.67 (s, 1H), 8.40 (s, 1H), 7.88 (d, J=1.4 Hz, 1H), 7.82 (s, 1H), 7.51 (d, J=3.6 Hz, 1H), 6.99 (d, J=3.6 Hz, 1H), 4.78 (s, 2H), 3.92-3.73 (m, 2H), 3.63-3.49 (m, 2H), 3.35 (s, 2H), 3.15-3.02 (m, 2H), 2.97 (tt, J=6.7, 6.9 Hz, 1H), 2.64-2.36 (m, 6H); $^{19}$F NMR (376 MHz, CD$_3$OD) δ −69.84 (s); LCMS (M+H)$^+$: 566.2.

Example 67

{trans-3-(4-{[4-(aminomethyl)-6-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

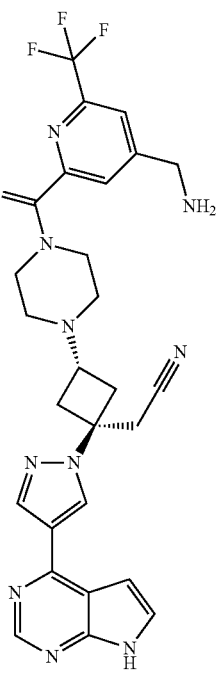

Triethylamine (6.0 µL, 0.043 mmol) and methanesulfonyl chloride (2.2 µL, 0.028 mmol) were added to a solution of {trans-3-(4-{[4-(hydroxymethyl)-6-(trifluoromethyl)pyridin-2-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (15 mg, 0.022 mmol, prepared as described in Example 68, Step A) in methylene chloride (0.75 mL). After 15 minutes, solvent was removed in vacuo and 7.0 M ammonia in methanol (0.3 mL, 2 mmol, Aldrich) was introduced. After 3.5 hours, the mixture was concentrated, the residue was dissolved in a 1:1 mixture of TFA:DCM, stirred for one hour, then concentrated again. The residue was redissolved in 1 mL MeOH, and 0.2 ml ethylenediamine was then added. When deprotection was complete, the product was purified via preparative HPLC-MS (C18 eluting with a gradient of MeCN/H$_2$O containing 0.15% NH$_4$OH), affording product as the free base (2.0 mg, 16%). $^1$H NMR (400 MHz, CD$_3$OD) δ 8.71 (s, 1H), 8.66 (s, 1H), 8.40 (s, 1H), 7.95-7.87 (m, 1H), 7.82 (s, 1H), 7.51 (d, J=3.6 Hz, 1H), 6.98 (d, J=3.6 Hz, 1H), 3.96 (s, 2H), 3.92-3.80 (m, 2H), 3.61-3.53 (m, 2H), 3.35 (s, 2H), 3.14-3.02 (m, 2H), 2.97 (tt, J=6.9, 7.0 Hz, 1H), 2.61-2.40 (m, 6H); $^{19}$F NMR (376 MHz, CD$_3$OD) δ −69.78 (s); LCMS (M+H)$^+$: 565.3

Example 68

{trans-3-(4-{[4-[(methylamino)methyl]-6-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

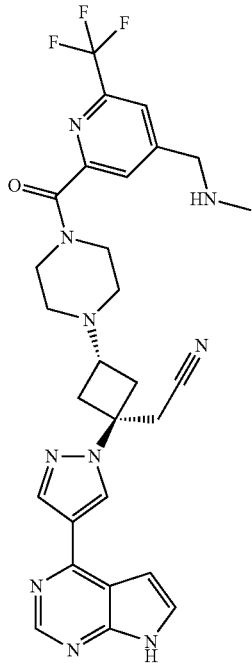 [SMILES: CNCc1cc(C(=O)N2CCN([C@H]3C[C@](CC#N)(n4cc(-c5ncnc6[nH]ccc56)cn4)C3)CC2)nc(C(F)(F)F)c1]

Step A. {trans-3-(4-{[4-(Hydroxymethyl)-6-(trifluoromethyl)pyridin-2-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile

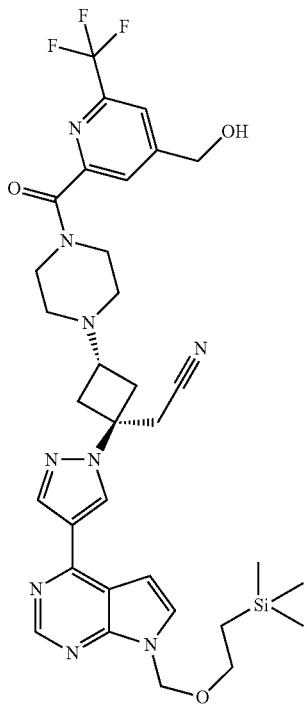 [SMILES: C[Si](C)(C)CCOCn1ccc2c(-c3cnn([C@]4(CC#N)C[C@@H](N5CCN(C(=O)c6cc(CO)cc(C(F)(F)F)n6)CC5)C4)c3)ncnc21]

Sodium tetrahydroborate (1.7 mg, 0.046 mmol) was added to a solution of {trans-3-(4-{[4-formyl-6-(trifluoromethyl)pyridin-2-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (32 mg, 0.046 mmol, Example 65, Step C) in ethanol (0.50 mL). After 30 minutes, the reaction was diluted with water and the product was extracted with EtOAc. The combined extracts were washed with water (3×), followed by brine, dried over sodium sulfate, filtered and concentrated to afford a near theoretical yield of product, used without further purification in Step B. LCMS (M+H)$^+$: 696.3.

Step B. {trans-3-(4-{[4-[(Methylamino)methyl]-6-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile Triethylamine (4.8 µL, 0.034 mmol) and methanesulfonyl chloride (1.7 µL, 0.022 mmol) were added to a solution of {trans-3-(4-{[4-(hydroxymethyl)-6-(trifluoromethyl)pyridin-2-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (12 mg, 0.017 mmol, from Step B) in methylene chloride (0.60 mL). After 15 minutes, solvent was removed in vacuo and methylamine 33 wt % in ethanol (50 mg, 0.5 mmol, Aldrich) was added. The reaction was continued for 1.5 hours, then solvent was again removed in vacuo. The crude product was dissolved in a 1:1 mixture of TFA:DCM, stirred for one hour, then concentrated again. The residue was redissolved in 1 mL of MeOH, and 0.2 mL ethylenediamine was added. When deprotection was determined complete by LCMS, the product was purified via preparative HPLC-MS (C18 eluting with a gradient of MeCN/H$_2$O containing 0.15% NH$_4$OH) to afford product as the free base (3.9 mg, 39%). $^1$H NMR (300 MHz, dmso) δ 12.11 (br s, 1H), 8.82 (s, 1H), 8.69 (s, 1H), 8.41 (s, 1H), 7.93 (d, J=1.3 Hz, 1H), 7.81 (s, 1H), 7.60 (d, J=3.6 Hz, 1H), 7.07 (d, J=3.6 Hz, 1H), 3.81 (s, 2H), 3.76-3.63 (m, 2H), 3.43 (s, 2H), 3.41-3.36 (m, 2H), 3.08-2.94 (m, 2H), 2.84 (tt, J=7.0, 7.0 Hz, 1H), 2.45-2.27 (m, 6H), 2.26 (s, 3H); $^{19}$F NMR (282 MHz, dmso) δ −66.83 (s); LCMS (M+H)$^+$: 579.2

Example 69

{trans-3-(4-{[6-(1-methoxy-1-methylethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

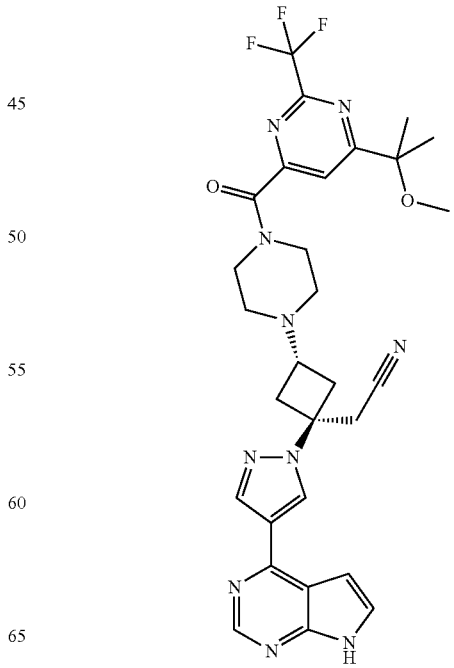

Step A. 6-(1-Methoxy-1-methylethyl)-2-(trifluoromethly)pyrimidine-4-carboxylic acid Sodium hydride (0.032 g, 0.80 mmol, 60% in mineral oil) and methyl iodide (0.031 mL, 0.50 mmol) were added to a solution of 6-(1-hydroxy-1-methylethyl)-2-(trifluoromethyl)pyrimidine-4-carboxylic acid (0.050 g, 0.20 mmol, Example 58, Step B) in N,N-dimethylformamide (1 mL, 10 mmol). After stirring overnight, water and lithium hydroxide monohydrate (0.050 g, 1.2 mmol) were added into the reaction. After stirring for 1.5 hours, the reaction was acidified by the addition of 1 N HCl to achieve pH between 3 and 4. The product was extracted with ethyl acetate (3×). The combined extracts were dried over sodium sulfate, filtered and concentrated. The residue was dissolved and rotovapped twice with MeOH to afford product which was used without further purification (0.045 g, 85%). $^1$H NMR (400 MHz, CD$_3$OD) δ 8.35 (s, 1H), 3.29 (s, 3H), 1.56 (s, 6H); LCMS (M+H)$^+$: 265.1

Step B. {trans-3-(4-{[6-(1-Methoxy-1-methylethyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile To a solution of 6-(1-methoxy-1-methylethyl)-2-(trifluoromethyl)pyrimidine-4-carboxylic acid (0.045 g, 0.17 mmol, from Step A) in N,N-dimethylformamide (4 mL) was added, sequentially, a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.0852 g, 0.173 mmol, from Step 1 of Example 1b) in N,N-dimethylformamide (2.5 mL), benzotriazol-1-yloxytris(dimethylamino)phosphonium hexafluorophosphate (90.4 mg, 0.204 mmol) and triethylamine (0.12 mL, 0.85 mmol). After stirring overnight, the reaction was worked up by partition between ethyl acetate and brine, and the aqueous layer was extracted with a further two portions of ethyl acetate. The combined organic extracts were dried over sodium sulfate, filtered and concentrated. The product was deprotected by stirring with TFA:DCM 1:1 for 1 hour, evaporating and stirring with excess ethylenediamine in methanol overnight. The solution was filtered and purified via preparative HPLC-MS (C18 eluting with a gradient of MeCN/H$_2$O containing 0.15% NH$_4$OH), frozen and lyophilized to afford product as the free base (0.03 g, 30%). $^1$H NMR (300 MHz, CDCl$_3$) δ 9.68 (s, 1H), 8.84 (s, 1H), 8.48 (s, 1H), 8.34 (s, 1H), 8.06 (s, 1H), 7.40 (dd, J=3.7, 2.2 Hz, 1H), 6.81 (dd, J=3.7, 1.8 Hz, 1H), 3.95-3.71 (m, 2H), 3.71-3.55 (m, 1H), 3.29 (s, 3H), 3.21 (s, 2H), 3.10-2.87 (m, 3H), 2.57-2.30 (m, 6H), 1.56 (s, 6H); LCMS (M+H)$^+$: 609.3

Example 70

{trans-3-(4-{[6-[1-(methylamino)cyclobutyl]-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

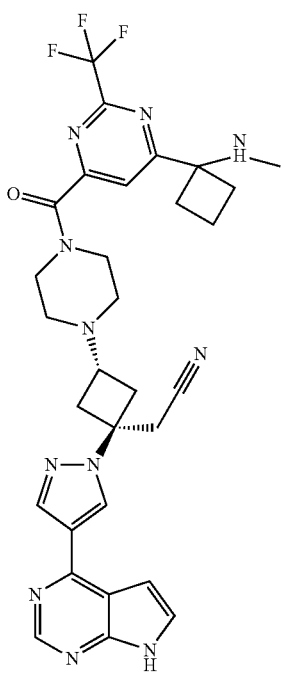 [SMILES: CNC1(c2cc(C(=O)N3CCN([C@H]4C[C@](CC#N)(n5cc(-c6ncnc7[nH]ccc67)cn5)C4)CC3)nc(C(F)(F)F)n2)CCC1]

To 1H-benzotriazole-1-methanol (3.0 mg, 0.020 mmol, Aldrich) in ethanol (0.30 mL) was added {trans-3-(4-{[6-(1-aminocyclobutyl)-2-(trifluoromethyl)pyrimidin-4-yl]carbonyl}piperazin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (15 mg, 0.020 mmol, Example 61, Step E). The solution was heated to 78° C. in a sealed vial for one hour. After cooling to room temperature, solvent was removed in vacuo and the residue was dissolved in tetrahydrofuran (0.60 mL). Sodium tetrahydroborate (4.6 mg, 0.12 mmol) was added and the mixture was stirred for 40 minutes before solvent was removed in vacuo again. The residue was redissolved in 2.0 mL of DCM and 0.40 mL of TFA was added dropwise. After stirring for 1.5 hours, the mixture was concentrated by rotary evaporation. Following this, the residue was stirred with ethylenediamine (0.10 mL) in MeOH (1.0 mL). When deprotection was complete, the product was purified via preparative HPLC-MS (C18 eluting with a gradient of MeCN/H$_2$O containing 0.15% NH$_4$OH) to afford the free base (2.0 mg, 16%). LCMS (M+H)$^+$: 620.4

Example 71

2-[(4-{trans-3-(cyanomethyl)-3-[4-(7H-pyrrolo[2,3-d]pyrimidin-4-yl)-1H-pyrazol-1-yl]cyclobutyl}piperazin-1-yl)carbonyl]-6-(trifluoromethyl)isonicotinonitrile

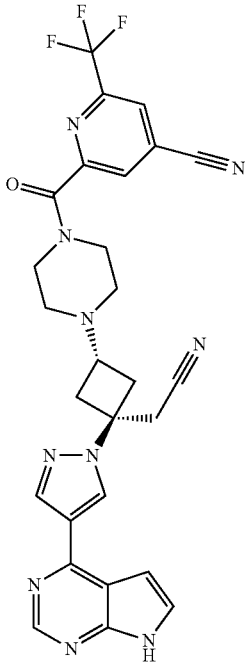 [SMILES: N#CC[C@]1(n2cc(-c3ncnc4[nH]ccc34)cn2)C[C@H](N2CCN(C(=O)c3cc(C#N)cc(C(F)(F)F)n3)CC2)C1]

Step A.
4-Cyano-6-(trifluoromethyl)pyridine-2-carboxylic acid

4-Bromo-6-(trifluoromethyl)pyridine-2-carboxylic acid (0.150 g, 0.556 mmol, Anichem) and zinc cyanide (0.39 g, 3.3 mmol) were mixed in N-methylpyrrolidinone (2 mL) and the mixture was degassed by bubbling a stream of nitrogen through the mixture for 10 minutes. Tetrakis(triphenylphosphine)palladium(0) (0.096 g, 0.083 mmol) was added, the degassing was continued for 5 minutes, then the reaction was sealed and heated in the microwave to a temperature of 160° C. for 15 minutes. The mixture was filtered and purified by preparative HPLC (eluting with a gradient from 18.8 to 40.9% MeCN/H$_2$O containing 0.1% TFA over 1-6 min at 60 mL/min thru C18 SunFire 30×100 mm, 5 um particle size) using UV detection. The product eluted at 5.25 minutes.

Step B. 2-[(4-{trans-3-(Cyanomethyl)-3-[4-(7H-pyrrolo[2,3-d]pyrimidin-4-yl)-1H-pyrazol-1-yl]cyclobutyl}piperazin-1-yl)carbonyl]-6-(trifluoromethyl)isonicotinonitrile 4-Cyano-6-(trifluoromethyl)pyridine-2-carboxylic acid (0.025 g, 0.12 mmol, from Step A) was dissolved in N,N-dimethylformamide (3 mL) and to this was added sequentially {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.0579 g, 0.117 mmol, from Step 1 of Example 1b) as a solution in N,N-dimethylformamide (1.7 mL), benzotriazol-1-yloxytris(dimethylamino)phosphonium hexafluorophosphate (61.4 mg, 0.139 mmol) and triethylamine (0.081 mL, 0.58 mmol). After stirring overnight, the reaction was worked up by partition between ethyl acetate and brine. The layers were separated and the aqueous was extracted with two further portions of ethyl acetate. The combined extracts were dried over sodium sulfate, filtered and concentrated. The SEM-protected intermediate was purified by flash chromatography on silica gel, eluting with a gradient of up to 100% EtOAc in Hexanes then 10-15% MeOH in DCM. A third of the material obtained was stirred with TFA:DCM 1:1 for 1 hour, evaporated, then stirred with 0.2 mL ethylenediamine in methanol for 30 minutes. The solution was then filtered and purified purified via preparative HPLC-MS (C18 eluting with a gradient of MeCN/H$_2$O containing 0.15% NH$_4$OH), frozen and lyophilized to afford product as the free base (5 mg, 20%). $^1$H NMR (400 MHz, CD$_3$OD) δ 8.71 (s, 1H), 8.66 (s, 1H), 8.40 (s, 1H), 8.33 (d, J=1.3 Hz, 1H), 8.26 (d, J=1.1 Hz, 1H), 7.51 (d, J=3.6 Hz, 1H), 6.98 (d, J=3.7 Hz, 1H), 3.89-3.80 (m, 2H), 3.62-3.53 (m, 2H), 3.35 (s, 2H), 3.12-3.03 (m, 2H), 2.97 (tt, J=7.1, 7.3 Hz, 1H), 2.67-2.29 (m, 6H); $^{19}$F NMR (376 MHz, CD$_3$OD) δ −70.18 (s); LCMS (M+H)$^+$: 561.0

Example 72

{trans-3-(4-{[6-(1-hydroxycyclobutyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile

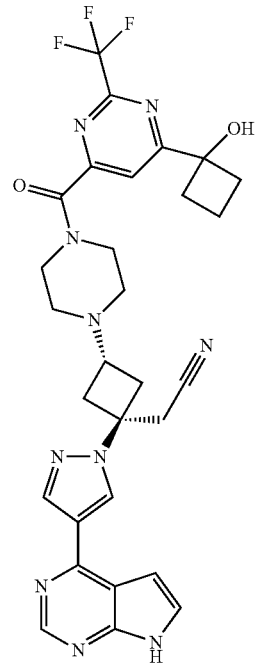 [SMILES: N#CC[C@]1(n2cc(-c3ncnc4[nH]ccc34)cn2)C[C@H](N2CCN(C(=O)c3cc(C4(O)CCC4)nc(C(F)(F)F)n3)CC2)C1]

Step A. 6-(1-Hydroxycyclobutyl)-2-(trifluoromethyl)pyrimidine-4-carboxylic acid To a solution of ethyl 6-cyclobutyl-2-(trifluoromethyl)pyrimidine-4-carboxylate (0.200 g, 0.729 mmol, Example 61, Step B) in Water (1 mL) and tert-butyl alcohol (1 mL) was added potassium permanganate (0.23 g, 1.4 mmol) followed quickly by sodium carbonate (0.15 g, 1.4 mmol). After stirring overnight, the mixture was filtered. The resulting mixture stood open to the air for a period of 3 days, during which time a brown precipitate formed. The mixture was filtered again and purified via preparative HPLC-MS (C18 eluting with a gradient of MeCN/H$_2$O containing 0.1% TFA) and evaporated to afford product with only a small amount of TFA present (0.01 g, 5%). $^1$H NMR (300 MHz, CD$_3$OD) δ 8.41 (s, 1H), 2.75-2.46 (m, 2H), 2.44-2.15 (m, 2H), 2.18-1.77 (m, 2H); $^{19}$F NMR (282 MHz, CD$_3$OD) δ −72.09 (s); LCMS (M+H)$^+$: 263.0

Step B. {trans-3-(4-{[6-(1-Hydroxycyclobutyl)-2-(trifluoromethyl)pyrimidin-4-yl]carbonyl}piperazin-1-yl)-1-[4-(7H-pyrrolo[2,3-d]pyrimidin-4-yl)-1H-pyrazol-1-yl]cyclobutyl}acetonitrile To 6-(1-hydroxycyclobutyl)-2-(trifluoromethyl)pyrimidine-4-carboxylic acid (0.010 g, 0.038 mmol, from Step A) and {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.019 g, 0.038 mmol, from Step 1 of Example 1b) in N,N-dimethylformamide (1 mL) was added benzotriazol-1-yloxytris(dimethylamino)phosphonium hexafluorophosphate (20.2 mg, 0.0458 mmol) and triethylamine (0.026 mL, 0.19 mmol). After stirring overnight, the reaction mixture was partitioned between water and ethyl acetate. The layers were separated and the aqueous was extracted with two further portions of ethyl acetate. The combined extracts were washed with brine, dried over sodium sulfate, decanted and concentrated. Deprotection was carried out by stirring with 1:1 TFA:DCM for 1 hour, evaporating, then stirring with ethylenediamine (0.2 mL) in methanol until deprotection was complete. The product was purified via preparative HPLC-MS (C18 eluting with a gradient of MeCN/H$_2$O containing 0.15% NH$_4$OH), frozen and lyophilized to afford product as the free base (15 mg, 65%). $^1$H NMR (500 MHz, CDCl$_3$) δ 9.83 (s, 1H), 8.84 (s, 1H), 8.48 (s, 1H), 8.34 (s, 1H), 8.09 (s, 1H), 7.40 (dd, J=3.7, 2.3 Hz, 1H), 6.81 (dd, J=3.7, 1.8 Hz, 1H), 3.92-3.75 (m, 2H), 3.70-3.64 (m, 2H), 3.64 (s, 1H), 3.21 (s, 2H), 3.10-3.01 (m, 2H), 2.98 (ft, J=6.7, 6.7 Hz, 1H), 2.69-2.57 (m, 2H), 2.57-2.37 (m, 8H), 2.20-1.93 (m, 2H). $^{19}$F NMR (376 MHz, CDCl$_3$) δ −70.72 (s); LCMS (M+H)$^+$: 607.2

Example 73

{trans-3-(4-{[4-(4,5-dihydro-1H-imidazol-2-yl)-6-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

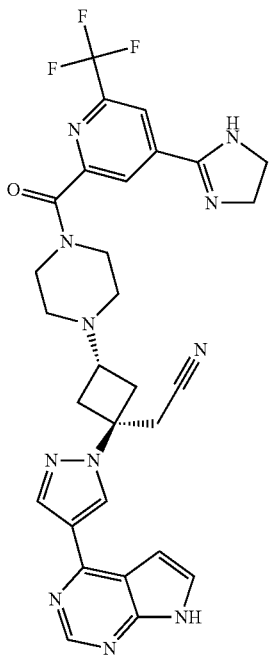 [SMILES: N#CC[C@]1(n2cc(-c3ncnc4[nH]ccc34)cn2)C[C@H](N2CCN(C(=O)c3cc(C4=NCCN4)cc(C(F)(F)F)n3)CC2)C1]

The procedure of Example 71 was followed, with the modification that during the deprotection, stirring with ethylenediamine was continued overnight rather than for 30 minutes. $^1$H NMR (300 MHz, dmso) δ 12.11 (br s, 1H), 8.83 (s, 1H), 8.69 (s, 1H), 8.42 (s, 1H), 8.28 (d, J=1.4 Hz, 1H), 8.21 (d, J=1.1 Hz, 1H), 7.60 (d, J=3.6 Hz, 1H), 7.46 (s, 1H), 7.07 (d, J=3.6 Hz, 1H), 3.89 (t, J=10.1 Hz, 2H), 3.77-3.61 (m, 2H), 3.49 (t, J=10.4 Hz, 2H), 3.44-3.36 (m, 4H), 3.07-2.96 (m, 2H), 2.84 (tt, J=6.8, 7.0 Hz, 1H), 2.47-2.14 (m, 6H); $^{19}$F NMR (282 MHz, dmso) δ −67.02 (s); LCMS (M+H)$^+$: 604.3

Example 74

{trans-3-(4-{3-(difluoromethyl)-5-[(dimethylamino)methyl]benzoyl}piperazin-1-yl)-1-[4-(7H-pyrrolo[2,3-d]pyrimidin-4-yl)-1H-pyrazol-1-yl]cyclobutyl}acetonitrile

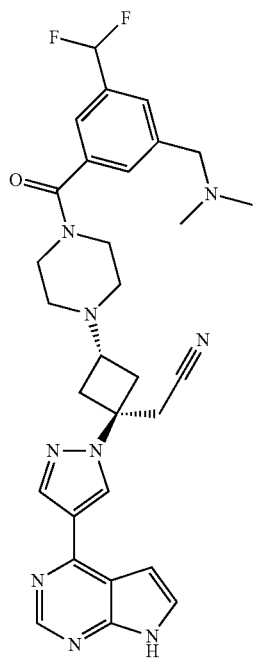 [SMILES: CN(C)Cc1cc(C(=O)N2CCN([C@H]3C[C@](CC#N)(n4cc(-c5ncnc6[nH]ccc56)cn4)C3)CC2)cc(C(F)F)c1]

Step A. Methyl 3-[(dimethylamino)methyl]-5-(hydroxymethyl)benzoate

To a reaction vial was added methyl 3-bromo-5-(hydroxymethyl)benzoate (1.2 g, 4.9 mmol, prepared as described in WO 2003/048111 from dimethyl 5-bromoisophthalate, Alfa Aesar), cesium carbonate (4.79 g, 14.7 mmol), dicyclohexyl(2',4',6'-triisopropylbiphenyl-2-yl)phosphine (280 mg, 0.59 mmol, Aldrich), potassium [(dimethylamino)methyl](trifluoro)borate(1-) (0.970 g, 5.88 mmol, Aldrich), palladium acetate (66 mg, 0.29 mmol) and THF:H$_2$O (10:1, 30 mL). The reaction mixture was degassed by purging with a stream of nitrogen for 10 minutes. The vial was sealed and heated at 80° C. for 17 hours. The reaction mixture was partitioned between water and ethyl acetate. The organic layer was was washed twice with water. The combined aqueous portions were then saturated with NaCl, and the product was extracted with eight portions of DCM. The extracts were dried over sodium sulfate, filtered and concentrated to afford product as a colorless oil (0.37 g, 34%). ¹H NMR (300 MHz, CDCl₃): δ 7.94 (s, 1H), 7.88 (s, 1H), 7.56 (s, 1H), 4.74 (s, 2H), 3.91 (s, 3H), 3.46 (s, 2H), 2.24 (s, 6H); LCMS (M+H)⁺: 224.1.

Step B. Methyl 3-[(dimethylamino)methyl]-5-formylbenzoate

Manganese(IV) oxide (0.72 g, 8.3 mmol) was added to methyl 3-[(dimethylamino)methyl]-5-(hydroxymethyl)benzoate (0.37 g, 1.6 mmol, from Step A) in toluene (15 mL). The mixture was heated to 105° C. for 2 hours, then was cooled to room temperature and filtered. Solvent was removed from the filtrate in vacuo to afford the product as a colorless oil (0.30 g, 82%). ¹H NMR (400 MHz, CDCl₃): δ 10.07 (s, 1H), 8.43 (dd, 1H), 8.25 (dd, 1H), 8.05 (dd, 1H), 3.96 (s, 3H), 3.54 (s, 2H), 2.26 (s, 6H); LCMS (M+H)⁺: 222.1.

Step C. Methyl 3-(difluoromethyl)-5-[(dimethylamino)methyl]benzoate

Methyl 3-[(dimethylamino)methyl]-5-formylbenzoate (99 mg, 0.45 mmol, from Step B), was stirred in deoxo-Fluor® (495 µL, 2.69 mmol) containing ethanol (5 µL, 0.09 mmol) for 24 hours. The mixture was quenched by dropwise addition into ice-cold saturated NaHCO₃ solution. The product was isolated by extraction using DCM. The organic extract was washed twice with water, once with brine, was dried over sodium sulfate, filtered and concentrated to afford product as a light yellow oil which was used without further purification (0.046 g, 30%). ¹H NMR (400 MHz, CDCl₃): δ 8.09 (s, 2H), 7.69 (s, 1H), 6.68 (t, 1H), 3.94 (s, 3H), 3.36 (s, 2H), 2.25 (s, 6H); LCMS (M+H)⁺: 244.1.

Step D. 3-(Difluoromethyl)-5-[(dimethylamino)methyl]benzoic acid

Lithium hydroxide, monohydrate (65.2 mg, 1.55 mmol) in water (0.7 mL) was added to a solution of methyl 3-(difluoromethyl)-5-[(dimethylamino)methyl]benzoate (45 mg, 0.13 mmol, from Step C) in tetrahydrofuran (2 mL). Upon stirring for 3.5 hours, the mixture was treated with 1N HCl to adjust the pH to 7, then THF was removed by rotary evaporation. Acetonitrile was added to make a 1:1 ACN: water mixture, the mixture was filtered, and the filtrate was purified via preparative HPLC-MS (C18 eluting with a gradient of MeCN/H₂O containing 0.15% NH₄OH) to afford product as a white solid (0.030 g, 100%). ¹H NMR (300 MHz, DMSO-d₆): δ 7.95 (s, 2H), 7.50 (s, 1H), 7.05 (t, 1H), 3.44 (s, 2H), 2.15 (s, 6H); LCMS (M+H)⁺: 230.1.

Step E. {trans-3-(4-{3-(Difluoromethyl)-5-[(dimethylamino)methyl]benzoyl}piperazin-1-yl)-1-[4-(7H-pyrrolo[2,3-d]pyrimidin-4-yl)-1H-pyrazol-1-yl]cyclobutyl}acetonitrile 3-(Difluoromethyl)-5-[(dimethylamino)methyl]benzoic acid (14.0 mg, 0.0609 mmol, from Step D) was dissolved in THF (0.56 mL). Triethylamine (28.3 µL, 0.203 mmol) and N,N,N',N'-tetramethyl-O-(7-azabenzotriazol-1-yl)uronium hexafluorophosphate (21.2 mg, 0.0558 mmol) were added and the mixture was stirred for 15 minutes. {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl] cyclobutyl}acetonitrile (25.0 mg, 0.0507 mmol, from Step 1 of Example 1b) was added, and the reaction was stirred for two hours. The reaction mixture was partitioned between water and ethyl acetate. The organic layer was washed with water, 0.1N NaOH and sat. NaCl, dried over sodium sulfate, filtered and concentrated. The residue was dissolved in a 1:1 mixture of DCM:TFA, stirred for 1 hour, concentrated again, then stirred with ethylenediamine (0.2 mL) in Methanol (1 mL) until deprotection was complete. The product was purified via preparative HPLC-MS (C18 eluting with a gradient of MeCN/H₂O containing 0.15% NH₄OH), frozen and lyophilized to afford the free base (11.8 mg, 40%). ¹H NMR (400 MHz, dmso) δ 8.83 (s, 1H), 8.69 (s, 1H), 8.42 (s, 1H), 7.60 (d, J=3.5 Hz, 1H), 7.58 (s, 1H), 7.45 (s, 2H), 7.26-6.77 (m, 2H), 3.66 (br m, 2H), 3.47 (s, 2H), 3.43 (s, 2H), 3.34 (br m, 2H), 3.07-2.89 (m, 2H), 2.83 (tt, J=7.3, 7.4 Hz, 1H), 2.43-2.21 (m, 6H), 2.15 (s, 6H); ¹⁹F NMR (376 MHz, dmso) δ −107.70 (d, J=55.9 Hz); LCMS (M+H)⁺: 574.3.

Example 75

{trans-3-(4-{[4-(1-hydroxy-1-methylethyl)-6-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

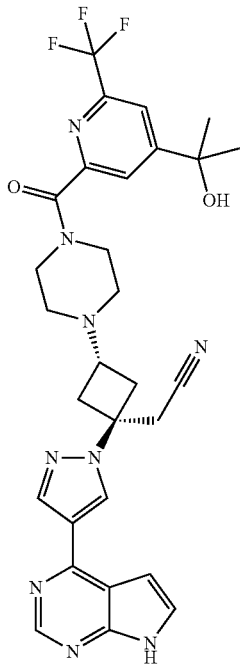 [SMILES: CC(C)(O)c1cc(C(=O)N2CCN([C@H]3C[C@](CC#N)(n4cc(-c5ncnc6[nH]ccc56)cn4)C3)CC2)nc(C(F)(F)F)c1]

Step A. 2-Chloro-6-(trifluoromethyl)isonicotinic acid and 2-chloro-6-(trifluoromethyl)nicotinic acid 2-Chloro-6-(trifluoromethyl)pyridine (20.0 g, 110 mmol, Synquest) was dissolved in tetrahydrofuran (400 mL) and then 1.0 M lithium chloride—chloro(2,2,6,6-tetramethylpiperidin-1-yl)magnesium (1:1) in THF (132 mL, 132 mmol, Aldrich) was added. The reaction was stirred at room temperature for 1 hour and was then cooled to −78° C., and 67 g of solid dry ice was added into the flask. The reaction was stirred at −78° C. for 1 hour and subsequently allowed to slowly warm to room temperature. Upon reaching room temperature, the reaction was quenched with water, and was poured into 1N NaOH and washed with diethyl ether. The aqueous phase was then acidified with c.HCl to pH~1 and extracted with diethyl ether. The combined extracts were washed with water, then sat'd NaCl, dried over $Na_2SO_4$, filtered concentrated to afford a 1.2:1 regioisomeric mixture of carboxylic acids (11.65 g, 47%). $^1$H NMR (400 MHz, $CDCl_3$) δ 8.43 (dd, J=7.9, 0.8 Hz, 1H), 8.17 (d, J=1.1 Hz, 1H), 8.11 (dd, J=1.1, 0.6 Hz, 1H), 7.71 (d, J=7.9 Hz, 1H).

Step B. 2-[2-Chloro-6-(trifluoromethyl)pyridin-4-yl]propan-2-ol (Desired Isomer Isolated)

To a solution of 2-chloro-6-(trifluoromethyl)nicotinic acid (0.45 g, 2.0 mmol) and 2-chloro-6-(trifluoromethyl)isonicotinic acid (0.55 g, 2.4 mmol) (as a mixture from Step A) in tetrahydrofuran (10 mL) cooled in an ice bath was added triethylamine (0.64 mL, 4.6 mmol) followed by isobutyl chloroformate (0.60 mL, 4.6 mmol, Aldrich). The reaction was stirred for 30 minutes, then was filtered through a pad of celite into a flask containing 3.0 M methylmagnesium bromide in diethyl ether (4.0 mL, 12 mmol, Aldrich) in tetrahydrofuran (5 mL) also cooled in an ice bath. The celite pad was rinsed with an additional 10 mL of THF. After warming to room temperature, an additional portion of 3.0 M methylmagnesium bromide in diethyl ether (4.0 mL, 12 mmol) was added to the reaction mixture. When the reaction was determined to be complete by LCMS, saturated ammonium chloride solution was added to the reaction. After stirring for 20 minutes, the mixture was transferred to a separatory funnel and was extracted with ethyl acetate. The combined organic extracts were washed with water and brine, dried over sodium sulfate, filtered and concentrated. Flash chromatography on silica gel, eluting with a gradient from 0-30% EtOAc/Hexanes afforded product (0.28 g, 58%). $^1$H NMR (400 MHz, $CDCl_3$) δ 7.70 (d, J=1.4 Hz, 1H), 7.63 (d, J=1.2 Hz, 1H), 1.60 (s, 6H); LCMS (M+H)$^+$: 240.1, 242.1.

Step C. 4-(1-Hydroxy-1-methylethyl)-6-(trifluoromethyl)pyridine-2-carbonitrile A solution of 2-[2-chloro-6-(trifluoromethyl)pyridin-4-yl]propan-2-ol (0.230 g, 0.960 mmol, from Step B) and zinc cyanide (0.676 g, 5.76 mmol) in N-methylpyrrolidinone (4 mL) was degassed by bubbling a stream of nitrogen through the solution for 10 minutes. Tetrakis(triphenylphosphine)palladium(0) (0.22 g, 0.19 mmol) was added and degassed similarly for 5 additional minutes. The vial was sealed and heated in the microwave to 140° C. for 10 minutes. The reaction mixture was worked up by partitioning between water and ethyl acetate, extracting (3×), and drying the combined extracts over sodium sulfate. The dried extract was then filtered and concentrated. Flash chromatography on silica gel, eluting with a gradient from 0-25% EtOAc/Hexanes afforded product (110 mg, 50%). $^1$H NMR (400 MHz, $CDCl_3$) δ 8.00 (d, J=1.5 Hz, 1H), 7.99 (d, J=1.6 Hz, 1H), 1.62 (s, 6H); $^{19}$F NMR (282 MHz, $CDCl_3$) δ −68.39 (s); LCMS (M+H)$^+$: 231.1.

Step D. 4-(1-Hydroxy-1-methylethyl)-6-(trifluoromethyl)pyridine-2-carboxylic acid To a solution of 4-(1-hydroxy-1-methylethyl)-6-(trifluoromethyl)pyridine-2-carbonitrile (0.088 g, 0.38 mmol, from Step C) in ethanol (4 mL) was added 1.0 M sodium hydroxide in water (1.5 mL, 1.5 mmol) and the reaction was heated to 90° C. for 20 minutes. Upon cooling to room temperature, the reaction was acidified by the addition of 1 N HCl to achieve pH 5 and the ethanol was removed in vacuo. The remaining aqueous mixture was extracted with ethyl acetate (3×). The combined extracts were dried over sodium sulfate, decanted and concentrated to afford product, used without further purification (80 mg, 84%). $^1$H NMR (400 MHz, $CD_3OD$) δ 8.43 (d, J=1.6 Hz, 1H), 8.10 (d, J=1.6 Hz, 1H), 1.57 (s, 6H); $^{19}$F NMR (376 MHz, $CD_3OD$) δ −69.39 (s); LCMS (M+H)$^+$: 250.1.

Step E. {trans-3-(4-{[4-(1-Hydroxy-1-methylethyl)-6-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile 4-(1-Hydroxy-1-methylethyl)-6-(trifluoromethyl)pyridine-2-carboxylic acid (0.0498 g, 0.200 mmol, from Step D) was dissolved in N,N-dimethylformamide (5 mL) and to this was added {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.100 g, 0.203 mmol, from Step 1 of Example 1b), followed by benzotriazol-1-yloxytris(dimethylamino)phosphonium hexafluorophosphate (106.1 mg, 0.2398 mmol) and triethylamine (0.14 mL, 1.0 mmol). The reaction was stirred overnight, then was partitioned between ethyl acetate and brine. The aqueous portion was extracted with two further portions of ethyl acetate. The combined extracts were dried over sodium sulfate, filtered and concentrated. The crude product was stirred with TFA:DCM 1:1 for 1 hour, then evaporated and stirred with excess ethylenediamine in methanol until the deprotection was complete. The product was purified via preparative HPLC-MS (C18 eluting with a gradient of MeCN/$H_2O$ containing 0.15% $NH_4OH$), frozen and lyophilized to afford the free base (62 mg, 52%). $^1$H NMR (300 MHz, $CDCl_3$) δ 9.79 (br s, 1H), 8.83 (s, 1H), 8.48 (s, 1H), 8.34 (s, 1H), 8.00 (d, J=1.5 Hz, 1H), 7.87 (d, J=1.6 Hz, 1H), 7.39 (d, J=3.7 Hz, 1H), 6.81 (d, J=3.6 Hz, 1H), 3.93-3.80 (m, 2H), 3.77-3.64 (m, 2H), 3.22 (s, 2H), 3.13-2.87 (m, 3H), 2.58-2.35 (m, 6H), 1.61 (s, 6H); $^{19}$F NMR (282 MHz, $CDCl_3$) δ −68.19 (s); LCMS (M+H)$^+$: 594.3.

Example 76

{trans-3-(4-{[4-(methoxymethyl)-6-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile

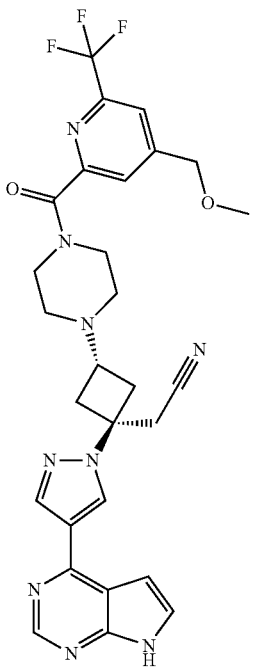 [SMILES: COCc1cc(C(=O)N2CCN([C@H]3C[C@](CC#N)(n4cc(-c5ncnc6[nH]ccc56)cn4)C3)CC2)nc(C(F)(F)F)c1]

Step A. [2-Chloro-6-(trifluoromethyl)pyridin-4-yl]methanol and [2-chloro-6-(trifluoromethyl)pyridin-3-yl]methanol To a solution of 2-chloro-6-(trifluoromethyl)nicotinic acid (0.90 g, 4.0 mmol) and 2-chloro-6-(trifluoromethyl)isonicotinic acid (1.1 g, 4.9 mmol) (a mixture of regioisomers prepared in Example 75, Step A) in tetrahydrofuran (20 mL) cooled in an ice bath was added triethylamine (1.3 mL, 9.2 mmol) followed by isobutyl chloroformate (1.2 mL, 9.2 mmol, Aldrich). The reaction was stirred for 30 minutes, then was filtered through a short pad of celite into a flask containing sodium tetrahydroborate (1.0 g, 26 mmol) in water (10 mL) which was also cooled in an ice bath. Additional THF (10 mL) was used as a rinse through the celite into the reaction flask. After warming to room temperature, water was added and the layers separated. The THF layer was reserved and the aqueous was extracted with three portions of ethyl acetate which were combined with the original THF organic layer. The combined organic extracts were washed with brine, dried over sodium sulfate, filtered and concentrated. Theoretical yield was assumed and the product used without further purification, as a mixture of regioisomers. $^1$H NMR (300 MHz, CDCl$_3$) δ 8.11 (dq, J=7.8, 0.9 Hz, 1H), 7.68 (d, J=7.8 Hz, 1H), 7.61 (s, 1H), 7.55 (s, 1H), 4.85 (s, 2H), 4.83 (s, 2H); LCMS (M+H)$^+$: 212.0.

Step B. 2-Chloro-4-(methoxymethyl)-6-(trifluoromethyl)pyridine (Desired Isomer Isolated)

To a solution of [2-chloro-6-(trifluoromethyl)pyridin-4-yl]methanol (0.84 g, 4.0 mmol) and [2-chloro-6-(trifluoromethyl)pyridin-3-yl]methanol (0.84 g, 4.0 mmol) (as a mixture of regioisomers from Step A) in N,N-dimethylformamide (8.6 mL) was added potassium carbonate (3.3 g, 24 mmol), followed by methyl iodide (0.99 mL, 16 mmol). The reaction was stirred overnight. Additional DMF (10 mL), methyl iodide (2.0 mL, 32 mmol) and potassium carbonate (3.3 g, 24 mmol) were added and the reaction was stirred for 72 hours. Water was added into the reaction and the product was extracted with three portions of ethyl acetate. The combined organic extracts were dried over sodium sulfate, filtered and concentrated. Flash chromatography on silica gel, eluting with a gradient from 0-25% EtOAc/Hexanes allowed for isolation of desired isomer, contaminated with a small amount of the undesired isomer. Desired isomer: $^1$H NMR (300 MHz, CDCl$_3$) δ 7.56 (s, 1H), 7.50 (s, 1H), 4.53 (dd, 2H), 3.48 (s, 3H).

Step C. 4-(Methoxymethyl)-6-(trifluoromethyl)pyridine-2-carbonitrile

A solution of 2-chloro-4-(methoxymethyl)-6-(trifluoromethyl)pyridine (0.5 g, 2 mmol, from Step B) and zinc cyanide (1.56 g, 13.3 mmol) in N-methylpyrrolidinone (8 mL) was degassed by bubbling a stream of nitrogen through the solution for 10 minutes. Tetrakis(triphenylphosphine)palladium(0) (0.51 g, 0.44 mmol) was added and the mixture was degassed similarly for 5 minutes. The reaction vial was sealed and heated in the microwave to 140° C. for 10 minutes. The reaction mixture was partitioned between water and ethyl acetate, and the aqueous portion was extracted with two further portions of ethyl acetate. The combined organic extracts were washed with water, followed by brine, dried over sodium sulfate, filtered and concentrated. Flash chromatography on silica gel, eluting with a gradient from 0-30% EtOAc/Hexanes afforded purified product (0.36 g, 80%). $^1$H NMR (400 MHz, CDCl$_3$) δ 7.87-7.83 (m, 2H), 4.60 (dd, J=0.9 Hz, 2H), 3.51 (s, 3H); $^{19}$F NMR (376 MHz, CDCl$_3$) δ −68.55 (s); LCMS (M+H)$^+$: 217.1.

Step D. 4-(Methoxymethyl)-6-(trifluoromethyl)pyridine-2-carboxylic acid

To a solution of 4-(methoxymethyl)-6-(trifluoromethyl)pyridine-2-carbonitrile (0.36 g, 1.7 mmol, from Step C) in ethanol (20 mL) was added 1.0 M sodium hydroxide in water (6.5 mL, 6.5 mmol) and the reaction was heated in an oil bath held at 90° C. for 4 hours. Upon cooling to room temperature, 1N HCl was added to achieve pH 2, and the product was extracted with ethyl acetate (3×). The combined extracts were dried over sodium sulfate, decanted and concentrated to afford a crystalline solid which was used without further purification. $^1$H NMR (300 MHz, CD$_3$OD) δ 8.29 (s, 1H), 7.95 (s, 1H), 4.66 (s, 2H), 3.49 (s, 3H); $^{19}$F NMR (282 MHz, CD$_3$OD) δ −69.56 (s); LCMS (M+H)$^+$: 236.0.

Step E. {trans-3-(4-{[4-(Methoxymethyl)-6-(trifluoromethyl)pyridin-2-yl]carbonyl}piperazin-1-yl)-1-[4-(7H-pyrrolo[2,3-d]pyrimidin-4-yl)-1H-pyrazol-1-yl]cyclobutyl}acetonitrile 4-(Methoxymethyl)-6-(trifluoromethyl)pyridine-2-carboxylic acid (0.0470 g, 0.200 mmol, from Step D) was dissolved in N,N-dimethylformamide (5 mL) and to this was added {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.100 g, 0.203 mmol, from Step 1 of Example 1b), followed by benzotriazol-1-yloxytris(dimethylamino)phosphonium hexafluorophosphate (106.1 mg, 0.2398 mmol) and triethylamine (0.14 mL, 1.0 mmol). After stirring overnight, the reaction mixture was partitioned between ethyl acetate and brine. The aqueous portion was extracted a further two times with ethyl acetate. The combined extracts were dried over sodium sulfate, filtered and concentrated. The crude product was stirred with TFA:DCM 1:1 for 1 hour, evaporated, then stirred with excess ethylenediamine in methanol until the deprotection was complete. The product was purified via preparative HPLC-MS (C18 eluting with a gradient of MeCN/H$_2$O containing 0.15% NH$_4$OH), frozen and lyophilized to afford the free base (49 mg, 42%). $^1$H NMR (300 MHz, CDCl$_3$) δ 10.14 (br s, 1H), 8.85 (s, 1H), 8.48 (s, 1H), 8.34 (s, 1H), 7.84 (s, 1H), 7.74 (d, J=1.4 Hz, 1H), 7.41 (d, J=3.7 Hz, 1H), 6.81 (d, J=3.6 Hz, 1H), 4.57 (s, 2H), 3.94-3.80 (m, 2H), 3.76-3.61 (m, 2H), 3.48 (s, 3H), 3.22 (s, 2H), 3.12-2.80 (m, 3H), 2.60-2.34 (m, 6H); $^{19}$F NMR (282 MHz, CDCl$_3$) δ −68.34 (s); LCMS (M+H)$^+$: 580.3.

Example 77

{cis-3-(4-{[6-(1-hydroxy-1-methylethyl)-2-(trifluoromethyl)pyrimidin-4-yl]carbonyl}piperazin-1-yl)-1-[4-(1H-pyrrolo[2,3-b]pyridin-4-yl)-1H-pyrazol-1-yl]cyclobutyl}acetonitrile

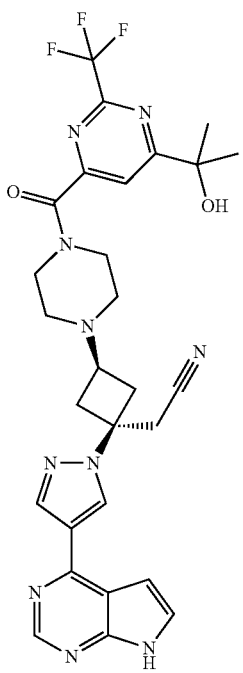 [SMILES: CC(C)(O)c1cc(C(=O)N2CCN([C@H]3C[C@@](CC#N)(n4cc(-c5ncnc6[nH]ccc56)cn4)C3)CC2)nc(C(F)(F)F)n1]

Step A. {3-{[tert-Butyl(diphenyl)silyl]oxy}-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (a mixture of diastereomers)

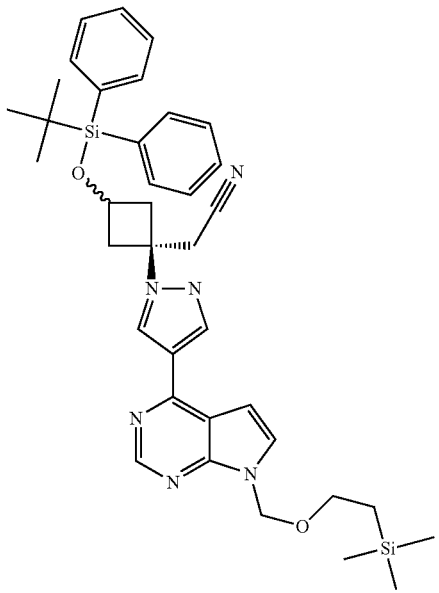

To a solution of (3-{[tert-butyl(diphenyl)silyl]oxy}cyclobutylidene)acetonitrile (4.0 g, 8.7 mmol, from Step 4 of Example 1a) and 4-(1H-pyrazol-4-yl)-1-{[2-(trimethylsilyl)ethoxy]methyl}-1H-pyrrolo[2,3-b]pyridine (1.50 g, 4.77 mmol, US 20090181959) in acetonitrile (10 mL, 200 mmol) was added 1,8-diazabicyclo[5.4.0]undec-7-ene (0.68 mL, 4.6 mmol). The reaction was stirred overnight. A further portion of 1,8-diazabicyclo[5.4.0]undec-7-ene (0.7 mL, 5 mmol) was added and the reaction was allowed to continue for an additional 72 hours. Acetonitrile was removed in vacuo. Flash chromatography on silica gel, eluting with 0%-30% EtOAc/Hexanes, was used to purify product, which was obtained as a mixture of diastereomers (2 g, 60%). $^1$H NMR (300 MHz, CDCl$_3$) δ 8.33 (d, J=5.0 Hz, 1H major), 8.29 (d, J=5.0 Hz, 1H minor), 8.06 (s, 1H major), 8.03 (s, 1H major), 8.00 (s, 1H minor), 7.93 (s, 1H minor), 7.70-7.31 (m, 10H major and 10H minor), 7.19 (d, J=5.0 Hz, 1H major), 7.11 (d, J=5.0 Hz, 1H minor), 6.74 (d, J=3.6 Hz, 1H major), 6.63 (d, J=3.7 Hz, 1H minor), 5.71 (s, 2H major), 5.69 (s, 2H minor), 4.49-4.39 (m, 1H minor), 4.33 (tt, J=7.0, 7.0 Hz, 1H major), 3.67-3.45 (m, 2H major and 2H minor), 3.22 (s, 2H minor), 3.11-2.95 (m, 2H minor), 2.92-2.77 (m, 6H major), 2.65-2.50 (m, 2H minor), 1.08 (s, 9H minor), 1.03 (s, 9H major), 0.98-0.80 (m, 2H major and 2H minor), −0.06 (s, 9H major), −0.08 (s, 9H minor); LCMS (M+H)$^+$: 662.1.

Step B. {3-hydroxy-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (A Mixture of Diastereomers)

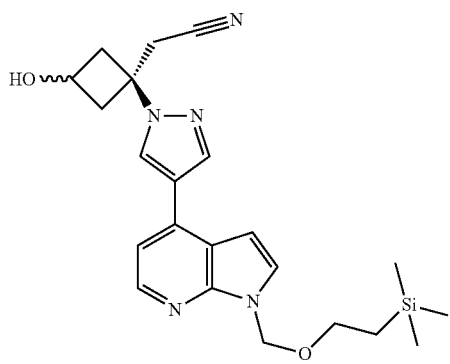

To {3-{[tert-butyl(diphenyl)silyl]oxy}-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (2.0 g, 3.0 mmol, a mixture of diastereomers from Step A) ethanol (82 mL) was added 5.0 M sodium hydroxide in water (9 mL, 50 mmol). The reaction was stirred overnight. The reaction mixture was diluted with water and ethanol was removed in vacuo. The aqueous mixture was extracted with ethyl acetate (3×). The combined organic extracts were washed with water, then brine, dried over sodium sulfate, decanted and concentrated. The product, as a mixture of diastereomers, was used without further purification in Step C. LCMS (M+H)+: 424.2.

Step C. {3-oxo-1-[4-(1-{[2-(trimethylsilyl)ethoxy]methyl}-1H-pyrrolo[2,3-b]pyridin-4-yl)-1H-pyrazol-1-yl]cyclobutyl}acetonitrile

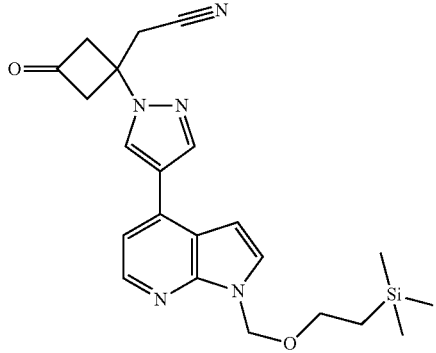 [SMILES: C[Si](C)(C)CCOCn1ccc2c(-c3cnn(C4(CC#N)CC(=O)C4)c3)ccnc21]

To a solution of {3-hydroxy-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (1.3 g, 3.1 mmol, a mixture of diastereomers from Step B) in methylene chloride (40 mL) was added Dess-Martin periodinane (1.63 g, 3.84 mmol). After stirring for 1 hour and 15 minutes, the reaction mixture was poured into 1N NaOH and extracted with three portions of DCM. The combined extracts were washed with 1N NaOH, then brine, dried over sodium sulfate, decanted and solvent was removed in vacuo. Flash chromatography on silica gel, eluting with an initial gradient from 0-30% EtOAc/Hexanes, then a rapid gradient up to 100% EtOAc afforded product (1.1 g, 85%). $^1$H NMR (300 MHz, CDCl$_3$) δ 8.34 (d, J=5.0 Hz, 1H), 8.14 (s, 1H), 8.11 (s, 1H), 7.42 (d, J=3.7 Hz, 1H), 7.18 (d, J=5.0 Hz, 1H), 6.71 (d, J=3.7 Hz, 1H), 5.71 (s, 2H), 4.10-3.97 (m, 2H), 3.74-3.61 (m, 2H), 3.61-3.47 (m, 2H), 3.28 (s, 2H), 0.98-0.86 (m, 2H), −0.07 (s, 9H); LCMS (M+H)+: 422.2.

Step D. tert-butyl 4-{cis-3-(cyanomethyl)-3-[4-(1-{[2-(trimethylsilyl)ethoxy]methyl}-1H-pyrrolo[2,3-b]pyridin-4-yl)-1H-pyrazol-1-yl]cyclobutyl}piperazine-1-carboxylate and tert-butyl 4-{trans-3-(cyanomethyl)-3-[4-(1-{[2-(trimethylsilyl)ethoxy]methyl}-1H-pyrrolo[2,3-b]pyridin-4-yl)-1H-pyrazol-1-yl]cyclobutyl}piperazine-1-carboxylate (Each Diastereomer Isolated)

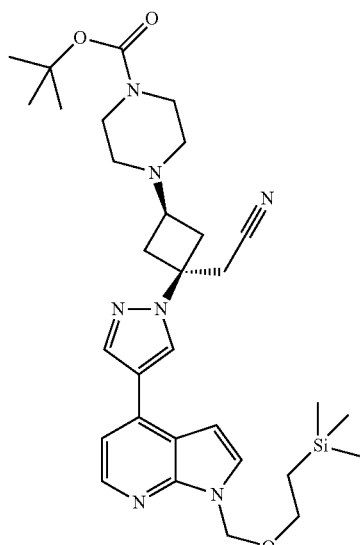

and

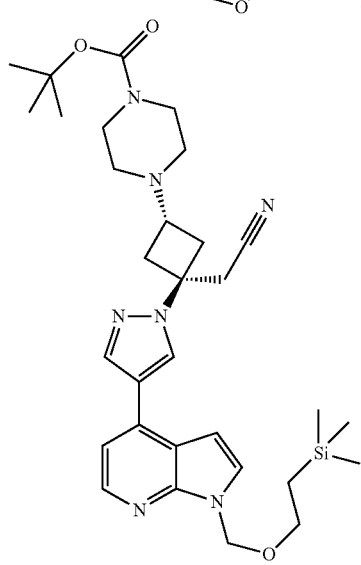

Zinc dichloride (0.210 g, 1.54 mmol) and sodium cyanoborohydride (0.194 g, 3.08 mmol) were combined in methanol (6.5 mL) (according to the procedure found in JOC 1985, 50, 1927-1932) and stirred for 2 hours. After the reducing mixture was generated, {3-oxo-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (1.10 g, 2.61 mmol, from Step C) and tert-butyl piperazine-1-carboxylate (1.15 g, 6.17 mmol, Aldrich) were combined in methanol (30 mL) to dissolve, then the reducing solution generated by the combination of Zinc dichloride and sodium cyanoborohydride was added. The reaction was stirred overnight. Methanol was removed in vacuo. Saturated sodium bicarbonate solution was added and the solution was extracted with three portions of ethyl acetate. The combined extracts were dried over sodium sulfate, filtered and concentrated. Flash chromatograpy on silica gel, eluting with a gradient from 0-10% MeOH in DCM afforded product (1.27 g, 82%) as a mixture of diastereomers: $^1$H NMR (300 MHz, CDCl$_3$) δ 8.32 (d, J=5.1 Hz, 1H), 8.31 (d, J=5.0 Hz, 1H), 8.12 (s, 1H), 8.08 (s, 1H), 8.04 (s, 1H), 8.04 (s, 1H), 7.41 (d, J=3.7 Hz, 1H), 7.40 (d, J=3.7 Hz, 1H), 7.19 (d, J=5.1 Hz, 1H), 7.17 (d, J=5.8 Hz, 1H), 6.73 (d, J=3.1 Hz, 1H), 6.71 (d, 1H), 5.71 (s, 4H), 3.59-3.50 (m, 4H), 3.45 (m, 8H), 3.19 (s, 2H), 3.11 (s, 2H), 3.07-2.95 (m, 2H), 2.94-2.60 (m, 6H), 2.53-2.39 (m, 2H), 2.33 (m, 8H), 1.61 (s, 18H), 0.99-0.73 (m, 4H), -0.07 (d, J=0.7 Hz, 18H).

Chiral HPLC was used to separate the cis and trans isomers: CHIRALPAK IA column, 30% EtOH/Hexanes at 14 mL/min, 75 mg/injection, Peak 1 retention time: 9.725 min; Peak 2 retention time: 12.804 min.

Step E. {cis-3-Piperazin-1-yl-1-[4-(1-{[2-(trimethylsilyl)ethoxy]methyl}-1H-pyrrolo[2,3-b]pyridin-4-yl)-1H-pyrazol-1-yl]cyclobutyl}acetonitrile

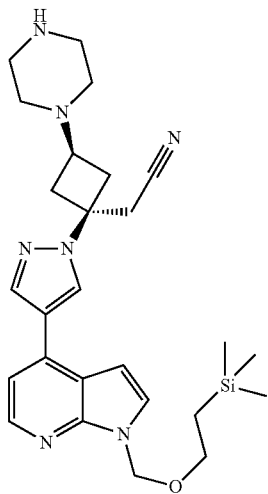 [SMILES: C[Si](C)(C)CCOCn1ccc2c(-c3cnn([C@]4(CC#N)C[C@H](N5CCNCC5)C4)c3)ccnc21]

tert-Butyl 4-{cis-3-(cyanomethyl)-3-[4-(1-{[2-(trimethylsilyl)ethoxy]methyl}-1H-pyrrolo[2,3-b]pyridin-4-yl)-1H-pyrazol-1-yl]cyclobutyl}piperazine-1-carboxylate (0.7 g, 1 mmol, peak 1 from Step D) was dissolved in 1,4-dioxane (14 mL) and 4.0 M hydrogen chloride in dioxane (10 mL, 40 mmol) was added. After stirring for 72 hours, water (10 mL) was added and the heterogeneous mixture became a solution, and the reaction then proceeded. After stirring for 5 hours, the reaction mixture was poured into saturated sodium bicarbonate solution to neutralize and dioxane was removed in vacuo. The aqueous mixture was extracted with ethyl acetate (4×) and the combined extracts were dried over sodium sulfate, filtered and concentrated. (0.56 g, 93%). LCMS (M+H)$^+$: 492.1.

Step F. {cis-3-(4-{[6-(1-Hydroxy-1-methylethyl)-2-(trifluoromethyl)pyrimidin-4-yl]carbonyl}piperazin-1-yl)-1-[4-(1H-pyrrolo[2,3-b]pyridin-4-yl)-1H-pyrazol-1-yl]cyclobutyl}acetonitrile 6-(1-Hydroxy-1-methylethyl)-2-(trifluoromethyl)pyrimidine-4-carboxylic acid (0.0125 g, 0.0501 mmol, Example 58, Step B) was dissolved in N,N-dimethylformamide (1 mL), and to this was added {cis-3-piperazin-1-yl-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (0.025 g, 0.051 mmol, from Step E, stemming from Peak 1 of Step D), followed by benzotriazol-1-yloxytris(dimethylamino)phosphonium hexafluorophosphate (26.57 mg, 0.06008 mmol) and triethylamine (0.035 mL, 0.25 mmol). After stirring overnight, the reaction mixture was partitioned between ethyl acetate and brine, and the aqueous portion was extracted with ethyl acetate a further two times. The combined extracts were dried over sodium sulfate, filtered and concentrated. The crude product was stirred with TFA:DCM 1:1 for 1 hour, evaporated, then stirred with ethylenediamine (1.5 mL) in methanol (5 mL) overnight. The product was purified via preparative HPLC-MS (C18 eluting with a gradient of MeCN/H$_2$O containing 0.15% NH$_4$OH), frozen and lyophilized to afford the free base (5 mg, 20%). $^1$H NMR (500 MHz, CDCl$_3$) δ 9.05 (s, 1H), 8.30 (d, J=5.0 Hz, 1H), 8.06 (s, 1H), 8.05 (s, 2H), 7.37 (d, J=3.5 Hz, 1H), 7.18 (d, J=5.1 Hz, 1H), 6.72 (d, J=3.6 Hz, 1H), 3.90-3.78 (m, 2H), 3.69-3.58 (m, 2H), 3.12 (s, 2H), 2.94 (tt, J=7.2, 7.7 Hz, 1H), 2.88-2.78 (m, 2H), 2.78-2.63 (m, 2H), 2.57-2.50 (m, 2H), 2.50-2.41 (m, 2H), 1.62 (s, 6H). $^{19}$F NMR (282 MHz, cdcl$_3$) δ -70.71 (s); LCMS (M+H)$^+$: 594.1.

Example 78

{trans-3-(4-{[6-(1-hydroxy-1-methylethyl)-2-(trifluoromethyl)pyrimidin-4-yl]carbonyl}piperazin-1-yl)-1-[4-(1H-pyrrolo[2,3-b]pyridin-4-yl)-1H-pyrazol-1-yl]cyclobutyl}acetonitrile

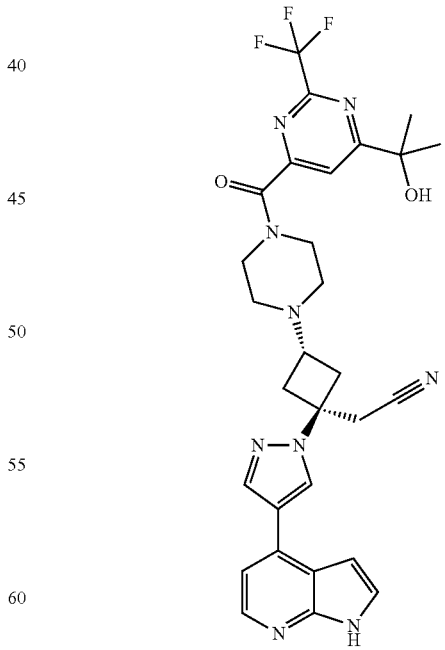

The title compound was prepared in the manner of Example 77, starting with Peak 2 from Step D to afford product as the free base (5 mg, 20%). $^1$H NMR (500 MHz, CDCl$_3$) δ 10.00 (s, 1H), 8.31 (d, J=5.0 Hz, 1H), 8.14 (s, 1H), 8.10 (s, 1H), 8.08 (s, 1H), 7.40 (d, J=3.5 Hz, 1H), 7.19 (d, J=5.0 Hz, 1H), 6.72 (d, J=3.5 Hz, 1H), 3.97-3.83 (m, 2H), 3.76-3.51 (m, 2H), 3.19 (s, 2H), 3.11-3.00 (m, 2H), 2.98 (tt, J=6.5, 6.8 Hz, 1H), 2.59-2.39 (m, 6H), 1.62 (s, 6H); $^{19}$F NMR (282 MHz, cdcl$_3$) δ −70.71 (s); LCMS (M+H)$^+$: 594.1.

Example 79

4-{trans-3-(cyanomethyl)-3-[4-(7H-pyrrolo[2,3-d]pyrimidin-4-yl)-1H-pyrazol-1-yl]cyclobutyl}-N-isopropyl-N-methylpiperazine-1-carboxamide

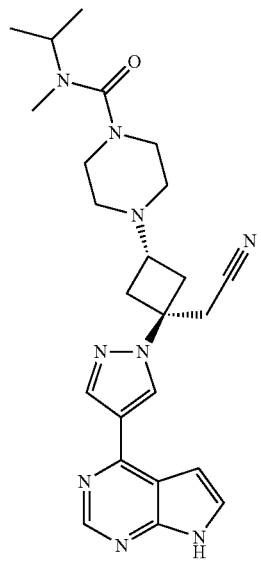 [SMILES: CC(C)N(C)C(=O)N1CCN([C@H]2C[C@](CC#N)(n3cc(-c4ncnc5[nH]ccc45)cn3)C2)CC1]

To N-methyl-2-propanamine (13.4 μL, 0.183 mmol, Aldrich), in acetonitrile (0.5 mL) was added 1.89 M phosgene in toluene (0.193 mL, 0.365 mmol) followed by N,N-diisopropylethylamine (0.0318 mL, 0.183 mmol). After stirring for 1 hour, solvents and excess reagents were removed in vacuo. The residue was reconstituted in 1:1 MeCN:DCM and N,N-diisopropylethylamine (0.0318 mL, 0.183 mmol) was added, followed by {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Step 1 of Example 1b) and the reaction mixture was stirred overnight. The mixture was diluted with water, and extracted with EtOAc. The extract was washed with water, brine, dried over sodium sulfate and concentrated. The residue was stirred with 1:1 TFA:DCM for 1 hour, evaporated, then stirred with 0.2 mL ethylenediamine in methanol. The product was purified by preparative HPLC-MS (C18 eluting with a gradient of MeCN/H$_2$O containing 0.15% NH$_4$OH), frozen and lyophilized to afford product as the free base (12.8 mg, 46%). $^1$H NMR (400 MHz, dmso) δ 12.06 (br s, 1H), 8.82 (s, 1H), 8.69 (s, 1H), 8.42 (s, 1H), 7.60 (d, 1H), 7.07 (d, 1H), 3.90 (hept, 1H), 3.42 (s, 2H), 3.14-3.04 (m, 4H), 3.04-2.94 (m, 2H), 2.79 (tt, J=7.2, 7.3 Hz, 1H), 2.60 (s, 3H), 2.42-2.21 (m, 6H), 1.04 (d, 6H); LCMS (M+H)$^+$: 462.3.

Example 80

4-{trans-3-(cyanomethyl)-3-[4-(7H-pyrrolo[2,3-d]pyrimidin-4-yl)-1H-pyrazol-1-yl]cyclobutyl}-N-methyl-N-propylpiperazine-1-carboxamide

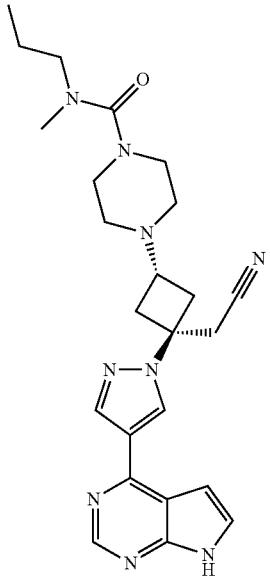 [SMILES: CCCN(C)C(=O)N1CCN([C@H]2C[C@](CC#N)(n3cc(-c4ncnc5[nH]ccc45)cn3)C2)CC1]

The title compound was prepared according to the procedure of Example 79, using N-methyl-n-propylamine (18.7 μL, 0.183 mmol, Acros) to afford product as the free base (13 mg, 46%). $^1$H NMR (400 MHz, dmso) δ 12.10 (br s, 1H), 8.82 (s, 1H), 8.69 (s, 1H), 8.42 (s, 1H), 7.60 (d, 1H), 7.07 (d, 1H), 3.42 (s, 2H), 3.10 (m, 4H), 3.06-2.92 (m, 4H), 2.78 (tt, J=7.5, 7.8 Hz, 1H), 2.72 (s, 3H), 2.40-2.18 (m, 6H), 1.54-1.38 (m, 2H), 0.79 (t, 3H); LCMS (M+H)$^+$: 462.3.

Example 81

4-{trans-3-(cyanomethyl)-3-[4-(7H-pyrrolo[2,3-d]pyrimidin-4-yl)-1H-pyrazol-1-yl]cyclobutyl}-N-ethylpiperazine-1-carboxamide

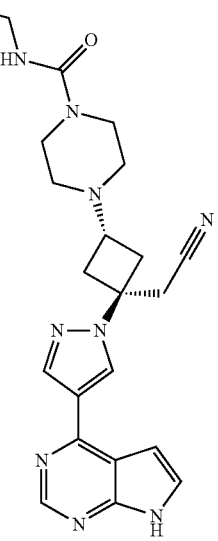

{trans-3-Piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (30.0 mg, 0.0609 mmol, from Step 1 of Example 1b) was dissolved in acetonitrile (0.40 mL) and ethane, isocyanato- (8.6 mg, 0.12 mmol, Aldrich) was added. After stirring for 1 hour, solvent and excess reagent was removed in vacuo. The residue was stirred with 1:1 TFA:DCM for 1 hour, evaporated, then stirred with 0.2 mL ethylenediamine in methanol until deprotection was complete. The product was purified by preparative HPLC-MS (C18 eluting with a gradient of MeCN/H$_2$O containing 0.15% NH$_4$OH), frozen and lyophilized to afford product as the free base (16.7 mg, 63%). $^1$H NMR (400 MHz, dmso) δ 12.06 (br s, 1H), 8.82 (s, 1H), 8.69 (s, 1H), 8.42 (s, 1H), 7.60 (d, 1H), 7.07 (d, 1H), 6.47 (t, 1H), 3.42 (s, 2H), 3.32-3.21 (m, 4H), 3.08-2.93 (m, 4H), 2.76 (tt, J=7.3, 7.3 Hz, 1H), 2.40-2.30 (m, 2H), 2.28-2.15 (m, 4H), 0.99 (t, J=7.1 Hz, 3H); LCMS (M+H)$^+$: 434.1.

Example 82

4-{trans-3-(cyanomethyl)-3-[4-(7H-pyrrolo[2,3-d]pyrimidin-4-yl)-1H-pyrazol-1-yl]cyclobutyl}-N-[3-(dimethylamino)propyl]-N-methylpiperazine-1-carboxamide

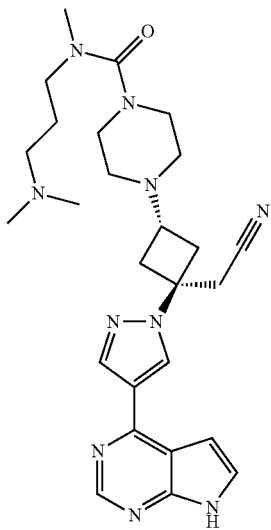 [SMILES: CN(C)CCCN(C)C(=O)N1CCN([C@H]2C[C@](CC#N)(n3cc(-c4ncnc5[nH]ccc45)cn3)C2)CC1]

To N,N,N'-trimethylpropane-1,3-diamine (0.0212 g, 0.183 mmol, Alfa Aesar) in acetonitrile (0.5 mL) was added 1.89 M phosgene in toluene (0.193 mL, 0.365 mmol). After stirring for 1 hour, solvent was removed in vacuo. The residue was dissolved in 1:1 MeCN:DCM and {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Step 1 of Example 1b) and N,N-diisopropylethylamine (64 µL, 0.36 mmol) were added and the mixture was stirred overnight. The mixture was diluted with water and was extracted with EtOAc. The extract was washed with water, brine, dried over sodium sulfate and concentrated. The residue was stirred with 1:1 TFA:DCM for 1 hour, evaporated, then stirred with 0.2 mL ethylenediamine in methanol until deprotection was complete. The product was purified by preparative HPLC-MS (C18 eluting with a gradient of MeCN/H$_2$O containing 0.15% NH$_4$OH), frozen and lyophilized to afford product as the free base (10.3 mg, 34%). $^1$H NMR (400 MHz, dmso) δ 12.10 (s, 1H), 8.82 (s, 1H), 8.69 (s, 1H), 8.42 (s, 1H), 7.60 (d, J=3.5 Hz, 1H), 7.07 (d, J=3.6 Hz, 1H), 3.42 (s, 2H), 3.14-2.93 (m, 8H), 2.77 (tt, J=7.4, 7.5 Hz, 1H), 2.73 (s, 3H), 2.40-2.23 (m, 6H), 2.13 (t, J=7.0 Hz, 2H), 2.09 (s, 6H), 1.58 (p, J=7.0 Hz, 2H); LCMS (M+H)$^+$: 505.2.

Example 83

4-{trans-3-(cyanomethyl)-3-[4-(7H-pyrrolo[2,3-d]pyrimidin-4-yl)-1H-pyrazol-1-yl]cyclobutyl}-N-cyclopropyl-N-methylpiperazine-1-carboxamide

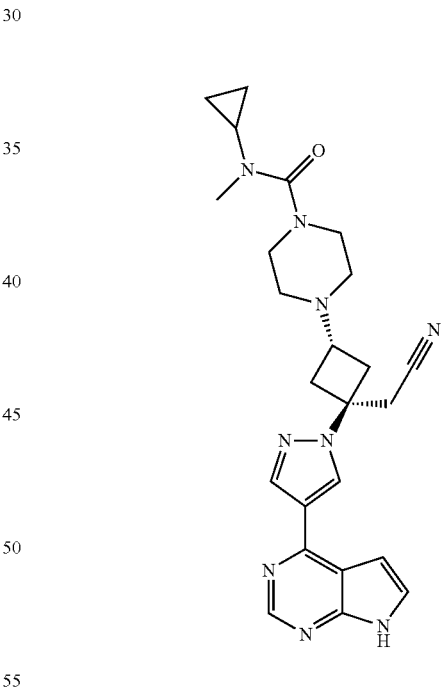

The title compound was prepared by the method of Example 79, using N-methylcyclopropanamine hydrochloride (0.0196 g, 0.183 mmol, Accela ChemBio, Inc.) to afford product as the free base (21.8 mg, 78%). $^1$H NMR (400 MHz, dmso) δ 11.98 (br s, 1H), 8.82 (s, 1H), 8.69 (s, 1H), 8.42 (s, 1H), 7.60 (d, J=3.6 Hz, 1H), 7.07 (d, J=3.6 Hz, 1H), 3.42 (s, 2H), 3.26-3.17 (m, 4H), 3.04-2.94 (m, 2H), 2.78 (tt, J=7.3, 7.4 Hz, 1H), 2.70 (s, 3H), 2.57 (tt, J=6.9, 3.7 Hz, 1H), 2.39-2.31 (m, 2H), 2.31-2.22 (m, 4H), 0.63 (td, J=6.9, 4.9 Hz, 2H), 0.50-0.44 (m, 2H); LCMS (M+H)$^+$: 460.3.

Example 84

4-{trans-3-(cyanomethyl)-3-[4-(7H-pyrrolo[2,3-d]pyrimidin-4-yl)-1H-pyrazol-1-yl]cyclobutyl}-N-methyl-N-(2,2,2-trifluoroethyl)piperazine-1-carboxamide

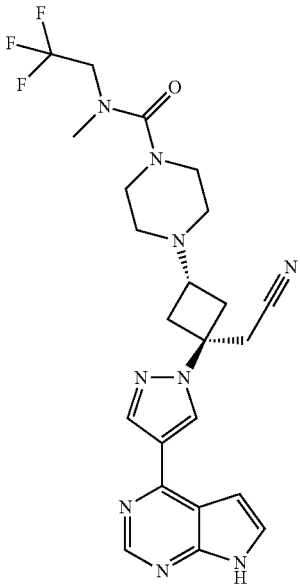 [SMILES: CN(CC(F)(F)F)C(=O)N1CCN([C@H]2C[C@](CC#N)(n3cc(-c4ncnc5[nH]ccc45)cn3)C2)CC1]

The title compound was prepared by the method of Example 79, using 2,2,2-trifluoro-N-methylethanamine hydrochloride (0.0273 g, 0.183 mmol, Matrix Scientific) to afford product as the free base (11.5 mg, 38%). $^1$H NMR (376 MHz, dmso) δ 12.11 (br s, 1H), 8.82 (s, 1H), 8.69 (s, 1H), 8.42 (s, 1H), 7.60 (d, J=3.6 Hz, 1H), 7.07 (d, J=3.6 Hz, 1H), 4.04 (q, J=9.8 Hz, 2H), 3.42 (s, 2H), 3.24-3.11 (m, 4H), 3.04-2.96 (m, 2H), 2.94 (s, 3H), 2.79 (tt, J=7.3, 7.3 Hz, 1H), 2.40-2.26 (m, 6H); $^{19}$F NMR (376 MHz, dmso) δ −70.04 (t, J=9.7 Hz); LCMS (M+H)$^+$: 502.2.

Example 85

4-{trans-3-(cyanomethyl)-3-[4-(7H-pyrrolo[2,3-d]pyrimidin-4-yl)-1H-pyrazol-1-yl]cyclobutyl}-N-isopropylpiperazine-1-carboxamide

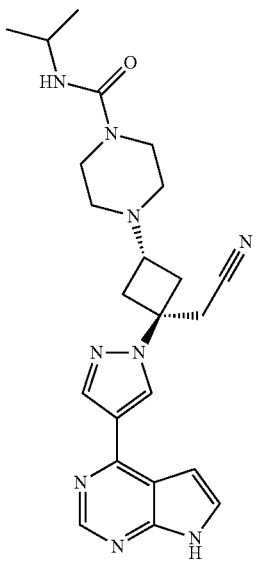 [SMILES: CC(C)NC(=O)N1CCN([C@H]2C[C@](CC#N)(n3cc(-c4ncnc5[nH]ccc45)cn3)C2)CC1]

To a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Step 1 of Example 1b) in methylene chloride (1 mL) was added N,N-diisopropylethylamine (26 µL, 0.15 mmol) followed by 2-isocyanatopropane (7 µL, 0.07 mmol, Aldrich) and the reaction was stirred for two hours. TFA (1 mL) was added and the reaction was stirred for 1 hour, then evaporated. The residue was redissolved in methanol (1.8 mL) and ethylenediamine (0.2 mL) was added. After stirring for 30 minutes, the product was purified by preparative HPLC-MS (C18 eluting with a gradient of MeCN/H$_2$O containing 0.15% NH$_4$OH), the eluent was frozen and lyophilized to afford product as the free base (9 mg, 30%). $^1$H NMR (300 MHz, CD$_3$OD) δ 8.71 (s, 1H), 8.66 (s, 1H), 8.39 (s, 1H), 7.50 (d, J=3.7 Hz, 1H), 6.98 (d, J=3.6 Hz, 1H), 3.94-3.78 (m, 1H), 3.49-3.37 (m, 4H), 3.33 (s, 2H), 3.14-3.00 (m, 2H), 2.97-2.85 (m, 1H), 2.57-2.43 (m, 2H), 2.43-2.31 (m, 4H), 1.12 (d, J=6.7 Hz, 6H); LCMS (M+H)$^+$: 448.1.

Example 86

4-{trans-3-(cyanomethyl)-3-[4-(7H-pyrrolo[2,3-d]pyrimidin-4-yl)-1H-pyrazol-1-yl]cyclobutyl}-N-(trans-4-hydroxycyclohexyl)piperazine-1-carboxamide

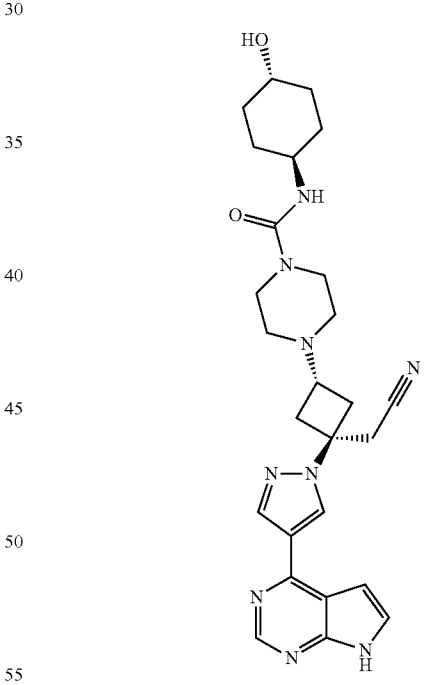

To a vial containing Phoxime® resin (0.19 g, Aldrich) was added trans-4-aminocyclohexanol (56 mg, 0.49 mmol, Aldrich) in methylene chloride (2.5 mL). The reaction was stirred overnight. The resin was collected by filtration and washed with DCM, then with MeOH. The collected resin was returned to a reaction vial and swelled with 1,2-Dichloro ethane (2 mL). {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.040 g, 0.081 mmol, from Step 1 of Example 1b) as a solution in methylene chloride (1 mL) was added, followed by Toluene (5 mL). The vials was sealed and heated to 80° C. overnight. After cooling to room temperature, the resin was removed by filtration and washed with DCM and MeOH, and the filtrate was evaporated. The residue was stirred with 1:1 TFA:DCM for 1 hour, evaporated, then stirred with ethylenediamine (0.2 mL) in methanol (1.5 mL) until the deprotection was complete. The product was purified by preparative HPLC-MS (C18 eluting with a gradient of MeCN/H$_2$O containing 0.15% NH$_4$OH), the eluent was frozen and lyophilized to afford product as the free base (5 mg, 10%). $^1$H NMR (400 MHz, CD$_3$OD) δ 8.71 (s, 1H), 8.66 (s, 1H), 8.39 (s, 1H), 7.51 (d, J=3.6 Hz, 1H), 6.98 (d, J=3.6 Hz, 1H), 3.56-3.44 (m, 2H), 3.44-3.37 (m, 4H), 3.33 (s, 2H), 3.13-3.02 (m, 2H), 2.95-2.83 (m, 1H), 2.55-2.44 (m, 2H), 2.41-2.33 (m, 4H), 1.98-1.80 (m, 4H), 1.40-1.20 (m, 4H); LCMS (M+H)$^+$: 504.4.

Phoxime® resin. Purified to afford product as the free base (5 mg, 10%). $^1$H NMR (300 MHz, CD$_3$OD) δ 8.71 (s, 1H), 8.66 (s, 1H), 8.39 (s, 1H), 7.51 (d, J=3.7 Hz, 1H), 6.98 (d, J=3.6 Hz, 1H), 4.34-4.17 (m, 1H), 3.98-3.81 (m, 2H), 3.76 (td, J=8.3, 6.1 Hz, 1H), 3.56 (dd, J=9.1, 4.3 Hz, 1H), 3.50-3.38 (m, 4H), 3.33 (s, 2H), 3.14-2.95 (m, 2H), 2.98-2.83 (m, 1H), 2.56-2.43 (m, 2H), 2.44-2.32 (m, 4H), 2.18 (dq, J=14.8, 7.4 Hz, 1H), 1.92-1.72 (m, 1H); LCMS (M+H)$^+$: 476.2.

Example 88

4-{trans-3-(cyanomethyl)-3-[4-(7H-pyrrolo[2,3-d]pyrimidin-4-yl)-1H-pyrazol-1-yl]cyclobutyl}-N-(2-hydroxycyclopentyl)piperazine-1-carboxamide (racemic)

Example 87

4-{trans-3-(cyanomethyl)-3-[4-(7H-pyrrolo[2,3-d]pyrimidin-4-yl)-1H-pyrazol-1-yl]cyclobutyl}-N-[(3R)-tetrahydrofuran-3-yl]piperazine-1-carboxamide

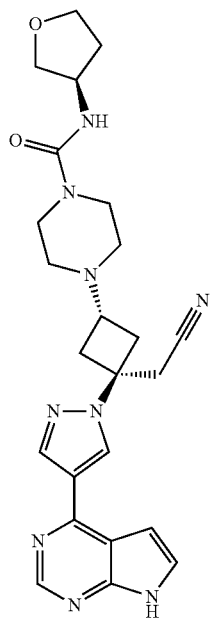 [SMILES: N#CC[C@]1(n2cc(-c3ncnc4[nH]ccc34)cn2)C[C@H](N2CCN(C(=O)N[C@@H]3CCOC3)CC2)C1]

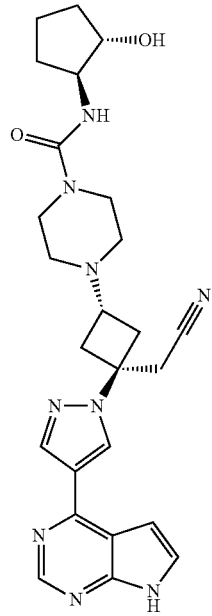 [SMILES: N#CC[C@]1(n2cc(-c3ncnc4[nH]ccc34)cn2)C[C@H](N2CCN(C(=O)N[C@H]3CCC[C@@H]3O)CC2)C1]

The title compound was prepared according to the method of Example 86, starting with (3R)-tetrahydrofuran-3-amine 4-methylbenzenesulfonate (0.13 g, 0.49 mmol, Fluka), which was stirred with triethylamine (0.068 mL, 0.49 mmol) in DCM (2.5 mL) before adding the resulting mixture to the The title compound was prepared by the method of Example 87 using a mixture of trans-2-aminocyclopentanol hydrochloride (67 mg, 0.49 mmol, racemic) and triethylamine (0.068 mL, 0.49 mmol) in methylene chloride (2.5 mL). The racemic product was obtained as the free base (5 mg, 10%). $^1$H NMR (400 MHz, CD$_3$OD) δ 8.62 (s, 1H), 8.57 (s, 1H), 8.31 (s, 1H), 7.42 (d, J=3.6 Hz, 1H), 6.89 (d, J=3.7 Hz, 1H), 3.83 (q, J=6.2 Hz, 1H), 3.74-3.63 (m, 1H), 3.39-3.30 (m, 4H), 3.23 (s, 2H), 3.04-2.90 (m, 2H), 2.86-2.71 (m, 1H), 2.45-2.36 (m, 2H), 2.36-2.25 (m, 4H), 2.05-1.89 (m, 1H), 1.89-1.77 (m, 1H), 1.67-1.51 (m, 2H), 1.51-1.25 (m, 2H); LCMS (M+H)$^+$: 490.4.

Example 89

4-{trans-3-(cyanomethyl)-3-[4-(7H-pyrrolo[2,3-d]pyrimidin-4-yl)-1H-pyrazol-1-yl]cyclobutyl}-N-[(1S,2R)-2-hydroxycyclopentyl]piperazine-1-carboxamide (Single Enantiomer Produced)

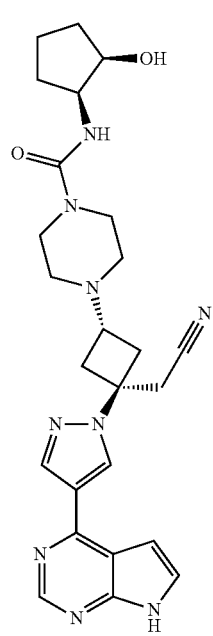

To a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Step 1 of Example 1b) in acetonitrile (1 mL) was added 1.89 M phosgene in toluene (0.042 mL, 0.079 mmol) followed by N,N-diisopropylethylamine (0.021 mL, 0.12 mmol). After stirring for 1 hour, solvent and excess reagents were removed in vacuo. The residue was redissolved in methylene chloride (0.2 mL) and (1R,2S)-2-aminocyclopentanol hydrochloride (0.025 g, 0.18 mmol, Fluka) followed by N,N-diisopropylethylamine (0.04 mL, 0.2 mmol) were added. After 45 minutes, additional (1R,2S)-2-aminocyclopentanol hydrochloride (0.025 g, 0.18 mmol) and N,N-diisopropylethylamine (0.04 mL, 0.2 mmol) were added. TFA (0.2 mL) was added, the reaction was stirred for 3 hours, and then the solvent was removed. Deprotection was completed by stirring with excess ethylenediamine in methanol and the product was purified via preparative HPLC-MS (C18 eluting with a gradient of MeCN/H$_2$O containing 0.15% NH$_4$OH) to afford the free base (13 mg, 44%). $^1$H NMR (400 MHz, CD$_3$OD) δ 8.71 (s, 1H), 8.66 (s, 1H), 8.40 (s, 1H), 7.51 (d, J=3.6 Hz, 1H), 6.98 (d, J=3.7 Hz, 1H), 4.07 (td, J=4.5, 2.0 Hz, 1H), 3.86 (ddd, J=9.9, 7.6, 4.4 Hz, 1H), 3.49-3.42 (m, 4H), 3.34 (s, 2H), 3.11-3.03 (m, 2H), 2.91 (tt, J=6.7, 6.8 Hz, 1H), 2.55-2.45 (m, 2H), 2.44-2.36 (m, 4H), 1.96-1.71 (m, 3H), 1.71-1.48 (m, 3H); LCMS (M+H)$^+$: 490.1.

Example 90

4-{trans-3-(cyanomethyl)-3-[4-(7H-pyrrolo[2,3-d]pyrimidin-4-yl)-1H-pyrazol-1-yl]cyclobutyl}-N-cyclopentylpiperazine-1-carboxamide

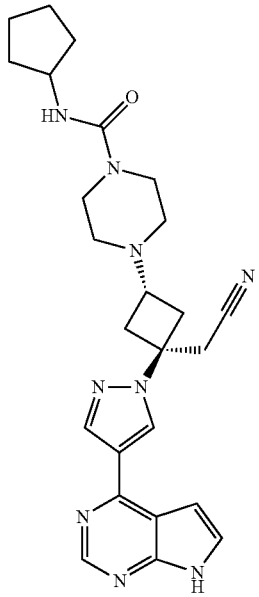 [SMILES: N#CC[C@]1(n2cc(-c3ncnc4[nH]ccc34)cn2)C[C@H](N2CCN(C(=O)NC3CCCC3)CC2)C1]

The title compound was prepared by the method of Example 85, using isocyanatocyclopentane (8.2 uL, 0.073 mmol, Aldrich) and omitting DIPEA, to afford the product as the free base (13 mg, 45%). $^1$H NMR (400 MHz, CD$_3$OD) δ 8.71 (s, 1H), 8.66 (s, 1H), 8.39 (s, 1H), 7.51 (d, J=3.6 Hz, 1H), 6.98 (d, J=3.7 Hz, 1H), 4.07-3.86 (m, 2H), 3.48-3.37 (m, 4H), 3.32 (s, 2H), 3.13-2.99 (m, 2H), 2.91 (tt, J=7.3, 7.6 Hz, 1H), 2.56-2.43 (m, 2H), 2.44-2.29 (m, 4H), 1.99-1.76 (m, 2H), 1.80-1.62 (m, 2H), 1.62-1.47 (m, 2H), 1.48-1.27 (m, 2H); LCMS (M+H)$^+$: 474.1.

Example 91

{trans-3-(4-{[(3S)-3-hydroxypyrrolidin-1-yl]carbonyl}piperazin-1-yl)-1-[4-(7H-pyrrolo[2,3-d]pyrimidin-4-yl)-1H-pyrazol-1-yl]cyclobutyl}acetonitrile

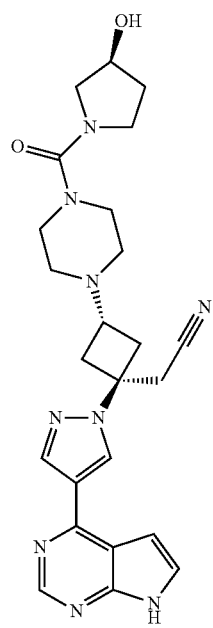 [SMILES: N#CC[C@]1(n2cc(-c3ncnc4[nH]ccc34)cn2)C[C@H](N2CCN(C(=O)N3CC[C@H](O)C3)CC2)C1]

(3S)-Pyrrolidin-3-ol (0.011 g, 0.12 mmol, Aldrich) was dissolved in methylene chloride (0.2 mL) and acetonitrile (1 mL) and 1.89 M phosgene in toluene (0.097 mL, 0.18 mmol) and N,N-diisopropylethylamine (0.021 mL, 0.12 mmol) were added. The reaction mixture was stirred at room temperature for 1 hour, followed by evaporation of solvent and excess reagent. N,N-Diisopropylethylamine (0.062 mL, 0.35 mmol) was again added followed by acetonitrile (0.5 mL), and a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Step 1 of Example 1b) in methylene chloride (1 mL) was added. The reaction was stirred overnight. TFA (1 mL) was added and the reaction was stirred for 1 hour. Solvents were evaporated and replaced with methanol (1.8 mL) and ethylenediamine (0.2 mL). After stirring for 30 minutes, the product was purified via preparative HPLC-MS (C18 eluting with a gradient of MeCN/$H_2O$ containing 0.15% $NH_4OH$) to afford the free base (3 mg, 10%). $^1$H NMR (400 MHz, $CD_3OD$) δ 8.72 (s, 1H), 8.67 (s, 1H), 8.40 (s, 1H), 7.51 (d, J=3.6 Hz, 1H), 6.99 (d, J=3.6 Hz, 1H), 4.41-4.29 (m, 1H), 3.70-3.50 (m, 2H), 3.45-3.15 (m, 8H), 3.14-3.00 (m, 2H), 2.93 (tt, J=7.0, 7.0 Hz, 1H), 2.56-2.32 (m, 6H), 2.04-1.68 (m, 2H); LCMS (M+H)$^+$: 476.1.

Example 92

4-{trans-3-(cyanomethyl)-3-[4-(7H-pyrrolo[2,3-d]pyrimidin-4-yl)-1H-pyrazol-1-yl]cyclobutyl}-N-(cyclopropylmethyl)piperazine-1-carboxamide trifluoroacetate salt

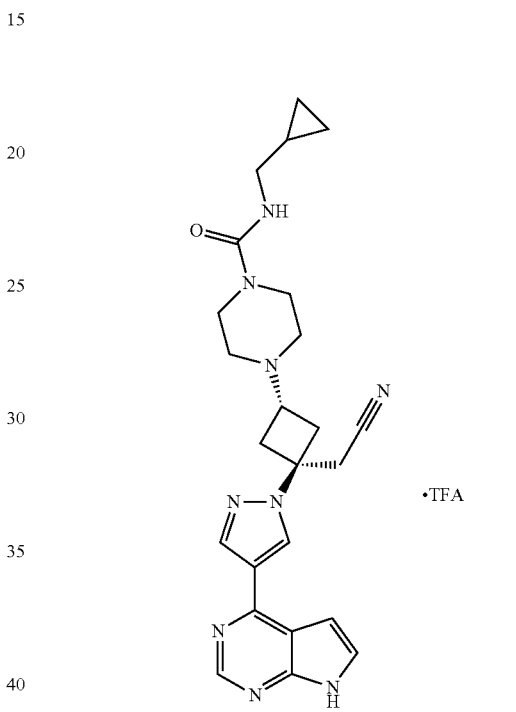

To a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.021 g, 0.043 mmol, from Step 1 of Example 1b) in acetonitrile (1 mL) was added 1.89 M phosgene in toluene (0.042 mL, 0.079 mmol) followed by N,N-diisopropylethylamine (0.021 mL, 0.12 mmol). After stirring for 1 hour, excess reagents and solvent were removed in vacuo. The product was reconstituted in methylene chloride (0.2 mL) and 1-cyclopropylmethanamine hydrochloride (80 mg, 0.74 mmol, Aldrich) followed by N,N-diisopropylethylamine (0.080 mL, 0.46 mmol) were added. The reaction was stirred overnight and then evaporated under a stream of nitrogen. The residue was reconstituted in DCM and TFA was added (1:1). After 1 hour, these solvents were evaporated and replaced with ethylenediamine (0.2 mL) in methanol. When deprotection was complete, the product was purified via two successive preparative HPLC-MS runs (first: C18 eluting with a gradient of MeCN/$H_2O$ containing 0.15% $NH_4OH$; followed by C18 eluting with a gradient of MeCN/$H_2O$ containing 0.1% TFA) to afford the product as the trifluoroacetate salt (6 mg). $^1$H NMR (400 MHz, CD$_3$OD) δ 9.02 (s, 1H), 8.87 (s, 1H), 8.53 (s, 1H), 7.80 (d, J=3.7 Hz, 1H), 7.27 (d, J=3.7 Hz, 1H), 3.93 (tt, J=8.8, 9.1 Hz, 1H), 3.73 (br m, 4H), 3.51-3.36 (m, 4H), 3.21 (br m, 4H), 3.07-2.90 (m, 4H), 0.98 (dddd, J=14.9, 8.1, 7.2, 3.7 Hz, 1H), 0.45 (ddd, 2H), 0.18 (dt, J=6.0, 4.5 Hz, 2H); LCMS (M+H)$^+$: 460.2.

Example 93

4-{trans-3-(cyanomethyl)-3-[4-(7H-pyrrolo[2,3-d]pyrimidin-4-yl)-1H-pyrazol-1-yl]cyclobutyl}-N-[(1R)-1,2-dimethylpropyl]piperazine-1-carboxamide

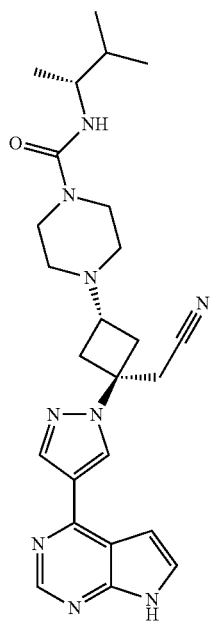 [SMILES: CC(C)[C@@H](C)NC(=O)N1CCN([C@H]2C[C@](CC#N)(n3cc(-c4ncnc5[nH]ccc45)cn3)C2)CC1]

The title compound was prepared by the method of Example 92, using (2R)-3-methylbutan-2-amine (0.05 g, 0.6 mmol, Aldrich) and purified by preparative HPLC-MS (C18 eluting with a gradient of MeCN/H$_2$O containing 0.15% NH$_4$OH) to afford product as the free base (7 mg, 30%). $^1$H NMR (400 MHz, CD$_3$OD) δ 8.71 (s, 1H), 8.66 (s, 1H), 8.39 (s, 1H), 7.50 (d, J=3.6 Hz, 1H), 6.98 (d, J=3.6 Hz, 1H), 3.64-3.52 (m, 1H), 3.51-3.38 (m, 4H), 3.33 (s, 2H), 3.13-2.98 (m, 2H), 2.91 (tt, J=7.3, 7.5 Hz, 1H), 2.54-2.46 (m, 2H), 2.45-2.34 (m, 4H), 1.66 (h, J=6.8 Hz, 1H), 1.07 (d, J=6.7 Hz, 3H), 0.89 (d, J=6.8 Hz, 3H), 0.88 (d, J=6.8 Hz, 3H); LCMS (M+H)$^+$: 476.3.

Example 94

4-{trans-3-(cyanomethyl)-3-[4-(7H-pyrrolo[2,3-d]pyrimidin-4-yl)-1H-pyrazol-1-yl]cyclobutyl}-N-[(1S)-1,2-dimethylpropyl]piperazine-1-carboxamide

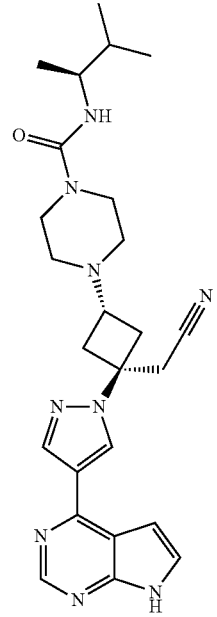 [SMILES: CC(C)[C@H](C)NC(=O)N1CCN([C@H]2C[C@](CC#N)(n3cc(-c4ncnc5[nH]ccc45)cn3)C2)CC1]

The title compound was prepared by the method of Example 92, using (2S)-3-methylbutan-2-amine (0.05 g, 0.6 mmol, Alfa Aesar) and purified by preparative HPLC-MS (C18 eluting with a gradient of MeCN/H$_2$O containing 0.15% NH$_4$OH) to afford product as the free base (7 mg, 30%). $^1$H NMR (400 MHz, CD$_3$OD) δ 8.71 (s, 1H), 8.66 (s, 1H), 8.40 (s, 1H), 7.51 (d, J=3.6 Hz, 1H), 6.98 (d, J=3.6 Hz, 1H), 3.58 (tt, 1H), 3.51-3.38 (m, 4H), 3.33 (s, 2H), 3.12-3.00 (m, 2H), 2.91 (tt, J=7.2, 7.2 Hz, 1H), 2.54-2.45 (m, 2H), 2.44-2.31 (m, 4H), 1.67 (dq, J=13.4, 6.6 Hz, 1H), 1.07 (d, J=6.7 Hz, 3H), 0.89 (d, J=6.8 Hz, 3H), 0.88 (d, J=6.8 Hz, 3H); LCMS (M+H)$^+$: 476.4.

Example 95

4-{trans-3-(cyanomethyl)-3-[4-(7H-pyrrolo[2,3-d]pyrimidin-4-yl)-1H-pyrazol-1-yl]cyclobutyl}piperazine-1-carboxamide

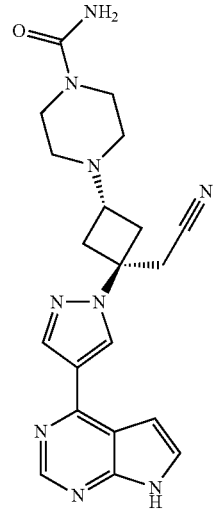 [SMILES: N#CC[C@]1(n2cc(-c3ncnc4[nH]ccc34)cn2)C[C@H](N2CCN(C(N)=O)CC2)C1]

The title compound was obtained as a by-product when following the procedure of Example 92 using (1R)-1-cyclopropylethanamine (0.05 mL, 0.5 mmol, Alfa Aesar). The cyclopropylethyl substituent was unstable to the TFA step of the deprotection. The byproduct was isolated in pure form via preparative HPLC-MS (C18 eluting with a gradient of MeCN/H$_2$O containing 0.15% NH$_4$OH) (7 mg, 40%). $^1$H NMR (400 MHz, CD$_3$OD) δ 8.71 (s, 1H), 8.66 (s, 1H), 8.39 (s, 1H), 7.50 (d, J=3.7 Hz, 1H), 6.98 (d, J=3.6 Hz, 1H), 3.52-3.42 (m, 4H), 3.33 (s, 2H), 3.11-2.96 (m, 2H), 2.91 (tt, J=7.0, 7.1 Hz, 1H), 2.56-2.44 (m, 2H), 2.44-2.33 (m, 4H); LCMS (M+H)$^+$: 406.1.

Example 96

4-{trans-3-(cyanomethyl)-3-[4-(7H-pyrrolo[2,3-d]pyrimidin-4-yl)-1H-pyrazol-1-yl]cyclobutyl}-N-[(1S)-1-cyclopropylethyl]piperazine-1-carboxamide

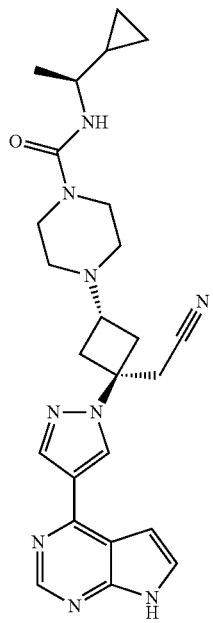 [SMILES: C[C@H](NC(=O)N1CCN([C@H]2C[C@](CC#N)(n3cc(-c4ncnc5[nH]ccc45)cn3)C2)CC1)C1CC1]

To a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.100 g, 0.203 mmol, from Step 1 of Example 1b) in DCM (1 mL) was added TFA (1 mL). After stirring for 1 hour, solvents were removed in vacuo. The residue was dissolved in MeOH (1.5 mL) and ethylenediamine (0.5 mL) was added and stirring continued until deprotection was determined to be complete by LCMS. Purification via preparative HPLC-MS (C18, eluting with a gradient of MeCN/H$_2$O containing 0.15% NH$_4$OH) afforded product as the free base (0.030 g, 41%; M+H=363.2). To a solution of {trans-3-piperazin-1-yl-1-[4-(7H-pyrrolo[2,3-d]pyrimidin-4-yl)-1H-pyrazol-1-yl]cyclobutyl}acetonitrile (0.015 g, 0.041 mmol) in acetonitrile (2 mL) and methylene chloride (2 mL), was added 1.89 M phosgene in toluene (0.022 mL, 0.041 mmol) followed by N,N-diisopropylethylamine (0.0072 mL, 0.041 mmol). After stirring for 15 minutes, (1S)-1-cyclopropylethanamine (0.023 mL, 0.24 mmol, Alfa Aesar) was added. The product was purified via preparative HPLC-MS (C18 eluting with a gradient of MeCN/H$_2$O containing 0.15% NH$_4$OH) to afford the free base (8 mg, 40%). $^1$H NMR (400 MHz, CD$_3$OD) δ 8.71 (s, 1H), 8.66 (s, 1H), 8.40 (s, 1H), 7.51 (d, J=3.6 Hz, 1H), 6.98 (d, J=3.7 Hz, 1H), 3.48-3.39 (m, 4H), 3.33 (s, 2H), 3.21-3.10 (m, 1H), 3.11-3.02 (m, 2H), 2.92 (tt, J=7.1, 7.4 Hz, 1H), 2.54-2.45 (m, 2H), 2.44-2.34 (m, 4H), 1.19 (d, J=6.7 Hz, 3H), 0.88 (tdd, J=8.3, 4.9, 3.4 Hz, 1H), 0.51-0.43 (m, 1H), 0.43-0.35 (m, 1H), 0.28 (ddd, J=9.8, 4.9 Hz, 1H), 0.15 (ddd, J=9.3, 4.8 Hz, 1H); LCMS (M+H)$^+$: 474.2.

Example 97

4-{trans-3-(cyanomethyl)-3-[4-(7H-pyrrolo[2,3-d]pyrimidin-4-yl)-1H-pyrazol-1-yl]cyclobutyl}-N-[(1R)-1-cyclopropylethyl]piperazine-1-carboxamide

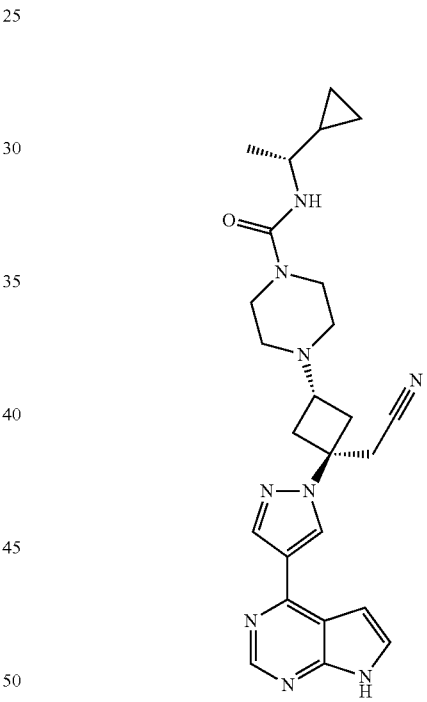

The procedure of Example 96 was followed, using {trans-3-piperazin-1-yl-1-[4-(7H-pyrrolo[2,3-d]pyrimidin-4-yl)-1H-pyrazol-1-yl]cyclobutyl}acetonitrile (0.010 g, 0.027 mmol, prepared as described in that Example) and (1R)-1-cyclopropylethanamine (0.010 mL, 0.11 mmol, Alfa Aesar). The product was obtained as the free base (5 mg, 40%). $^1$H NMR (300 MHz, CD$_3$OD) δ 8.71 (s, 1H), 8.66 (s, 1H), 8.40 (s, 1H), 7.51 (d, J=3.8 Hz, 1H), 6.98 (d, J=3.6 Hz, 1H), 3.48-3.39 (m, 4H), 3.33 (s, 2H), 3.21-3.01 (m, 3H), 2.99-2.81 (m, 1H), 2.59-2.45 (m, 2H), 2.45-2.32 (m, 4H), 1.19 (d, J=6.7 Hz, 3H), 1.03-0.65 (m, 1H), 0.59-0.33 (m, 2H), 0.34-0.22 (m, 1H), 0.22-0.09 (m, 1H); LCMS (M+H)$^+$: 474.2.

Example 98

4-{trans-3-(cyanomethyl)-3-[4-(7H-pyrrolo[2,3-d]pyrimidin-4-yl)-1H-pyrazol-1-yl]cyclobutyl}-N-cyclopropylpiperazine-1-carboxamide

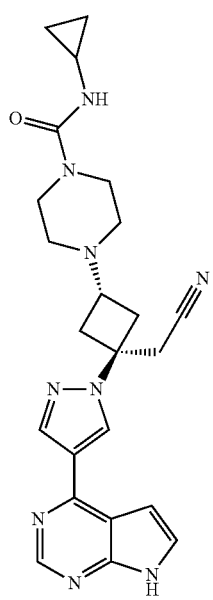 [SMILES: N#CC[C@]1(n2cc(-c3ncnc4[nH]ccc34)cn2)C[C@H](N2CCN(C(=O)NC3CC3)CC2)C1]

To a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Step 1 of Example 1b) in acetonitrile (1 mL) was added 1.89 M phosgene in toluene (0.032 mL, 0.061 mmol) followed by N,N-diisopropylethylamine (0.011 mL, 0.061 mmol). When formation of the carbamoyl chloride was complete, cyclopropylamine (0.010 g, 0.18 mmol, TCI) was added and the reaction was stirred until deemed complete by LCMS analysis. The solvent was then evaporated. The product was deprotected by stirring in 1:1 TFA:DCM for 1 hour, then ethylenediamine (0.2 mL) in methanol until the deprotection was complete. The product was purified via preparative HPLC-MS (C18 eluting with a gradient of MeCN/H$_2$O containing 0.15% NH$_4$OH) to afford the free base (5 mg, 20%). $^1$H NMR (300 MHz, CD$_3$OD) δ 8.70 (s, 1H), 8.66 (s, 1H), 8.39 (s, 1H), 7.50 (d, J=3.7 Hz, 1H), 6.98 (d, J=3.7 Hz, 1H), 3.46-3.38 (m, 4H), 3.33 (s, 2H), 3.13-3.00 (m, 2H), 2.90 (tt, J=7.0, 7.3 Hz, 1H), 2.59-2.43 (m, 3H), 2.43-2.31 (m, 4H), 0.69-0.60 (m, 2H), 0.48-0.39 (m, 2H); LCMS (M+H)$^+$: 446.1.

Example 99

4-{trans-3-(cyanomethyl)-3-[4-(7H-pyrrolo[2,3-d]pyrimidin-4-yl)-1H-pyrazol-1-yl]cyclobutyl}-N-cyclobutylpiperazine-1-carboxamide

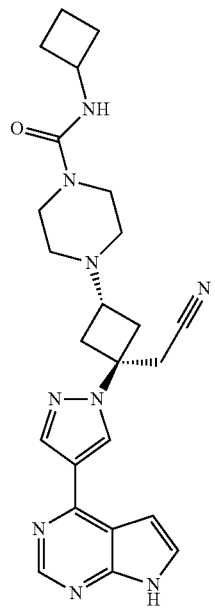 [SMILES: N#CC[C@]1(n2cc(-c3ncnc4[nH]ccc34)cn2)C[C@H](N2CCN(C(=O)NC3CCC3)CC2)C1]

The title compound was prepared according to the method of Example 98, using cyclobutanamine (0.013 g, 0.18 mmol, Aldrich) to afford the product as the free base (5 mg, 20%). $^1$H NMR (400 MHz, CD$_3$OD) δ 8.66 (s, 1H), 8.64 (s, 1H), 8.36 (s, 1H), 7.50 (d, J=3.7 Hz, 1H), 6.98 (d, J=3.6 Hz, 1H), 4.22-4.12 (m, 1H), 3.45-3.37 (m, 4H), 3.34 (s, 2H), 2.94 (tt, J=7.0, 7.2 Hz, 1H), 2.85-2.73 (m, 2H), 2.73-2.58 (m, 2H), 2.47-2.30 (m, 4H), 2.23 (dtt, J=8.7, 7.3, 2.8 Hz, 2H), 2.00-1.86 (m, 2H), 1.72-1.57 (m, 2H); LCMS (M+H)$^+$: 460.1.

Example 100

4-{trans-3-(cyanomethyl)-3-[4-(7H-pyrrolo[2,3-d]pyrimidin-4-yl)-1H-pyrazol-1-yl]cyclobutyl}-N-(2,2-dimethylpropyl)piperazine-1-carboxamide

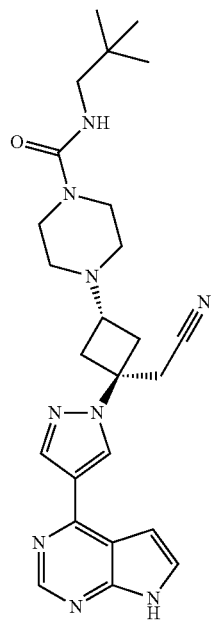 [SMILES: CC(C)(C)CNC(=O)N1CCN([C@H]2C[C@](CC#N)(n3cc(-c4ncnc5[nH]ccc45)cn3)C2)CC1]

To a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Step 1 of Example 1b) in acetonitrile (1 mL) was added 1.89 M phosgene in toluene (0.035 mL, 0.067 mmol) followed by N,N-diisopropylethylamine (0.011 mL, 0.061 mmol). When formation of carbamoyl chloride was complete, neopentylamine (0.016 g, 0.18 mmol, TCI) was added. When urea formation was complete, solvents were evaporated. The crude product was then stirred with 1:1 TFA in DCM for 1 hour, evaporated and stirred with ethylenediamine (0.2 mL) in methanol until the deprotection was complete. The product was purified via preparative HPLC-MS (C18 eluting with a gradient of MeCN/H$_2$O containing 0.15% NH$_4$OH) to afford the free base (6 mg, 20%). $^1$H NMR (400 MHz, CD$_3$OD) δ 8.71 (s, 1H), 8.66 (s, 1H), 8.39 (s, 1H), 7.50 (d, J=3.6 Hz, 1H), 6.98 (d, J=3.6 Hz, 1H), 6.40 (t, J=6.2 Hz, 1H), 3.49-3.41 (m, 4H), 3.33 (s, 2H), 3.11-3.02 (m, 2H), 2.99 (d, 2H), 2.91 (tt, J=7.2, 7.3 Hz, 1H), 2.55-2.44 (m, 2H), 2.44-2.30 (m, 4H), 0.86 (s, 9H); LCMS (M+H)$^+$: 476.3.

Example 101

4-{trans-3-(cyanomethyl)-3-[4-(7H-pyrrolo[2,3-d]pyrimidin-4-yl)-1H-pyrazol-1-yl]cyclobutyl}-N-isobutylpiperazine-1-carboxamide

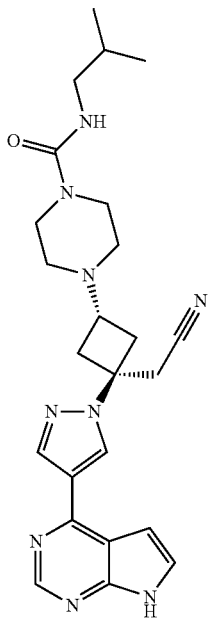

The title compound was prepared according to the procedure of Example 100, using {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.020 g, 0.040 mmol, from Step 1 of Example 1b), 1.89 M phosgene in toluene (0.030 mL, 0.057 mmol), N,N-diisopropylethylamine (0.0078 mL, 0.045 mmol) and 2-methyl-1-propanamine (9 mg, 0.12 mmol, Aldrich). Purification via preparative HPLC-MS (C18 eluting with a gradient of MeCN/H$_2$O containing 0.15% NH$_4$OH) afforded product as the free base (5 mg, 30%). $^1$H NMR (400 MHz, CD$_3$OD) δ 8.72 (s, 1H), 8.66 (s, 1H), 8.40 (s, 1H), 7.51 (d, J=3.6 Hz, 1H), 6.98 (d, J=3.6 Hz, 1H), 3.49-3.41 (m, 4H), 3.33 (s, 2H), 3.11-3.02 (m, 2H), 2.95 (d, J=7.1 Hz, 2H), 2.91 (tt, J=7.1, 7.4 Hz, 1H), 2.55-2.45 (m, 2H), 2.44-2.36 (m, 4H), 1.75 (hept, J=6.5 Hz, 1H), 0.88 (d, J=6.7 Hz, 6H); LCMS (M+H)$^+$: 462.1.

Example 102

4-{trans-3-(cyanomethyl)-3-[4-(7H-pyrrolo[2,3-d]pyrimidin-4-yl)-1H-pyrazol-1-yl]cyclobutyl}-N-[(1R)-1-methylpropyl]piperazine-1-carboxamide

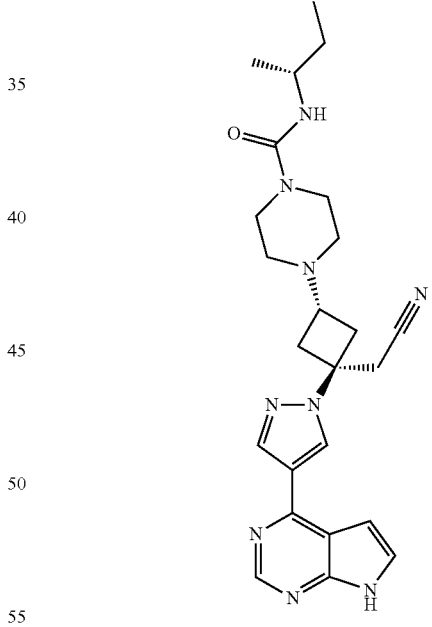

The title compound was prepared by the method of Example 101 using (2R)-butan-2-amine (9 mg, 0.12 mmol, Aldrich) to afford product as the free base (7 mg, 40%). $^1$H NMR (400 MHz, CD$_3$OD) δ 8.71 (s, 1H), 8.66 (s, 1H), 8.40 (s, 1H), 7.51 (d, J=3.6 Hz, 1H), 6.98 (d, J=3.6 Hz, 1H), 3.67 (h, J=6.6 Hz, 1H), 3.47-3.39 (m, 4H), 3.33 (s, 2H), 3.12-3.01 (m, 2H), 2.90 (tt, J=7.2, 7.2 Hz, 1H), 2.55-2.43 (m, 2H), 2.43-2.34 (m, 4H), 1.53-1.38 (m, 2H), 1.10 (d, J=6.6 Hz, 3H), 0.88 (t, J=7.4 Hz, 3H); LCMS (M+H)$^+$: 462.2.

Example 103

4-{trans-3-(cyanomethyl)-3-[4-(7H-pyrrolo[2,3-d]pyrimidin-4-yl)-1H-pyrazol-1-yl]cyclobutyl}-N-[(1S)-1-methylpropyl]piperazine-1-carboxamide

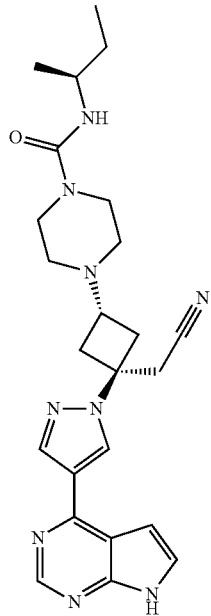 [SMILES: CC[C@H](C)NC(=O)N1CCN([C@H]2C[C@](CC#N)(n3cc(-c4ncnc5[nH]ccc45)cn3)C2)CC1]

The title compound was prepared by the method of Example 101 using (2S)-butan-2-amine (9 mg, 0.12 mmol, Aldrich) to afford product as the free base (7 mg, 40%). $^1$H NMR (400 MHz, CD$_3$OD) δ 8.71 (s, 1H), 8.66 (s, 1H), 8.40 (s, 1H), 7.51 (d, J=3.6 Hz, 1H), 6.98 (d, J=3.6 Hz, 1H), 3.68 (hept, J=6.6, 6.2 Hz, 1H), 3.50-3.40 (m, 4H), 3.33 (s, 2H), 3.13-3.00 (m, 2H), 2.90 (tt, J=7.1, 7.2 Hz, 1H), 2.55-2.44 (m, 2H), 2.42-2.35 (m, 4H), 1.54-1.36 (m, 2H), 1.10 (d, J=6.6 Hz, 3H), 0.88 (t, J=7.4 Hz, 3H); LCMS (M+H)$^+$: 462.2.

Example 104

4-{cis-3-(cyanomethyl)-3-[4-(7H-pyrrolo[2,3-d]pyrimidin-4-yl)-1H-pyrazol-1-yl]cyclobutyl}-N-cyclobutylpiperazine-1-carboxamide

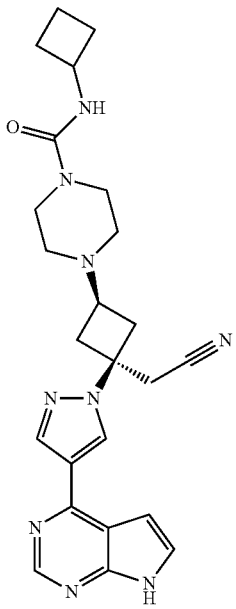 [SMILES: N#CC[C@]1(n2cc(-c3ncnc4[nH]ccc34)cn2)C[C@@H](N2CCN(C(=O)NC3CCC3)CC2)C1]

To a solution of {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.040 g, 0.081 mmol, from Step 9 of Example 1a) in methylene chloride (2.0 mL) was added 1.89 M phosgene in toluene (0.0472 mL, 0.0893 mmol). After 15 minutes, cyclobutanamine (0.029 g, 0.40 mmol, Aldrich) was added. When reaction was deemed complete by LCMS, TFA was added (1 mL) and stirred for 1 hour. Solvents were then evaporated and the residue was dissolved in MeOH and ethylenediamine (0.2 mL) was added. When deprotection was complete, the reaction was purified via preparative HPLC-MS (C18 eluting with a gradient of MeCN/H$_2$O containing 0.15% NH$_4$OH. Eluent containing product was frozen and lyophilized to afford product as the free base (0.01 g, 30%). $^1$H NMR (400 MHz, CD$_3$OD) δ 8.65 (s, 1H), 8.63 (s, 1H), 8.36 (s, 1H), 7.50 (d, J=3.7 Hz, 1H), 6.97 (d, J=3.6 Hz, 1H), 4.23-4.08 (m, 1H), 3.45-3.36 (m, 4H), 3.33 (s, 2H), 2.94 (tt, J=7.7, 7.8 Hz, 1H), 2.83-2.74 (m, 2H), 2.73-2.56 (m, 2H), 2.44-2.30 (m, 4H), 2.28-2.13 (m, 2H), 2.00-1.85 (m, 2H), 1.72-1.55 (m, 2H).

LCMS (M+H)$^+$: 460.3.

Example 105

4-{cis-3-(cyanomethyl)-3-[4-(7H-pyrrolo[2,3-d]pyrimidin-4-yl)-1H-pyrazol-1-yl]cyclobutyl}-N-[(1R)-1-methylpropyl]piperazine-1-carboxamide

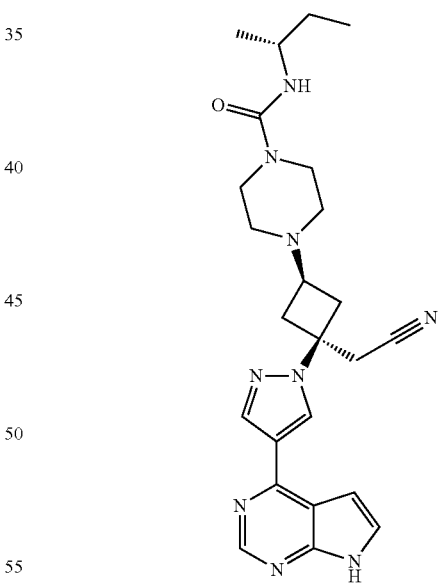

The procedure of Example 104 was followed, using (2R)-butan-2-amine (30. mg, 0.40 mmol, Aldrich) to afford product as the free base (0.01 g, 30%). $^1$H NMR (400 MHz, CD$_3$OD) δ 8.66 (s, 1H), 8.64 (s, 1H), 8.37 (s, 1H), 7.50 (d, J=3.6 Hz, 1H), 6.98 (d, J=3.7 Hz, 1H), 3.67 (h, J=6.7 Hz, 1H), 3.46-3.37 (m, 4H), 3.34 (s, 2H), 2.95 (tt, J=7.6, 7.7 Hz, 1H), 2.80 (ddd, J=9.9, 6.9, 2.9 Hz, 2H), 2.69 (ddd, J=10.7, 8.0, 2.3 Hz, 2H), 2.48-2.33 (m, 4H), 1.56-1.34 (m, 2H), 1.10 (d, J=6.6 Hz, 3H), 0.89 (t, J=7.4 Hz, 3H); LCMS (M+H)$^+$: 462.3.

Example 106

4-{cis-3-(cyanomethyl)-3-[4-(7H-pyrrolo[2,3-d]pyrimidin-4-yl)-1H-pyrazol-1-yl]cyclobutyl}-N-[(1S)-1-methylpropyl]piperazine-1-carboxamide

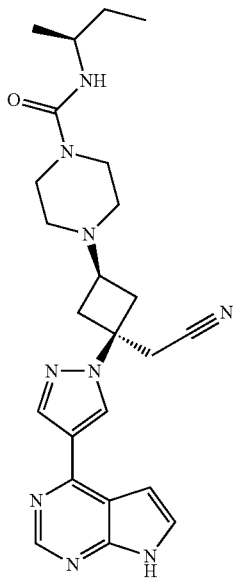 [SMILES: CC[C@H](C)NC(=O)N1CCN([C@H]2C[C@@](CC#N)(n3cc(-c4ncnc5[nH]ccc45)cn3)C2)CC1]

The procedure of Example 104 was followed, using (2S)-butan-2-amine (30. mg, 0.40 mmol, Aldrich) to afford product as the free base (0.01 g, 30%). $^1$H NMR (400 MHz, CD$_3$OD) δ 8.66 (s, 1H), 8.64 (s, 1H), 8.37 (s, 1H), 7.50 (d, J=3.6 Hz, 1H), 6.98 (d, J=3.6 Hz, 1H), 3.67 (h, J=6.7 Hz, 1H), 3.47-3.37 (m, 4H), 3.34 (s, 2H), 2.95 (tt, J=7.5, 7.6 Hz, 1H), 2.80 (ddd, J=9.8, 7.1, 2.6 Hz, 2H), 2.74-2.62 (m, 2H), 2.45-2.30 (m, 4H), 1.54-1.36 (m, 2H), 1.10 (d, J=6.6 Hz, 3H), 0.89 (t, J=7.4 Hz, 3H); LCMS (M+H)$^+$: 462.2.

Example 107

4-{cis-3-(cyanomethyl)-3-[4-(7H-pyrrolo[2,3-d]pyrimidin-4-yl)-1H-pyrazol-1-yl]cyclobutyl}-N-cyclopropylpiperazine-1-carboxamide

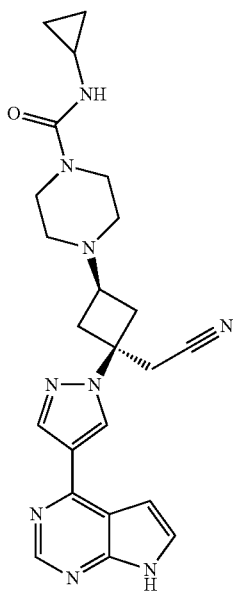 [SMILES: N#CC[C@]1(n2cc(-c3ncnc4[nH]ccc34)cn2)C[C@@H](N2CCN(C(=O)NC3CC3)CC2)C1]

The procedure of Example 104 was followed, using cyclopropylamine (23 mg, 0.40 mmol, TCI) to afford product as the free base (0.005 g, 14%). $^1$H NMR (400 MHz, CD$_3$OD) δ 8.65 (s, 1H), 8.63 (s, 1H), 8.36 (s, 1H), 7.49 (d, J=3.6 Hz, 1H), 6.96 (d, J=3.7 Hz, 1H), 3.43-3.35 (m, 4H), 3.33 (s, 2H), 2.93 (tt, J=7.6, 7.7 Hz, 1H), 2.79 (ddd, J=9.7, 7.0, 2.5 Hz, 2H), 2.72-2.62 (m, 2H), 2.52 (tt, J=7.1, 3.7 Hz, 1H), 2.42-2.34 (m, 4H), 0.64 (td, J=6.9, 4.9 Hz, 2H), 0.46-0.40 (m, 2H); LCMS (M+H)$^+$: 446.1.

Example 108

4-{cis-3-(cyanomethyl)-3-[4-(7H-pyrrolo[2,3-d]pyrimidin-4-yl)-1H-pyrazol-1-yl]cyclobutyl}-N-isopropylpiperazine-1-carboxamide

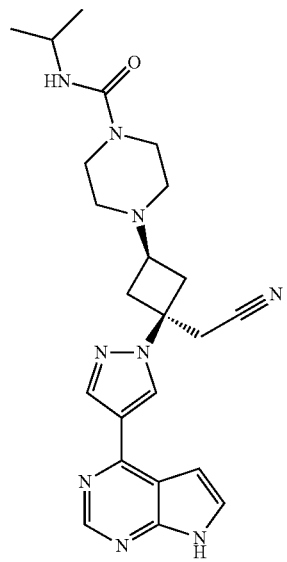 [SMILES: CC(C)NC(=O)N1CCN([C@H]2C[C@@](CC#N)(n3cc(-c4ncnc5[nH]ccc45)cn3)C2)CC1]

To a solution of {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.040 g, 0.081 mmol, from Step 9 of Example 1a) in methylene chloride (1 mL) was added 2-isocyanatopropane (16 μL, 0.16 mmol, Aldrich) and the reaction was stirred for 2 hours. Methanol was added and then solvents were removed in vacuo. The crude product was deprotected by stirring in 1:1 TFA:DCM for 1 hour, followed by evaporation and stirring with ethylenediamine (0.2 mL) in methanol until the deprotection was complete. The product was purified via preparative HPLC-MS (C18 eluting with a gradient of MeCN/H$_2$O containing 0.15% NH$_4$OH). Eluent containing the product was frozen and lyophilized to afford the free base (0.009 g, 20%). $^1$H NMR (400 MHz, CD$_3$OD) δ 8.65 (s, 1H), 8.64 (s, 1H), 8.36 (s, 1H), 7.50 (d, J=3.6 Hz, 1H), 6.97 (d, J=3.6 Hz, 1H), 3.87 (hept, J=6.7 Hz, 1H), 3.45-3.36 (m, 4H), 3.33 (s, 2H), 2.94 (tt, J=7.6, 7.7 Hz, 1H), 2.80 (ddd, J=9.6, 7.0, 2.4 Hz, 2H), 2.73-2.59 (m, 2H), 2.44-2.36 (m, 4H), 1.12 (d, J=6.6 Hz, 6H); LCMS (M+H)$^+$: 448.2.

Example 109

4-{cis-3-(cyanomethyl)-3-[4-(7H-pyrrolo[2,3-d]pyrimidin-4-yl)-1H-pyrazol-1-yl]cyclobutyl}-N-cyclopentylpiperazine-1-carboxamide

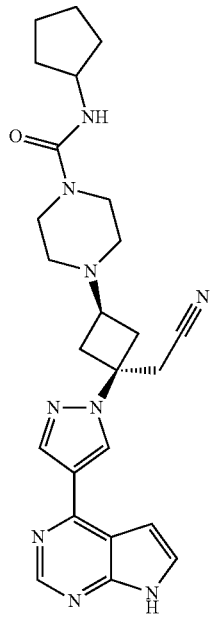 [SMILES: N#CC[C@]1(n2cc(-c3ncnc4[nH]ccc34)cn2)C[C@@H](N2CCN(C(=O)NC3CCCC3)CC2)C1]

The procedure of Example 108 was followed, using isocyanatocyclopentane (18 μL, 0.16 mmol, Aldrich) to afford product as the free base (7 mg, 18%). $^1$H NMR (400 MHz, CD$_3$OD) δ 8.66 (s, 1H), 8.64 (s, 1H), 8.36 (s, 1H), 7.50 (d, J=3.6 Hz, 1H), 6.97 (d, J=3.6 Hz, 1H), 3.99 (p, J=7.3 Hz, 1H), 3.45-3.38 (m, 4H), 3.33 (s, 2H), 2.94 (tt, J=7.6, 7.7 Hz, 1H), 2.80 (ddd, J=9.6, 7.0, 2.6 Hz, 2H), 2.72-2.62 (m, 2H), 2.54-2.20 (m, 4H), 1.97-1.84 (m, 2H), 1.76-1.62 (m, 2H), 1.62-1.48 (m, 2H), 1.48-1.36 (m, 2H); LCMS (M+H)$^+$: 474.2.

Example 110

4-{cis-3-(cyanomethyl)-3-[4-(7H-pyrrolo[2,3-d]pyrimidin-4-yl)-1H-pyrazol-1-yl]cyclobutyl}-N-[(1R)-1,2-dimethylpropyl]piperazine-1-carboxamide

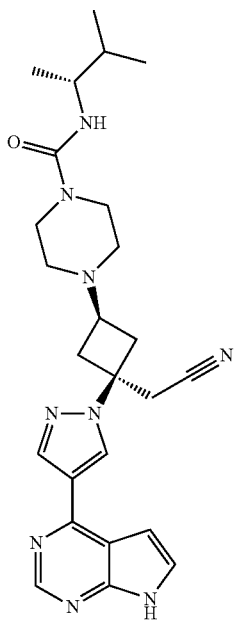 [SMILES: CC(C)[C@@H](C)NC(=O)N1CCN([C@H]2C[C@@](CC#N)(n3cc(-c4ncnc5[nH]ccc45)cn3)C2)CC1]

The procedure of Example 104 was followed, using (2R)-3-methylbutan-2-amine (0.045 mL, 0.40 mmol, Aldrich) to afford product as the free base (5 mg, 10%). $^1$H NMR (400 MHz, CD$_3$OD) δ 8.66 (s, 1H), 8.65 (s, 1H), 8.37 (s, 1H), 7.51 (d, J=3.6 Hz, 1H), 6.99 (d, J=3.6 Hz, 1H), 6.11 (d, J=8.5 Hz, 1H), 3.64-3.53 (m, 1H), 3.47-3.38 (m, 4H), 3.34 (s, 2H), 2.96 (tt, J=7.5, 7.5 Hz, 1H), 2.81 (ddd, J=9.9, 7.0, 2.8 Hz, 2H), 2.75-2.63 (m, 2H), 2.46-2.36 (m, 4H), 1.67 (h, J=6.8 Hz, 1H), 1.08 (d, J=6.8 Hz, 3H), 0.89 (d, J=6.8 Hz, 3H), 0.89 (d, J=6.8 Hz, 3H); LCMS (M+H)$^+$: 476.2.

Example 111

4-{cis-3-(cyanomethyl)-3-[4-(7H-pyrrolo[2,3-d]pyrimidin-4-yl)-1H-pyrazol-1-yl]cyclobutyl}-N-[(1S)-1,2-dimethylpropyl]piperazine-1-carboxamide

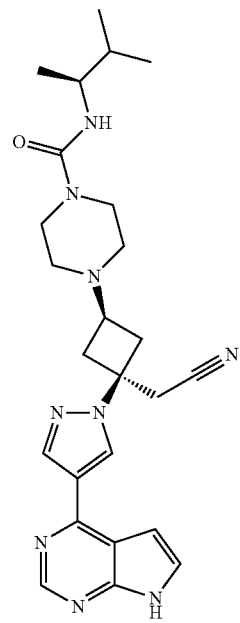 [SMILES: CC(C)[C@H](C)NC(=O)N1CCN([C@H]2C[C@@](CC#N)(n3cc(-c4ncnc5[nH]ccc45)cn3)C2)CC1]

The procedure of Example 104 was followed, using (2S)-3-methylbutan-2-amine (0.035 g, 0.40 mmol, Alfa Aesar) to afford product as the free base (5 mg, 10%). $^1$H NMR (400 MHz, CD$_3$OD) δ 8.66 (s, 1H), 8.65 (s, 1H), 8.37 (s, 1H), 7.51 (d, J=3.6 Hz, 1H), 6.99 (d, J=3.7 Hz, 1H), 6.11 (d, J=8.4 Hz, 1H), 3.64-3.52 (m, 1H), 3.46-3.39 (m, 4H), 3.34 (s, 2H), 2.96 (tt, J=7.2, 7.2 Hz, 1H), 2.86-2.73 (m, 2H), 2.74-2.63 (m, 2H), 2.46-2.35 (m, 4H), 1.66 (dq, J=13.6, 6.8 Hz, 1H), 1.08 (d, J=6.8 Hz, 3H), 0.89 (d, J=6.7 Hz, 3H), 0.89 (d, J=6.8 Hz, 3H); LCMS (M+H)$^+$: 476.2.

Example 112

4-{trans-3-(cyanomethyl)-3-[4-(7H-pyrrolo[2,3-d]pyrimidin-4-yl)-1H-pyrazol-1-yl]cyclobutyl}-N-methylpiperazine-1-carboxamide

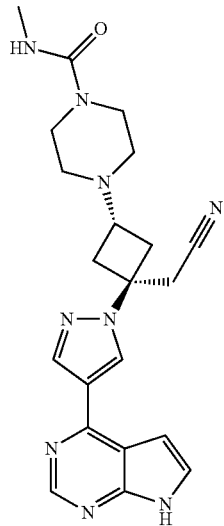 [SMILES: CNC(=O)N1CCN([C@H]2C[C@](CC#N)(n3cc(-c4ncnc5[nH]ccc45)cn3)C2)CC1]

The procedure of Example 108 was followed, using {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Step 1 of Example 1b) and Methyl Isocyanate (3.98 µL, 0.0670 mmol, Supelco) to yield product as the free base (0.02 g, 80%). $^1$H NMR (300 MHz, CD$_3$OD) δ 8.71 (s, 1H), 8.66 (s, 1H), 8.39 (s, 1H), 7.51 (d, J=3.6 Hz, 1H), 6.98 (d, J=3.6 Hz, 1H), 3.48-3.38 (m, 4H), 3.33 (s, 2H), 3.14-3.00 (m, 2H), 2.90 (tt, J=6.3, 6.7 Hz, 1H), 2.70 (s, 3H), 2.58-2.43 (m, 2H), 2.43-2.33 (m, 4H); LCMS (M+H)$^+$: 420.1.

Example 113

4-{trans-3-(cyanomethyl)-3-[4-(7H-pyrrolo[2,3-d]pyrimidin-4-yl)-1H-pyrazol-1-yl]cyclobutyl}-N-[(1R)-2,2,2-trifluoro-1-methylethyl]piperazine-1-carboxamide

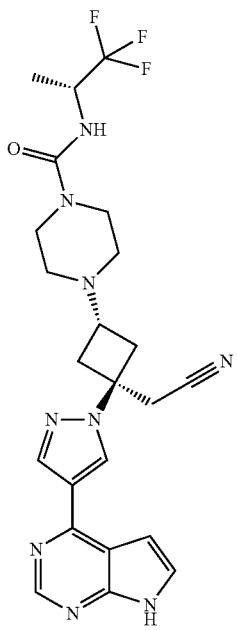 [SMILES: C[C@@H](NC(=O)N1CCN([C@H]2C[C@](CC#N)(n3cc(-c4ncnc5[nH]ccc45)cn3)C2)CC1)C(F)(F)F]

To a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.040 g, 0.081 mmol, from Step 1 of Example 1b) in methylene chloride (1.0 mL) was added 1.89 M phosgene in toluene (0.0472 mL, 0.0893 mmol) and this was stirred for 15 minutes. During this time a mixture of (2R)-1,1,1-trifluoropropan-2-amine hydrochloride (0.024 g, 0.16 mmol, Synquest) and N,N-diisopropylethylamine (0.028 mL, 0.16 mmol) in methylene chloride (1.0 mL) was prepared, which was then added to the mixture of starting material and phosgene. The reaction vial was sealed and heated at a temperature of 50° C. for an hour, then stood at room temperature overnight. Methanol was added and then the solvents were evaporated to dryness with a stream of nitrogen. The residue was reconstituted in MeCN and 1N NaOH, filtered and purified via preparative HPLC-MS (C18 eluting with a gradient of MeCN/H$_2$O containing 0.15% NH$_4$OH). Eluent containing the product was evaporated. The product was deprotected by stirring with 4 mL of TFA:DCM (1:1) for 2 hours. Solvents were evaporated and the residue was dissolved in methanol. Ethylenediamine (0.2 mL) was added. After 1 hour, the product was purified via preparative HPLC-MS (C18 eluting with a gradient of MeCN/H$_2$O containing 0.15% NH$_4$OH) to afford product as the free base (1.2 mg, 3%). LCMS (M+H)$^+$: 502.1.

Example 114

4-{trans-3-(cyanomethyl)-3-[4-(7H-pyrrolo[2,3-d]pyrimidin-4-yl)-1H-pyrazol-1-yl]cyclobutyl}-N-[(1S)-2,2,2-trifluoro-1-methylethyl]piperazine-1-carboxamide

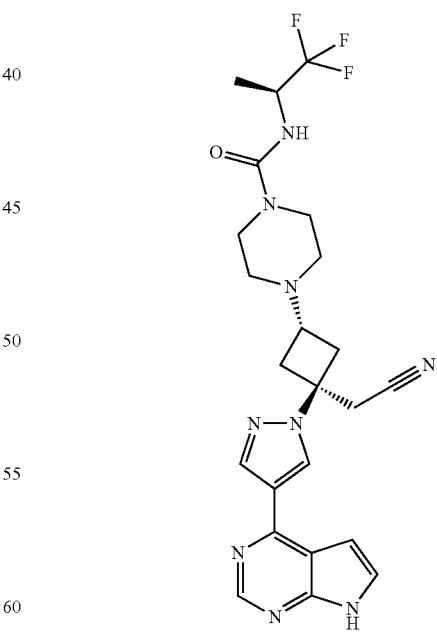

The title compound was prepared by the method of Example 113, using (2S)-1,1,1-trifluoropropan-2-amine hydrochloride (0.024 g, 0.16 mmol, Synquest) to afford product as the free base (1.9 mg, 5%). LCMS (M+H)$^+$: 502.0.

Example 115

4-{trans-3-(cyanomethyl)-3-[4-(7H-pyrrolo[2,3-d]pyrimidin-4-yl)-1H-pyrazol-1-yl]cyclobutyl}-N-[(1S)-1-(trifluoromethyl)propyl]piperazine-1-carboxamide

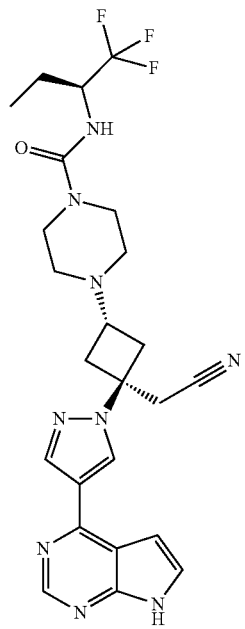 [SMILES: CC[C@H](NC(=O)N1CCN([C@H]2C[C@](CC#N)(n3cc(-c4ncnc5[nH]ccc45)cn3)C2)CC1)C(F)(F)F]

To a solution of (2S)-1,1,1-trifluorobutan-2-amine (0.050 g, 0.39 mmol, Oakwood) in methylene chloride (1 mL) was added pyridine (32 µL, 0.39 mmol) and p-nitrophenyl chloroformate (0.087 g, 0.43 mmol). After stirring overnight, the reaction mixture was partitioned between water and ethyl acetate, and the aqueous portion was extracted with a further two portions of ethyl acetate. The combined extracts were dried over sodium sulfate, decanted and concentrated. The crude product was dissolved in 1,4-dioxane (1 mL) and {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.060 g, 0.12 mmol, from Step 1 of Example 1b) and N,N-diisopropylethylamine (42 µL, 0.24 mmol) were then added. The mixture was heated to 60° C. for 1 hour, then cooled to room temperature. The dioxane was removed in vacuo. The residue was stirred with 1:1 TFA:DCM for 1 hour, then with 0.2 mL ethylenediamine in methanol until the deprotection was complete. The product was purified via preparative HPLC-MS (C18 eluting with a gradient of MeCN/H$_2$O containing 0.15% NH$_4$OH). The eluent was frozen and lyophilized to afford product as the free base (0.01 g, 16%). $^1$H NMR (400 MHz, dmso) δ 12.11 (br s, 1H), 8.82 (s, 1H), 8.69 (s, 1H), 8.42 (s, 1H), 7.60 (d, J=3.6 Hz, 1H), 7.07 (d, J=3.6 Hz, 1H), 6.75 (d, J=8.7 Hz, 1H), 4.42-4.09 (m, 1H), 3.42 (s, 2H), 3.41-3.35 (m, 4H), 3.06-2.93 (m, 2H), 2.78 (tt, J=7.2, 7.3 Hz, 1H), 2.42-2.31 (m, 2H), 2.31-2.20 (m, 4H), 1.76-1.48 (m, 2H), 0.87 (t, J=7.3 Hz, 3H); $^{19}$F NMR (376 MHz, dmso) δ −75.22 (d, J=8.3 Hz); LCMS (M+H)$^+$: 516.3.

Example 116

[trans-1-[4-(7H-pyrrolo[2,3-d]pyrimidin-4-yl)-1H-pyrazol-1-yl]-3-(4-{[(2R)-2-(trifluoromethyl)pyrrolidin-1-yl]carbonyl}piperazin-1-yl)cyclobutyl]acetonitrile

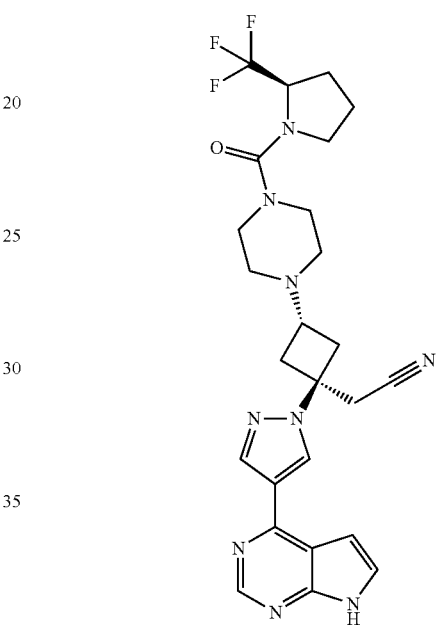

A solution of (2R)-2-(trifluoromethyl)pyrrolidine (0.013 g, 0.091 mmol, Aldrich) and N,N-carbonyldiimidazole (0.015 g, 0.091 mmol) in methylene chloride (0.4 mL) and tetrahydrofuran (0.1 mL) was stirred overnight. A solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.030 g, 0.061 mmol, from Step 1 of Example 1b) in Tetrahydrofuran (0.2 mL) was then added. Stirring was continued for 96 hours at room temperature. The reaction was then heated to 70° C. in a sealed vial overnight, then to 90° C. for 3 hours. After cooling, solvent was removed in vacuo and the residue was deprotected by stirring with 1:1 TFA:DCM for 1 hour, followed by evaporation and stirring with 0.2 mL ethylenediamine in methanol until the deprotection was complete. The product was purified via preparative HPLC-MS (C18 eluting with a gradient of MeCN/H$_2$O containing 0.15% NH$_4$OH). The eluent was frozen and lyophilized to afford product as the free base (2 mg, 6%). $^1$H NMR (500 MHz, CDCl$_3$) δ 9.12 (s, 1H), 8.84 (s, 1H), 8.47 (s, 1H), 8.33 (s, 1H), 7.39-7.33 (m, 1H), 6.85-6.74 (m, 1H), 5.07-4.67 (m, 1H), 3.65-1.74 (m, 21H); LCMS (M+H)$^+$: 528.4.

Example 117

[trans-1-[4-(7H-pyrrolo[2,3-d]pyrimidin-4-yl)-1H-pyrazol-1-yl]-3-(4-{[(2S)-2-(trifluoromethyl)pyrrolidin-1-yl]carbonyl}piperazin-1-yl)cyclobutyl]acetonitrile

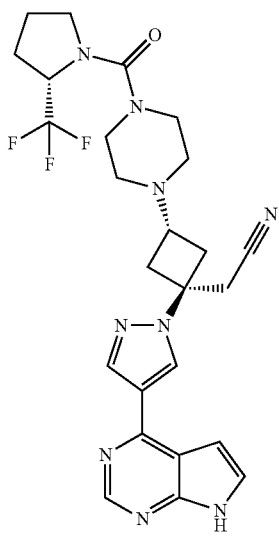 [SMILES: N#CC[C@]1(n2cc(-c3ncnc4[nH]ccc34)cn2)C[C@H](N2CCN(C(=O)N3CCC[C@H]3C(F)(F)F)CC2)C1]

The title compound was prepared as described for Example 116, using (2S)-2-(trifluoromethyl)pyrrolidine (0.013 g, 0.091 mmol, Aldrich) to afford product as free base (3 mg, 9%). $^1$H NMR (500 MHz, CDCl$_3$) δ 9.38 (s, 1H), 8.84 (s, 1H), 8.47 (s, 1H), 8.33 (s, 1H), 7.38 (dd, J=3.7, 2.2 Hz, 1H), 6.81 (dd, J=3.6, 1.8 Hz, 1H), 4.99-4.90 (m, 1H), 3.64-3.45 (m, 2H), 3.43-3.30 (m, 4H), 3.23 (s, 2H), 3.12-2.83 (m, 3H), 2.61-2.23 (m, 6H), 2.24-2.07 (m, 1H), 2.06-1.88 (m, 2H), 1.88-1.74 (m, 1H); LCMS (M+H)$^+$: 528.4.

Example 118

N'-cyano-4-{trans-3-(cyanomethyl)-3-[4-(7H-pyrrolo[2,3-d]pyrimidin-4-yl)-1H-pyrazol-1-yl]cyclobutyl}-N,N-dimethylpiperazine-1-carboximidamide

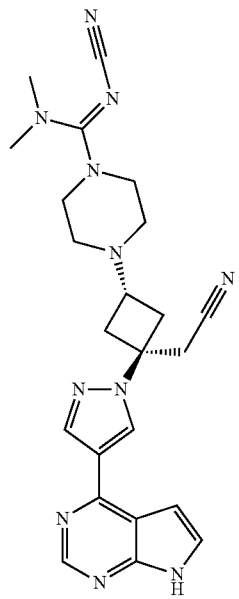 [SMILES: CN(C)/C(=N\C#N)N1CCN([C@H]2C[C@](CC#N)(n3cc(-c4ncnc5[nH]ccc45)cn3)C2)CC1]

To {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.025 g, 0.051 mmol, from Step 1 of Example 1b) in tetrahydrofuran (0.5 mL) was added diphenyl cyanocarbonimidate (0.0121 g, 0.0507 mmol, Aldrich). After stirring overnight, 2.0 M dimethylamine in THF (0.5 mL, 1 mmol, Aldrich) was added and the reaction was stirred for 2 hours. Solvent was removed in vacuo. The crude product was stirred with 1:1 TFA:DCM for 1 hour, solvent was again evaporated, and the residue was stirred with NH$_4$OH in methanol overnight. The product was purified via preparative HPLC-MS (C18 eluting with a gradient of MeCN/H$_2$O containing 0.15% NH$_4$OH) and was afforded as the free base (2 mg, 9%). $^1$H NMR (400 MHz, CD$_3$OD) δ 8.71 (s, 1H), 8.66 (s, 1H), 8.40 (s, 1H), 7.51 (d, J=3.7 Hz, 1H), 6.98 (d, J=3.6 Hz, 1H), 3.53-3.42 (m, 4H), 3.35 (s, 2H), 3.11-3.02 (m, 2H), 2.99 (s, 6H), 2.99-2.91 (m, 1H), 2.57-2.44 (m, 6H); LCMS (M+H)$^+$: 458.1.

Example 119

{trans-3-[4-(methylsulfonyl)piperazin-1-yl]-1-[4-(7H-pyrrolo[2,3-d]pyrimidin-4-yl)-1H-pyrazol-1-yl]cyclobutyl}acetonitrile

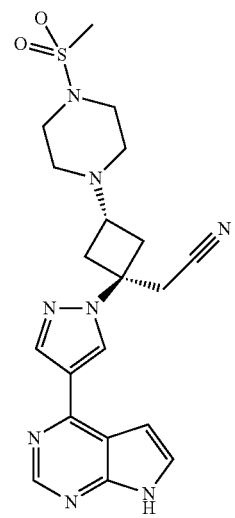

The title compound was obtained as a byproduct during Step E of Example 47, due to impurity resulting from incomplete amide formation in the previous step (Step D). The byproduct was isolated using preparative HPLC-MS (C18 eluting with a gradient of MeCN/H$_2$O containing 0.15% NH$_4$OH) in the amount of 3 mg. $^1$H NMR (400 MHz, CD$_3$OD) δ 8.71 (s, 1H), 8.66 (s, 1H), 8.40 (s, 1H), 7.51 (d, J=3.6 Hz, 1H), 6.98 (d, J=3.6 Hz, 1H), 3.33 (s, 2H), 3.28-3.23 (m, 4H), 3.11-3.02 (m, 2H), 2.96 (tt, J=7.1, 7.1 Hz, 1H), 2.85 (s, 3H), 2.58-2.44 (m, 6H); LCMS (M+H)$^+$: 441.0.

Example 120 isopropyl 4-{trans-3-(cyanomethyl)-3-[4-(7H-pyrrolo[2,3-d]pyrimidin-4-yl)-1H-pyrazol-1-yl]cyclobutyl}piperazine-1-carboxylate

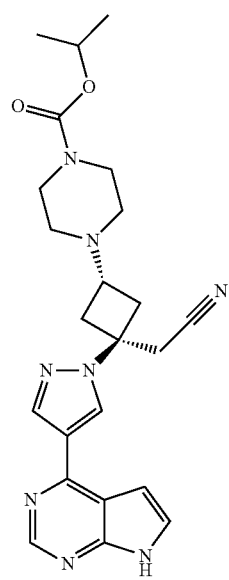 [SMILES: CC(C)OC(=O)N1CCN([C@H]2C[C@](CC#N)(n3cc(-c4ncnc5[nH]ccc45)cn3)C2)CC1]

To a solution of {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.040 g, 0.081 mmol, from Step 1 of Example 1b) in methylene chloride (1 mL) was added triethylamine (0.023 mL, 0.16 mmol) followed by 1.0 M isopropyl chloroformate in toluene (0.097 mL, 0.097 mmol, Aldrich). The reaction was stirred for 2 hours. Methanol was added to the reaction, then solvent was removed in vacuo. The crude product was stirred with 1:1 TFA:DCM for 1 hour, then with excess ethylenediamine in methanol until the deprotection was complete. The product was purified via preparative HPLC-MS (C18 eluting with a gradient of MeCN/H$_2$O containing 0.15% NH$_4$OH) to yield 0.01 g (30%). $^1$H NMR (400 MHz, dmso) δ 12.13 (s, 1H), 8.82 (s, 1H), 8.69 (s, 1H), 8.41 (s, 1H), 7.60 (dd, J=3.6, 2.3 Hz, 1H), 7.07 (dd, J=3.6, 1.6 Hz, 1H), 4.76 (hept, 1H), 3.42 (s, 2H), 3.38-3.32 (m, 4H), 3.06-2.94 (m, 2H), 2.83-2.71 (m, 1H), 2.40-2.30 (m, 2H), 2.30-2.17 (m, 4H), 1.17 (d, J=6.2 Hz, 6H); LCMS (M+H)$^+$: 449.2.

Example 121

{cis-3-(4-{[4-(methoxymethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile (Single Isomer Isolated)

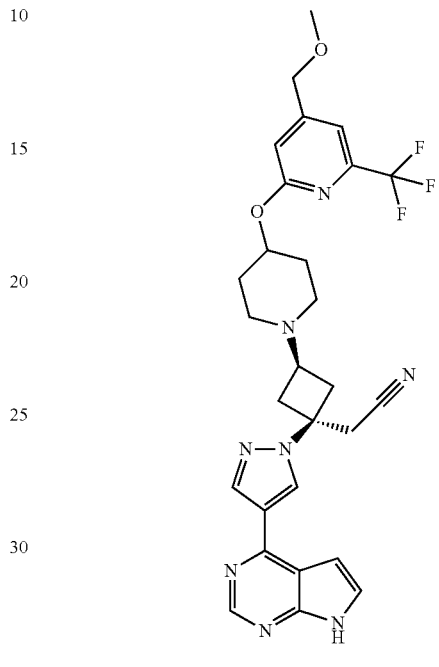

Step A. [2-Chloro-6-(trifluoromethyl)pyridin-4-yl]methanol

Sodium tetrahydroborate (74 mg, 2.0 mmol) was added to a solution of ethyl 2-chloro-6-(trifluoromethyl)isonicotinate (0.50 g, 2.0 mmol, Anichem) in ethanol (17 mL) at 0° C. The mixture was stirred at 0° C. for one hour, then was allowed to warm to room temperature and stir for 2 hours. The mixture was recooled in an ice bath and was quenched by the dropwise addition of 4.0 mL 1N HCl. The pH was then adjusted to 7 by the addition of saturated sodium bicarbonate solution. The reaction was further diluted with water, and then was extracted with EtOAc. The extract was washed with brine, dried over sodium sulfate, filtered and concentrated. Flash chromatography on silica gel, eluting with a gradient from 0-40% EtOAc in Hexanes afforded product as an oil (0.33 g, 79%). $^1$H NMR (300 MHz, CDCl$_3$) δ 7.61 (s, 1H), 7.56 (s, 1H), 4.84 (d, J=5.2 Hz, 2H), 2.20 (t, J=5.6 Hz, 1H); LCMS (M+H)$^+$: 212.1.

Step B. 2-Chloro-4-(methoxymethyl)-6-(trifluoromethyl)pyridine

To a solution of [2-chloro-6-(trifluoromethyl)pyridin-4-yl]methanol (130 mg, 0.614 mmol, from Step A) and methyl iodide (42 µL, 0.68 mmol) in N,N-dimethylformamide (0.65 mL, 8.4 mmol) was added potassium carbonate (250 mg, 1.8 mmol). The mixture was sealed and stirred at room temperature for 24 hours. Additional methyl iodide (42 µL, 0.68 mmol) was added. The mixture was stirred again for 24 hours, then was diluted with water and extracted with EtOAc. The extract was washed with water (3x), followed by brine, dried over sodium sulfate, filtered and concentrated. Flash chromatography on silica gel, eluting with a gradient from 0-20% EtOAc in Hexanes, afforded product as a colorless oil (56 mg, 40%). $^1$H NMR (300 MHz, CDCl$_3$) δ 7.56 (s, 1H), 7.50 (s, 1H), 4.53 (s, 2H), 3.48 (s, 3H); $^{19}$F NMR (282 MHz, CDCl$_3$) δ −68.45 (s); LCMS (M+H)$^+$: 226.1.

Step C. tert-Butyl 4-{[4-(methoxymethyl)-6-(trifluoromethyl)pyridin-2-yl]oxy}piperidine-1-carboxylate To sodium hydride (18 mg, 0.45 mmol, 60% in mineral oil) in tetrahydrofuran (0.50 mL) was added tert-butyl 4-hydroxypiperidine-1-carboxylate (91 mg, 0.45 mmol, Aldrich). The mixture was stirred for 45 minutes, followed by the addition of 2-chloro-4-(methoxymethyl)-6-(trifluoromethyl)pyridine (51 mg, 0.23 mmol, from Step B) in tetrahydrofuran (0.30 mL). The vial was sealed and stirred at room temperature overnight. The mixture was quenched and diluted with water and extracted with EtOAc. The extract was washed with water, brine, dried over sodium sulfate, filtered and concentrated. Flash chromatography on silica gel, eluting with a gradient from 0-10% EtOAc in hexanes afforded product as an oil (42 mg, 48%). $^1$H NMR (300 MHz, CDCl$_3$) δ 7.19 (s, 1H), 6.85 (s, 1H), 5.26 (tt, J=7.7, 4.0 Hz, 1H), 4.46 (s, 2H), 3.73 (dq, J=11.1, 3.9 Hz, 2H), 3.44 (s, 3H), 3.32 (ddd, J=13.6, 8.3, 3.7 Hz, 2H), 1.98 (ddq, J=10.3, 6.9, 3.5 Hz, 2H), 1.73 (ddt, J=16.0, 7.5, 3.6 Hz, 2H), 1.47 (s, 9H); $^{19}$F NMR (282 MHz, CDCl$_3$) δ −68.88 (s); LCMS (M−tBu+H)$^+$: 335.1.

Step D. 4-(Methoxymethyl)-2-(piperidin-4-yloxy)-6-(trifluoromethyl)pyridine

To a solution of tert-butyl 4-{[4-(methoxymethyl)-6-(trifluoromethyl)pyridin-2-yl]oxy}piperidine-1-carboxylate (40. mg, 0.10 mmol, from Step C) in Methylene chloride (1.0 mL) was added 4.0 M Hydrogen chloride in dioxane (0.50 mL, 2.0 mmol). The reaction mixture was stirred for one hour. The solvent was removed in vacuo. The residue was dissolved in DCM, and this solution was washed with saturated sodium bicarbonate, water (2x), brine, dried over sodium sulfate, filtered and concentrated to give product which was used without further purification (30 mg, 100%). $^1$H NMR (400 MHz, CDCl$_3$) δ 7.18 (s, 1H), 6.84 (s, 1H), 5.19 (tt, J=8.4, 3.6 Hz, 1H), 4.45 (s, 2H), 3.44 (s, 3H), 3.19-3.03 (m, 2H), 2.88-2.70 (m, 2H), 2.13-1.97 (m, 2H), 1.73-1.53 (m, 2H); $^{19}$F NMR (376 MHz, CDCl$_3$) δ −68.89 (s); LCMS (M+H)$^+$: 291.1.

Step E. {cis-3-(4-{[4-(Methoxymethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile (Single Isomer)

Sodium cyanoborohydride (7.8 mg, 0.12 mmol) and zinc dichloride (8.4 mg, 0.062 mmol) were precombined in methanol (0.5 mL) and stirred for 2 hours, according to the procedure found in JOC 1985, 50, 1927-1932. Following this, {3-oxo-1-[4-{7-{[2-(trimethylsilyl)ethoxy]methyl}-7H-pyrrolo[2,3-d]pyrimidin-4-yl)-1H-pyrazol-1-yl]cyclobutyl}acetonitrile (58 mg, 0.12 mmol, from Step 7 of Example 1a) and 4-(methoxymethyl)-2-(piperidin-4-yloxy)-6-(trifluoromethyl)pyridine (30. mg, 0.10 mmol, from Step D) in methanol (0.9 mL, 20 mmol) was stirred to dissolve and then the reducing solution generated from the zinc dichloride and sodium cyanoborohydride was added. The reaction was stirred overnight. Purification via preparative HPLC-MS (Waters XBridge C18, 30×100 mm, eluting with a gradient from 53.8% to 71.8% MeCN/H$_2$O containing 0.15% NH$_4$OH over 12 min at 60 mL/min) afforded two SEM protected isomers: Peak 1, 1st peak eluted (LCMS (M+H)$^+$: 697.4), 13.6 mg; Peak 2, 2nd peak eluted (LCMS (M+H)$^+$: 697.4), 13.9 mg. Peak 1 was deprotected by stirring with 1:1 TFA/DCM for one hour, removal of solvents, then stirring in 1.0 mL MeOH containing 0.10 mL ethylenediamine until deprotection was complete. Purification via preparative HPLC-MS (C18 eluting with a gradient of MeCN/H$_2$O containing 0.15% NH$_4$OH) afforded the cis product as the free base (6.7 mg, 11%). Peak 1: cis, $^1$H NMR (500 MHz, CDCl$_3$) δ 10.67 (s, 1H), 8.80 (s, 1H), 8.28 (s, 1H), 8.24 (s, 1H), 7.35 (dd, J=3.7, 2.1 Hz, 1H), 7.24 (s, 1H), 7.16 (s, 1H), 6.82 (s, 1H), 6.75-6.68 (m, 1H), 5.17-5.10 (m, 1H), 4.43 (s, 2H), 3.42 (s, 3H), 3.12 (s, 2H), 2.90 (tt, J=7.4, 7.5 Hz, 1H), 2.83-2.71 (m, 4H), 2.66 (br m, 2H), 2.28 (br m, J=11.1 Hz, 2H), 2.11-1.99 (m, 2H), 1.90-1.75 (m, 2H); $^{19}$F NMR (376 MHz, CDCl$_3$) δ −69.01 (s); LCMS (M+H)$^+$: 567.2.

Example 122

{trans-3-(4-{[4-(methoxymethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile (Single Isomer)

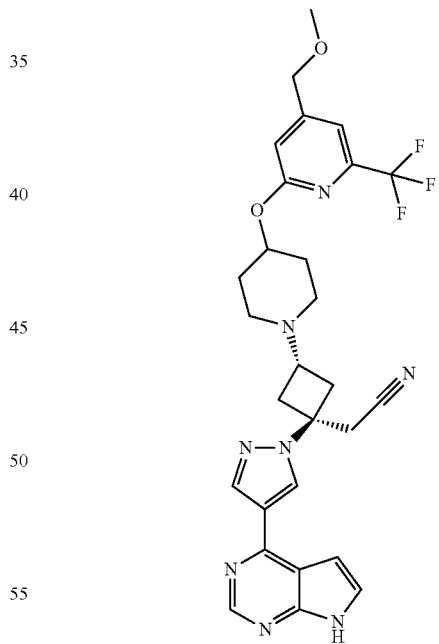

The title compound was prepared by the method of Example 121, Step E using Peak 2 from separation of the SEM-protected intermediates in that step, to afford product as the free base (7.2 mg, 12%). $^1$H NMR (500 MHz, CDCl$_3$) δ 10.98 (s, 1H), 8.87 (s, 1H), 8.50 (s, 1H), 8.36 (s, 1H), 7.43 (dd, J=3.7, 2.0 Hz, 1H), 7.18 (s, 1H), 6.84 (s, 1H), 6.81 (dd, J=3.6, 1.6 Hz, 1H), 5.17-5.10 (m, 1H), 4.45 (s, 2H), 3.43 (s, 3H), 3.23 (s, 2H), 3.07-2.99 (m, 2H), 2.94 (tt, J=6.8, 6.9 Hz, 1H), 2.66 (br m, 2H), 2.53-2.41 (m, 2H), 2.27 (br m, J=10.5

Hz, 2H), 2.13-2.03 (m, 2H), 1.88-1.75 (m, 2H); $^{19}$F NMR (376 MHz, CDCl$_3$) δ −68.93 (s); LCMS (M+H)$^+$: 567.2.

Example 123

{trans-3-(4-{[4-(hydroxymethyl)-6-(trifluoromethyl) pyridin-2-yl]oxy}piperidin-1-yl)-1-[4-(7H-pyrrolo[2, 3-d]pyrimidin-4-yl)-1H-pyrazol-1-yl] cyclobutyl}acetonitrile (Single Isomer Isolated)

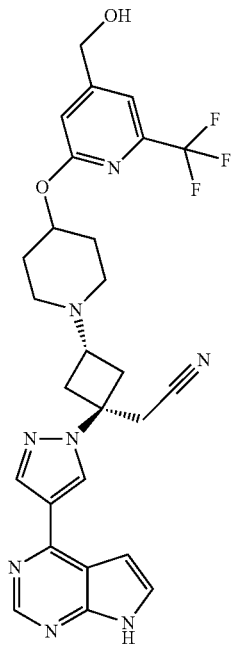 [SMILES: N#CC[C@]1(n2cc(-c3ncnc4[nH]ccc34)cn2)C[C@H](N2CCC(Oc3cc(CO)cc(C(F)(F)F)n3)CC2)C1]

Step A. 4-({[tert-Butyl(diphenyl)silyl]oxy}methyl)-2-chloro-6-(trifluoromethyl)pyridine To a solution of [2-chloro-6-(trifluoromethyl)pyridin-4-yl]methanol (142 mg, 0.671 mmol, Example 121, Step A) in methylene chloride (1.0 mL) at 0° C. was added 1H-imidazole (55 mg, 0.80 mmol) followed by tert-Butylchlorodiphenylsilane (190 μL, 0.74 mmol) and 4-dimethylaminopyridine (4 mg, 0.03 mmol). The reaction was stirred with warming to room temperature for 64 hours. The reaction mixture was diluted with diethyl ether and was washed with water followed by brine, dried over sodium sulfate, decanted and concentrated. Flash chromatography on silica gel, eluting with a gradient from 0-4% EtOAc in hexanes afforded product as a white solid (0.20 g, 66%). $^1$H NMR (300 MHz, CDCl$_3$) δ 7.70-7.58 (m, 4H), 7.55-7.34 (m, 8H), 4.77 (s, 2H), 1.12 (s, 9H); $^{19}$F NMR (282 MHz, CDCl$_3$) δ −68.49 (s); LCMS (M+H)$^+$: 450.1.

Step B. tert-Butyl 4-{[4-({[tert-butyl(diphenyl)silyl] oxy}methyl)-6-(trifluoromethyl)pyridin-2-yl] oxy}piperidine-1-carboxylate To sodium hydride (36 mg, 0.89 mmol, 60% in mineral oil) in tetrahydrofuran (1.0 mL) was added tert-butyl 4-hydroxypiperidine-1-carboxylate (0.18 g, 0.89 mmol, Aldrich). After stirring for 45 minutes, 4-({[tert-butyl(diphenyl)silyl] oxy}methyl)-2-chloro-6-(trifluoromethyl)pyridine (0.20 g, 0.44 mmol, from Step A) in tetrahydrofuran (0.60 mL) was added and the mixture was stirred overnight. The reaction was quenched and diluted with water and extracted with ether. The extract was washed with water, brine, dried over sodium sulfate, filtered and concentrated. Flash chromatography on silica gel, eluting with a gradient from 0-5% EtOAc in hexanes afforded product as an oil (0.19 g, 52%). LCMS (M−tBu+H)$^+$: 559.2

Step C. 4-({[tert-Butyl(diphenyl)silyl]oxy}methyl)-2-(piperidin-4-yloxy)-6-(trifluoromethyl)pyridine To a solution of tert-butyl 4-{[4-({[tert-butyl(diphenyl) silyl]oxy}methyl)-6-(trifluoromethyl)pyridin-2-yl] oxy}piperidine-1-carboxylate (0.19 g, 0.23 mmol, from Step B) in 1,4-dioxane (2.0 mL) was added 4.0 M hydrogen chloride in dioxane (0.50 mL, 2.0 mmol). The reaction mixture was stirred for one hour. Additional 4.0 M hydrogen chloride in dioxane (0.50 mL, 2.0 mmol) was added and stirring was continued for two hours. The mixture was diluted with water, saturated sodium bicarbonate was used to adjust the pH to between 7 and 8, and then the product was extracted with two portions of DCM. The combined extracts were washed with brine, dried over sodium sulfate, filtered and concentrated. Flash chromatography on silica gel, eluting with a gradient from 0-15% MeOH in DCM afforded product as an oil (62 mg, 52%). $^1$H NMR (400 MHz, CDCl$_3$) δ 7.69-7.62 (m, 4H), 7.48-7.34 (m, 6H), 7.14-7.11 (m, 1H), 6.91 (s, 1H), 5.17 (tt, J=8.7, 4.0 Hz, 1H), 4.71 (s, 2H), 3.13 (dt, J=12.7, 4.5 Hz, 2H), 2.78 (ddd, J=12.7, 9.7, 3.0 Hz, 2H), 2.07 (dq, J=12.2, 4.1 Hz, 2H), 1.67 (dtd, J=13.0, 9.4, 3.9 Hz, 2H), 1.11 (s, 9H); LCMS (M+H)$^+$: 515.2.

Step D. {3-(4-{[4-({[tert-Butyl(diphenyl)silyl] oxy}methyl)-6-(trifluoromethyl)pyridin-2-yl] oxy}piperidin-1-yl)-1-[4-(7-{[2-(trimethylsilyl) ethoxy]methyl}-7H-pyrrolo[2,3-d]pyrimidin-4-yl)-1H-pyrazol-1-yl]cyclobutyl}acetonitrile (A Mixture of Cis- and Trans-Isomers)

Sodium cyanoborohydride (8.8 mg, 0.14 mmol) and zinc dichloride (9.5 mg, 0.070 mmol) were combined in methanol (0.56 mL, 14 mmol) and stirred for 2 hours to generate the reducing solution referenced in JOC 1985, 50, 1927-1932. Subsequently, {3-oxo-1-[4-(7-{[2-(trimethylsilyl) ethoxy]methyl}-7H-pyrrolo[2,3-d]pyrimidin-4-yl)-1H-pyrazol-1-yl]cyclobutyl}acetonitrile (66 mg, 0.14 mmol, from Step 7 of Example 1a) and 4-({[tert-butyl(diphenyl) silyl]oxy}methyl)-2-(piperidin-4-yloxy)-6-(trifluoromethyl) pyridine (60. mg, 0.12 mmol, from Step C) were combined in Methanol (2.0 mL) to dissolve, then the above generated reducing mixture was added. The reaction was stirred overnight. An additional 0.3 eq of the prestirred NaCNBH$_3$/ZnCl$_2$ mixture was added. After stirring for 3 hours, the mixture was diluted with EtOAc and was washed with saturated sodium bicarbonate solution, followed by brine, dried over sodium sulfate, filtered and concentrated. Flash chromatography on silica gel, eluting with a gradient from 0-80% EtOAc in hexanes afforded product as a mixture of cis- and trans-isomers (43 mg, 40%). LCMS (M+2H)$^{2+}$: 461.4.

Step E. {cis-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile and {trans-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (Each Diastereomer Isolated)

To {3-(4-{[4-({[tert-butyl(diphenyl)silyl]oxy}methyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.35 g, 0.38 mmol, a mixture of cis- and trans-isomers from Step D) in ethanol (10. mL, 180 mmol) was added 5.0 M sodium hydroxide in water (1.5 mL, 7.6 mmol). After stirring for 3 hours, the reaction mixture was partitioned between DCM and brine. The aqueous layer was extracted with an additional portion of DCM. The combined extracts were dried over sodium sulfate, filtered and concentrated. Flash chromatography on silica gel, eluting with a gradient from 0-10% MeOH in DCM afforded a mixture of isomers (0.22 g, 76%). The isomers were separated by chiral HPLC (Phenomenex Lux-Cellulose 2 column, eluting with 45% EtOH in hexanes at 18 mL/min, ~44 mg/injection). Peak 1 retention time: 6.0 min, Peak 2 retention time: 10.2 min. Peak 1, trans isomer, 83 mg: $^1$H NMR (500 MHz, CDCl$_3$) δ 8.84 (s, 1H), 8.47 (s, 1H), 8.33 (s, 1H), 7.40 (d, J=3.7 Hz, 1H), 7.21 (s, 1H), 6.89 (s, 1H), 6.81 (d, J=3.7 Hz, 1H), 5.68 (s, 2H), 5.15 (br m, 1H), 4.73 (s, 2H), 3.61-3.45 (m, 2H), 3.22 (s, 2H), 3.08-2.97 (m, 2H), 2.97-2.84 (m, 1H), 2.67 (br m, 2H), 2.48 (br m, 2H), 2.25 (br m, 2H), 2.07 (br m, 2H), 1.84 (br m, 2H), 0.98-0.84 (m, 2H), −0.05 (s, 9H); LCMS (M+H)$^+$: 683.4. Peak 2, cis isomer, 78 mg: $^1$H NMR (500 MHz, CDCl$_3$) δ 8.83 (s, 1H), 8.39 (s, 1H), 8.29 (s, 1H), 7.39 (d, J=3.7 Hz, 1H), 7.21 (s, 1H), 6.90 (s, 1H), 6.80 (d, J=3.7 Hz, 1H), 5.67 (s, 2H), 5.20-5.06 (m, 1H), 4.73 (s, 2H), 3.64-3.46 (m, 2H), 3.14 (s, 2H), 2.90 (tt, J=7.4, 7.8 Hz, 1H), 2.84-2.76 (m, 2H), 2.75-2.52 (m, 4H), 2.28 (br m, 2H), 2.04 (br m, 2H), 1.81 (br m, 2H), 1.69 (s, 2H), 1.01-0.81 (m, 2H), −0.06 (s, 9H); LCMS (M+H)$^+$: 683.3.

Step F. {trans-3-(4-{[4-(Hydroxymethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile {trans-3-(4-{[4-(Hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (30. mg, 0.044 mmol, Peak 1 from Step E) was dissolved in methylene chloride (3.0 mL) and trifluoroacetic acid (3.0 mL, 39 mmol) was added. After stirring for 1.5 hours, the solvent was removed in vacuo. The residue was dissolved in 1.0 mL methanol, and 0.10 mL ethylenediamine was added. When deprotection was complete as determined by LCMS, purification via preparative HPLC-MS (C18 eluting with a gradient of MeCN/H$_2$O containing 0.15% NH$_4$OH) afforded product as the free base (18 mg, 75%). $^1$H NMR (400 MHz, dmso) δ 12.13 (s, 1H), 8.83 (s, 1H), 8.69 (s, 1H), 8.42 (s, 1H), 7.60 (dd, J=3.6, 2.3 Hz, 1H), 7.37 (s, 1H), 7.08 (dd, J=3.6, 1.7 Hz, 1H), 6.99 (s, 1H), 5.57 (t, J=5.8 Hz, 1H), 5.00 (tt, J=8.5, 4.2 Hz, 1H), 4.56 (d, J=5.7 Hz, 2H), 3.42 (s, 2H), 3.09-2.93 (m, 2H), 2.81 (tt, J=7.3, 7.3 Hz, 1H), 2.65 (br m, J=11.5 Hz, 2H), 2.41-2.28 (m, 2H), 2.17 (br m, 2H), 2.01 (br m, 2H), 1.69 (br m, J=11.1 Hz, 2H); $^{19}$F NMR (376 MHz, dmso) δ −67.39 (s); LCMS (M+H)$^+$: 553.2.

Example 124

{cis-3-(4-{[4-(hydroxymethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile (Single Isomer Isolated)

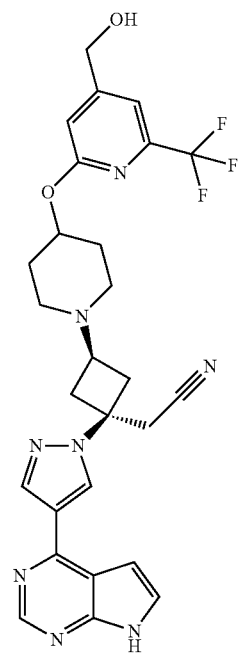 [SMILES: N#CC[C@]1(n2cc(-c3ncnc4[nH]ccc34)cn2)C[C@@H](N2CCC(Oc3cc(CO)cc(C(F)(F)F)n3)CC2)C1]

The procedure of Example 123, Step F was followed using Peak 2 from Example 123, Step E to afford product as the free base. LCMS (M+H)$^+$: 553.2.

Example 125

{trans-3-(4-{[4-(1-hydroxy-1-methylethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile (Single Isomer Isolated)

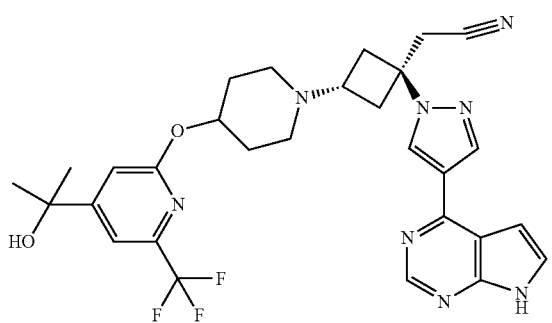 [SMILES: CC(C)(O)c1cc(OC2CCN([C@H]3C[C@](CC#N)(n4cc(-c5ncnc6[nH]ccc56)cn4)C3)CC2)nc(C(F)(F)F)c1]

Step A. 2-[2-Chloro-6-(trifluoromethyl)pyridin-4-yl]propan-2-ol

To a solution of ethyl 2-chloro-6-(trifluoromethyl)isonicotinate (0.200 g, 0.789 mmol, Anichem) in tetrahydrofuran (5 mL) at 0° C. was added 3.0 M methylmagnesium bromide in diethyl ether (0.66 mL, 2.0 mmol). After 30 minutes, the reaction was quenched by the addition of saturated ammonium chloride solution and extracted with three portions of ethyl acetate. The combined extracts were dried over sodium sulfate, decanted and concentrated. Used without further purification in Step B. $^1$H NMR (300 MHz, CDCl$_3$) δ 7.70 (d, J=1.4 Hz, 1H), 7.66-7.59 (m, 1H), 1.59 (s, 6H); $^{19}$F NMR (282 MHz, CDCl$_3$) δ −68.30 (s); LCMS (M+H)$^+$: 240.1.

Step B. 2-[2-(piperidin-4-yloxy)-6-(trifluoromethyl)pyridin-4-yl]propan-2-ol Tert-butyl 4-hydroxypiperidine-1-carboxylate (0.95 g, 4.7 mmol, Aldrich) was added to Sodium hydride (0.19 g, 4.7 mmol, 60% in mineral oil) in tetrahydrofuran (7 mL, 80 mmol). After stirring for 4 hours additional tetrahydrofuran (5 mL) was added, followed by 2-[2-chloro-6-(trifluoromethyl)pyridin-4-yl]propan-2-ol (0.189 g, 0.789 mmol, from Step A) as a solution in tetrahydrofuran (7 mL). The reaction was heated to 50° C. for 4 hours, then raised to 65° C. and stirred overnight. Upon cooling to room temperature, water was added and the product was extracted with three portions of ethyl acetate. The combined extracts were dried with sodium sulfate, decanted and concentrated. The product was purified via preparative HPLC-MS (C18 eluting with a gradient of MeCN/H$_2$O containing 0.1% TFA). Intermediate Boc-protected product: $^1$H NMR (400 MHz, CDCl$_3$) δ 7.33 (s, 1H), 6.97 (s, 1H), 5.29-5.21 (m, 1H), 3.71 (ddd, J=13.7, 6.9, 3.8 Hz, 2H), 3.30 (ddd, J=13.1, 8.3, 3.6 Hz, 2H), 2.64 (s, 1H), 1.99-1.91 (m, 2H), 1.77-1.65 (m, 2H), 1.55 (s, 6H), 1.45 (s, 9H); $^{19}$F NMR (376 MHz, CDCl$_3$) δ −68.72 (s).

A portion of this product (87 mg) was Boc-deprotected by stirring in 1,4-Dioxane (5 mL) containing 4.0 M Hydrogen chloride in Dioxane (2 mL, 8 mmol) overnight. The reaction mixture was poured into sufficient saturated sodium bicarbonate solution to make the mixture basic. The product was then extracted with four portions of ethyl acetate. The combined extracts were dried over sodium sulfate, decanted and concentrated. LCMS (M+H)$^+$: 305.1.

Step C. {trans-3-(4-{[4-(1-hydroxy-1-methylethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile (Single Isomer Isolated)

To zinc dichloride (0.017 g, 0.13 mmol) in methanol (1 mL, 20 mmol) was added sodium cyanoborohydride (0.0161 g, 0.256 mmol). This solution was stirred for 2 hours and is referred to as Solution A. Then, 2-[2-(piperidin-4-yloxy)-6-(trifluoromethyl)pyridin-4-yl]propan-2-ol (0.078 g, 0.26 mmol, from Step B) and {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.108 g, 0.256 mmol, from Step 7 of Example 1a) were combined in methanol (2 mL) to form solution B. After a few minutes, solution A was added to solution B and the reaction was stirred for 40 hours. Water was added and the product was extracted with three portions of ethyl acetate. The combined extracts were washed with brine, dried over sodium sulfate, decanted and concentrated. Flash chromatography on silica gel, eluting with a gradient from 0-10% MeOH/DCM afforded SEM-protected products as a mixture of cis and trans isomers. Chiral HPLC was used to separate the isomers (Phenomenex Lux-Cellulose 2; 30% EtOH/Hx, 22 mL/min, 22 mg/inj). Retention time of first isomer to elute (Peak 1): 6.65 min; retention time of second isomer to elute (Peak 2): 11.45 min. Peak 1 was stirred with 1:1 TFA:DCM for 1.5 hours, solvents were evaporated, then the residue was stirred with 0.7 mL ethylenediamine in methanol for 2 hours. Purification via preparative HPLC-MS (C18 eluting with a gradient of MeCN/H$_2$O containing 0.15% NH$_4$OH), followed by lyophilization afforded product as the free base. $^1$H NMR (500 MHz, CDCl$_3$) δ 9.56 (s, 1H), 8.84 (s, 1H), 8.49 (s, 1H), 8.34 (s, 1H), 7.38 (dd, J=3.7, 1.6 Hz, 1H), 7.33 (d, J=1.4 Hz, 1H), 6.96 (s, 1H), 6.81 (d, J=4.0 Hz, 1H), 5.16 (ddd, J=11.2, 7.4, 3.6 Hz, 1H), 3.23 (s, 2H), 3.07-3.00 (m, 2H), 2.94 (tt, J=6.8, 7.0 Hz, 1H), 2.67 (br m, 2H), 2.52-2.40 (m, 2H), 2.26 (br m, 2H), 2.08 (br m, 2H), 1.85 (br m, J=4.3 Hz, 3H), 1.56 (s, 6H); $^{19}$F NMR (282 MHz, CDCl$_3$) δ −68.72 (s); LCMS (M+H)$^+$: 581.3.

Example 126

{cis-3-(4-{[4-(1-hydroxy-1-methylethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile (Single Isomer Isolated)

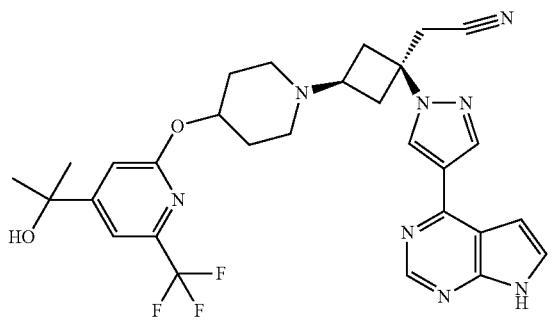 [SMILES: CC(C)(O)c1cc(OC2CCN([C@H]3C[C@@](CC#N)(n4cc(-c5ncnc6[nH]ccc56)cn4)C3)CC2)nc(C(F)(F)F)c1]

The title compound was prepared as described in Example 125, Step C, using Peak 2 from the chiral HPLC run in that step. $^1$H NMR (500 MHz, CDCl$_3$) δ 9.81 (s, 1H), 8.82 (s, 1H), 8.34 (s, 1H), 8.28 (s, 1H), 7.36 (d, J=3.6 Hz, 1H), 7.33 (d, J=1.3 Hz, 1H), 6.97 (s, 1H), 6.77 (d, J=3.6 Hz, 1H), 5.15 (ddd, J=11.4, 7.6, 3.3 Hz, 1H), 3.14 (s, 2H), 2.92 (tt, J=7.5, 7.5 Hz, 1H), 2.84-2.58 (m, 6H), 2.30 (br m, 2H), 2.13-1.99 (m, 2H), 1.94-1.74 (m, 2H), 1.56 (s, 6H); $^{19}$F NMR (282 MHz, CDCl$_3$) δ −68.72 (s); LCMS (M+H)$^+$: 581.3.

Example 127

{trans-3-(4-{[4-[(tert-butylamino)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

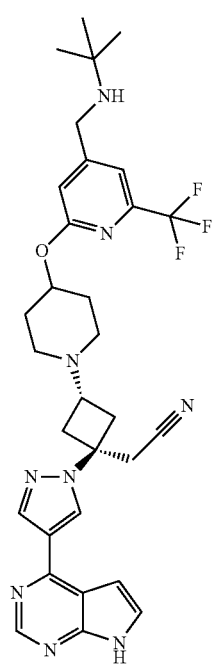 [SMILES: CC(C)(C)NCc1cc(OC2CCN([C@H]3C[C@](CC#N)(n4cc(-c5ncnc6[nH]ccc56)cn4)C3)CC2)nc(C(F)(F)F)c1]

N,N-Diisopropylethylamine (7.6 μL, 0.044 mmol) and methanesulphonic anhydride (5.4 mg, 0.031 mmol, Aldrich) were added to a solution of {trans-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (15 mg, 0.022 mmol, Peak 1 from Example 123, Step E) in methylene chloride (0.30 mL). After stirring for one hour, solvent was removed in vacuo and tetrahydrofuran (0.20 mL) and tert-butylamine (34 μL, 0.33 mmol, Aldrich) were added. The mixture was sealed in a vial and heated to 50° C. for 2 hours. Solvent and excess amine were removed in vacuo. The residue was stirred in a 1:1 mixture of TFA/DCM for one hour, the solvents were evaporated, and the residue was stirred in Methanol (1 mL) containing ethylenediamine (0.1 mL) until deprotection was complete. Purification via preparative HPLC-MS (C18 eluting with a gradient of MeCN/H$_2$O containing 0.15% NH$_4$OH), followed by lyophilization afforded product as the free base (5.5 mg, 41%). $^1$H NMR (300 MHz, dmso) δ 12.12 (s, 1H), 8.83 (s, 1H), 8.69 (s, 1H), 8.42 (s, 1H), 7.60 (d, J=3.6 Hz, 1H), 7.43 (s, 1H), 7.08 (d, J=3.6 Hz, 1H), 7.06 (s, 1H), 5.04-4.94 (m, 1H), 3.71 (d, J=6.4 Hz, 2H), 3.42 (s, 2H), 3.08-2.96 (m, 2H), 2.81 (tt, J=7.6, 7.7 Hz, 1H), 2.63 (br m, 2H), 2.40-2.28 (m, 2H), 2.20-1.90 (m, 4H), 1.68 (d, J=10.4 Hz, 2H), 1.05 (s, 9H); $^{19}$F NMR (282 MHz, dmso) δ −67.26 (s); LCMS (M+H)$^+$: 608.4.

Example 128

{cis-3-(4-{[4-[(tert-butylamino)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

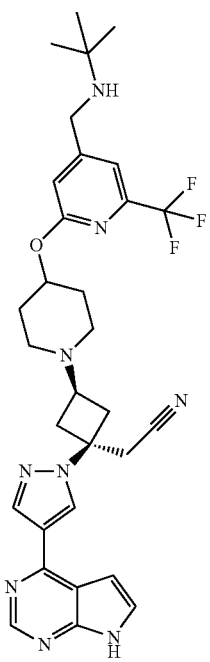 [SMILES: CC(C)(C)NCc1cc(OC2CCN([C@H]3C[C@@](CC#N)(n4cc(-c5ncnc6[nH]ccc56)cn4)C3)CC2)nc(C(F)(F)F)c1]

The title compound was prepared according to the procedure of Example 127, using {cis-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (15 mg, 0.022 mmol, Peak 2 from Example 123, Step E) to afford the product as the free base (6.3 mg, 47%). $^1$H NMR (300 MHz, dmso) δ 12.12 (br s, 1H), 8.70 (s, 1H), 8.68 (s, 1H), 8.40-8.38 (m, 1H), 7.60 (d, J=3.6 Hz, 1H), 7.43 (s, 1H), 7.09-7.00 (m, 2H), 5.05-4.93 (m, 1H), 3.71 (d, J=6.6 Hz, 2H), 3.47 (s, 2H), 2.93 (tt, J=7.4, 7.7 Hz, 1H), 2.70-2.55 (m, 4H), 2.25-1.89 (m, 6H), 1.77-1.52 (m, 2H), 1.05 (s, 9H); $^{19}$F NMR (282 MHz, dmso) δ −67.25 (s); LCMS (M+H)$^+$: 608.4.

225
Example 129

{trans-3-(4-{[4-(aminomethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

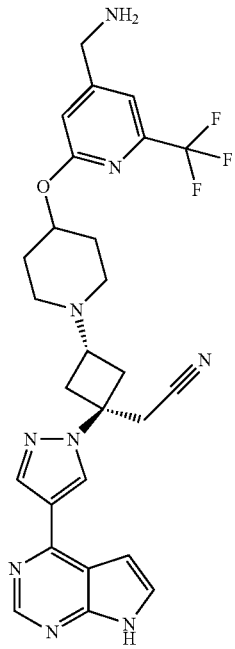

The title compound was prepared according to the method of Example 127, using 7.0 M Ammonia in methanol (0.16 mL, 1.1 mmol, Aldrich) at room temperature overnight (7.7 mg, 64%). $^1$H NMR (400 MHz, dmso) δ 12.13 (br s, 1H), 8.83 (s, 1H), 8.69 (s, 1H), 8.42 (s, 1H), 7.60 (d, J=3.6 Hz, 1H), 7.43 (s, 1H), 7.08 (d, J=3.6 Hz, 1H), 7.04 (s, 1H), 5.06-4.92 (m, 1H), 3.74 (s, 2H), 3.42 (s, 2H), 3.07-2.93 (m, 2H), 2.81 (tt, J=7.2, 7.4 Hz, 1H), 2.65 (br m, J=14.0 Hz, 2H), 2.40-2.29 (m, 2H), 2.16 (br m, 2H), 2.01 (br m, 2H), 1.77-1.52 (m, 2H); $^{19}$F NMR (376 MHz, dmso) δ −67.26 (s); LCMS (M+H)$^+$: 551.8.

226
Example 130

{trans-3-(4-{[4-[(dimethylamino)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

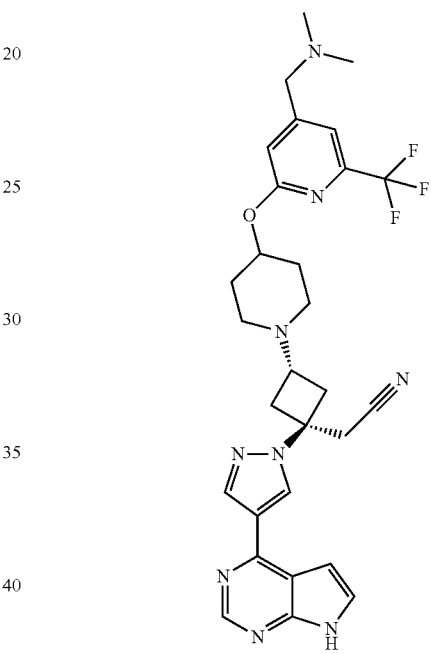

The title compound was prepared according to the method of Example 127, using 2.0 M Dimethylamine in THF (0.11 mL, 0.22 mmol, Aldrich) at room temperature for 2 hours (8.3 mg, 65%). $^1$H NMR (400 MHz, dmso) δ 12.13 (br s, 1H), 8.83 (s, 1H), 8.69 (s, 1H), 8.42 (s, 1H), 7.60 (d, J=3.6 Hz, 1H), 7.36 (s, 1H), 7.08 (d, J=3.6 Hz, 1H), 6.99 (s, 1H), 5.04-4.96 (m, 1H), 3.46 (s, 2H), 3.42 (s, 2H), 3.06-2.94 (m, 2H), 2.81 (tt, J=7.3, 7.4 Hz, 1H), 2.65 (br m, 2H), 2.42-2.21 (m, 2H), 2.22-2.07 (m, 8H), 2.00 (br m, J=8.4 Hz, 2H), 1.75-1.63 (m, 2H); $^{19}$F NMR (376 MHz, dmso) δ −67.35 (s); LCMS (M+H)$^+$: 580.3.

227

Example 131

{trans-3-(4-{[4-[(ethylamino)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

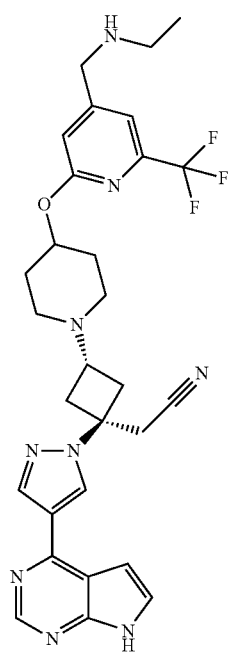 [SMILES: CCNCc1cc(OC2CCN([C@H]3C[C@](CC#N)(n4cc(-c5ncnc6[nH]ccc56)cn4)C3)CC2)nc(C(F)(F)F)c1]

The title compound was prepared according to the procedure of Example 127, using Ethylamine (0.124 mL, 2.20 mmol, Aldrich) at room temperature overnight (6.2 mg, 49%). $^1$H NMR (400 MHz, dmso) δ 12.13 (s, 1H), 8.83 (s, 1H), 8.69 (s, 1H), 8.42 (s, 1H), 7.60 (d, J=3.6 Hz, 1H), 7.41 (s, 1H), 7.08 (d, J=3.6 Hz, 1H), 7.03 (s, 1H), 4.99 (tt, J=8.0, 3.2 Hz, 1H), 3.73 (s, 2H), 3.42 (s, 2H), 3.08-2.95 (m, 2H), 2.81 (tt, J=7.4, 7.5 Hz, 1H), 2.65 (br m, J=12.8 Hz, 2H), 2.48 (q, J=7.1 Hz, 2H), 2.40-2.31 (m, 2H), 2.17 (br m, J=10.7 Hz, 2H), 2.00 (br m, 2H), 1.77-1.55 (m, 2H), 1.01 (t, J=7.1 Hz, 3H); $^{19}$F NMR (376 MHz, dmso) δ −67.29 (s); LCMS (M+H)$^+$: 580.3.

228

Example 132

{trans-3-(4-{[4-[(methylamino)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

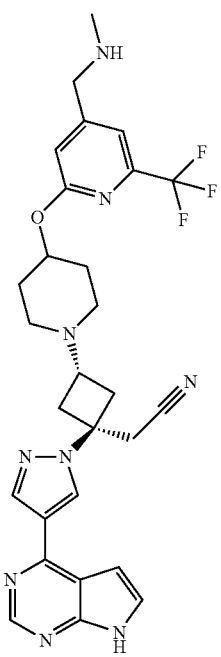 [SMILES: CNCc1cc(OC2CCN([C@H]3C[C@](CC#N)(n4cc(-c5ncnc6[nH]ccc56)cn4)C3)CC2)nc(C(F)(F)F)c1]

The title compound was prepared according to the procedure of Example 127, using 33 wt % methylamine in ethanol (69 mg, 0.73 mmol) at room temperature overnight (4.7 mg, 57%). $^1$H NMR (300 MHz, dmso) δ 12.13 (s, 1H), 8.83 (s, 1H), 8.69 (s, 1H), 8.42 (s, 1H), 7.60 (d, J=3.6 Hz, 1H), 7.41 (s, 1H), 7.08 (d, J=3.6 Hz, 1H), 7.02 (s, 1H), 5.05-4.95 (m, 1H), 3.68 (s, 2H), 3.42 (s, 2H), 3.07-2.95 (m, 2H), 2.81 (tt, J=7.3, 7.5 Hz, 1H), 2.64 (br m, 2H), 2.41-2.30 (m, 2H), 2.23 (s, 3H), 2.21-2.09 (m, 2H), 2.01 (br m, 3H), 1.80-1.54 (m, 2H); $^{19}$F NMR (282 MHz, dmso) δ −67.30 (s); LCMS (M+H)$^+$: 566.3.

Example 133

2-[(1-{cis-3-(cyanomethyl)-3-[4-(7H-pyrrolo[2,3-d]pyrimidin-4-yl)-1H-pyrazol-1-yl]cyclobutyl}piperidin-4-yl)oxy]-6-(trifluoromethyl)isonicotinonitrile (Single Isomer)

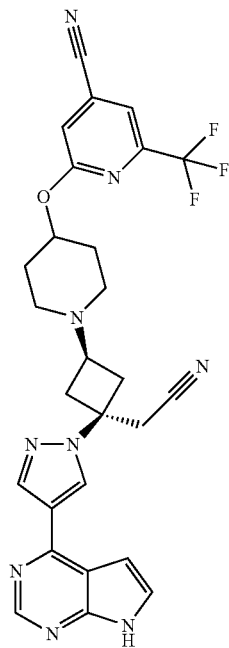 [SMILES: N#CC[C@]1(n2cc(-c3ncnc4[nH]ccc34)cn2)C[C@@H](N2CCC(Oc3cc(C#N)cc(C(F)(F)F)n3)CC2)C1]

Step A.
2-Chloro-6-(trifluoromethyl)isonicotinonitrile

2-Chloro-4-iodo-6-(trifluoromethyl)pyridine (0.50 g, 1.5 mmol, prepared according to the method described in European Journal of Organic Chemistry, (18) 3793-3798; 2004) and copper cyanide (0.52 g, 5.8 mmol) were mixed in N-methylpyrrolidinone (2 mL). The reaction vial was sealed and heated in the microwave to 120° C. for 10 minutes. The mixture was diluted with water and EtOAc and was filtered. The organic layer was washed with water (3×), followed by brine, dried over sodium sulfate and concentrated. Flash chromatography on silica gel, eluting with a gradient from 0-15% EtOAc in hexanes afforded product as a colorless oil (0.24 g, 64%).

Step B. tert-Butyl 4-{[4-(aminocarbonyl)-6-(trifluoromethyl)pyridin-2-yl]oxy}piperidine-1-carboxylate Tert-butyl 4-hydroxypiperidine-1-carboxylate (0.37 g, 1.8 mmol, Aldrich) was added to sodium hydride (74 mg, 1.8 mmol, 60% in mineral oil) in tetrahydrofuran (2.1 mL). After stirring for 45 minutes, 2-chloro-6-(trifluoromethyl)isonicotinonitrile (0.24 g, 0.93 mmol, from Step A) in tetrahydrofuran (1.3 mL) was introduced. After stirring overnight, the mixture was diluted with water and extracted with EtOAc. The combined extracts were washed with water, brine, dried over sodium sulfate, filtered and concentrated. Flash chromatography, eluting with a gradient from 0-40% EtOAc in hexanes afforded product (0.20 g, 44%). $^1$H NMR (300 MHz, CDCl$_3$) δ 7.58 (d, J=1.2 Hz, 1H), 7.23 (dd, J=1.3, 0.6 Hz, 1H), 6.15 (s, 1H), 5.75 (s, 1H), 5.30 (tt, J=7.7, 3.8 Hz, 1H), 3.95-3.62 (m, 4H), 3.33 (ddd, J=13.5, 8.4, 3.7 Hz, 2H), 3.02 (ddd, J=13.3, 9.8, 3.4 Hz, 2H), 1.58 (s, 9H); $^{19}$F NMR (282 MHz, CDCl$_3$) δ −68.97 (s); LCMS (M+Na)$^+$: 412.0.

Step C. 2-(Piperidin-4-yloxy)-6-(trifluoromethyl)isonicotinamide tert-Butyl 4-{[4-(aminocarbonyl)-6-(trifluoromethyl)pyridin-2-yl]oxy}piperidine-1-carboxylate (0.20 g, 0.41 mmol, from Step B) was dissolved in 1,4-dioxane (3.0 mL, 38 mmol) and treated with 4.0 M hydrogen chloride in dioxane (2.4 mL, 9.8 mmol). After 2.5 hours, the mixture was treated with ammonium hydroxide to achieve pH 11, and 15 mL of acetonitrile was added. The mixture was filtered and purified via preparative HPLC-MS (C18 eluting with a gradient of MeCN/H$_2$O containing 0.15% NH$_4$OH) to afford product (72 mg, 60%). $^1$H NMR (400 MHz, dmso) δ 8.35 (s, 1H), 7.91 (s, 1H), 7.76 (d, J=1.2 Hz, 1H), 7.49 (s, 1H), 5.05 (tt, J=8.9, 4.1 Hz, 1H), 2.95 (dt, J=12.6, 4.2 Hz, 2H), 2.57 (ddd, J=12.7, 10.0, 2.9 Hz, 2H), 2.01-1.87 (m, 2H), 1.60-1.41 (m, 2H); $^{19}$F NMR (376 MHz, dmso) δ −67.49 (s); LCMS (M+H)$^+$: 290.1.

Step D. 2-[(1-{cis-3-(Cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperidin-4-yl)oxy]-6-(trifluoromethyl)isonicotinamide and 2-[(1-{trans-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperidin-4-yl)oxy]-6-(trifluoromethyl)isonicotinamide (Each Diastereomer Isolated)

Sodium cyanoborohydride (21 mg, 0.34 mmol) and zinc dichloride (23 mg, 0.17 mmol) were combined in methanol (1.2 mL) and stirred for 2 hours. Separately, {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.11 g, 0.27 mmol, from Step 7 of Example 1a) and 2-(piperidin-4-yloxy)-6-(trifluoromethyl)isonicotinamide (70. mg, 0.24 mmol, from Step C) were stirred in methanol (3.4 mL) to dissolve, then the solution combining ZnCl$_2$ and NaCNBH$_3$ was added. After stirring overnight, the mixture was purified via preparative HPLC-MS (C18 eluting with a gradient of MeCN/H$_2$O containing 0.15% NH$_4$OH) to afford two isomers: Peak 1 (1st peak eluted) was the cis-isomer (49 mg, 29%); Peak 2 (second peak to elute) was the trans-isomer (56 mg, 33%).

Peak 1, Cis-: $^1$H NMR (300 MHz, CDCl$_3$) δ 8.90 (s, 1H), 8.45 (s, 1H), 8.36 (s, 1H), 7.63 (d, J=1.2 Hz, 1H), 7.46 (d, J=3.7 Hz, 1H), 7.28 (s, 1H), 6.86 (d, J=3.7 Hz, 1H), 6.17 (s, 1H), 5.80 (s, 1H), 5.73 (s, 2H), 5.29-5.19 (m, 1H), 3.72-3.44 (m, 2H), 3.21 (s, 2H), 3.06-2.49 (m, 7H), 2.48-2.22 (m, 2H), 2.24-2.01 (m, 2H), 1.99-1.80 (m, 2H), 1.08-0.87 (m, 2H), 0.00 (s, 9H); $^{19}$F NMR (282 MHz, CDCl$_3$) δ −68.97 (s); LCMS (M+H)$^+$: 696.1. Peak 2, Trans-: $^1$H NMR (300 MHz, CDCl$_3$) δ 8.85 (s, 1H), 8.48 (s, 1H), 8.33 (s, 1H), 7.57 (d, J=1.2 Hz, 1H), 7.41 (d, J=3.7 Hz, 1H), 7.22 (s, 1H), 6.82 (d, J=3.7 Hz, 1H), 6.12 (s, 1H), 5.74 (s, 1H), 5.68 (s, 2H), 5.19 (tt, J=7.5, 3.9 Hz, 1H), 3.62-3.46 (m, 2H), 3.22 (s, 2H), 3.11-2.99 (m, 2H), 2.93 (tt, J=6.4, 7.0 Hz, 1H), 2.66 (br m, 2H), 2.57-2.41 (m, 2H), 2.27 (br m, 2H), 2.05 (br m, 2H), 1.93-1.76 (m, 2H), 1.01-0.77 (m, 2H), −0.06 (s, 9H); $^{19}$F NMR (282 MHz, CDCl$_3$) δ −68.97 (s); LCMS (M+H)$^+$: 696.1.

Step E. 2-[(1-{cis-3-(cyanomethyl)-3-[4-(7H-pyrrolo[2,3-d]pyrimidin-4-yl)-1H-pyrazol-1-yl]cyclobutyl}piperidin-4-yl)oxy]-6-(trifluoromethyl)isonicotinonitrile Triethylamine (16 μL, 0.11 mmol) followed by trichloroacetic anhydride (16 μL, 0.086 mmol, Aldrich) was added to a solution of 2-[(1-{cis-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperidin-4-yl)oxy]-6-(trifluoromethyl)isonicotinamide (20. mg, 0.029 mmol, Peak 1 from Step D) in methylene chloride (1.5 mL) at 0° C. After 25 minutes, 1.5 mL TFA was added to the reaction. After stirring for one hour, TFA and DCM removed in vacuo. The residue was dissolved in 1.0 mL methanol, and 0.20 mL ethylenediamine was added. After deprotection was complete, preparative HPLC-MS (C18 eluting with a gradient of MeCN/H$_2$O containing 0.15% NH$_4$OH) was used to afford product as the free base (13 mg, 83%). $^1$H NMR (400 MHz, dmso) δ 12.13 (s, 1H), 8.70 (s, 1H), 8.68 (s, 1H), 8.39 (s, 1H), 8.00 (s, 1H), 7.78 (s, 1H), 7.60 (d, J=3.5 Hz, 1H), 7.06 (d, J=3.5 Hz, 1H), 5.04 (tt, J=7.5, 3.2 Hz, 1H), 3.47 (s, 2H), 2.94 (tt, J=7.6, 7.7 Hz, 1H), 2.75-2.55 (m, 6H), 2.19 (br m, J=10.5 Hz, 2H), 2.01 (br m, 2H), 1.78-1.58 (m, 2H); $^{19}$F NMR (376 MHz, dmso) δ −67.77 (s); LCMS (M+H)$^+$: 548.0.

Example 134

2-1(1-{trans-3-(cyanomethyl)-3-[4-(7H-pyrrolo[2,3-d]pyrimidin-4-yl)-1H-pyrazol-1-yl]cyclobutyl}piperidin-4-yl)oxyl-6-(trifluoromethyl)isonicotinonitrile (Single Isomer Prepared)

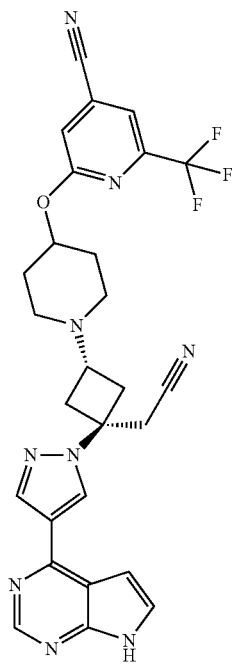 [SMILES: N#CC[C@]1(n2cc(-c3ncnc4[nH]ccc34)cn2)C[C@H](N2CCC(Oc3cc(C#N)cc(C(F)(F)F)n3)CC2)C1]

The title compound was prepared according to the procedure of Example 133, Step E, using 2-[(1-{trans-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperidin-4-yl)oxy]-6-(trifluoromethyl)isonicotinamide (48 mg, 0.069 mmol, Peak 2 from Example 133, Step D) to afford product as the free base (29 mg, 77%). $^1$H NMR (400 MHz, dmso) δ 12.13 (s, 1H), 8.83 (s, 1H), 8.69 (s, 1H), 8.42 (d, J=0.6 Hz, 1H), 8.00 (d, J=1.0 Hz, 1H), 7.77 (s, 1H), 7.60 (d, J=3.6 Hz, 1H), 7.08 (d, J=3.6 Hz, 1H), 5.09-4.94 (m, 1H), 3.42 (s, 2H), 3.08-2.96 (m, 2H), 2.82 (tt, J=7.4, 7.4 Hz, 1H), 2.66 (br m, J=12.3 Hz, 2H), 2.41-2.28 (m, 2H), 2.15 (br m, J=10.8 Hz, 2H), 2.03 (br m, 2H), 1.81-1.52 (m, 2H); $^{19}$F NMR (376 MHz, dmso) δ −67.78 (s); LCMS (M+H)$^+$: 548.0.

Example 135

{cis-3-{4-[3-[(dimethylamino)methyl]-5-(trifluoromethyl)benzoyl]piperazin-1-yl}-1-[4-(7H-pyrrolo[2,3-d]pyrimidin-4-yl)-1H-pyrazol-1-yl]cyclobutyl}acetonitrile

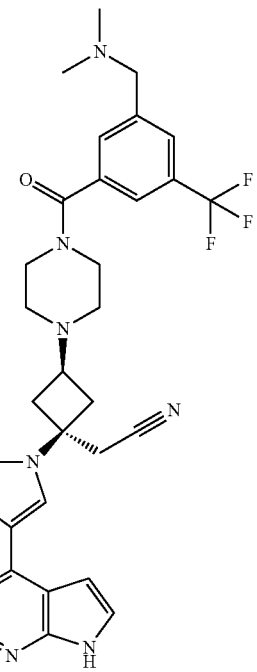

Lithium 3-[(dimethylamino)methyl]-5-(trifluoromethyl)benzoate (23.1 mg, 0.0913 mmol, US 2010/197924) was dissolved in tetrahydrofuran (0.67 mL), triethylamine (33.9 μL, 0.244 mmol) and N,N,N',N'-tetramethyl-O-(7-azabenzotriazol-1-yl)uronium hexafluorophosphate (32.4 mg, 0.0852 mmol) were added, the mixture was stirred for 15 minutes. {cis-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (30.0 mg, 0.0609 mmol, from Step 9 of Example 1a) was then added, and the reaction was stirred for two hours. Ethyl acetate and water were added and the layers were separated. The organic layer was washed with water, 0.1N NaOH and sat. NaCl, dried over sodium sulfate, and concentrated. The residue was dissolved in a 1:1 mixture of DCM:TFA, stirred for 1 hour, and concentrated again. Methanol (1 mL) was added, followed by 0.2 mL of ethylenediamine. The reaction was stirred until deprotection was complete. Purification via preparative HPLC-MS (C18 eluting with a gradient of MeCN/H$_2$O containing 0.15% NH$_4$OH) followed by lyophilization afforded product as the free base (20 mg, 40%). ¹H NMR (400 MHz, dmso) δ 12.14 (br s, 1H), 8.70 (s, 1H), 8.68 (s, 1H), 8.40 (s, 1H), 7.71 (br m, 1H), 7.62 (br m, 1H), 7.61 (d, J=3.6 Hz, 1H), 7.59 (br m, 1H), 7.06 (d, J=3.6 Hz, 1H), 3.64 (br m, 2H), 3.51 (s, 2H), 3.47 (s, 2H), 3.30 (br m, 2H), 2.95 (tt, J=7.6, 7.7 Hz, 1H), 2.69-2.54 (m, 4H), 2.40 (br m, 2H), 2.29 (br m, 2H), 2.15 (s, 6H); ¹⁹F NMR (376 MHz, dmso) δ −61.46 (s); LCMS (M+H)⁺: 592.3.

Example 136

3-[(4-{trans-3-(cyanomethyl)-3-[4-(7H-pyrrolo[2,3-d]pyrimidin-4-yl)-1H-pyrazol-1-yl] cyclobutyl}piperazin-1-yl)carbonyl]-5-[(dimethyl-amino)methyl]benzonitrile

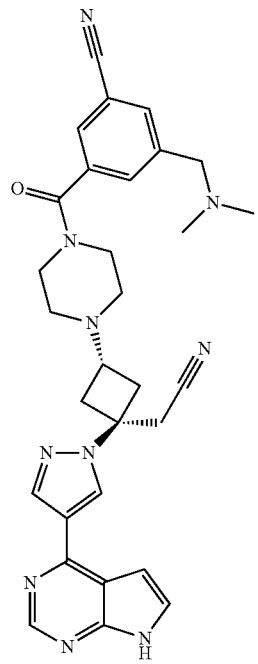 [SMILES: CN(C)Cc1cc(C#N)cc(C(=O)N2CCN([C@H]3C[C@](CC#N)(n4cc(-c5ncnc6[nH]ccc56)cn4)C3)CC2)c1]

Methyl 3-bromo-5-[(dimethylamino)methyl]benzoate (0.30 g, 1.1 mmol, from Example 43, Step A) was hydrolyzed by stirring with lithium hydroxide monohydrate (0.555 g, 13.2 mmol) in a mixture of THF (20 mL) and water (6 mL) for 3 hours. The mixture was acidified by the addition of 1 N HCl to achieve pH 10, and the solvents were removed in vacuo. Purification by preparative HPLC-MS (C18 eluting with a gradient of MeCN/H₂O containing 0.15% NH₄OH) to afford 0.26 g of product (91%). A portion of the 3-bromo-5-[(dimethylamino)methyl]benzoic acid (31.4 mg, 0.122 mmol) obtained by hydrolysis was dissolved in tetrahydrofuran (0.90 mL), and triethylamine (45.3 µL, 0.325 mmol) and N,N,N',N'-tetramethyl-O-(7-azabenzotriazol-1-yl)uronium hexafluorophosphate (43.2 mg, 0.114 mmol) were added. The mixture was stirred for 15 minutes, then {trans-3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (40.0 mg, 0.0812 mmol, from Step 1 of Example 1b) was added. The reaction was stirred for two hours and the reaction mixture was partitioned between ethyl acetate and water. The layers were separated and the organic layer was washed with water, 0.1 N NaOH and sat. NaCl, dried over sodium sulfate and concentrated. The residue was dissolved in N,N-dimethylformamide (1.0 mL) and zinc cyanide (57 mg, 0.49 mmol) was added. The reaction mixture was degassed by bubbling a stream of nitrogen through the mixture for 10 minutes. Tetrakis(triphenylphosphine)palladium(0) (19 mg, 0.016 mmol) was then added. The reaction was heated to 120° C. in the microwave for 30 minutes. The reaction mixture was partitioned between water and ethyl acetate. After separation of layers, the organic layer was washed twice with water, once with brine, dried over sodium sulfate and concentrated. The residue was stirred in a 1:1 mixture of DCM:TFA for one hour, then concentrated. To complete the deprotection, the residue was redissolved in methanol (1 mL) and 0.2 mL of ethylenediamine was added and stirred until deprotection was complete. Purification via two successive preparative HPLC-MS runs (C18 eluting first with acidic method, using a gradient of MeCN/H₂O containing 0.1% TFA, then via basic method: C18 eluting with a gradient of MeCN/H₂O containing 0.15% NH₄OH) followed by lyophilization, afforded the product as the free base (14.1 mg, 31%). ¹H NMR (400 MHz, dmso) δ 12.13 (br s, 1H), 8.83 (s, 1H), 8.69 (s, 1H), 8.42 (s, 1H), 7.80 (dd, 1H), 7.77 (dd, 1H), 7.62 (dd, 1H), 7.60 (d, J=3.6 Hz, 1H), 7.07 (d, J=3.6 Hz, 1H), 3.65 (br m, 2H), 3.46 (s, 2H), 3.43 (s, 2H), 3.31 (br m, 2H), 3.07-2.93 (m, 2H), 2.83 (tt, J=7.2, 7.3 Hz, 1H), 2.44-2.21 (m, 6H), 2.14 (s, 6H); LCMS (M+H)⁺: 549.2.

Example 137

3-[(1-{trans-3-(cyanomethyl)-3-[4-(7H-pyrrolo[2,3-d]pyrimidin-4-yl)-1H-pyrazol-1-yl] cyclobutyl}piperidin-4-yl)oxy]-5-[(dimethylamino) methyl]benzonitrile

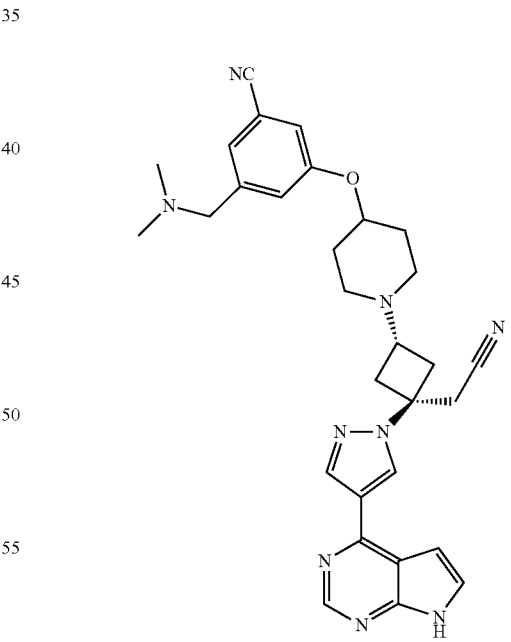

Step 1. tert-Butyl 4-[3-bromo-5-(methoxycarbonyl) phenoxy]piperidine-1-carboxylate The title compound was prepared according to the method of Example 40, Step 5 using methyl 3-bromo-5-hydroxybenzoate as starting material. LCMS (M+H−100)⁺: 314.0, 316.0.

Step 2. tert-Butyl 4-[3-bromo-5-(hydroxymethyl) phenoxy]piperidine-1-carboxylate To a solution of tert-butyl 4-[3-bromo-5-(methoxycarbonyl)phenoxy]piperidine-1-carboxylate (520 mg, 1.2 mmol) in THF (10 mL) was added lithium tetrahydroborate (27.3 mg, 1.26 mmol). The resulting solution was stirred at room temperature for 1 hour. The reaction was quenched with 1 N HCl. The organic solution was washed with brine, dried over $Na_2SO_4$, filtered and concentrated. The crude was purified by flash chromatography on a silica gel column to give the desired product. LCMS (M+Na)$^+$: 408.1, 410.1.

Step 3. tert-Butyl 4-(3-bromo-5-formylphenoxy) piperidine-1-carboxylate

To a solution of tert-butyl 4-[3-bromo-5-(hydroxymethyl) phenoxy]piperidine-1-carboxylate (0.47 g, 1.2 mmol) in DCM (20 mL) at 0° C. was added Dess-Martin periodinane (0.67 g, 1.6 mmol). After stirring for 2 hours, the reaction solution was poured into saturated $NaHCO_3$, and extracted with DCM (3×). The combined extracts were washed with brine. The organic layer was dried over sodium sulfate, decanted and evaporated to give the desired product that was used without further purification.

Step 4. tert-Butyl 4-{3-bromo-5-[(E)-(hydroxyimino)methyl]phenoxy}piperidine-1-carboxylate To the solution of tert-butyl 4-(3-bromo-5-formylphenoxy)piperidine-1-carboxylate (205 mg, 0.533 mmol) in ethanol (1.9 mL) and water (0.6 mL), hydroxylamine hydrochloride (40.8 mg, 0.587 mmol) and sodium acetate (61.3 mg, 0.747 mmol) were added sequentially, then the resulting solution was refluxed for 1 hour. The most organic solvent was removed in vacuo and the solution was diluted with water. The resultant precipitate was collected and dried under vacuum to give the desired product as white solid. LCMS (M+H)$^+$: 399.1, 401.1.

Step 5. tert-Butyl 4-(3-bromo-5-cyanophenoxy)piperidine-1-carboxylate

To a solution of tert-butyl 4-{3-bromo-5-[(E)-(hydroxyimino)methyl]phenoxy}piperidine-1-carboxylate (157 mg, 0.393 mmol) in pyridine (1.2 mL) was added methanesulfonyl chloride (0.12 mL, 1.6 mmol). The reaction mixture was heated at 60° C. for 2 hours. The reaction solution was diluted with ethyl acetate and saturated $CuSO_4$ solution. The organic layer was washed with $CuSO_4$ twice, 1 N HCl, brine, dried over $Na_2SO_4$, filtered and concentrated. The residue was purified by flash chromatography on a silica gel column to give the desired product as white solid. LCMS (M+H)$^+$: 381.1, 383.1.

Step 6. tert-Butyl 4-{3-cyano-5-[(dimethylamino)methyl]phenoxy}piperidine-1-carboxylate This compound was prepared according to the method of Example 40, Step 6 using tert-butyl 4-(3-bromo-5-cyanophenoxy)piperidine-1-carboxylate as starting material. LCMS (M+H)$^+$: 360.1.

Step 7. 3-[(Dimethylamino)methyl]-5-(piperidin-4-yloxy)benzonitrile

This compound was prepared according to the method of Example 40, Step 7 using tert-butyl 4-{3-cyano-5-[(dimethylamino)methyl]phenoxy}piperidine-1-carboxylate as starting material. LCMS (M+H)$^+$: 260.1.

Step 8. 3-[(1-{trans-3-(Cyanomethyl)-3-[4-(7-{[2-(trimethylsilyl)ethoxy]methyl}-7H-pyrrolo[2,3-d]pyrimidin-4-yl)-1H-pyrazol-1-yl] cyclobutyl}piperidin-4-yl)oxy]-5-[(dimethylamino) methyl]benzonitrile, 3-[(1-{trans-3-(cyanomethyl)-3-[4-(7-{[2-(trimethylsilyl)ethoxy]methyl}-7H-pyrrolo[2,3-d]pyrimidin-4-yl)-1H-pyrazol-1-yl] cyclobutyl}piperidin-4-yl)oxy]-5-[(dimethylamino) methyl]benzonitrile These compounds were prepared according to the method of Example 40, Step 8 using 3-[(dimethylamino)methyl]-5-(piperidin-4-yloxy)benzonitrile as starting material. LCMS (M+H)$^+$: 666.3

Step 9. 3-[(1-{trans-3-(Cyanomethyl)-3-[4-(7H-pyrrolo[2,3-d]pyrimidin-4-yl)-1H-pyrazol-1-yl] cyclobutyl}piperidin-4-yl)oxy]-5-[(dimethylamino) methyl]benzonitrile The title compounds were prepared according to the method of Example 40, Step 9 using 3-[(1-{trans-3-(cyanomethyl)-3-[4-(7-{[2-(trimethylsilyl)ethoxy]methyl}-7H-pyrrolo[2,3-d]pyrimidin-4-yl)-1H-pyrazol-1-yl] cyclobutyl}piperidin-4-yl)oxy]-5-[(dimethylamino)methyl] benzonitrile as starting materials. LCMS (M+H)$^+$: 536.3.

Example 138

{trans-3-{4-[3-[(dimethylamino)methyl]-5-(trifluoromethyl)phenoxy]piperidin-1-yl}-1-[4-(7H-pyrrolo [2,3-d]pyrimidin-4-yl)-1H-pyrazol-1-yl] cyclobutyl}acetonitrile

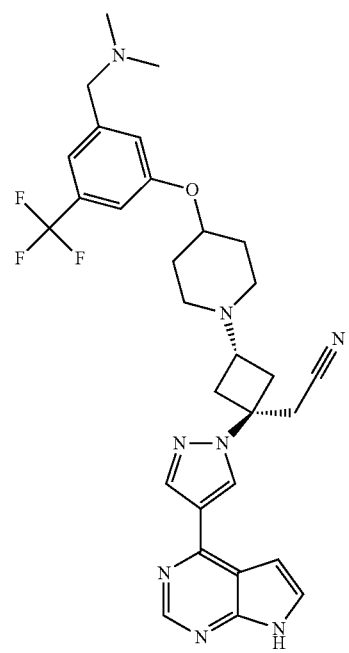 [SMILES: CN(C)Cc1cc(OC2CCN([C@H]3C[C@](CC#N)(n4cc(-c5ncnc6[nH]ccc56)cn4)C3)CC2)cc(C(F)(F)F)c1]

Step 1. Methyl 3-(4,4,5,5-tetramethyl-1,3,2-dioxaborolan-2-yl)-5-(trifluoromethyl)benzoate The mixture of methyl 3-bromo-5-(trifluoromethyl)benzoate (6.72 g, 23.7 mmol), 4,4,5,5,4',4',5'5'-octamethy-[2,2'] bi[1,3,2]dioxaborolayl] (6.63, 26.1 mmol), Pd (dppf) (0.58 g, 0.71 mmol), and potassium acetate (7.0 g, 71 mmol) in dioxane (50 mL) was degassed with $N_2$ and heated at 100° C. for 14 hours. The reaction mixture was cooled to room temperature. The reaction mixture was filtered through a pad of celite and washed with EtOAc. The filtrates were concentrated and the crude residue was purified by flash chromatography on a silica gel column to give the desired product. (7.2 g, 92%). LCMS (M+H)$^+$: 331.1.

Step 2. 3-Hydroxy-5-(trifluoromethyl)benzoic acid

A mixture of copper(II) sulfate pentahydrate (0.43 g, 1.7 mmol), o-phenanthroline (0.62 g, 3.4 mmol), methyl 3-(4,4,5,5-tetramethyl-1,3,2-dioxaborolan-2-yl)-5-(trifluoromethyl)benzoate (5.70 g, 17.3 mmol), and potassium hydroxide (3.42 g, 51.8 mmol) in water (90 mL) was stirred at room temperature open to air overnight. The reaction was acidified with 6 M HCl and diluted with ethyl acetate. The aqueous layer was extracted with ethyl acetate once. The combined organic solutions were washed with brine, dried over $Na_2SO_4$, filtered, and concentrated. The crude was used in the next step without purification.

Step 3. Methyl 3-hydroxy-5-(trifluoromethyl)benzoate

To a solution of 3-hydroxy-5-(trifluoromethyl)benzoic acid (3.56 g, 17.3 mmol) in methanol (110 mL) was added 4.0 M hydrogen chloride in dioxane (110 mL, 460 mmol). The resulting mixture was stirred at room temperature overnight. The solvent was concentrated. The residue was purified by flash chromatography on a silica gel column to give the desired product as white solid.

Step 4. tert-Butyl 4-[3-(methoxycarbonyl)-5-(trifluoromethyl)phenoxy]piperidine-1-carboxylate The title compound was prepared according to the method of Example 40, Step 5 using methyl 3-hydroxy-5-(trifluoromethyl)benzoate as starting material. LCMS (M+H–100)$^+$: 304.0.

Step 5. tert-Butyl 4-[3-(hydroxymethyl)-5-(trifluoromethyl)phenoxy]piperidine-1-carboxylate The title compound was prepared according to the method of Example 137, Step 2 (this is a LiBH$_4$ reduction) using tert-butyl 4-[3-(methoxycarbonyl)-5-(trifluoromethyl)phenoxy]piperidine-1-carboxylate as starting material. LCMS (M+H–56)$^+$: 320.0.

Step 6. tert-Butyl 4-[3-formyl-5-(trifluoromethyl)phenoxy]piperidine-1-carboxylate The title compound was prepared according to the method of Example 137, Step 3 using tert-butyl 4-[3-(methoxycarbonyl)-5-(trifluoromethyl)phenoxy]piperidine-1-carboxylate as starting material. LCMS (M+H–56)$^+$: 318.0.

Step 7. tert-Butyl 4-[3-[(dimethylamino)methyl]-5-(trifluoromethyl)phenoxy]piperidine-1-carboxylate The title compound was prepared according to the method of Example 41, Step 2 using tert-butyl 4-[3-formyl-5-(trifluoromethyl)phenoxy]piperidine-1-carboxylate and dimethylamine as starting materials. LCMS (M+H)$^+$: 403.2.

Step 8. N,N-Dimethyl-1-[3-(piperidin-4-yloxy)-5-(trifluoromethyl)phenyl]methanamine This compound was prepared according to the method of Example 40, Step 7 using tert-butyl 4-[3-[(dimethylamino)methyl]-5-(trifluoromethyl)phenoxy]piperidine-1-carboxylate as starting material. LCMS (M+H)$^+$: 303.1.

Step 9. {trans-3-{4-[3-[(dimethylamino)methyl]-5-(trifluoromethyl)phenoxy]piperidin-1-yl}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile This compound was prepared according to the method of Example 40, Step 8 using N,N-dimethyl-1-[3-(piperidin-4-yloxy)-5-(trifluoromethyl)phenyl]methanamine as starting material. LCMS (M+H)$^+$: 709.3.

Step 10. {trans-3-{4-[3-[(Dimethylamino)methyl]-5-(trifluoromethyl)phenoxy]piperidin-1-yl}-1-[4-(7H-pyrrolo[2,3-d]pyrimidin-4-yl)-1H-pyrazol-1-yl]cyclobutyl}acetonitrile The title compound was prepared according to the method of Example 40, Step 9 sing {trans-3-{4-[3-[(dimethylamino)methyl]-5-(trifluoromethyl)phenoxy]piperidin-1-yl}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile as starting materials. LCMS (M+H)$^+$: 579.2.

Example 139

{trans-3-{4-[3-[(diethylamino)methyl]-5-(trifluoromethyl)phenoxy]piperidin-1-yl}-1-[4-(7H-pyrrolo[2,3-d]pyrimidin-4-yl)-1H-pyrazol-1-yl]cyclobutyl}acetonitrile

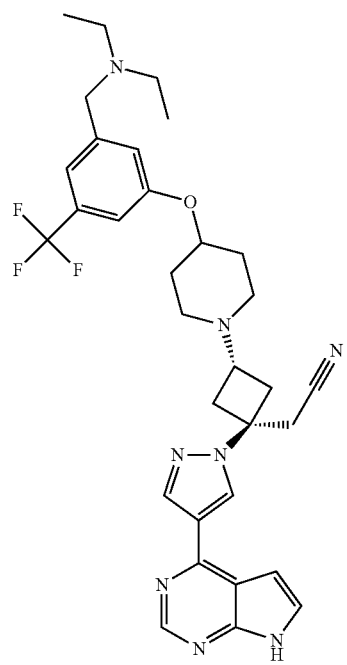 [SMILES: CCN(CC)Cc1cc(OC2CCN([C@H]3C[C@](CC#N)(n4cc(-c5ncnc6[nH]ccc56)cn4)C3)CC2)cc(C(F)(F)F)c1]

239

Step 1. tert-Butyl 4-[3-[(diethylamino)methyl]-5-(trifluoromethyl)phenoxy]piperidine-1-carboxylate trifluoroacetate The title compound was prepared according to the method of Example 41, Step 2 using tert-butyl 4-[3-formyl-5-(trifluoromethyl)phenoxy]piperidine-1-carboxylate and diethylamine as starting materials. LCMS (M+H−100)⁺: 331.2.

Step 2. N N-Ethyl-N-[3-(piperidin-4-yloxy)-5-(trifluoromethyl)benzyl]ethanamine

This compound was prepared according to the method of Example 40, Step 7 using tert-butyl 4-[3-[(diethylamino)methyl]-5-(trifluoromethyl)phenoxy]piperidine-1-carboxylate trifluoroacetate as starting material. LCMS (M+H)⁺: 331.2.

Step 3. {cis-3-{4-[3-[(Diethylamino)methyl]-5-(trifluoromethyl)phenoxy]piperidin-1-yl}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile, {trans-3-{4-[3-[(diethylamino)methyl]-5-(trifluoromethyl)phenoxy]piperidin-1-yl}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile These compounds were prepared according to the method of Example 40, Step 8 using N,N-ethyl-N-[3-(piperidin-4-yloxy)-5-(trifluoromethyl)benzyl]ethanamine as starting material. LCMS (M+H)⁺: 737.3

Step 4. {trans-3-{4-[3-[(diethylamino)methyl]-5-(trifluoromethyl)phenoxy]piperidin-1-yl}-1-[4-(7H-pyrrolo[2,3-d]pyrimidin-4-yl)-1H-pyrazol-1-yl]cyclobutyl}acetonitrile The title compound was prepared according to the method of Example 40, Step 9 using {trans-3-{4-[3-[(diethylamino)methyl]-5-(trifluoromethyl)phenoxy]piperidin-1-yl}-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile as starting materials. LCMS (M+H)⁺: 607.3.

240

Example 140

{trans-3-(4-{3-(difluoromethyl)-5-[(dimethylamino)methyl]phenoxy}piperidin-1-yl)-1-[4-(7H-pyrrolo[2,3-d]pyrimidin-4-yl)-1H-pyrazol-1-yl]cyclobutyl}acetonitrile

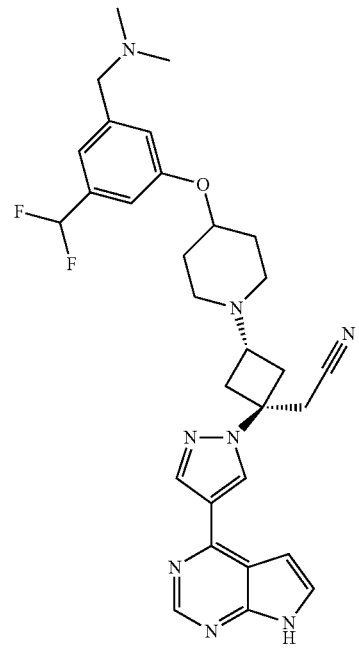 [SMILES: CN(C)Cc1cc(OC2CCN([C@H]3C[C@](CC#N)(n4cc(-c5ncnc6[nH]ccc56)cn4)C3)CC2)cc(C(F)F)c1]

Step 1. tert-Butyl 4-{3-(difluoromethyl)-5-[(dimethylamino)methyl]phenoxy}piperidine-1-carboxylate This compound was prepared according to the method of Example 40, Step 6 using tert-butyl 4-[3-bromo-5-(difluoromethyl)phenoxy]piperidine-1-carboxylate as starting material. LCMS (M+H−100)⁺: 331.2.

Step 2. 1-[3-(Difluoromethyl)-5-(piperidin-4-yloxy)phenyl]-N,N-dimethylmethanamine This compound was prepared according to the method of Example 40, Step 7 using tert-butyl 4-{3-(difluoromethyl)-5-[(dimethylamino)methyl]phenoxy}piperidine-1-carboxylate as starting material. LCMS (M+H)⁺: 331.2.

Step 3. {cis-3-(4-{3-(Difluoromethyl)-5-[(dimethylamino)methyl]phenoxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile, {trans-3-(4-{3-(difluoromethyl)-5-[(dimethylamino)methyl]phenoxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonarile These compounds were prepared according to the method of Example 40, Step 8 using 1-[3-(difluoromethyl)-5-(piperidin-4-yloxy)phenyl]-N,N-dimethylmethanamine as starting material. LCMS (M+H)⁺: 691.3.

Step 4. {trans-3-(4-{3-(Difluoromethyl)-5-[(dimethylamino)methyl]phenoxy}piperidin-1-yl)-1-[4-(7H-pyrrolo[2,3-c]pyrimidin-4-yl)-1H-pyrazol-1-yl]cyclobutyl}acetonarile The title compound was prepared according to the method of Example 40, Step 9 using {trans-3-(4-{3-(difluoromethyl)-5-[(dimethylamino)methyl]phenoxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile as starting materials. $^1$H NMR (300 MHz, DMSO): δ 12.06 (brs, 1H), 8.77 (s, 1H), 8.63 (s, 1H), 8.36 (s, 1H), 7.54 (d, 1H), 6.94 (m, 5H), 4.40 (m, 1H), 3.31 (m, 4H), 3.95 (m, 2H), 2.73 (m, 2H), 2.55 (m, 2H), 2.27 (m, 2H), 2.05 (m, 8H), 1.91 (m, 2H), 1.59 (m, 2H)☐; ; LCMS (M+H)$^+$: 561.3.

Example 141

{trans-3-[4-({6-chloro-4-[(dimethylamino)methyl]pyridin-2-yl}oxy)piperidin-1-yl]-1-[4-(7H-pyrrolo[2,3-d]pyrimidin-4-yl)-1H-pyrazol-1-yl]cyclobutyl}acetonitrile

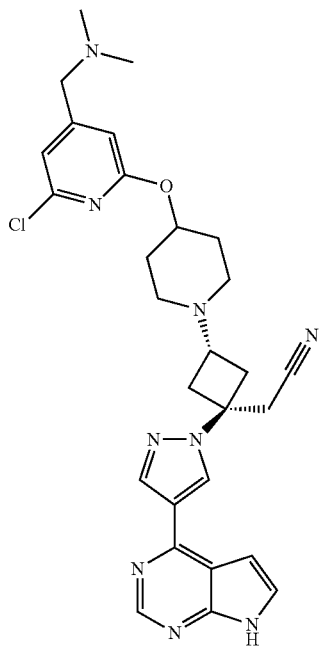 [SMILES: CN(C)Cc1cc(Cl)nc(OC2CCN([C@H]3C[C@](CC#N)(n4cc(-c5ncnc6[nH]ccc56)cn4)C3)CC2)c1]

Step 1. tert-Butyl 4-({6-chloro-4-[(dimethylamino)methyl]pyridin-2-yl}oxy)piperidine-1-carboxylate To a solution of tert-butyl 4-hydroxypiperidine-1-carboxylate (44.2 mg, 0.219 mmol) in DMF (0.7 mL) was added sodium hydride (13.2 mg, 0.329 mmol). After stirring for 30 minutes, 1-(2,6-dichloropyridin-4-yl)-N,N-dimethylmethanamine (45 mg, 0.22 mmol) was added to the reaction vial. The reaction solution was heated at 100° C. overnight. The reaction solution was diluted with methanol and purified with preparative LCMS to give the desired product. LCMS (M+H)$^+$: 370.1.

Step 2. 1-[2-Chloro-6-(piperidin-4-yloxy)pyridin-4-yl]-N,N-dimethylmethanamine This compound was prepared according to the method of Example 40, Step 7 using tert-butyl 4-({6-chloro-4-[(dimethylamino)methyl]pyridin-2-yl}oxy)piperidine-1-carboxylate as starting material. LCMS (M+H)$^+$: 270.1.

Step 3. {cis-3-[4-({6-Chloro-4-[(dimethylamino)methyl]pyridin-2-yl}oxy)piperidin-1-yl]-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile, {trans-3-[4-({6-chloro-4-[(dimethylamino)methyl]pyridin-2-yl}oxy)piperidin-1-yl]-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile These compounds were prepared according to the method of Example 40, Step 8 using 1-[2-chloro-6-(piperidin-4-yloxy)pyridin-4-yl]-N,N-dimethylmethanamine as starting material. LCMS (M+H)$^+$: 676.3

Step 4. {trans-3-(4-{3-(Difluoromethyl)-5-[(dimethylamino)methyl]phenoxy}piperidin-1-yl)-1-[4-(7H-pyrrolo[2,3-d]pyrimidin-4-yl)-1H-pyrazol-1-yl]cyclobutyl}acetonitrile The title compound was prepared according to the method of Example 40, Step 9 using {trans-3-[4-({6-chloro-4-[(dimethylamino)methyl]pyridin-2-yl}oxy)piperidin-1-yl]-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile as starting materials. $^1$H NMR (400 MHz, DMSO): δ; LCMS (M+H)$^+$: 546.3.

Example 142

{trans-3-(4-{[6-[(dimethylamino)methyl]-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile

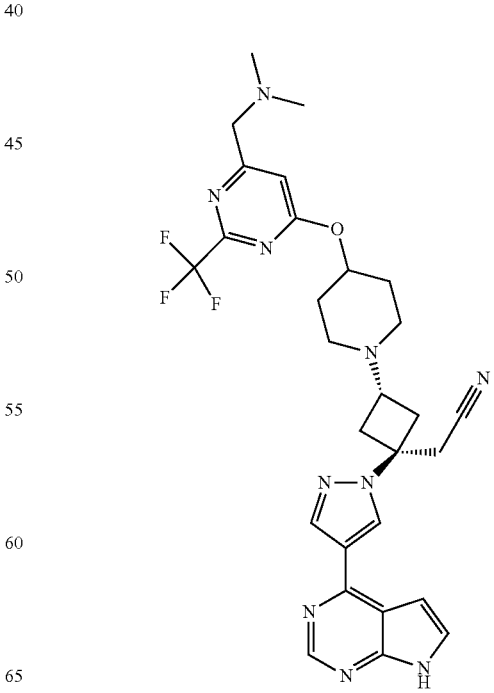

Step 1. tert-Butyl 4-{[6-chloro-2-(trifluoromethyl) pyrimidin-4-yl]oxy}piperidine-1-carboxylate In a reaction flask, tert-butyl 4-hydroxypiperidine-1-carboxylate (2.02 g, 10.0 mmol) and 4,6-dichloro-2-(trifluoromethyl)pyrimidine (2.18 g, 10.0 mmol) were dissolved in THF (19.7 mL) and cooled to 0° C. Sodium hydride (0.603 g, 15.1 mmol) was added and then the mixture was stirred for 30 minutes at 0° C. and at 25° C. for another 16 hours. The reaction was quenched with water, and was extracted with ethyl acetate and the organic extracts were washed with water, brine, dried over MgSO$_4$, filtered and concentrated in vacuo. The residue was purified by silica gel chromatography to give the product.

Step 2. tert-Butyl 4-{[2-(trifluoromethyl)-6-vinylpyrimidin-4-yl]oxy}piperidine-1-carboxylate To a solution of tert-butyl 4-{[6-chloro-2-(trifluoromethyl)pyrimidin-4-yl]oxy}piperidine-1-carboxylate (0.742 g, 1.94 mmol) in DMF (8.7 mL) was added (2-ethenyl)tri-n-butyltin (0.682 mL, 2.33 mmol) and tetrakis(triphenylphosphine)palladium(0) (112 mg, 0.0972 mmol). The reaction solution was stirred at 65° C. overnight. The reaction solution was diluted with ethyl acetate and saturated KF solution. The aqueous layer was extracted with ethyl acetate three times. The combined organic solutions were dried over Na$_2$SO$_4$, 6569 filtered and concentrated. The residue was purified with silica gel column to give the desired product as light brown oil. LCMS (M+H)$^+$: 374.2.

Step 3. tert-Butyl 4-{[6-(1,2-dihydroxyethyl)-2-(trifluoromethyl)pyrimidin-4-yl]oxy}piperidine-1-carboxylate To a solution of tert-butyl 4-{[2-(trifluoromethyl)-6-vinylpyrimidin-4-yl]oxy}piperidine-1-carboxylate (614 mg, 1.64 mmol) in methanol (7 mL) and tert-butyl alcohol (5.2 mL) was added N-methylmorpholine N-oxide (212 mg, 1.81 mmol) and water (5.2 mL). To this solution was then added osmium tetraoxide (20.9 mg, 0.0822 mmol). After stirring for 3 hours, another equivalent of N-methylmorpholine N-oxide was added. The reaction was stirred at room temperature overnight. The solution was concentrated and diluted with water and extracted with ethyl acetate twice, washed with brine, dried over Na$_2$SO$_4$, filtered and concentrated. The crude was purified by flash chromatography on a silica gel column to give the desired product. LCMS (M+H)$^+$: 408.2.

Step 4. tert-Butyl 4-{[6-formyl-2-(trifluoromethyl) pyrimidin-4-yl]oxy}piperidine-1-carboxylate To a solution of tert-butyl 4-{[6-(1,2-dihydroxyethyl)-2-(trifluoromethyl)pyrimidin-4-yl]oxy}piperidine-1-carboxylate (542 mg, 1.33 mmol) in THF (10. mL) and water (6.0 mL) was added acetic acid (20. μL, 0.35 mmol) and sodium periodate (854 mg, 3.99 mmol) at −5° C. After stirring for 30 minutes, the reaction mixture was diluted with ether and water. The aqueous layer was extracted with ethyl acetate once and the combined organic layers were washed with brine and dried over anhydrous Na$_2$SO$_4$. The organic solvent was removed in vacuo and the residue was purified with silica gel column to give the desired product as colorless oil. LCMS (M+H)$^+$: 376.1.

Step 5. tert-Butyl 4-{[6-[(dimethylamino)methyl]-2-(trifluoromethyl)pyrimidin-4-yl]oxy}piperidine-1-carboxylate The title compound was prepared according to the method of Example 41, Step 2 using tert-butyl 4-{[6-formyl-2-(trifluoromethyl)pyrimidin-4-yl]oxy}piperidine-1-carboxylate and dimethylamine as starting materials. LCMS (M+H−100)$^+$: 405.2.

Step 6. N,N-Dimethyl-1-[6-(piperidin-4-yloxy)-2-(trifluoromethyl)pyrimidin-4-yl]methanamine This compound was prepared according to the method of Example 40, Step 7 using tert-butyl 4-{[6-[(dimethylamino)methyl]-2-(trifluoromethyl)pyrimidin-4-yl]oxy}piperidine-1-carboxylate as starting material. LCMS (M+H)$^+$: 305.1.

Step 7. {cis-3-(4-{[6-[(Dimethylamino)methyl]-2-(trifluoromethyl)pyrimidin-4-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile, {trans-3-(4-{[6-[(dimethylamino)methyl]-2-(trifluoromethyl)pyrimidin-4-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile These compounds were prepared according to the method of Example 40, Step 8 using N,N-dimethyl-1-[6-(piperidin-4-yloxy)-2-(trifluoromethyl)pyrimidin-4-yl]methanamine as starting material. LCMS (M+H)$^+$: 711.3

Step 8. {trans-3-(4-{[6-[(Dimethylamino)methyl]-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile The title compound was prepared according to the method of Example 40, Step 9 using {trans-3-(4-{[6-[(dimethylamino)methyl]-2-(trifluoromethyl)pyrimidin-4-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile as starting materials. $^1$H NMR (400 MHz, CD$_3$OD): δ 8.74 (s, 1H), 8.67 (s, 1H), 8.41 (s, 1H), 7.52 (d, 1H), 7.06 (s, 1H), 6.99 (d, 1H), 5.26 (m, 1H), 3.59 (m, 2H), 3.30 (m, 1H), 3.09 (m, 2H), 2.96 (m, 2H), 2.76 (m, 2H), 2.49 (m, 2H), 2.30 (m, 8H), 2.14 (m, 2H), 1.91 (m, 2H); LCMS (M+H)$^+$: 581.3.

Example 143

{trans-3-(4-{[6-[(ethylamino)methyl]-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile

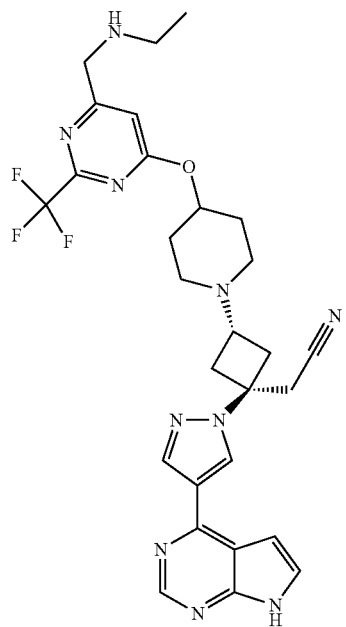 [SMILES: CCNCc1cc(OC2CCN([C@H]3C[C@](CC#N)(n4cc(-c5ncnc6[nH]ccc56)cn4)C3)CC2)nc(C(F)(F)F)n1]

Step 1. tert-Butyl 4-{[6-[(ethylamino)methyl]-2-(trifluoromethyl)pyrimidin-4-yl]oxy}piperidine-1-carboxylate This compound was prepared according to the method of Example 41, Step 2 using tert-butyl 4-{[6-formyl-2-(trifluoromethyl)pyrimidin-4-yl]oxy}piperidine-1-carboxylate and ethylamine as starting materials. LCMS (M+H)$^+$: 405.2.

Step 2. N-{[6-(Piperidin-4-yloxy)-2-(trifluoromethyl)pyrimidin-4-yl]methyl}ethanamine This compound was prepared according to the method of Example 40, Step 7 using tert-butyl 4-{[6-[(ethylamino)methyl]-2-(trifluoromethyl)pyrimidin-4-yl]oxy}piperidine-1-carboxylate as starting material. LCMS (M+H)$^+$: 305.2.

Step 3. {cis-3-(4-{[6-[(Ethylamino)methyl]-2-(trifluoromethyl)pyrimidin-4-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonarile, {trans-3-(4-{[6-[(ethylamino)methyl]-2-(trifluoromethyl)pyrimidin-4-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonarile These compounds were prepared according to the method of Example 40, Step 8 using N-{[6-(piperidin-4-yloxy)-2-(trifluoromethyl)pyrimidin-4-yl]methyl}ethanamine as starting material. LCMS (M+H)$^+$: 711.3.

Step 4. {trans-3-(4-{[6-[(Ethylamino)methyl]-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonarile The title compounds were prepared according to the method of Example 40, Step 9 using {trans-3-(4-{[6-[(ethylamino)methyl]-2-(trifluoromethyl)pyrimidin-4-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile as starting materials. LCMS (M+H)$^+$: 581.3.

Example 144

{trans-3-(4-{[6-[(3-hydroxyazetidin-1-yl)methyl]-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile

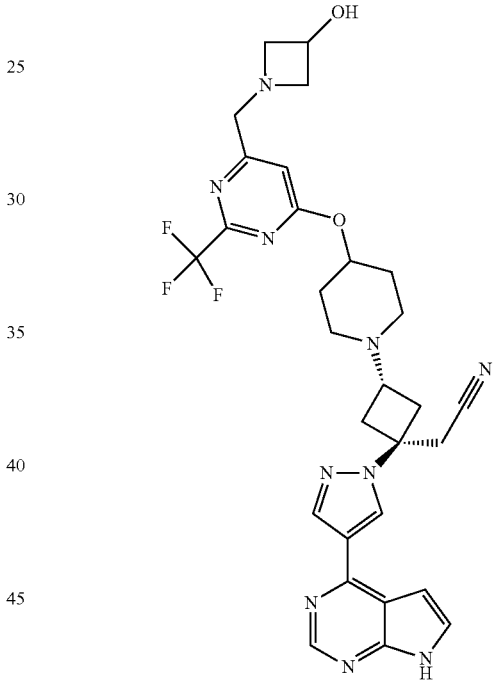

Step 1. tert-Butyl 4-{[6-[(3-hydroxyazetidin-1-yl)methyl]-2-(trifluoromethyl)pyrimidin-4-yl]oxy}piperidine-1-carboxylate This compound was prepared according to the method of Example 41, Step 2 using tert-butyl 4-{[6-formyl-2-(trifluoromethyl)pyrimidin-4-yl]oxy}piperidine-1-carboxylate and azetidin-3-ol as starting materials. LCMS (M+H)$^+$: 433.3.

Step 2. 1-{[6-(Piperidin-4-yloxy)-2-(trifluoromethyl)pyrimidin-4-yl]methyl}azetidin-3-ol This compound was prepared according to the method of Example 40, Step 7 using tert-butyl 4-{[6-[(3-hydroxyazetidin-1-yl)methyl]-2-(trifluoromethyl)pyrimidin-4-yl]oxy}piperidine-1-carboxylate as starting material. LCMS (M+H)$^+$: 333.1.

Step 3. {Cis-3-(4-{[6-[(3-Hydroxyazetidin-1-yl)
methyl]-2-(trifluoromethyl)pyrimidin-4-yl]
oxy}piperidin-1-yl)-1-[4-(7-{[2-(trimethylsilyl)
ethoxy]methyl}-7H-pyrrolo[2,3-d]pyrimidin-4-yl)-
1H-pyrazol-1-yl]cyclobutyl}acetonarile, {trans-3-(4-
{[6-[(3-hydroxyazetidin-1-yl)methyl]-2-
(trifluoromethyl)pyrimidin-4-yl]oxy}piperidin-1-yl)-
1-[4-(7-{[2-(trimethylsilyl)ethoxy]methyl}-7H-
pyrrolo[2,3-d]pyrimidin-4-yl)-1H-pyrazol-1-yl]
cyclobutyl}acetonarile These compounds were prepared according to the method of Example 40, Step 8 using 1-{[6-(piperidin-4-yloxy)-2-(trifluoromethyl)pyrimidin-4-yl]methyl}azetidin-3-ol as starting material. LCMS (M+H)⁺: 739.3.

Step 4. {trans-3-(4-{[6-[(3-Hydroxyazetidin-1-yl)
methyl]-2-(trifluoromethyl)pyrimidin-4-yl]
oxy}piperidin-1-yl)-1-[4-(7H-pyrrolo[2,3-d]pyrimi-
din-4-yl)-1H-pyrazol-1-yl]cyclobutyl}acetonitrile The title compound was prepared according to the method of Example 40, Step 9 using {trans-3-(4-{[6-[(3-hydroxyazetidin-1-yl)methyl]-2-(trifluoromethyl)pyrimidin-4-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile as starting materials. LCMS (M+H)⁺: 609.2.

Example 145

{trans-3-(4-{[6-methyl-2-(trifluoromethyl)pyrimi-
din-4-yl]oxy}piperidin-1-yl)-1-[4-(7H-pyrrolo[2,3-d]
pyrimidin-4-yl)-1H-pyrazol-1-yl]
cyclobutyl}acetonitrile

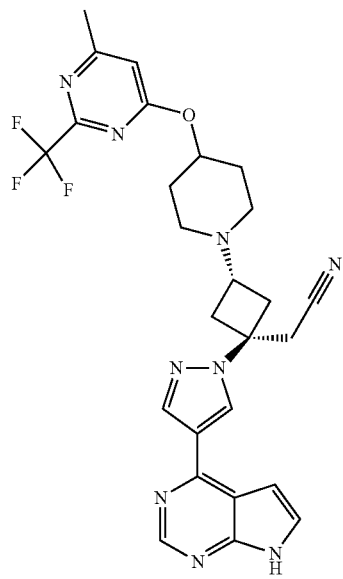 [SMILES: Cc1cc(OC2CCN([C@H]3C[C@](CC#N)(n4cc(-c5ncnc6[nH]ccc56)cn4)C3)CC2)nc(C(F)(F)F)n1]

Step 1.
6-Methyl-2-(trifluoromethyl)pyrimidin-4(3H)-one

To a solution of 2,2,2-trifluoroethanimidamide (3.02 g, 22.9 mmol) and 3-oxobutanoic acid, methyl ester (2.60 mL, 24.0 mmol) in methanol (25 mL) was added 25 wt % sodium methoxide (10.5 mL, 45.8 mmol). The reaction solution was stirred at room temperature overnight. The solvent was removed in vacuo and diluted with ethyl acetate and 5 M HCl. The aqueous layer was extracted with ethyl acetate once. The organic solutions were washed with brine, dried over sodium sulfate, filtered and concentrated. The residue was purified by flash chromatography on a silica gel column to give the desired product as white solid.

Step 2. tert-Butyl 4-{[6-methyl-2-(trifluoromethyl)
pyrimidin-4-yl]oxy}piperidine-1-carboxylate The title compound was prepared according to the method of Example 40, Step 5 using 6-methyl-2-(trifluoromethyl)pyrimidin-4(3H)-one as starting material. LCMS (M+H)⁺: 362.2.

Step 3. 4-Methyl-6-(piperidin-4-yloxy)-2-(trifluo-
romethyl)pyrimidine trifluoroacetate This compound was prepared according to the method of Example 40, Step 7 using tert-butyl 4-{[6-methyl-2-(trifluoromethyl)pyrimidin-4-yl]oxy}piperidine-1-carboxylate as starting material. LCMS (M+H)⁺: 333.1.

Step 4. {cis-3-(4-{[6-Methyl-2-(trifluoromethyl)
pyrimidin-4-yl]oxy}piperidin-1-yl)-1-[4-(7-{[2-
(trimethylsilyl)ethoxy]methyl}-7H-pyrrolo[2,3-d]
pyrimidin-4-yl)-1H-pyrazol-1-yl]
cyclobutyl}acetonitrile, {trans-3-(4-{[6-methyl-2-
(trifluoromethyl)pyrimidin-4-yl]oxy}piperidin-1-yl)-
1-[4-(7-{[2-(trimethylsilyl)ethoxy]methyl}-7H-
pyrrolo[2,3-d]pyrimidin-4-yl)-1H-pyrazol-1-yl]
cyclobutyl}acetonitrile These compounds were prepared according to the method of Example 40, Step 8 using 4-methyl-6-(piperidin-4-yloxy)-2-(trifluoromethyl)pyrimidine trifluoroacetate as starting material. LCMS (M+H)⁺: 668.3.

Step 5. {trans-3-(4-{[6-Methyl-2-(trifluoromethyl)
pyrimidin-4-yl]oxy}piperidin-1-yl)-1-[4-(7H-pyrrolo
[2,3-d]pyrimidin-4-yl)-1H-pyrazol-1-yl]
cyclobutyl}acetonitrile The title compound was prepared according to the method of Example 40, Step 9 using {trans-3-(4-{[6-methyl-2-(trifluoromethyl)pyrimidin-4-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile as starting materials. LCMS (M+H)⁺: 538.2.

Example 146

{trans-3-(4-{[6-(hydroxymethyl)-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile

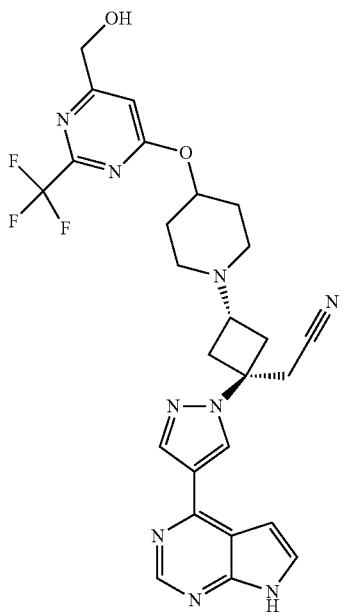 [SMILES: N#CC[C@]1(n2cc(-c3ncnc4[nH]ccc34)cn2)C[C@H](N2CCC(Oc3cc(CO)nc(C(F)(F)F)n3)CC2)C1]

Step 1. tert-Butyl 4-{[6-(hydroxymethyl)-2-(trifluoromethyl)pyrimidin-4-yl]oxy}piperidine-1-carboxylate To a solution of tert-butyl 4-{[6-formyl-2-(trifluoromethyl)pyrimidin-4-yl]oxy}piperidine-1-carboxylate (202 mg, 0.538 mmol) in methanol (2.0 mL) was added sodium tetrahydroborate (20.4 mg, 0.538 mmol). The reaction solution was stirred at room temperature for 4 hours. The reaction was quenched with water and extracted with ethyl acetate (2×). The organic solutions were washed with brine, dried over $Na_2SO_4$, filtered and concentrated. The crude was purified with silica gel column to give the desired product. LCMS (M+H)$^+$: 378.2.

Step 2. [6-(Piperidin-4-yloxy)-2-(trifluoromethyl)pyrimidin-4-yl]methanol

This compound was prepared according to the method of Example 40, Step 7 using tert-butyl 4-{[6-(hydroxymethyl)-2-(trifluoromethyl)pyrimidin-4-yl]oxy}piperidine-1-carboxylate as starting material. LCMS (M+H)$^+$: 278.2.

Step 3. {cis-3-(4-{[6-(Hydroxymethyl)-2-(trifluoromethyl)pyrimidin-4-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile, {trans-3-(4-{[6-(hydroxymethyl)-2-(trifluoromethyl)pyrimidin-4-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile These compounds were prepared according to the method of Example 40, Step 8 using [6-(piperidin-4-yloxy)-2-(trifluoromethyl)pyrimidin-4-yl]methanol as starting material. LCMS (M+H)$^+$: 684.3.

Step 4. {trans-3-(4-{[6-(Hydroxymethyl)-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile The title compound was prepared according to the method of Example 40, Step 9 using {trans-3-(4-{[6-(hydroxymethyl)-2-(trifluoromethyl)pyrimidin-4-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile as starting materials. LCMS (M+H)$^+$: 554.2.

Example 147

{trans-3-(4-{[6-(aminomethyl)-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile

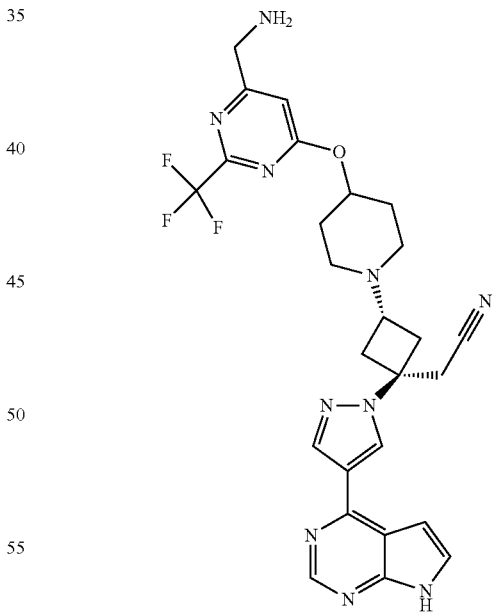

Step 1. [6-[(1-{trans-3-(Cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperidin-4-yl)oxy]-2-(trifluoromethyl)pyrimidin-4-yl]methyl methanesulfonate To a solution of {trans-3-(4-{[6-(hydroxymethyl)-2-(trifluoromethyl)pyrimidin-4-yl]oxy}piperidin-1-yl)-1-[4-(7-

{[2-(trimethylsilyl)ethoxy]methyl}-7H-pyrrolo[2,3-d]pyrimidin-4-yl)-1H-pyrazol-1-yl]cyclobutyl}acetonitrile (98.5 mg, 0.144 mmol) in DCM (1.0 mL) was added methanesulfonyl chloride (13.4 μL, 0.173 mmol) and N,N-diisopropylethylamine (37.6 μL, 0.216 mmol) at 0° C. The solution was stirred at same temperature for 1 hour. The reaction solution was diluted with DCM and water. The organic layer was washed with brine, dried over Na₂SO₄, filtered and concentrated to give the desired product. The crude was used in the next without purification. LCMS (M+H)⁺: 762.2.

Step 2. {trans-3-(4-{[6-(Aminomethyl)-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile To a vial charged with 6-[(1-{trans-3-(cyanomethyl)-3-[4-(7-{[2-(trimethylsilyl)ethoxy]methyl}-7H-pyrrolo[2,3-d]pyrimidin-4-yl)-1H-pyrazol-1-yl]cyclobutyl}piperidin-4-yl)oxy]-2-(trifluoromethyl)pyrimidin-4-yl]methyl methanesulfonate (23 mg, 0.030 mmol) was added 7.0 M Ammonia in methanol (0.6 mL, 4 mmol). After stirring for 2 h at room temperature, the mixture was concentrated. The residue was treated under the conditions was used in Example 40, Step 9 to give the desired product. LCMS (M+H)⁺: 553.2.

Examples 148-150

The examples in the table below were made by procedures analogous to those for producing Example 147.

| Ex. | Structure | Name | M + H |
|---|---|---|---|
| 148 | | {trans-3-(4-{[6-(pyrrolidin-1-ylmethyl)-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile | 607.3 |
| 149 | 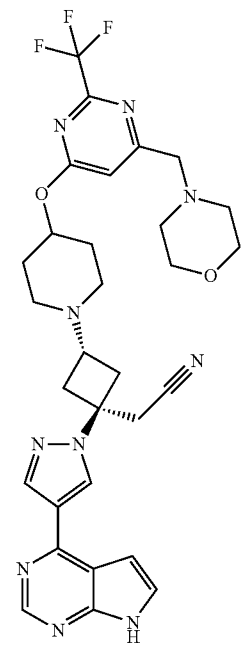 [SMILES: N#CC[C@]1(n2cc(-c3ncnc4[nH]ccc34)cn2)C[C@H](N2CCC(Oc3cc(CN4CCOCC4)nc(C(F)(F)F)n3)CC2)C1] | {trans-3-(4-{[6-(morpholin-4-ylmethyl)-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile | 623.3 |
| 150 | 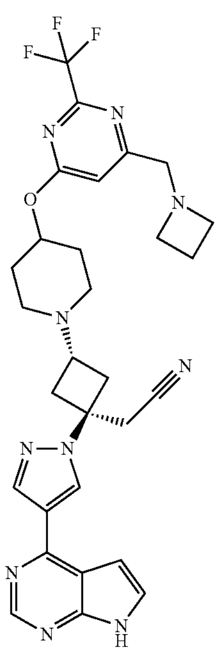 [SMILES: N#CC[C@]1(n2cc(-c3ncnc4[nH]ccc34)cn2)C[C@H](N2CCC(Oc3cc(CN4CCC4)nc(C(F)(F)F)n3)CC2)C1] | {cis-3-(4-{[6-(azetidin-1-ylmethyl)-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile | 593.3 |

Example 151

{trans-3-(4-{[4-methyl-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

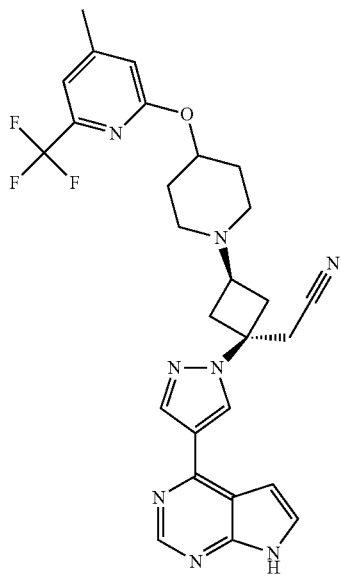 [SMILES: Cc1cc(OC2CCN([C@H]3C[C@@](CC#N)(n4cc(-c5ncnc6[nH]ccc56)cn4)C3)CC2)nc(C(F)(F)F)c1]

Step 1. 4-Methyl-6-(trifluoromethyl)-2H-pyran-2-one

To a solution of trifluoroacetic anhydride (10.63 g, 50.61 mmol) and 3,3-dimethylacryloyl chloride (5.0 g, 42 mmol) in chloroform (85 mL) at 0° C. was added triethylamine (12.91 mL, 92.60 mmol). The resulting reaction mixture was stirred at same temperature for 1 h, then allowed to warm to room temperature overnight. The reaction solution was washed with water (2×), saturated sodium bicarbonate, water, and brine, and then dried over $Na_2SO_4$, filtered and concentrated. The crude residue was used in next step.

Step 2. 4-Methyl-6-(trifluoromethyl)pyridin-2(1H)-one

To a solution of crude 4-methyl-6-(trifluoromethyl)-2H-pyran-2-one (28.8 g, 162 mmol) in acetic acid (330 mL) was added ammonium acetate (25.0 g, 324 mmol). The reaction solution was heated at 120° C. over weekend. The solvent was removed in vacuo. The residue was diluted with ethyl acetate and washed with saturated $NaHCO_3$ and brine, dried over $Na_2SO_4$, filtered and concentrated. The crude was purified with pad silica gel. The solvent was removed. The solid was washed with 10:1 hexanes/ethyl acetate to give the desired product as white solid. LCMS (M+H)$^+$: 178.0.

Step 3. tert-Butyl 4-{[4-methyl-6-(trifluoromethyl)pyridin-2-yl]oxy}piperidine-1-carboxylate The title compound was prepared according to the method of Example 40, Step 5 using 4-methyl-6-(trifluoromethyl)pyridin-2(1H)-one as starting material. LCMS (M+H−56)$^+$: 305.1.

Step 4. 4-Methyl-6-(piperidin-4-yloxy)-2-(trifluoromethyl)pyridine

This compound was prepared according to the method of Example 40, Step 7 using tert-butyl 4-{[4-methyl-6-(trifluoromethyl)pyridin-2-yl]oxy}piperidine-1-carboxylate as starting material. LCMS (M+H)$^+$: 261.1.

Step 5. {cis-3-(4-{[4-Methyl-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile, {trans-3-(4-{[4-methyl-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile These compounds were prepared according to the method of Example 40, Step 8 using 4-methyl-6-(piperidin-4-yloxy)-2-(trifluoromethyl)pyridine as starting material. LCMS (M+H)$^+$: 667.3.

Step 6. {trans-3-(4-{[4-Methyl-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile The title compound was prepared according to the method of Example 40, Step 9 using {trans-3-(4-{[4-methyl-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile as starting materials. LCMS (M+H)$^+$: 537.2.

Example 152

4-{trans-3-(Cyanomethyl)-3-[4-(7H-pyrrolo[2,3-d]pyrimidin-4-yl)-1H-pyrazol-1-yl]cyclobutyl}-N-[2,2,2-trifluoro-1-(trifluoromethyl)ethyl]piperazine-1-carboxamide

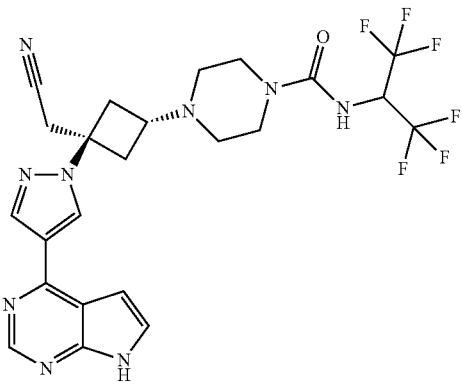 [SMILES: N#CC[C@]1(n2cc(-c3ncnc4[nH]ccc34)cn2)C[C@H](N2CCN(C(=O)NC(C(F)(F)F)C(F)(F)F)CC2)C1]

Step 1. 3,3,3-Trifluoro-2-(trifluoromethyl)propanoyl chloride 3,3,3-Trifluoro-2-(trifluoromethyl)propanoic acid (4.63 g, 23.6 mmol) and phosphorus pentachloride (5.21 g, 25.0 mmol) were stirred for 1 minute, solids were mostly dissolved. The mixture was refluxed for 2 hours and then cooled to room temperature. The acid chloride was isolated by fractional distillation: oil temp: 100-130 C.; vapor temp: 30-35 C. Collected 3.9 g colorless liquid (77% yield). ¹H NMR (300 MHz, CDCl₃): δ 4.45 (m, 1H).

Step 2. 1,1,1,3,3,3-Hexafluoro-2-isocyanatopropane

Sodium azide (5.0 g, 77 mmol) in water (15 mL, 830 mmol) and 1,3-dimethyl-benzene (10.0 mL, 81.8 mmol) at 0° C. were added a solution of 3,3,3-trifluoro-2-(trifluoromethyl)propanoyl chloride (1.0 mL, 7.6 mmol) in 1,3-dimethyl-benzene (5 mL, 40 mmol) over 1 minute. After 1 hour, the ice bath was removed. After stirring for 3 hours at room temperature, the organic phase was separated and was dried to give the acyl azide intermediate in xylene. The azide solution was heated at 70° C. for 1 hour to give the isocyanate as a solution in xylene.

Step 3. 4-(3-(Cyanomethyl)-3-(4-(7-((2-(trimethylsilyl)ethoxy)methyl)-7H-pyrrolo[2,3-d]pyrimidin-4-yl)-1H-pyrazol-1-yl)cyclobutyl)-N-(1,1,1,3,3,3-hexafluoropropan-2-yl)piperazine-1-carboxamide To a solution of {3-piperazin-1-yl-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (0.10 g, 0.20 mmol) in methylene chloride (5 mL, 80 mmol) was added. 0.21 M 1,1,1,3,3,3-hexafluoro-2-isocyanatopropane in m-xylene (1.2 mL, 0.24 mmol) was added, followed by N,N-diisopropylethylamine (71 μL, 0.41 mmol). The reaction was stirred overnight. The reaction was rotovaped and ethyl acetate was added, washed with sat. NH₄Cl (×2), sat. NaHCO₃, and sat. NaCl. The extracts were dried and the solvent removed by rotary evaporation to give 164 mg of an orange oil. The crude oil was purified by column chromatography on 40 g silica gel using a gradient of 0-8% MeOH/DCM, 0-0.8% NH₄Cl. The product was collected as 82 mg of a glass (59% yield). LCMS (M+1): 586.

Step 4. 4-{trans-3-(Cyanomethyl)-3-[4-(7H-pyrrolo[2,3-d]pyrimidin-4-yl)-1H-pyrazol-1-yl]cyclobutyl}-N-[2,2,2-trifluoro-1-(trifluoromethyl)ethyl]piperazine-1-carboxamide A solution of 4-(3-(cyanomethyl)-3-(4-(7-((2-(trimethylsilyl)ethoxy)methyl)-7H-pyrrolo[2,3-d]pyrimidin-4-yl)-1H-pyrazol-1-yl)cyclobutyl)-N-(1,1,1,3,3,3-hexafluoropropan-2-yl)piperazine-1-carboxamide in 3 mL DCM and 3 mL TFA was stirred for 1 hour. The solvent was removed by rotary evaporation and the residue was stirred in 3 mL MeOH and 0.3 mL ethylenediamine for 0.5 hour. The reaction purified by LCMS (C18 column eluting with a gradient MeCN/H₂O containing 0.15% NH₄OH at 5 mL/min) to give 43 mg white solid (64% yield). ¹H NMR (400 MHz, dmso) δ 12.12 (Br, 1H), 8.81 (s, 1H), 8.68 (s, 1H), 8.41 (s, 1H), 7.80 (d, J=9.3 Hz, 1H), 7.59 (d, J=3.6 Hz, 1H), 7.06 (d, J=3.6 Hz, 1H), 5.69 (q, J=8.0 Hz, 1H), 3.46-3.39 (m, 5H), 3.05-2.95 (m, 2H), 2.78 (t, J=7.3 Hz, 1H), 2.40-2.30 (m, 2H), 2.27 (s, 3H). LCMS (M+1): 556.

Example 153

{trans-3-(4-{[4-{[(2-hydroxy-1,1-dimethylethyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

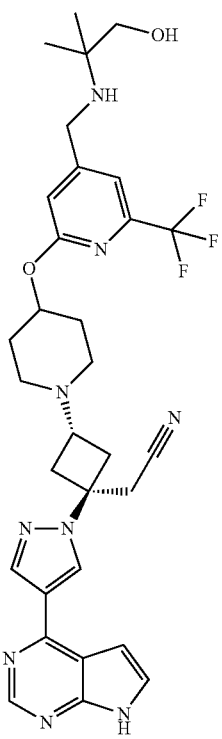 [SMILES: CC(C)(CO)NCc1cc(OC2CCN([C@H]3C[C@](CC#N)(n4cc(-c5ncnc6[nH]ccc56)cn4)C3)CC2)nc(C(F)(F)F)c1]

This compound was prepared according to the method of Example 127, using {trans-3-(4-{[4-(hydroxymethyl)-6-(trifluoromethyl)pyridin-2-yl]oxy}piperidin-1-yl)-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (25 mg, 0.037 mmol, Peak 1 from Example 123, Step E), N,N-diisopropylethylamine (13 μL, 0.073 mmol) and methanesulphonic anhydride (8.9 mg, 0.051 mmol) in methylene chloride (0.50 mL), followed by 2-amino-2-methyl-1-propanol (52 μL, 0.55 mmol, Fluka) in tetrahydrofuran (0.50 mL) at 50° C. for 1 hour, followed by deprotection (first using 1:1 TFA:DCM, followed by evaporation and then ethylenediamine (0.4 mL) in methanol (2 mL)). Purification under the conditions of Example 127 afforded product as the free base (11 mg, 48%). ¹H NMR (400 MHz, dmso) δ 12.13 (br s, 1H), 8.83 (s, 1H), 8.69 (s, 1H), 8.42 (s, 1H), 7.60 (d, J=3.6 Hz, 1H), 7.42 (s, 1H), 7.08 (d, J=3.6 Hz, 1H), 7.06 (s, 1H), 5.04-4.91 (m, 1H), 4.58 (t, J=5.5 Hz, 1H), 3.71 (s, 2H), 3.42 (s, 2H), 3.20 (d, J=5.0 Hz, 2H), 3.10-2.93 (m, 2H), 2.81 (tt, J=7.4, 7.4 Hz, 1H), 2.70-2.57 (br m, 2H), 2.42-2.28 (m, 2H), 2.21-2.10 (br m, 2H), 2.06-1.95 (br m, 2H), 1.73-1.62 (br m, 2H), 0.95 (s, 6H); ¹⁹F NMR (376 MHz, dmso) δ −67.25 (s); LCMS (M+H)⁺: 624.3.

Example 154

{trans-3-(4-{[4-{[(2-hydroxyethyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

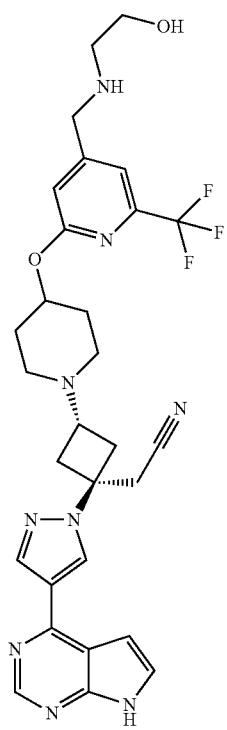 [SMILES: N#CC[C@]1(n2cc(-c3ncnc4[nH]ccc34)cn2)C[C@H](N2CCC(Oc3cc(CNCCO)cc(C(F)(F)F)n3)CC2)C1]

This compound was prepared according to Example 153, using ethanolamine (33 µL, 0.55 mmol, Aldrich) in the displacement step (14 mg, 64%). $^1$H NMR (400 MHz, dmso) δ 12.13 (br s, 1H), 8.83 (s, 1H), 8.69 (s, 1H), 8.42 (s, 1H), 7.60 (d, J=3.6 Hz, 1H), 7.42 (s, 1H), 7.08 (d, J=3.6 Hz, 1H), 7.04 (s, 1H), 5.22-4.61 (m, 1H), 4.50 (t, J=5.4 Hz, 1H), 3.76 (s, 2H), 3.47-3.42 (m, 2H), 3.42 (s, 2H), 3.10-2.95 (m, 2H), 2.81 (tt, J=7.4, 7.5 Hz, 1H), 2.72-2.56 (br m, 2H), 2.55-2.50 (m, 2H), 2.41-2.23 (m, 2H), 2.22-2.08 (br m, 2H), 2.06-1.93 (br m, 2H), 1.75-1.60 (br m, 2H); $^{19}$F NMR (376 MHz, dmso) δ −67.28 (s); LCMS (M+H)$^+$: 596.3.

Example 155

{trans-3-(4-{[4-{[(3-hydroxypropyl)amino]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

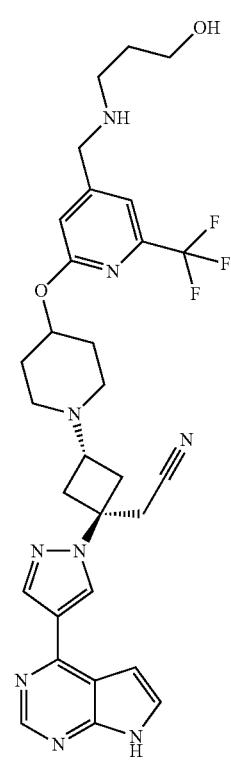 [SMILES: N#CC[C@]1(n2cc(-c3ncnc4[nH]ccc34)cn2)C[C@H](N2CCC(Oc3cc(CNCCCO)cc(C(F)(F)F)n3)CC2)C1]

The procedure of Example 153 was followed, using 3-amino-1-propanol (42 µL, 0.55 mmol, Aldrich) overnight at room temperature (13 mg, 58%). $^1$H NMR (400 MHz, dmso) δ 12.13 (br s, 1H), 8.83 (s, 1H), 8.69 (s, 1H), 8.42 (s, 1H), 7.60 (d, J=3.6 Hz, 1H), 7.42 (s, 1H), 7.08 (d, J=3.6 Hz, 1H), 7.03 (s, 1H), 5.13-4.67 (m, 1H), 4.41 (br s, 1H), 3.72 (s, 2H), 3.49-3.38 (m, 4H), 3.10-2.94 (m, 2H), 2.81 (tt, J=7.51, 7.52 Hz, 1H), 2.72-2.55 (m, 2H), 2.52-2.47 (m, 2H), 2.41-2.27 (m, 2H), 2.23-2.08 (br m, 2H), 2.07-1.94 (br m, 2H), 1.80-1.61 (m, 2H), 1.56 (tt, J=6.6, 6.7 Hz, 2H); $^{19}$F NMR (376 MHz, dmso) δ −67.28 (s); LCMS (M+H)$^+$: 610.1.

Example 156

{trans-3-(4-{[4-(azetidin-1-ylmethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

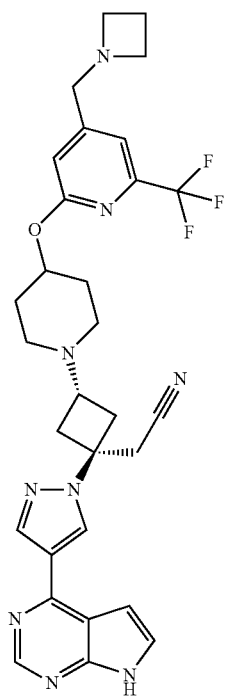 [SMILES: N#CC[C@]1(n2cc(-c3ncnc4[nH]ccc34)cn2)C[C@H](N2CCC(Oc3cc(CN4CCC4)cc(C(F)(F)F)n3)CC2)C1]

The procedure of Example 153 was followed, using azetidine (37 μL, 0.55 mmol, Aldrich) overnight at room temperature (9 mg, 40%). ¹H NMR (400 MHz, dmso) δ 12.13 (br s, 1H), 8.83 (s, 1H), 8.69 (s, 1H), 8.42 (s, 1H), 7.60 (d, J=3.6 Hz, 1H), 7.31 (s, 1H), 7.08 (d, J=3.6 Hz, 1H), 6.94 (s, 1H), 5.21-4.67 (m, 1H), 3.59 (s, 2H), 3.42 (s, 2H), 3.16 (t, J=7.0 Hz, 4H), 3.07-2.93 (m, 2H), 2.81 (tt, J=7.4 Hz, 1H), 2.70-2.55 (m, 2H), 2.40-2.25 (m, 2H), 2.23-2.07 (m, 2H), 2.07-1.92 (m, 4H), 1.74-1.59 (m, 2H); ¹⁹F NMR (376 MHz, dmso) δ −67.37 (s); LCMS (M+H)⁺: 592.1.

Example 157

{trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile The procedure of Example 153 was followed, using N,N-diisopropylethylamine (64 μL, 0.37 mmol) and azetidin-3-ol hydrochloride (30 mg, 0.3 mmol, Oakwood) in the displacement step. After stirring overnight at room temperature, methanol (0.20 mL) was added to afford a homogenous solution, which was stirred for a further 2.5 hours at room temperature and treated according to the deprotection and purification conditions given in Example 153 to afford product as the free base (9.7 mg, 44%). ¹H NMR (400 MHz, dmso) δ 12.12 (br s, 1H), 8.81 (s, 1H), 8.67 (s, 1H), 8.40 (s, 1H), 7.59 (d, J=3.6 Hz, 1H), 7.29 (s, 1H), 7.06 (d, J=3.6 Hz, 1H), 6.93 (s, 1H), 5.34 (d, J=6.4 Hz, 1H), 5.05-4.77 (m, 1H), 4.19 (h, J=6.1 Hz, 1H), 3.60 (s, 2H), 3.50 (td, J=6.1, 2.0 Hz, 2H), 3.40 (s, 2H), 3.06-2.92 (m, 2H), 2.86-2.71 (m, 3H), 2.68-2.53 (m, 2H), 2.38-2.22 (m, 2H), 2.22-2.07 (br m, 2H), 2.05-1.95 (br m, 2H), 1.75-1.48 (m, 2H); ¹⁹F NMR (376 MHz, dmso) δ −67.36 (s); LCMS (M+H)⁺: 608.2.

Example 158

{trans-3-(4-{[4-(pyrrolidin-1-ylmethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

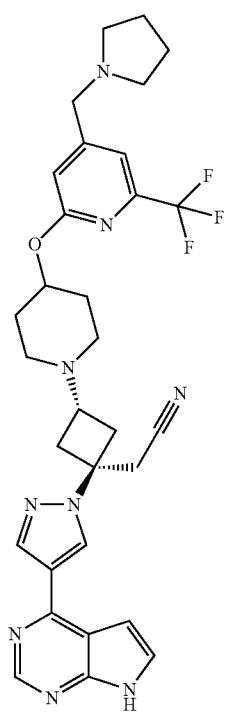 [SMILES: N#CC[C@]1(n2cc(-c3ncnc4[nH]ccc34)cn2)C[C@H](N2CCC(Oc3cc(CN4CCCC4)cc(C(F)(F)F)n3)CC2)C1]

The method of Example 127 was followed, except that the displacement of mesylate with amine was carried out with pyrrolidine (10 μL, 0.2 mmol, Aldrich) in methanol (0.30 mL) at room temperature for one hour. The deprotection was carried out as described in that example, but 0.3 mL of ethylenediamine was used. The product was obtained in pure form as the free base by the method described in that example (8.7 mg, 65%). $^1$H NMR (400 MHz, dmso) δ 12.12 (br s, 1H), 8.83 (s, 1H), 8.69 (s, 1H), 8.42 (s, 1H), 7.60 (d, J=3.6 Hz, 1H), 7.36 (s, 1H), 7.08 (d, J=3.6 Hz, 1H), 7.00 (s, 1H), 5.00 (tt, J=7.6, 3.8 Hz, 1H), 3.64 (s, 2H), 3.42 (s, 2H), 3.09-2.94 (m, 2H), 2.81 (tt, J=7.4, 7.4 Hz, 1H), 2.71-2.57 (br m, 2H), 2.47-2.40 (m, 4H), 2.38-2.27 (m, 2H), 2.23-2.08 (br m, 2H), 2.06-1.95 (br m, 2H), 1.81-1.49 (m, 6H); $^{19}$F NMR (376 MHz, dmso) δ −67.32 (s); LCMS (M+H)$^+$: 606.1.

Example 159

{trans-3-(4-{[4-(morpholin-4-ylmethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

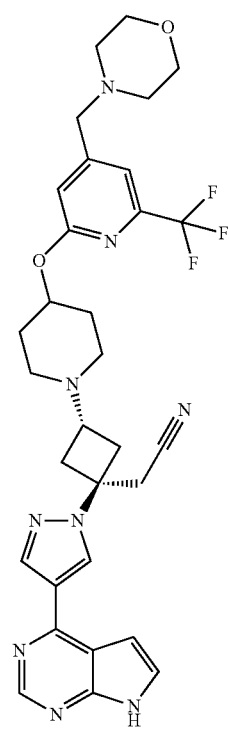 [SMILES: N#CC[C@]1(n2cc(-c3ncnc4[nH]ccc34)cn2)C[C@H](N2CCC(Oc3cc(CN4CCOCC4)cc(C(F)(F)F)n3)CC2)C1]

This compound was prepared according to method of Example 158, using Morpholine (20 μL, 0.2 mmol, Aldrich) in the displacement step, for 1 hour at room temperature (8.1 mg, 59%). $^1$H NMR (400 MHz, dmso) δ 12.12 (br s, 1H), 8.83 (s, 1H), 8.69 (s, 1H), 8.42 (s, 1H), 7.60 (d, J=3.6 Hz, 1H), 7.38 (s, 1H), 7.08 (d, J=3.6 Hz, 1H), 7.02 (s, 1H), 5.00 (tt, J=8.1, 3.8 Hz, 1H), 3.58 (dd, J=4.6 Hz, 4H), 3.55 (s, 2H), 3.41 (s, 2H), 3.08-2.92 (m, 2H), 2.81 (tt, J=7.4, 7.4 Hz, 1H), 2.71-2.57 (br m, 2H), 2.42-2.25 (m, 6H), 2.23-2.08 (br m, 2H), 2.07-1.94 (br m, 2H), 1.76-1.57 (m, 2H); $^{19}$F NMR (376 MHz, dmso) δ −67.33 (s); LCMS (M+H)$^+$: 622.2.

263

Example 160

{trans-3-(4-{[4-[(3,3-difluoropyrrolidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

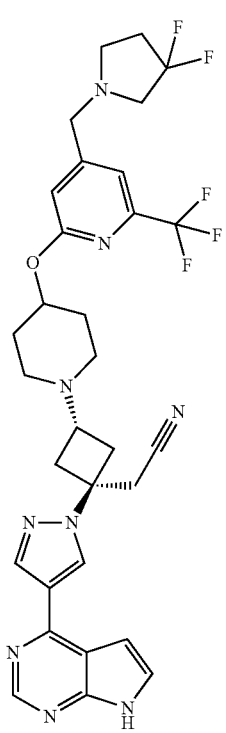 [SMILES: N#CC[C@]1(n2cc(-c3ncnc4[nH]ccc34)cn2)C[C@H](N2CCC(Oc3cc(CN4CCC(F)(F)C4)cc(C(F)(F)F)n3)CC2)C1]

The method of Example 158 was followed, except that the displacement of mesylate with amine was carried out using 3,3-difluoropyrrolidine hydrochloride (20 mg, 0.2 mmol, Oakwood), and N,N-diisopropylethylamine (30 μL, 0.2 mmol) at room temperature overnight (5.6 mg, 40%). $^1$H NMR (400 MHz, dmso) δ 12.13 (br s, 1H), 8.83 (s, 1H), 8.69 (s, 1H), 8.42 (s, 1H), 7.60 (d, J=3.6 Hz, 1H), 7.45-7.31 (m, 1H), 7.08 (d, J=3.6 Hz, 1H), 7.02 (s, 1H), 5.26-4.62 (m, 1H), 3.70 (s, 2H), 3.42 (s, 2H), 3.09-2.96 (m, 2H), 2.90 (t, J=13.3 Hz, 2H), 2.81 (tt, J=7.7, 7.8 Hz, 1H), 2.72 (t, J=7.0 Hz, 2H), 2.69-2.56 (m, 2H), 2.45-2.09 (m, 6H), 2.07-1.94 (br m, 2H), 1.77-1.58 (m, 2H); $^{19}$F NMR (376 MHz, dmso) δ −67.35 (s), −91.48 (p, J=14.4 Hz); LCMS (M+H)$^+$: 642.1.

264

Example 161

{trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

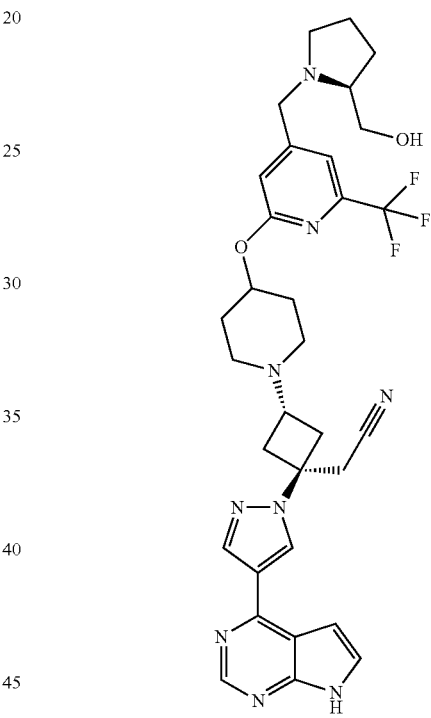

The method of Example 158 was followed, except that the displacement of mesylate with amine was carried out using (2S)-pyrrolidin-2-ylmethanol (20 μL, 0.2 mmol, Aldrich), at room temperature overnight (8.3 mg, 59%). $^1$H NMR (500 MHz, DMSO) δ 12.09 (br s, 1H), 8.81 (s, 1H), 8.69 (s, 1H), 8.41 (s, 1H), 7.59 (d, J=3.5 Hz, 1H), 7.39 (s, 1H), 7.06 (d, J=3.6 Hz, 1H), 7.03 (s, 1H), 5.00 (tt, J=8.4, 3.9 Hz, 1H), 4.48 (s, 1H), 4.12 (d, J=14.8 Hz, 1H), 3.45 (d, J=15.0 Hz, 1H), 3.41 (s, 2H), 3.42-3.25 (m, 2H), 3.06-2.97 (m, 2H), 2.87-2.77 (m, 2H), 2.69-2.62 (m, 2H), 2.59 (dddd, J=5.8, 5.8, 5.8, 8.1 Hz, 1H), 2.41-2.31 (m, 2H), 2.22-2.09 (m, 3H), 2.08-1.95 (m, 2H), 1.83 (dddd, J=8.1, 8.1, 8.3, 12.2 Hz, 1H), 1.75-1.46 (m, 5H); $^{19}$F NMR (376 MHz, dmso) δ −67.24 (s); LCMS (M+H)$^+$: 636.3.

Example 162

{trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile

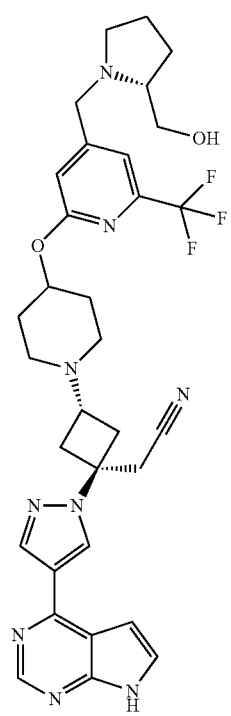 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1]

The method of Example 158 was followed, except that the displacement of mesylate with amine was carried out using (2R)-pyrrolidin-2-ylmethanol (20 μL, 0.2 mmol, Aldrich) at room temperature overnight (8.3 mg, 59%). $^1$H NMR (400 MHz, dmso) δ 12.14 (br s, 1H), 8.83 (s, 1H), 8.69 (s, 1H), 8.42 (s, 1H), 7.60 (d, J=3.6 Hz, 1H), 7.39 (s, 1H), 7.08 (d, J=3.6 Hz, 1H), 7.03 (s, 1H), 5.04-4.94 (m, 1H), 4.52 (t, J=5.4 Hz, 1H), 4.12 (d, J=14.9 Hz, 1H), 3.52-3.22 (m, 5H), 3.09-2.92 (m, 2H), 2.86-2.73 (m, 2H), 2.70-2.53 (m, 3H), 2.42-2.27 (m, 2H), 2.22-2.09 (m, 3H), 2.06-1.87 (m, 2H), 1.82 (dddd, J=8.0, 8.0, 8.4, 11.9 Hz, 1H), 1.77-1.37 (m, 5H); $^{19}$F NMR (376 MHz, dmso) δ −67.24 (s); LCMS (M+H)$^+$: 636.3.

Example 163

{trans-3-(4-{[4-(1-hydroxy-1-methylethyl)-6-(trifluoromethyl)pyridin-2-yl]carbonyl}piperazin-1-yl)-1-[4-(1H-pyrrolo[2,3-b]pyridin-4-yl)-1H-pyrazol-1-yl]cyclobutyl}acetonitrile

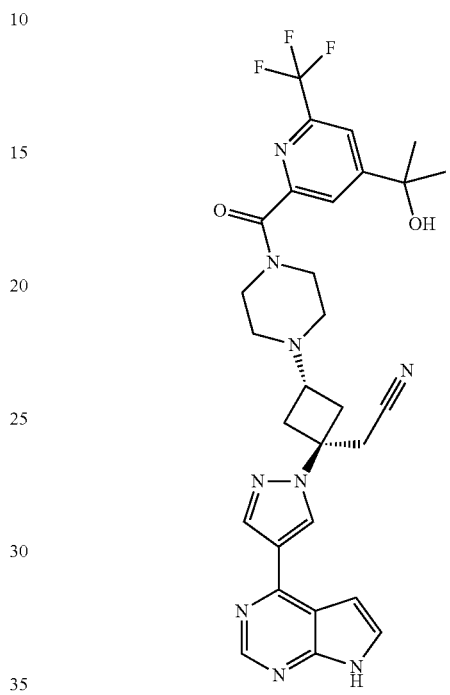

4-(1-Hydroxy-1-methylethyl)-6-(trifluoromethyl)pyridine-2-carboxylic acid (0.0125 g, 0.0501 mmol, from Example 75, Step D) was dissolved in N,N-dimethylformamide (1 mL) and to this was added {trans-3-piperazin-1-yl-1-[4-(1-{[2-(trimethylsilyl)ethoxy]methyl}-1H-pyrrolo[2,3-b]pyridin-4-yl)-1H-pyrazol-1-yl]cyclobutyl}acetonitrile (0.0250 g, 0.0508 mmol, obtained by treatment of Peak 2 of Step D from Example 77 with the conditions found in Step E of Example 77), followed by benzotriazol-1-yloxytris(dimethylamino)phosphonium hexafluorophosphate (26.57 mg, 0.06008 mmol) and Triethylamine (0.035 mL, 0.25 mmol). The reaction was stirred for 6 hours and was worked up by partitioning between ethyl acetate and brine. The aqueous portion was extracted a total of 3 times with ethyl acetate. The combined extracts were washed with water twice, then brine, dried over sodium sulfate, filtered and concentrated. The crude product was deprotected by stirring with TFA:DCM (1:1) for 1 hour, evaporated, then with ethylenediamine (1.5 mL) in methanol overnight. Purification by preparative HPLC-MS (C18, eluting with a gradient of MeCN/H$_2$O containing 0.15% NH$_4$OH) afforded product as the free base (0.01 g, 30%). $^1$H NMR (300 MHz, CD$_3$OD) δ 8.53 (d, J=0.7 Hz, 1H), 8.20 (s, J=0.7 Hz, 1H), 8.15 (d, J=5.2 Hz, 1H), 7.99 (d, J=1.6 Hz, 1H), 7.97-7.92 (m, 1H), 7.43 (d, J=3.6 Hz, 1H), 7.31 (d, J=5.2 Hz, 1H), 6.82 (d, J=3.6 Hz, 1H), 3.99-3.74 (m, 2H), 3.64-3.47 (m, 2H), 3.17-3.01 (m, 2H), 2.96 (tt, J=6.7, 7.0 Hz, 1H), 2.60-2.40 (m, 6H), 1.55 (s, 6H); $^{19}$F NMR (282 MHz, CD$_3$OD) δ −69.03 (s); LCMS (M+H)$^+$: 593.1.

Example 164

{cis-3-(4-{[6-(2-hydroxyethyl)-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile and {trans-3-(4-{[6-(2-hydroxyethyl)-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile (Each Diastereomer Isolated)

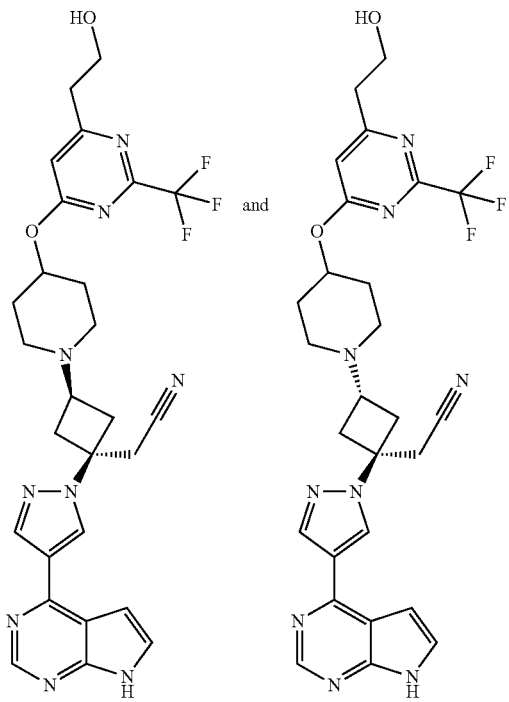 [SMILES: N#CC[C@]1(n2cc(-c3ncnc4[nH]ccc34)cn2)C[C@@H](N2CCC(Oc3cc(CCO)nc(C(F)(F)F)n3)CC2)C1 ; "and" ; N#CC[C@]1(n2cc(-c3ncnc4[nH]ccc34)cn2)C[C@H](N2CCC(Oc3cc(CCO)nc(C(F)(F)F)n3)CC2)C1]

Step 1. Methyl [6-hydroxy-2-(trifluoromethyl)pyrimidin-4-yl]acetate 2,2,2-Trifluoroethanimidamide (6.7 g, 50. mmol, Oakwood) was dissolved in 0.5 M sodium methoxide in methanol (120 mL, 60. mmol) and 3-oxo-pentanedioic acid dimethyl ester (8.4 mL, 55 mmol, Aldrich) was added. The reaction solution was stirred at room temperature for 72 hours, followed by heating to 50° C. for 42 hours. The solvent was removed in vacuo. 1 N HCl (50 mL) was added, this resulted in pH 5. After stirring overnight, 4 M HCl (10 mL) and ethyl acetate were added, and layers separated. The aqueous layer was extracted with ethyl acetate. The combined organic extract was washed with brine, dried over sodium sulfate, filtered and concentrated. Flash chromatography, on 120 g silica gel cartridge, eluting with a gradient (solvent A=hexane; solvent B=3% iPrOH/EtOAc) from 0-30% solvent B in A over 40 minutes and hold at 30% for 20 minutes at a flow rate of 60 mL/min. The residue obtained on evaporation of product-containing fractions was mixed with DCM and the resulting white ppt (impurity) was removed by filtration. The filtrate was evaporated and the resulting residue was repurified (A=hexane; solvent B=iPrOH) on a 120 g silica gel cartridge, eluting with a gradient from 0-20% B in A over 25 minutes and hold at 20% B at a flow rate of 60 mL/min. Evaporated to afford an oil which crystallized on standing (5.2 g, 75% pure). A portion of the material was purified via preparative HPLC-MS (C18, eluting with a gradient of MeCN/H$_2$O containing 0.1% TFA) to afford product used in the subsequent step. $^1$H NMR (300 MHz, CDCl$_3$) δ 6.76 (s, 1H), 3.76 (s, 3H), 3.75 (s, 2H).

Step 2. tert-Butyl 4-{[6-(2-methoxy-2-oxoethyl)-2-(trifluoromethyl)pyrimidin-4-yl]oxy}piperidine-1-carboxylate To tert-butyl 4-hydroxypiperidine-1-carboxylate (213 mg, 1.06 mmol, Aldrich) in tetrahydrofuran (2.0 mL) was added Triphenylphosphine (0.284 g, 1.08 mmol), followed by diisopropyl azodicarboxylate (0.215 mL, 1.09 mmol). After 10 minutes, methyl [6-hydroxy-2-(trifluoromethyl)pyrimidin-4-yl]acetate (0.20 g, 0.85 mmol, from Step 1) was added. The reaction was stirred for 1 hour and solvent was removed in vacuo. Flash chromatography on a 40 g silica gel cartridge, eluting with a gradient from 0-20% EtOAc in hexanes afforded product as a viscous oil (127 mg, 25%). LCMS (M+H)$^+$: 420.0.

Step 3. tert-Butyl 4-{[6-(2-hydroxyethyl)-2-(trifluoromethyl)pyrimidin-4-yl]oxy}piperidine-1-carboxylate Sodium tetrahydroborate (32 mg, 0.83 mmol) was added to a solution of tert-butyl 4-{[6-(2-methoxy-2-oxoethyl)-2-(trifluoromethyl)pyrimidin-4-yl]oxy}piperidine-1-carboxylate (125 mg, 0.209 mmol, from Step 2) in tetrahydrofuran (2.0 mL). Methanol (0.21 mL) was added in portions. After stirring for 2 hours, the mixture was quenched by the addition of saturated ammonium chloride solution. The reaction was diluted with additional water, and the product was extracted with EtOAc. The combined extracts were washed with brine, dried over sodium sulfate, filtered and concentrated. Flash chromatography on a 12 g silica gel column, eluting with a gradient from 0-30% EtOAc in hexanes afforded product (26 mg, 32%). $^1$H NMR (400 MHz, CDCl$_3$) δ 6.74 (s, 1H), 5.35 (tt, J=7.8, 3.7 Hz, 1H), 4.07-3.96 (m, 2H), 3.81-3.61 (m, 2H), 3.31 (ddd, J=13.5, 8.4, 3.7 Hz, 2H), 2.99 (t, J=5.4 Hz, 2H), 2.03-1.92 (m, 2H), 1.79-1.68 (m, 2H), 1.47 (s, 9H); $^{19}$F NMR (376 MHz, CDCl$_3$) δ −71.37 (s); LCMS (M+Na)$^+$: 414.0.

Step 4. {cis-3-(4-{[6-(2-hydroxyethyl)-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile and {trans-3-(4-{[6-(2-hydroxyethyl)-2-(trifluoromethyl)pyrimidin-4-yl]oxy}piperidin-1-yl)-1-[4-(7H-pyrrolo[2,3-d]pyrimidin-4-yl)-1H-pyrazol-1-yl]cyclobutyl}acetonitrile (Each Diastereomer Isolated)

tert-Butyl 4-{[6-(2-hydroxyethyl)-2-(trifluoromethyl)pyrimidin-4-yl]oxy}piperidine-1-carboxylate (26.0 mg, 0.0664 mmol, from Step 3) was dissolved in 4.0 M hydrogen chloride in dioxane (0.50 mL, 2.0 mmol) and the mixture was stirred for 30 minutes. The mixture was neutralized by the addition of saturated sodium bicarbonate solution and was extracted with DCM (6 times). The combined extracts were dried over sodium sulfate, filtered and concentrated. Sodium cyanoborohydride (5.9 mg, 0.093 mmol) and zinc dichloride (6.3 mg, 0.046 mmol) were combined in methanol (0.34 mL) and stirred for two hours. Following this, the deprotected piperidine, generated above, and {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (34 mg, 0.080 mmol, from Step 7 of Example 1a) were mixed in methanol (0.95 mL) and stirred to dissolve, then the reducing mixture generated by the combination of sodium cyanoborohydride and zinc dichloride was added. The reaction was stirred overnight, then was diluted with DCM and washed with saturated sodium bicarbonate solution. The aqueous phase was extracted with two further portions of DCM, the combined extracts were dried over sodium sulfate, filtered and concentrated. The residue was dissolved in a 1:1 mixture of TFA:DCM, stirred for one hour, then concentrated, re-dissolved in 2.0 mL methanol, and 0.20 mL ethylenediamine was added. Purification via preparative HPLC-MS (C18, eluting with a gradient of MeCN/H$_2$O containing 0.15% NH$_4$OH) afforded 12 mg product, as a mixture of cis- and trans-isomers, 32% yield. Chiral HPLC was used to separate the isomers (Phenomenex Lux Cellulose-2, 21.1×250 mm, eluting with 45% EtOH in hexanes at 18 mL/min, 6 mg per injection). Peak 1, trans isomer, eluted at 8.84 minutes (4.6 mg, 12% overall yield). $^1$H NMR (400 MHz, dmso) δ 12.13 (br s, 1H), 8.70 (s, 1H), 8.68 (s, 1H), 8.40 (s, 1H), 7.60 (d, J=3.6 Hz, 1H), 7.09 (s, 1H), 7.07 (d, J=3.6 Hz, 1H), 5.11 (tt, J=8.6, 3.7 Hz, 1H), 4.74 (t, J=5.2 Hz, 1H), 3.79-3.72 (m, 2H), 3.47 (s, 2H), 2.94 (tt, J=7.7, 7.8 Hz, 1H), 2.86 (t, J=6.3 Hz, 2H), 2.71-2.54 (m, 6H), 2.28-2.10 (m, 2H), 2.07-1.89 (m, 2H), 1.81-1.59 (m, 2H); $^{19}$F NMR (376 MHz, dmso) δ −69.87 (s); LCMS (M+H)$^+$: 568.0; Peak 2, cis isomer, eluted at 12.55 minutes (4.3 mg, 11% overall yield). $^1$H NMR (400 MHz, dmso) δ 12.13 (s, 1H), 8.83 (s, 1H), 8.69 (s, 1H), 8.42 (s, 1H), 7.60 (d, J=3.6 Hz, 1H), 7.13-6.99 (m, 2H), 5.10 (tt, J=9.0, 4.3 Hz, 1H), 4.74 (t, J=5.3 Hz, 1H), 3.78-3.72 (m, 2H), 3.42 (s, 2H), 3.06-2.96 (m, 2H), 2.86 (t, J=6.2 Hz, 2H), 2.81 (tt, J=7.4, 7.4 Hz, 1H), 2.70-2.55 (m, 2H), 2.40-2.30 (m, 2H), 2.26-2.12 (m, 2H), 2.08-1.96 (m, 2H), 1.79-1.63 (m, 2H); $^{19}$F NMR (376 MHz, dmso) δ −69.87 (s); LCMS (M+H)$^+$: 568.0.

Example 165

{cis-3-(4-{[4-[(2-oxo-1,3-oxazolidin-3-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile and {trans-3-(4-{[4-[(2-oxo-1,3-oxazolidin-3-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile (Each Diastereomer Isolated)

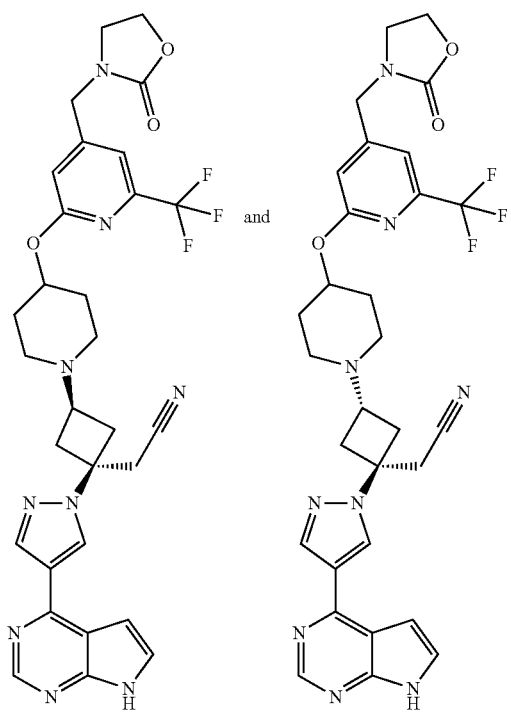 [SMILES: N#CC[C@]1(n2cc(-c3ncnc4[nH]ccc34)cn2)C[C@@H](N2CCC(Oc3cc(CN4CCOC4=O)cc(C(F)(F)F)n3)CC2)C1 ; "and" ; N#CC[C@]1(n2cc(-c3ncnc4[nH]ccc34)cn2)C[C@H](N2CCC(Oc3cc(CN4CCOC4=O)cc(C(F)(F)F)n3)CC2)C1]

Step 1. tert-Butyl 2-chloro-6-(trifluoromethyl)isonicotinate

2-Chloro-6-(trifluoromethyl)pyridine (20.00 g, 110.2 mmol, Oakwood) was dissolved in tetrahydrofuran (400 mL) and 1.0 M lithium chloride—chloro(2,2,6,6-tetramethylpiperidin-1-yl)magnesium (1:1) in THF (132.2 mL, 132.2 mmol, Aldrich) was added at 25° C. The reaction was stirred at 25° C. for 1 hour and was cooled to −78° C., and di-tert-butyldicarbonate (48.1 g, 220 mmol, Aldrich) in tetrahydrofuran (135 mL) was added. The reaction was allowed to warm to room temperature, and after the reaction was complete as determined by analytical LCMS, the reaction was quenched by the addition of saturated NH$_4$Cl solution and the product was extracted with EtOAc. The combined organic extracts were washed with 1N HCl, satd. NaHCO$_3$ solution, dried over sodium sulfate, filtered and the solvents were removed in vacuo. Flash chromatography on silica gel eluting with 5% EtOAc/hexanes afforded desired product as a light yellow solid (14.0 g, 45%). $^1$H NMR (300 MHz, CDCl$_3$) δ 8.07 (d, J=1.2 Hz, 1H), 8.01 (dq, J=1.1, 0.6

Hz, 1H), 1.62 (s, 9H); $^{19}$F NMR (282 MHz, CDCl$_3$) δ −68.43 (s); LCMS (M+H)$^+$: 282.0.

Step 2. tert-Butyl 4-{[4-(hydroxymethyl)-6-(trifluoromethyl)pyridin-2-yl]oxy}piperidine-1-carboxylate To a mixture of sodium hydride (1.1 g, 28 mmol, 60% in mineral oil) in tetrahydrofuran (45 mL) at 0° C. was added tert-butyl 4-hydroxypiperidine-1-carboxylate (5.8 g, 29 mmol, Aldrich). The mixture was then stirred at room temperature for 50 minutes. A solution of tert-butyl 2-chloro-6-(trifluoromethyl)isonicotinate (3.0 g, 11 mmol, from Step 1) in tetrahydrofuran (15 mL) was added, and the mixture was stirred at rt over three nights. The mixture was then quenched by the addition of 15 mL of 1N NaOH. After stirring for 2 hours, the mixture was further diluted with water and extracted with two portions of diethyl ether. The aqueous layer was acidified to pH 6 by the addition of conc. HCl, solid sodium chloride was added to saturate and the product was extracted with EtOAc (3×). The combined extracts were dried over sodium sulfate, filtered and concentrated to afford 4.2 g of yellow solid. The solid was dissolved in methanol (100 mL) and cooled to 0° C. A solution of 2.0 M trimethylsilyldiazomethane in ether was added in sufficient quantity to effect complete conversion to the methyl ester as determined by TLC and analytical LCMS. Excess reagent was quenched by the addition of acetic acid to the mixture which was still at 0° C. Saturated sodium bicarbonate solution was introduced to achieve pH in the range of 7-8 and brine was also added. The product was extracted in one portion of EtOAc and this extract was dried over sodium sulfate, filtered and concentrated to afford a yellow solid. Sodium tetrahydroborate (1.2 g, 32 mmol) was added to a solution of this product in ethanol (60. mL) at 0° C., and the reaction mixture was allowed to warm to room temperature and stir for 3.5 hours. The reaction was quenched by the addition of saturated ammonium chloride solution. The mixture was further diluted with water and extracted with two portions of EtOAc. The combined organic extracts were washed with brine, dried over sodium sulfate, filtered and concentrated. The alcohol product was purified by flash chromatography on silica gel (120 g), eluting with a gradient of 0-40% EtOAc in hexanes to afford the product as a colorless oil (2.8 g, 70%). LCMS (M+Na)$^+$: 399.1.

Step 3. tert-Butyl 4-{[4-[(2-oxo-1,3-oxazolidin-3-yl)methyl]-6-(trifluoromethyl)pyridin-2-yl]oxy}piperidine-1-carboxylate Triethylamine (220 µL, 1.6 mmol) and then methanesulfonyl chloride (82 µL, 1.1 mmol) were added to a solution of tert-butyl 4-{[4-(hydroxymethyl)-6-(trifluoromethyl)pyridin-2-yl]oxy}piperidine-1-carboxylate (0.20 g, 0.53 mmol, from Step 2) in methylene chloride (2 mL) at 0° C. After stirring at this temperature for 30 minutes, the reaction mixture was partitioned between water and EtOAc. The organic layer was washed with brine, dried over sodium sulfate, filtered and concentrated. The crude mesylate intermediate was dissolved in N,N-dimethylformamide (2.0 mL), and oxazolidin-2-one (230 mg, 2.6 mmol) was added. The mixture was cooled to 0° C. and sodium hydride (53 mg, 1.3 mmol, 60% in mineral oil) was added. The reaction was warmed to room temperature and stirred for 40 minutes, then was quenched with water, and extracted with EtOAc. The organic extract was washed with water, brine, dried over sodium sulfate, filtered and concentrated. Flash chromatography, eluting with a gradient from 0-70% EtOAc in hexanes afforded product (95 mg, 40%). $^1$H NMR (400 MHz, CDCl$_3$) δ 7.14 (s, 1H), 6.79 (s, 1H), 5.27 (tt, J=7.7, 4.1 Hz, 1H), 4.44 (s, 2H), 4.44-4.38 (m, 2H), 3.80-3.68 (m, 2H), 3.58-3.47 (m, 2H), 3.31 (ddd, J=13.6, 8.5, 3.6 Hz, 2H), 1.99 (ddt, J=13.2, 6.3, 3.0 Hz, 2H), 1.78-1.67 (m, 2H), 1.47 (s, 9H); $^{19}$F NMR (376 MHz, CDCl$_3$) δ −68.89 (s); LCMS (M+Na)$^+$: 468.0.

Step 4. {cis-3-(4-{[4-[(2-oxo-1,3-oxazolidin-3-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile and {trans-3-(4-{[4-[(2-oxo-1,3-oxazolidin-3-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile
(Each Diastereomer Isolated)

tert-Butyl 4-{[4-[(2-oxo-1,3-oxazolidin-3-yl)methyl]-6-(trifluoromethyl)pyridin-2-yl]oxy}piperidine-1-carboxylate (93 mg, 0.21 mmol, from Step 3) was dissolved in 4.0 M hydrogen chloride in dioxane (1.6 mL, 6.3 mmol) and was stirred for 30 minutes. The mixture was neutralized with saturated sodium bicarbonate solution, then extracted with chloroform (6×). The combined extracts were dried over sodium sulfate, filtered and concentrated. The crude product and {3-oxo-1-[4-(7-{[2-(trimethylsilyl)ethoxy]methyl}-7H-pyrrolo[2,3-d]pyrimidin-4-yl)-1H-pyrazol-1-yl]cyclobutyl}acetonitrile (97 mg, 0.23 mmol, from Step 7 of Example 1a) were mixed in methanol (3.0 mL) and stirred to dissolve, then a solution prepared from the combination of sodium cyanoborohydride (18 mg, 0.29 mmol) and zinc dichloride (20. mg, 0.15 mmol) in methanol (1.1 mL) that had been pre-stirred for 50 minutes was added. After stirring for 3 hours, the SEM-protected cis- and trans-intermediates were purified and isolated separately via preparative HPLC-MS (Waters XBridge, 30×100 mm, eluting with a gradient over 12 minutes from 45.7 to 63.7% MeCN in H$_2$O containing 0.15% NH$_4$OH). Peak 1 retention time: 9.5 min, Peak 2 retention time: 10.3 min. After evaporating solvent, each of Peak 1 and Peak 2 were deprotected separately by stirring in a 1:1 mixture of TFA:DCM for one hour, evaporation, then stirring in 2.0 mL methanol containing 0.20 mL ethylenediamine until deprotection was complete as determined by analytical LCMS. Purification of deprotected Peak 1 via preparative HPLC-MS (C18 eluting with a gradient of MeCN/H$_2$O containing 0.15% NH$_4$OH) afforded the cis-isomer (16.8 mg, 13% yield). $^1$H NMR (400 MHz, dmso) δ 12.13 (br s, 1H), 8.70 (s, 1H), 8.68 (s, 1H), 8.39 (d, J=0.6 Hz, 1H), 7.60 (d, J=3.6 Hz, 1H), 7.36 (d, J=0.6 Hz, 1H), 7.07 (d, J=3.6 Hz, 1H), 7.00 (s, 1H), 5.02 (ddd, J=11.6, 7.5, 3.4 Hz, 1H), 4.43 (s, 2H), 4.38-4.27 (m, 2H), 3.55-3.49 (m, 2H), 3.47 (s, 2H), 2.93 (ft, J=7.5, 7.6 Hz, 1H), 2.70-2.56 (m, 6H), 2.27-2.09 (m, 2H), 2.06-1.94 (m, 2H), 1.74-1.60 (m, 2H); $^{19}$F NMR (376 MHz, dmso) δ −67.40 (s); LCMS (M+H)$^+$: 622.2. Purification of deprotected Peak 2 via preparative HPLC-MS (C18 eluting with a gradient of MeCN/H$_2$O containing 0.15% NH$_4$OH) afforded the trans-isomer (21.6 mg, 17% yield). $^1$H NMR (400 MHz, dmso) δ 12.13 (s, 2H), 8.83 (s, 1H), 8.69 (s, 1H), 8.42 (s, 1H), 7.60 (d, J=3.6 Hz, 1H), 7.36 (s, 1H), 7.08 (d, J=3.6 Hz, 1H), 6.99 (s, 1H), 5.05-4.97 (m, 1H), 4.43 (s, 2H), 4.38-4.27 (m, 2H), 3.57-3.47 (m, 2H), 3.42 (s, 2H), 3.13-2.90 (m, 2H), 2.82 (tt, J=7.4, 7.5 Hz, 1H), 2.72-2.58 (m, 2H), 2.42-2.29 (m, 2H), 2.24-

2.09 (m, 2H), 2.09-1.88 (m, 2H), 1.78-1.62 (m, 2H); $^{19}$F NMR (376 MHz, dmso) δ −67.40 (s); LCMS (M+H)$^+$: 622.2.

Example A

In Vitro JAK Kinase Assay

Compounds herein were tested for inhibitory activity of JAK targets according to the following in vitro assay described in Park et al., *Analytical Biochemistry* 1999, 269, 94-104. The catalytic domains of human JAK1 (a.a. 837-1142) and JAK2 (a.a. 828-1132) with an N-terminal His tag were expressed using baculovirus in insect cells and purified. The catalytic activity of JAK1 and JAK2 was assayed by measuring the phosphorylation of a biotinylated peptide. The phosphorylated peptide was detected by homogenous time resolved fluorescence (HTRF). IC$_{50}$s of compounds were measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM IC$_{50}$ measurements, ATP concentration in the reactions was 1 mM. Reactions were carried out at room temperature for 1 hour and then stopped with 20 μL 45 mM EDTA, 300 nM SA-APC, 6 nM Eu-Py20 in assay buffer (Perkin Elmer, Boston, Mass.). Binding to the Europium labeled antibody took place for 40 minutes and HTRF signal was measured on a Fusion plate reader (Perkin Elmer, Boston, Mass.). See Tables A-F for data related to compounds of the Examples (at 1 mM). Data is indicated as ranges, wherein "+" is less than 10 nM; "++" is 10 nM to 25 nM; "+++" is greater than 25 nM to 100 nM; and "++++" is greater than 100 nM. Greater than 25 nM to 100 nM specifies a range with a lower endpoint "at greater than 25 nM" and an upper endpoint at 100 nM.

TABLE A

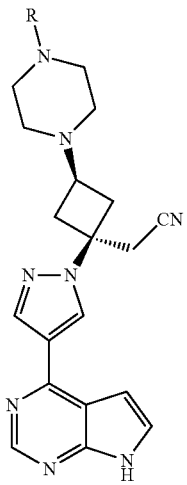

| Ex No. | R = | JAK1 IC$_{50}$ (nM) | JAK2 IC$_{50}$ (nM) |
|---|---|---|---|
| 1a | 3,5-F,CN-benzyl | + | ++++ |
| 2a | N(CH$_3$)$_2$, F, CN-benzyl | + | +++ |
| 3a | CF$_3$, F-anilide amide | +++ | ++++ |
| 4a | 2-methylpyrrolidine amide | +++ | ++++ |
| 6a | 2-CF$_3$, 3-F-pyridyl ketone | ++ | ++++ |
| 7a | 2-CF$_3$-pyrimidinyl ketone | ++ | ++++ |
| 8a | 3,5-F-benzoyl | + | +++ |

TABLE A-continued

| Ex No. | R = | JAK1 IC$_{50}$ (nM) | JAK2 IC$_{50}$ (nM) |
|---|---|---|---|
| 12a | 3-fluoro-5-cyanobenzoyl | + | +++ |
| 13a | 4-(trifluoromethyl)thiazole-2-carbonyl | + | +++ |
| 14a | 6-(trifluoromethyl)pyrazine-2-carbonyl | + | +++ |
| 17 | 3-fluoro-5-(trifluoromethyl)benzoyl | + | +++ |
| 15a | 3,4-difluorobenzoyl | + | +++ |
| 11a | 3-fluoro-2-(difluoromethyl)pyridine-4-carbonyl | ++ | ++++ |
| 20a | 6-(trifluoromethyl)pyridine-2-carbonyl | + | +++ |
| 10a | 5-fluoropyridine-3-carbonyl | + | ++++ |
| 22 | 2-fluoro-3-(trifluoromethyl)benzoyl | + | +++ |
| 21a | 6-(difluoromethyl)pyridine-2-carbonyl | + | +++ |
| 23a | 2-(5-fluoropyridin-3-yl)ethyl | ++ | ++++ |
| 24a | 2-isopropylpyrimidine-4-carbonyl | ++ | ++++ |

TABLE A-continued

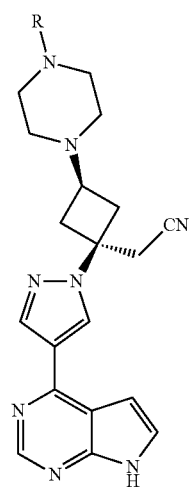

| Ex No. | R = | JAK1 IC$_{50}$ (nM) | JAK2 IC$_{50}$ (nM) |
|---|---|---|---|
| 26 | 4-F, 3-OCF$_3$ benzoyl | ++ | +++ |
| 27 | 3-F, 5-CF$_3$ pyridyl-2-carbonyl | + | +++ |
| 16a | 2,6-diF, 3-Cl benzyl | + | ++ |
| 9a | 2-Cl, 5-F pyridyl-3-carbonyl | ++ | ++++ |
| 28 | 4-Cl benzoyl | + | ++ |
| 29 | 2-F, 4-CF$_3$ benzoyl | ++ | +++ |

TABLE B

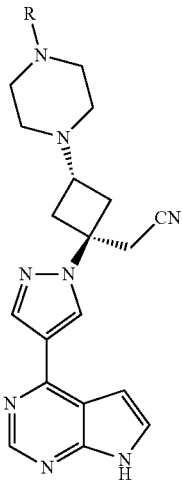

| Ex | R = | JAK1 IC$_{50}$ (nM) | JAK2 IC$_{50}$ (nM) |
|---|---|---|---|
| 1b | 3-F, 5-CN benzyl | + | +++ |
| 2b | 3-NMe$_2$, 2-CN, 4-F benzyl | + | +++ |
| 3b | 2-CF$_3$, 4-F phenylcarbamoyl | ++ | ++++ |
| 4b | 2-methylpyrrolidin-1-yl carbonyl | + | ++++ |
| 5 | 2-ethylpyrrolidin-1-yl carbonyl | + | ++++ |
| 6b | 3-F, 2-CF$_3$ pyridyl-4-carbonyl | + | +++ |

TABLE B-continued

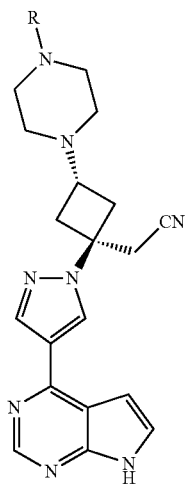

| Ex | R = | JAK1 IC$_{50}$ (nM) | JAK2 IC$_{50}$ (nM) |
|----|-----|---------------------|---------------------|
| 7b | (4-pyrimidinyl-2-CF$_3$)C(O)– | + | +++ |
| 8b | (3,5-difluorophenyl)C(O)– | + | + |
| 9b | (2-Cl-5-F-pyridin-3-yl)C(O)– | + | ++ |
| 10b | (5-fluoropyridin-3-yl)C(O)– | + | +++ |
| 11b | (3-F-2-CHF$_2$-pyridin-4-yl)C(O)– | + | +++ |
| 12b | (3-F-5-CN-phenyl)C(O)– | + | ++ |

TABLE B-continued

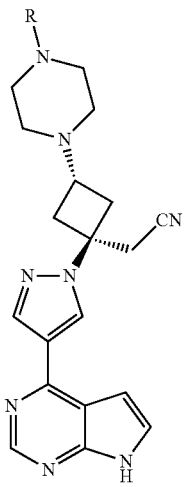

| Ex | R = | JAK1 IC$_{50}$ (nM) | JAK2 IC$_{50}$ (nM) |
|----|-----|---------------------|---------------------|
| 13b | (4-CF$_3$-thiazol-2-yl)C(O)– | + | +++ |
| 14b | (6-CF$_3$-pyrazin-2-yl)C(O)– | + | +++ |
| 15b | (3,4-difluorophenyl)C(O)– | + | ++ |
| 16b | (3-Cl-2,6-difluorobenzyl)– | + | +++ |
| 18 | (2-F-4-CF$_3$-phenyl)C(O)– | + | ++ |
| 19 | pyrrolidin-1-yl-C(O)– | ++ | ++++ |
| 20b | (6-CF$_3$-pyridin-2-yl)C(O)– | + | +++ |

TABLE B-continued

| Ex | R = | JAK1 IC$_{50}$ (nM) | JAK2 IC$_{50}$ (nM) |
|---|---|---|---|
| 21b | 6-(difluoromethyl)pyridine-2-carbonyl | + | ++ |
| 23b | (5-fluoropyridin-3-yl)methyl | + | +++ |
| 25 | piperidine-1-carbonyl | +++ | ++++ |
| 24b | 2-isopropylpyrimidine-4-carbonyl | ++ | +++ |
| 32 | N,N-dimethylcarbamoyl | + | ++++ |
| 33 | 3-fluoro-5-((dimethylamino)methyl)benzoyl | + | + |

TABLE B-continued

| Ex | R = | JAK1 IC$_{50}$ (nM) | JAK2 IC$_{50}$ (nM) |
|---|---|---|---|
| 34 | 3-fluoro-5-((dimethylamino)methyl)phenethyl | + | ++ |
| 35 | ethylsulfonyl | + | + |
| 36 | cyclopropylsulfonyl | + | + |
| 37 | N,N-dimethylsulfamoyl | + | + |
| 38 | N-ethyl-N-methylcarbamoyl | + | +++ |
| 39 | 3-(trifluoromethyl)-5-((dimethylamino)methyl)benzoyl | + | +++ |

TABLE C

R group attached to piperazine-cyclobutane-pyrazole-pyrrolopyrimidine scaffold with CN substituent (D-labeled stereochemistry).

| Ex | R = | JAK1 IC$_{50}$ (nM) | JAK2 IC$_{50}$ (nM) |
|---|---|---|---|
| 30 | pyrimidine-CF$_3$ ketone | + | ++++ |

TABLE D

Same scaffold as Table C.

| Ex | R = | JAK1 IC$_{50}$ (nM) | JAK2 IC$_{50}$ (nM) |
|---|---|---|---|
| 31 | pyrimidine-CF$_3$ ketone | + | +++ |

TABLE E

| Ex. No. | Salt Form | JAK1 IC$_{50}$ (nM) at 1 mM | JAK2 IC$_{50}$ (nM) + |
|---|---|---|---|
| 40, isomer 1 | — | + | ++ |
| 40, isomer 2 | — | + | + |
| 41, isomer 1 | — | + | ++ |
| 41, isomer 2 | — | + | + |

TABLE F

| Example | JAK1 IC$_{50}$ (nM) at 1 mM ATP | JAK2 IC$_{50}$ (nM) at 1 mM ATP |
|---|---|---|
| 42 | + | ++++ |
| 43 | +++ | ++++ |
| 44 | ++ | ++++ |
| 45 | ++++ | ++++ |
| 46 | +++ | ++++ |
| 47 | + | +++ |
| 48 | ++ | ++++ |
| 49 | + | +++ |
| 50 | + | +++ |
| 51 | + | +++ |
| 52 | + | +++ |
| 53 | + | +++ |
| 54 | + | +++ |
| 55 | + | +++ |
| 56 | + | +++ |
| 57 | + | ++ |
| 58 | + | ++ |
| 59 | + | +++ |
| 60 | + | +++ |
| 61 | + | + |
| 62 | + | + |
| 63 | + | +++ |
| 64 | + | +++ |
| 65 | + | +++ |
| 66 | + | +++ |
| 67 | + | +++ |
| 68 | + | ++ |
| 69 | + | +++ |
| 70 | + | + |
| 71 | + | +++ |
| 72 | + | ++ |
| 73 | + | ++ |
| 74 | + | ++ |
| 75 | + | ++ |
| 76 | + | ++ |
| 77 | + | +++ |
| 78 | + | +++ |
| 79 | +++ | ++++ |
| 80 | + | +++ |
| 81 | + | +++ |
| 82 | ++ | ++++ |
| 83 | + | +++ |
| 84 | +++ | ++++ |
| 85 | + | +++ |
| 86 | ++ | +++ |
| 87 | ++ | ++++ |
| 88 | + | +++ |
| 89 | + | +++ |
| 90 | + | ++ |
| 91 | +++ | ++++ |
| 92 | + | +++ |
| 93 | + | +++ |
| 94 | + | +++ |
| 95 | + | +++ |
| 96 | + | +++ |
| 97 | + | +++ |
| 98 | + | ++++ |
| 99 | + | +++ |
| 100 | ++ | ++++ |
| 101 | + | +++ |
| 102 | + | +++ |
| 103 | + | +++ |
| 104 | ++ | ++++ |
| 105 | ++ | +++ |

TABLE F-continued

| Example | JAK1 IC$_{50}$ (nM) at 1 mM ATP | JAK2 IC$_{50}$ (nM) at 1 mM ATP |
|---|---|---|
| 106 | ++ | ++++ |
| 107 | ++ | ++++ |
| 108 | ++ | ++++ |
| 109 | + | +++ |
| 110 | + | ++++ |
| 111 | ++ | ++++ |
| 112 | ++ | +++ |
| 113 | + | ++++ |
| 114 | + | ++++ |
| 115 | + | ++++ |
| 116 | +++ | ++++ |
| 117 | +++ | ++++ |
| 118 | ++ | +++ |
| 119 | + | ++ |
| 120 | + | +++ |
| 121 | +++ | ++++ |
| 122 | + | ++++ |
| 123 | + | ++++ |
| 124 | +++ | ++++ |
| 125 | + | +++ |
| 126 | ++ | ++++ |
| 127 | + | +++ |
| 128 | +++ | ++++ |
| 129 | + | +++ |
| 130 | + | ++++ |
| 131 | + | +++ |
| 132 | + | +++ |
| 133 | +++ | ++++ |
| 134 | + | ++++ |
| 135 | ++ | ++++ |
| 136 | + | +++ |
| 137 | ++ | ++++ |
| 138 | ++ | ++++ |
| 139 | + | ++++ |
| 140 | ++ | ++++ |
| 141 | + | + |
| 142 | ++ | ++++ |
| 143 | ++ | +++ |
| 144 | ++ | ++++ |
| 145 | ++ | ++++ |
| 146 | ++ | ++++ |
| 147 | ++ | +++ |
| 148 | ++ | ++++ |
| 149 | +++ | ++++ |
| 150 | ++ | ++++ |
| 151 | + | +++ |
| 152 | + | ++++ |
| 153 | + | +++ |
| 154 | + | +++ |
| 155 | + | +++ |
| 156 | + | +++ |
| 157 | + | +++ |
| 158 | + | +++ |
| 159 | + | +++ |
| 160 | ++ | ++++ |
| 161 | + | +++ |
| 162 | + | ++++ |
| 163 | + | +++ |
| 164, peak 1 | ++ | ++++ |
| 164, peak 2 | +++ | ++++ |
| 165, peak 1 | +++ | ++++ |
| 165, peak 2 | + | +++ |

Example B

Cellular Assays

Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds can be added to the cells in DMSO/media (final concentration 0.2% DMSO) and incubated for 72 hours at 37° C., 5% CO$_2$. The effect of compound on cell viability is assessed using the CellTiter-Glo Luminescent Cell Viability Assay (Promega) followed by TopCount (Perkin Elmer, Boston, Mass.) quantitation. Potential off-target effects of compounds are measured in parallel using a non-JAK driven cell line with the same assay readout. All experiments are typically performed in duplicate.

The above cell lines can also be used to examine the effects of compounds on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those schooled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those schooled in the art.

Compounds herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. Nature 434:1144-1148; Staerk, J., et al. JBC 280:41893-41899). Endpoints include the effects of compounds on cell survival, proliferation, and phosphorylated JAK, STAT, Akt, or Erk proteins.

Certain compounds herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 µg/ml streptomycin) at a density of 2×10$^6$ cells/ml at 37° C. for up to 2 days. For IL-2 stimulated cell proliferation analysis, T-cells are first treated with Phytohemagglutinin (PHA) at a final concentration of 10 µg/mL for 72 h. After washing once with PBS, 6000 cells/well are plated in 96-well plates and treated with compounds at different concentrations in the culture medium in the presence of 100 U/mL human IL-2 (ProSpec-Tany TechnoGene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol* J. 2:42-53, 2001). Tumor bearing animals can then be randomized into drug or vehicle treatment groups and different doses of compounds can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound(s) can be assessed using xenograft tumor models that are driven by other know kinases (e.g. Bcr-Abl) such as the K562 tumor model.

Example D

Murine Skin Contact Delayed Hypersensitivity Response Test

Compounds herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* 1998 January; 19(1):37-44). Murine DTH shares multiple characteristics with psoriasis, including the immune infiltrate, the accompanying increase in inflammatory cytokines, and keratinocyte hyperproliferation. Furthermore, many classes of agents that are efficacious in treating psoriasis in the clinic are also effective inhibitors of the DTH response in mice (Agents Actions. 1993 January; 38(1-2):116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 µL (10 µL on the internal pinna and 10 µL on the external pinna) at a concentration of 0.2%. Twenty-four to seventy-two hours after the challenge, ears are measured again. Treatment with the test compounds is given throughout the sensitization and challenge phases (day −1 to day 7) or prior to and throughout the challenge phase (usually afternoon of day 4 to day 7). Treatment of the test compounds (in different concentration) is administered either systemically or topically (topical application of the treatment to the ears). Efficacies of the test compounds are indicated by a reduction in ear swelling comparing to the situation without the treatment. Compounds causing a reduction of 20% or more were considered efficacious. In some experiments, the mice are challenged but not sensitized (negative control).

The inhibitive effect (inhibiting activation of the JAK-STAT pathways) of the test compounds can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with test compounds, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds herein. These models are well established in the research community and are familiar to those schooled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003.).

Example F

Animal Models for the Treatment of Dry Eye, Uveitis, and Conjunctivitis

Agents may be evaluated in one or more preclinical models of dry eye known to those schooled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent auto-immune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those schooled in the art. These include, but are not limited to, models of experimental autoimmune uveitis (EAU) and endotoxin induced uveitis (EIU). EAU experiements may be performed in the rabbit, rat, or mouse and may involve passive or activate immunization. For instance, any of a number or retinal antigens may be used to sensitize animals to a relevant immunogen after which animals may be challenged ocularly with the same antigen. The EIU model is more acute and involves local or systemic administration of lipopolysaccaride at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those schooled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Example G

In Vivo Protection of Bone

Compounds may be evaluated in various preclinical models of osteopenia, osteoporosis, or bone resorption known to those schooled in the art. For example, ovariectomized rodents may be used to evaluate the ability of compounds to affect signs and markers of bone remodeling and/or density (W. S. S. Jee and W. Yao, J Musculoskel. Nueron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds on bone resorption and density may be evaluable in the rodent models of arthritis discussed above (Example E). Endpoints for all these models may vary but often include histological and radiological assessments as well as immunohisotology and appropriate biochemical markers of bone remodeling.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula I:

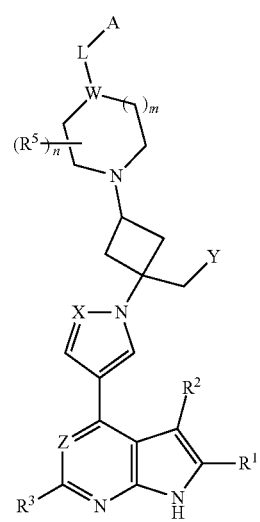

or a pharmaceutically acceptable salt thereof; wherein:
X is N;
Y is H, cyano, halo, $C_{1-3}$ alkyl, or $C_{1-3}$ haloalkyl;
Z is $CR^4$;
W is N;
L is $C(R^6)_2$, $C(=O)$, $C(=O)O$, $C(=O)N(R^7)$, $C(=O)C(R^6)_2$, $S(=O)$, $S(=O)_2$, $S(=O)N(R^7)$, $S(=O)_2N(R^7)$, or $C(=NR^{7a})N(R^7)$;
$R^1$, $R^2$, $R^3$, and $R^4$ are each independently H, hydroxy, halo, $C_{1-3}$ alkyl, or $C_{1-3}$ haloalkyl;
each $R^5$ is independently hydroxy, $C_{1-4}$ alkoxy, fluorine, $C_{1-4}$ alkyl, hydroxy-$C_{1-4}$-alkyl, $C_{1-4}$ alkoxy-$C_{1-4}$-alkyl, or $C_{1-4}$ fluoroalkyl;
each $R^6$ is, independently, H or $C_{1-4}$ alkyl; or
two $R^6$ groups, together with the carbon atom to which they are attached, form a 3-, 4-, 5-, or 6-membered cycloalkyl ring;
$R^7$ is H or $C_{1-4}$ alkyl;
$R^{7a}$ is H, OH, CN, $C_{1-4}$ alkoxy, or $C_{1-4}$ alkyl;
or $R^7$ and $R^{7a}$, taken together with the $C(=N)N$ moiety to which they are attached, form a 4-, 5-, 6-, or 7-membered heterocycloalkyl ring or a 5- or 6-membered heteroaryl ring;
A is H, $C_{1-6}$ alkyl, $C_{3-10}$ cycloalkyl, $C_{2-10}$ heterocycloalkyl, $C_{6-10}$ aryl, or $C_{1-10}$ heteroaryl;
wherein said $C_{1-6}$ alkyl, $C_{3-10}$ cycloalkyl, $C_{2-10}$ heterocycloalkyl, $C_{6-10}$ aryl, and $C_{1-10}$ heteroaryl are each optionally substituted with p independently selected $R^8$ substituents; wherein p is 1, 2, 3, 4, or 5; provided when L is O, S, $C(=O)$, $C(=O)O$, $S(=O)$, or $S(=O)_2$, then A is not H;
each $R^8$ is independently selected from halo, cyano, nitro, $C_{1-6}$ alkyl, $C_{1-6}$ haloalkyl, $C_{2-6}$ alkenyl, $C_{2-6}$ alkynyl, $C_{3-10}$ cycloalkyl, $C_{3-10}$ cycloalkyl-$C_{1-4}$-alkyl, $C_{2-10}$ heterocycloalkyl, $C_{2-10}$ heterocycloalkyl-$C_{1-4}$-alkyl, $C_{6-10}$ aryl, $C_{6-10}$ aryl-$C_{1-4}$-alkyl, $C_{1-10}$ heteroaryl, $C_{1-10}$ heteroaryl-$C_{1-4}$-alkyl, $—OR^a$, $—SR^a$, $—S(=O)_2R^b$, $—S(=O)_2R^b$, $—S(=O)_2NR^eR^f$, $—C(=O)R^b$, $—C(=O)OR^a$, $—C(=O)NR^eR^f$, $—OC(=O)R^b$, $—OC(=O)NR^eR^f$, $—NR^eR^f$, $—NR^cC(=O)R^d$, $—NR^cC(=O)$ OR$^d$, —NR$^c$S(=O)$_2$R$^d$, and —NR$^c$S(=O)$_2$NR$^e$R$^f$; wherein said C$_{1-6}$ alkyl, C$_{2-6}$ alkenyl, C$_{2-6}$ alkynyl, C$_{3-10}$ cycloalkyl, C$_{3-10}$ cycloalkyl-C$_{1-4}$-alkyl, C$_{2-10}$ heterocycloalkyl, C$_{2-10}$ heterocycloalkyl-C$_{1-4}$-alkyl, C$_{6-10}$ aryl, C$_{6-10}$ aryl-C$_{1-4}$-alkyl, C$_{1-10}$ heteroaryl, and C$_{1-10}$ heteroaryl-C$_{1-4}$-alkyl are each optionally substituted by 1, 2, 3, or 4 independently selected R$^g$ groups;

each R$^a$, R$^c$, R$^d$, R$^e$, and R$^f$ is independently selected from H, C$_{1-6}$ alkyl, C$_{1-6}$ haloalkyl, C$_{2-6}$ alkenyl, C$_{2-6}$ alkynyl, C$_{3-10}$ cycloalkyl, C$_{3-10}$ cycloalkyl-C$_{1-4}$-alkyl, C$_{2-10}$ heterocycloalkyl, C$_{2-10}$ heterocycloalkyl-C$_{1-4}$-alkyl, C$_{6-10}$ aryl, C$_{6-10}$ aryl-C$_{1-4}$-alkyl, C$_{1-10}$ heteroaryl, and C$_{1-10}$ heteroaryl-C$_{1-4}$-alkyl; wherein said C$_{1-6}$ alkyl, C$_{2-6}$ alkenyl, C$_{2-6}$ alkynyl, C$_{3-10}$ cycloalkyl, C$_{3-10}$ cycloalkyl-C$_{1-4}$-alkyl, C$_{2-10}$ heterocycloalkyl, C$_{2-10}$ heterocycloalkyl-C$_{1-4}$-alkyl, C$_{6-10}$ aryl, C$_{6-10}$ aryl-C$_{1-4}$-alkyl, C$_{1-10}$ heteroaryl, and C$_{1-10}$ heteroaryl-C$_{1-4}$-alkyl are each optionally substituted by 1, 2, 3, or 4 independently selected R$^g$ groups;

each R$^b$ is independently selected from C$_{1-6}$ alkyl, C$_{1-6}$ haloalkyl, C$_{2-6}$ alkenyl, C$_{2-6}$ alkynyl, C$_{3-10}$ cycloalkyl, C$_{3-10}$ cycloalkyl-C$_{1-4}$-alkyl, C$_{2-10}$ heterocycloalkyl, C$_{2-10}$ heterocycloalkyl-C$_{1-4}$-alkyl, C$_{6-10}$ aryl, C$_{6-10}$ aryl-C$_{1-4}$-alkyl, C$_{1-10}$ heteroaryl, and C$_{1-10}$ heteroaryl-C$_{1-4}$-alkyl; wherein said C$_{1-6}$ alkyl, C$_{2-6}$ alkenyl, C$_{2-6}$ alkynyl, C$_{3-10}$ cycloalkyl, C$_{3-10}$ cycloalkyl-C$_{1-4}$-alkyl, C$_{2-10}$ heterocycloalkyl, C$_{2-10}$ heterocycloalkyl-C$_{1-4}$-alkyl, C$_{6-10}$ aryl, C$_{6-10}$ aryl-C$_{1-4}$-alkyl, C$_{1-10}$ heteroaryl, and C$_{1-10}$ heteroaryl-C$_{1-4}$-alkyl are each optionally substituted by 1, 2, 3, or 4 independently selected R$^g$ groups;

each R$^g$ is independently selected from halo, cyano, nitro, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ cycloalkyl-C$_{1-3}$-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, C$_{1-7}$ heteroaryl-C$_{1-3}$-alkyl, —OR$^{a1}$, —SR$^{a1}$, —S(=O)R$^{b1}$, —S(=O)$_2$R$^{b1}$, —S(=O)$_2$NR$^{e1}$R$^{f1}$, —C(=O)R$^{b1}$, —C(=O)OR$^{a1}$, —C(=O)NR$^{e1}$R$^{f1}$, —OC(=O)R$^{b1}$, —OC(=O)NR$^{e1}$R$^{f1}$, —NR$^{e1}$R$^{f1}$, —NR$^{c1}$C(=O)R$^{d1}$, —NR$^{c1}$C(=O)OR$^{a1}$, —NR$^{c1}$S(=O)$_2$R$^{d1}$, and —NR$^{c1}$S(=O)$_2$NR$^{e1}$R$^{f1}$; wherein said C$_{1-6}$ alkyl, C$_{2-6}$ alkenyl, C$_{2-6}$ alkynyl, C$_{3-7}$ cycloalkyl, C$_{3-7}$ cycloalkyl-C$_{1-3}$-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, and C$_{1-7}$ heteroaryl-C$_{1-3}$-alkyl are each optionally substituted with 1, 2, 3, or 4 independently selected R$^h$ groups;

each R$^{a1}$, R$^{c1}$, R$^{d1}$, R$^{e1}$, and R$^{f1}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ cycloalkyl-C3-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, and C$_{1-7}$ heteroaryl-C$_{1-3}$-alkyl; wherein said C$_{1-6}$ alkyl, C$_{2-6}$ alkenyl, C$_{2-6}$ alkynyl, C$_{3-7}$ cycloalkyl, C$_{3-7}$ cycloalkyl-C$_{1-3}$-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, and C$_{1-7}$ heteroaryl-C$_{1-3}$-alkyl are each optionally substituted by 1, 2, 3, or 4 independently selected R$^h$ groups;

each R$^{b1}$ is independently selected from C$_{1-6}$ alkyl, C$_{1-6}$ haloalkyl, C$_{2-6}$ alkenyl, C$_{2-6}$ alkynyl, C$_{3-7}$ cycloalkyl, C$_{3-7}$ cycloalkyl-C$_{1-3}$-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, and C$_{1-7}$ heteroaryl-C$_{1-3}$-alkyl; wherein said C$_{1-6}$ alkyl, C$_{2-6}$ alkenyl, C$_{2-6}$ alkynyl, C$_{3-7}$ cycloalkyl, C$_{3-7}$ cycloalkyl-C$_{1-3}$-alkyl, C$_{2-7}$ heterocycloalkyl, C$_{2-7}$ heterocycloalkyl-C$_{1-3}$-alkyl, phenyl, phenyl-C$_{1-3}$-alkyl, C$_{1-7}$ heteroaryl, and C$_{1-7}$ heteroaryl-C$_{1-3}$-alkyl are each optionally substituted by 1, 2, 3, or 4 independently selected R$^h$ groups;

each R$^h$ is independently selected from cyano, halo, hydroxy, C$_{1-4}$ alkyl, C$_{1-4}$ haloalkyl, C$_{1-4}$ alkoxy, C$_{1-4}$ haloalkoxy, amino, C$_{1-4}$ alkylamino, di-C$_{1-4}$-alkylamino, hydroxy-C$_{1-4}$ alkyl, C$_{1-4}$ alkoxy-C$_{1-4}$ alkyl, cyano-C$_{1-4}$ alkyl, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino;

m is 0, 1, or 2; and n is 0, 1, 2, 3, or 4.

2. The compound of claim 1, or a pharmaceutically acceptable salt thereof, wherein Z is CH.

3. The compound of claim 1, or a pharmaceutically acceptable salt thereof, wherein L is C(R$^6$)$_2$, C(=O), C(=O)O, C(=O)N(R$^7$), S(=O)$_2$, S(=O)$_2$N(R$^7$) or C(=NR$^{7a}$)N(R$^7$).

4. The compound of claim 3, or a pharmaceutically acceptable salt thereof, wherein R$^6$ is H, R$^7$ is H or methyl, and R$^{7a}$ is CN.

5. The compound of claim 1, or a pharmaceutically acceptable salt thereof, wherein Y is cyano.

6. The compound of claim 1, or a pharmaceutically acceptable salt thereof, wherein R$^1$, R$^2$, R$^3$, and R$^4$ are each H.

7. The compound of claim 1, or a pharmaceutically acceptable salt thereof, wherein n is 0.

8. The compound of claim 1, or a pharmaceutically acceptable salt thereof, wherein m is 1.

9. The compound of claim 1, or a pharmaceutically acceptable salt thereof, wherein A is H, methyl, ethyl, propyl, isopropyl, isobutyl, sec-butyl, 1,2-dimethylpropyl, 1-(tert-butyl)methyl, cyclopropyl, cyclobutyl, cyclopentyl, cyclohexyl, phenyl, a tetrahydropyran ring, a pyrrolidine ring, a piperidine ring, a pyridine ring, a pyrimidine ring, a thiazole ring, or a pyrazine ring; each of which is optionally substituted with p independently selected R$^8$ substituents; provided when L is O, S, C(=O), C(=O)O, S(=O), or S(=O)$_2$, then A is not H.

10. The compound of claim 1, or a pharmaceutically acceptable salt thereof, wherein each R$^8$ is independently selected from halo, cyano, C$_{1-6}$ alkyl, C$_{1-6}$ haloalkyl, C$_{3-7}$ cycloalkyl, C$_{2-7}$ heterocycloalkyl, —OR$^a$, —C(=O)OR$^a$, or —NR$^e$R$^f$; wherein said C$_{1-6}$ alkyl is optionally substituted by 1, 2, 3, or 4 independently selected R$^g$ groups; and wherein each R$^a$, R$^e$, and R$^f$ is independently selected from H, C$_{1-6}$ alkyl, and C$_{1-6}$ haloalkyl.

11. The compound of claim 1, or a pharmaceutically acceptable salt thereof, wherein each R$^g$ is independently selected from C$_{2-7}$ heterocycloalkyl, —OR$^{a1}$, and —NR$^{e1}$R$^{f1}$; wherein said C$_{2-7}$ heterocycloalkyl is optionally substituted by 1 or 2 R$^h$ groups independently selected from fluoro, OH, C$_{1-3}$ alkyl, C$_{1-3}$ alkoxy, and hydroxy-C$_{1-4}$ alkyl;

and wherein each $R^{a1}$, $R^{e1}$ and $R^{f1}$ are independently selected from H, $C_{3-7}$ cycloalkyl, and $C_{1-6}$ alkyl.

12. The compound of claim 1, or a pharmaceutically acceptable salt thereof, wherein each $R^h$ is independently selected from fluoro, OH, $C_{1-3}$ alkyl, $C_{1-3}$ alkoxy, and hydroxy-$C_{1-4}$ alkyl.

13. The compound of claim 1, or a pharmaceutically acceptable salt thereof, wherein:
  $R^1$, $R^2$, and $R^3$ are each H;
  Y is cyano;
  L is $C(R^6)_2$, $C(=O)$, $C(=O)N(R')$, $S(=O)_2$, or $S(=O)_2N(R^7)$;
  A is $C_{1-6}$ alkyl, $C_{3-10}$ cycloalkyl, $C_{2-10}$ heterocycloalkyl, $C_{6-10}$ aryl, or $C_{1-10}$ heteroaryl;
  wherein said $C_{1-6}$ alkyl, $C_{3-10}$ cycloalkyl, $C_{2-10}$ heterocycloalkyl, $C_{6-10}$ aryl, and $C_{1-10}$ heteroaryl are each optionally substituted with p independently selected $R^8$ substituents; wherein p is 1, 2, 3, 4, or 5;
    each $R^8$ is independently selected from halo, cyano, nitro, $C_{1-6}$ alkyl, $C_{1-6}$ haloalkyl, —$OR^a$, —$SR^a$, —$S(=O)R^b$, —$S(=O)_2R^b$, —$S(=O)_2NR^eR^f$, —$C(=O)R^b$, —$C(=O)OR^a$, —$C(=O)NR^eR^f$, —$OC(=O)R^b$, —$OC(=O)NR^eR^f$, —$NR^eR^f$, —$NR^cC(=O)R^d$, —$NR^cC(=O)OR^d$, —$NR^cS(=O)_2R^d$, and —$NR^cS(=O)_2NR^eR^f$;
    wherein said $C_{1-6}$ alkyl is optionally substituted by 1, 2, 3, or 4 independently selected $R^g$ groups;
    each $R^g$ is independently selected from halo, cyano, $C_{1-6}$ alkyl, $C_{1-6}$ haloalkyl, $C_{3-7}$ cycloalkyl, $C_{2-7}$ heterocycloalkyl, —$OR^{a1}$, —$S(=O)_2R^{b1}$, —$S(=O)_2NR^{e1}R^{f1}$, —$C(=O)R^{b1}$, —$C(=O)OR^{a1}$, and —$NR^{e1}R^{f1}$; wherein said $C_{1-6}$ alkyl, $C_{3-7}$ cycloalkyl, and $C_{2-7}$ heterocycloalkyl are each optionally substituted by 1, 2, 3, or 4 independently selected $R^h$ groups;
    each $R^a$, $R^c$, $R^d$, $R^e$, and $R^f$ is independently selected from H, $C_{1-6}$ alkyl, and $C_{1-6}$ haloalkyl;
    each $R^{b1}$ is independently selected from $C_{1-6}$ alkyl and $C_{1-6}$ haloalkyl;
    each $R^{a1}$, $R^{e1}$, and $R^{f1}$ is independently selected from H, $C_{1-6}$ alkyl, and $C_{1-6}$ haloalkyl;
    each $R^{b1}$ is independently selected from $C_{1-6}$ alkyl and $C_{1-6}$ haloalkyl;
  n is 0; and
  m is 1.

14. The compound accordingly to claim 1, or a pharmaceutically acceptable salt thereof, wherein:
  $R^1$, $R^2$, and $R^3$ are each H;
  Y is cyano;
  L is $C(R^6)_2$, $C(=O)$, $C(=O)O$, $C(=O)N(R')$, $S(=O)_2$, or $S(=O)_2N(R^7)$; or
  $R^6$ is H;
  $R^7$ is H or methyl;
  A is methyl, ethyl, propyl, isopropyl, isobutyl, sec-butyl, 1,2-dimethylpropyl, 1-(tert-butyl)methyl, cyclopropyl, cyclobutyl, cyclopentyl, cyclohexyl, phenyl, a tetrahydropyran ring, a pyrrolidine ring, a piperidine ring, a pyridine ring, a pyrimidine ring, a thiazole ring, or a pyrazine ring; each of which is optionally substituted with p independently selected $R^8$ substituents;
    each $R^8$ is independently selected from halo, cyano, $C_{1-6}$ alkyl, $C_{1-6}$ haloalkyl, $C_{3-7}$ cycloalkyl, $C_{2-7}$ heterocycloalkyl, —$OR^a$, —$C(=O)OR^a$, or —$NR^eR^f$; wherein said $C_{1-6}$ alkyl is optionally substituted by 1, 2, 3, or 4 independently selected $R^g$ groups; and wherein each $R^a$, $R^e$, and $R^f$ is independently selected from H, $C_{1-6}$ alkyl, and $C_{1-6}$ haloalkyl;
    each $R^g$ is independently selected from $C_{2-7}$ heterocycloalkyl, —$OR^{a1}$, and —$NR^{e1}R^{f1}$;
  wherein said $C_{2-7}$ heterocycloalkyl is optionally substituted by 1 or 2 $R^h$ groups independently selected from fluoro, OH, $C_{1-3}$ alkyl, $C_{1-3}$ alkoxy, and hydroxy-$C_{1-4}$ alkyl; and wherein each $R^{a1}$, $R^{e1}$ and $R^{f1}$ are independently selected from H, $C_{3-7}$ cycloalkyl, and $C_{1-6}$ alkyl;
  p is 1, 2, or 3;
  m is 1; and
  n is 0.

15. The compound of claim 1, selected from:
  {cis-3-(4-{[6-(1-hydroxy-1-methylethyl)-2-(trifluoromethyl)pyrimidin-4-yl]carbonyl}piperazin-1-yl)-1-[4-(1H-pyrrolo[2,3-b]pyridin-4-yl)-1H-pyrazol-1-yl]cyclobutyl}acetonitrile;
  {trans-3-(4-{[6-(1-hydroxy-1-methylethyl)-2-(trifluoromethyl)pyrimidin-4-yl]carbonyl}piperazin-1-yl)-1-[4-(1H-pyrrolo[2,3-b]pyridin-4-yl)-1H-pyrazol-1-yl]cyclobutyl)}acetonitrile; and
  {trans-3-(4-{[4-(1-hydroxy-1-methylethyl)-6-(trifluoromethyl)pyridin-2-yl]carbonyl}piperazin-1-yl)-1-[4-(1H-pyrrolo[2,3-b]pyridin-4-yl)-1H-pyrazol-1-yl]cyclobutyl}acetonitrile;
  or a pharmaceutically acceptable salt of any of the aforementioned.

16. The compound according to claim 1, or a pharmaceutically acceptable salt thereof, wherein the cyclobutyl ring in Formula I is the cis form.

17. The compound according to claim 1, or a pharmaceutically acceptable salt thereof, wherein the cyclobutyl ring in Formula I is the trans form.

18. A composition comprising a compound according to claim 1, or a pharmaceutically acceptable salt thereof, and at least one pharmaceutically acceptable carrier.

19. A method of modulating an activity of JAK1 comprising contacting JAK1 with a compound according to claim 1, or a pharmaceutically acceptable salt thereof.

20. The method according to claim 19, wherein said compound, or pharmaceutically acceptable salt thereof, is selective for JAK1 over JAK2.

* * * * *

UNITED STATES PATENT AND TRADEMARK OFFICE
CERTIFICATE OF CORRECTION

PATENT NO. : 10,640,506 B2  
APPLICATION NO. : 16/047544  
DATED : May 5, 2020  
INVENTOR(S) : James D. Rodgers et al.

Page 1 of 1

It is certified that error appears in the above-identified patent and that said Letters Patent is hereby corrected as shown below:

In the Claims

Column 290, Line 64, Claim 1, delete "—S(=O)$_2$R$^b$, —S(=O)$_2$R$^b$," and insert -- "—S(=O)R$^b$, —S(=O)$_2$R$^b$, --;

Column 291, Line 54, Claim 1, delete "-C3-alkyl," and insert -- -C$_{1-3}$-alkyl, --.

Column 293, Line 11, Claim 13, delete "N(R')," and insert -- N(R$^7$), --;

Column 293, Line 37, Claim 13, delete "R$^{b1}$" and insert -- R$^b$ --.

Column 293, Line 45, Claim 14, delete "accordingly" and insert -- according --;

Column 293, Line 49, Claim 14, delete "N(R')," and insert -- N(R$^7$), --.

Column 294, Line 32, Claim 15, delete "cyclobutyl)}" and insert -- cyclobutyl} --.

Signed and Sealed this  
Twenty-seventh Day of April, 2021

Drew Hirshfeld  
*Performing the Functions and Duties of the*  
*Under Secretary of Commerce for Intellectual Property and*  
*Director of the United States Patent and Trademark Office*